US007345178B2

(12) United States Patent
Nunes et al.

(10) Patent No.: US 7,345,178 B2
(45) Date of Patent: Mar. 18, 2008

(54) SIRTUIN MODULATING COMPOUNDS

(75) Inventors: Joseph J. Nunes, Andover, MA (US); Jill Milne, Brookline, MA (US); Jean Bemis, Arlington, MA (US); Roger Xie, Southborough, MA (US); Chi B. Vu, Arlington, MA (US); Pui Yee Ng, Boston, MA (US); Jeremy S. Disch, Natick, MA (US)

(73) Assignee: Sirtris Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 11/499,919

(22) Filed: Aug. 4, 2006

(65) Prior Publication Data

US 2007/0043050 A1 Feb. 22, 2007

Related U.S. Application Data

(60) Provisional application No. 60/705,612, filed on Aug. 4, 2005, provisional application No. 60/741,783, filed on Dec. 2, 2005, provisional application No. 60/779,370, filed on Mar. 3, 2006, provisional application No. 60/792,276, filed on Apr. 14, 2006.

(51) Int. Cl.
*C07D 513/00* (2006.01)
*A01N 43/78* (2006.01)
(52) U.S. Cl. .................................. 548/154; 514/366
(58) Field of Classification Search .............. 548/154
See application file for complete search history.

(56) References Cited

U.S. PATENT DOCUMENTS

| 4,018,932 | A  | 4/1977  | Spicer et al. |
| 2004/0176396 | A1 | 9/2004  | Biftu et al. |
| 2005/0245539 | A1 | 11/2005 | Mendla et al. |

FOREIGN PATENT DOCUMENTS

| GB | 1 402 689      | 8/1975  |
| JP | 50-76084       | 6/1975  |
| JP | 52-89689       | 7/1977  |
| JP | 07 291976      | 11/1995 |
| WO | WO-01/27119 A2 | 4/2001  |
| WO | WO-03/007959   | 1/2003  |
| WO | WP-03/11219    | 2/2003  |
| WO | WO-03/028725 A1| 4/2003  |
| WO | WO-03/028728 A1| 4/2003  |
| WO | WO-03/042188 A1| 5/2003  |
| WO | WO-2004/080481 A1 | 9/2004 |
| WO | WO-2005/058884 A2 | 6/2005 |
| WO | WO-2005/069998 A2 | 8/2005 |

OTHER PUBLICATIONS

Andreani, et al., "6-(Hydroxyphenyl) Imidazo [2,1-b]Thiazoles as Potential Antiinflammatory Agents: Effects on Human Neutrophil Functions," *Collection of Czechoslovak Chemical Communications*, 65:267-279 (2000).

Andreani, et al., "Synthesis and antitubercular activity of imidazol[2,1-*b*]thiazoles," *European Journal of Medicinal Chemistry*, 36:743-746 (2001).

Andreani, et al., "Synthesis and antitumor activity of substituted 3-(5-imidazo[2,1-b]thiazolylmethylene)-2-indolinones," *Anti-Cancer Drug Design*, 16:167-174 (2001).

Andreani, et al., "Thienylimidazo[2,1-*b*]thiazoles as Inhibitors of Mitochondrial NADH Dehydrogenase," *Journal of Medicinal Chemistry*, 38:1090-1097 (1995).

Barchechath, et al., "Inhibitors of Apoptosis in Lymphocytes: Synthesis and Biological Evaluation of Compounds Related to Pifithrin-α," *Journal of Medicinal Chemistry*, 48:6409-6422 (2005).

Bienayme and Bouzid et al., "A New Heterocyclic Multicomponent Reaction For the Combinatorial Synthesis of Fused 3-Aminoimidazoles," *Angewandte Chemie International Edition*, 37(16):2234-2237 (1998).

Forti, et al., "NADPH-generating system: influence on microsomal mono-oxygenase stability during incubation for the liver-microsomal assay with rat and mouse S9 fractions," *Mutation Research*, 129:291-297 (1984).

Freymann, et al., Efficient identification of inhibitors targeting the closed active site conformation of the HPRT from *Trypansoma cruzi*, *Chemistry and Biology*, 7:957-968 (2000).

Gemesi, et al., "Application of LC-MS analysis to the characterisation of the in vitro and in vivo metabolite profiles of RGH-1756 in the rat," *Journal of Pharmaceutical and Biomedical Analysis*, 24:877-885 (2001).

Hozien, et al., "An Efficient Route for Synthesis of 5,6-Diphenylimidazo-[2,1-*b*]thiazoles as Antibacterial Agents," *Journal of Heterocyclic Chemistry*, 37:943-949 (2000).

Ikeda, et al., "Functional analysis of four naturally occuring variants of human constitutive androslane receptor," *Molecular Genetics and Metabolism*, 86:314-319 (2005).

Jinno, et al., "Identification of Novel Alternative Splice Variants of Human Constitutive Androstane Receptor and Characterization of Their Expression in the Liver," *Molecular Pharmacology*, 65(3):496-502 (2004).

Laszlovszky, et al., "Substituted phenoxyalkylpiperazines as dopamine $D_3$ receptor ligands," *Pharmazie*, 56(4):287-289 (2001).

Lewis, et al., "Levamisole-Resistant Mutants of the Nematode *Caenorhabditis elegans* Appear to Lack Pharmacological Acetylcholine Receptors," *Neuroscience*, 5;967-989 (1980).

(Continued)

*Primary Examiner*—Kamal A. Saeed
*Assistant Examiner*—Robert Havlin
(74) *Attorney, Agent, or Firm*—Ropes & Gray LLP

(57) ABSTRACT

Provided herein are novel sirtuin-modulating compounds and methods of use thereof. The sirtuin-modulating compounds may be used for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benfit from increased mitochondrial activity. Also provided are compositions comprising a sirtuin-modulating compound in combination with another therapeutic agent.

30 Claims, 2 Drawing Sheets

OTHER PUBLICATIONS

Terjeki, et al., "An HPLC/UV method for the determination of RGH-1756 in dog and rat plasma," *Journal of Pharmaceutical and Biomedical Analysis*, 24:913-920 (2001).

Yagodinets, et al., "Convenient method for the synthesis of phosphorus-containing heterocyclic systems of imidazo[2,1-*b*]thiazoles, imidazo[2,1-*a*]pyridines and quinoxalines," *Zhurnal Obshchei Khimii*, 54(12):2789-2790 (1984).

Yueh, et al., "High Volume Bioassays to Assess CYP3A4-Mediated Drug Interactions: Induction and Inhibition in a Single Cell Line," *Drug Metabolism and Disposition*, 33(1):38-48 (2005).

Porcu, et al., "The emerging therapeutic potential of sirtuin-interacting drugs: from cell death to lifespan extension," TRENDS in Pharmacological Sciences, 26(2):94-103 (2005).

Database Chemcats Chemical Abstracts Service, Columbus, OH, US; Jan. 18, 2005 (Jan. 18, 2005), XP002384121 ON's STK199474, STK199472, STK199473, STK180355, STK174405, STK196060, STK115373, STK164162, STK136073, STK164152, STK120473, STK052285 -& "Interchim Intermediates" Jan. 18, 2005 (Jan. 18, 2005), Interchim, Montlucon, France, XP002386059.

SIRTUIN MODULATING COMPOUNDS

RELATED APPLICATIONS

This application claims the benefit of U.S. Provisional Application Nos. 60/705,612, filed Aug. 4, 2005, 60/741,783, filed Dec. 2, 2005, 60/779,370, filed Mar. 3, 2006 and 60/792,276, filed Apr. 14, 2006, the contents of which are incorporated by reference in their entirety.

BACKGROUND

The Silent Information Regulator (SIR) family of genes represents a highly conserved group of genes present in the genomes of organisms ranging from archaebacteria to a variety of eukaryotes (Frye, 2000). The encoded SIR proteins are involved in diverse processes from regulation of gene silencing to DNA repair. The proteins encoded by members of the SIR gene family show high sequence conservation in a 250 amino acid core domain. A well-characterized gene in this family is S. cerevisiae SIR2, which is involved in silencing HM loci that contain information specifying yeast mating type, telomere position effects and cell aging (Guarente, 1999; Kaeberlein et al., 1999; Shore, 2000). The yeast Sir2 protein belongs to a family of histone deacetylases (reviewed in Guarente, 2000; Shore, 2000). The Sir2 homolog, CobB, in *Salmonella typhimurium*, functions as an NAD (nicotinamide adenine dinucleotide)-dependent ADP-ribosyl transferase (Tsang and Escalante-Semerena, 1998).

The Sir2 protein is a class III deacetylase which uses NAD as a cosubstrate (Imai et al., 2000; Moazed, 2001; Smith et al., 2000; Tanner et al., 2000; Tanny and Moazed, 2001). Unlike other deacetylases, many of which are involved in gene silencing, Sir2 is insensitive to class I and II histone deacetylase inhibitors like trichostatin A (TSA) (Imai et al., 2000; Landry et al., 2000a; Smith et al., 2000).

Deacetylation of acetyl-lysine by Sir2 is tightly coupled to NAD hydrolysis, producing nicotinamide and a novel acetyl-ADP ribose compound (Tanner et al., 2000; Landry et al., 2000b; Tanny and Moazed, 2001). The NAD-dependent deacetylase activity of Sir2 is essential for its functions which can connect its biological role with cellular metabolism in yeast (Guarente, 2000; Imai et al., 2000; Lin et al., 2000; Smith et al., 2000). Mammalian Sir2 homologs have NAD-dependent histone deacetylase activity (Imai et al., 2000; Smith et al., 2000). Most information about Sir2 mediated functions comes from the studies in yeast (Gartenberg, 2000; Gottschling, 2000).

Biochemical studies have shown that Sir2 can readily deacetylate the amino-terminal tails of histones H3 and H4, resulting in the formation of 1-O-acetyl-ADP-ribose and nicotinamide. Strains with additional copies of SIR2 display increased rDNA silencing and a 30% longer life span. It has recently been shown that additional copies of the *C. elegans* SIR2 homolog, sir-2.1, and the *D. melanogaster* dSir2 gene greatly extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

SIRT3 is a homolog of SIRT1 that is conserved in prokaryotes and eukaryotes (P. Onyango et al., Proc. Natl. Acad. Sci. USA 99: 13653-13658 (2002)). The SIRT3 protein is targeted to the mitochondrial cristae by a unique domain located at the N-terminus. SIRT3 has NAD+-dependent protein deacetylase activity and is upbiquitously expressed, particularly in metabolically active tissues. Upon transfer to the mitochondria, SIRT3 is believed to be cleaved into a smaller, active form by a mitochondrial matrix processing peptidase (MPP) (B. Schwer et al., J. Cell Biol. 158: 647-657 (2002)).

Caloric restriction has been known for over 70 years to improve the health and extend the lifespan of mammals (Masoro, 2000). Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of this diet (Anderson et al., 2003; Helfand and Rogina, 2004). Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway (Lin et al., 2001).

SUMMARY

Provided herein are novel sirtuin-modulating compounds and methods of use thereof.

In one aspect, the invention provides sirtuin-modulating compounds of Formula (I):

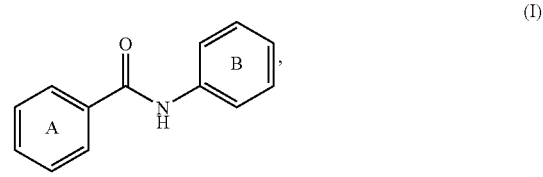

or a salt thereof, where:

Ring A is optionally substituted, fused to another ring or both; and

Ring B is substituted with at least one carboxy, substituted or unsubstituted arylcarboxamine, substituted or unsubstituted aralkylcarboxamine, substituted or unsubstituted heteroaryl group, substituted or unsubstituted heterocyclylcarbonylethenyl, or polycyclic aryl group or is fused to an aryl ring and is optionally substituted by one or more additional groups.

In another aspect, the invention provides sirtuin-modulating compounds of Formula (II):

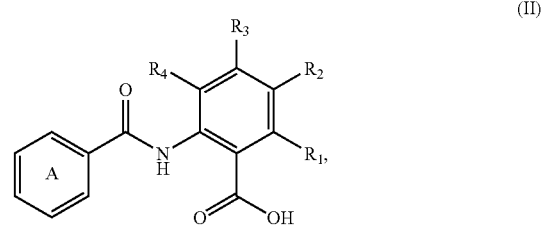

or a salt thereof, where:

Ring A is optionally substituted;

$R_1$, $R_2$, $R_3$ and $R_4$ are independently selected from the group consisting of —H, halogen, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;

$R_5$ and $R_6$ are independently —H, a substituted or unsubstituted alkyl group, a substituted or unsubstituted aryl group or a substituted or unsubstituted heterocyclic group; and n is 1 or 2.

In yet another aspect, the invention provides sirtuin-modulating compounds of Formula (III):

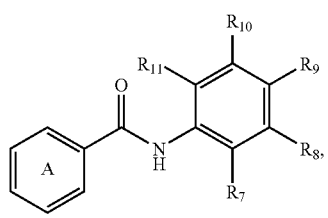

(III)

or a salt thereof, where:

Ring A is optionally substituted;

$R_5$ and $R_6$ are independently —H, a substituted or unsubstituted alkyl group, a substituted or unsubstituted aryl group or a substituted or unsubstituted heterocyclic group;

$R_7$, $R_9$, $R_{10}$ and $R_{11}$ are independently selected from the group consisting of —H, halogen, —$R_5$, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;

$R_8$ is a polycyclic aryl group; and n is 1 or 2.

In another aspect, the invention provides sirtuin-modulating compounds of Formula (IV):

(IV)

or a salt thereof, wherein:

each Ar and Ar' is independently an optionally substituted carbocyclic or heterocyclic aryl group;

L is an optionally substituted carbocyclic or heterocyclic arylene group;

each J and K is independently $NR_1'$, O, S, or is optionally independently absent; or when J is $NR_1'$, $R_1'$ is a C1-C4 alkylene or C2-C4 alkenylene attached to Ar' to form a ring fused to Ar'; or when K is $NR_1'$, $R_1'$ is a C1-C4 alkylene or C2-C4 alkenylene attached to L to form a ring fused to L;

each M is C(O), S(O), S(O)$_2$, or $CR_1'R_1'$;

each $R_1'$ is independently selected from H, C1-C10 alkyl; C2-C10 alkenyl; C2-C10 alkynyl; C3-C10 cycloalkyl; C4-C10 cycloalkenyl; aryl; $R_5'$; halo; haloalkyl; $CF_3$; $SR_2'$; $OR_2'$; $NR_2'R_2'$; $NR_2'R_3'$; $COOR_2'$; $NO_2$; CN; $C(O)R_2'$; $C(O)C(O)R_2'$; $C(O)NR_2'R_2'$; $OC(O)R_2'$; $S(O)_2R_2'$; $S(O)_2NR_2'R_2'$; $NR_2'C(O)NR_2'R_2'$; $NR_2'C(O)C(O)R_2'$; $NR_2'C(O)R_2'$; $NR_2'(COOR_2')$; $NR_2'C(O)R_5'$; $NR_2'S(O)_2NR_2'R_2'$; $NR_2'S(O)_2R_2'$; $NR_2'S(O)_2R_5'$; $NR_2'C(O)C(O)NR_2'R_2'$; $NR_2'C(O)C(O)NR_2'R_3'$; C1-C10 alkyl substituted with aryl, $R_4'$ or $R_5'$; or C2-C10 alkenyl substituted with aryl, $R_4'$ or $R_5'$;

each $R_2'$ is independently H; C1-C10 alkyl; C2-C10 alkenyl; C2-C10 alkynyl; C3-C10 cycloalkyl; C4-C10 cycloalkenyl; aryl; $R_6'$; C1-C10 alkyl substituted with 1-3 independent aryl, $R_4'$ or $R_6'$ groups; C3-C10 cycloalkyl substituted with 1-3 independent aryl, $R_4'$ or $R_6'$ groups; or C2-C10 alkenyl substituted with 1-3 independent aryl, $R_4'$ or $R_6'$;

each $R_3'$ is independently $C(O)R_2'$, $COOR_2'$, or $S(O)_2R_2'$;

each $R_4'$ is independently halo, $CF_3$, $SR_7'$, $OR_7'$, $OC(O)R_7'$, $NR_7'R_7'$, $NR_7'R_8'$, $NR_8'R_8'$, $COOR_7'$, $NO_2$, CN, $C(O)R_7'$, or $C(O)NR_7'R_7'$;

each $R_5'$ is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; aryl; $R_6'$; halo; sulfur; oxygen; $CF_3$; haloalkyl; $SR_2'$; $OR_2'$; $OC(O)R_2'$; $NR_2'R_2'$; $NR_2'R_3'$; $NR_3'R_3'$; $COOR_2'$; $NO_2$; CN; $C(O)R_2'$; $C(O)NR_2'R_2'$; C1-C10 alkyl substituted with 1-3 independent $R_4'$, $R_6'$, or aryl; or C2-C10 alkenyl substituted with 1-3 independent $R_4'$, $R_6'$, or aryl;

each $R_6'$ is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; halo; sulfur; oxygen; $CF_3$; haloalkyl; $SR_7'$; $OR_7'$; $NR_7'R_7'$; $NR_7'R_8'$; $NR_8'R_8'$; $COOR_7'$; $NO_2$; CN; $C(O)R_7'$; or $C(O)NR_7'R_7'$;

each $R_7'$ is independently H, C1-C10 alkyl; C2-C10 alkenyl; C2-C10 alkynyl; C3-C10 cycloalkyl; C4-C10 cycloalkenyl; haloalkyl; C1-C10 alkyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR_{10}'$, $SR_{10}'$, $NR_{10}'R_{10}'$, $COOR_{10}'$, $NO_2$, CN, $C(O)R_{10}'$, $C(O)NR_{10}'R_{10}'$, $NHC(O)R_{10}'$, or $OC(O)R_{10}'$; or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR_{10}'$, $SR_{10}'$, $NR_{10}'R_{10}'$, $COOR_{10}'$, $NO_2$, CN, $C(O)R_{10}'$, $C(O)NR_{10}'R_{10}'$, $NHC(O)R_{10}'$, or $OC(O)R_{10}'$;

each $R_8'$ is independently $C(O)R_7'$, $COOR_7'$, or $S(O)_2R_7'$;

each $R_9'$ is independently H, C1-C10 alkyl, C2-C10 alkenyl, C2-C10 alkynyl, C3-C10 cycloalkyl, C4-C10 cycloalkenyl, or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR_{10}'$, $SR_{10}'$, $NR_{10}'R_{10}'$, $COOR_{10}'$, $NO_2$, CN, $C(O)R_{10}'$, $C(O)NR_{10}'R_{10}'$, $NHC(O)R_{10}'$, or $OC(O)R_{10}'$;

each $R_{10}'$ is independently H; C1-C10 alkyl; C2-C10 alkenyl; C2-C10 alkynyl; C3-C10 cycloalkyl; C4-C10 cycloalkenyl; C1-C10 alkyl optionally substituted with halo, $CF_3$, $OR_{11}'$, $SR_{11}'$, $NR_{11}'R_{11}'$, $COOR_{11}'$, $NO_2$, CN; or phenyl optionally substituted with halo, $CF_3$, $OR_{11}'$, $SR_{11}'$, $NR_{11}'R_{11}'$, $COOR_{11}'$, $NO_2$, CN;

each $R_{11}'$ is independently H; C1-C10 alkyl; C3-C10 cycloalkyl or phenyl;

each haloalkyl is independently a C1-C10 alkyl substituted with one or more halogen atoms, selected from F, Cl, Br, or I, wherein the number of halogen atoms may not exceed that number that results in a perhaloalkyl group; and each aryl is independently optionally substituted with 1-3 independent C1-C10 alkyl; C2-C10 alkenyl; C2-C10 alkynyl; C3-C10 cycloalkyl; C4-C10 cycloalkenyl; R$_6$'; halo; haloalkyl; CF$_3$; OR$_9$'; SR$_9$'; NR$_9$'R$_9$'; COOR$_9$'; NO$_2$; CN; C(O)R$_9$'; C(O)C(O)R$_9$'; C(O)NR$_9$'R$_9$'; S(O)$_2$R$_9$'; N(R$_9$')C(O)R$_9$'; N(R$_9$')(COOR$_9$'); N(R$_9$')S(O)$_2$R$_9$'; S(O)$_2$NR$_9$'R$_9$'; OC(O)R$_9$'; NR$_9$'C(O)NR$_9$'R$_9$'; NR$_9$'C(O)C(O)R$_9$'; NR$_9$'C(O)R$_6$'; NR$_9$'S(O)$_2$NR$_9$'R$_9$'; NR$_9$'S(O)$_2$R$_6$'; NR$_9$'C(O)C(O)NR$_9$'R$_9$'; C1-C10 alkyl substituted with 1-3 independent R$_6$', halo, CF$_3$, OR$_9$', SR$_9$', NR$_9$'R$_9$', COOR$_9$', NO$_2$, CN, C(O)R$_9$', C(O)NR$_9$'R$_9$', NHC(O)R$_9$', NH(COOR$_9$'), S(O)$_2$NR$_9$'R$_9$', OC(O)R$_9$'; C2-C10 alkenyl substituted with 1-3 independent R$_6$', halo, CF$_3$, OR$_9$', SR$_9$', NR$_9$'R$_9$', COOR$_9$', NO$_2$, CN, C(O)R$_9$', C(O)NR$_9$'R$_9$', NHC(O)R$_9$', NH(COOR$_9$'), S(O)$_2$NR$_9$'R$_9$', OC(O)R$_9$'; or R$_9$'.

In a further aspect, the invention provides sirtuin-modulating compounds of Formula (IVa):

Het—L—Q—Ar'     (IVa)

or a salt thereof, where:

Het is an optionally substituted heterocyclic aryl group;

L is an optionally substituted carbocyclic or heterocyclic arylene group;

Ar' is an optionally substituted carbocyclic or heterocyclic aryl group; and

Q is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(O)—CR$_1$'R$_1$'—NR$_1$'—, —NR$_1$'—C(=NR$_1$')—NR$_1$'—, —C(O)—NR$_1$'—, —C(O)—NR$_1$'—S(O)$_2$—NR$_1$'—, —CR$_1$'R$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$'—C(O)—NR$_1$'—, —CR$_1$'R$_1$'—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R$_1$'—,

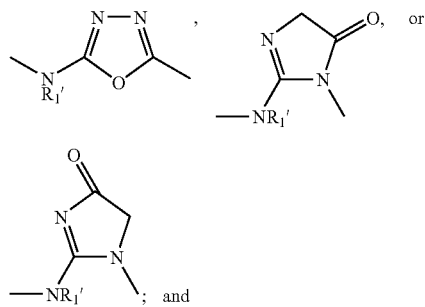

each R$_1$' is independently selected from H or optionally substituted C$_1$-C$_3$ straight or branched alkyl, wherein:

when Het is a polycyclic heteroaryl, L is an optionally substituted phenylene, Q and Het are attached to L in a meta orientation, and Ar' is optionally substituted phenyl;

then Q is not —NH—C(O)—.

In still yet another aspect, the invention provides sirtuin-modulating compounds of Formula (V):

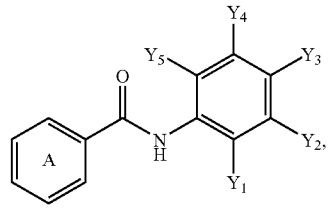

or a salt thereof, wherein:

Ring A is optionally substituted with at least one R$_1$' group;

Y$_1$, Y$_2$, Y$_3$, Y$_4$, and Y$_5$ are independently R$_1$';

each R$_1$' is independently selected from H, C1-C10 alkyl; C2-C10 alkenyl; C2-C10 alkynyl; C3-C10 cycloalkyl; C4-C10 cycloalkenyl; aryl; R$_5$'; halo; haloalkyl; CF$_3$; SR$_2$'; OR$_2$'; NR$_2$'R$_2$'; NR$_2$'R$_3$'; COOR$_2$'; NO$_2$; CN; C(O)R$_2$'; C(O)C(O)R$_2$'; C(O)NR$_2$'R$_2$'; OC(O)R$_2$'; S(O)$_2$R$_2$'; S(O)$_2$NR$_2$'R$_2$'; NR$_2$'C(O)NR$_2$'R$_2$'; NR$_2$'C(O)C(O)R$_2$'; NR$_2$'C(O)R$_2$'; NR$_2$'(COOR$_2$'); NR$_2$'C(O)R$_5$'; NR$_2$'S(O)$_2$NR$_2$'R$_2$'; NR$_2$'S(O)$_2$R$_2$'; NR$_2$'S(O)$_2$R$_5$'; NR$_2$'C(O)C(O)NR$_2$'R$_2$'; NR$_2$'C(O)C(O)NR$_2$'R$_3$'; C1-C10 alkyl substituted with aryl, R$_4$' or R$_5$'; or C2-C10 alkenyl substituted with aryl, R$_4$' or R$_5$';

each R$_2$' is independently H; C1-C10 alkyl; C2-C10 alkenyl; C2-C10 alkynyl; C3-C10 cycloalkyl; C4-C10 cycloalkenyl; aryl; R$_6$'; C1-C10 alkyl substituted with 1-3 independent aryl, R$_4$' or R$_6$' groups; C3-C10 cycloalkyl substituted with 1-3 independent aryl, R$_4$' or R$_6$' groups; or C2-C10 alkenyl substituted with 1-3 independent aryl, R$_4$' or R$_6$';

each R$_3$' is independently C(O)R$_2$', COOR$_2$', or S(O)$_2$R$_2$';

each R$_4$' is independently halo, CF$_3$, SR$_7$', OR$_7$', OC(O)R$_7$', NR$_7$'R$_7$', NR$_7$'R$_8$', NR$_8$'R$_8$', COOR$_7$', NO$_2$, CN, C(O)R$_7$', or C(O)NR$_7$'R$_7$';

each R$_5$' is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; aryl; R$_6$'; halo; sulfur; oxygen; CF$_3$; haloalkyl; SR$_2$'; OR$_2$'; OC(O)R$_2$'; NR$_2$'R$_2$'; NR$_2$'R$_3$'; NR$_3$'R$_3$'; COOR$_2$'; NO$_2$; CN; C(O)R$_2$'; C(O)NR$_2$'R$_2$'; C1-C10 alkyl substituted with 1-3 independent R$_4$', R$_6$', or aryl; or C2-C10 alkenyl substituted with 1-3 independent R$_4$', R$_6$', or aryl;

each R$_6$' is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; halo; sulfur; oxygen; CF$_3$; haloalkyl; SR$_7$'; OR$_7$'; NR$_7$'R$_7$'; NR$_7$'R$_8$'; NR$_8$'R$_8$'; COOR$_7$'; NO$_2$; CN; C(O)R$_7$'; or C(O)NR$_7$'R$_7$';

each R$_7$' is independently H, C1-C10 alkyl; C2-C10 alkenyl; C2-C10 alkynyl; C3-C10 cycloalkyl; C4-C10 cycloalkenyl; haloalkyl; C1-C10 alkyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR_{10}'$, $SR_{10}'$, $NR_{10}'R_{10}'$, $COOR_{10}'$, $NO_2$, CN, $C(O)R_{10}'$, $C(O)NR_{10}'R_{10}'$, $NHC(O)R_{10}'$, or $OC(O)R_{10}'$; or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR_{10}'$, $SR_{10}'$, $NR_{10}'R_{10}'$, $COOR_{10}'$, $NO_2$, CN, $C(O)R_{10}'$, $C(O)NR_{10}'R_{10}'$, $NHC(O)R_{10}'$, or $OC(O)R_{10}'$;

each $R_8'$ is independently $C(O)R_7'$, $COOR_7'$, or $S(O)_2R_7'$;

each $R_9'$ is independently H, C1-C10 alkyl, C2-C10 alkenyl, C2-C10 alkynyl, C3-C10 cycloalkyl, C4-C10 cycloalkenyl, or phenyl optionally substituted with 1-3 independent C1-C10 alkyl, C2-C10 alkenyl, C2-C10 alkynyl, C3-C10 cycloalkyl, C4-C10 cycloalkenyl, halo, $CF_3$, $OR_{10}'$, $SR_{10}'$, $NR_{10}'R_{10}'$, $COOR_{10}'$, $NO_2$, CN, $C(O)R_{10}'$, $C(O)NR_{10}'R_{10}'$, $NHC(O)R_{10}'$, or $OC(O)R_{10}'$;

each $R_{10}'$ is independently H; C1-C10 alkyl; C2-C10 alkenyl; C2-C10 alkynyl; C3-C10 cycloalkyl; C4-C10 cycloalkenyl; C1-C10 alkyl optionally substituted with halo, $CF_3$, $OR_{11}'$, $SR_{11}'$, $NR_{11}'R_{11}'$, $COOR_{11}'$, $NO_2$, CN; or phenyl optionally substituted with halo, $CF_3$, $OR_{11}'$, $SR_{11}'$, $NR_{11}'R_{11}'$, $COOR_{11}'$, $NO_2$, CN;

each $R_{11}'$ is independently H; C1-C10 alkyl; C3-C10 cycloalkyl or phenyl;

each haloalkyl is independently a C1-C10 alkyl substituted with one or more halogen atoms, selected from F, Cl, Br, or I, wherein the number of halogen atoms may not exceed that number that results in a perhaloalkyl group; and each aryl is independently a 5- to 7-membered monocyclic ring system or a 9- to 12-membered bicyclic ring system optionally substituted with 1-3 independent C1-C10 alkyl; C2-C10 alkenyl; C2-C10 alkynyl; C3-C10 cycloalkyl; C4-C10 cycloalkenyl; $R_6'$; halo; haloalkyl; $CF_3$; $OR_9'$; $SR_9'$; $NR_9'R_9'$; $COOR_9'$; $NO_2$; CN; $C(O)R_9'$; $C(O)C(O)R_9'$; $C(O)NR_9'R_9'$; $S(O)_2R_9'$; $N(R_9')C(O)R_9'$; $N(R_9')(COOR_9')$; $N(R_9')S(O)_2R_9'$; $S(O)_2NR_9'R_9'$; $OC(O)R_9'$; $NR_9'C(O)NR_9'R_9'$; $NR_9'C(O)C(O)R_9'$; $NR_9'C(O)R_6'$; $NR_9'S(O)_2NR_9'R_9'$; $NR_9'S(O)_2R_6'$; $NR_9'C(O)C(O)NR_9'R_9'$; C1-C10 alkyl substituted with 1-3 independent $R_6'$, halo, $CF_3$, $OR_9'$, $SR_9'$, $NR_9'R_9'$, $COOR_9'$, $NO_2$, CN, $C(O)R_9'$, $C(O)NR_9'R_9'$, $NHC(O)R_9'$, $NH(COOR_9')$, $S(O)_2NR_9'R_9'$, $OC(O)R_9'$; C2-C10 alkenyl substituted with 1-3 independent $R_6'$, halo, $CF_3$, $OR_9'$, $SR_9'$, $NR_9'R_9'$, $COOR_9'$, $NO_2$, CN, $C(O)R_9'$, $C(O)NR_9'R_9'$, $NHC(O)R_9'$, $NH(COOR_9')$, $S(O)_2NR_9'R_9'$, $OC(O)R_9'$; or $R_9'$.

In one aspect, the invention provides sirtuin-modulating compounds of Structural Formula (VI):

$$\text{Het}-N\underset{\underset{O}{\|}}{\overset{\frown}{N}}-C-NH-Ar', \quad (VI)$$

or a salt thereof, wherein:

Het is an optionally substituted heterocyclic aryl group; and

Ar' is an optionally substituted carbocyclic or heterocyclic aryl group.

The invention also includes prodrugs and metabolites of the compounds disclosed herein.

In another aspect, the invention provides sirtuin-modulating compounds of Structural Formula (VII):

(VII)

or a salt thereof, wherein:

each of $X_7$, $X_8$, $X_9$ and $X_{10}$ is independently selected from N, $CR^{20}$, or $CR_1'$, wherein:

each $R^{20}$ is independently selected from H or a solubilizing group;

each $R_1'$ is independently selected from H or optionally substituted $C_1$-$C_3$ straight or branched alkyl;

one of $X_7$, $X_8$, $X_9$ and $X_{10}$ is N and the others are selected from CR20 or $CR_1'$; and zero to one $R^{20}$ is a solubilizing group;

$R^{19}$ is selected from:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, S or O;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group;

zero to one $R_1'$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

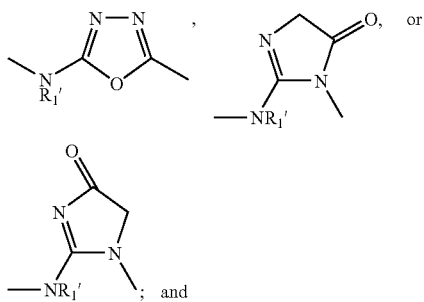

$R^{31}$ is selected from an optionally substituted monocyclic or bicyclic aryl, or an optionally substituted monocyclic or bicyclic heteroaryl, with the provisos that said compound is not:

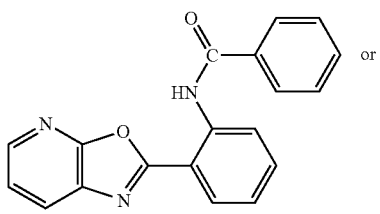

that when $R^{19}$ is

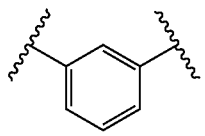

and $R^{21}$ is —NHC(O)—, $R^{31}$ is not an optionally substituted phenyl.

In certain embodiments, compounds of Structural Formula (VII) have the following values:

each of $X_7$, $X_8$, $X_9$ and $X_{10}$ is independently selected from N, $CR^{20}$, or $CR_1'$, wherein:

each $R^{20}$ is independently selected from H or a solubilizing group;

each $R_1'$ is independently selected from H or optionally substituted $C_1$-$C_3$ straight or branched alkyl;

one of $X_7$, $X_8$, $X_9$ and $X_{10}$ is N and the others are selected from $CR^{20}$ or $CR_1'$; and zero to one $R^{20}$ is a solubilizing group;

$R^{19}$ is selected from:

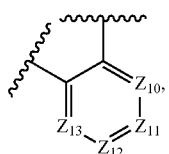 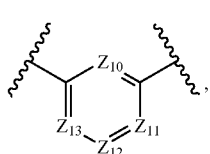

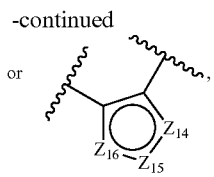

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl, with the provisos that:
said compound is not:

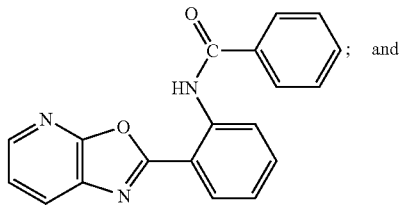

when $X_8$ and $X_9$ are each independently selected from $CR^{20}$ or $CR_1'$, $R^{19}$ is

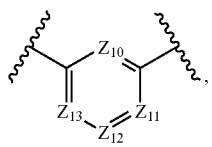

and each of $Z_{10}$, $Z_{11}$, $Z_{12}$ and $Z_{13}$ is independently selected from $CR^{20}$, or $CR_1'$, then:
a) at least one of $X_8$ and $X_9$ is not CH; or
b) at least one of $Z_{10}$, $Z_{11}$, $Z_{12}$ and $Z_{13}$ is $CR^{20}$, wherein $R^{20}$ is a solubilizing group.

In yet another embodiment, the invention provides sirtuin-modulating compounds of Structural Formula (VIII):

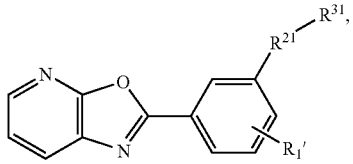
(VIII)

or a salt thereof, wherein:

$R_1'$ is selected from H or optionally substituted $C_1$-$C_3$ straight or branched alkyl;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

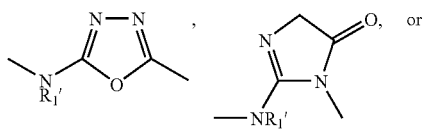
; and $R^{31}$ is selected from an optionally substituted monocyclic or bicyclic aryl, or an optionally substituted monocyclic or bicyclic heteroaryl, with the provisos that:

when $R_1'$ is methyl, and $R^{21}$ is —NH—C(O)—, $R^{31}$ is not

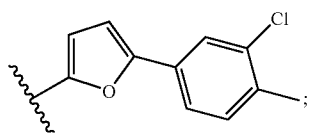

1-methoxynaphthyl; 2-methoxynaphthyl; or unsubstituted 2-thienyl;

when $R_1'$ is methyl, and $R^{21}$ is —NH—C(O)—CH=CH—, $R^{31}$ is not

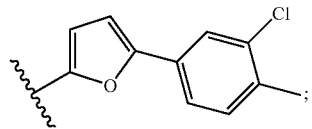
;

when $R_1'$ is methyl, and $R^{21}$ is —NH—C(O)—CH—O—, $R^{31}$ is not unsubstituted naphthyl; 2-methoxy, 4-nitrophenyl; 4-chloro, 2-methylphenyl; or 4-t-butylphenyl; and when $R^{21}$ is —NH—C(O)—, $R^{31}$ is not optionally substituted phenyl.

In a further embodiment, the invention provides sirtuin-modulating compounds of Structural Formula (IX):

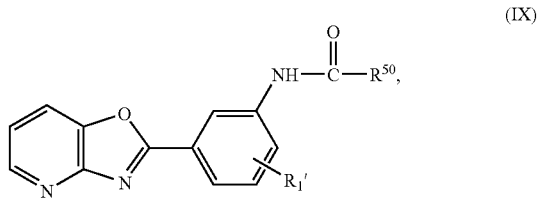
(IX)

or a salt thereof, wherein:

$R_1'$ is selected from H or optionally substituted $C_1$-$C_3$ straight or branched alkyl; and $R^{50}$ is selected from 2,3-dimethoxyphenyl, phenoxyphenyl, 2-methyl-3-methoxyphenyl, 2-methoxy-4-methylphenyl, or phenyl substituted with 1 to 3 substituents, wherein one of said substituents is a solubilizing group; with the provisos that $R^{50}$ is not substituted simultaneously with a solubilizing group and a nitro group, and $R^{50}$ is not singly substituted at the 4-position with cyclic solubilizing group or at the 2-position with a morpholino group.

In one aspect, the invention provides sirtuin-modulating compounds of Structural Formula (X):

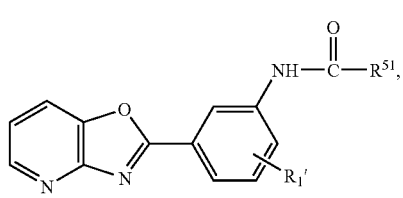
(X)

or a salt thereof, wherein:

$R_1'$ is selected from H or optionally substituted $C_1$-$C_3$ straight or branched alkyl; and $R^{51}$ is selected from an ooptionally substituted monocyclic heteroaryl, an optionally substituted bicyclic heteroaryl, or an optionally substituted naphthyl, wherein $R^{51}$ is not chloro-benzo(b)thienyl, unsubstituted benzodioxolyl, unsubstituted benzofuranyl, methyl-benzofuranyl, unsubstituted furanyl, phenyl-, bromo-, or nitro-furyl, chlorophenyl-isoxazolyl, oxobenzopyranyl, unsubstituted naphthyl, methoxy-, methyl-, or halo-naphthyl, unsubstituted thienyl, unsubstituted pyridinyl, or chloropyridinyl.

In another aspect, the invention provides sirtuin-modulating compounds of Structural Formula (XI):

(XI)

[Structure: oxazolopyridine with R22, R31, R1' substituents on phenyl]

or a salt thereof, wherein:

$R_1'$ is selected from H or optionally substituted $C_1$-$C_3$ straight or branched alkyl;

$R^{22}$ is selected —$NR^{23}$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O— or —$NR_1'$—C(O)—$CR_1'R_1'$—, wherein $R^{23}$ is an optionally substituted $C_1$-$C_3$ straight or branched alkyl; and $R^{31}$ is selected from an optionally substituted monocyclic or bicyclic aryl, or an optionally substituted monocyclic or bicyclic heteroaryl, with the provisos that:

when $R^{22}$ is —NH—C(O)—CH=CH—, $R^{31}$ is not unsubstituted furyl, 5-(2-methyl-3-chlorophenyl)-furanyl, 2,4-dichlorophenyl, 3,5-dichloro-2-methoxyphenyl, 3-nitrophenyl, 4-chlorophenyl, 4-chloro-3-nitrophenyl, 4-isopropylphenyl, 4-methoxyphenyl, 2-methoxy-5-bromophenyl, or unsubstituted phenyl;

when $R^{22}$ is —NH—C(O)—CH$_2$—, $R^{31}$ is not 3,4-dimethoxyphenyl, 4-chlorophenyl, or unsubstituted phenyl;

when $R^{22}$ is —NH—C(O)—CH$_2$—O—, $R^{31}$ is not 2,4-dimethyl-6-nitrophenyl, 2- or 4-nitrophenyl, 4-cyclohexylphenyl, 4-methoxyphenyl, unsubstituted naphthyl, or unsubstituted phenyl, or phenyl monosubstituted, disubstituted or trisubstituted solely with substituents selected from straight- or branched-chain alkyl or halo;

when $R^{22}$ is —NH—C(O)—CH(CH$_3$)—O—, $R^{31}$ is not 2,4-dichlorophenyl, 4-chlorophenyl, or unsubstituted phenyl; and when $R^{22}$ is —NH—S(O)$_2$—, $R^{31}$ is not unsubstituted phenyl.

In yet another aspect, the invention provides sirtuin-modulating compounds of Structural Formula (XII):

(XII)

[Structure: thiazole fused with pyridine-like ring bearing X7, X8, X9, X10, with R19, R21, R31 substituents]

or a salt thereof, wherein:

each of $X_7$, $X_8$, $X_9$ and $X_{10}$ is independently selected from N, $CR^{20}$, or $CR_1'$, wherein:

each $R^{20}$ is independently selected from H or a solubilizing group;

each $R_1'$ is independently selected from H or optionally substituted $C_1$-$C_3$ straight or branched alkyl;

one of $X_7$, $X_8$, $X_9$ and $X_{10}$ is N and the others are selected from $CR^{20}$ or $CR_1'$; and zero to one $R^{20}$ is a solubilizing group;

$R^{19}$ is selected from:

[Four ring structures with Z10, Z11, Z12, Z13 and Z14, Z15, Z16 labels]

wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, O or S;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group;

zero to one $R_1'$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

[Three small heterocyclic structures: oxadiazole with NR1', imidazolone with NR1', and imidazolone with NR1']

; and $R^{31}$ is selected from an optionally substituted monocyclic or bicyclic aryl, or an optionally substituted monocyclic or bicyclic heteroaryl, with the proviso that when $R^{19}$ is

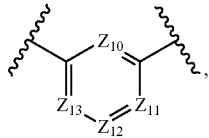

$Z_{10}$, $Z_{11}$, $Z_{12}$ and $Z_{13}$ are each CH, and $R^{21}$ is —NHC(O)—, $R^{31}$ is not an optionally substituted phenyl.

In certain embodiments, the compounds of Structural Formula (XI) have the following values:

each of $X_7$, $X_8$, $X_9$ and $X_{10}$ is independently selected from N, $CR^{20}$, or $CR_1'$, wherein:
 each $R^{20}$ is independently selected from H or a solubilizing group;
 each $R_1'$ is independently selected from H or optionally substituted $C_1$-$C_3$ straight or branched alkyl;
one of $X_7$, $X_8$, $X_9$ and $X_{10}$ is N and the others are selected from $CR^{20}$ or $CR_1'$; and
zero to one $R^{20}$ is a solubilizing group;
$R^{19}$ is selected from:

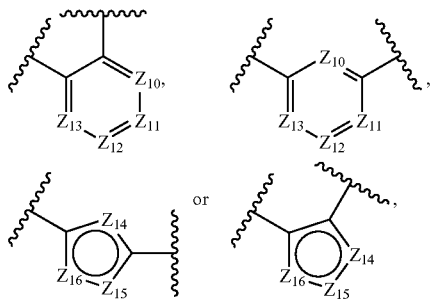

wherein:
 each $Z_{10}$, $Z_{11}$, $Z_{12}$ and $Z_{13}$ is independently selected from N, $CR^{20}$, or $CR_1'$; and
 each $Z_{14}$, $Z_{15}$ and $Z_{16}$ is independently selected from N, $NR_1'$, S, O, $CR^{20}$, or $CR_1'$, wherein:
 zero to two of $Z_{10}$, $Z_{11}$, $Z_{12}$ or $Z_{13}$ are N;
 at least one of $Z_{14}$, $Z_{15}$ and $Z_{16}$ is N, $NR_1'$, S or O;
 zero to one of $Z_{14}$, $Z_{15}$ and $Z_{16}$ is S or O;
 zero to two of $Z_{14}$, $Z_{15}$ and $Z_{16}$ are N or $NR_1'$;
 zero to one $R^{20}$ is a solubilizing group;
 zero to one $R_1'$ is an optionally substituted $C_1$-$C_3$ straight or branched alkyl; and
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—$CR_1'R_1'$—, —$NR_1'$—C(S)—

$NR_1'$—$CR_1'R_1'$—$CR_1'R_1'$—, —$NR_1'$—C(O)—O— or —$NR_1'$—C(O)—$CR_1'R_1'$—; and
$R^{31}$ is selected from an optionally substituted monocyclic or bicyclic aryl, or an optionally substituted monocyclic or bicyclic heteroaryl, with the proviso that:
 when $X_7$ is N, $R^{19}$ is

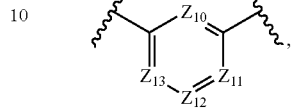

and each of $Z_{10}$, $Z_{11}$, $Z_{12}$ and $Z_{13}$ is independently selected from $CR^{20}$, or $CR_1'$, then:
 a) at least one of $X_8$, $X_9$ or $X_{10}$ is C—($C_1$-$C_3$ straight or branched alkyl) or C-(solubilizing group); or
 b) at least one of $Z_{10}$, $Z_{11}$, $Z_{12}$ and $Z_{13}$ is $CR^{20}$, wherein $R^{20}$ is a solubilizing group.

In a further aspect, the invention provides compounds of Structural Formula (XIII):

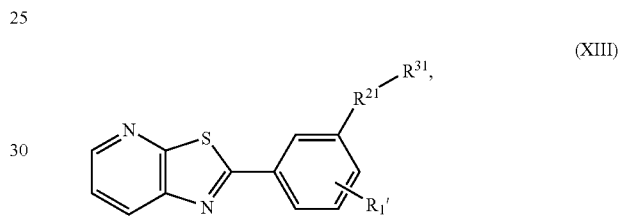

or a salt thereof, wherein:
$R_1'$ is selected from H or optionally substituted $C_1$-$C_3$ straight or branched alkyl;
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

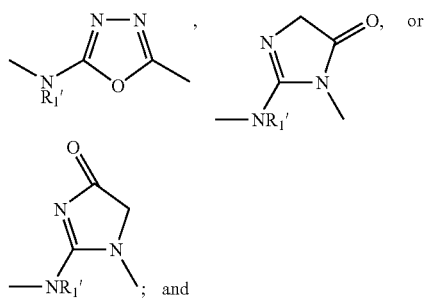

; and $R^{31}$ is selected from an optionally substituted monocyclic or bicyclic aryl, or an optionally substituted monocyclic or bicyclic heteroaryl, with the provisos that:

when $R^{21}$ is —NH—C(O)—, $R^{31}$ is not unsubstituted furyl, 5-bromofuryl, unsubstituted phenyl, phenyl monosubstituted with halo or methyl, 3- or 4-methoxyphenyl, 4-butoxyphenyl, 4-t-butylphenyl, 3-trifluoromethylphenyl, 2-benzoylphenyl, 2- or 4-ethoxyphenyl, 2,3-, 2,4-, 3,4-, or 3,5-dimethoxyphenyl, 3,4,5-trimethoxyphenyl, 2,4- or 2-6 difluorophenyl, 3,4-dioxymethylene phenyl, 3,4- or 3,5-dimethlyphenyl, 2-chloro-5-bromophenyl, 2-methoxy-5-chlorophenyl, unsubstituted quinolinyl, thiazolyl substituted simultaneously with methyl and phenyl, or ethoxy-substituted pyridinyl;

when $R^{21}$ is —NH—C(O)—CH(CH$_2$—CH$_3$)—, $R^{31}$ is not unsubstituted phenyl;

when $R^{21}$ is —NH—C(O)—CH$_2$—, $R^{31}$ is not unsubstituted phenyl, 3-methylphenyl, 4-chlorophenyl, 4-ethoxyphenyl, 4-fluorophenyl or 4-methoxyphenyl;

when $R^{21}$ is —NH—C(O)—CH$_2$—O—, $R^{31}$ is not unsubstituted phenyl or 4-chlorophenyl; and when $R^{21}$ is —NH—S(O)$_2$—, $R^{31}$ is not 3,4-dioxymethylene phenyl, 2,4,5-trimethylphenyl, 2,4,6-trimethylphenyl, 2,4- or 3,4-dimethylphenyl, 2,5-difluorophenyl, 2,5- or 3,4-dimethoxyphenyl, fluorophenyl, 4-chlorophenyl, 4-bromophenyl, 4-ethylphenyl, 4-methylphenyl, 3-methyl-4-methoxyphenyl, unsubstituted phenyl, unsubstituted pyridinyl, unsubstituted thienyl, chloro-substituted thienyl, or methyl-substituted benzothiazolyl.

In one aspect, the invention provides sirtuin-modulating compounds of Structural Formula (XIV):

(XIV)

or a salt thereof, wherein:

each of $R^{23}$ and $R^{24}$ is independently selected from H, —CH$_3$ or a solubilizing group;

$R^{25}$ is selected from H, or a solubilizing group; and $R^{19}$ is selected from:

, or , wherein:

each $Z_{10}$, $Z_{11}$, $Z_{12}$ and $Z_{13}$ is independently selected from N, CR$^{20}$, or CR$_1$'; and each $Z_{14}$, $Z_{15}$ and $Z_{16}$ is independently selected from N, NR$_1$', S, O, CR$^{20}$ or CR$_1$', wherein:

zero to two of $Z_{10}$, $Z_{11}$, $Z_{12}$ or $Z_{13}$ are N;

at least one of $Z_{14}$, $Z_{15}$ and $Z_{16}$ is N, NR$_1$', O or S;

zero to one of $Z_{14}$, $Z_{15}$ and $Z_{16}$ is S or O;

zero to two of $Z_{14}$, $Z_{15}$ and $Z_{16}$ are N or NR$_1$';

zero to one $R^{20}$ is a solubilizing group; and zero to one R$_1$' is an optionally substituted C$_1$-C$_3$ straight or branched alkyl;

each $R^{20}$ is independently selected from H or a solubilizing group;

$R^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R$_1$'—, —NR$_1$'—C(O)—CR$_1$'R$_1$'—NR$_1$'—, —NR$_1$'—C(=NR$_1$')—NR$_1$'—, —C(O)—NR$_1$'—, —C(O)—NR$_1$'—S(O)$_2$—, —NR$_1$'—CR$_1$'R$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$'—C(O)—NR$_1$'—, —CR$_1$'R$_1$'—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R$_1$'—O—, —NR$_1$'—C(O)—CR$_1$'R$_1$'—CR$_1$'R$_1$'—O—, —NR$_1$'—S(O)$_2$—CR$_1$'R$_1$'—, —NR$_1$'—S(O)$_2$—CR$_1$'R$_1$'—CR$_1$'R$_1$'—, —NR$_1$'—C(O)—CR$_1$'R$_1$'—; —NR$_1$'—C(O)—CR$_1$'R$_1$'—CR$_1$'R$_1$'—, —NR$_1$'—C(S)—NR$_1$'—CR$_1$'R$_1$'—CR$_1$'R$_1$'—, —NR$_1$'—C(O)—O—, , or

;

each R$_1$' is independently selected from H or optionally substituted C$_1$-C$_3$ straight or branched alkyl; and $R^{31}$ is selected from an optionally substituted monocyclic or bicyclic aryl, or an optionally substituted monocyclic or bicyclic heteroaryl, wherein when $R^{19}$ is

, $R^{21}$ is —NH—C(O)— and $R^{25}$ is —H, $R^{31}$ is not an optionally substituted phenyl group, and wherein said compound is not 2-chloro-N-[3-[3-(cyclohexylamino)imidazo[1,2-a]pyridin-2-yl]phenyl]-4-nitrobenzamide.

In another aspect, the invention provides sirtuin-modulating compounds of Structural Formula (XV):

(XV)

or a salt thereof, wherein:

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'$—$R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

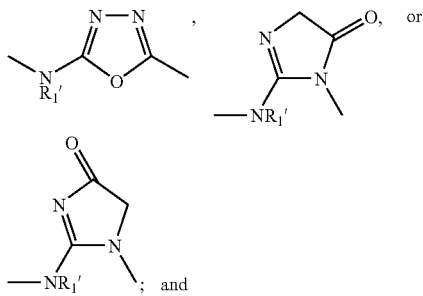

; and each $R_1'$ is independently selected from H or optionally substituted $C_1$-$C_3$ straight or branched alkyl; and $R^{32}$ is selected from an optionally substituted bicyclic aryl, or an optionally substituted monocyclic or bicyclic heteroaryl, wherein:

when $R^{21}$ is —NH—C(O)—, $R^{32}$ is not unsubstituted 2-furyl, 2-(3-bromofuryl), unsubstituted 2-thienyl, unsubstituted 3-pyridyl, unsubstituted 4-pyridyl,

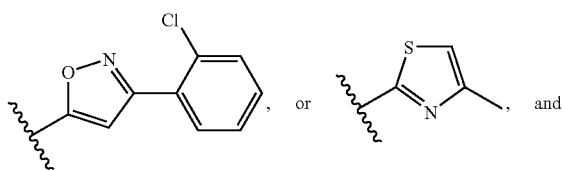

when $R^{21}$ is —$NR_1'$—S(O)$_2$—, $R^{32}$ is not unsubstituted 2-thienyl or unsubstituted naphthyl.

In yet another aspect, the invention provides sirtuin-modulating compounds of Structural Formula (XVI):

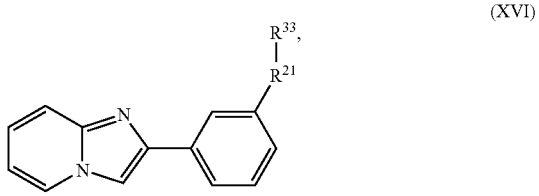

or a salt thereof, wherein:

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

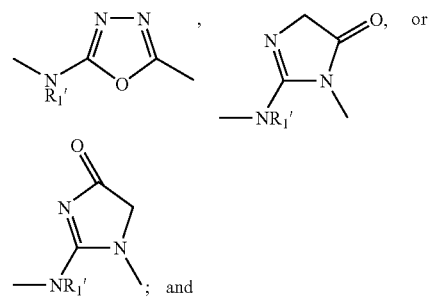

; and each $R_1'$ is independently selected from H or optionally substituted $C_1$-$C_3$ straight or branched alkyl; and $R^{33}$ is an optionally substituted phenyl, wherein:

when $R^{21}$ is —NH—C(O)—, $R^{33}$ is a substituted phenyl other than phenyl singly substituted with halo, methyl, nitro or methoxy; 2-carboxyphenyl; 4-n-pentylphenyl; 4-ethoxyphenyl; 2-carboxy-3-nitrophenyl; 2-chloro-4-nitrophenyl; 2-methoxy-5-ethylphenyl; 2,4-dimethoxyphenyl; 3,4,5-trimethoxyphenyl; 2,4 dichlorophenyl; 2,6-difluorophenyl; 3,5-dinitrophenyl; or 3,4-dimethylphenyl;

when $R^{21}$ is —$NR_1'$—C(O)—$CR_1'R_1'$ or —NH—C(O)—CH(CH$_3$)—O, $R^{33}$ is a substituted phenyl;

when $R^{21}$ is —NH—C(O)—CH$_2$, $R^{33}$ is not unsubstituted phenyl, 4-methoxyphenyl; 3,4-dimethoxyphenyl or 4-chlorophenyl;

when $R^{21}$ is —NH—C(O)—CH$_2$—O, $R^{33}$ is not 2,4-bis(1,1-dimethylpropyl)phenyl;

when $R^{21}$ is —NH—C(O)—NH—, $R^{33}$ is not 4-methoxyphenyl; and when $R^{21}$ is —NH—S(O)$_2$—, $R^{33}$ is a substituted phenyl other than 3-methylphenyl, 3-trifluoromethylphenyl, 2,4,5- or 2,4,6-trimethylphenyl, 2,4- or 3,4-dimethylphenyl, 2,5- or 3,4-dimethoxyphenyl, 2,5-dimethoxy-4-chlorophenyl, 3,6-dimethoxy, 4-methylphenyl, 2,5- or 3,4-dichlorophenyl, 2,5-diethoxyphenyl, 2-methyl-5-nitrophenyl, 2-ethoxy-5-bromophenyl, 2-methoxy-5-bromophenyl, 2-methoxy-3,4-dichlorophenyl, 2-methoxy-4-methyl-5-bromophenyl, 3,5-dinitro-4-methylphenyl, 3-methyl-4-methoxyphenyl, 3-nitro-4-methylphenyl, 3-methoxy-4-halophenyl, 3-methoxy-5-chlorophenyl, 4-n-butoxyphenyl, 4-halophenyl, 4-ethylphenyl, 4-methylphenyl, 4-nitrophenyl, 4-ethoxyphenyl, 4-acetylaminophenyl, 4-methoxyphenyl, 4-t-butylphenyl, or para-biphenyl.

In a further ascept, the invention provides sirtuin-modulating compounds of Structural Formula (XVII):

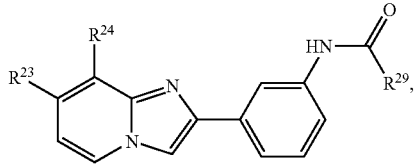
(XVII)

or a salt thereof, wherein:
each of $R^{23}$ and $R^{24}$ is independently selected from H or —$CH_3$, wherein at least one of $R^{23}$ and $R^{24}$ is H; and
$R^{29}$ is phenyl substituted with:
a) two —O—$CH_3$ groups;
b) three —O—$CH_3$ groups located at the 2,3 and 4 positions; or
c) one —$N(CH_3)_2$ group; and;
d) when $R^{23}$ is $CH_3$, one —O—$CH_3$ group at the 2 or 3 position, wherein $R^{29}$ is optionally additionally substituted with a solubilizing group.

In one aspect, the invention provides sirtuin-modulating compounds of Structural Formula (XVIII):

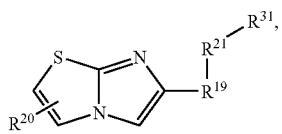
(XVIII)

or a salt thereof, wherein
$R^{19}$ is selected from:

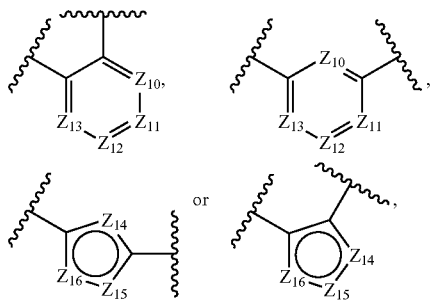

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$,
wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group; and
zero to one $R_1'$ is an optionally substituted $C_1$-$C_3$ straight or branched alkyl;
each $R^{20}$ is independently selected from H or a solubilizing group;
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

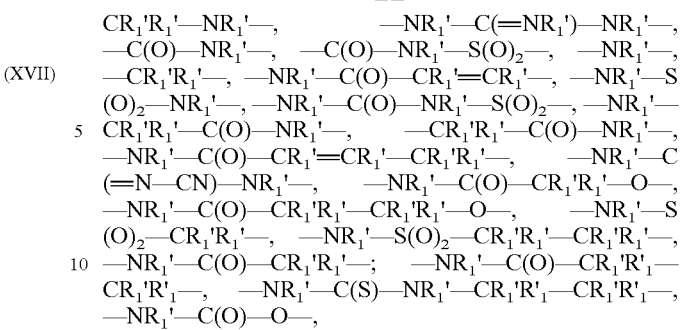

wherein each $R_1'$ is independently selected from H or optionally substituted $C_1$-$C_3$ straight or branched alkyl; and
$R^{31}$ is selected from an optionally substituted monocyclic or bicyclic aryl, or an optionally substituted monocyclic or bicyclic heteroaryl, with the proviso that when $R^{19}$ is

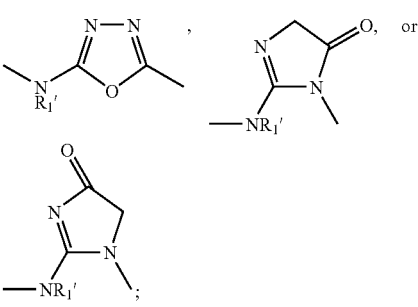

$Z_{10}$, $Z_{11}$, $Z_{12}$ and $Z_{13}$ are each CH, $R^{20}$ is H, and $R^{21}$ is —NHC(O)—, $R^{31}$ is not an optionally substituted phenyl.

In another aspect, the invention provides sirtuin-modulating compounds of Structural Formula (XX):

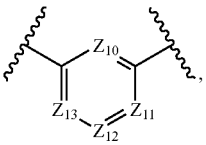
(XX)

or a salt thereof, wherein
$R^{19}$ is selected from:

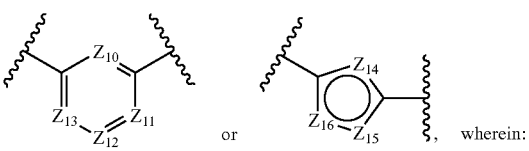, wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, O or S;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group; and zero to one $R_1'$ is an optionally substituted $C_1$-$C_3$ straight or branched alkyl;

each $R^{20}$ is independently selected from H or a solubilizing group;

$R^{20a}$ is independently selected from H or a solubilizing group;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

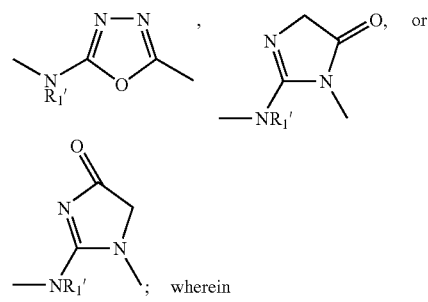

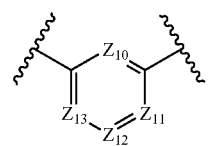; wherein each $R_1'$ is independently selected from H or optionally substituted $C_1$-$C_3$ straight or branched alkyl; and $R^{31}$ is selected from an optionally substituted monocyclic or bicyclic aryl, or an optionally substituted monocyclic or bicyclic heteroaryl, wherein when $R^{19}$ is and $Z_{10}$, $Z_{11}$, $Z_{12}$ and $Z_{13}$ are each CH, $R^{20a}$ is a solubilizing group.

In yet another aspect, the invention provides sirtuin-modulating compounds of Structural Formula (XXI):

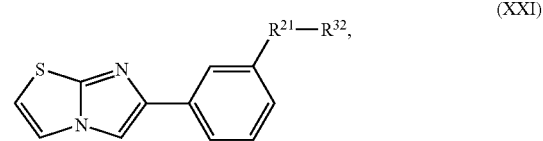

or a salt thereof, wherein $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

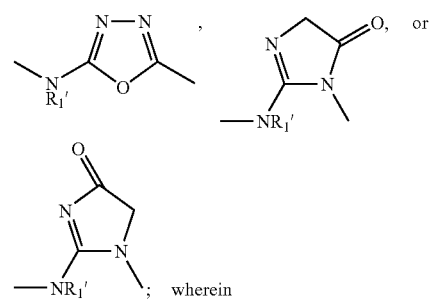; wherein each $R_1'$ is independently selected from H or optionally substituted $C_1$-$C_3$ straight or branched alkyl; and $R^{32}$ is an optionally substituted monocyclic or bicyclic heteroaryl, or an optionally substituted bicyclic aryl, wherein:

when $R^{21}$ is —NH—C(O)—$CH_2$—, $R^{32}$ is not unsubstituted thien-2-yl;

when $R^{21}$ is —NH—C(O)—, $R^{32}$ is not furan-2-yl, 5-bromofuran-2-yl, or 2-phenyl-4-methylthiazol-5-yl;

when $R^{21}$ is —NH—S(O)$_2$—, $R^{32}$ is not unsubstituted naphthyl or 5-chlorothien-2-yl.

In a further aspect, the invention provides sirtuin-modulating compounds of Structural Formula (XXII):

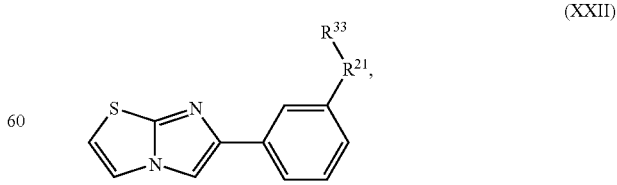

or a salt thereof, wherein:

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —NR$_1$'—C(S)—NR$_1$'—CR$_1$'R$_1$'—, —NR$_1$'—C(O)—CR$_1$'R$_1$'—NR$_1$'—, —NR$_1$'—C(=NR$_1$')—NR$_1$'—, —C(O)—NR$_1$'—, —C(O)—NR$_1$'—S(O)$_2$—, —NR$_1$'—CR$_1$'R$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$'—C(O)—NR$_1$'—, —CR$_1$'R$_1$'—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R$_1$'—O—, —NR$_1$'—C(O)—CR$_1$'R$_1$'—CR$_1$'R$_1$'—O—, —NR$_1$'—S(O)$_2$—CR$_1$'R$_1$'—, —NR$_1$'—S(O)$_2$—CR$_1$'R$_1$'—CR$_1$'R$_1$'—, —NR$_1$'—C(O)—CR$_1$'R$_1$'—; —NR$_1$'—C(O)—CR$_1$'R$_1$'—CR$_1$'R$_1$'—, —NR$_1$'—C(S)—NR$_1$'—CR$_1$'R$_1$'—CR$_1$'R$_1$'—, —NR$_1$'—C(O)—O—, wherein each R$_1$' is independently selected from H or optionally substituted C$_1$-C$_3$ straight or branched alkyl; and R$^{33}$ is an optionally substituted phenyl, wherein:

when R$^{21}$ is —NR$_1$'—C(O)—, R$_1$' is not H;

when R$^{21}$ is —NH—C(O)—CH$_2$ or —NH—C(O)—CH$_2$—O—, R$^{33}$ is not unsubstituted phenyl or 4-halophenyl; and when R$^{21}$ is —NH—S(O)$_2$—, R$^{33}$ is not unsubstituted phenyl, 2,4- or 3,4-dimethylphenyl, 2,4-dimethyl-5-methoxyphenyl, 2-methoxy-3,4-dichlorophenyl, 2-methoxy, 5-bromophenyl-3,4-dioxyethylenephenyl, 3,4-dimethoxyphenyl, 3,4-dichlorophenyl, 3,4-dimethylphenyl, 3- or 4-methylphenyl, 4-alkoxyphenyl, 4-phenoxyphenyl, 4-halophenyl, 4-biphenyl, or 4-acetylaminophenyl.

In one aspect, the invention provides sirtuin-modulating compounds of Structural Formula (XXII):

(XXII)

or a salt thereof wherein:

R$^{21}$ is selected from —NH—C(O)—, or —NH—C(O)—CH$_2$—; and

R$^{33}$ is phenyl substituted with a) one —N(CH$_3$)$_2$ group;

b) one CN group at the 3 position;

c) one —S(CH$_3$) group; or d)

bridging the 3 and 4 positions.

In another aspect, the invention provides sirtuin-modulating compounds of Structural Formula (XXIII):

(XXIII)

or a salt thereof, wherein:

each R$^{20}$ and R$^{20a}$ is independently selected from H or a solubilizing group;

each R$_1$', R$_1$" and R$_1$'" is independently selected from H or optionally substituted C$_1$-C$_3$ straight or branched alkyl;

R$^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R$_1$'—, —NR$_1$'—C(O)—CR$_1$'R$_1$'—NR$_1$'—, —NR$_1$'—C(=NR$_1$')—NR$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$'—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R$_1$'—O—, —NR$_1$'—C(O)—CR$_1$'R$_1$'—CR$_1$'R$_1$'—O—, —NR$_1$'—S(O)$_2$—CR$_1$'R$_1$'—, —NR$_1$'—S(O)$_2$—CR$_1$'R$_1$'—CR$_1$'R$_1$'—, or —NR$_1$'—C(O)—CR$_1$'R$_1$'—; and R$^{31}$ is selected from an optionally substituted monocyclic or bicyclic aryl, or an optionally substituted monocyclic or bicyclic heteroaryl, with the provisos that:

when R$^{21}$ is —NH—C(O)—, R$^{31}$ is not is not 3,5-dinitrophenyl, 4-butoxyphenyl, when R$^{21}$ is —NH—C(O)— and each of R$^{20}$, R$^{20a}$, R$_1$', R$_1$" and R$_1$'" is hydrogen, R$^{31}$ is not

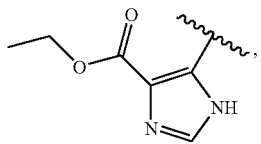

unsubstituted phenyl, 2- or 4-nitrophenyl, 2,4-dinitrophenyl, 2- or 4-chlorophenyl, 2-bromophenyl, 4-fluorophenyl, 2,4-dichlorophenyl, 2-carboxyphenyl, 2-azidophenyl, 2- or 4-aminophenyl, 2-acetamidophenyl, 4-methylphenyl, or 4-methoxyphenyl;

when $R^{21}$ is —NH—C(O)—, $R_1''$ is methyl; and each of $R^{20}$, $R^{20a}$, $R_1'$ and $R_1'''$ is hydrogen, $R^{31}$ is not 2-methylaminophenyl,

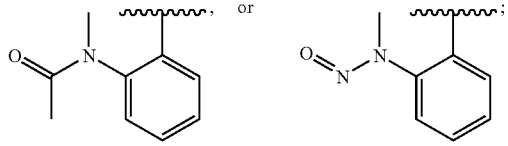

when $R^{21}$ is —NH—C(O)—CH$_2$— or NH—C(S)—NH—, and each of $R^{20}$, $R^{20a}$, $R_1'$, $R_1''$ and $R_1'''$ is hydrogen, $R^{31}$ is not unsubstituted phenyl;

when $R^{21}$ is —NH—S(O)$_2$—, $R_1''$ is hydrogen or methyl, and each of $R^{20}$, $R^{20a}$, $R_1'$ and $R_1'''$ is hydrogen, $R^{31}$ is not 4-methylphenyl; and when $R^{21}$ is —NH—S(O)$_2$—, $R^{20a}$ is hydrogen or —CH$_2$—N(CH$_2$CH$_3$)$_2$, and each of $R^{20}$, $R_1'$, $R_1''$ and $R_1'''$ is hydrogen, $R^{31}$ is not

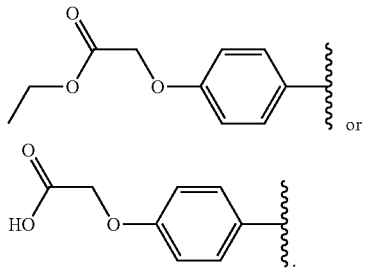

In a particular aspect, the invention provides sirtuin-modulating compounds of Structural Formula (XXIII):

(XXIII)

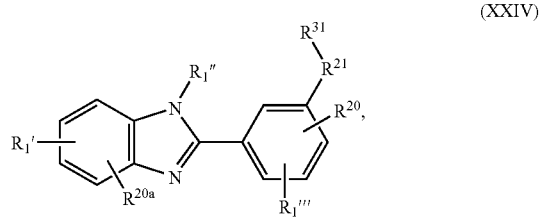

or a salt thereof, wherein:

each $R^{20}$ and $R^{20a}$ is independently selected from H or a solubilizing group;

each $R_1'$, $R_1''$ and $R_1'''$ is independently selected from H or optionally substituted C$_1$-C$_3$ straight or branched alkyl;

$R^{21}$ is selected from —NR$_1'$—C(O)—, —NR$_1'$—S(O)$_2$—, —NR$_1'$—C(O)—NR$_1'$—, —NR$_1'$—C(S)—NR$_1'$—, —NR$_1'$—C(S)—NR$_1'$—CR$_1'$R$_1'$—, —NR$_1'$—C(O)—CR$_1'$R$_1'$—NR$_1'$—, —NR$_1'$—C(=NR$_1'$)—NR$_1'$—, —NR$_1'$—C(O)—CR$_1'$=CR$_1'$—, —NR$_1'$—S(O)$_2$—NR$_1'$—, —NR$_1'$—C(O)—NR$_1'$—S(O)$_2$—, —NR$_1'$—CR$_1'$R$_1'$—C(O)—NR$_1'$—, —NR$_1'$—C(O)—CR$_1'$=CR$_1'$—CR$_1'$R$_1'$—, —NR$_1'$—C(=N—CN)—NR$_1'$—, —NR$_1'$—C(O)—CR$_1'$R$_1'$—O—, —NR$_1'$—C(O)—CR$_1'$R$_1'$—CR$_1'$R$_1'$—O—, —NR$_1'$—S(O)$_2$—CR$_1'$R$_1'$—, —NR$_1'$—S(O)$_2$—CR$_1'$R$_1'$—CR$_1'$R$_1'$—, or —NR$_1'$—C(O)—CR$_1'$R$_1'$—; and $R^{31}$ is selected from an optionally substituted monocyclic or bicyclic aryl, or an optionally substituted monocyclic or bicyclic heteroaryl, wherein:
i) at least one $R^{20}$ is a solubilizing group or at least one $R_1'''$ is an optionally substituted C$_1$-C$_3$ straight or branched alkyl or both; or
ii) $R^{20a}$ is a solubilizing group other than CH$_2$—N(CH$_2$CH$_3$)$_2$.

In yet another aspect, the invention provides sirtuin-modulating compounds of Structural Formula (XXIV):

(XXIV)

or a salt thereof, wherein:

each $R^{20}$ and $R^{20a}$ is independently selected from H or a solubilizing group;

each $R_1'$, $R_1''$ and $R_1'''$ is independently selected from H or optionally substituted C$_1$-C$_3$ straight or branched alkyl;

$R^{21}$ is selected from —NR$^{23}$—C(O)—, —NR$_1'$—S(O)$_2$—, —NR$_1'$—C(O)—NR$_1'$—, —NR$_1'$—C(S)—NR$_1'$—, —NR$_1'$—C(S)—NR$_1'$—CR$_1'$R$_1'$—, —NR$_1'$—C(O)—CR$_1'$R$_1'$—NR$_1'$—, —NR$_1'$—C(=NR$_1'$)—NR$_1'$—, —NR$_1'$—C(O)—CR$_1'$=CR$_1'$—, —NR$_1'$—S(O)$_2$—NR$_1'$—, —NR$_1'$—C(O)—NR$_1'$—S(O)$_2$—, —NR$_1'$—CR$_1'$R$_1'$—C(O)—NR$_1'$—, —NR$_1'$—C(O)—CR$_1'$=CR$_1'$—CR$_1'$R$_1'$—, —NR$_1'$—C(=N—CN)—NR$_1'$—, —NR$_1'$—C(O)—CR$_1'$R$_1'$—O—, —NR$_1'$—C(O)—CR$_1'$R$_1'$—CR$_1'$R$_1'$—O—, —NR$_1'$—S(O)$_2$—CR$_1'$R$_1'$—, —NR$_1'$—S(O)$_2$—CR$_1'$R$_1'$—CR$_1'$R$_1'$—, or —NR$_1'$—C(O)—CR$_1'$R$_1'$—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—CH$_2$—, $R^{31}$ is not 2-methylphenyl, or 3,4-dimethoxyphenyl;

when $R^{21}$ is —NH—C(O)—CH=CH—, $R^{31}$ is not 2-chlorophenyl;

when $R^{21}$ is —NH—C(O)—NH—, $R^{31}$ is not unsubstituted benzimidazolyl;

when $R^{21}$ is —NH—S(O)$_2$—, and each of $R^{20}$, $R^{20a}$, $R_1'$, $R_1''$ and $R_1'''$ is hydrogen, $R^{31}$ is not unsubstituted phenyl, 4-chlorophenyl, 4-methylphenyl, or 4-acetamidophenyl;

when $R^{21}$ is —NH—S(O)$_2$—, each of $R_1'$ and $R_1'''$ is methyl or hydrogen, and each of $R^{20}$, $R^{20a}$, and $R_1''$ is hydrogen, $R^{31}$ is not 4-nitrophenyl;

when $R^{21}$ is —NH—C(O)—CH$_2$—O—, $R_1'''$ is methyl or hydrogen, and each of $R^{20}$, $R^{20a}$, $R_1'$, and $R_1''$ is hydrogen, $R^{31}$ is not 2,3-, 2,5-, 2,6-, 3,4- or 3,5-dimethylphenyl, 2,4-dichloromethyl, 2,4-dimethyl-6-bromophenyl, 2- or 4-chlorophenyl, 2-(1-methylpropyl)phenyl, 5-methyl-2-(1-methylethyl)phenyl, 2- or 4-methylphenyl, 2,4-dichloro-6-methylphenyl, nitrophenyl, 2,4-dimethyl-6-nitrophenyl, 2- or 4-methoxyphenyl, 4-acetyl-2-methoxyphenyl, 4-chloro-3,5-dimethylphenyl, 3-ethylphenyl, 4-bromophenyl, 4-cyclohexyphenyl, 4-(1-methylpropyl)phenyl, 4-(1-methylethyl)phenyl, 4-(1,1-dimethylethyl)phenyl, or unsubstituted phenyl;

when $R^{21}$ is —NH—C(O)—CH$_2$—, $R_1'''$ is methyl or hydrogen, and each of $R^{20}$, $R^{20a}$, $R_1'$, and $R_1''$ is hydrogen, $R^{31}$ is not unsubstituted naphthyl, 4-chlorophenyl, 4-nitrophenyl, 4-methoxyphenyl, unsubstituted phenyl, unsubstituted thienyl

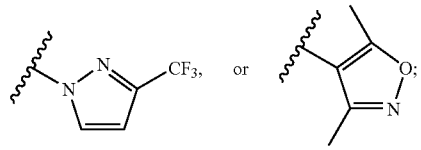

when $R^{21}$ is —NH—C(O)—CH$_2$—, $R_1'$ is methyl, and each of $R^{20}$, $R^{20a}$, $R_1''$, and $R_1'''$ is hydrogen, $R^{31}$ is not unsubstituted phenyl;

when $R^{21}$ is —NH—C(O)—CH=CH, $R_1'''$ is methyl or hydrogen, and each of $R^{20}$, $R^{20a}$, $R_1'$, and $R_1''$ is hydrogen, $R^{31}$ is not unsubstituted furyl, nitrophenyl-substituted furyl, 2,4-dichlorophenyl, 3,5-dichloro-2-methoxyphenyl, 3- or 4-nitrophenyl, 4-methoxyphenyl, unsubstituted phenyl, or nitro-substituted thienyl;

when $R^{21}$ is —NH—C(O)—CH(CH$_2$CH$_3$)—, and each of $R^{20}$, $R^{20a}$, $R_1'$, $R_1''$, and $R_1'''$ is hydrogen, $R^{31}$ is not unsubstituted phenyl;

when $R^{21}$ is —NH—C(O)—CH(CH$_3$)—O—, $R_1'''$ is methyl or hydrogen, and each of $R^{20}$, $R^{20a}$, $R_1'$, and $R_1''$ is hydrogen, $R^{31}$ is not 2,4-dichlorophenyl.

In a particular aspect, the invention provides sirtuin-modulating compounds of Structural Formula (XXIV):

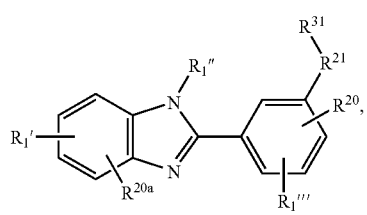

(XXIV)

or a salt thereof, wherein:

each $R^{20}$ and $R^{20a}$ is independently selected from H or a solubilizing group and at least one of $R^{20}$ and $R^{20a}$ is a solubilizing group;

each $R_1'$, $R_1''$ and $R_1'''$ is independently selected from H or optionally substituted C$_1$-C$_3$ straight or branched alkyl;

$R_{21}$ is selected from —NR$^{23}$—C(O)—, —NR$_1'$—S(O)$_2$—, —NR$_1'$—C(O)—NR$_1'$—, —NR$_1'$—C(S)—NR$_1'$—, —NR$_1'$—C(S)—NR$_1'$—CR$_1'$R$_1'$—, —NR$_1'$—C(O)—CR$_1'$R$_1'$—NR$_1'$—, —NR$_1'$—C(=NR$_1'$)—NR$_1'$—, —NR$_1'$—C(O)—CR$_1'$=CR$_1'$—, —NR$_1'$—S(O)$_2$—NR$_1'$—, —NR$_1'$—C(O)—NR$_1'$—S(O)$_2$—, —NR$_1'$—CR$_1'$R$_1'$—C(O)—NR$_1'$—, —NR$_1'$—C(O)—CR$_1'$=CR$_1'$R$_1'$—, —NR$_1'$—C(=N—CN)—NR$_1'$—, —NR$_1'$—C(O)—CR$_1'$R$_1'$—O—, —NR$_1'$—C(O)—CR$_1'$R$_1'$—CR$_1'$R$_1'$—O—, —NR$_1'$—S(O)$_2$—CR$_1'$R$_1'$—, —NR$_1'$—S(O)$_2$—CR$_1'$R$_1'$—CR$_1'$R$_1'$—, or —NR$_1'$—C(O)—CR$_1'$R$_1'$—, wherein $R^{23}$ is an optionally substituted C$_1$-C$_3$ straight or branched alkyl; and $R^{31}$ is selected from an optionally substituted monocyclic or bicyclic aryl, or an optionally substituted monocyclic or bicyclic heteroaryl.

In a further aspect, the invention provides sirtuin-modulating compounds of Structural Formula (XXV):

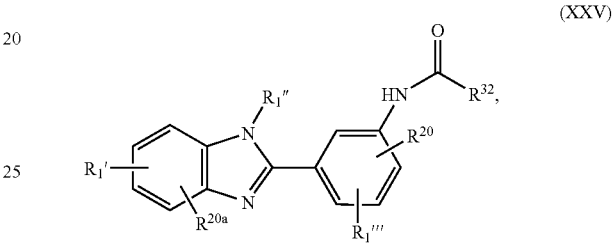

(XXV)

or a salt thereof, wherein:

each $R^{20}$ and $R^{20a}$ is independently selected from H or a solubilizing group, wherein at least one of $R^{20}$ and $R^{20a}$ is a solubilizing group;

each $R_1'$, $R_1''$ and $R_1'''$ is independently selected from H or optionally substituted C$_1$-C$_3$ straight or branched alkyl; and $R^{32}$ is an optionally substituted phenyl.

In one aspect, the invention provides sirtuin-modulating compounds of Structural Formula (XXVI):

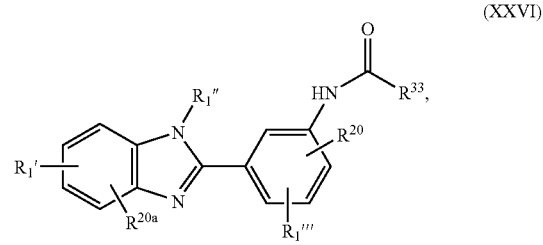

(XXVI)

or a salt thereof, wherein:

each $R^{20}$ and $R^{20a}$ is independently selected from H or a solubilizing group;

each $R_1'$, $R_1''$ and $R_1'''$ is independently selected from H or optionally substituted C$_1$-C$_3$ straight or branched alkyl; and $R^{33}$ is selected from an optionally substituted heteroaryl or an optionally substituted bicyclic aryl, with the provisos that:

when each of $R_1'$ and $R_1'''$ is hydrogen or methyl and each of $R_1''$, $R_{20}$ and $R_{20a}$ is hydrogen, $R^{33}$ is not 5,6,7,8-tetrahydronaphthyl, unsubstituted benzofuryl, unsubstituted benzothiazolyl, chloro- or nitro-substituted benzothienyl, unsubstituted furyl, phenyl-, bromo- or nitro-substituted furyl, dimethyl-substituted isoxazolyl, unsubstituted naphthyl, 5-bromonaphthyl, 4-methylnaphthyl, 1- or 3-methoxynaphthyl, azo-substituted naphthyl, unsubstituted pyrazinyl, S-methyl-substituted pyridyl, unsubstituted pyridyl, thienyl- or phenyl-substituted quinolinyl, chloro-, bromo- or nitro-substituted thienyl, unsubstituted thienyl, or

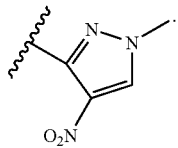

In a particular aspect, the invention provides sirtuin-modulating compounds of Structural Formula (XXVI):

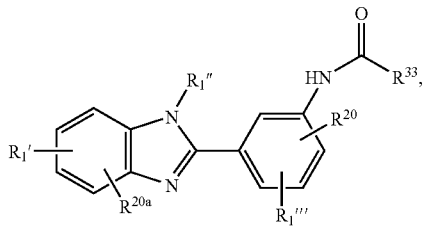

(XXVI)

or a salt thereof, wherein:
each $R^{20}$ and $R^{20a}$ is independently selected from H or a solubilizing group, wherein at least one of $R^{20}$ or $R^{20a}$ is a solubilizing group;
each $R_1'$, $R_1''$ and $R_1'''$ is independently selected from H or optionally substituted $C_1$-$C_3$ straight or branched alkyl; and
$R^{33}$ is selected from an optionally substituted heteroaryl or an optionally substituted bicyclic aryl.

In another aspect, the invention provides sirtuin-modulating compounds of Structural Formula (XXVII):

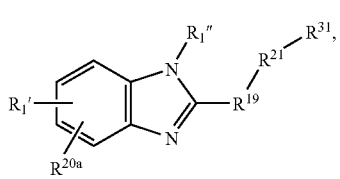

(XXVII)

or a salt thereof, wherein:
each $R^{20}$ and $R^{20a}$ is independently selected from H or a solubilizing group;
each $R_1'$ and $R_1''$ is independently selected from H or optionally substituted $C_1$-$C_3$ straight or branched alkyl;
$R^{19}$ is selected from:

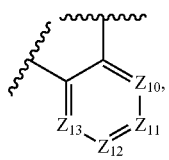 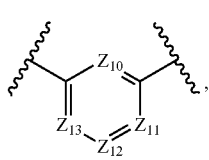

-continued

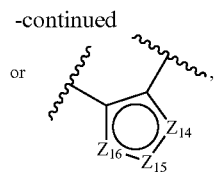

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and
$R^{31}$ is selected from an optionally substituted monocyclic or bicyclic aryl, or an optionally substituted monocyclic or bicyclic heteroaryl,
provided that when $R^{21}$ is —NH—C(O)— and $R^{19}$ is

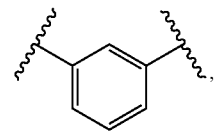

$R^{31}$ is not unsubstituted pyridyl, 2,6-dimethoxyphenyl, 3,4,5-trimethoxyphenyl or unsubstituted furyl.

In a particular aspect, the invention provides sirtuin-modulating compounds of Structural Formula (XXVII):

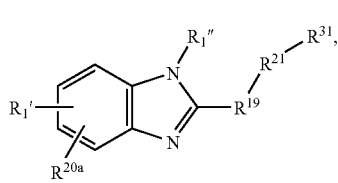

(XXVII)

or a salt thereof, wherein:
each $R^{20}$ and $R^{20a}$ is independently selected from H or a solubilizing group;
each $R_1'$ and $R_1''$ is independently selected from H or optionally substituted $C_1$-$C_3$ straight or branched alkyl;

$R^{19}$ is selected from:

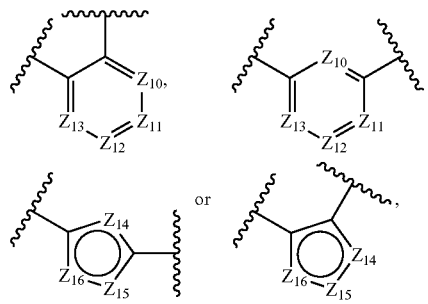

wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, S or O;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group;

zero to one $R_1'$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—, $R^{19}$ is not pyrazolyl;

when $R^{21}$ is —NH—, and $R^{19}$ is thiazolyl, $R^{31}$ is not optionally substituted phenyl or optionally substituted pyridyl;

when $R^{21}$ is —NH—C(O)—CH$_2$—, and $R^{19}$ is pyrazolyl, $R^{31}$ is not unsubstituted indolyl or unsubstituted phenyl;

when $R^{21}$ is —NH—C(O)—CH$_2$—, and $R^{19}$ is

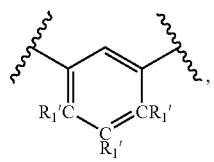

$R^{31}$ is not 2-methylphenyl or 3,4-dimethoxyphenyl;

when $R^{21}$ is —NH—C(O)—CH=CH—, and $R^{19}$ is

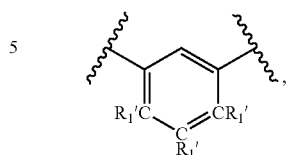

$R^{31}$ is not 2-chlorophenyl;

when $R^{21}$ is —NH—C(O)—NH—, and $R^{19}$ is pyrazolyl, $R^{31}$ is not unsubstituted isoxazolyl, unsubstituted naphthyl, unsubstituted phenyl, 2,6-difluorophenyl, 2,5-dimethylphenyl, 3,4-dichlorophenyl, or 4-chlorophenyl;

when $R^{21}$ is —NH—C(O)—NH—, and $R^{19}$ is

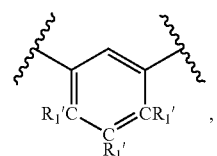

$R^{31}$ is not unsubstituted benzimidazolyl;

when $R^{21}$ is —NH—, and $R^{19}$ is pyrazolyl, $R^{31}$ is not unsubstituted pyridyl;

when $R^{20a}$ is a solubilizing group, $R^{19}$ is 1-methylpyrrolyl and $R^{21}$ is —NH—C(O)—, $R^{31}$ is not unsubstituted phenyl, unsubstituted furyl, unsubstituted pyrrolyl, unsubstituted pyrazolyl, unsubstituted isoquinolinyl, unsubstituted benzothienyl, chloro-substituted benzothienyl, 2-fluoro-4-chlorophenyl or phenyl singly substituted with a solubilizing group;

when $R^{20a}$ is a solubilizing group, $R^{19}$ is thienyl and $R^{21}$ is —NH—C(O)—, $R^{31}$ is not unsubstituted phenyl;

when $R^{20a}$ is a solubilizing group, $R^{19}$ is methylimidazolyl and $R^{21}$ is —NH—C(O)—, $R^{31}$ is not 1-methyl-4-(1,1-dimethylethyloxycarbonylamino)pyrrol-2-yl or phenyl singly substituted with a solubilizing group;

when $R^{21}$ is —NH— and $R^{19}$ is pyridyl, oxadiazolyl or thiadiazolyl, $R^{31}$ is not unsubstituted phenyl, 3-methoxyphenyl or 4-methoxyphenyl;

when $R^{21}$ is —NH—C(O)— and $R^{19}$ is thiazolyl or pyrimidinyl, $R^{31}$ is not unsubstituted phenyl;

when $R^{21}$ is —NH—C(O)— and $R^{19}$ is

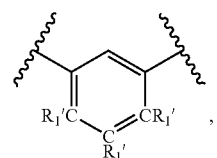

$R^{31}$ is not unsubstituted pyridyl, unsubstituted thienyl, unsubstituted phenyl, 2-methylphenyl, 4-fluorophenyl, 4-methoxyphenyl, 4-methylphenyl, 3,4-dioxyethylenephenyl, 3-acetylamino-4-methylphenyl, 3-[(6-amino-1-oxohexyl)amino]-4-methylphenyl, 3-amino-4-methylphenyl, 2,6-dimethoxyphenyl, 3,5-dimethoxyphenyl, 3-halo-4-methoxyphenyl, 3-nitro-4-methylphenyl, 4-propoxyphenyl, 3,4,5-trimethoxyphenyl or unsubstituted furyl;

when $R^{21}$ is —NH—C(O)— and $R^{19}$ is

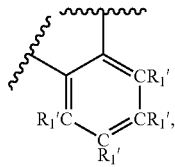

$R^{31}$ is not 3,5-dinitrophenyl, 4-butoxyphenyl,

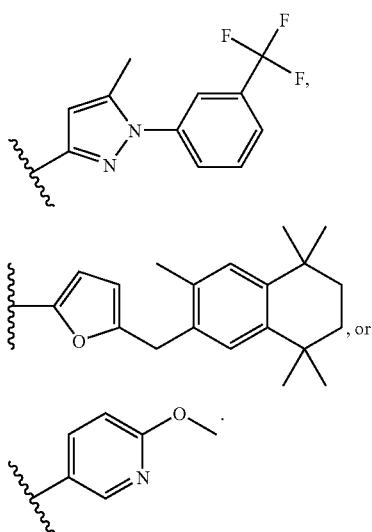

In a more particular embodiment, the invention provides sirtuin-modulating compounds of Structural Formula (XXVII):

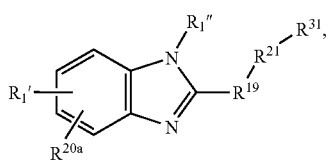

(XXVII)

or a salt thereof, wherein:

each $R^{20}$ and $R^{20a}$ is independently selected from H or a solubilizing group;

each $R_1'$ and $R_1''$ is independently selected from H or optionally substituted $C_1$-$C_3$ straight or branched alkyl;

$R^{19}$ is selected from:

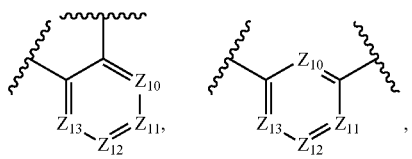

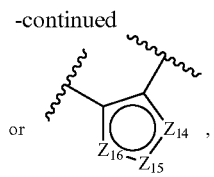

-continued wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

one to two of $Z_{10}$, $Z_{11}$, $Z_{12}$ or $Z_{13}$ are N;

at least one of $Z_{14}$, $Z_{15}$ and $Z_{16}$ is N, $NR_1'$, S or O;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group;

zero to one $R_1'''$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—, $R^{19}$ is not pyrazolyl;

when $R^{21}$ is —NH—C(O)—$CH_2$—, and $R^{19}$ is pyrazolyl, $R^{31}$ is not unsubstituted indolyl or unsubstituted phenyl;

when $R^{21}$ is —NH—C(O)—NH—, and $R^{19}$ is pyrazolyl, $R^{31}$ is not unsubstituted isoxazolyl, unsubstituted naphthyl, unsubstituted phenyl, 2,6-difluorophenyl; 2,5-dimethylphenyl; 3,4-dichlorophenyl; or 4-chlorophenyl;

when $R^{20a}$ is a solubilizing group, $R^{19}$ is 1-methylpyrrolyl and $R^{21}$ is —NH—C(O)—, $R^{31}$ is not unsubstituted phenyl; unsubstituted furyl; unsubstituted pyrrolyl; unsubstituted pyrazolyl; unsubstituted isoquinolinyl; unsubstituted benzothienyl; chloro-substituted benzothienyl; 2-fluoro-4-chlorophenyl or phenyl singly substituted with a solubilizing group;

when $R^{20a}$ is a solubilizing group, $R^{19}$ is thienyl and $R^{21}$ is —NH—C(O)—, $R^{31}$ is not unsubstituted phenyl;

when $R^{20a}$ is a solubilizing group, $R^{19}$ is methylimidazolyl and $R^{21}$ is —NH—C(O)—, $R^{31}$ is not 1-methyl-4-(1,1-dimethylethyloxycarbonylamino)pyrrol-2-yl or phenyl singly substituted with a solubilizing group; and when $R^{21}$ is —NH—C(O)— and $R^{19}$ is thiazolyl or pyrimidinyl, $R^{31}$ is not unsubstituted phenyl.

In yet another aspect, the invention provides compounds of Structural Formula (XXVIII):

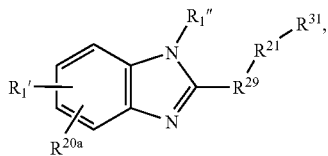

(XXVIII)

or a salt thereof, wherein:

each $R^{20}$ and $R^{20a}$ is independently selected from H or a solubilizing group;

each $R_1'$ and $R_1''$ is independently selected from H or optionally substituted $C_1$-$C_3$ straight or branched alkyl;

$R^{29}$ is selected from:

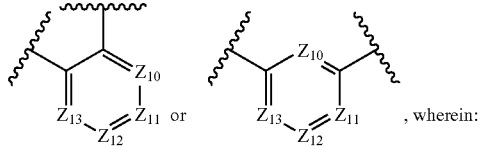

, wherein:

each $Z_{10}$, $Z_{11}$, $Z_{12}$ and $Z_{13}$ is independently selected from N, $CR^{20}$, or $CR_1'$, wherein one of $Z_{10}$, $Z_{11}$, $Z_{12}$ or $Z_{13}$ is N; and zero to one $R^{20}$ is a solubilizing group;

zero to one $R_1'''$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl.

Also provided are pharmaceutical compositions comprising one or more compounds of Formulas (I)-(XXVIII) or a salt, prodrug or metabolite thereof.

In another aspect, the invention provides methods for using sirtuin-modulating compounds, or compostions comprising sirtuin-modulating compounds. In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, chemotherapeutic induced neuropathy, neuropathy associated with an ischemic event, ocular diseases and/or disorders, cardiovascular disease, blood clotting disorders, inflammation, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods comprise administering to a subject in need thereof a pharmaceutically effective amount of a sirtuin-modulating compound.

In certain aspects, the sirtuin-modulating compounds may be administered alone or in combination with other compounds, including other sirtuin-modulating compounds, or other therapeutic agents.

DETAILED DESCRIPTION

1. Definitions

Figure 1:
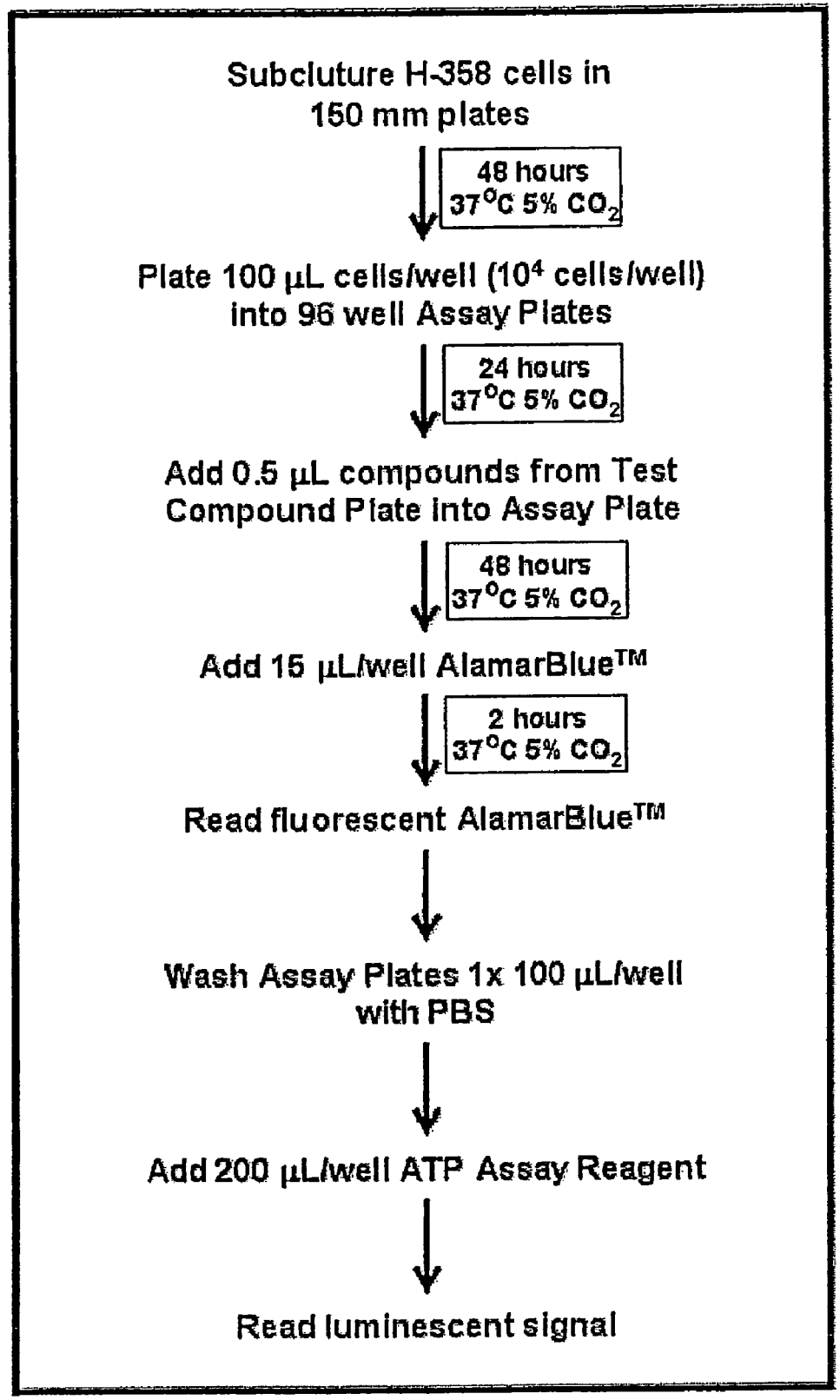
FIG. 1 shows a schematic of the Cellular ATP Assay described in Example 5.

As used herein, the following terms and phrases shall have the meanings set forth below. Unless defined otherwise, all technical and scientific terms used herein have the same meaning as commonly understood to one of ordinary skill in the art.

The singular forms "a," "an," and "the" include plural reference unless the context clearly dictates otherwise.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

The term "bioavailable" when referring to a compound is art-recognized and refers to a form of a compound that allows for it, or a portion of the amount of compound administered, to be absorbed by, incorporated to, or otherwise physiologically available to a subject or patient to whom it is administered.

"Biologically active portion of a sirtuin" refers to a portion of a sirtuin protein having a biological activity, such as the ability to deacetylate. Biologically active portions of a sirtuin may comprise the core domain of sirtuins. Biologically active portions of SIRT1 having GenBank Accession No. NP_036370 that encompass the NAD+ binding domain and the substrate binding domain, for example, may include without limitation, amino acids 62-293 of GenBank Accession No. NP_036370, which are encoded by nucleotides 237 to 932 of GenBank Accession No. NM_012238. Therefore, this region is sometimes referred to as the core domain. Other biologically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238.

The term "companion animals" refers to cats and dogs. As used herein, the term "dog(s)" denotes any member of the species *Canis familiaris*, of which there are a large number of different breeds. The term "cat(s)" refers to a feline animal including domestic cats and other members of the family Felidae, genus *Felis*.

The terms "comprise" and "comprising" are used in the inclusive, open sense, meaning that additional elements may be included.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

A "direct activator" of a sirtuin is a molecule that activates a sirtuin by binding to it. A "direct inhibitor" of a sirtuin is a molecule inhibits a sirtuin by binding to it.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "hyperinsulinemia" refers to a state in an individual in which the level of insulin in the blood is higher than normal.

The term "including" is used to mean "including but not limited to". "Including" and "including but not limited to" are used interchangeably.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

The term "livestock animals" refers to domesticated quadrupeds, which includes those being raised for meat and various byproducts, e.g., a bovine animal including cattle and other members of the genus *Bos*, a porcine animal including domestic swine and other members of the genus *Sus*, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*.

The term "mammal" is known in the art, and exemplary mammals include humans, primates, livestock animals (including bovines, porcines, etc.), companion animals (e.g., canines, felines, etc.) and rodents (e.g., mice and rats).

The term "naturally occurring form" when referring to a compound means a compound that is in a form, e.g., a composition, in which it can be found naturally. For example, since resveratrol can be found in red wine, it is present in red wine in a form that is naturally occurring. A compound is not in a form that is naturally occurring if, e.g., the compound has been purified and separated from at least some of the other molecules that are found with the compound in nature. A "naturally occurring compound" refers to a compound that can be found in nature, i.e., a compound that has not been designed by man. A naturally occurring compound may have been made by man or by nature.

A "naturally occurring compound" refers to a compound that can be found in nature, i.e., a compound that has not been designed by man. A naturally occurring compound may have been made by man or by nature. For example, resveratrol is a naturally-occurring compound. A "non-naturally occurring compound" is a compound that is not known to exist in nature or that does not occur in nature.

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection and infusion.

A "patient", "subject", "individual" or "host" refers to either a human or a non-human animal.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences.

Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "polynucleotide", and "nucleic acid" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The term "recombinant" polynucleotide means a polynucleotide of genomic, cDNA, semisynthetic, or synthetic origin which either does not occur in nature or is linked to another polynucleotide in a nonnatural arrangement.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "protecting group" is art-recognized and refers to temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed by Greene and Wuts in *Protective Groups in Organic Synthesis* ($2^{nd}$ ed., Wiley: New York, 1991).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 20%, 30%, 40%, 50%, 60% or between 20% and 70%, 30% and 60%, 40% and 60% or more using methods described herein.

"Sirtuin-activating compound" refers to a compound that increases the level of a sirtuin protein and/or increases at least one activity of a sirtuin protein. In an exemplary embodiment, a sirtuin-activating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin-inhibiting compound" refers to a compound that decreases the level of a sirtuin protein and/or decreases at least one activity of a sirtuin protein. In an exemplary embodiment, a sirtuin-inhibiting compound may decrease at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

"Sirtuin-modulating compound" refers to a compound of Formulas (I)-(XXVIII) as described herein. In exemplary embodiments, a sirtuin-modulating compound may either up regulate (e.g., activate or stimulate), down regulate (e.g., inhibit or suppress) or otherwise change a functional property or biological activity of a sirtuin protein. Sirtuin-modulating compounds may act to modulate a sirtuin protein either directly or indirectly. In certain embodiments, a sirtuin-modulating compound may be a sirtuin-activating compound or a sirtuin-inhibiting compound.

"Sirtuin protein" refers to a member of the sirtuin deacetylase protein family, or preferably to the sir2 family, which include yeast Sir2 (GenBank Accession No. P53685), C. elegans Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273). Preferred sirtuins are those that share more similarities with SIRT1, i.e., hSIRT1, and/or Sir2 than with SIRT2, such as those members having at least part of the N-terminal sequence present in SIRT1 and absent in SIRT2 such as SIRT3 has.

"SIRT1 protein" refers to a member of the sir2 family of sirtuin deacetylases. In one embodiment, a SIRT1 protein includes yeast Sir2 (GenBank Accession No. P53685), C. elegans Sir-2.1 (GenBank Accession No. NP_501912), human SIRT1 (GenBank Accession No. NM_012238 or NP_036370 (or AF083106)), and human SIRT2 (GenBank Accession No. NM_012237, NM_030593, NP_036369, NP_085096, or AF083107) proteins, and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

"SIRT3 protein" refers to a member of the sirtuin deacetylase protein family and/or to a homolog of a SIRT1 protein. In one embodiment, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In one embodiment, a SIRT3 protein includes a fragment of SIRT3 protein that is produced by cleavage with a mitochondrial matrix processing peptidase (MPP) and/or a mitochondrial intermediate peptidase (MIP).

The term "substantially homologous" when used in connection with amino acid sequences, refers to sequences which are substantially identical to or similar in sequence with each other, giving rise to a homology of conformation and thus to retention, to a useful degree, of one or more biological (including immunological) activities. The term is not intended to imply a common evolution of the sequences.

The term "synthetic" is art-recognized and refers to production by in vitro chemical or enzymatic synthesis.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions described herein may be administered in a sufficient amount to produce a desired effect at a reasonable benefit/risk ratio applicable to such treatment.

"Transcriptional regulatory sequence" is a generic term used throughout the specification to refer to DNA sequences, such as initiation signals, enhancers, and promoters, which induce or control transcription of protein coding sequences with which they are operable linked. In preferred embodiments, transcription of one of the recombinant genes is under the control of a promoter sequence (or other transcriptional regulatory sequence) which controls the expression of the recombinant gene in a cell-type which expression is intended. It will also be understood that the recombinant gene can be under the control of transcriptional regulatory sequences which are the same or which are different from those sequences which control transcription of the naturally-occurring forms of genes as described herein.

"Treating" a condition or disease refers to curing as well as ameliorating at least one symptom of the condition or disease.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions. As used herein, "expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

2. Sirtuin Modulators

In one aspect, the invention provides novel sirtuin-modulating compounds for treating and/or preventing a wide variety of diseases and disorders including, for example, diseases or disorders related to aging or stress, diabetes, obesity, neurodegenerative diseases, ocular diseases and disorders, cardiovascular disease, blood clotting disorders, inflammation, cancer, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. Other compounds disclosed herein may be suitable for use in a pharmaceutical composition and/or one or more methods disclosed herein.

In one embodiment, sirtuin-modulating compounds of the invention are represented by Structural Formula (I):

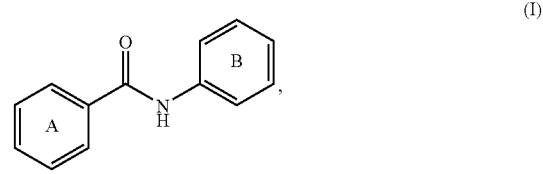

(I)

or a salt thereof, where:

Ring A is optionally substituted; and

Ring B is substituted with at least one carboxy, substituted or unsubstituted arylcarboxamine, substituted or unsubstituted aralkylcarboxamine, substituted or unsubstituted heteroaryl group, substituted or unsubstituted heterocyclylcarbonylethenyl, or polycyclic aryl group or is fused to an aryl ring and is optionally substituted by one or more additional groups.

In certain embodiments, Ring B is substituted with at least a carboxy group.

In certain embodiments, Ring B is substituted with at least a substituted or unsubstituted arylcarboxamine, a substituted or unsubstituted aralkylcarboxamine or a polycyclic aryl group.

In certain embodiments, Ring B is substituted with at least a substituted or unsubstituted heteroaryl group or a substituted or unsubstituted heterocyclylcarbonylethenyl group.

In another embodiment, sirtuin-modulating compounds of the invention are represented by Structural Formula (II):

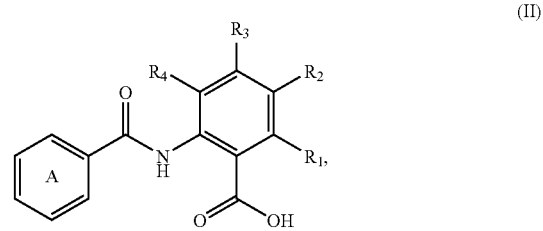

(II)

or a salt thereof, where:

Ring A is optionally substituted;

$R_1$, $R_2$, $R_3$ and $R_4$ are independently selected from the group consisting of —H, halogen, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;

$R_5$ and $R_6$ are independently —H, a substituted or unsubstituted alkyl group, a substituted or unsubstituted aryl group or a substituted or unsubstituted heterocyclic group; and n is 1 or 2.

In a further embodiment, sirtuin-modulating compounds of the invention are represented by Structural Formula (IIa):

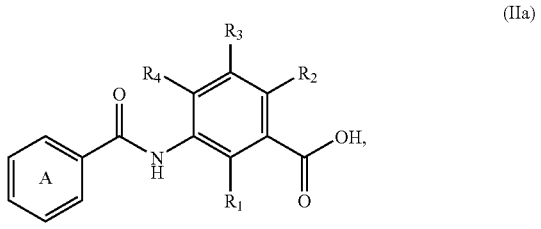

(IIa)

or a salt thereof, where:

Ring A is optionally substituted;

$R_1$, $R_2$, $R_3$ and $R_4$ are independently selected from the group consisting of —H, halogen, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;

$R_5$ and $R_6$ are independently —H, a substituted or unsubstituted alkyl group, a substituted or unsubstituted aryl group or a substituted or unsubstituted heterocyclic group; and n is 1 or 2.

In yet another embodiment, sirtuin-modulating compounds of the invention are represented by Structural Formula (II):

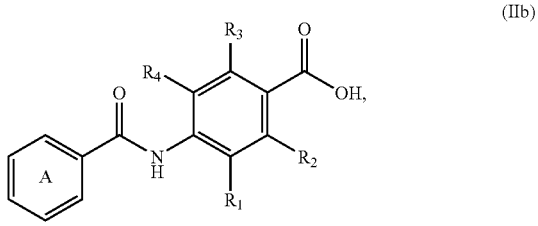

(IIb)

or a salt thereof, where:

Ring A is optionally substituted;

$R_1$, $R_2$, $R_3$ and $R_4$ are independently selected from the group consisting of —H, halogen, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;

$R_5$ and $R_6$ are independently —H, a substituted or unsubstituted alkyl group, a substituted or unsubstituted aryl group or a substituted or unsubstituted heterocyclic group; and n is 1 or 2.

In certain embodiments, $R_1$, $R_2$, $R_3$ and $R_4$ in Structural Formulas (II)-(IIb) are independently selected from the group consisting of —H, —$OR_5$ and —$SR_5$, particularly —H and —$OR_5$ (e.g., —H, —OH, —$OCH_3$).

Ring A is preferably substituted. Suitable substituents include halogens (e.g., bromine), acyloxy groups (e.g., acetoxy), aminocarbonyl groups (e.g., arylaminocarbonyl such as substituted, particularly carboxy-substituted, phenylaminocarbonyl groups) and alkoxy (e.g., methoxy, ethoxy) groups.

In yet another aspect, the invention provides novel sirtuin-modulating compounds of Formula (III):

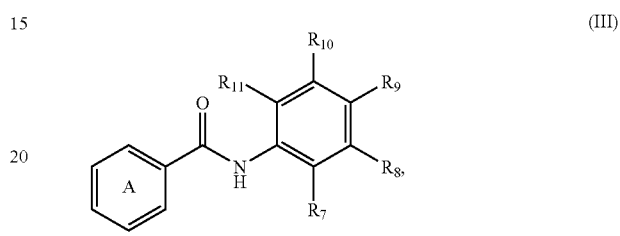

(III)

or a salt thereof, where:

Ring A is optionally substituted;

$R_5$ and $R_6$ are independently —H, a substituted or unsubstituted alkyl group, a substituted or unsubstituted aryl group or a substituted or unsubstituted heterocyclic group;

$R_7$, $R_9$, $R_{10}$ and $R_{11}$ are independently selected from the group consisting of —H, halogen, —$R_5$, —$OR_5$, —CN, —$CO_2R_5$, —$OCOR_5$, —$OCO_2R_5$, —$C(O)NR_5R_6$, —$OC(O)NR_5R_6$, —$C(O)R_5$, —$COR_5$, —$SR_5$, —$OSO_3H$, —$S(O)_nR_5$, —$S(O)_nOR_5$, —$S(O)_nNR_5R_6$, —$NR_5R_6$, —$NR_5C(O)OR_6$, —$NR_5C(O)R_6$ and —$NO_2$;

$R_8$ is a polycyclic aryl group; and n is 1 or 2.

In certain embodiments, one or more of $R_7$, $R_9$, $R_{10}$ and $R_{11}$ are —H. In particular embodiments, $R_7$, $R_9$, $R_{10}$ and $R_{11}$ are each —H.

In certain embodiments, $R_8$ is a heteroaryl group, such as an oxazolo[4,5-b]pyridyl group. In particular embodiments, $R_8$ is a heteroaryl group and one or more of $R_7$, $R_9$, $R_{10}$ and $R_{11}$ are —H.

Ring A is preferably substituted. Suitable substituents include halogens (e.g., bromine), acyloxy groups (e.g., acetoxy), aminocarbonyl groups (e.g., arylaminocarbonyl, such as substituted, particularly carboxy-substituted, phenylaminocarbonyl groups) and alkoxy (e.g., methoxy, ethoxy) groups, particularly alkoxy groups. In certain embodiments, Ring A is substituted with at least one alkoxy or halo group, particularly methoxy.

In certain embodiments, Ring A is optionally substituted with up to 3 substituents independently selected from ($C_1$-$C_3$ straight or branched alkyl), O—($C_1$-$C_3$ straight or branched alkyl), N($C_1$-$C_3$ straight or branched alkyl)$_2$, halo, or a 5 to 6-membered heterocycle.

In certain embodiments, Ring A is not substituted with a nitrile or pyrrolidyl group.

In certain embodiments, $R_8$ is a substituted or unsubstituted bicyclic heteroaryl group, such as a bicyclic heteroaryl group that includes a ring N atom and 1 to 2 additional ring heteroatoms independently selected from N, O or S. Preferably, $R_8$ is attached to the remainder of the compound by a carbon-carbon bond. In certain such embodiments, 2 additional ring heteroatoms are present, and typically at least one of said additional ring heteroatoms is O or S. In certain such embodiments, 2 total ring nitrogen atoms are present (with zero or one O or S present), and the nitrogen atoms are typically each in a different ring. In certain such embodiments, $R_8$ is not substituted with a carbonyl-containing moiety, particularly when $R_8$ is thienopyrimidyl or thienopyridinyl.

In certain such embodiments, $R_8$ is selected from oxazolopyridyl, benzothienyl, benzofuryl, indolyl, quinoxalinyl, benzothiazolyl, benzoxazolyl, benzimidazolyl, quinolinyl, isoquinolinyl or isoindolyl. In certain such embodiments, $R_8$ is selected from thiazolopyridyl, imidazothiazolyl, benzoxazinonyl, or imidazopyridyl.

Particular examples of $R_8$, where

cates attachment to the remainder of Structural Formula (III), include:

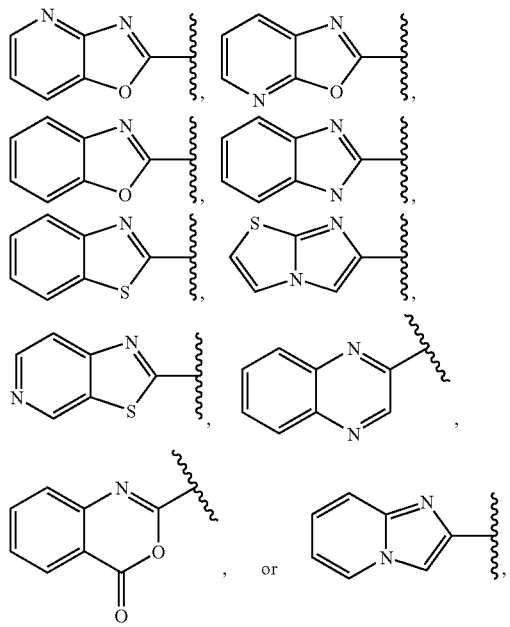

where up to 2 ring carbons not immediately adjacent to the indicated attachment point are independently substituted with O—$C_1$-$C_3$ straight or branched alkyl, $C_1$-$C_3$ straight or branched alkyl or halo, particularly $C_1$-$C_3$ straight or branched alkyl or halo. In certain embodiments, $R_8$ is

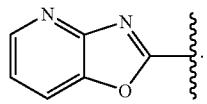

In certain embodiments (e.g., when the modulator is a sirtuin activator), $R_8$ is

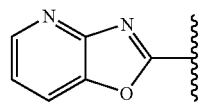

and Ring A is optionally substituted with up to 3 substituents independently selected from ($C_1$-$C_3$ straight or branched alkyl), O—($C_1$-$C_3$ straight or branched alkyl), N($C_1$-$C_3$ straight or branched alkyl)$_2$, halo, or a 5 to 6-membered heterocycle. In certain such embodiments, Ring A is not simultaneously substituted at the 2- and 6-positions with O—($C_1$-$C_3$ straight or branched alkyl). In certain such embodiments, Ring A is not simultaneously substituted at the 2-, 4- and 6-positions with O—($C_1$-$C_3$ straight or branched alkyl). In certain such embodiments, Ring A is not simultaneously substituted at the 2-, 3-, and 4-positions with O—($C_1$-$C_3$ straight or branched alkyl). In certain such embodiments, Ring A is not substituted at the 4-position with a 5 to 6-membered heterocycle. In certain such embodiments, Ring A is not singly substituted at the 3- or 4-position (typically 4-position) with O—($C_1$-$C_3$ straight or branched alkyl). In certain such embodiments, Ring A is not substituted at the 4-position with O—($C_1$-$C_3$ straight or branched alkyl) and at the 2- or 3-position with $C_1$-$C_3$ straight or branched alkyl.

In certain embodiments, $R_8$ is

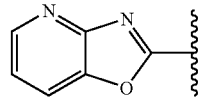

and Ring A is optionally substituted with up to 3 substituents independently selected from ($C_1$-$C_3$ straight or branched alkyl), ($C_1$-$C_3$ straight or branched haloalkyl, where a haloalkyl group is an alkyl group substituted with one or more halogen atoms), O—($C_1$-$C_3$ straight or branched alkyl), N($C_1$-$C_3$ straight or branched alkyl)$_2$, halo, or a 5 to 6-membered heterocycle. In certain such embodiments, Ring A is not singly substituted at the 3- or 4-position with O—($C_1$-$C_3$ straight or branched alkyl). In certain such embodiments, Ring A is not substituted at the 4-position with O—($C_1$-$C_3$ straight or branched alkyl) and at the 2- or 3-position with $C_1$-$C_3$ straight or branched alkyl.

In certain embodiments, $R_8$ is

(e.g., where one or both halo is chlorine) and Ring A is optionally substituted with up to 3 substituents independently selected from ($C_1$-$C_3$ straight or branched alkyl), O—($C_1$-$C_3$ straight or branched alkyl), N($C_1$-$C_3$ straight or branched alkyl)$_2$, halo, or a 5 to 6-membered heterocycle, but not singly substituted at the 3-position with O—($C_1$-$C_3$ straight or branched alkyl).

In certain embodiments, such as when $R_8$ has one of the values described above, Ring A is substituted with up to 3 substituents independently selected from chloro, methyl, O-methyl, $N(CH_3)_2$ or morpholino. In certain such embodiments, $R_8$ is selected from
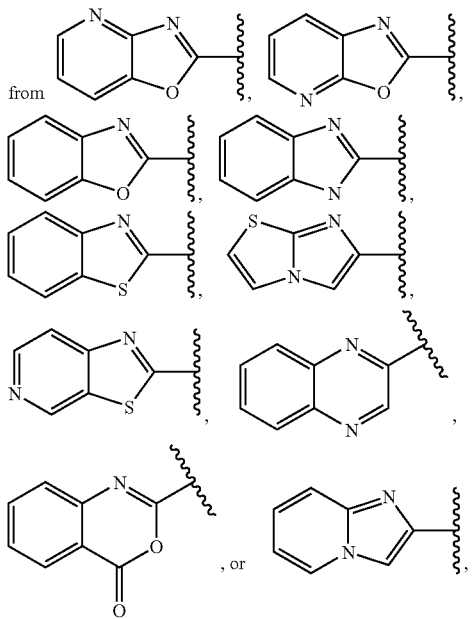
, or where up to 2 ring carbons not immediately adjacent to the indicated attachment point are independently substituted with $C_1$-$C_3$ straight or branched alkyl or halo; each of $R_7$, $R_9$, and $R_{11}$ is —H; and $R_{10}$ is selected from —H, —$CH_2OH$, —$CO_2H$, —$CO_2CH_3$, —$CH_2$-piperazinyl, $CH_2N(CH_3)_2$, —C(O)—NH—$(CH_2)_2$—$N(CH_3)_2$, or —C(O)-piperazinyl. In certain such embodiments, when $R_8$ is

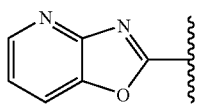

and Ring A is 3-dimethylaminophenyl, none of $R_7$, $R_9$, $R_{10}$ and $R_{11}$ is —$CH_2$—$N(CH_3)_2$ or —C(O)—NH—$(CH_2)_2$—N$(CH_3)_2$, and/or when $R_8$ is

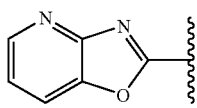

and Ring A is 3,4 dimethoxyphenyl, none of $R_7$, $R_9$, $R_{10}$ and $R_{11}$ is $C(O)OCH_3$ or $C(O)OH$.

In certain embodiments, such as when $R_8$ has one of the values described above and/or Ring A is optionally substituted as described above, at least one of $R_7$, $R_9$, $R_{10}$ and $R_{11}$ is —H. In certain such embodiments, each of $R_7$, $R_9$, $R_{10}$ and $R_{11}$ is —H.

In certain embodiments, $R_7$, $R_9$, $R_{10}$ or $R_{11}$ is selected from —C(O)OH, —$N(CH_3)_2$, —$CH_2OH$, —$CH_2OCH_3$, —$CH_2$-piperazinyl, —$CH_2$-methylpiperazinyl, —$CH_2$-pyrrolidyl, —$CH_2$-piperidyl, —$CH_2$-morpholino, —$CH_2$—N$(CH_3)_2$, —C(O)—NH—$(CH_2)_n$-piperazinyl, —C(O)—NH—$(CH_2)_n$-methylpiperazinyl, —C(O)—NH—$(CH_2)_n$-pyrrolidyl, —C(O)—NH—$(CH_2)_n$-morpholino, —C(O)—NH—$(CH_2)_n$-piperidyl, or —C(O)—NH—$(CH_2)_n$N$(CH_3)_2$, wherein n is 1 or 2. In certain such embodiments, $R_{10}$ is selected from —C(O)OH, —$N(CH_3)_2$, —$CH_2OH$, —$CH_2OCH_3$, —$CH_2$-piperazinyl, —$CH_2$-methylpiperazinyl, —$CH_2$-pyrrolidyl, —$CH_2$-piperidyl, —$CH_2$-morpholino, —$CH_2$—N$(CH_3)_2$, —C(O)—NH—$(CH_2)_n$-piperazinyl, —C(O)—NH—$(CH_2)_n$-methylpiperazinyl, —C(O)—NH—$(CH_2)_n$-pyrrolidyl, —C(O)—NH—$(CH_2)_n$-morpholino, —C(O)—NH—$(CH_2)_n$-piperidyl, or —C(O)—NH—$(CH_2)_n$N$(CH_3)_2$, wherein n is 1 or 2, and each of $R_7$, $R_9$, and $R_{11}$ is H.

In certain embodiments, Ring A is substituted with a nitrile group or is substituted at the para position with a 5- or 6-membered heterocycle. Typical examples of the heterocycle include pyrrolidyl, piperidinyl and morpholinyl.

In yet another aspect, the invention provides novel sirtuin-modulating compounds of Formula (IV):

$$Ar—L—J—M—K—Ar' \quad (IV)$$

or a salt thereof, wherein:

each Ar and Ar' is independently an optionally substituted carbocyclic or heterocyclic aryl group;

L is an optionally substituted carbocyclic or heterocyclic arylene group;

each J and K is independently $NR_1'$, O, S, or is optionally independently absent; or when J is $NR_1'$, $R_1'$ is a C1-C4 alkylene or C2-C4 alkenylene attached to Ar' to form a ring fused to Ar'; or when K is $NR_1'$, $R_1'$ is a C1-C4 alkylene or C2-C4 alkenylene attached to L to form a ring fused to L;

each M is C(O), S(O), S(O)$_2$, or $CR_1'R_1'$;

each $R_1'$ is independently selected from H, C1-C10 alkyl; C2-C10 alkenyl; C2-C10 alkynyl; C3-C10 cycloalkyl; C4-C10 cycloalkenyl; aryl; $R_5'$; halo; haloalkyl; $CF_3$; $SR_2'$; $OR_2'$; $NR_2'R_2'$; $NR_2'R_3'$; $COOR_2'$; $NO_2$; CN; C(O)$R_2'$; C(O)C(O)$R_2'$; C(O)NR$_2'R_2'$; OC(O)$R_2'$; S(O)$_2R_2'$; S(O)$_2NR_2'R_2'$; NR$_2'C(O)NR_2'R_2'$; NR$_2'C(O)C(O)R_2'$; NR$_2'C(O)R_2'$; NR$_2'$(COOR$_2'$); NR$_2'C(O)R_5'$; NR$_2'S(O)_2NR_2'R_2'$; NR$_2'S(O)_2R_2'$; NR$_2'S(O)_2R_5'$; NR$_2'C(O)C(O)NR_2'R_2'$; NR$_2'C(O)C(O)NR_2'R_3'$; C1-C10 alkyl substituted with aryl, $R_4'$ or $R_5'$; or C2-C10 alkenyl substituted with aryl, $R_4'$ or $R_5'$;

each $R_2'$ is independently H; C1-C10 alkyl; C2-C10 alkenyl; C2-C10 alkynyl; C3-C10 cycloalkyl; C4-C10 cycloalkenyl; aryl; $R_6'$; C1-C10 alkyl substituted with 1-3 independent aryl, $R_4'$ or $R_6'$ groups; C3-C10 cycloalkyl substituted with 1-3 independent aryl, $R_4'$ or $R_6'$ groups; or C2-C10 alkenyl substituted with 1-3 independent aryl, $R_4'$ or $R_6'$;

each $R_3'$ is independently C(O)$R_2'$, COOR$_2'$, or S(O)$_2R_2'$;

each $R_4'$ is independently halo, $CF_3$, $SR_7'$, $OR_7'$, OC(O) $R_7'$, $NR_7'R_7'$, $NR_7'R_8'$, $NR_8'R_8'$, COOR$_7'$, $NO_2$, CN, C(O) $R_7'$, or C(O)NR$_7'R_7'$;

each $R_5'$ is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; aryl; $R_6'$; halo; sulfur; oxygen; $CF_3$; haloalkyl; $SR_2'$; $OR_2'$; OC(O)$R_2'$; NR$_2'R_2'$; NR$_2'R_3'$; NR$_3'R_3'$; COOR$_2'$; $NO_2$; CN; C(O)$R_2'$;

C(O)NR$_2$'R$_2$'; C1-C10 alkyl substituted with 1-3 independent R$_4$', R$_6$', or aryl; or C2-C10 alkenyl substituted with 1-3 independent R$_4$', R$_6$', or aryl;

each R$_6$' is independently a 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, or S, which may be saturated or unsaturated, and wherein 0, 1, 2 or 3 atoms of each ring may be substituted by a substituent independently selected from C1-C10 alkyl; C2-C10 alkenyl; C2-C10 alkynyl; C3-C10 cycloalkyl; C4-C10 cycloalkenyl; halo; sulfur; oxygen; CF$_3$; haloalkyl; SR$_7$'; OR$_7$'; NR$_7$'R$_7$'; NR$_7$'R$_8$'; NR$_8$'R$_8$'; COOR$_7$'; NO$_2$; CN; C(O)R$_7$'; or C(O)NR$_7$'R$_7$';

each R$_7$' is independently H, C1-C10 alkyl; C2-C10 alkenyl; C2-C10 alkynyl; C3-C10 cycloalkyl; C4-C10 cycloalkenyl; haloalkyl; C1-C10 alkyl optionally substituted with 1-3 independent C1-C10 alkyl, C2-C10 alkenyl, C2-C10 alkynyl, C3-C10 cycloalkyl, C4-C10 cycloalkenyl, halo, CF$_3$, OR$_{10}$', SR$_{10}$', NR$_{10}$'R$_{10}$', COOR$_{10}$', NO$_2$, CN, C(O)R$_{10}$', C(O)NR$_{10}$'R$_{10}$', NHC(O)R$_{10}$', or OC(O)R$_{10}$'; or phenyl optionally substituted with 1-3 independent C1-C10 alkyl, C2-C10 alkenyl, C2-C10 alkynyl, C3-C10 cycloalkyl, C4-C10 cycloalkenyl, halo, CF$_3$, OR$_{10}$', SR$_{10}$', NR$_{10}$'R$_{10}$', COOR$_{10}$', NO$_2$, CN, C(O)R$_{10}$', C(O)NR$_{10}$'R$_{10}$', NHC(O)R$_{10}$', or OC(O)R$_{10}$';

each R$_8$' is independently C(O)R$_7$', COOR$_7$', or S(O)$_2$R$_7$';

each R$_9$' is independently H, C1-C10 alkyl, C2-C10 alkenyl, C2-C10 alkynyl, C3-C10 cycloalkyl, C4-C10 cycloalkenyl, or phenyl optionally substituted with 1-3 independent C1-C10 alkyl, C2-C10 alkenyl, C2-C10 alkynyl, C3-C10 cycloalkyl, C4-C10 cycloalkenyl, halo, CF$_3$, OR$_{10}$', SR$_{10}$', NR$_{10}$'R$_{10}$', COOR$_{10}$', NO$_2$, CN, C(O)R$_{10}$', C(O)NR$_{10}$'R$_{10}$', NHC(O)R$_{10}$', or OC(O)R$_{10}$';

each R$_{10}$' is independently H; C1-C10 alkyl; C2-C10 alkenyl; C2-C10 alkynyl; C3-C10 cycloalkyl; C4-C10 cycloalkenyl; C1-C10 alkyl optionally substituted with halo, CF$_3$, OR$_{11}$', SR$_{11}$', NR$_{11}$'R$_{11}$', COOR$_{11}$', NO$_2$, CN; or phenyl optionally substituted with halo, CF$_3$, OR$_{11}$', SR$_{11}$', NR$_{11}$'R$_{11}$', COOR$_{11}$', NO$_2$, CN;

each R$_{11}$' is independently H; C1-C10 alkyl; C3-C10 cycloalkyl or phenyl;

each haloalkyl is independently a C1-C10 alkyl substituted with one or more halogen atoms, selected from F, Cl, Br, or I, wherein the number of halogen atoms may not exceed that number that results in a perhaloalkyl group; and each aryl is independently optionally substituted with 1-3 independent C1-C10 alkyl; C2-C10 alkenyl; C2-C10 alkynyl; C3-C10 cycloalkyl; C4-C10 cycloalkenyl; R$_6$'; halo; haloalkyl; CF$_3$; OR$_9$'; SR$_9$'; NR$_9$'R$_9$'; COOR$_9$'; NO$_2$; CN; C(O)R$_9$'; C(O)C(O)R$_9$'; C(O)NR$_9$'R$_9$'; S(O)$_2$R$_9$'; N(R$_9$')C(O)R$_9$'; N(R$_9$')(COOR$_9$'); N(R$_9$')S(O)$_2$R$_9$'; S(O)$_2$NR$_9$'R$_9$'; OC(O)R$_9$'; NR$_9$'C(O)NR$_9$'R$_9$'; NR$_9$'C(O)C(O)R$_9$'; NR$_9$'C(O)R$_6$'; NR$_9$'S(O)$_2$NR$_9$'R$_9$'; NR$_9$'S(O)$_2$R$_6$'; NR$_9$'C(O)C(O)NR$_9$'R$_9$'; C1-C10 alkyl substituted with 1-3 independent R$_6$', halo, CF$_3$, OR$_9$', SR$_9$', NR$_9$'R$_9$', COOR$_9$', NO$_2$, CN, C(O)R$_9$', C(O)NR$_9$'R$_9$', NHC(O)R$_9$', NH(COOR$_9$'), S(O)$_2$NR$_9$'R$_9$', OC(O)R$_9$'; C2-C10 alkenyl substituted with 1-3 independent R$_6$', halo, CF$_3$, OR$_9$', SR$_9$', NR$_9$'R$_9$', COOR$_9$', NO$_2$, CN, C(O)R$_9$', C(O)NR$_9$'R$_9$', NHC(O)R$_9$', NH(COOR$_9$'), S(O)$_2$NR$_9$'R$_9$', OC(O)R$_9$'; or R$_9$'.

In a preferred embodiment of the invention, each Ar, L, and Ar' is independently an optionally substituted 5- to 7-membered monocyclic ring system or an optionally substituted 9- to 12-membered bicyclic ring system.

According to another preferred embodiment, Ar is

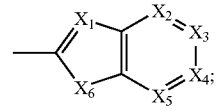

X$_1$, X$_2$, X$_3$, X$_4$, and X$_5$ are independently selected from CR$_1$' and N; and X$_6$ is selected from NR$_1$', O, and S;

According to yet another preferred embodiment, X$_1$ and X$_2$ are N; X$_3$, X$_4$, and X$_5$ are CR$_1$'; and X$_6$ is O.

According to still yet another preferred embodiment, X$_1$ and X$_3$ are N; X$_2$, X$_4$, and X$_5$ are CR$_1$'; and X$_6$ is O.

According to still yet another preferred embodiment, X$_1$ and X$_4$ are N; X$_2$, X$_3$, and X$_5$ are CR$_1$'; and X$_6$ is O.

According to still yet another preferred embodiment, X$_1$ and X$_5$ are N; X$_2$, X$_3$, and X$_4$ are CR$_1$'; and X$_6$ is O.

In another embodiment, the compounds of the formula above are those wherein J is NR$_1$', K is absent, and M is C(O).

In yet another embodiment, the compounds of the formula above are those wherein J is absent, K is NR$_1$', and M is C(O).

In a further embodiment, compounds of formula (IV) are those where when J is absent and K is NR$_1$', M is not C(O) and when J is NR$_1$' and K is absent, M is not C(O).

In a preferred embodiment, the compounds above are those wherein L is an optionally substituted 5- to 7-membered carbocyclic or heterocyclic aryl group.

In yet another preferred embodiment, the compounds are those wherein L is an optionally substituted phenylene, pyridinylene, imidazolylene, oxazolylene, or thiazolylene.

In a particularly preferred embodiment, L is an optionally substituted phenylene.

In another particularly preferred embodiment, L is an optionally substituted pyridinylene.

In an even more preferred embodiment, L is phenylene.

In another even more preferred embodiment, L is pyridinylene.

In either of these embodiments, Ar and J may be attached to L at the ortho-, meta-, or para-positions. Particularly preferred are those embodiments where attachment is at the meta-position.

In certain embodiments, L is not phenylene when Ar' is phenyl. Examples of such embodiments include embodiments where L is an optionally substituted heterocyclic aryl group and Ar' is an optionally substituted carbocyclic or heterocyclic aryl group, or wherein L is an optionally substituted carbocyclic or heterocyclic aryl group and Ar' is an optionally substituted heterocyclic aryl group.

In yet another aspect, the invention provides novel sirtuin-modulating compounds of Formula (I) or a salt thereof, wherein Ring A is substituted with at least one R$_1$' group;

R$_1$', R$_2$', R$_3$', R$_4$', R$_5$', R$_6$', R$_7$', R$_8$', R$_9$', R$_{10}$', and R$_{11}$' are as defined above;

each haloalkyl is independently a C1-C10 alkyl substituted with one or more halogen atoms, selected from F, Cl, Br, or I, wherein the number of halogen atoms may not exceed that number that results in a perhaloalkyl group;

each aryl is independently a 5- to 7-membered monocyclic ring system or a 9- to 12-membered bicyclic ring system optionally substituted with 1-3 independent C1-C10 alkyl;

C2-C10 alkenyl; C2-C10 alkynyl; C3-C10 cycloalkyl; C4-C10 cycloalkenyl; R$_6$'; halo; haloalkyl; CF$_3$; OR$_9$'; SR$_9$'; NR$_9$'R$_9$'; COOR$_9$'; NO$_2$; CN; C(O)R$_9$'; C(O)C(O)R$_9$'; C(O)NR$_9$'R$_9$'; S(O)$_2$R$_9$'; N(R$_9$')C(O)R$_9$'; N(R$_9$')(COOR$_9$'); N(R$_9$')S(O)$_2$R$_9$'; S(O)$_2$NR$_9$'R$_9$'; OC(O)R$_9$'; NR$_9$'C(O)NR$_9$'R$_9$'; NR$_9$'C(O)C(O)R$_9$'; NR$_9$'C(O)R$_6$'; NR$_9$'S(O)$_2$NR$_9$'R$_9$'; NR$_9$'S(O)$_2$R$_6$'; NR$_9$'C(O)C(O)NR$_9$'R$_9$'; C1-C10 alkyl substituted with 1-3 independent R$_6$', halo, CF$_3$, OR$_9$', SR$_9$', NR$_9$'R$_9$', COOR$_9$', NO$_2$, CN, C(O)R$_9$', C(O)NR$_9$'R$_9$', NHC(O)R$_9$', NH(COOR$_9$'), S(O)$_2$NR$_9$'R$_9$', OC(O)R$_9$'; C2-C10 alkenyl substituted with 1-3 independent R$_6$', halo, CF$_3$, OR$_9$', SR$_9$', NR$_9$'R$_9$', COOR$_9$', NO$_2$, CN, C(O)R$_9$', C(O)NR$_9$'R$_9$', NHC(O)R$_9$', NH(COOR$_9$'), S(O)$_2$NR$_9$'R$_9$', OC(O)R$_9$'; or R$_9$'; and Ring B is substituted with at least one

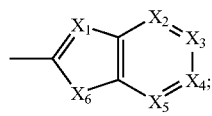

wherein

X$_1$, X$_2$, X$_3$, X$_4$, and X$_5$ are independently selected from CR$_1$' and N; and X$_6$ is selected from NR$_1$', O, and S.

In a preferred embodiment, Ring B is phenyl or pyridinyl.

In a further aspect, the invention provides novel sirtuin-modulating compounds of Formula (IVa):

Het—L—Q—Ar'  (IVa)

or a salt thereof, wherein:

Het is an optionally substituted heterocyclic aryl group;

L is an optionally substituted carbocyclic or heterocyclic arylene group;

Ar' is an optionally substituted carbocyclic or heterocyclic aryl group; and

Q is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(O)—CR$_1$'R'$_1$—NR$_1$'—, —NR$_1$'—C(=NR$_1$')—NR$_1$'—, —C(O)—NR$_1$'—, —C(O)—NR$_1$'—S(O)$_2$—, —NR$_1$'—, —CR$_1$'R'$_1$—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R'$_1$—C(O)—NR$_1$'—, —CR$_1$'R'$_1$—C(O)—NR$_1$'—, —NR$_1$'—C(O)—CR$_1$'=CR$_1$'—CR$_1$'R'$_1$—, —NR$_1$'—C(=N—CN)—NR$_1$'—, —NR$_1$'—C(O)—CR$_1$'R'$_1$—,

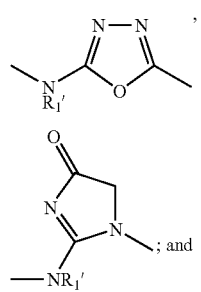

each R$_1$' is independently selected from H or optionally substituted C$_1$-C$_3$ straight or branched alkyl, wherein:

when Het is a polycyclic heteroaryl, L is an optionally substituted phenylene, Q and Het are attached to L in a meta orientation, and Ar' is optionally substituted phenyl; then Q is not —NH—C(O)—.

In certain embodiments, when Het is a polycyclic heteroaryl, L is optionally substituted phenylene, and Ar' is optionally substituted phenyl; then Q is not —NH—C(O)—.

In certain embodiments (e.g., when the compound is a sirtuin activator), Het and Q are attached to L in a 1-, 2- or 1-,3-configuration (e.g., when L is phenylene, Het and Q are attached in an ortho or a meta orientation). In certain embodiments where Het and Q are attached to L in a 1-,3-configuration, if Het is benzoxazolyl, L is pyridylene and Q is —NH—C(O)—NH, then Ar' is not 3,4 dioxymethlyene phenyl; if Het is methyl thiazolyl, L is phenylene and Q is —NH—C(O)—, then Ar' is not 3-dimethylamino phenyl; if Het is oxazolopyridyl, L is pyridylene and Q is —NH—C(O)—NH, then Ar' is not 4-dimethylamino phenyl; if Het is oxazolopyridyl or benzoxazolyl and L is

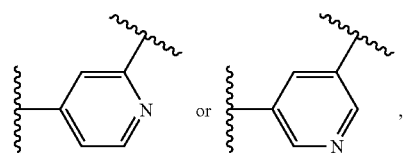

then Q is not —NH—(SO)$_2$—; and if Het is oxazolopyridyl, L is

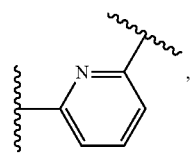

and Q is —NH—C(O)—, then Ar' is not 3,4 dimethoxyphenyl or pyridyl.

When Het is substituted, it is typically substituted at up to 2 carbon atoms with a substituent independently selected from R$_{12}$, N(R$_{12}$)$_2$, NH(R$_{12}$), OR$_{12}$, C(O)—NH—R$_{12}$, C(O)—N(R$_{12}$)$_2$, N(R$_{12}$)—OR$_{12}$, CH$_2$—N(R$_{12}$)$_2$, C(O)OR$_{12}$, C(O)OH,

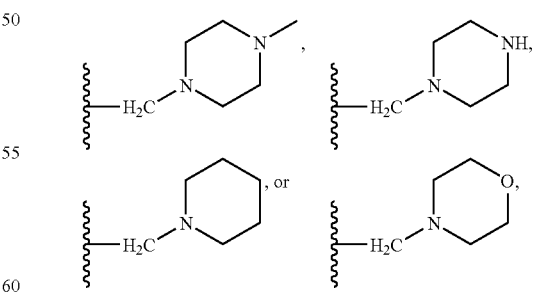

where each R$_{12}$ is independently selected from optionally substituted C$_1$-C$_3$ straight or branched alkyl.

In certain embodiments, Het is selected from oxazolopyridyl, benzothienyl, benzofuryl, indolyl, quinoxalinyl, benzothiazolyl, benzoxazolyl, benzimidazolyl, quinolinyl, isoquinolinyl or isoindolyl. In other embodiments, Het comprises one ring N heteroatom and 1 to 2 additional ring heteroatoms independently selected from N, O or S, such as thiazolyl, triazolyl, oxadiazolyl, thiazolopyridyl, imidazothiazolyl, benzoxazinonyl, or imidazopyridyl.

Particular examples of Het include:

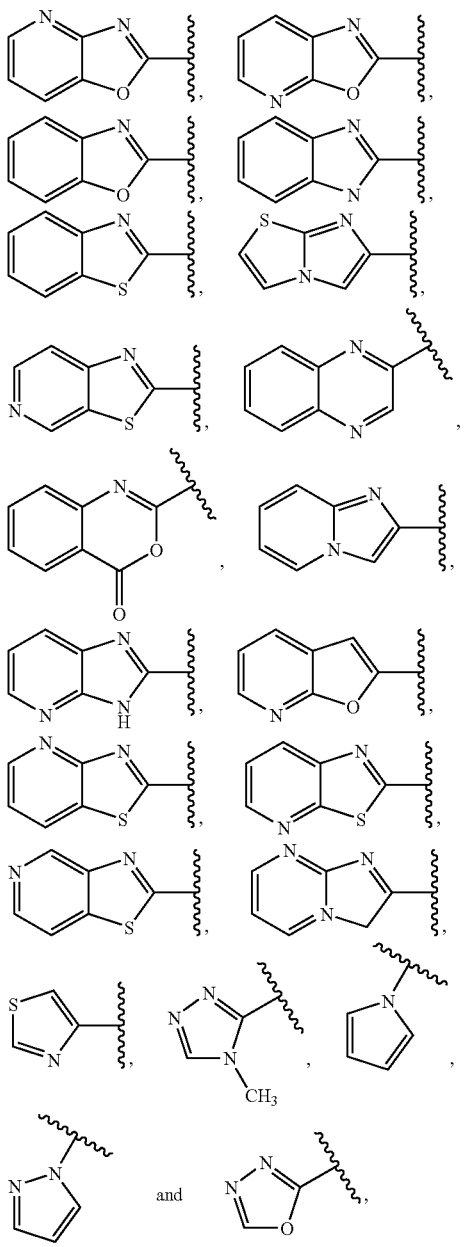

where up to 2 ring carbons not immediately adjacent to the indicated attachment point are independently substituted with optionally substituted $C_1$-$C_3$ straight or branched alkyl, phenyl, halo, $N(R_{12})_2$, $NH(R_{12})$, $OR_{12}$, $C(O)$—$NH$—$R_{12}$, $C(O)$—$N(R_{12})_2$, $N(R_{12})$—

$OR_{12}$, $CH_2$—$N(R_{12})_2$, $C(O)OR_{12}$, $C(O)OH$,

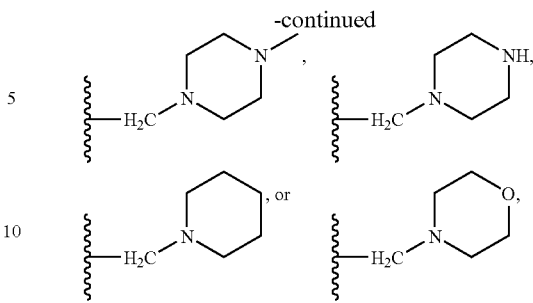

wherein each $R_{12}$ is independently selected from optionally substituted $C_1$-$C_3$ straight or branched alkyl.

In certain embodiments, L is selected from

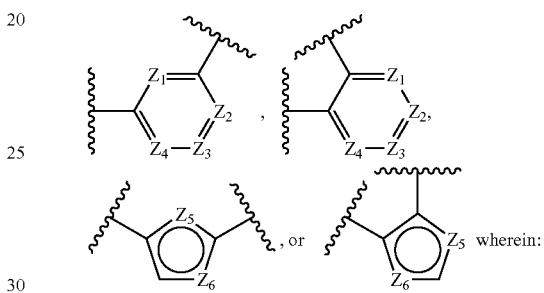

wherein:

each of $Z_1$, $Z_2$, $Z_3$ and $Z_4$ is independently selected from CH or N, wherein not more than three of said $Z_1$, $Z_2$, $Z_3$ or $Z_4$ is N;

each of $Z_5$ and $Z_6$ is independently selected from C, N, O or S, provided that at least one of $Z_5$ and $Z_6$ is N; and L is optionally substituted at 1 to 2 carbon atoms with a substituent independently selected from $R_{12}$, $N(R_{12})_2$, $NH(R_{12})$, $OR_{12}$, $C(O)$—$NH$—$R_{12}$, $C(O)$—$N(R_{12})_2$, $N(R_{12})$—$OR_{12}$, $CH_2$—$N(R_{12})_2$, $C(O)OR_{12}$, $C(O)OH$,

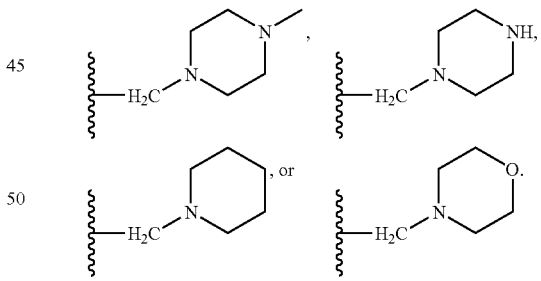

In preferred embodiments, L is selected from phenylene or pyridylene, such as unsubstituted phenylene or phenylene substituted with a single substituent selected from $C(O)OCH_3$, $C(O)OH$, $CH_2OH$, $N(CH_3)_2$, or $CH_2N(CH_3)_2$, or unsubstituted pyridylene.

In certain embodiments, Q is selected from —NH—C(O)—, —NH—S(O)$_2$—, —NH—C(O)—NH—, —C(O)—NH—, —CH$_2$—, —N(CH$_3$)—C(O)—NH—, —NH—C(O)—N(CH$_3$)—, or —NH—S(O)$_2$—NH—, particularly —NH—C(O)—, —C(O)—NH—, —NH—, —NH—C(O)—NH, or —NH—S(O)$_2$—.

In certain embodiments, Ar' is selected from optionally substituted phenyl, benzothiazolyl, or benzoxazolyl. When Ar' is phenyl, typical optional substituents are 1 to 3 substituents independently selected from halo, (optionally substituted $C_1$-$C_3$ straight or branched alkyl), O-(optionally substituted $C_1$-$C_3$ straight or branched alkyl), S-(optionally substituted $C_1$-$C_3$ straight or branched alkyl), $N(CH_3)_2$ or optionally substituted heterocyclyl, or wherein two substituents on adjacent ring atoms are taken together to form a dioxymethylene.

In certain embodiments, Het is selected from

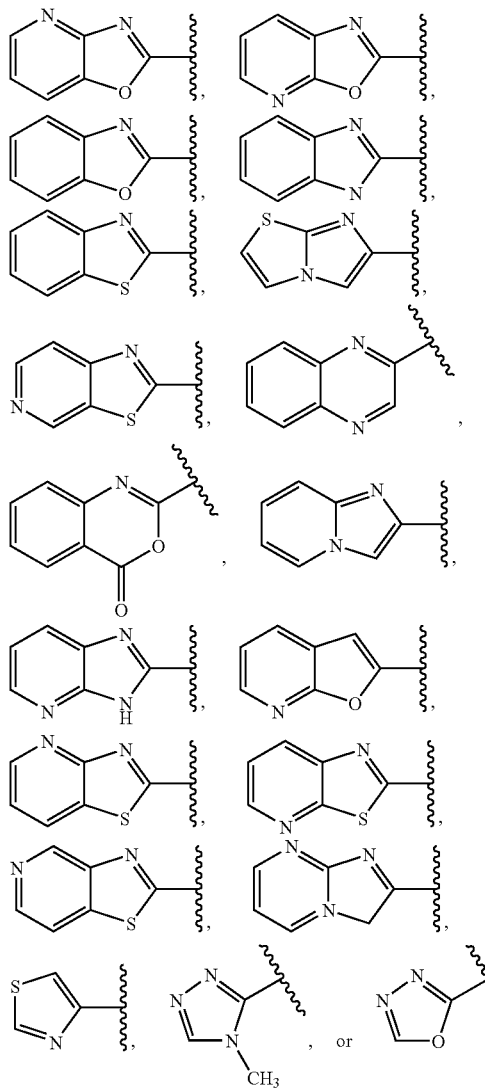

and wherein up to 2 ring carbons not immediately adjacent to the indicated attachment point are independently substituted with optionally substituted $C_1$-$C_3$ straight or branched alkyl, phenyl or halo;

L is selected from unsubstituted phenylene, phenylene substituted with a single substituent selected from C(O)OCH₃, C(O)OH, CH₂OH, N(CH₃)₂, or CH₂N(CH₃)₂, or unsubstituted pyridylene;

Q is selected from —NH—C(O)—, —C(O)—NH—, —NH—, —NH—C(O)—NH, or —NH—S(O)₂—; and

Ar' is selected from optionally substituted phenyl, benzothiazolyl, or benzoxazolyl, wherein said phenyl is optionally substituted with 1 to 3 substituents independently selected from chloro, methyl, O-methyl, S-methyl, N(CH₃)₂, morpholino, or 3,4 dioxymethylene.

In certain embodiments, Q is selected from —NH—C(O)—, —C(O)—NH—, —NH— or —NH—C(O)—NH.

In certain embodiments, the substituents on Ar' are selected from chloro, methyl, O-methyl, S-methyl or N(CH₃)₂. In certain embodiments, the only substituent on Ar' is an O-methyl group, particularly an O-methyl group ortho or meta to Q. In certain embodiments, when there are two or more O-methyl groups or Ar', at least one is ortho or meta to Q.

In certain embodiments, L is pyridyl and Het and Q are at the 1,3- or 2,4-position with respect to the pyridyl nitrogen atom. In certain such embodiments, Q is —NH—S(O)₂—.

In certain embodiments where L is further substituted, the substituent is typically meta to both Het and Q.

In certain embodiments, Q is —NH— and Het is thiazolyl or oxazolopyridyl.

In certain embodiments, Q is —NH— and Ar is benzothiazolyl or benzoxazolyl.

In certain embodiments, such as when the sirtuin modulator is a sirtuin activator, L is

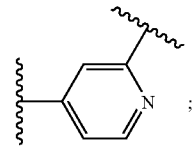

and Q is —NH—(SO)₂—. In certain such embodiments, Het is oxazolopyridyl. When L, Q and optionally Het have these values, Ar' is advantageously naphthyl or phenyl, where Ar' is optionally substituted with 1 to 3 substituents independently selected from CN, halo, ($C_1$-$C_3$ straight or branched alkyl), O—($C_1$-$C_3$ straight or branched alkyl), N($C_1$-$C_3$ straight or branched alkyl)₂, or a 5 to 6-membered heterocycle.

In certain embodiments, such as when the sirtuin modulator is a sirtuin activator, L is

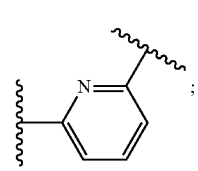

and Q is —NH—C(O)—. In certain such embodiments, Het is oxazolopyridyl. When L, Q and optionally Het have these values, Ar' is advantageously pyridyl or phenyl optionally substituted with 1 to 3 substituents independently selected from CN, halo, (C1-C3 straight or branched alkyl), O—(C1-C3 straight or branched alkyl), N(C1-C3 straight or branched alkyl)2, or a 5 to 6-membered heterocycle.

In certain embodiments, such as when the sirtuin modulatory is a sirtuin inhibitor, Het comprises one N heteroatom and 1 to 2 additional heteroatoms independently selected from N, O or S;

L is

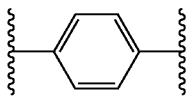

and is optionally substituted;

Q is —NH—C(O)—; and

Ar' is phenyl substituted with 1 to 3 substituents independently selected from CN, halo, $C_1$-$C_3$ straight or branched alkyl, O—($C_1$-$C_3$ straight or branched alkyl), N($C_1$-$C_3$ straight or branched alkyl)$_2$, or a 5 to 6-membered heterocycle, wherein when $R_8$ is unsubstituted

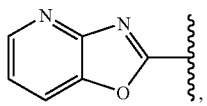

then ring A is:
a) not simultaneously substituted at the 2- and 6-positions with O—($C_1$-$C_3$ straight or branched alkyl);
b) not simultaneously substituted at the 2-position with $C_1$-$C_3$ straight or branched alkyl or O—($C_1$-$C_3$ straight or branched alkyl) and at the 3-position with O—($C_1$-$C_3$ straight or branched alkyl);
c) not substituted at the 4-position with O—($C_1$-$C_3$ straight or branched alkyl) unless simultaneously substituted at the 3-position with halo or O—($C_1$-$C_3$ straight or branched alkyl) and unsubstituted at all other positions;

not substituted at the 4-position with N($C_1$-$C_3$ straight or branched alkyl)$_2$, or said 5 to 6-membered heterocycle. In certain such embodiments, L is unsubstituted and/or Het is oxazolopyridyl.

In yet another aspect, the invention provides novel sirtuin-modulating compounds of Formula (V):

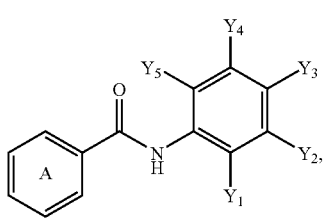

or a salt thereof, wherein:

Ring A is optionally substituted with at least one $R_1'$ group;

$Y_1$, $Y_2$, $Y_3$, $Y_4$, and $Y_5$ are independently $R_1'$;

$R_1'$, $R_2'$, $R_3'$, $R_4'$, $R_5'$, $R_6'$, $R_7'$, $R_8'$, $R_9'$, $R_{10}'$, and $R_{11}'$ are as defined above;

each haloalkyl is independently a C1-C10 alkyl substituted with one or more halogen atoms, selected from F, Cl, Br, or I, wherein the number of halogen atoms may not exceed that number that results in a perhaloalkyl group; and each aryl is independently a 5- to 7-membered monocyclic ring system or a 9- to 12-membered bicyclic ring system optionally substituted with 1-3 independent C1-C10 alkyl; C2-C10 alkenyl; C2-C10 alkynyl; C3-C10 cycloalkyl; C4-C10 cycloalkenyl; $R_6'$; halo; haloalkyl; $CF_3$; $OR_9'$; $SR_9'$; $NR_9'R_9'$; $COOR_9'$; $NO_2$; CN; $C(O)R_9'$; $C(O)C(O)R_9'$; $C(O)NR_9'R_9'$; $S(O)_2R_9'$; $N(R_9')C(O)R_9'$; $N(R_9')(COOR_9')$; $N(R_9')S(O)_2R_9'$; $S(O)_2NR_9'R_9'$; $OC(O)R_9'$; $NR_9'C(O)NR_9'R_9'$; $NR_9'C(O)C(O)R_9'$; $NR_9'C(O)R_6'$; $NR_9'S(O)_2NR_9'R_9'$; $NR_9'S(O)_2R_6'$; $NR_9'C(O)C(O)NR_9'R_9'$; C1-C10 alkyl substituted with 1-3 independent $R_6'$, halo, $CF_3$, $OR_9'$, $SR_9'$, $NR_9'R_9'$, $COOR_9'$, $NO_2$, CN, $C(O)R_9'$, $C(O)NR_9'R_9'$, $NHC(O)R_9'$, $NH(COOR_9')$, $S(O)_2NR_9'R_9'$, $OC(O)R_9'$; C2-C10 alkenyl substituted with 1-3 independent $R_6'$, halo, $CF_3$, $OR_9'$, $SR_9'$, $NR_9'R_9'$, $COOR_9'$, $NO_2$, CN, $C(O)R_9'$, $C(O)NR_9'R_9'$, $NHC(O)R_9'$, $NH(COOR_9')$, $S(O)_2NR_9'R_9'$, $OC(O)R_9'$; or $R_9'$.

In a preferred embodiment of the above compound, either $Y_2$ or $Y_3$ is

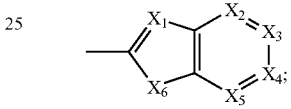

$X_1$, $X_2$, $X_3$, $X_4$, and $X_5$ are independently selected from $CR_1'$ and N; and $X_6$ is selected from $NR_1'$, O, and S.

According to an even more preferred embodiment, $X_1$ and $X_2$ are N; $X_3$, $X_4$, and $X_5$ are $CR_1'$; and $X_6$ is O.

According to another even more preferred embodiment, $X_1$ and $X_3$ are N; $X_2$, $X_4$, and $X_5$ are $CR_1'$; and $X_6$ is O.

According to another even more preferred embodiment, $X_1$ and $X_4$ are N; $X_2$, $X_3$, and $X_5$ are $CR_1'$; and $X_6$ is O.

According to another even more preferred embodiment, $X_1$ and $X_5$ are N; $X_2$, $X_3$, and $X_4$ are $CR_1'$; and $X_6$ is O.

In another aspect, the invention provides sirtuin-modulating compounds of Structural Formula (VII):

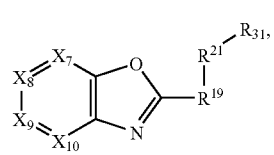

or a salt thereof, wherein:

each of $X_7$, $X_8$, $X_9$ and $X_{10}$ is independently selected from N, $CR^{20}$, or $CR_1'$, wherein:

each $R^{20}$ is independently selected from H or a solubilizing group;

each $R_1'$ is independently selected from H or optionally substituted $C_1$-$C_3$ straight or branched alkyl;

one of $X_7$, $X_8$, $X_9$ and $X_{10}$ is N and the others are selected from $CR^{20}$ or $CR_1'$; and zero to one $R^{20}$ is a solubilizing group;

$R^{19}$ is selected from:

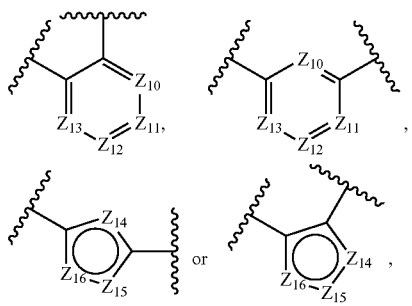

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and
$R^{21}$ is selected from $-NR_1'-C(O)-$, $-NR_1'-S(O)_2-$, $-NR_1'-C(O)-NR_1'-$, $-NR_1'-C(S)-NR_1'-$, $-NR_1'-C(S)-NR_1'-CR_1'R_1'-$, $-NR_1'-C(O)-CR_1'R_1'-NR_1'-$, $-NR_1'-C(=NR_1')-NR_1'-$, $-C(O)-NR_1'-$, $-C(O)-NR_1'-S(O)_2-$, $-NR_1'-CR_1'R_1'-$, $-NR_1'-C(O)-CR_1'=CR_1'-$, $-NR_1'-S(O)_2-NR_1'-$, $-NR_1'-C(O)-NR_1'-S(O)_2-$, $-NR_1'-CR_1'R_1'-C(O)-NR_1'-$, $-CR_1'R_1'-C(O)-NR_1'-$, $-NR_1'-C(O)-CR_1'=CR_1'-CR_1'R_1'-$, $-NR_1'-C(=N-CN)-NR_1'-$, $-NR_1'-C(O)-CR_1'R_1'-O-$, $-NR_1'-C(O)-CR_1'R_1'-CR_1'R_1'-O-$, $-NR_1'-S(O)_2-CR_1'R_1'-$, $-NR_1'-S(O)_2-CR_1'R_1'-CR_1'R_1'-$, or $-NR_1'-C(O)-CR_1'R_1'-$; and
$R^{31}$ is selected from an optionally substituted monocyclic or bicyclic aryl, or an optionally substituted monocyclic or bicyclic heteroaryl, with the provisos that said compound is not:

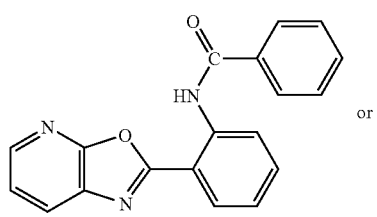

that when $R^{19}$ is

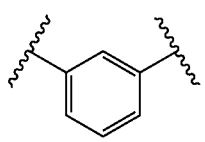

$R^{21}$ is $-NHC(O)-$, $R^{31}$ is not an optionally substituted phenyl.

In certain embodiments, compounds of Structural Formula (VII) have the following values:
each of $X_7$, $X_8$, $X_9$ and $X_{10}$ is independently selected from N, $CR^{20}$, or $CR_1'$, wherein:
each $R^{20}$ is independently selected from H or a solubilizing group;
each $R_1'$ is independently selected from H or optionally substituted $C_1$-$C_3$ straight or branched alkyl;
one of $X_7$, $X_8$, $X_9$ and $X_{10}$ is N and the others are selected from $CR^{20}$ or $CR_1'$; and
zero to one $R^{20}$ is a solubilizing group;
$R^{19}$ is selected from:

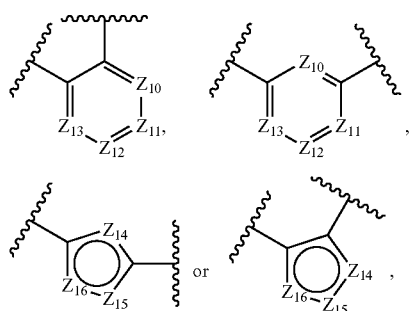

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and
$R^{21}$ is selected from $-NR_1'-C(O)-$, $-NR_1'-S(O)_2-$, $-NR_1'-C(O)-NR_1'-$, $-NR_1'-C(S)-NR_1'-$, $-NR_1'-C(S)-NR_1'-CR_1'R_1'-$, $-NR_1'-C(O)-CR_1'R_1'-NR_1'-$, $-NR_1'-C(=NR_1')-NR_1'-$, $-C(O)-NR_1'-$, $-C(O)-NR_1'-S(O)_2-$, $-NR_1'-CR_1'R_1'-$, $-NR_1'-C(O)-CR_1'=CR_1'-$, $-NR_1'-S(O)_2-NR_1'-$, $-NR_1'-C(O)-NR_1'-S(O)_2-$, $-NR_1'-CR_1'R_1'-C(O)-NR_1'-$, $-CR_1'R_1'-C(O)-NR_1'-$, $-NR_1'-C(O)-CR_1'=CR_1'-CR_1'R_1'-$, $-NR_1'-C(=N-CN)-NR_1'-$, $-NR_1'-C(O)-CR_1'R_1'-O-$, $-NR_1'-C(O)-CR_1'R_1'-CR_1'R_1'-O-$, $-NR_1'-S(O)_2-CR_1'R_1'-$, $-NR_1'-S(O)_2-CR_1'R_1'-CR_1'R_1'-$, or $-NR_1'-C(O)-CR_1'R_1'-$; and
$R^{31}$ is selected from an optionally substituted monocyclic or bicyclic aryl, or an optionally substituted monocyclic or bicyclic heteroaryl, with the provisos that:

said compound is not:

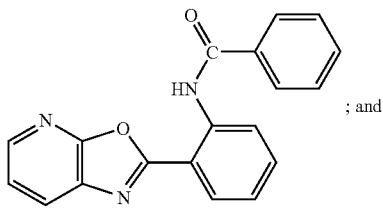
; and when $X_8$ and $X_9$ are each independently selected from $CR^{20}$ or $CR_1'$, $R^{19}$ is

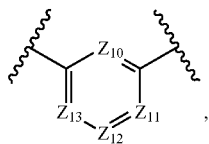
, and each of $Z_{10}$, $Z_{11}$, $Z_{12}$ and $Z_{13}$ is independently selected from $CR^{20}$, or $CR_1'$, then:

a) at least one of $X_8$ and $X_9$ is not CH; or b) at least one of $Z_{10}$, $Z_{11}$, $Z_{12}$ and $Z_{13}$ is $CR^{20}$, wherein $R^{20}$ is a solubilizing group.

In certain embodiments, when $Z_{12}$ is $CR^{20}$ and $R^{20}$ is a solubilizing group, the solubilizing group is not —C(O)OCH$_2$CH$_3$, —COOH,

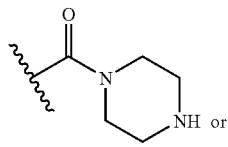 or

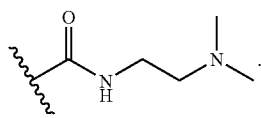

In certain embodiments, when $X_8$ and $X_9$ are each independently selected from $CR^{20}$ or $CR_1'$ $R^{19}$ is

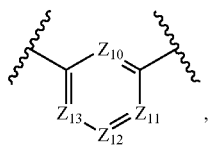
, and each of $Z_{10}$, $Z_{11}$, $Z_{12}$ and $Z_{13}$ is independently selected from $CR^{20}$, or $CR_1'$, then:

a) at least one of $X_8$ and $X_9$ is not CH; or b) at least one of $Z_{10}$, $Z_{11}$ and $Z_{13}$ is $CR^{20}$, wherein $R^{20}$ is a solubilizing group.

In certain embodiments, when $R^{19}$ is

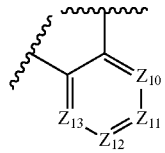

and each of $Z_{10}$, $Z_{11}$, $Z_{12}$ and $Z_{13}$ is $CR^{20}$, or $CR_1'$; $X_8$ and $X_9$ are $CR^{20}$ or $CR_1'$; $R^{21}$ is —NHC(O)—; and $R^{31}$ is optionally substituted phenyl, then $R^{31}$ is a substituted phenyl, at least one $R_1'$ in a $CR_1'$ moiety is optionally substituted $C_1$-$C_3$ straight or branched alkyl or at least one $R^{20}$ in a $CR^{20}$ is a solubilizing group, or a combination thereof.

In certain embodiments, $R^{19}$ is selected from phenyl, pyridyl, thienyl or furyl.

In certain embodiments, $R^{19}$ is

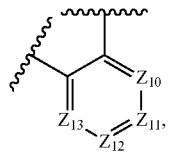
, wherein each of $Z_{10}$, $Z_{11}$, $Z_{12}$ and $Z_{13}$ is independently selected from $CR^{20}$ or $CR_1'$; and $R^{21}$ is —NH—C(O)—; and $R^{31}$ is a substituted phenyl.

In certain such embodiments, when $X_9$ is N, $R^{31}$ is not 2,4 dimethoxyphenyl and/or when $X_{10}$ is N, $R^{31}$ is not halo substituted phenyl; 3,4-dioxoethylenephenyl; or 3,5-dimethoxyphenyl.

In preferred embodiments, $R^{31}$ is optionally substituted with 1 to 3 substituents independently selected from —OCH$_3$, —CH$_3$, —N(CH$_3$)$_2$, pyrazinoxy or a solubilizing group. Suitable examples of $R^{31}$ include 3-methoxy-4-((4-methylpiperazin-1-yl)methyl)phenyl, 3-methoxy-4-morpholinomethylphenyl, 3-methoxy-4-diaminomethylphenyl, 3-methoxy-4-((pyrrolidin-1-yl)methyl)phenyl, 3,4-dimethoxyphenyl, 3,5-dimethoxyphenyl, 2,3,4-trimethoxyphenyl, 3,4,5-trimethoxyphenyl, 2-dimethylaminophenyl, 3-dimethylaminophenyl, 4-dimethylaminophenyl, or 3,5-dimethylphenyl.

In certain embodiments, $R^{19}$ is selected from

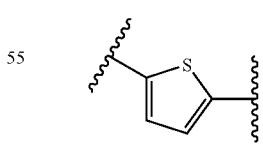 or 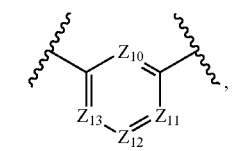, wherein one of $Z_{10}$, $Z_{11}$, $Z_{12}$, and $Z_{13}$ is N and the others are independently selected from $CR^{20}$ or $CR_1'$;

$R^{21}$ is selected from —NH—, —NH—C(O)—, —NH—C(O)—NH, —NH—C(S)—NH— or —NH—S(O)$_2$—; and $R^{31}$ is selected from an optionally substituted phenyl, an optionally substituted naphthyl, or an optionally substituted heteroaryl.

In certain such embodiments,
a) when R²¹ is —NH—S(O)₂—, either:
   i) Z₁₀ is N; or
   ii) Z₁₁ is N and R³¹ is halophenyl or 2-methoxy-5-methylphenyl;
b) when R¹⁹ is

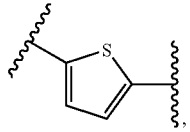

R³¹ is not 4-dimethylaminophenyl, 2,3,4-trimethoxyphenyl, or 3,5 dimethoxyphenyl; and/or
c) when R²¹ is —NH—C(O)—NH— and Z₁₀ is N, R³¹ is not 4-dimethylaminophenyl.

In certain such embodiments, R³¹ is selected from optionally substituted phenyl, benzothiazolyl, or benzoxazolyl.

In yet another embodiment, the invention provides sirtuin-modulating compounds of Structural Formula (VIII):

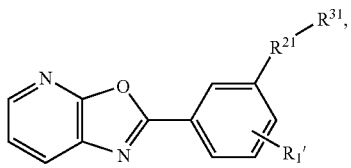

(VIII)

or a salt thereof, wherein:
R₁' is selected from H or optionally substituted C₁-C₃ straight or branched alkyl;
R²¹ is selected from —NR₁'—C(O)—, —NR₁'—S(O)₂—, —NR₁'—C(O)—NR₁'—, —NR₁'—C(S)—NR₁'—, —NR₁'—C(S)—NR₁'—CR₁'R₁'—, —NR₁'—C(O)—CR₁'R₁'—NR₁'—, —NR₁'—C(=NR₁')—NR₁'—, —C(O)—NR₁'—, —C(O)—NR₁'—S(O)₂—, —NR₁'—, —CR₁'R₁'—, —NR₁'—C(O)—CR₁'=CR₁'—, —NR₁'—S(O)₂—NR₁'—, —NR₁'—C(O)—NR₁'—S(O)₂—, —NR₁'—CR₁'R₁'—C(O)—NR₁'—, —CR₁'R₁'—C(O)—NR₁'—, —NR₁'—C(O)—CR₁'=CR₁'—CR₁'R₁'—, —NR₁'—C(=N—CN)—NR₁'—, —NR₁'—C(O)—CR₁'R₁'—O—, —NR₁'—C(O)—CR₁'R₁'—CR₁'R₁'—O—, —NR₁'—S(O)₂—CR₁'R₁'—, —NR₁'—S(O)₂—CR₁'R₁'—CR₁'R₁'—, or —NR₁'—C(O)—CR₁'R₁'—; and
R³¹ is selected from an optionally substituted monocyclic or bicyclic aryl, or an optionally substituted monocyclic or bicyclic heteroaryl, with the provisos that:
when R₁' is methyl, and R²¹ is —NH—C(O)—, R₃₁ is not

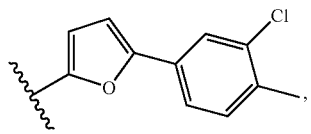

1-methoxynaphthyl, 2-methoxynaphthyl, or unsubstituted 2-thienyl;
when R₁' is methyl, and R²¹ is —NH—C(O)—CH=CH—, R³¹ is not

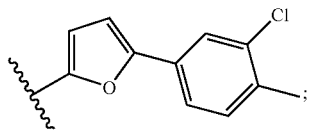

when R₁' is methyl, and R²¹ is —NH—C(O)—CH—O—, R³¹ is not unsubstituted naphthyl, 2-methoxy, 4-nitrophenyl, 4-chloro-2-methylphenyl, or 4-t-butylphenyl; and
when R²¹ is —NH—C(O)—, R³¹ is not optionally substituted phenyl.

In certain embodiments, R²¹ is —NH—C(O)—; and R³¹ is phenyl optionally substituted with 1 to 3 substituents independently selected from —OCH₃, —CH₃, —N(CH₃)₂, or a solubilizing group.

In certain such embodiments, R²¹ is —NH—C(O)— and R³¹ is selected from unsubstituted phenyl, 2-methoxyphenyl, 3-methoxyphenyl, 2,3,4-trimethoxyphenyl, 3,4,5-trimethoxyphenyl, 2,4-dimethoxyphenyl, 3,5-dimethoxyphenyl, 2-methyl-3-methoxyphenyl, 2-morpholinophenyl, 2-methoxy-4-methylphenyl, 2-dimethylaminophenyl, 4-dimethylaminophenyl, or

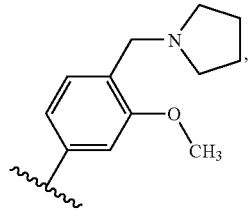

particularly phenyl; 2-methoxyphenyl; 3-methoxyphenyl; 2,3,4-trimethoxyphenyl; 3,4,5-trimethoxyphenyl; 2,4-dimethoxyphenyl; 3,5-dimethoxyphenyl; 2-methyl-3-methoxyphenyl; 2-morpholinophenyl; 2-methoxy-4-methylphenyl; 2-dimethylaminophenyl; or 4-dimethylaminophenyl.

In a further embodiment, the invention provides sirtuin-modulating compounds of Structural Formula (IX):

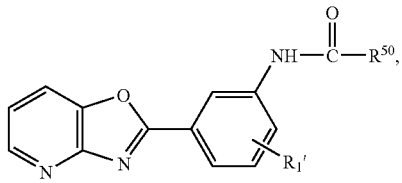

(IX)

or a salt thereof, wherein:
R₁' is selected from H or optionally substituted C₁-C₃ straight or branched alkyl; and
R⁵⁰ is selected from 2,3-dimethoxyphenyl, phenoxyphenyl, 2-methyl-3-methoxyphenyl, 2-methoxy-4-methylphenyl, or phenyl substituted with 1 to 3 substituents, wherein one of said substituents is a solubilizing group; with the provisos that R⁵⁰ is not substituted simultaneously with a solubilizing group and a nitro group, and R⁵⁰ is not singly substituted at the 4-position with cyclic solubilizing group or at the 2-position with a morpholino group.

In one aspect, the invention provides sirtuin-modulating compounds of Structural Formula (X):

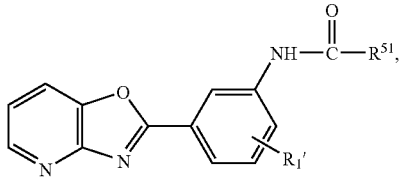
(X)

or a salt thereof, wherein:

$R_1'$ is selected from H or optionally substituted $C_1$-$C_3$ straight or branched alkyl; and $R^{51}$ is selected from an optionally substituted monocyclic heteroaryl, an optionally substituted bicyclic heteroaryl, or an optionally substituted naphthyl, wherein $R^{51}$ is not chloro-benzo(b)thienyl, unsubstituted benzodioxolyl, unsubstituted benzofuranyl, methyl-benzofuranyl, unsubstituted furanyl, phenyl-, bromo-, or nitro-furyl, chlorophenyl-isoxazolyl, oxobenzopyranyl, unsubstituted naphthyl, methoxy-, methyl-, or halo-naphthyl, unsubstituted thienyl, unsubstituted pyridinyl, or chloropyridinyl.

In certain embodiments, $R^{51}$ is selected from pyrazolyl, thiazolyl, oxazolyl, pyrimidinyl, furyl, thienyl, pyridyl, isoxazolyl, indolyl, benzopyrazolyl, benzothiazolyl, benzoxazolyl, quinoxalinyl, benzofuranyl, benzothienyl, quinolinyl, benzoisoxazolyl, benzotriazinyl, triazinyl, naphthyl, or

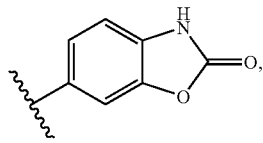

and wherein $R^{51}$ is optionally substituted. In certain such embodiments, $R^{51}$ is selected from pyrazolyl, thiazolyl, oxazolyl, pyrimidinyl, indolyl, pyrazinyl, triazinyl, or

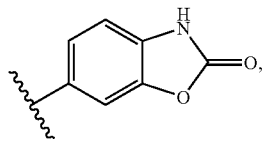

and $R^{51}$ is optionally substituted.

In another aspect, the invention provides sirtuin-modulating compounds of Structural Formula (XI):

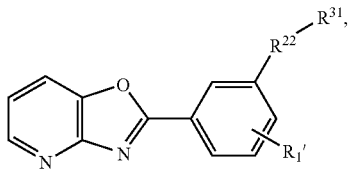
(XI)

or a salt thereof, wherein:

$R_1'$ is selected from H or optionally substituted $C_1$-$C_3$ straight or branched alkyl;

$R^{22}$ is selected from $-NR^{23}-C(O)-$, $-NR_1'-S(O)_2-$, $-NR_1'-C(O)-NR_1'-$, $-NR_1'-C(S)-NR_1'-$, $-NR_1'-C(S)-NR_1'-CR_1'R_1'-$, $-NR_1'-C(O)-CR_1'R_1'-NR_1'-$, $-NR_1'-C(=NR_1')-NR_1'-$, $-C(O)-NR_1'-$, $-C(O)-NR_1'-S(O)_2-$, $-NR_1'-CR_1'R_1'-$, $-NR_1'-C(O)-CR_1'=CR_1'-$, $-NR_1'-S(O)_2-NR_1'-$, $-NR_1'-C(O)-NR_1'-S(O)_2-$, $-NR_1'-CR_1'R_1'-C(O)-NR_1'-$, $-CR_1'R_1'-C(O)-NR_1'-$, $-NR_1'-C(O)-CR_1'=CR_1'-CR_1'R_1'-$, $-NR_1'-C(=N-CN)-NR_1'-$, $-NR_1'-C(O)-CR_1'R_1'-O-$, $-NR_1'-C(O)-CR_1'R_1'-CR_1'R_1'-O-$, $-NR_1'-S(O)_2-CR_1'R_1'-$, $-NR_1'-S(O)_2-CR_1'R_1'-CR_1'R_1'-$, or $-NR_1'-C(O)-CR_1'R_1'-$, wherein $R^{23}$ is an optionally substituted $C_1$-$C_3$ straight or branched alkyl; and $R^{31}$ is selected from an optionally substituted monocyclic or bicyclic aryl, or an optionally substituted monocyclic or bicyclic heteroaryl, with the provisos that:

when $R^{22}$ is $-NH-C(O)-CH=CH-$, $R^{31}$ is not unsubstituted furyl, 5-(2-methyl-3-chlorophenyl)-furanyl, 2,4-dichlorophenyl, 3,5-dichloro-2-methoxyphenyl, 3-nitrophenyl, 4-chlorophenyl, 4-chloro-3-nitrophenyl, 4-isopropylphenyl, 4-methoxyphenyl, 2-methoxy-5-bromophenyl, or unsubstituted phenyl;

when $R^{22}$ is $-NH-C(O)-CH_2-$, $R^{31}$ is not 3,4-dimethoxyphenyl, 4-chlorophenyl, or unsubstituted phenyl;

when $R^{22}$ is $-NH-C(O)-CH_2-O-$, $R^{31}$ is not 2,4-dimethyl-6-nitrophenyl, 2- or 4-nitrophenyl, 4-cyclohexylphenyl, 4-methoxyphenyl, unsubstituted naphthyl, or unsubstituted phenyl, or phenyl monosubstituted, disubstituted or trisubstituted solely with substituents selected from straight- or branched-chain alkyl or halo;

when $R^{22}$ is $-NH-C(O)-CH(CH_3)-O-$, $R^{31}$ is not 2,4-dichlorophenyl, 4-chlorophenyl, or unsubstituted phenyl; and when $R^{22}$ is $-NH-S(O)_2-$, $R^{31}$ is not unsubstituted phenyl.

In certain embodiments, $R^{22}$ is selected from $-C(O)-NH-$, $-NH-$, or $-C(O)-NH-CH_3$.

In certain embodiments, such as when $R^{22}$ is selected from $-C(O)-NH-$, $-NH-$, or $-C(O)-NH-CH_3$, $R^{31}$ is selected from optionally substituted phenyl, benzothiazolyl, quinoxalinyl, or benzoxazolyl.

In yet another aspect, the invention provides sirtuin-modulating compounds of Structural Formula (XII):

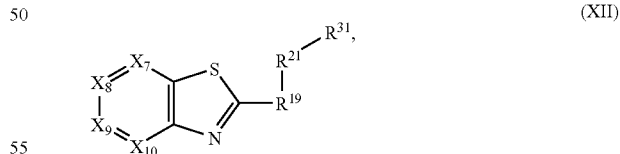
(XII)

or a salt thereof, wherein:

each of $X_7$, $X_8$, $X_9$ and $X_{10}$ is independently selected from N, $CR^{20}$, or $CR_1'$, wherein:

each $R^{20}$ is independently selected from H or a solubilizing group;

each $R_1'$ is independently selected from H or optionally substituted $C_1$-$C_3$ straight or branched alkyl;

one of $X_7$, $X_8$, $X_9$ and $X_{10}$ is N and the others are selected from $CR^{20}$ or $CR_1'$; and zero to one $R^{20}$ is a solubilizing group;

$R^{19}$ is selected from:

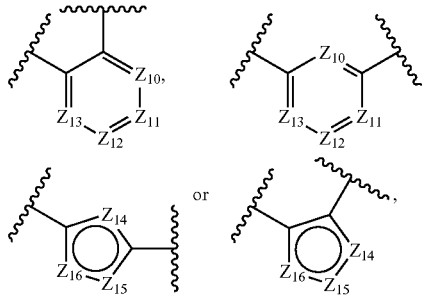

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, O or S;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and
$R^{31}$ is selected from an optionally substituted monocyclic or bicyclic aryl, or an optionally substituted monocyclic or bicyclic heteroaryl, with the proviso that when $R^{19}$ is

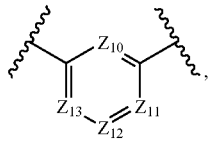

$Z_{10}$, $Z_{11}$, $Z_{12}$ and $Z_{13}$ are each CH, and $R^{21}$ is —NHC(O)—, $R^{31}$ is not an optionally substituted phenyl.

In certain embodiments, the compounds of Structural Formula (XI) have the following values:
each of $X_7$, $X_8$, $X_9$ and $X_{10}$ is independently selected from N, $CR^{20}$, or $CR_1'$, wherein:
each $R^{20}$ is independently selected from H or a solubilizing group;
each $R_1'$ is independently selected from H or optionally substituted $C_1$-$C_3$ straight or branched alkyl;
one of $X_7$, $X_8$, $X_9$ and $X_{10}$ is N and the others are selected from $CR^{20}$ or $CR_1'$; and
zero to one $R^{20}$ is a solubilizing group;

$R^{19}$ is selected from:

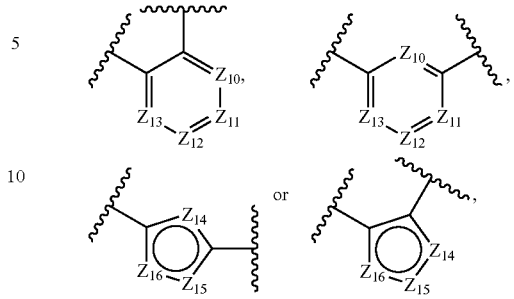

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'$ is an optionally substituted $C_1$-$C_3$ straight or branched alkyl; and
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and
$R^{31}$ is selected from an optionally substituted monocyclic or bicyclic aryl, or an optionally substituted monocyclic or bicyclic heteroaryl, with the proviso that:
when $X_7$ is N, $R^{19}$ is

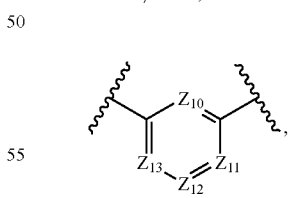

and each of $Z_{10}$, $Z_{11}$, $Z_{12}$ and $Z_{13}$ is independently selected from $CR^{20}$, or $CR_1'$, then:
a) at least one of $X_8$, $X_9$ or $X_{10}$ is C—($C_1$-$C_3$ straight or branched alkyl) or C-(solubilizing group); or
b) at least one of $Z_{10}$, $Z_{11}$, $Z_{12}$ and $Z_{13}$ is $CR^{20}$, wherein $R^{20}$ is a solubilizing group.

In certain embodiments, $R^{21}$ is —NH—C(O)— and $R^{19}$ is selected from:

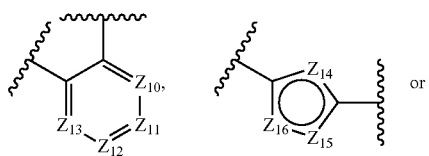

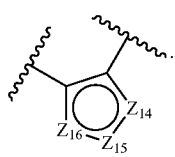

In certain embodiments, $R^{19}$ is selected from optionally substituted phenyl, optionally substituted pyridyl, optionally substituted thienyl or optionally substituted furyl.

In certain embodiments, $R^{19}$ is

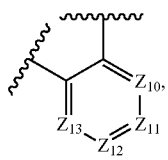

wherein each of $Z_{10}$, $Z_{11}$, $Z_{12}$ and $Z_{13}$ is independently selected from $CR^{20}$ or $CR_1'$; and $R^{21}$ is selected from —NH—C(O)—, —NH—C(O)—CH(CH$_3$)—O—, —NH—C(O)—CH$_2$—O—, or —NH—S(O)$_2$—CH$_2$—CH$_2$—; and $R^{31}$ is selected from an optionally substituted aryl, or an optionally substituted heteroaryl.

In certain such embodiments, $R^{31}$ is optionally substituted with 1 to 3 substituents independently selected from —OCH$_3$, —CH$_3$, —N(CH$_3$)$_2$, phenyl, phenoxy, 3,4-dioxymethylene, fluoro, or another solubilizing group. Suitable examples of $R^{31}$ include unsubstituted quinolinyl, 2,4-dimethoxyphenyl, 3,4-dimethoxyphenyl, 3,5-dimethoxyphenyl, 3,4,5-trimethoxyphenyl, 2,3,4-trimethoxyphenyl, 2-dimethylaminophenyl, 3-dimethylaminophenyl, 4-dimethylaminophenyl, 3,5-dimethylphenyl, 3,5-difluorophenyl, 3-trifluoromethoxyphenyl, unsubstituted quinoxalinyl, unsubstituted benzopyrimidinyl,

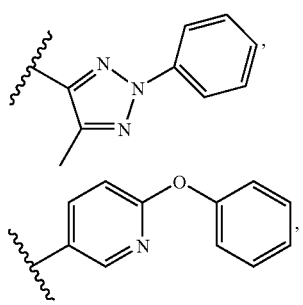

-continued

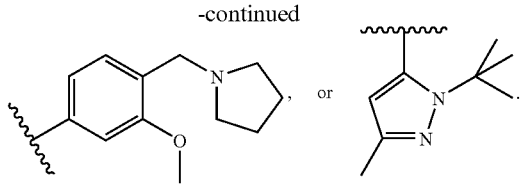

In certain such embodiments, $R^{31}$ is not phenyl-substituted furyl.

In certain embodiments, $R^{19}$ is selected from

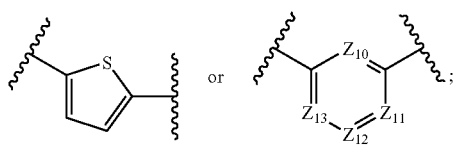

each of $Z_{10}$, $Z_{11}$, $Z_{12}$ and $Z_{13}$ is independently selected from $CR^{20}$, or $CR_1'$;

$R^{21}$ is selected from —NH—C(O)—, NH—C(O)—CH$_2$—CH(CH$_3$)—O, —NH—C(O)—NH—, —NH—C(S)—NH—, —NH—C(S)—NH—CH$_2$—, or —NH—S(O)$_2$—; and $R^{31}$ is selected from an optionally substituted phenyl, an optionally substituted naphthyl, or an optionally substituted heteroaryl.

In certain such embodiments, $R^{31}$ is selected from phenyl, naphthyl, pyrazolyl, furyl, thienyl, pyridyl, isoxazolyl, benzopyrazolyl, benzofuryl, benzothienyl, quinolinyl, benzoisoxazolyl, or

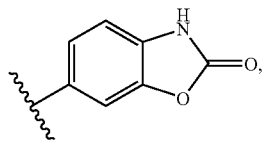

and $R^{31}$ is optionally substituted (e.g., optionally substituted with up to three substituents independently selected from —OCH$_3$, —CH$_3$, —N(CH$_3$)$_2$, —O-phenyl, or another solubilizing group). Suitable examples of $R^{31}$ include unsubstituted phenyl, 3-methoxyphenyl, 4-methoxyphenyl, 2,3 dimethoxyphenyl, 2,4-dimethoxyphenyl, 2,5-bis(trifluoromethyl)phenyl, 3,4-dimethoxyphenyl, 3,5-dimethoxyphenyl, 3,4,5-trimethoxyphenyl, 2,3,4-trimethoxyphenyl, 2-methoxy-4-methylphenyl, 2-phenoxyphenyl, 3-dimethylaminophenyl, 4-dimethylaminophenyl, unsubstituted 2-furanyl, unsubstituted 2-thienyl, 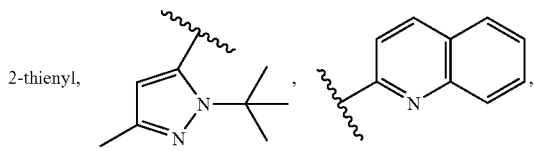

-continued

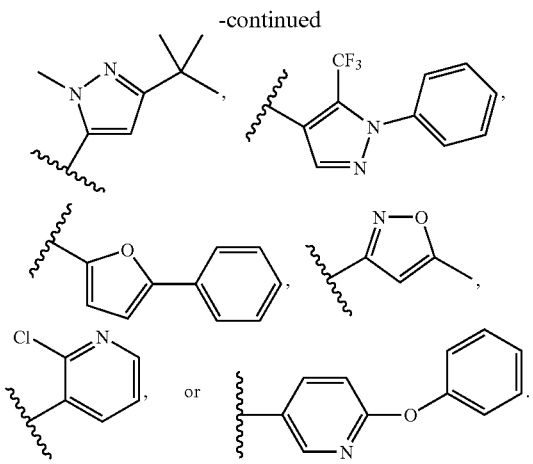

In certain embodiments, one or more of the following conditions applies:

when $X_8$ is N, $R^{21}$ is —NH—C(S)—NH—, and $R^{19}$ is phenyl, $R^{31}$ is not 2-methoxy-5-nitrophenyl, 2-S-methylphenyl or 2-acetylphenyl;

when $X_8$ is N, $R^{21}$ is —NH—S(O)$_2$—, and $R^{19}$ is phenyl, $R^{31}$ is not thiadiazole-substituted thienyl or 4-methylsulfonylphenyl;

when $X_8$ is N, $R^{21}$ is —NH—CO—, and $R^{19}$ is phenyl, $R^{31}$ is not 2,4-difluorophenyl, pyridyl-substituted thienyl, 3,4-dichlorophenyl, 4-t-butylphenyl, or 3-benzyloxyphenyl;

when $X_9$ is N, $R^{21}$ is —NH—C(O)— and $R^{19}$ is

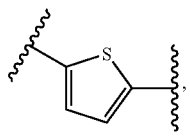

$R^{31}$ is not 2,3,4-trimethoxyphenyl or 3,5-dimethoxyphenyl; and when $X_9$ is N, $R^{21}$ is —NH—C(O)— and $R^{19}$ is phenyl, $R^{31}$ is not 3,5-dimethoxyphenyl.

In a further embodiment, the invention provides compounds of Structural Formula (XIII):

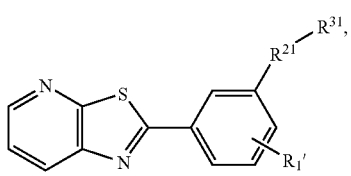

(XIII)

or a salt thereof, wherein:

$R_1'$ is selected from H or optionally substituted $C_1$-$C_3$ straight or branched alkyl;

$R^{21}$ is selected from —NR$_1'$—C(O)—, —NR$_1'$—S(O)$_2$—, —NR$_1'$—C(O)—NR$_1'$—, —NR$_1'$—C(S)—NR$_1'$—, —NR$_1'$—C(S)—NR$_1'$—CR$_1'$R$_1'$—, —NR$_1'$—C(O)—CR$_1'$R$_1'$—NR$_1'$—, —NR$_1'$—C(=NR$_1'$)—NR$_1'$—, —C(O)—NR$_1'$—, —C(O)—NR$_1'$—S(O)$_2$—, —NR$_1'$—CR$_1'$R$_1'$—, —NR$_1'$—C(O)—CR$_1'$=CR$_1'$—, —NR$_1'$—S(O)$_2$—NR$_1'$—, —NR$_1'$—C(O)—NR$_1'$—S(O)$_2$—, —NR$_1'$—CR$_1'$R$_1'$—C(O)—NR$_1'$—, —CR$_1'$R$_1'$—C(O)—NR$_1'$—, —NR$_1'$—C(O)—CR$_1'$=CR$_1'$—CR$_1'$R$_1'$—, —NR$_1'$—C(=N—CN)—NR$_1'$—, —NR$_1'$—C(O)—CR$_1'$R$_1'$—O—, —NR$_1'$—C(O)—CR$_1'$R$_1'$—CR$_1'$R$_1'$—O—, —NR$_1'$—S(O)$_2$—CR$_1'$R$_1'$—, —NR$_1'$—S(O)$_2$—CR$_1'$R$_1'$—CR$_1'$R$_1'$—, or —NR$_1'$—C(O)—CR$_1'$R$_1'$—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—, $R^{31}$ is not unsubstituted furyl, 5-bromofuryl, unsubstituted phenyl, phenyl monosubstituted with halo or methyl, 3- or 4-methoxyphenyl, 4-butoxyphenyl, 4-t-butylphenyl, 3-trifluoromethylphenyl, 2-benzoylphenyl, 2- or 4-ethoxyphenyl, 2,3-, 2,4-, 3,4-, or 3,5-dimethoxyphenyl, 3,4,5-trimethoxyphenyl, 2,4- or 2-6 difluorophenyl, 3,4-dioxymethylene phenyl, 3,4- or 3,5-dimethlphenyl, 2-chloro-5-bromophenyl, 2-methoxy-5-chlorophenyl, unsubstituted quinolinyl, thiazolyl substituted simultaneously with methyl and phenyl, or ethoxy-substituted pyridinyl;

when $R^{21}$ is —NH—C(O)—CH(CH$_2$—CH$_3$)—, $R^{31}$ is not unsubstituted phenyl;

when $R^{21}$ is —NH—C(O)—CH$_2$—, $R^{31}$ is not unsubstituted phenyl, 3-methylphenyl, 4-chlorophenyl, 4-ethoxyphenyl, 4-fluorophenyl or 4-methoxyphenyl;

when $R^{21}$ is —NH—C(O)—CH$_2$—O—, $R^{31}$ is not unsubstituted phenyl or 4-chlorophenyl; and when $R^{21}$ is —NH—S(O)$_2$—, $R^{31}$ is not 3,4-dioxymethylene phenyl, 2,4,5-trimethylphenyl, 2,4,6-trimethylphenyl, 2,4- or 3,4-dimethylphenyl, 2,5-difluorophenyl, 2,5- or 3,4-dimethoxyphenyl, fluorophenyl, 4-chlorophenyl, 4-bromophenyl, 4-ethylphenyl, 4-methylphenyl, 3-methyl-4-methoxyphenyl, unsubstituted phenyl, unsubstituted pyridinyl, unsubstituted thienyl, chloro-substituted thienyl, or methyl-substituted benzothiazolyl.

In certain embodiments, $R_1'$ is selected from H or optionally substituted $C_1$-$C_3$ straight or branched alkyl;

$R^{21}$ is selected from —NR$_1'$—C(O)—, —NR$_1'$—S(O)$_2$—, —NR$_1'$—C(O)—NR$_1'$—, —NR$_1'$—C(S)—NR$_1'$—, —NR$_1'$—C(S)—NR$_1'$—CR$_1'$R$_1'$—, —NR$_1'$—C(O)—CR$_1'$R$_1'$—NR$_1'$—, —NR$_1'$—C(=NR$_1'$)—NR$_1'$—, —C(O)—NR$_1'$—, —C(O)—NR$_1'$—S(O)$_2$—, —NR$_1'$—, —CR$_1'$R$_1'$—, —NR$_1'$—C(O)—CR$_1'$=CR$_1'$—, —NR$_1'$—S(O)$_2$—NR$_1'$—, —NR$_1'$—C(O)—NR$_1'$—S(O)$_2$—, —NR$_1'$—CR$_1'$R$_1'$—C(O)—NR$_1'$—, —CR$_1'$R$_1'$—C(O)—NR$_1'$—, —NR$_1'$—C(O)—CR$_1'$=CR$_1'$—CR$_1'$R$_1'$—, —NR$_1'$—C(=N—CN)—NR$_1'$—, —NR$_1'$—C(O)—CR$_1'$R$_1'$—O—, —NR$_1'$—C(O)—CR$_1'$R$_1'$—CR$_1'$R$_1'$—O—, —NR$_1'$—S(O)$_2$—CR$_1'$R$_1'$—, —NR$_1'$—S(O)$_2$—CR$_1'$R$_1'$—CR$_1'$R$_1'$—, or —NR$_1'$—C(O)—CR$_1'$R$_1'$—; and $R^{31}$ is selected from a monocyclic or bicyclic aryl or a monocyclic or bicyclic heteroaryl, and comprises a solubilizing group substituent.

In certain embodiments, $R^{31}$ is selected from phenyl, naphthyl, pyrazolyl, furyl, thienyl, pyridyl, isoxazolyl, benzopyrazolyl, benzofuryl, benzothienyl, quinolinyl, benzoisoxazolyl, or

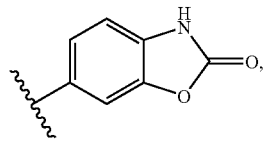

and $R^{31}$ is optionally substituted.

In certain embodiments, $R^{21}$ is selected from —NH—C(O)—, NH—C(O)—CH$_2$—CH(CH$_3$)—O, —NH—C(O)—NH—, —NH—C(S)—NH—, —NH—C(S)—NH—CH$_2$—, or —NH—S(O)$_2$—; and $R^{31}$ is selected from an optionally substituted phenyl, an optionally substituted naphthyl, or an optionally substituted heteroaryl.

In certain such embodiments, particularly when $R^{21}$ is —NH—C(O)—, $R^{31}$ is selected from $R^{31}$ is selected from unsubstituted phenyl, 3-methoxyphenyl, 4-methoxyphenyl, 2,3 dimethoxyphenyl, 2,4-dimethoxyphenyl, 2,5-bis(trifluoromethyl)phenyl, 3,4-dimethoxyphenyl, 3,5-dimethoxyphenyl, 3,4,5-trimethoxyphenyl, 2,3,4-trimethoxyphenyl, 2-methoxy-4-methylphenyl, 2-phenoxyphenyl, 3-dimethylaminophenyl, 4-dimethylaminophenyl, unsubstituted 2-furanyl, unsubstituted 2-thienyl,

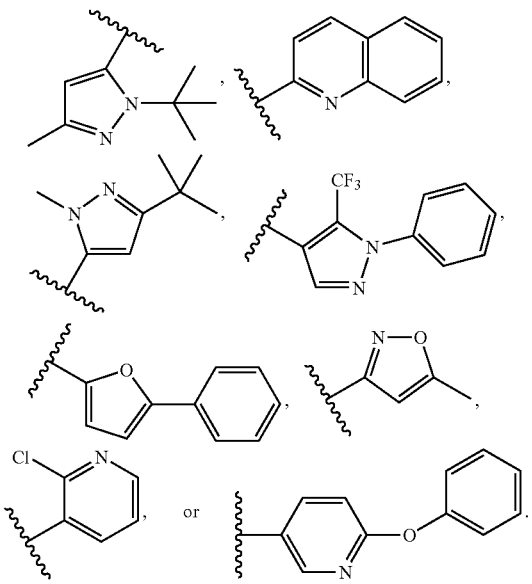

In one aspect, the invention provides sirtuin-modulating compounds of Structural Formula (XIV):

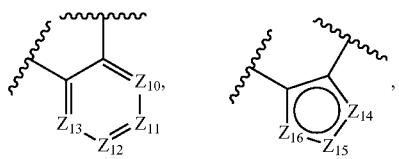

(XIV)

or a salt thereof, wherein:
each of $R^{23}$ and $R^{24}$ is independently selected from H, —CH$_3$ or a solubilizing group;
$R^{25}$ is selected from H or a solubilizing group; and
$R^{19}$ is selected from:

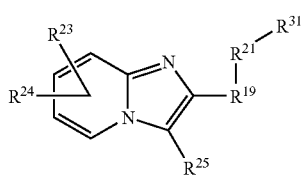

each $Z_{10}$, $Z_{11}$, $Z_{12}$ and $Z_{13}$ is independently selected from N, CR$^{20}$, or CR$_1$'; and each $Z_{14}$, $Z_{15}$ and $Z_{16}$ is independently selected from N, NR$_1$', S, O, CR$^{20}$, or CR$_1$', wherein:

zero to two of $Z_{10}$, $Z_{11}$, $Z_{12}$ or $Z_{13}$ are N;

at least one of $Z_{14}$, $Z_{15}$ and $Z_{16}$ is N, NR$_1$', O or S;

zero to one of $Z_{14}$, $Z_{15}$ and $Z_{16}$ is S or O;

zero to two of $Z_{14}$, $Z_{15}$ and $Z_{16}$ are N or NR$_1$';

zero to one $R^{20}$ is a solubilizing group; and zero to one R$_1$' is an optionally substituted C$_1$-C$_3$ straight or branched alkyl;

each $R^{20}$ is independently selected from H or a solubilizing group;

$R^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R$_1$'—, —NR$_1$'—C(O)—CR$_1$'R$_1$'—NR$_1$'—, —NR$_1$'—C(=NR$_1$')—NR$_1$'—, —C(O)—NR$_1$'—, —C(O)—NR$_1$'—S(O)$_2$—, —NR$_1$'—CR$_1$'R$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$'—C(O)—NR$_1$'—, —CR$_1$'R$_1$'—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R$_1$'—O—, —NR$_1$'—C(O)—CR$_1$'R$_1$'—CR$_1$'R$_1$'—O—, —NR$_1$'—S(O)$_2$—CR$_1$'R$_1$'—, —NR$_1$'—S(O)$_2$—CR$_1$'R$_1$'—CR$_1$'R$_1$'—, —NR$_1$'—C(O)—CR$_1$'R$_1$'—CR$_1$'R$_1$'—, —NR$_1$'—C(S)—NR$_1$'—CR$_1$'R$_1$'—CR$_1$'R$_1$'—, —NR$_1$'—C(O)—O— or —NR$_1$'—C(O)—CR$_1$'R$_1$'—; and each R$_1$' is independently selected from H or optionally substituted C$_1$-C$_3$ straight or branched alkyl; and $R^{31}$ is selected from an optionally substituted monocyclic or bicyclic aryl, or an optionally substituted monocyclic or bicyclic heteroaryl,
wherein when $R^{19}$ is

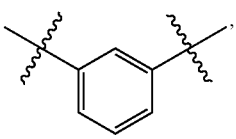

$R^{21}$ is —NH—C(O)— and $R^{25}$ is —H, $R^{31}$ is not an optionally substituted phenyl group, and wherein said compound is not 2-chloro-N-[3-[3-(cyclohexylamino)imidazo[1,2-a]pyridin-2-yl]phenyl]-4-nitrobenzamide.

In certain embodiments, each of $R^{23}$ and $R^{24}$ is independently selected from H, —CH$_3$ or a solubilizing group;

$R^{25}$ is selected from H, or a solubilizing group; and
$R^{19}$ is selected from:

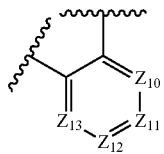 or 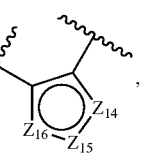, wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, O or S;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group; and zero to one $R_1'$ is an optionally substituted $C_1$-$C_3$ straight or branched alkyl;

each $R^{20}$ is independently selected from H or a solubilizing group;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O— or —$NR_1'$—C(O)—$CR_1'R_1'$— (particularly —NH—C(O)—); and each $R_1'$ is independently selected from H or optionally substituted $C_1$-$C_3$ straight or branched alkyl; and $R^{31}$ is selected from an optionally substituted monocyclic or bicyclic aryl, or an optionally substituted monocyclic or bicyclic heteroaryl.

In certain such embodiments, $R^{31}$ is not 2,4-dimethoxyphenyl.

Typically, $R^{25}$ is selected from H, —CH$_2$—N(CH$_3$)$_2$, or

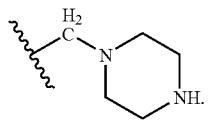

Typically, $R^{23}$ and $R^{24}$ are H.

Typically, $R^{19}$ is selected from phenyl, pyridyl, thienyl or furyl, particularly optionally substituted phenyl. Preferably, a phenyl is optionally substituted with:

a) up to three —O—CH$_3$ groups; or b) one —N(CH$_3$)$_2$ group.

In certain embodiments, each of $R^{23}$ and $R^{24}$ is independently selected from H, —CH$_3$ or a solubilizing group;

$R^{25}$ is selected from H, or a solubilizing group; and
$R^{19}$ is selected from:

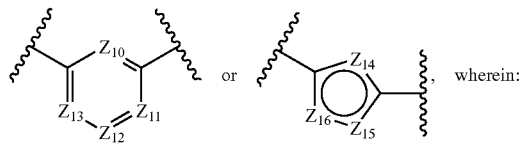, wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, O or S;

zero to one of $Z_{14}$, $Z_{15}$ and $Z_{16}$ is S or O;

zero to two of $Z_{14}$, $Z_{15}$ and $Z_{16}$ is N or $NR_1'$;

zero to one $R^{20}$ is a solubilizing group; and zero to one $R_1'$ is an optionally substituted $C_1$-$C_3$ straight or branched alkyl;

each $R^{20}$ is independently selected from H or a solubilizing group;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O— or —$NR_1'$—C(O)—$CR_1'R_1'$— (particularly —NH—C(O)—); and each $R_1'$ is independently selected from H or optionally substituted $C_1$-$C_3$ straight or branched alkyl; and $R^{31}$ is selected from an optionally substituted monocyclic or bicyclic aryl, or an optionally substituted monocyclic or bicyclic heteroaryl, wherein when $R^{19}$ is phenyl, at least one of $R^{23}$, $R^{24}$, or $R^{25}$ is a solubilizing group and wherein said compound is not 2-chloro-N-[3-[3-(cyclohexylamino)imidazo[1,2-a]pyridin-2-yl]phenyl]-4-nitrobenzamide.

Typically, $R^{25}$ is selected from H, —CH$_2$—N(CH$_3$)$_2$, or

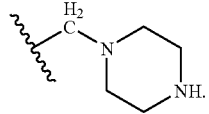

Typically, $R^{23}$ and $R^{24}$ are H.

Typically, $R^{19}$ is selected from phenyl, pyridyl, thienyl or furyl, particularly optionally substituted phenyl. Preferably, a phenyl is optionally substituted with:

b) up to three —O—CH$_3$ groups; or b) one —N(CH$_3$)$_2$ group.

In another aspect, the invention provides sirtuin-modulating compounds of Structural Formula (XV):

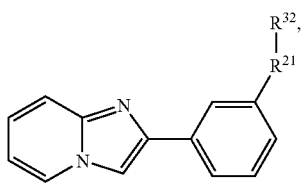

(XV)

or a salt thereof, wherein:

$R^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R'$_1$—, —NR$_1$'—C(O)—CR$_1$'R'$_1$—NR$_1$'—, —NR$_1$'—C(=NR$_1$')—NR$_1$'—, —C(O)—NR$_1$'—, —C(O)—NR$_1$'—S(O)$_2$—, —NR$_1$'—, —CR$_1$'R'$_1$—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R'$_1$—C(O)—NR$_1$'—, —CR$_1$'R'$_1$—C(O)—NR$_1$'—, —NR$_1$'—C(O)—CR$_1$'=CR$_1$'—CR$_1$'R'$_1$—, —NR$_1$'—C(=N—CN)—NR$_1$'—, —NR$_1$'—C(O)—CR$_1$'R'$_1$—O—, —NR$_1$'—C(O)—CR$_1$'R'$_1$—CR$_1$'R'$_1$—O—, —NR$_1$'—S(O)$_2$—CR$_1$'R'$_1$—, —NR$_1$'—S(O)$_2$—CR$_1$'R'$_1$—CR$_1$'R'$_1$—, —NR$_1$'—C(O)—CR$_1$'R'$_1$—CR$_1$'R'$_1$—, —NR$_1$'—C(S)—NR$_1$'—CR$_1$'R'$_1$—CR$_1$'R'$_1$—, —NR$_1$'—C(O)—O— or —NR$_1$'—C(O)—CR$_1$'R'$_1$— (particularly —NH—C(O)—); and each $R_1$' is independently selected from H or optionally substituted $C_1$-$C_3$ straight or branched alkyl; and $R^{32}$ is selected from an optionally substituted bicyclic aryl, or an optionally substituted monocyclic or bicyclic heteroaryl, wherein:

when $R^{21}$ is —NH—C(O)—, $R^{32}$ is not unsubstituted 2-furyl, 2-(3-bromofuryl), unsubstituted 2-thienyl, unsubstituted 3-pyridyl, unsubstituted 4-pyridyl,

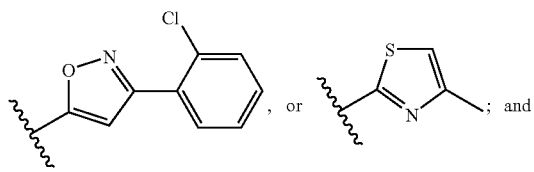

when $R^{21}$ is —NR$_1$'—S(O)$_2$—, $R^{32}$ is not unsubstituted 2-thienyl or unsubstituted naphthyl.

In yet another aspect, the invention provides sirtuin-modulating compounds of Structural Formula (XVI):

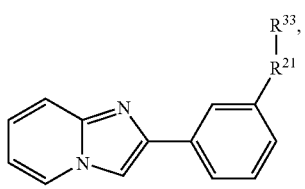

(XVI)

or a salt thereof, wherein:

$R^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R'$_1$—, —NR$_1$'—C(O)—CR$_1$'R'$_1$—NR$_1$'—, —NR$_1$'—C(=NR$_1$')—NR$_1$'—, —C(O)—NR$_1$'—, —C(O)—NR$_1$'—S(O)$_2$—, —NR$_1$'—, —CR$_1$'R'$_1$—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R'$_1$—C(O)—NR$_1$'—, —CR$_1$'R'$_1$—C(O)—NR$_1$'—, —NR$_1$'—C(O)—CR$_1$'R'$_1$—O—, —NR$_1$'—C(O)—CR$_1$'R'$_1$—CR$_1$'R'$_1$—O—, —NR$_1$'—S(O)$_2$—CR$_1$'R'$_1$—, —NR$_1$'—S(O)$_2$—CR$_1$'R'$_1$—CR$_1$'R'$_1$—, —NR$_1$'—C(O)—CR$_1$'=CR$_1$'—CR$_1$'R'$_1$—, —NR$_1$'—C(=N—CN)—NR$_1$'—, or —NR$_1$'—C(O)—CR$_1$'R'$_1$—; and each $R_1$' is independently selected from H or optionally substituted $C_1$-$C_3$ straight or branched alkyl;

$R^{22}$ is an optionally substituted $C_1$-$C_3$ straight or branched alkyl; and $R^{33}$ is phenyl comprising a solubilizing group substituent, wherein: when $R^{21}$ is —NH—S(O)$_2$ said phenyl comprises an additional substituent.

In certain embodiments, $R^{21}$ is selected from —NR$^{22}$—C(O)—, —NR$_1$'—C(S)—NR$_1$'—, —NR$_1$'—C(S)—NR$_1$'—

$R^{33}$ is an optionally substituted phenyl, wherein:

when $R^{21}$ is —NH—C(O)—, $R^{33}$ is a substituted phenyl other than phenyl singly substituted with halo, methyl, nitro or methoxy; 2-carboxyphenyl; 4-n-pentylphenyl; 4-ethoxyphenyl; 2-carboxy-3-nitrophenyl; 2-chloro-4-nitrophenyl; 2-methoxy-5-ethylphenyl; 2,4-dimethoxyphenyl; 3,4,5-trimethoxyphenyl; 2,4 dichlorophenyl; 2,6-difluorophenyl; 3,5-dinitrophenyl; or 3,4-dimethylphenyl;

when $R^{21}$ is —NR$_1$'—C(O)—CR$_1$'R'$_1$— or —NH—C(O)—CH(CH$_3$)—O, $R^{33}$ is a substituted phenyl;

when $R^{21}$ is —NH—C(O)—CH$_2$, $R^{33}$ is not unsubstituted phenyl, 4-methoxyphenyl; 3,4-dimethoxyphenyl or 4-chlorophenyl;

when $R^{21}$ is —NH—C(O)—CH$_2$—O, $R^{33}$ is not 2,4-bis(1,1-dimethylpropyl)phenyl;

when $R^{21}$ is —NH—C(O)—NH—, $R^{33}$ is not 4-methoxyphenyl; and when $R^{21}$ is —NH—S(O)$_2$—, $R^{33}$ is a substituted phenyl other than 3-methylphenyl, 3-trifluoromethylphenyl, 2,4,5- or 2,4,6-trimethylphenyl, 2,4- or 3,4-dimethylphenyl, 2,5- or 3,4-dimethoxyphenyl, 2,5-dimethoxy-4-chlorophenyl, 3,6-dimethoxy, 4-methylphenyl, 2,5- or 3,4-dichlorophenyl, 2,5-diethoxyphenyl, 2-methyl-5-nitrophenyl, 2-ethoxy-5-bromophenyl, 2-methoxy-5-bromophenyl, 2-methoxy-3,4-dichlorophenyl, 2-methoxy-4-methyl-5-bromophenyl, 3,5-dinitro-4-methylphenyl, 3-methyl-4-methoxyphenyl, 3-nitro-4-methylphenyl, 3-methoxy-4-halophenyl, 3-methoxy-5-chlorophenyl, 4-n-butoxyphenyl, 4-halophenyl, 4-ethylphenyl, 4-methylphenyl, 4-nitrophenyl, 4-ethoxyphenyl, 4-acetylaminophenyl, 4-methoxyphenyl, 4-t-butylphenyl, or para-biphenyl.

In certain embodiments, $R^{21}$ is selected from —NR$^{22}$—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R'$_1$—, —NR$_1$'—C(O)—CR$_1$'R'$_1$—NR$_1$'—, —NR$_1$'—C(=NR$_1$')—NR$_1$'—, —C(O)—NR$_1$'—, —C(O)—NR$_1$'—S(O)$_2$—, —NR$_1$'—, —CR$_1$'R'$_1$—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R'$_1$—C(O)—NR$_1$'—, —CR$_1$'R'$_1$—C(O)—NR$_1$'—, —NR$_1$'—C(O)—CR$_1$'R'$_1$—O—, —NR$_1$'—C(O)—CR$_1$'R'$_1$—CR$_1$'R'$_1$—O—, —NR$_1$'—S(O)$_2$—CR$_1$'R'$_1$—, —NR$_1$'—S(O)$_2$—CR$_1$'R'$_1$—CR$_1$'R'$_1$—, —NR$_1$'—C(O)—CR$_1$'=CR$_1$'—CR$_1$'R'$_1$—, —NR$_1$'—C(=N—CN)—NR$_1$'—, or —NR$_1$'—C(O)—CR$_1$'R'$_1$—; and each $R_1$' is independently selected from H or optionally substituted $C_1$-$C_3$ straight or branched alkyl;

$R^{22}$ is an optionally substituted $C_1$-$C_3$ straight or branched alkyl; and $R^{33}$ is phenyl comprising a solubilizing group substituent, wherein: when $R^{21}$ is —NH—S(O)$_2$ said phenyl comprises an additional substituent.

In certain embodiments, $R^{21}$ is selected from —NR$^{22}$—C(O)—, —NR$_1$'—C(S)—NR$_1$'—, —NR$_1$'—C(S)—NR$_1$'—

$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'$=$CR_1'$—$CR_1'R_1'$—, or —$NR_1'$—C(=N—CN)—$NR_1'$—, each $R_1'$ is independently selected from H or optionally substituted $C_1$-$C_3$ straight or branched alkyl; and $R^{22}$ is an optionally substituted $C_1$-$C_3$ straight or branched alkyl.

In certain embodiments, $R^{33}$ is optionally substituted on up to three carbon atoms with a substituent independently selected from —O—$CH_3$, —$CH_3$, —N($CH_3$)$_2$, —S($CH_3$), or CN; or substituted on adjacent carbon atoms with bridging said adjacent carbon atoms.

In a further embodiment, the invention provides sirtuin-modulating compounds of Structural Formula (XVII):

(XVII)

or a salt thereof, wherein:
each of $R^{23}$ and $R^{24}$ is independently selected from H or —$CH_3$, wherein at least one of $R^{23}$ and $R^{24}$ is H; and
$R^{29}$ is phenyl substituted with:
a) two —O—$CH_3$ groups;
b) three —O—$CH_3$ groups located at the 2,3 and 4 positions; or
c) one —N($CH_3$)$_2$ group; and
d) when $R^{23}$ is $CH_3$, one —O—$CH_3$ group at the 2 or 3 position, wherein $R^{29}$ is optionally additionally substituted with a solubilizing group.

In certain embodiments, $R^{29}$ is phenyl substituted with:
a) three —O—$CH_3$ groups located at the 2,3 and 4 positions; or
b) one —N($CH_3$)$_2$ group.

In one aspect, the invention provides sirtuin-modulating compounds of Structural Formula (XVIII):

(XVIII)

or a salt thereof, wherein
$R^{19}$ is selected from:

wherein:
each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$,
wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group; and
zero to one $R_1'$ is an optionally substituted $C_1$-$C_3$ straight or branched alkyl;
each $R^{20}$ is independently selected from H or a solubilizing group;
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—, wherein each $R_1'$ is independently selected from H or optionally substituted $C_1$-$C_3$ straight or branched alkyl; and
$R^{31}$ is selected from an optionally substituted monocyclic or bicyclic aryl, or an optionally substituted monocyclic or bicyclic heteroaryl, with the proviso that when $R^{19}$ is

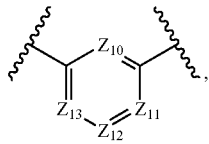

$Z_{10}$, $Z_{11}$, $Z_{12}$ and $Z_{13}$ are each CH, $R^{20}$ is H, and $R^{21}$ is —NHC(O)—, $R^{31}$ is not an optionally substituted phenyl.

In certain embodiments, $R^{19}$ is selected from:

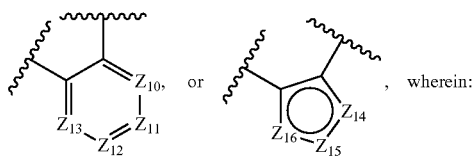, wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, O or S;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group; and zero to one $R_1'$ is an optionally substituted $C_1$-$C_3$ straight or branched alkyl;

each $R^{20}$ is independently selected from H or a solubilizing group;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

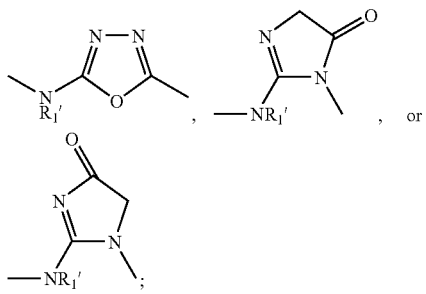

each $R_1'$ is independently selected from H or optionally substituted $C_1$-$C_3$ straight or branched alkyl; and $R^{31}$ is selected from an optionally substituted monocyclic or bicyclic aryl, or an optionally substituted monocyclic or bicyclic heteroaryl.

In certain such embodiments, compounds of Structural Formula (XVIII) have the formula:

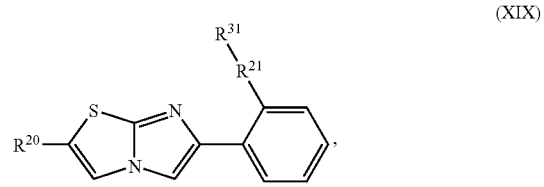

(XIX)

or a salt thereof, wherein $R^{20}$ is selected from H or a solubilizing group;

$R^{21}$ is selected from —NH—C(O)—, or —NH—C(O)—CH$_2$—; and $R^{31}$ is selected from an optionally substituted monocyclic or bicyclic aryl, or an optionally substituted monocyclic or bicyclic heteroaryl.

Typically, $R^{19}$ in compounds of Structural Formula (XVIII) is selected from phenyl, pyridyl, thienyl or furyl, particularly optionally substituted phenyl.

Typically, $R^{20}$ is selected from H, —CH$_2$—N(CH$_3$)$_2$,

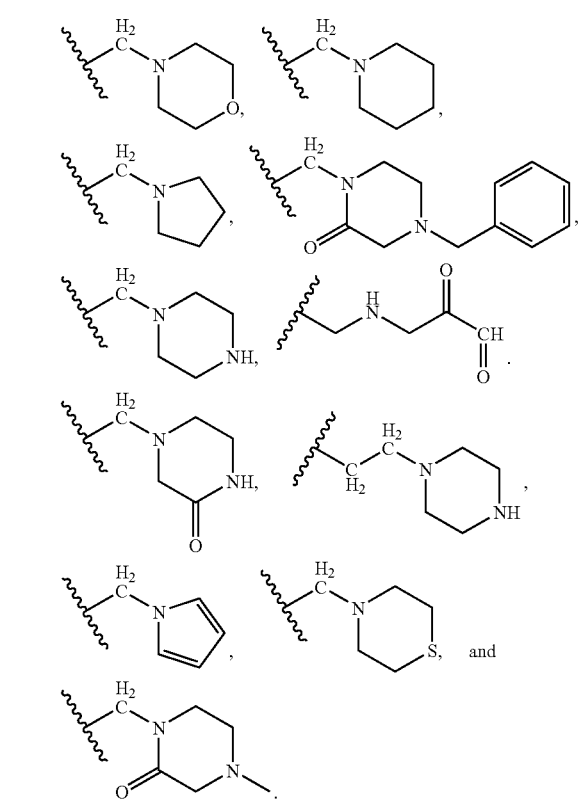

Typically, $R^{31}$ is selected from phenyl, pyrazolyl, furyl, pyridyl, pyrimidinyl, thienyl, naphthyl, benzopyrazolyl, benzofuryl, quinolinyl, quinoxalinyl, or benzothienyl and wherein $R^{31}$ is optionally substituted.

Typically, $R^{21}$ is selected from —NH—C(O)— or —NH—C(O)—CH$_2$—.

In certain such embodiments, when $R^{21}$ is —$NR_1$'—C(O)—, $R^{31}$ is not 4-cyanophenyl or

[structure: benzofurazan-5-yl];

and/or when $R^{21}$ is —$NR_1$'—$S(O)_2$—, $R^{31}$ is not 4-methoxyphenyl or 4-t-butylphenyl.

In certain such embodiments, when $R^{19}$ is

[structure: 5-membered ring with $Z_{14}$, $Z_{15}$, $Z_{16}$]  or

[structure: 5-membered ring with $Z_{14}$, $Z_{15}$, $Z_{16}$]

and $R^{21}$ is —$NR_1$'—C(O)—, $R^{31}$ is not 4-cyanophenyl or

[structure: benzofurazan-5-yl];

and/or when $R^{19}$ is

[structure: 5-membered ring with $Z_{14}$, $Z_{15}$, $Z_{16}$]  or  [structure: 5-membered ring with $Z_{14}$, $Z_{15}$, $Z_{16}$]

and $R^{21}$ is —$NR_1$'—$S(O)_2$—, $R^{31}$ is not 4-methoxyphenyl or 4-t-butylphenyl.

In another aspect, the invention provides sirtuin-modulating compounds of Structural Formula (XX):

(XX)

[structure of formula XX with $R^{20a}$, $R^{31}$, $R^{21}$, $R^{19}$]

or a salt thereof, wherein
$R^{19}$ is selected from:

[structure with $Z_{10}$, $Z_{11}$, $Z_{12}$, $Z_{13}$]  or  [structure with $Z_{14}$, $Z_{15}$, $Z_{16}$], wherein:

each $Z_{10}$, $Z_{11}$, $Z_{12}$ and $Z_{13}$ is independently selected from N, $CR^{20}$, or $CR_1$'; and each $Z_{14}$, $Z_{15}$ and $Z_{16}$ is independently selected from N, $NR_1$', S, O, $CR^{20}$, or $CR_1$', wherein:
zero to two of $Z_{10}$, $Z_{11}$, $Z_{12}$ or $Z_{13}$ are N;
at least one of $Z_{14}$, $Z_{15}$ and $Z_{16}$ is N, $NR_1$', O or S;
zero to one of $Z_{14}$, $Z_{15}$ and $Z_{16}$ is S or O;
zero to two of $Z_{14}$, $Z_{15}$ and $Z_{16}$ are N or $NR_1$';
zero to one $R^{20}$ is a solubilizing group; and
zero to one $R_1$' is an optionally substituted $C_1$-$C_3$ straight or branched alkyl;

each $R^{20}$ is independently selected from H or a solubilizing group;

$R^{20a}$ is independently selected from H or a solubilizing group;

$R^{21}$ is selected from —$NR_1$'—C(O)—, —$NR_1$'—$S(O)_2$—, —$NR_1$'—C(O)—$NR_1$'—, —$NR_1$'—C(S)—$NR_1$'—, —$NR_1$'—C(S)—$NR_1$'—$CR_1$'$R_1$'—, —$NR_1$'—C(O)—$CR_1$'$R_1$'—$NR_1$'—, —$NR_1$'—C(=$NR_1$')—$NR_1$'—, —C(O)—$NR_1$'—, —C(O)—$NR_1$'—$S(O)_2$—, —$NR_1$'—$CR_1$'$R_1$'—, —$NR_1$'—C(O)—$CR_1$'=$CR_1$'—, —$NR_1$'—$S(O)_2$—$NR_1$'—, —$NR_1$'—C(O)—$NR_1$'—$S(O)_2$—, —$NR_1$'—$CR_1$'$R_1$'—C(O)—$NR_1$'—, —$CR_1$'$R_1$'—C(O)—$NR_1$'—, —$NR_1$'—C(O)—$CR_1$'=$CR_1$'—$CR_1$'$R_1$'—, —$NR_1$'—C(=N—CN)—$NR_1$'—, —$NR_1$'—C(O)—$CR_1$'$R_1$'—O—, —$NR_1$'—C(O)—$CR_1$'$R_1$'—$CR_1$'$R_1$'—O—, —$NR_1$'—$S(O)_2$—$CR_1$'$R_1$'—, —$NR_1$'—$S(O)_2$—$CR_1$'$R_1$'—$CR_1$'$R_1$'—, —$NR_1$'—C(O)—$CR_1$'$R_1$'—; —$NR_1$'—C(O)—$CR_1$'$R'_1$—$CR_1$'$R'_1$—, —$NR_1$'—C(S)—$NR_1$'—$CR_1$'$R'_1$—$CR_1$'$R'_1$—, —$NR_1$'—C(O)—O—,

[structures: oxadiazole with —$NR_1$', imidazolinone with —$NR_1$', or imidazolinone with —$NR_1$']; wherein each $R_1$' is independently selected from H or optionally substituted $C_1$-$C_3$ straight or branched alkyl; and $R^{31}$ is selected from an optionally substituted monocyclic or bicyclic aryl, or an optionally substituted monocyclic or bicyclic heteroaryl, wherein when $R^{19}$ is

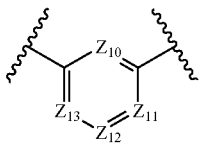

and $Z_{10}$, $Z_{11}$, $Z_{12}$ and $Z_{13}$ are each CH, $R^{20a}$ is a solubilizing group.

Typically, $R^{19}$ in compounds of Structural Formula (XX) is selected from phenyl, pyridyl, thienyl or furyl, particularly optionally substituted phenyl.

Typically, $R^{20a}$ is selected from H, —$CH_2$—$N(CH_3)_2$,

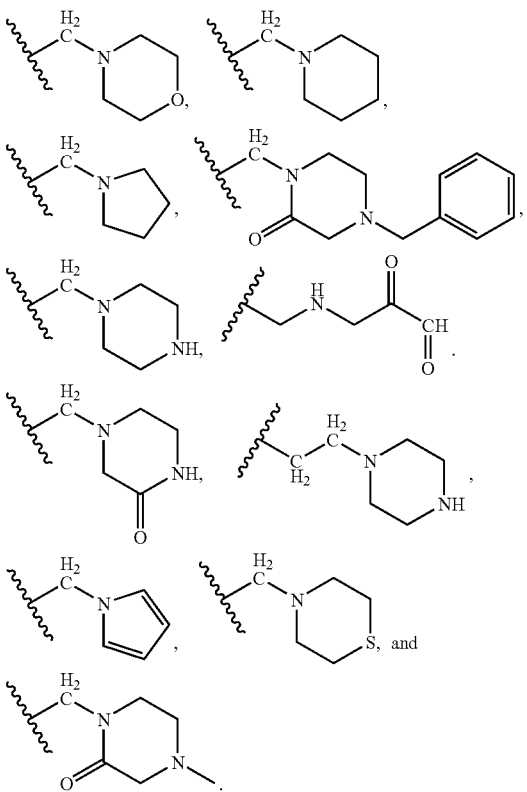

Typically, $R^{31}$ is selected from phenyl, pyrazolyl, furyl, pyridyl, pyrimidinyl, thienyl, naphthyl, benzopyrazolyl, benzofuryl, quinolinyl, quinoxalinyl, or benzothienyl and wherein $R^{31}$ is optionally substituted.

Typically, $R^{21}$ is selected from —NH—C(O)— or —NH—C(O)—$CH_2$—.

In yet another aspect, the invention provides sirtuin-modulating compounds of Structural Formula (XXI):

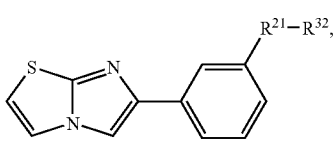

or a salt thereof, wherein $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

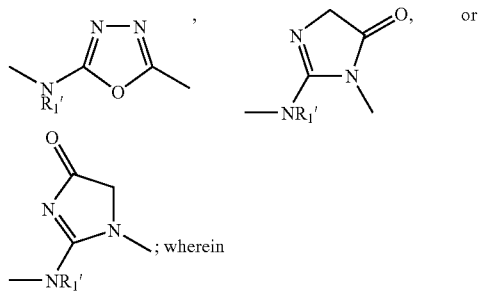

each $R_1'$ is independently selected from H or optionally substituted $C_1$-$C_3$ straight or branched alkyl; and $R^{32}$ is an optionally substituted monocyclic or bicyclic heteroaryl, or an optionally substituted bicyclic aryl, wherein:

when $R^{21}$ is —NH—C(O)—$CH_2$—, $R^{32}$ is not unsubstituted thien-2-yl;

when $R^{21}$ is —NH—C(O)—, $R^{32}$ is not furan-2-yl, 5-bromofuran-2-yl, or 2-phenyl-4-methylthiazol-5-yl;

when $R^{21}$ is —NH—S(O)$_2$—, $R^{32}$ is not unsubstituted naphthyl or 5-chlorothien-2-yl.

In certain embodiments, $R^{32}$ is selected from pyrrolyl, pyrazolyl, pyrazinyl, furyl, pyridyl, pyrimidinyl, or thienyl, and $R^{32}$ is optionally substituted and is optionally benzo-fused.

In certain embodiments, $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, —$NR_1'$—C(O)—$CR_1'R_1'$—; —$NR_1'$—C(O)—$CR_1'R_1'$—$CR_1'R_1'$—, —$NR_1'$—C(S)—$NR_1'$—$CR_1'R_1'$—$CR_1'R_1'$—, —$NR_1'$—C(O)—O—,

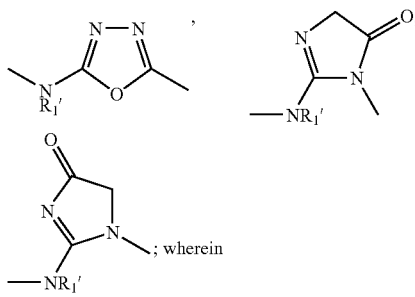

each $R_1'$ is independently selected from H or optionally substituted $C_1$-$C_3$ straight or branched alkyl; and $R^{32}$ is selected from benzofuryl, methylfuryl, benzothienyl, pyridyl, pyrazinyl, pyrimidinyl, pyrazolyl, wherein said methyfuryl, pyridyl, pyrazinyl, pyrimidinyl or pyrazolyl is optionally benzofused and wherein $R^{32}$ is optionally substituted or further substituted.

In a further aspect, the invention provides sirtuin-modulating compounds of Structural Formula (XXII):

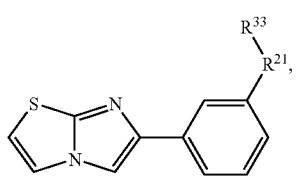

(XXII)

or a salt thereof, wherein:

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—, —$NR_1'$—C(O)—$CR_1'R_1'$—$CR_1'R_1'$—O—, —$NR_1'$—C(O)—$CR_1'R_1'$—O—, —$NR_1'$—S(O)$_2$—$CR_1'R_1'$—, —$NR_1'$—S(O)$_2$—$CR_1'R_1'$—$CR_1'R_1'$—,

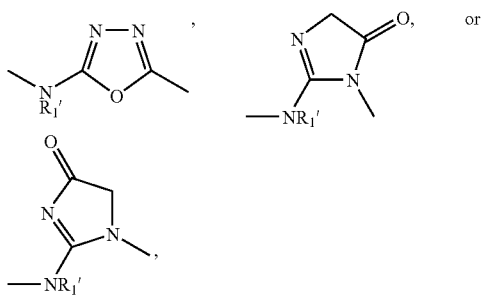

wherein each $R_1'$ is independently selected from H or optionally substituted $C_1$-$C_3$ straight or branched alkyl; and $R^{33}$ is an optionally substituted phenyl, wherein:
when $R^{21}$ is —$NR_1'$—C(O)—, $R_1'$ is not H;
when $R^{21}$ is —NH—C(O)—$CH_2$ or —NH—C(O)—$CH_2$—O—, $R^{33}$ is not unsubstituted phenyl or 4-halophenyl; and
when $R^{21}$ is —NH—S(O)$_2$—, $R^{33}$ is not unsubstituted phenyl, 2,4- or 3,4-dimethylphenyl, 2,4-dimethyl-5-methoxyphenyl, 2-methoxy-3,4-dichlorophenyl, 2-methoxy, 5-bromophenyl-3,4-dioxyethylenephenyl, 3,4-dimethoxyphenyl, 3,4-dichlorophenyl, 3,4-dimethylphenyl, 3- or 4-methylphenyl, 4-alkoxyphenyl, 4-phenoxyphenyl, 4-halophenyl, 4-biphenyl, or 4-acetylaminophenyl.

Preferably, $R^{21}$ is selected from —NH—C(O)— or —NH—C(O)—$CH_2$—.

In one aspect, the invention provides sirtuin-modulating compounds of Structural Formula (XXII):

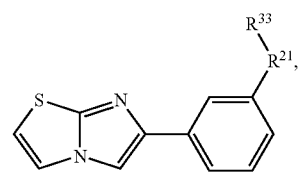

(XXII)

or a salt thereof wherein:
$R^{21}$ is selected from —NH—C(O)—, or —NH—C(O)—$CH_2$—; and
$R^{33}$ is phenyl substituted with
e) one —N(CH$_3$)$_2$ group;
f) one CN group at the 3 position;
g) one —S(CH$_3$) group; or

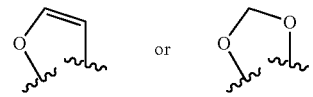

bridging the 3 and 4 positions.

In another aspect, the invention provides sirtuin-modulating compounds of Structural Formula (XXIII):

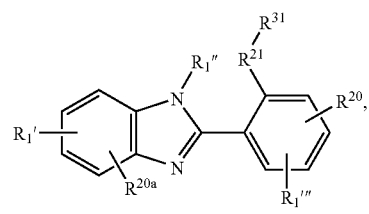

(XXIII)

or a salt thereof, wherein:
each $R^{20}$ and $R^{20a}$ is independently selected from H or a solubilizing group;
each $R_1'$, $R_1''$ and $R_1'''$ is independently selected from H or optionally substituted $C_1$-$C_3$ straight or branched alkyl;
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—

$NR_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—, $R^{31}$ is not is not 3,5-dinitrophenyl, 4-butoxyphenyl,

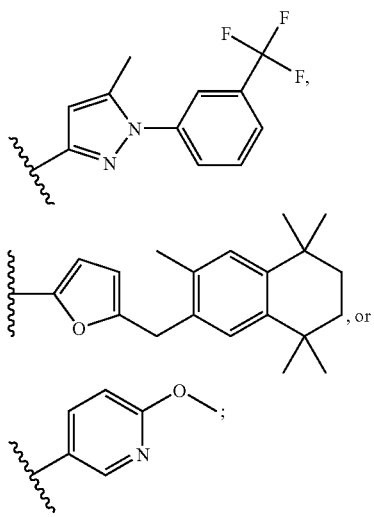

when $R^{21}$ is —NH—C(O)— and each of $R^{20}$, $R^{20a}$, $R_1'$, $R_1''$ and $R_1'''$ is hydrogen, $R^{31}$ is not

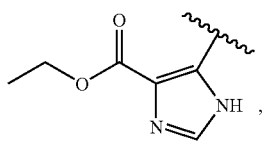

unsubstituted phenyl, 2- or 4-nitrophenyl, 2,4-dinitrophenyl, 2- or 4-chlorophenyl, 2-bromophenyl, 4-fluorophenyl, 2,4-dichlorophenyl, 2-carboxyphenyl, 2-azidophenyl, 2- or 4-aminophenyl, 2-acetamidophenyl, 4-methylphenyl, or 4-methoxyphenyl;

when $R^{21}$ is —NH—C(O)—, $R_1''$ is methyl; and each of $R^{20}$, $R^{20a}$, $R_1'$ and $R_1'''$ is hydrogen, $R^{31}$ is not 2-methylaminophenyl,

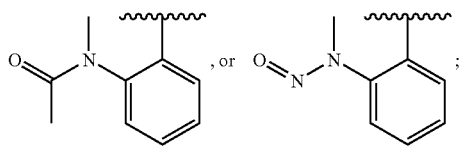

when $R^{21}$ is —NH—C(O)—CH$_2$— or NH—C(S)—NH—, and each of $R^{20}$, $R^{20a}$, $R_1'$, $R_1''$ and $R_1'''$ is hydrogen, $R^{31}$ is not unsubstituted phenyl;

when $R^{21}$ is —NH—S(O)$_2$—, $R_1''$ is hydrogen or methyl, and each of $R^{20}$, $R^{20a}$, $R_1'$ and $R_1'''$ is hydrogen, $R^{31}$ is not 4-methylphenyl; and when $R^{21}$ is —NH—S(O)$_2$—, $R^{20a}$ is hydrogen or —CH$_2$—N(CH$_2$CH$_3$)$_2$, and each of $R^{20}$, $R_1'$, $R_1''$ and $R_1'''$ is hydrogen, $R^{31}$ is not

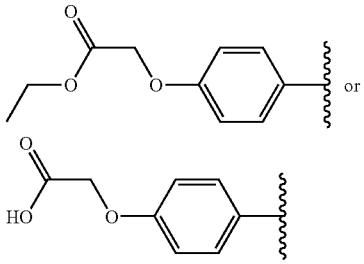

In certain embodiments, $R^{21}$ is selected from —NH—C(O)—, or —NH—C(O)—$NR_1'$—.

In certain embodiments, $R^{31}$ is selected from optionally substituted phenyl, quinoxalinyl or quinolinyl. For example, $R^{31}$ is optionally substituted with up to 3 substituents independently selected from —OCH$_3$, —N(CH$_3$)$_2$, or a solubilizing group. Suitable examples of $R^{31}$ include 4-dimethylaminophenyl, 3,4-dimethoxyphenyl, 3,5-dimethoxyphenyl, 3,4,5-tnimethoxyphenyl, 3-methoxy-4-((piperazin-1-yl)methyl)phenyl, 3-methoxy-4-((morpholino)methyl)phenyl, 3-methoxy-4-((pyrrolidin-1-yl)methyl)phenyl, unsubstituted phenyl, unsubstituted quinoxalinyl, and unsubstituted quinolinyl.

In a particular aspect, the invention provides sirtuin-modulating compounds of Structural Formula (XXIII):

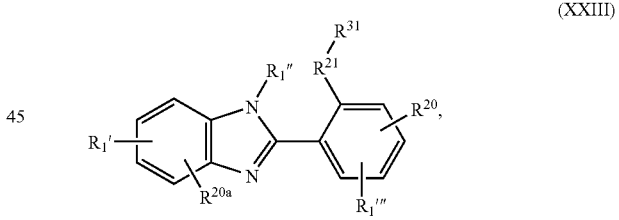

(XXIII)

or a salt thereof, wherein:

each $R^{20}$ and $R^{20a}$ is independently selected from H or a solubilizing group;

each $R_1'$, $R_1''$ and $R_1'''$ is independently selected from H or optionally substituted $C_1$-$C_3$ straight or branched alkyl;

$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R\alpha_1$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S $(O)_2$—$CR_1'R_1'$—, —$NR_1'$—$S(O)_2$—$CR_1'R_1'$—$CR_1'R_1'$—, or —$NR_1'$—$C(O)$—$CR_1'R_1'$—; and $R^{31}$ is selected from an optionally substituted monocyclic or bicyclic aryl, or an optionally substituted monocyclic or bicyclic heteroaryl, wherein:
i) at least one $R^{20}$ is a solubilizing group or at least one $R_1'''$ is an optionally substituted $C_1$-$C_3$ straight or branched alkyl or both; or
ii) $R^{20a}$ is a solubilizing group other than $CH_2$—$N(CH_2CH_3)_2$.

In certain embodiments, $R^{21}$ is selected from —NH—C(O)—, or —NH—C(O)—$NR_1'$—.

In certain embodiments, $R^{31}$ is selected from optionally substituted phenyl, quinoxalinyl or quinolinyl. For example, $R^{31}$ is optionally substituted with up to 3 substituents independently selected from —$OCH_3$, —$N(CH_3)_2$, or a solubilizing group. Suitable examples of $R^{31}$ include 4-dimethylaminophenyl, 3,4-dimethoxyphenyl, 3,5-dimethoxyphenyl, 3,4,5-trimethoxyphenyl, 3-methoxy-4-((piperazin-1-yl)methyl)phenyl, 3-methoxy-4-((morpholino)methyl)phenyl, 3-methoxy-4-((pyrrolidin-1-yl)methyl)phenyl, unsubstituted phenyl, unsubstituted quinoxalinyl, and unsubstituted quinolinyl.

In yet another aspect, the invention provides sirtuin-modulating compounds of Structural Formula (XXIV):

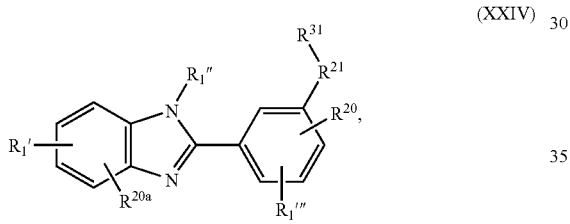

(XXIV)

or a salt thereof, wherein:
each $R^{20}$ and $R^{20a}$ is independently selected from H or a solubilizing group;
each $R_1'$, $R_1''$ and $R_1'''$ is independently selected from H or optionally substituted $C_1$-$C_3$ straight or branched alkyl;
$R^{21}$ is selected from —$NR^{23}$—C(O)—, —$NR_1'$—$S(O)_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —$NR_1'$—C(O)—$CR_1'$=$CR_1'$—, —$NR_1'$—$S(O)_2$—$NR_1'$—, —$NR_1'$—C(O)—$NR_1'$—$S(O)_2$—, —$NR_1'$—$CR_1'R_1'$—C(O)—$NR_1'$—, —$NR_1'$—C(O)—$CR_1'$=$CR_1'$—$CR_1'R_1'$—, —$NR_1'$—C(=N—CN)$NR_1'$—, —$NR_1'$—C(O)—$CR_1'R_1'$—O—, —$NR_1'$—C(O)—$CR_1'R_1'$—$CR_1'R_1'$—O—, —$NR_1'$—$S(O)_2$—$CR_1'R_1'$—, —$NR_1'$—$S(O)_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—$CH_2$—, $R^{31}$ is not 2-methylphenyl, or 3,4-dimethoxyphenyl;
when $R^{21}$ is —NH—C(O)—CH=CH—, $R^{31}$ is not 2-chlorophenyl;
when $R^{21}$ is —NH—C(O)—NH—, $R^{31}$ is not unsubstituted benzimidazolyl;

when $R^{21}$ is —NH—$S(O)_2$—, and each of $R^{20}$, $R^{20a}$, $R_1'$, $R_1''$ and $R_1'''$ is hydrogen, $R^{31}$ is not unsubstituted phenyl, 4-chlorophenyl, 4-methylphenyl, or 4-acetoamidophenyl;
when $R^{21}$ is —NH—$S(O)_2$—, each of $R_1'$ and $R_1'''$ is methyl or hydrogen, and each of $R^{20}$, $R^{20a}$, and $R_1''$ is hydrogen, $R^{31}$ is not 4-nitrophenyl;
when $R^{21}$ is —NH—C(O)—$CH_2$—O—, $R_1'''$ is methyl or hydrogen, and each of $R^{20}$, $R^{20a}$, $R_1'$, and $R_1''$ is hydrogen, $R^{31}$ is not 2,3-, 2,5-, 2,6-, 3,4- or 3,5-dimethylphenyl, 2,4-dichloromethyl, 2,4-dimethyl-6-bromophenyl, 2- or 4-chlorophenyl, 2-(1-methylpropyl)phenyl, 5-methyl-2-(1-methylethyl)phenyl, 2- or 4-methylphenyl, 2,4-dichloro-6-methylphenyl, nitrophenyl, 2,4-dimethyl-6-nitrophenyl, 2- or 4-methoxyphenyl, 4-acetyl-2-methoxyphenyl, 4-chloro-3,5-dimethylphenyl, 3-ethylphenyl, 4,-bromophenyl, 4-cyclohexyphenyl, 4-(1-methylpropyl)phenyl, 4-(1-methylethyl)phenyl, 4-(1,1-dimethylethyl)phenyl, or unsubstituted phenyl;
when $R^{21}$ is —NH—C(O)—$CH_2$—, $R_1'''$ is methyl or hydrogen, and each of $R^{20}$, $R^{20a}$, $R_1'$, and $R_1''$ is hydrogen, $R^{31}$ is not unsubstituted naphthyl, 4-chlorophenyl, 4-nitrophenyl, 4-methoxyphenyl, unsubstituted phenyl, unsubstituted thienyl

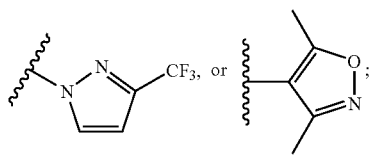

when $R^{21}$ is —NH—C(O)—$CH_2$—, $R_1'$ is methyl, and each of $R^{20}$, $R^{20a}$, $R_1''$, and $R_1'''$ is hydrogen, $R^{31}$ is not unsubstituted phenyl;
when $R^{21}$ is —NH—C(O)—CH=CH, $R_1'''$ is methyl or hydrogen, and each of $R^{20}$, $R^{20a}$, $R_1'$, and $R_1''$ is hydrogen, $R^{31}$ is not unsubstituted furyl, nitrophenyl-substituted furyl, 2,4-dichlorophenyl, 3,5-dichloro-2-methoxyphenyl, 3- or 4-nitrophenyl, 4-methoxyphenyl, unsubstituted phenyl, or nitro-substituted thienyl;
when $R^{21}$ is —NH—C(O)—CH($CH_2CH_3$)—, and each of $R^{20}$, $R^{20a}$, $R_1'$, $R_1''$, and $R_1'''$ is hydrogen, $R^{31}$ is not unsubstituted phenyl;
when R is —NH—C(O)—CH($CH_3$)—O—, $R_1'''$ is methyl or hydrogen, and each of $R^{20}$, $R^{20a}$, $R_1'$, and $R_1''$ is hydrogen, $R^{31}$ is not 2,4-dichlorophenyl.

In a particular aspect, the invention provides sirtuin-modulating compounds of Structural Formula (XXIV):

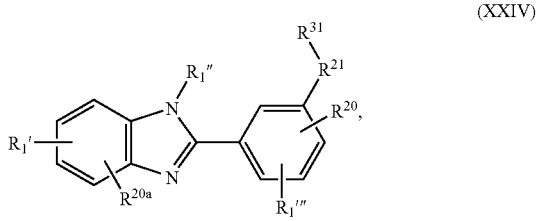

(XXIV)

or a salt thereof, wherein:
  each $R^{20}$ and $R^{20a}$ is independently selected from H or a solubilizing group and at least one of $R^{20}$ and $R^{20a}$ is a solubilizing group;
  each $R_1'$, $R_1''$ and $R_1'''$ is independently selected from H or optionally substituted $C_1$-$C_3$ straight or branched alkyl;
  $R^{21}$ is selected from —$NR^{23}$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—, wherein $R^{23}$ is an optionally substituted $C_1$-$C_3$ straight or branched alkyl; and
  $R^{31}$ is selected from an optionally substituted monocyclic or bicyclic aryl, or an optionally substituted monocyclic or bicyclic heteroaryl.

In certain embodiments, when $R^{21}$ is —NH—C(O)—$CH_2$—, $R^{31}$ is not 2-methylphenyl; or 3,4-dimethoxyphenyl; when $R^{21}$ is —NH—C(O)—CH=CH—, $R^{31}$ is not 2-chlorophenyl; and/or when $R^{21}$ is —NH—C(O)—NH—, $R^{31}$ is not unsubstituted benzimidazolyl.

In a further aspect, the invention provides sirtuin-modulating compounds of Structural Formula (XXV):

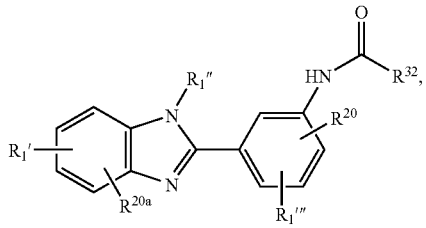

(XXV)

or a salt thereof, wherein:
  each $R^{20}$ and $R^{20a}$ is independently selected from H or a solubilizing group, wherein at least one of $R^{20}$ and $R^{20a}$ is a solubilizing group;
  each $R_1'$, $R_1''$ and $R_1'''$ is independently selected from H or optionally substituted $C_1$-$C_3$ straight or branched alkyl; and
  $R^{32}$ is an optionally substituted phenyl.

In certain embodiments, $R^{32}$ is selected from 3,4-dimethoxyphenyl, 2,6-dimethoxyphenyl, or 2,4-dimethoxyphenyl; wherein $R^{32}$ is further optionally substituted with a solubilizing group.

In certain embodiments, $R^{32}$ is not unsubstituted thienyl; unsubstituted phenyl; 2-methylphenyl; 4-fluorophenyl; 4-methoxyphenyl; 4-methylphenyl; 3,4-dioxyethylenephenyl; 3-acetylamino-4-methylphenyl; 3-[(6-amino-1-oxohexyl)amino]-4-methylphenyl; 3-amino-4-methylphenyl; 3,5-dimethoxyphenyl; 3-halo-4-methoxyphenyl; 3-nitro-4-methylphenyl; or 4-propoxyphenyl.

In one aspect, the invention provides sirtuin-modulating compounds of Structural Formula (XXVI):

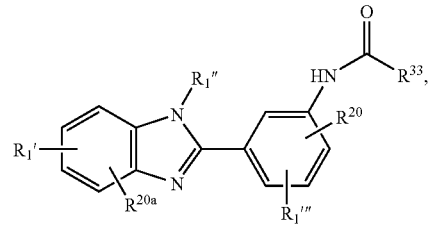

(XXVI)

or a salt thereof, wherein:
  each $R^{20}$ and $R^{20a}$ is independently selected from H or a solubilizing group;
  each $R_1'$, $R_1''$ and $R_1'''$ is independently selected from H or optionally substituted $C_1$-$C_3$ straight or branched alkyl; and
  $R^{33}$ is selected from an optionally substituted heteroaryl or an optionally substituted bicyclic aryl, with the provisos that:
  when each of $R_1'$ and $R_1'''$ is hydrogen or methyl and each of $R_1''$, $R_{20}$ and $R_{20a}$ is hydrogen, $R^{33}$ is not 5,6,7,8-tetrahydronaphthyl, unsubstituted benzofuryl, unsubstituted benzothiazolyl, chloro- or nitro-substituted benzothienyl, unsubstituted furyl, phenyl—, bromo- or nitro-substituted furyl, dimethyl-substituted isoxazolyl, unsubstituted naphthyl, 5-bromonaphthyl, 4-methylnaphthyl, 1- or 3-methoxynaphthyl, azo-substituted naphthyl, unsubstituted pyrazinyl, S-methyl-substituted pyridyl, unsubstituted pyridyl, thienyl- or phenyl-substituted quinolinyl, chloro- , bromo- or nitro-substituted thienyl, unsubstituted thienyl,

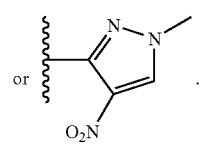

or

In a particular aspect, the invention provides sirtuin-modulating compounds of Structural Formula (XXVI):

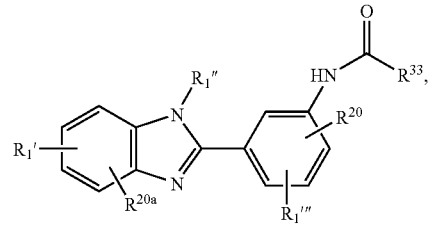

(XXVI)

or a salt thereof, wherein:
  each $R^{20}$ and $R^{20a}$ is independently selected from H or a solubilizing group, wherein at least one of $R^{20}$ or $R^{20a}$ is a solubilizing group;
  each $R_1'$, $R_1''$ and $R_1'''$ is independently selected from H or optionally substituted $C_1$-$C_3$ straight or branched alkyl; and
  $R^{33}$ is selected from an optionally substituted heteroaryl or an optionally substituted bicyclic aryl.

In another aspect, the invention provides sirtuin-modulating compounds of Structural Formula (XXVII):

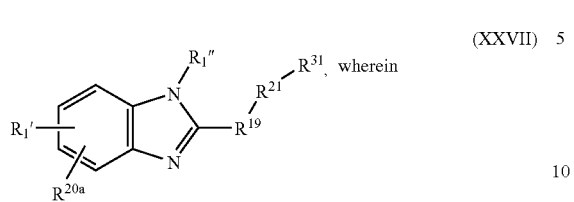 (XXVII)

wherein each $R^{20}$ and $R^{20a}$ is independently selected from H or a solubilizing group;

each $R_1'$ and $R_1''$ is independently selected from H or optionally substituted $C_1$-$C_3$ straight or branched alkyl;

$R^{19}$ is selected from:

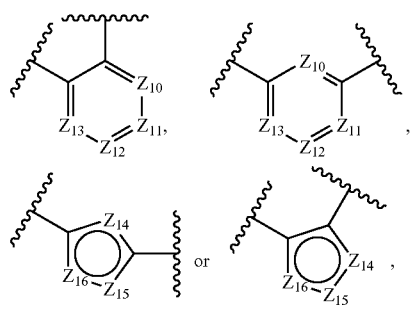

wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, S or O;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group;

zero to one $R_1'$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—,—$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and $R^{31}$ is selected from an optionally substituted monocyclic or bicyclic aryl, or an optionally substituted monocyclic or bicyclic heteroaryl, provided that when $R^{21}$ is —NH—C(O)— and $R^{19}$ is

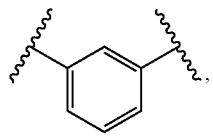, $R^{31}$ is not unsubstituted pyridyl, 2,6-dimethoxyphenyl, 3,4,5-trimethoxyphenyl or unsubstituted furyl.

In a particular aspect, the invention provides sirtuin-modulating compounds of Structural Formula (XXVII):

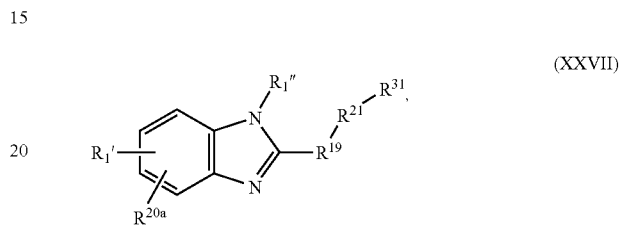 (XXVII)

or a salt thereof, wherein:

each $R^{20}$ and $R^{20a}$ is independently selected from H or a solubilizing group;

each $R_1'$ and $R_1''$ is independently selected from H or optionally substituted $C_1$-$C_3$ straight or branched alkyl;

$R^{19}$ is selected from:

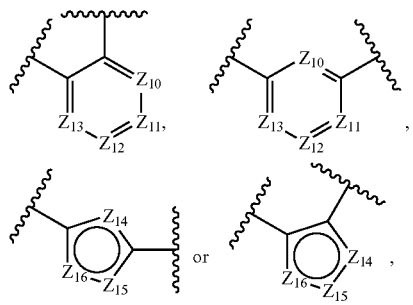

wherein:

each $Z_{10}$, $Z_{11}$, $Z_{12}$ and $Z_{13}$ is independently selected from N, $CR^{20}$, or $CR_1'$; and each $Z_{14}$, $Z_{15}$ and $Z_{16}$ is independently selected from N, $NR_1'$, S, O, $CR^{20}$, or $CR_1'$, wherein:

zero to two of $Z_{10}$, $Z_{11}$, $Z_{12}$ or $Z_{13}$ are N;

at least one of $Z_{14}$, $Z_{15}$ and $Z_{16}$ is N, $NR_1'$, S or O;

zero to one of $Z_{14}$, $Z_{15}$ and $Z_{16}$ is S or O;

zero to two of $Z_{14}$, $Z_{15}$ and $Z_{16}$ are N or $NR_1'$;

zero to one $R^{20}$ is a solubilizing group;

zero to one $R_1'$ is an optionally substituted $C_1$-$C_3$ straight or branched alkyl; and $R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —C(O)—$NR_1'$—, —C(O)—$NR_1'$—S(O)$_2$—, —$NR_1'$—, —$CR_1'R_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$CR_1'R_1'$—C(O)—$NR_1'$—, —$NR_1'$—C (O)—CR₁'=CR₁'—CR₁'R₁'—, —NR₁'—C(=N—CN)—NR₁'—, —NR₁'—C(O)—CR₁'R₁'—O—, —NR₁'—C(O)—CR₁'R₁'—CR₁'R₁'—O—, —NR₁'—S(O)₂—CR₁'R₁'—, —NR₁'—S(O)₂—CR₁'R₁'—CR₁'R₁'—, or —NR₁'—C(O)—CR₁'R₁'—; and $R^{31}$ is selected from an optionally substituted monocyclic or bicyclic aryl, or an optionally substituted monocyclic or bicyclic heteroaryl, with the provisos that:

when $R^{21}$ is —NH—C(O)—, $R^9$ is not pyrazolyl;

when $R^{21}$ is —NH—, and $R^{19}$ is thiazolyl, $R^{31}$ is not optionally substituted phenyl or optionally substituted pyridyl;

when $R^{21}$ is —NH—C(O)—CH₂—, and $R^{19}$ is pyrazolyl, $R^{31}$ is not unsubstituted indolyl or unsubstituted phenyl;

when $R^{21}$ is —NH—C(O)—CH₂—, and $R^{19}$ is

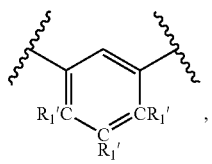

$R^{31}$ is not 2-methylphenyl or 3,4-dimethoxyphenyl;

when $R^{21}$ is —NH—C(O)—CH=CH—, and $R^{19}$ is

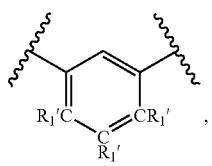

$R^{31}$ is not 2-chlorophenyl;

when $R^{21}$ is —NH—C(O)—NH—, and $R^9$ is pyrazolyl, $R^{31}$ is not unsubstituted isoxazolyl, unsubstituted naphthyl, unsubstituted phenyl, 2,6-difluorophenyl, 2,5-dimethylphenyl, 3,4-dichlorophenyl, or 4-chlorophenyl;

when $R^{21}$ is —NH—C(O)—NH—, and $R^{19}$ is

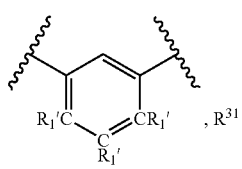

is not unsubstituted benzimidazolyl;

when $R^{21}$ is —NH—, and $R^{19}$ is pyrazolyl, $R^{31}$ is not unsubstituted pyridyl;

when $R^{20a}$ is a solubilizing group, $R^{19}$ is 1-methylpyrrolyl and $R^{21}$ is —NH—C(O)—, $R^{31}$ is not unsubstituted phenyl, unsubstituted furyl, unsubstituted pyrrolyl, unsubstituted pyrazolyl, unsubstituted isoquinolinyl, unsubstituted benzothienyl, chloro-substituted benzothienyl, 2-fluoro-4-chlorophenyl or phenyl singly substituted with a solubilizing group;

when $R^{20a}$ is a solubilizing group, $R^{19}$ is thienyl and $R^{21}$ is —NH—C(O)—, $R^{31}$ is not unsubstituted phenyl;

when $R^{20a}$ is a solubilizing group, $R^{19}$ is methylimidazolyl and $R^{21}$ is —NH—C(O)—, $R^{31}$ is not 1-methyl-4-(1,1-dimethylethyloxycarbonylamino)pyrrol-2-yl or phenyl singly substituted with a solubilizing group;

when $R^{21}$ is —NH— and $R^{19}$ is pyridyl, oxadiazolyl or thiadiazolyl, $R^{31}$ is not unsubstituted phenyl, 3-methoxyphenyl or 4-methoxyphenyl;

when $R^{21}$ is —NH—C(O)— and $R^{19}$ is thiazolyl or pyrimidinyl, $R^{31}$ is not unsubstituted phenyl;

when $R^{21}$ is —NH—C(O)— and $R^{19}$ is

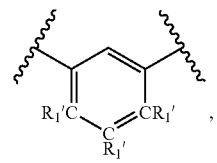

$R^{31}$ is not unsubstituted pyridyl, unsubstituted thienyl, unsubstituted phenyl, 2-methylphenyl, 4-fluorophenyl, 4-methoxyphenyl, 4-methylphenyl, 3,4-dioxyethylenephenyl, 3-acetylamino-4-methylphenyl, 3-[(6-amino-1-oxohexyl)amino]-4-methylphenyl, 3-amino-4-methylphenyl, 2,6-dimethoxyphenyl, 3,5-dimethoxyphenyl, 3-halo-4-methoxyphenyl, 3-nitro-4-methylphenyl, 4-propoxyphenyl, 3,4,5-trimethoxyphenyl or unsubstituted furyl;

when $R^{21}$ is —NH—C(O)— and $R^{19}$ is

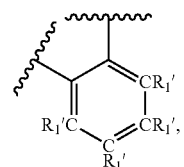

$R^{31}$ is not 3,5-dinitrophenyl, 4-butoxyphenyl,

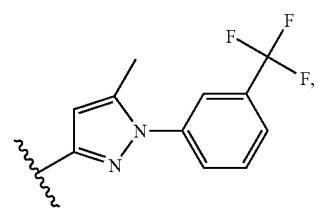

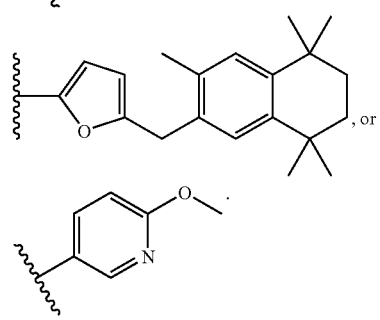

In certain embodiments, $R^{21}$ is selected from —NH—C(O)— or —NH—C(O)—NR₁'—, preferably —NH—C(O)—.

In certain embodiments, $R^{31}$ is selected from optionally substituted phenyl, quinoxalinyl or quinolinyl; preferably optionally substituted phenyl. For example, $R^{31}$ is optionally substituted with up to 3 substituents independently selected from —$OCH_3$, —$N(CH_3)_2$, or a solubilizing group. Suitable examples of $R^{31}$ include 4-dimethylaminophenyl; 3,4-dimethoxyphenyl; 3,5-dimethoxyphenyl; 3,4,5-trimethoxyphenyl; 3-methoxy-4-((piperazin-1-yl)methyl)phenyl; 3-methoxy-4-((morpholino)methyl)phenyl; 3-methoxy-4-((pyrrolidin-1-yl)methyl)phenyl; unsubstituted phenyl; unsubstituted quinoxalinyl; and unsubstituted quinolinyl. Preferred examples of $R^{31}$ include 3,4-dimethoxyphenyl; 2,6-dimethoxyphenyl; or 2,4-dimethoxyphenyl; wherein $R^{31}$ is further optionally substituted with a solubilizing group.

In preferred embodiments, $R^{21}$ is —NH—C(O)— and $R^{31}$ is selected from 3-methoxyphenyl; 3,4-dimethoxyphenyl; 3,4,5-trimethoxyphenyl; or 4-dimethylaminophenyl.

In certain embodiments, when $R^{21}$ is —NH—C(O)—, $R^{19}$ is not

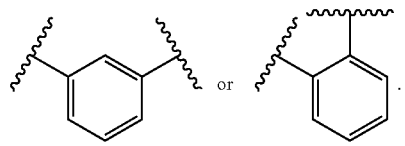

In certain embodiments, when $R^{21}$ is —NH—C(O)—, $R^{19}$ is not optionally substituted pyrazolyl, thiazolyl, thienyl, pyrrolyl or pyrimidinyl; when $R^{21}$ is —NH—C(O)—CH2— or —NH—C(O)—NH—, $R^{19}$ is not pyrazolyl; and/or when $R^{21}$ is —NH—, $R^{19}$ is not optionally substituted pyridyl, thiazolyl, pyrazolyl, thiadiazolyl, or oxadiazolyl.

In a more particular aspect, the invention provides sirtuin-modulating compounds of Structural Formula (XXVII):

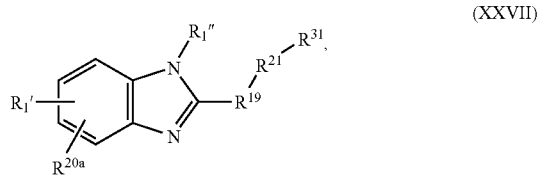

(XXVII)

or a salt thereof, wherein:
each $R^{20}$ and $R^{20a}$ is independently selected from H or a solubilizing group;
each $R_1'$ and $R_1''$ is independently selected from H or optionally substituted $C_1$-$C_3$ straight or branched alkyl;
$R^{19}$ is selected from:

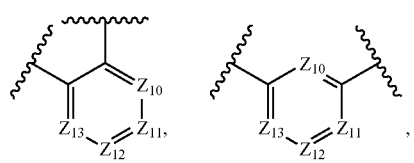

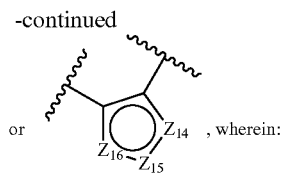, wherein:

each $Z_{10}$, $Z_{11}$, $Z_{12}$ and $Z_{13}$ is independently selected from N, $CR^{20}$, or $CR_1'$; and
each $Z_{14}$, $Z_{15}$ and $Z_{16}$ is independently selected from N, $NR_1'$, S, O, $CR^{20}$, or $CR_1'$, wherein:
one to two of $Z_{10}$, $Z_{11}$, $Z_{12}$ or $Z_{13}$ are N;
at least one of $Z_{14}$, $Z_{15}$ and $Z_{16}$ is N, $NR_1'$, S or O;
zero to one of $Z_{14}$, $Z_{15}$ and $Z_{16}$ is S or O;
zero to two of $Z_{14}$, $Z_{15}$ and $Z_{16}$ are N or $NR_1'$;
zero to one $R^{20}$ is a solubilizing group;
zero to one $R_1'''$ is an optionally substituted $C_1$-$C_3$ straight or branched alkyl; and
$R^{21}$ is selected from —$NR_1'$—C(O)—, —$NR_1'$—S(O)$_2$—, —$NR_1'$—C(O)—$NR_1'$—, —$NR_1'$—C(S)—$NR_1'$—, —$NR_1'$—C(S)—$NR_1'$—$CR_1'R_1'$—, —$NR_1'$—C(O)—$CR_1'R_1'$—$NR_1'$—, —$NR_1'$—C(=$NR_1'$)—$NR_1'$—, —$NR_1'$—C(O)—$CR_1'$=$CR_1'$—, —$NR_1'$—S(O)$_2$—$NR_1'$—, —$NR_1'$—C(O)—$NR_1'$—S(O)$_2$—, —$NR_1'$—$CR_1'R_1'$—C(O)—$NR_1'$—, —$NR_1'$—C(O)—$CR_1'$=$CR_1'$—$CR_1'R_1'$—, —$NR_1'$—C(=N—CN)—$NR_1'$—, —$NR_1'$—C(O)—$CR_1'R_1'$—O—, —$NR_1'$—C(O)—$CR_1'R_1'$—$CR_1'R_1'$—O—, —$NR_1'$—S(O)$_2$—$CR_1'R_1'$—, —$NR_1'$—S(O)$_2$—$CR_1'R_1'$—$CR_1'R_1'$—, or —$NR_1'$—C(O)—$CR_1'R_1'$—; and
$R^{31}$ is selected from an optionally substituted monocyclic or bicyclic aryl, or an optionally substituted monocyclic or bicyclic heteroaryl, with the provisos that:
when $R^{21}$ is —NH—C(O)—, $R^{19}$ is not pyrazolyl;
when $R^{21}$ is —NH—C(O)—CH$_2$—, and $R^{19}$ is pyrazolyl, $R^{31}$ is not unsubstituted indolyl or unsubstituted phenyl;
when $R^{21}$ is —NH—C(O)—NH—, and $R^{19}$ is pyrazolyl, $R^{31}$ is not unsubstituted isoxazolyl, unsubstituted naphthyl, unsubstituted phenyl, 2,6-difluorophenyl; 2,5-dimethylphenyl; 3,4-dichlorophenyl; or 4-chlorophenyl;
when $R^{20a}$ is a solubilizing group, $R^{19}$ is 1-methylpyrrolyl and $R^{21}$ is —NH—C(O)—, $R^{31}$ is not unsubstituted phenyl; unsubstituted furyl; unsubstituted pyrrolyl; unsubstituted pyrazolyl; unsubstituted isoquinolinyl; unsubstituted benzothienyl; chloro-substituted benzothienyl; 2-fluoro-4-chlorophenyl or phenyl singly substituted with a solubilizing group;
when $R^{20a}$ is a solubilizing group, $R^{19}$ is thienyl and $R^{21}$ is —NH—C(O)—, $R^{31}$ is not unsubstituted phenyl;
when $R^{20a}$ is a solubilizing group, $R^{19}$ is methylimidazolyl and $R^{21}$ is —NH—C(O)—, $R^{31}$ is not 1-methyl-4-(1,1-dimethylethyloxycarbonylamino)pyrrol-2-yl or phenyl singly substituted with a solubilizing group; and
when $R^{21}$ is —NH—C(O)— and $R^{19}$ is thiazolyl or pyrimidinyl, $R^{31}$ is not unsubstituted phenyl.

In certain embodiments, $R^{21}$ is selected from —NH—C(O)— or —NH—C(O)—$NR_1'$—, preferably —NH—C(O)—.

In certain embodiments, $R^{31}$ is selected from optionally substituted phenyl, quinoxalinyl or quinolinyl; preferably optionally substituted phenyl. For example, $R^{31}$ is optionally substituted with up to 3 substituents independently selected from —OCH$_3$, —N(CH$_3$)$_2$, or a solubilizing group. Suitable examples of R$^{31}$ include 4-dimethylaminophenyl; 3,4-dimethoxyphenyl; 3,5-dimethoxyphenyl; 3,4,5-trimethoxyphenyl; 3-methoxy-4-((piperazin-1-yl)methyl)phenyl; 3-methoxy-4-((morpholino)methyl)phenyl; 3-methoxy-4-((pyrrolidin-1-yl)methyl)phenyl; unsubstituted phenyl; unsubstituted quinoxalinyl; and unsubstituted quinolinyl. Preferred examples of R$^{31}$ include 3,4-dimethoxyphenyl; 2,6-dimethoxyphenyl; or 2,4-dimethoxyphenyl; wherein R$^{31}$ is further optionally substituted with a solubilizing group.

In preferred embodiments, R$^{21}$ is —NH—C(O)— and R$^{31}$ is selected from 3-methoxyphenyl; 3,4-dimethoxyphenyl; 3,4,5-trimethoxyphenyl; or 4-dimethylaminophenyl.

In yet another aspect, the invention provides compounds of Structural Formula (XXVIII):

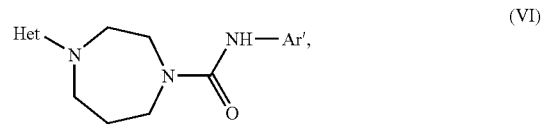
(XXVIII)

or a salt thereof, wherein:
each R$^{20}$ and R$^{20a}$ is independently selected from H or a solubilizing group;
each R$_1$' and R$_1$'' is independently selected from H or optionally substituted C$_1$-C$_3$ straight or branched alkyl;
R$^{29}$ is selected from:

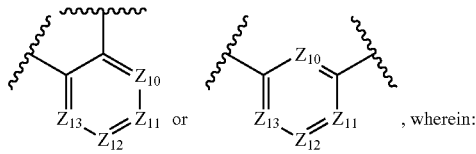
, wherein:

each Z$_{10}$, Z$_{11}$, Z$_{12}$ and Z$_{13}$ is independently selected from N, CR$^{20}$, or CR$_1$', wherein one of Z$_{10}$, Z$_{11}$, Z$_{12}$ or Z$_{13}$ is N; and
zero to one R$^{20}$ is a solubilizing group;
zero to one R$_1$''' is an optionally substituted C$_1$-C$_3$ straight or branched alkyl; and
R$^{21}$ is selected from —NR$_1$'—C(O)—, —NR$_1$'—S(O)$_2$—, —NR$_1$'—C(O)—NR$_1$'—, —NR$_1$'—C(S)—NR$_1$'—, —NR$_1$'—C(S)—NR$_1$'—CR$_1$'R'$_1$—, —NR$_1$'—C(O)—CR$_1$'R$_1$'—NR$_1$'—, —NR$_1$'—C(=NR$_1$')—NR$_1$'—, —NR$_1$'—C(O)—CR$_1$'=CR$_1$'—, —NR$_1$'—S(O)$_2$—NR$_1$'—, —NR$_1$'—C(O)—NR$_1$'—S(O)$_2$—, —NR$_1$'—CR$_1$'R$_1$—C(O)—NR$_1$'—, —NR$_1$'—C(O)—CR$_1$'=CR$_1$'—CR$_1$'R$_1$'—, —NR$_1$'—C(=N—CN)—NR$_1$'—, —NR$_1$'—C(O)—CR$_1$'R'$_1$O—, —NR$_1$'—C(O)—CR$_1$'R$_1$'—CR$_1$'R$_1$'—O—, —NR$_1$'—S(O)$_2$—CR$_1$'R'$_1$—, —NR$_1$'—S(O)$_2$—CR$_1$'R$_1$'—CR$_1$'R$_1$'—, or —NR$_1$'—C(O)—CR$_1$'R$_1$'—; and
R$^{31}$ is selected from an optionally substituted monocyclic or bicyclic aryl, or an optionally substituted monocyclic or bicyclic heteroaryl.

In certain embodiments, R$^{31}$ is optionally substituted phenyl, such as 3-methoxyphenyl, 3,4-dimethoxyphenyl, 3,4,5-trimethoxyphenyl, or 4-dimethylaminophenyl.

In certain embodiments, R$^{21}$ is —NH—C(O)—.

In preferred embodiments, R$^{21}$ is —NH—C(O)— and R$^{31}$ is an optionally substituted phenyl, such as 3-methoxyphenyl, 3,4-dimethoxyphenyl, 3,4,5-trimethoxyphenyl, or 4-dimethylaminophenyl.

In a further aspect, such as when the sirtuin modulator is a sirtuin inhibitor, the invention provides novel sirtuin-modulating compounds of Formula (VI):

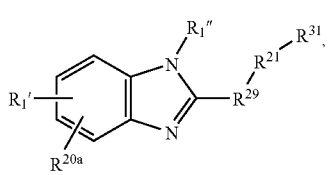
(VI)

or a salt thereof, wherein:
Het is an optionally substituted heterocyclic aryl group; and
Ar' is an optionally substituted carbocyclic or heterocyclic aryl group.

In certain embodiments, Het comprises one N heteroatom and 1 to 2 additional heteroatoms independently selected from N, O or S, such as oxazolopyridyl.

In certain embodiments, Ar' is selected from optionally substituted phenyl, benzothiazolyl, or benzoxazolyl. When Ar' is substituted phenyl, typically it is substituted with 1 to 3 substituents independently selected from halo, methyl, O-methyl, S-methyl or N(CH$_3$)$_2$, morpholino, or 3,4 dioxymethylene.

Compounds of the invention, including novel compounds of the invention, can also be used in the methods described herein.

The compounds and salts thereof described herein also include their corresponding hydrates (e.g., hemihydrate, monohydrate, dihydrate, trihydrate, tetrahydrate) and solvates. Suitable solvents for preparation of solvates and hydrates can generally be selected by a skilled artisan.

The compounds and salts thereof can be present in amorphous or crystalline (including co-crystalline and polymorph) forms.

In the compounds described above, bivalent groups disclosed as possible values for variables can have either orientation, provided that such orientation results in a stable molecule. Preferably, however, the left hand side of a bivalent group (e.g., —NR$_1$'—C(O)—) is attached to a bivalent arylene or heteroarylene group (e.g., R$^{19}$) and the right hand side of a bivalent group is attached to a monovalent aryl group (e.g., R$^{31}$).

Sirtuin-modulating compounds of the invention having hydroxyl substituents, unless otherwise indicated, also include the related secondary metabolites, such as phosphate, sulfate, acyl (e.g., acetyl, fatty acid acyl) and sugar (e.g., glucurondate, glucose) derivatives (e.g., of hydroxyl groups), particularly the sulfate, acyl and sugar derivatives. In other words, substituent groups -OH also include —OSO$_3^-$M$^+$, where M$^+$ is a suitable cation (preferably H$^+$, NH$_4^+$ or an alkali metal ion such as Na$^+$ or K$^+$) and sugars such as

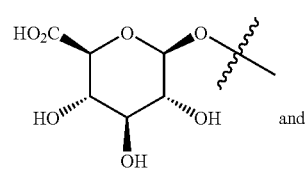
and

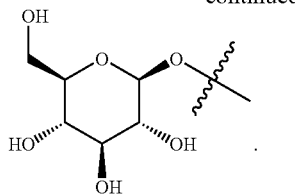

These groups are generally cleavable to —OH by hydrolysis or by metabolic (e.g., enzymatic) cleavage.

In certain embodiments, the compounds of the invention exclude one or more of the species disclosed in Tables 4-6. In certain such embodiments, the compounds of the invention exclude compound 7.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

An alkyl group is a straight chained, branched or cyclic non-aromatic hydrocarbon which is completely saturated. Typically, a straight chained or branched alkyl group has from 1 to about 20 carbon atoms, preferably from 1 to about 10, and a cyclic alkyl group has from 3 to about 10 carbon atoms, preferably from 3 to about 8. Examples of straight chained and branched alkyl groups include methyl, ethyl, n-propyl, iso-propyl, n-butyl, sec-butyl, tert-butyl, pentyl, hexyl, pentyl and octyl. A C1-C4 straight chained or branched alkyl group is also referred to as a "lower alkyl" group.

An alkenyl group is a straight chained, branched or cyclic non-aromatic hydrocarbon which contains one or more double bonds. Typically, the double bonds are not located at the terminus of the alkenyl group, such that the double bond is not adjacent to another functional group.

An alkynyl group is a straight chained, branched or cyclic non-aromatic hydrocarbon which contains one or more triple bonds. Typically, the triple bonds are not located at the terminus of the alkynyl group, such that the triple bond is not adjacent to another functional group.

A ring (e.g., 5- to 7-membered ring) or cyclic group includes carbocyclic and heterocyclic rings. Such rings can be saturated or unsaturated, including aromatic. Heterocyclic rings typically contain 1 to 4 heteroatoms, although oxygen and sulfur atoms cannot be adjacent to each other.

Aromatic (aryl) groups include carbocyclic aromatic groups such as phenyl, naphthyl, and anthracyl, and heteroaryl groups such as imidazolyl, thienyl, furyl, pyridyl, pyrimidyl, pyranyl, pyrazolyl, pyrroyl, pyrazinyl, thiazolyl, oxazolyl, and tetrazolyl.

Aromatic groups also include fused polycyclic aromatic ring systems in which a carbocyclic aromatic ring or heteroaryl ring is fused to one or more other heteroaryl rings. Examples include benzothienyl, benzofuryl, indolyl, quinolinyl, benzothiazole, benzoxazole, benzimidazole, quinolinyl, isoquinolinyl and isoindolyl.

Non-aromatic heterocyclic rings are non-aromatic carbocyclic rings which include one or more heteroatoms such as nitrogen, oxygen or sulfur in the ring. The ring can be five, six, seven or eight-membered. Examples include tetrahydrofuryl, tetrahyrothiophenyl, morpholino, thiomorpholino, pyrrolidinyl, piperazinyl, piperidinyl, and thiazolidinyl, along with the cyclic form of sugars.

A ring fused to a second ring shares at least one common bond.

Suitable substituents on an alkyl, alkenyl, alkynyl, aryl, non-aromatic heterocyclic or aryl group (carbocyclic and heteroaryl) are those which do not substantially interfere with the ability of the disclosed compounds to have one or more of the properties disclosed herein. A substituent substantially interferes with the properties of a compound when the magnitude of the property is reduced by more than about 50% in a compound with the substituent compared with a compound without the substituent. Examples of suitable substituents include —OH, halogen (—Br, —Cl, —I and —F), —OR$^a$, —O—COR$^a$, —COR$^a$, —C(O)R$^a$, —CN, —NO$^2$, —COOH, —COOR$^a$, —OCO$_2$R$^a$, —C(O)NR$^a$R$^b$, —OC(O)NR$^a$R$^b$, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, CR$^c$=CHR$^a$, —CR$^c$=CR$^a$R$^b$, CCR$^a$, —SH, —SO$_k$R$^a$ (k is 0, 1 or 2), —S(O)$_k$OR$^a$ (k is 0 or 1 or 2) and —NH—C(=NH)—NH$_2$. R$^a$—R$^d$ are each independently an aliphatic, substituted aliphatic, benzyl, substituted benzyl, aromatic or substituted aromatic group, preferably an alkyl, benzylic or aryl group. In addition, —NR$^a$R$^b$, taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

A hydrogen-bond donating group is a functional group having a partially positively-charged hydrogen atom (e.g., —OH, —NH$_2$, —SH) or a group (e.g., an ester) that metabolizes into a group capable of donating a hydrogen bond.

As used herein, a "solubilizing group" is a moiety that has hydrophilic character sufficient to improve or increase the water-solubility of the compound in which it is included, as compared to an analog compound that does not include the group. The hydrophilic character can be achieved by any means, such as by the inclusion of functional groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups (e.g., O, S, N, NH, N—$(CH_2)_y$—$R^a$, N—$(CH_2)_y$—$C(O)R^a$, N—$(CH_2)_y$—$C(O)OR^a$, N—$(CH_2)_y$—$S(O)_2R^a$, N—$(CH_2)_y$—$S(O)_2OR^a$, N—$(CH_2)_y$—$C(O)NR^aR^a$, etc., wherein $R^a$ is selected from hydrogen, lower alkyl, lower cycloalkyl, (C6-C14) aryl, phenyl, naphthyl, (C7-C20) arylalkyl and benzyl, wherein $R^a$ is optionally substituted; and y is an integer ranging from 0 to 6), optionally substituted heterocyclic groups (e.g., —$(CH_2)_n$—$R^b$, —$(CH_2)_n$—$C(O)$—$R^b$, —$(CH_2)_n$—O—$(CH_2)_n$—$R^b$, wherein $R^b$ is selected from an optionally substituted saturated monocyclic heterocycle, an optionally substituted saturated bicyclic fused heterocycle, an optionally substituted saturated bicyclic spiro heterocycle, an optionally substituted heteroaryl and an optionally substituted partially substituted non-aryl heterocycle; and n is an integer ranging from 0 to 2). It should be understood that substituents present on $R^a$ or $R^b$ need not improve or increase water solubility over their unsubstituted counterparts to be within the scope of this definition. All that is required is that such substituents do not significantly reverse the improvement in water-solubility afforded by the unsubstituted $R^a$ or $R^b$ moiety.

In one embodiment, the solubilizing group increases the water-solubility of the corresponding compound lacking the solubilizing group at least 5-fold, preferably at least 10-fold, more preferably at least 20-fold and most preferably at least 50-fold.

In one preferred embodiment, the solubilizing group is a moiety of the formula: —$(CH_2)_n$—$R^{100}$—$N(R^{101})(R^{101})$, wherein:

n is selected from 0, 1 or 2;

$R^{100}$ is selected from a bond, —C(O)—, or —$O(CH_2)_n$; and each $R^{101}$ is independently selected from:
a. hydrogen;
b. $C_1$-$C_4$ straight or branched alkyl, wherein said alkyl is optionally substituted with halo, CN, OH, O—($C_1$-$C_4$ straight or branched alkyl), $N(R_1')(R_1')$, or =O;

c. 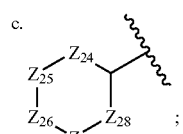

d. 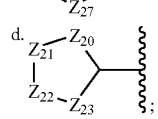

e. 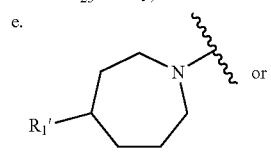

f. both $R^{101}$ moieties are taken together with the nitrogen atom to which they are bound to form a ring of the structure

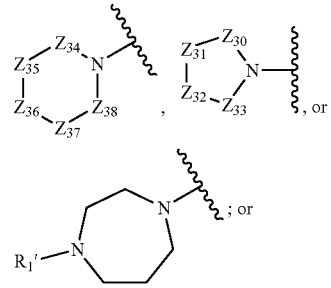

g. both $R^{101}$ moieties are taken together with the nitrogen atom to which they are bound to form a 5-membered heteroaryl ring containing 1 to 3 additional N atoms, wherein said heteroaryl ring is optionally substituted with $R_1'$;

wherein:
each Z is independently selected from —O—, —S—, —$NR_1'$—, or —$C(R^{50})(R^{50})$—, wherein:
at least three of $Z_{20}$, $Z_{21}$, $Z_{22}$, and $Z_{23}$ are —$C(R^{50})(R^{50})$—;
at least three of $Z_{24}$, $Z_{25}$, $Z_{26}$, $Z_{27}$, and $Z_{28}$ are —$C(R^{50})(R^{50})$—;
at least four of $Z_{30}$, $Z_{31}$, $Z_{32}$, and $Z_{33}$ are —$C(R^{50})(R^{50})$—; and
at least four of $Z_{34}$, $Z_{35}$, $Z_{36}$, $Z_{37}$, and $Z_{38}$ are —$C(R^{50})(R^{50})$—;

each $R_1'$ is independently selected from hydrogen or a $C_1$-$C_3$ straight or branched alkyl optionally substituted with one or more substituent independently selected from halo, —CN, —OH, —$OCH_3$, —$NH_2$, —$NH(CH_3)$, —$N(CH_3)_2$, or =O;

each $R^{50}$ is independently selected from $R_1'$, halo, CN, OH, O—($C_1$-$C_4$ straight or branched alkyl), $N(R_1')(R_1')$, =$CR_1'$, $SR_1'$, =$NR_1'$, =$NOR_1'$, or =O;

any two suitable non-cyclic $R^{50}$ are optionally bound to one another directly or via a $C_1$ to $C_2$ alkylene, alkenylene or alkanediylidene bridge to produce a bicyclic fused or spiro ring; and

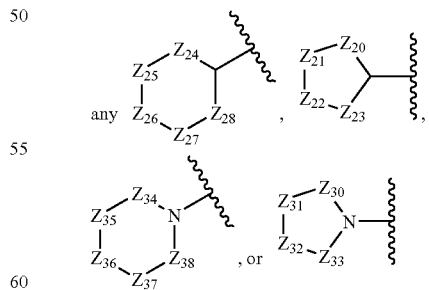

ring structure is optionally benzofused or fused to a monocyclic heteroaryl to produce a bicyclic ring.

For clarity, the term "$C_1$ to $C_2$ alkylene, alkenylene or alkanediylidene bridge" means the multivalent structures —$CH_2$—, —$CH_2$—$CH_2$—, —CH=, =CH—, —CH═CH—, or ═CH—CH═. The two $R^{50}$ moieties that are optionally bound to one another can be either on the same carbon atom or different carbon atoms. The former produces a spiro bicyclic ring, while the latter produces a fused bicyclic ring. It will be obvious to those of skill in the art that when two $R^{50}$ are bound to one another to form a ring (whether directly or through one of the recited bridges), one or more terminal hydrogen atoms on each $R^{50}$ will be lost. Accordingly, a "suitable non-cyclic $R^{50}$" moiety available for forming a ring is a non-cyclic $R^{50}$ that comprises at least one terminal hydrogen atom.

In another preferred embodiment, the solubilizing group is a moiety of the formula: —$(CH_2)_n$—O—$R^{101}$, wherein n and $R^{101}$ are as defined above.

In another preferred embodiment, the solubilizing group is a moiety of the formula: —$(CH_2)_n$—C(O)—$R_1'$, wherein n and $R_1'$ are as defined above.

In a more preferred embodiment, a solubilizing group is selected from —$(CH_2)_n$—$R^{102}$, wherein n is 0, 1 or 2; and $R^{102}$ is selected from

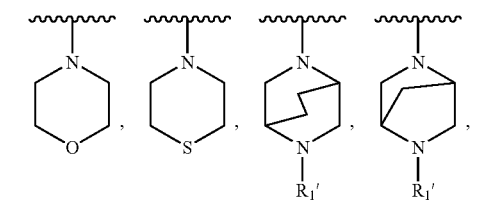

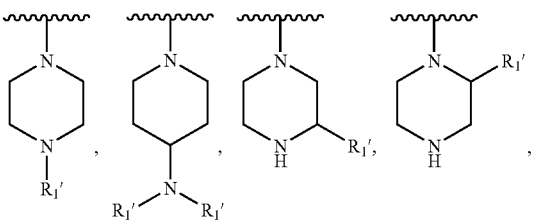

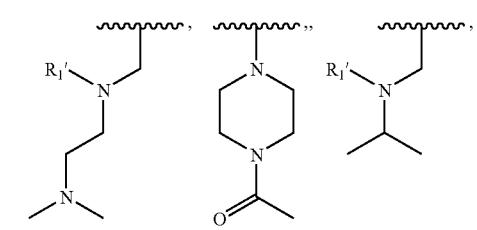

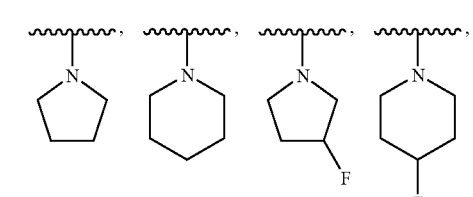

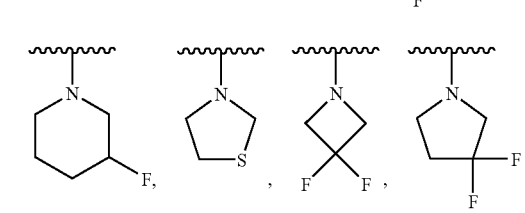

-continued

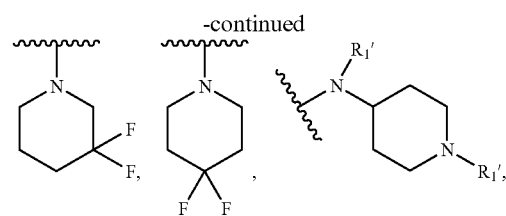

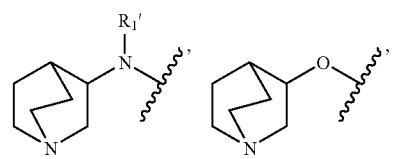

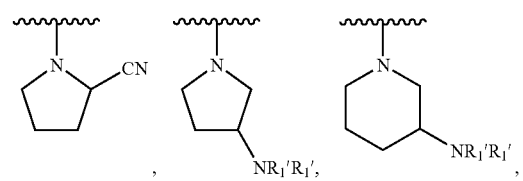

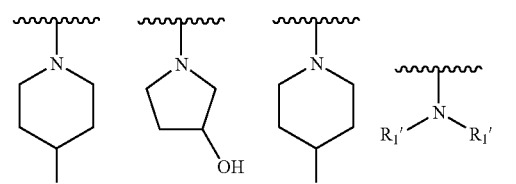

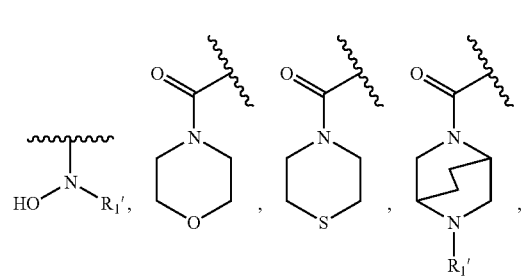

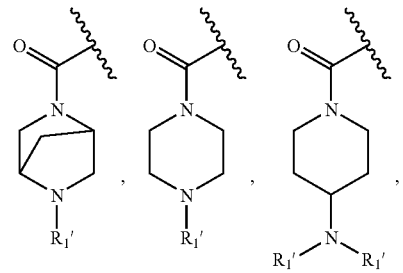

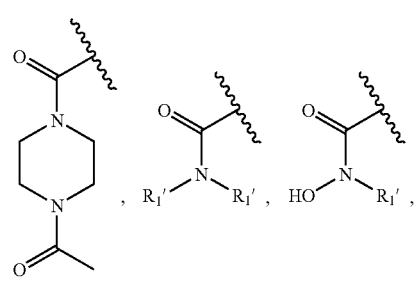

-continued

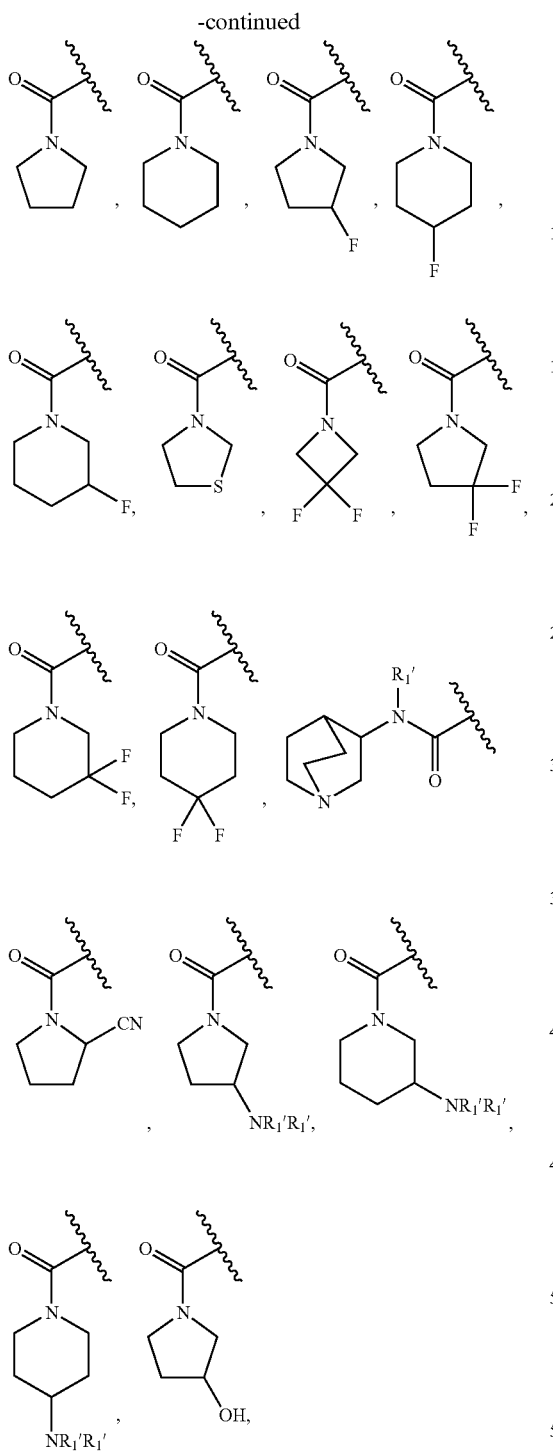

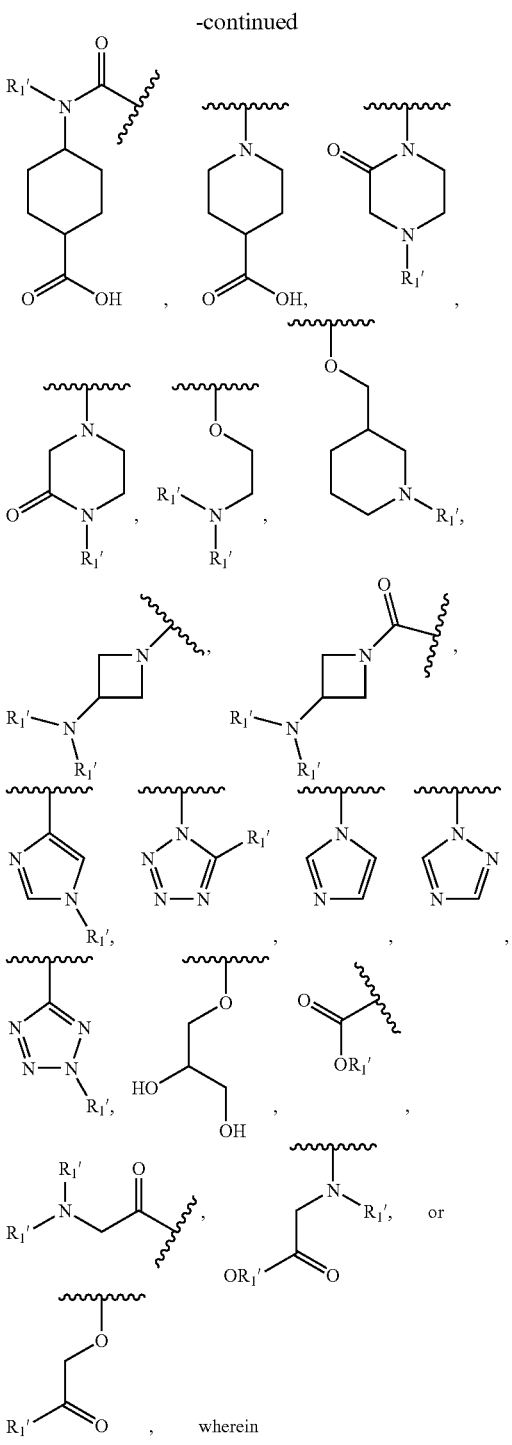

wherein $R_1'$ are as defined above.

In an even more preferred embodiment, a solubilizing group is selected from 2-dimethylaminoethylcarbamoyl, piperazin-1-ylcarbonyl, piperazinylmethyl, dimethylaminomethyl, 4-methylpiperazin-1-ylmethyl, 4-aminopiperidin-1-yl-methyl, 4-fluoropiperidin-1-yl-methyl, morpholinomethyl, pyrrolidin-1-ylmethyl, 2-oxo-4-benzylpiperazin-1-ylmethyl, 4-benzylpiperazin-1-ylmethyl, 3-oxopiperazin-1-ylmethyl, piperidin-1-ylmethyl, piperazin-1-ylethyl, 2,3-dioxopropylaminomethyl, thiazolidin-3-ylmethyl, 4-acetylpiperazin-1-ylmethyl, 4-acetylpiperazin-1-yl, morpholino, 3,3-difluoroazetidin-1-ylmethyl, 2H-tetrazol-5-ylmethyl, thiomorpholin-4-ylmethyl, 1-oxothiomorpholin-4-ylmethyl, 1,1-dioxothiomorpholin-4-ylmethyl, 1H-imidazol-1-ylmethyl, 3,5-dimethylpiperazin-1ylmethyl, 4-hydroxypiperidin-1-ylmethyl, N-methyl(1-acetylpiperidin-4-yl)-aminomethyl, N-methylquinuclidin-3-ylaminomethyl, 1H-1,2,4-triazol-1-ylmethyl, 1-methylpiperidin-3-yloxymethyl, or 4-fluoropiperidin-1-yl.

To the extent not included within any of the definitions set forth above, the term "solubilizing group" also includes moieties disclosed as being attached to the 7-position of 1-cyclopropyl-6-fluoro-1,4-dihydro-4-oxoquinoline-3-carboxylic acid (ciprofloxacin) and its derivatives, as disclosed in PCT publications WO 2005026165, WO 2005049602, and WO 2005033108, and European Patent publications EP 0343524, EP 0688772, EP 0153163, EP 0159174; as well as "water-solubilizing groups" described in United States patent publication 2006/0035891. The disclosure of each of these patent publications is incorporated herein by reference.

Double bonds indicated in a structure as:

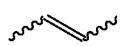

are intended to include both the (E)- and (Z)-configuration. Preferably, double bonds are in the (E)-configuration.

A sugar is an aldehyde or ketone derivative of a straight-chain polyhydroxy alcohol, which contains at least three carbon atoms. A sugar can exist as a linear molecule or, preferably, as a cyclic molecule (e.g., in the pyranose or furanose form). Preferably, a sugar is a monosaccharide such as glucose or glucuronic acid. In embodiments of the invention where, for example, prolonged residence of a compound derivatized with a sugar is desired, the sugar is preferably a non-naturally occurring sugar. For example, one or more hydroxyl groups are substituted with another group, such as a halogen (e.g., chlorine). The stereochemical configuration at one or more carbon atoms can also be altered, as compared to a naturally occurring sugar. One example of a suitable non-naturally occurring sugar is sucralose.

A fatty acid is a carboxylic acid having a long-chained hydrocarbon moiety. Typically, a fatty acid has an even number of carbon atoms ranging from 12 to 24, often from 14 to 20. Fatty acids can be saturated or unsaturated and substituted or unsubstituted, but are typically unsubstituted. Fatty acids can be naturally or non-naturally occurring. In embodiments of the invention where, for example, prolonged residence time of a compound having a fatty acid moiety is desired, the fatty acid is preferably non-naturally occurring. The acyl group of a fatty acid consists of the hydrocarbon moiety and the carbonyl moiety of the carboxylic acid functionality, but excludes the —OH moiety associated with the carboxylic acid functionality.

Also included in the present invention are salts, particularly pharmaceutically acceptable salts, of the sirtuin-modulating compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

According to another embodiment, the present invention provides methods of producing the above-defined sirtuin-modulating compounds. The compounds may be synthesized using conventional techniques. Advantageously, these compounds are conveniently synthesized from readily available starting materials.

Thus, one embodiment relates to a method of making a compound of the structure described herein using the following synthesis scheme:

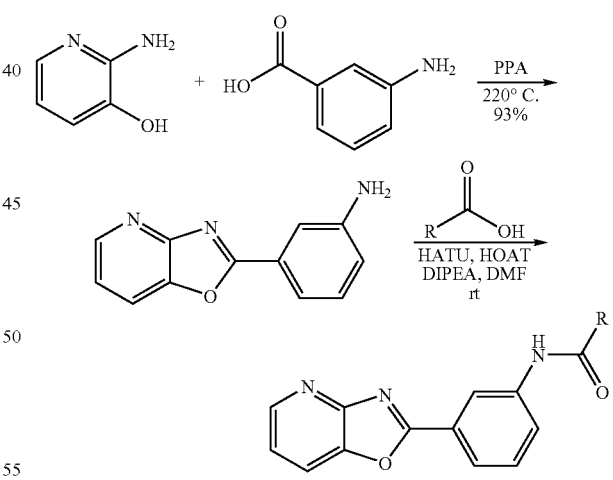

One of skill in the art would recognize that this synthetic scheme, or similar variants, usefully allows the incorporation of a variety of R groups into compounds falling within the scope of the instant invention, for example, compounds of the tables below.

As can be appreciated by the skilled artisan, the above synthetic scheme is not intended to comprise a comprehensive list of all means by which the compounds described and claimed in this application may be synthesized. Further methods will be evident to those of ordinary skill in the art.

Additionally, the various synthetic steps described above may be performed in an alternate sequence or order to give the desired compounds. Synthetic chemistry transformations and methodologies useful in synthesizing the sirtuin-modulating compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

In an exemplary embodiment, a sirtuin-modulating compound may traverse the cytoplasmic membrane of a cell. For example, a compound may have a cell-permeability of at least about 20%, 50%, 75%, 80%, 90% or 95%.

Sirtuin-modulating compounds described herein may also have one or more of the following characteristics: the compound may be essentially non-toxic to a cell or subject; the sirtuin-modulating compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a sirtuin-modulating compound may be more stable in solution than resveratrol by at least a factor of about 50%, 2 fold, 5 fold, 10 fold, 30 fold, 50 fold or 100 fold; a sirtuin-modulating compound may promote deacetylation of the DNA repair factor Ku70; a sirtuin-modulating compound may promote deacetylation of Re1A/p65; a compound may increase general turnover rates and enhance the sensitivity of cells to TNF-induced apoptosis.

In certain embodiments, a sirtuin-modulating compound does not have any substantial ability to inhibit a histone deacetylase (HDACs) class I, a HDAC class II, or HDACs I and II, at concentrations (e.g., in vivo) effective for modulating the deacetylase activity of the sirtuin. For instance, in preferred embodiments the sirtuin-modulating compound is a sirtuin-activating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, a sirtuin-modulating compound does not have any substantial ability to modulate sirtuin homologs. In one embodiment, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-activating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as *Candida, S. cerevisiae*, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as *Candida, S. cerevisiae*, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In one embodiment, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In one embodiment, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In one embodiment, a SIRT3 modulator does not have any substantial ability to modulate a SIRT1 protein.

In certain embodiments, a sirtuin-modulating compound may have a binding affinity for a sirtuin protein of about $10^{-9}$M, $10^{-10}$M, $10^{-11}$M, $10^{-12}$M or less. A sirtuin-modulating compound may reduce (activator) or increase (inhibitor) the apparent Km of a sirtuin protein for its substrate or NAD+ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an ED50 for modulating the deacetylase activity of a SIRT1 and/or SIRT3 protein of less than about 1nM, less than about 10 nM, less than about 100 nM, less than about 1 µM, less than about 10 µM, less than about 100 µM, or from about 1-10 nM, from about 10-100 nM, from about 0.1-1 µM, from about 1-10 µM or from about 10-100 µM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-activating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an ED50 for modulating SIRT5 that is at least about 10 fold, 20 fold, 30 fold, 50 fold greater than that for modulating SIRT1 and/or SIRT3.

3. Exemplary Uses

In certain aspects, the invention provides methods for modulating the level and/or activity of a sirtuin protein and methods of use thereof.

In certain embodiments, the invention provides methods for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of a sirtuin-modulating compound, e.g., a sirtuin-activating compound.

In other embodiments, the invention provides methods for using sirtuin-modulating compounds wherein the sirtuin-modulating compounds decrease sirtuin activity, e.g., decrease the level and/or activity of a sirtuin protein. Sirtuin-modulating compounds that decrease the level and/or activity of a sirtuin protein may be useful for a variety of therapeutic application including, for example, increasing cellular sensitivity to stress (including increasing radiosensitivity and/or chemosensitivity), increasing the amount and/or rate of apoptosis, treatment of cancer (optionally in combination another chemotherapeutic agent), stimulation of appetite, and/or stimulation of weight gain, etc. The methods comprise administering to a subject in need thereof a pharmaceutically effective amount of a sirtuin-modulating compound, e.g., a sirtuin-inhibiting compound.

While Applicants do not wish to be bound by theory, it is believed that activators and inhibitors of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In one embodiment, a mixture of two or more sirtuin-modulating compounds may be administered to a subject in need thereof. In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid. In another embodiment, a sirtuin-modulating compound that decreases the level and/or activity of a sirtuin protein may be administered with one or more of the following compounds: nicotinamide (NAM), suranim; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin choloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8,3',4'-hexahydroxyflavone), sirtinol; and splitomicin (see e.g., Howitz et al. (2003) Nature 425:191; Grozinger et al. (2001) *J. Biol. Chem.* 276:38837; Dedalov et al. (2001) *PNAS* 98:15113; and Hirao et al. (2003) *J. Biol. Chem* 278:52773). In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, ageing, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the sirtuin modulating compound(s) and other therapeutic agent(s) are in separate vessels). When using separate formulations, the sirtuin-modulating compound may be administered at the same, intermittent, staggered, prior to, subsequent to, or combinations thereof, with the administration of another therapeutic agent.

In certain embodiments, methods for reducing, preventing or treating diseases or disorders using a sirtuin-modulating compound may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042. The nucleic acid may be under the control of a promoter that regulates the expression of the SIRT1 and/or SIRT3 nucleic acid. Alternatively, the nucleic acid may be introduced into the cell at a location in the genome that is downstream of a promoter. Methods for increasing the level of a protein using these methods are well known in the art.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 (GenBank Accession No. NP_036370) and/or SIRT3 (GenBank Accession No. AAH01042) protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 (GenBank Accession No. NM_012238) and/or SIRT3 (e.g., GenBank Accession No. BC001042) protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM-012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods for modulating sirtuin protein levels also include methods for modulating the transcription of genes encoding sirtuins, methods for stabilizing/destabilizing the corresponding mRNAs, and other methods known in the art.

Aging/Stress

In one embodiment, the invention provides a method extending the lifespan of a cell, extending the proliferative capacity of a cell, slowing ageing of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods comprise contacting the cell with a sirtuin-activating compound.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one embodiment, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another embodiment, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first—, second- or third-degree burns and/or a thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In one embodiment, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods for decreasing the rate of senescence of a subject, e.g., after onset of senescence; methods for extending the lifespan of a subject; methods for treating or preventing a disease or condition relating to lifespan; methods for treating or preventing a disease or condition relating to the proliferative capacity of cells; and methods for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amniotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In one embodiment, a sirtuin-modulating compound that increases the level and/or activity of a sirtuin protein may be administered as part of a combination therapeutic with another cardiovascular agent including, for example, an anti-arrhythmic agent, an antihypertensive agent, a calcium channel blocker, a cardioplegic solution, a cardiotonic agent, a fibrinolytic agent, a sclerosing solution, a vasoconstrictor agent, a vasodilator agent, a nitric oxide donor, a potassium channel blocker, a sodium channel blocker, statins, or a naturiuretic agent.

In one embodiment, a sirtuin-modulating compound that increases the level and/or activity of a sirtuin protein may be administered as part of a combination therapeutic with an anti-arrhythmia agent. Anti-arrhythmia agents are often organized into four main groups according to their mechanism of action: type I, sodium channel blockade; type II, beta-adrenergic blockade; type III, repolarization prolongation; and type IV, calcium channel blockade. Type I antiarrhythmic agents include lidocaine, moricizine, mexiletine, tocainide, procainamide, encainide, flecanide, tocainide, phenytoin, propafenone, quinidine, disopyramide, and flecainide. Type II anti-arrhythmic agents include propranolol and esmolol. Type III includes agents that act by prolonging the duration of the action potential, such as amiodarone, artilide, bretylium, clofilium, isobutilide, sotalol, azimilide, dofetilide, dronedarone, ersentilide, ibutilide, tedisamil, and trecetilide. Type IV anti-arrhythmic agents include verapamil, diltaizem, digitalis, adenosine, nickel chloride, and magnesium ions.

In another embodiment, a sirtuin-modulating compound that increases the level and/or activity of a sirtuin protein may be administered as part of a combination therapeutic with another cardiovascular agent. Examples of cardiovascular agents include vasodilators, for example, hydralazine; angiotensin converting enzyme inhibitors, for example, captopril; anti-anginal agents, for example, isosorbide nitrate, glyceryl trinitrate and pentaerythritol tetranitrate; anti-arrhythmic agents, for example, quinidine, procainaltide and lignocaine; cardioglycosides, for example, digoxin and digitoxin; calcium antagonists, for example, verapamil and nifedipine; diuretics, such as thiazides and related compounds, for example, bendrofluazide, chlorothiazide, chlorothalidone, hydrochlorothiazide and other diuretics, for example, fursemide and triamterene, and sedatives, for example, nitrazepam, flurazepam and diazepam.

Other exemplary cardiovascular agents include, for example, a cyclooxygenase inhibitor such as aspirin or indomethacin, a platelet aggregation inhibitor such as clopidogrel, ticlopidene or aspirin, fibrinogen antagonists or a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, angiotensin II antagonists such as losartan, irbesartan or valsartan, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or animal salivary gland plasminogen activators, calcium channel blocking agents such as verapamil, nifedipine or diltiazem, thromboxane receptor antagonists such as ifetroban, prostacyclin mimetics, or phosphodiesterase inhibitors. Such combination products if formulated as a fixed dose employ the compounds of this invention within the dose range described above and the other pharmaceutically active agent within its approved dose range.

Yet other exemplary cardiovascular agents include, for example, vasodilators, e.g., bencyclane, cinnarizine, citicoline, cyclandelate, cyclonicate, ebumamonine, phenoxezyl, flunarizine, ibudilast, ifenprodil, lomerizine, naphlole, nikamate, nosergoline, nimodipine, papaverine, pentifylline, nofedoline, vincamin, vinpocetine, vichizyl, pentoxifylline, prostacyclin derivatives (such as prostaglandin E1 and prostaglandin I2), an endothelin receptor blocking drug (such as bosentan), diltiazem, nicorandil, and nitroglycerin. Examples of the cerebral protecting drug include radical scavengers (such as edaravone, vitamin E, and vitamin C), glutamate antagonists, AMPA antagonists, kainate antagonists, NMDA antagonists, GABA agonists, growth factors, opioid antagonists, phosphatidylcholine precursors, serotonin agonists, $Na^+/Ca^{2+}$ channel inhibitory drugs, and $K^+$ channel opening drugs. Examples of the brain metabolic stimulants include amantadine, tiapride, and gamma-aminobutyric acid. Examples of the anticoagulant include heparins (such as heparin sodium, heparin potassium, dalteparin sodium, dalteparin calcium, heparin calcium, pamaparin sodium, reviparin sodium, and danaparoid sodium), warfarin, enoxaparin, argatroban, batroxobin, and sodium citrate. Examples of the antiplatelet drug include ticlopidine hydrochloride, dipyridamole, cilostazol, ethyl icosapentate, sarpogrelate hydrochloride, dilazep hydrochloride, trapidil, a nonsteroidal antiinflammatory agent (such as aspirin), beraprostsodium, iloprost, and indobufene. Examples of the thrombolytic drug include urokinase, tissue-type plasminogen activators (such as alteplase, tisokinase, nateplase, pamiteplase, monteplase, and rateplase), and nasaruplase. Examples of the antihypertensive drug include angiotensin converting enzyme inhibitors (such as captopril, alacepril, lisinopril, imidapril, quinapril, temocapril, delapril, benazepril, cilazapril, trandolapril, enalapril, ceronapril, fosinopril, imadapril, mobertpril, perindopril, ramipril, spirapril, and randolapril), angiotensin II antagonists (such as losartan, candesartan, valsartan, eprosartan, and irbesartan), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendilin, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline), β-adrenaline receptor blocking drugs (propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, xybenolol, and esmolol), α-receptor blocking drugs (such as amosulalol, prazosin, terazosin, doxazosin, bunazosin, urapidil, phentolamine, arotinolol, dapiprazole, fenspiride, indoramin, labetalol, naftopidil, nicergoline, tamsulosin, tolazoline, trimazosin, and yohimbine), sympathetic nerve inhibitors (such as clonidine, guanfacine, guanabenz, methyldopa, and reserpine), hydralazine, todralazine, budralazine, and cadralazine. Examples of the anti anginal drug include nitrate drugs (such as amyl nitrite, nitroglycerin, and isosorbide), β-adrenaline receptor blocking drugs (such as propranolol, pindolol, indenolol, carteolol, bunitrolol, atenolol, acebutolol, metoprolol, timolol, nipradilol, penbutolol, nadolol, tilisolol, carvedilol, bisoprolol, betaxolol, celiprolol, bopindolol, bevantolol, labetalol, alprenolol, amosulalol, arotinolol, befunolol, bucumolol, bufetolol, buferalol, buprandolol, butylidine, butofilolol, carazolol, cetamolol, cloranolol, dilevalol, epanolol, levobunolol, mepindolol, metipranolol, moprolol, nadoxolol, nevibolol, oxprenolol, practol, pronetalol, sotalol, sufinalol, talindolol, tertalol, toliprolol, andxybenolol), calcium channel blocking drugs (such as aranidipine, efonidipine, nicardipine, bamidipine, benidipine, manidipine, cilnidipine, nisoldipine, nitrendipine, nifedipine, nilvadipine, felodipine, amlodipine, diltiazem, bepridil, clentiazem, phendiline, galopamil, mibefradil, prenylamine, semotiadil, terodiline, verapamil, cilnidipine, elgodipine, isradipine, lacidipine, lercanidipine, nimodipine, cinnarizine, flunarizine, lidoflazine, lomerizine, bencyclane, etafenone, and perhexiline) trimetazidine, dipyridamole, etafenone, dilazep, trapidil, nicorandil, enoxaparin, and aspirin. Examples of the diuretic include thiazide diuretics (such as hydrochlorothiazide, methyclothiazide, trichlormethiazide, benzylhydrochlorothiazide, and penflutizide), loop diuretics (such as furosemide, etacrynic acid, bumetanide, piretanide, azosemide, and torasemide), K$^+$ sparing diuretics (spironolactone, triamterene, and potassium can renoate), osmotic diuretics (such as isosorbide, D-mannitol, and glycerin), nonthiazide diuretics (such as meticrane, tripamide, chlorthalidone, and mefruside), and acetazolamide. Examples of the cardiotonic include digitalis formulations (such as digitoxin, digoxin, methyldigoxin, deslanoside, vesnarinone, lanatoside C, and proscillaridin), xanthine formulations (such as aminophylline, choline theophylline, diprophylline, and proxyphylline), catecholamine formulations (such as dopamine, dobutamine, and docarpamine), PDE III inhibitors (such as amrinone, olprinone, and milrinone), denopamine, ubidecarenone, pimobendan, levosimendan, aminoethylsulfonic acid, vesnarinone, carperitide, and colforsin daropate. Examples of the antiarrhythmic drug include ajmaline, pirmenol, procainamide, cibenzoline, disopyramide, quinidine, aprindine, mexiletine, lidocaine, phenyloin, pilsicainide, propafenone, flecainide, atenolol, acebutolol, sotalol, propranolol, metoprolol, pindolol, amiodarone, nifekalant, diltiazem, bepridil, and verapamil. Examples of the antihyperlipidemic drug include atorvastatin, simvastatin, pravastatin sodium, fluvastatin sodium, clinofibrate, clofibrate, simfibrate, fenofibrate, bezafibrate, colestimide, and colestyramine. Examples of the immunosuppressant include azathioprine, mizoribine, cyclosporine, tacrolimus, gusperimus, and methotrexate.

Cell Death/Cancer

Sirtuin-modulating compounds that increase the level and/or activity of a sirtuin protein may be administered to subjects who have recently received or are likely to receive a dose of radiation or toxin. In one embodiment, the dose of radiation or toxin is received as part of a work-related or medical procedure, e.g., working in a nuclear power plant, flying an airplane, an X-ray, CAT scan, or the administration of a radioactive dye for medical imaging; in such an embodiment, the compound is administered as a prophylactic measure. In another embodiment, the radiation or toxin exposure is received unintentionally, e.g., as a result of an industrial accident, habitation in a location of natural radiation, terrorist act, or act of war involving radioactive or toxic material. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer (see e.g., Bordone and Guarente, Nat. Rev. Mol. Cell Biol. (2005 epub); Guarente and Picard, Cell 120: 473-82 (2005); Berrigan, et al., Carcinogenesis 23: 817-822 (2002); and Heilbronn and Ravussin, Am. J. Clin. Nutr. 78: 361-369 (2003)). Additionally, the Sir2 protein from yeast has been shown to be required for lifespan extension by glucose restriction (see e.g., Lin et al., Science 289: 2126-2128 (2000); Anderson et al., Nature 423: 181-185 (2003)), a yeast model for calorie restriction. Accordingly, an increase in the level and/or activity of a sirtuin protein may be useful for treating and/or preventing the incidence of age-related disorders, such as, for example, cancer. In other embodiments, sirtuin-modulating compounds that decrease the level and/or activity of a sirtuin protein may be used for treating or preventing cancer. For example, inhibitory compounds may be used to stimulate acetylation of substrates such as p53 and thereby increase apoptosis, as well as to reduce the lifespan of cells and organisms, render them more sensitive to stress, and/or increase the radiosensitivity and/or chemosensitivity of a cell or organism. Thus, inhibitory compounds may be used, e.g., for treating cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth can also be treated, e.g., warts. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents that may be coadministered with modulating compounds described herein as having anti-cancer activity (e.g., compounds that induce apoptosis, compounds that reduce lifespan or compounds that render cells sensitive to stress) include: aminoglutethimide, amsacrine, anastrozole, asparaginase, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine(cladribine)); anti-proliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins(teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus(rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), atmsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; chromatin disruptors.

These chemotherapeutic agents may be used by themselves with a sirtuin-modulating compound described herein as inducing cell death or reducing lifespan or increasing sensitivity to stress and/or in combination with other chemotherapeutics agents. Many combinatorial therapies have been developed, including but not limited to those listed in Table 1.

TABLE 1

Exemplary combinatorial therapies for the treatment of cancer.

| Name | Therapeutic agents |
|---|---|
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/ Bleomycin |

TABLE 1-continued

Exemplary combinatorial therapies for the treatment of cancer.

| Name | Therapeutic agents |
|---|---|
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisone |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |

TABLE 1-continued

Exemplary combinatorial therapies for the treatment of cancer.

| Name | Therapeutic agents |
|---|---|
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |

TABLE 1-continued

Exemplary combinatorial therapies for the treatment of cancer.

| Name | Therapeutic agents |
|---|---|
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In addition to conventional chemotherapeutics, the sirtuin-modulating compounds described herein as capable of inducing cell death or reducing lifespan can also be used with antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a chronic, incurable, and unstoppable CNS disorder that occurs gradually, resulting in memory loss, unusual behavior, personality changes, and a decline in thinking abilities. These losses are related to the death of specific types of brain cells and the breakdown of connections and their supporting network (e.g. glial cells) between them. AD has been described as childhood development in reverse. In most people with AD, symptoms appear after the age 60. The earliest symptoms include loss of recent memory, faulty judgment, and changes in personality. Later in the disease, those with AD may forget how to do simple tasks like washing their hands. Eventually people with AD lose all reasoning abilities and become dependent on other people for their everyday care. Finally, the disease becomes so debilitating that patients are bedridden and typically develop coexisting illnesses.

PD is a chronic, incurable, and unstoppable CNS disorder that occurs gradually and results in uncontrolled body movements, rigidity, tremor, and dyskinesia. These motor system problems are related to the death of brain cells in an area of the brain that produces dopamine, a chemical that helps control muscle activity. In most people with PD, symptoms appear after age 50. The initial symptoms of PD are a pronounced tremor affecting the extremities, notably in the hands or lips. Subsequent characteristic symptoms of PD are stiffness or slowness of movement, a shuffling walk, stooped posture, and impaired balance. There are wide ranging secondary symptoms such as memory loss, dementia, depression, emotional changes, swallowing difficulties, abnormal speech, sexual dysfunction, and bladder and bowel problems. These symptoms will begin to interfere with routine activities, such as holding a fork or reading a newspaper. Finally, people with PD become so profoundly disabled that they are bedridden.

ALS (motor neuron disease) is a chronic, incurable, and unstoppable CNS disorder that attacks the motor neurons, components of the CNS that connect the brain to the skeletal muscles. In ALS, the motor neurons deteriorate and eventually die, and though a person's brain normally remains fully functioning and alert, the command to move never reaches the muscles. Most people who get ALS are between 40 and 70 years old. The first motor neurons that weaken are those controlling the arms or legs. Those with ALS may have trouble walking, they may drop things, fall, slur their speech, and laugh or cry uncontrollably. Eventually the muscles in the limbs begin to atrophy from disuse. This muscle weakness will become debilitating and a person will need a wheel chair or become unable to function out of bed.

The causes of these neurological diseases have remained largely unknown. They are conventionally defined as distinct diseases, yet clearly show extraordinary similarities in basic processes and commonly demonstrate overlapping symptoms far greater than would be expected by chance alone. Current disease definitions fail to properly deal with the issue of overlap and a new classification of the neurodegenerative disorders has been called for.

HD is another neurodegenerative disease resulting from genetically programmed degeneration of neurons in certain areas of the brain. This degeneration causes uncontrolled movements, loss of intellectual faculties, and emotional disturbance. HD is a familial disease, passed from parent to child through a dominant mutation in the wild-type gene. Some early symptoms of HD are mood swings, depression, irritability or trouble driving, learning new things, remembering a fact, or making a decision. As the disease progresses, concentration on intellectual tasks becomes increasingly difficult and the patient may have difficulty feeding himself or herself and swallowing.

Tay-Sachs disease and Sandhoff disease are glycolipid storage diseases caused by the lack of lysosomal β-hexosaminidase (Gravel et al., in The Metabolic Basis of Inherited Disease, eds. Scriver et al., McGraw-Hill, New York, pp. 2839-2879, 1995). In both disorders, GM2 ganglioside and related glycolipidssubstrates for β-hexosaminidase accumulate in the nervous system and trigger acute neurodegeneration. In the most severe forms, the onset of symptoms begins in early infancy. A precipitous neurodegenerative course then ensues, with affected infants exhibiting motor dysfunction, seizure, visual loss, and deafness. Death usually occurs by 2-5 years of age. Neuronal loss through an apoptotic mechanism has been demonstrated (Huang et al., Hum. Mol. Genet. 6: 1879-1885, 1997).

It is well-known that apoptosis plays a role in AIDS pathogenesis in the immune system. However, HIV-1 also induces neurological disease. Shi et al. (J. Clin. Invest. 98: 1979-1990, 1996) examined apoptosis induced by HIV-1 infection of the CNS in an in vitro model and in brain tissue from AIDS patients, and found that HIV-1 infection of primary brain cultures induced apoptosis in neurons and astrocytes in vitro. Apoptosis of neurons and astrocytes was also detected in brain tissue from 10/11 AIDS patients, including 5/5 patients with HIV-1 dementia and 4/5 nondemented patients.

There are four main peripheral neuropathies associated with HIV, namely sensory neuropathy, AIDP/CIPD, drug-induced neuropathy and CMV-related.

The most common type of neuropathy associated with AIDS is distal symmetrical polyneuropathy (DSPN). This syndrome is a result of nerve degeneration and is characterized by numbness and a sensation of pins and needles. DSPN causes few serious abnormalities and mostly results in numbness or tingling of the feet and slowed reflexes at the ankles. It generally occurs with more severe immunosuppression and is steadily progressive. Treatment with tricyclic antidepressants relieves symptoms but does not affect the underlying nerve damage.

A less frequent, but more severe type of neuropathy is known as acute or chronic inflammatory demyelinating polyneuropathy (AIDP/CIDP). In AIDP/CIDP there is damage to the fatty membrane covering the nerve impulses. This kind of neuropathy involves inflammation and resembles the muscle deterioration often identified with long-term use of AZT. It can be the first manifestation of HIV infection, where the patient may not complain of pain, but fails to respond to standard reflex tests. This kind of neuropathy may be associated with seroconversion, in which case it can sometimes resolve spontaneously. It can serve as a sign of HIV infection and indicate that it might be time to consider antiviral therapy. AIDP/CIDP may be auto-immune in origin.

Drug-induced, or toxic, neuropathies can be very painful. Antiviral drugs commonly cause peripheral neuropathy, as do other drugs e.g. vincristine, dilantin (an anti-seizure medication), high-dose vitamins, isoniazid, and folic acid antagonists. Peripheral neuropathy is often used in clinical trials for antivirals as a dose-limiting side effect, which means that more drugs should not be administered. Additionally, the use of such drugs can exacerbate otherwise minor neuropathies. Usually, these drug-induced neuropathies are reversible with the discontinuation of the drug.

CMV causes several neurological syndromes in AIDS, including encephalitis, myelitis, and polyradiculopathy.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. The most common cause of distal axonopathy is diabetes, and the most common distal axonopathy is diabetic neuropathy. The most distal portions of axons are usually the first to degenerate, and axonal atrophy advances slowly towards the nerve's cell body. If the noxious stimulus is removed, regeneration is possible, though prognosis decreases depending on the duration and severity of the stimulus. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy. Clinical manifestations of diabetic neuropathy include, for example, sensorimotor polyneuropathy such as numbness, sensory loss, dysesthesia and nighttime pain; autonomic neuropathy such as delayed gastric emptying or gastroparesis; and cranial neuropathy such as oculomotor (3rd) neuropathies or Mononeuropathies of the thoracic or lumbar spinal nerves.

Peripheral neuropathy is the medical term for damage to nerves of the peripheral nervous system, which may be caused either by diseases of the nerve or from the side-effects of systemic illness. Peripheral neuropathies vary in their presentation and origin, and may affect the nerve or the neuromuscular junction. Major causes of peripheral neuropathy include seizures, nutritional deficiencies, and HIV, though diabetes is the most likely cause. Mechanical pressure from staying in one position for too long, a tumor, intraneural hemorrhage, exposing the body to extreme conditions such as radiation, cold temperatures, or toxic substances can also cause peripheral neuropathy.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chromic inflammatory demyelinating polyneuropathy (CIDP), or symptoms associated therewith.

MS is a chronic, often disabling disease of the central nervous system. Various and converging lines of evidence point to the possibility that the disease is caused by a disturbance in the immune function, although the cause of this disturbance has not been established. This disturbance permits cells of the immune system to "attack" myelin, the fat containing insulating sheath that surrounds the nerve axons located in the central nervous system ("CNS"). When myelin is damaged, electrical pulses cannot travel quickly or normally along nerve fiber pathways in the brain and spinal cord. This results in disruption of normal electrical conductivity within the axons, fatigue and disturbances of vision, strength, coordination, balance, sensation, and bladder and bowel function.

As such, MS is now a common and well-known neurological disorder that is characterized by episodic patches of inflammation and demyelination which can occur anywhere in the CNS. However, almost always without any involvement of the peripheral nerves associated therewith. Demyelination produces a situation analogous to that resulting from cracks or tears in an insulator surrounding an electrical cord. That is, when the insulating sheath is disrupted, the circuit is "short circuited" and the electrical apparatus associated therewith will function intermittently or nor at all. Such loss of myelin surrounding nerve fibers results in short circuits in nerves traversing the brain and the spinal cord that thereby result in symptoms of MS. It is further found that such demyelination occurs in patches, as opposed to along the entire CNS. In addition, such demyelination may be intermittent. Therefore, such plaques are disseminated in both time and space.

It is believed that the pathogenesis involves a local disruption of the blood brain barrier which causes a localized immune and inflammatory response, with consequent damage to myelin and hence to neurons.

Clinically, MS exists in both sexes and can occur at any age. However, its most common presentation is in the relatively young adult, often with a single focal lesion such as a damage of the optic nerve, an area of anesthesia (loss of sensation), or paraesthesia (localize loss of feeling), or muscular weakness. In addition, vertigo, double vision, localized pain, incontinence, and pain in the arms and legs may occur upon flexing of the neck, as well as a large variety of less common symptoms.

An initial attack of MS is often transient, and it may be weeks, months, or years before a further attack occurs. Some individuals may enjoy a stable, relatively event free condition for a great number of years, while other less fortunate ones may experience a continual downhill course ending in complete paralysis. There is, most commonly, a series of remission and relapses, in which each relapse leaves a patient somewhat worse than before. Relapses may be triggered by stressful events, viral infections or toxins. Therein, elevated body temperature, i.e., a fever, will make the condition worse, or as a reduction of temperature by, for example, a cold bath, may make the condition better.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders, such as the ones described below. The PNS is composed of the nerves that lead to or branch off from the spinal cord and CNS. The peripheral nerves handle a diverse array of functions in the body, including sensory, motor, and autonomic functions. When an individual has a peripheral neuropathy, nerves of the PNS have been damaged. Nerve damage can arise from a number of causes, such as disease, physical injury, poisoning, or malnutrition. These agents may affect either afferent or efferent nerves. Depending on the cause of damage, the nerve cell axon, its protective myelin sheath, or both may be injured or destroyed.

The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

Peripheral neuropathy is a widespread disorder, and there are many underlying causes. Some of these causes are common, such as diabetes, and others are extremely rare, such as acrylamide poisoning and certain inherited disorders. The most common worldwide cause of peripheral neuropathy is leprosy. Leprosy is caused by the bacterium Mycobacterium leprae, which attacks the peripheral nerves of affected people.

Leprosy is extremely rare in the United States, where diabetes is the most commonly known cause of peripheral neuropathy. It has been estimated that more than 17 million people in the United States and Europe have diabetes-related polyneuropathy. Many neuropathies are idiopathic; no known cause can be found. The most common of the inherited peripheral neuropathies in the United States is Charcot-Marie-Tooth disease, which affects approximately 125,000 persons.

Another of the better known peripheral neuropathies is Guillain-Barré syndrome, which arises from complications associated with viral illnesses, such as cytomegalovirus, Epstein-Barr virus, and human immunodeficiency virus (HIV), or bacterial infection, including Campylobacter jejuni and Lyme disease. The worldwide incidence rate is approximately 1.7 cases per 100,000 people annually. Other well-known causes of peripheral neuropathies include chronic alcoholism, infection of the varicella-zoster virus, botulism, and poliomyelitis. Peripheral neuropathy may develop as a primary symptom, or it may be due to another disease. For example, peripheral neuropathy is only one symptom of diseases such as amyloid neuropathy, certain cancers, or inherited neurologic disorders. Such diseases may affect the PNS and the CNS, as well as other body tissues.

Other PNS diseases treatable with sirtuin-modulating compounds that increase the level and/or activity of a sirtuin protein include: Brachial Plexus Neuropathies (diseases of the cervical and first thoracic roots, nerve trunks, cords, and peripheral nerve components of the brachial plexus. Clinical manifestations include regional pain, paresthesia; muscle weakness, and decreased sensation in the upper extremity. These disorders may be associated with trauma, including birth injuries; thoracic outlet syndrome; neoplasms, neuritis, radiotherapy; and other conditions. See Adams et al., Principles of Neurology, 6th ed, pp1351-2); Diabetic Neuropathies (peripheral, autonomic, and cranial nerve disorders that are associated with diabetes mellitus). These conditions usually result from diabetic microvascular injury involving small blood vessels that supply nerves (vasa nervorum). Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy (see Adams et al., Principles of Neurology, 6th ed, p1325); mononeuropathies (disease or trauma involving a single peripheral nerve in isolation, or out of proportion to evidence of diffuse peripheral nerve dysfunction). Mononeuritis multiplex refers to a condition characterized by multiple isolated nerve injuries. Mononeuropathies may result from a wide variety of causes, including ischemia; traumatic injury; compression; connective tissue diseases; cumulative trauma disorders; and other conditions; Neuralgia (intense or aching pain that occurs along the course or distribution of a peripheral or cranial nerve); Peripheral Nervous System Neoplasms (neoplasms which arise from peripheral nerve tissue). This includes neurofibromas; Schwannomas; granular cell tumors; and malignant peripheral nerve sheath tumors (see DeVita Jr et al., Cancer: Principles and Practice of Oncology, 5th ed, pp1750-1); and Nerve Compression Syndromes (mechanical compression of nerves or nerve roots from internal or external causes). These may result in a conduction block to nerve impulses, due to, for example, myelin sheath dysfunction, or axonal loss. The nerve and nerve sheath injuries may be caused by ischemia; inflammation; or a direct mechanical effect; Neuritis (a general term indicating inflammation of a peripheral or cranial nerve). Clinical manifestation may include pain; paresthesias; paresis; or hyperesthesia; Polyneuropathies (diseases of multiple peripheral nerves). The various forms are categorized by the type of nerve affected (e.g., sensory, motor, or autonomic), by the distribution of nerve injury (e.g., distal vs. proximal), by nerve component primarily affected (e.g., demyelinating vs. axonal), by etiology, or by pattern of inheritance.

In another embodiment, a sirtuin activating compound may be used to treat or prevent chemotherapeutic induced neuropathy. The sirtuin modulating compounds may be administered prior to administration of the chemotherapeutic agent, concurrently with administration of the chemotherapeutic drug, and/or after initiation of administration of the chemotherapeutic drug. If the sirtuin activating compound is administered after the initiation of administration of the chemotherapeutic drug, it is desirable that the sirtuin activating compound be administered prior to, or at the first signs, of chemotherapeutic induced neuropathy.

Chemotherapy drugs can damage any part of the nervous system. Encephalopathy and myelopathy are fortunately very rare. Damage to peripheral nerves is much more common and can be a side effect of treatment experienced by people with cancers, such as lymphoma. Most of the neuropathy affects sensory rather than motor nerves. Thus, the common symptoms are tingling, numbness or a loss of balance. The longest nerves in the body seem to be most sensitive hence the fact that most patients will report numbness or pins and needles in their hands and feet.

The chemotherapy drugs which are most commonly associated with neuropathy, are the Vinca alkaloids (anti-cancer drugs originally derived from a member of the periwinkle— the Vinca plant genus) and a platinum-containing drug called Cisplatin. The Vinca alkaloids include the drugs vinblastine, vincristine and vindesine. Many combination chemotherapy treatments for lymphoma for example CHOP and CVP contain vincristine, which is the drug known to cause this problem most frequently. Indeed, it is the risk of neuropathy that limits the dose of vincristine that can be administered.

Studies that have been performed have shown that most patients will lose some reflexes in their legs as a result of treatment with vincristine and many will experience some degree of tingling (paresthesia) in their fingers and toes. The neuropathy does not usually manifest itself right at the start of the treatment but generally comes on over a period of a few weeks. It is not essential to stop the drug at the first onset of symptoms, but if the neuropathy progresses this may be necessary. It is very important that patients should report such symptoms to their doctors, as the nerve damage is largely reversible if the drug is discontinued. Most doctors will often reduce the dose of vincristine or switch to another form of Vinca alkaloid such as vinblastine or vindesine if the symptoms are mild. Occasionally, the nerves supplying the bowel are affected causing abdominal pain and constipation.

In another embodiment, a sirtuin activating compound may be used to treat or prevent a polyglutamine disease. Huntington's Disease (HD) and Spinocerebellar ataxia type 1 (SCA1) are just two examples of a class of genetic diseases caused by dynamic mutations involving the expansion of triplet sequence repeats. In reference to this common mechanism, these disorders are called trinucleotide repeat diseases. At least 14 such diseases are known to affect human beings. Nine of them, including SCA1 and Huntington's disease, have CAG as the repeated sequence (see Table 2 below). Since CAG codes for an amino acid called glutamine, these nine trinucleotide repeat disorders are collectively known as polyglutamine diseases.

Although the genes involved in different polyglutamine diseases have little in common, the disorders they cause follow a strikingly similar course. Each disease is characterized by a progressive degeneration of a distinct group of nerve cells. The major symptoms of these diseases are similar, although not identical, and usually affect people in midlife. Given the similarities in symptoms, the polyglutamine diseases are hypothesized to progress via common cellular mechanisms. In recent years, scientists have made great strides in unraveling what the mechanisms are.

Above a certain threshold, the greater the number of glutamine repeats in a protein, the earlier the onset of disease and the more severe the symptoms. This suggests that abnormally long glutamine tracts render their host protein toxic to nerve cells.

To test this hypothesis, scientists have generated genetically engineered mice expressing proteins with long polyglutamine tracts. Regardless of whether the mice express full-length proteins or only those portions of the proteins containing the polyglutamine tracts, they develop symptoms of polyglutamine diseases. This suggests that a long polyglutamine tract by itself is damaging to cells and does not have to be part of a functional protein to cause its damage.

For example, it is thought that the symptoms of SCA1 are not directly caused by the loss of normal ataxin-1 function but rather by the interaction between ataxin-1 and another protein called LANP. LANP is needed for nerve cells to communicate with one another and thus for their survival. When the mutant ataxin-1 protein accumulates inside nerve cells, it "traps" the LANP protein, interfering with its normal function. After a while, the absence of LANP function appears to cause nerve cells to malfunction.

TABLE 2

Summary of Polyglutamine Diseases.

| Disease | Gene name | Chromosomal location | Pattern of inheritance | Protein | Normal repeat length | Disease repeat length |
|---|---|---|---|---|---|---|
| Spinobulbar muscular atrophy (Kennedy disease) | AR | Xq13-21 | X-linked recessive | androgen receptor (AR) | 9-36 | 38-62 |
| Huntington's disease | HD | 4p16.3 | autosomal dominant | huntingtin | 6-35 | 36-121 |
| Dentatorubral-pallidoluysian atrophy (Haw River syndrome) | DRPLA | 12p13.31 | autosomal dominant | atrophin-1 | 6-35 | 49-88 |
| Spinocerebellar ataxia type 1 | SCA1 | 6p23 | autosomal dominant | ataxin-1 | 6-44 | 39-82 |
| Spinocerebellar ataxia type 2 | SCA2 | 12q24.1 | autosomal dominant | ataxin-2 | 15-31 | 36-63 |
| Spinocerebellar ataxia type 3 (Machado-Joseph disease) | SCA3 | 14q32.1 | autosomal dominant | ataxin-3 | 12-40 | 55-84 |
| Spinocerebellar ataxia type 6 | SCA6 | 19p13 | autosomal dominant | $\alpha 1_A$-voltage-dependent calcium channel subunit | 4-18 | 21-33 |
| Spinocerebellar ataxia type 7 | SCA7 | 3p12-13 | autosomal dominant | ataxin-7 | 4-35 | 37-306 |
| Spinocerebellar ataxia type 17 | SCA17 | 6q27 | autosomal dominant | TATA binding protein | 25-42 | 45-63 |

Many transcription factors have also been found in neuronal inclusions in different diseases. It is possible that these transcription factors interact with the polyglutamine-containing proteins and then become trapped in the neuronal inclusions. This in turn might keep the transcription factors from turning genes on and off as needed by the cell. Another observation is hypoacetylation of histones in affected cells. This has led to the hypothesis that Class I/II Histone Deacetylase (HDAC I/II) inhibitors, which are known to increase histone acetylation, may be a novel therapy for polyglutamine diseases (U.S. patent application Ser. No. 10/476,627; "Method of treating neurodegenerative, psychiatric, and other disorders with deacetylase inhibitors").

In yet another embodiment, the invention provides a method for treating or preventing neuropathy related to ischemic injuries or diseases, such as, for example, coronary heart disease (including congestive heart failure and myocardial infarctions), stroke, emphysema, hemorrhagic shock, peripheral vascular disease (upper and lower extremities) and transplant related injuries.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. By way of example, the normal amount of perfusion to brain gray matter in humans is about 60 to 70 mL/100 g of brain tissue/min. Death of central nervous system cells typically occurs when the flow of blood falls below approximately 8-10 mL/100 g of brain tissue/min, while at slightly higher levels (i.e. 20-35 mL/100 g of brain tissue/min) the tissue remains alive but not able to function. In one embodiment, apoptotic or necrotic cell death may be prevented. In still a further embodiment, ischemic-mediated damage, such as cytoxic edema or central nervous system tissue anoxemia, may be prevented. In each embodiment, the central nervous system cell may be a spinal cell or a brain cell.

Another aspect encompasses administrating a sirtuin activating compound to a subject to treat a central nervous system ischemic condition. A number of central nervous system ischemic conditions may be treated by the sirtuin activating compounds described herein. In one embodiment, the ischemic condition is a stroke that results in any type of ischemic central nervous system damage, such as apoptotic or necrotic cell death, cytoxic edema or central nervous system tissue anoxia. The stroke may impact any area of the brain or be caused by any etiology commonly known to result in the occurrence of a stroke. In one alternative of this embodiment, the stroke is a brain stem stroke. Generally speaking, brain stem strokes strike the brain stem, which control involuntary life-support functions such as breathing, blood pressure, and heartbeat. In another alternative of this embodiment, the stroke is a cerebellar stroke. Typically, cerebellar strokes impact the cerebellum area of the brain, which controls balance and coordination. In still another embodiment, the stroke is an embolic stroke. In general terms, embolic strokes may impact any region of the brain and typically result from the blockage of an artery by a vaso-occlusion. In yet another alternative, the stroke may be a hemorrhagic stroke. Like ischemic strokes, hemorrhagic stroke may impact any region of the brain, and typically result from a ruptured blood vessel characterized by a hemorrhage (bleeding) within or surrounding the brain. In a further embodiment, the stroke is a thrombotic stroke. Typically, thrombotic strokes result from the blockage of a blood vessel by accumulated deposits.

In another embodiment, the ischemic condition may result from a disorder that occurs in a part of the subject's body outside of the central nervous system, but yet still causes a reduction in blood flow to the central nervous system. These disorders may include, but are not limited to a peripheral vascular disorder, a venous thrombosis, a pulmonary embolus, arrhythmia (e.g. atrial fibrillation), a myocardial infarction, a transient ischemic attack, unstable angina, or sickle cell anemia. Moreover, the central nervous system ischemic condition may occur as result of the subject undergoing a surgical procedure. By way of example, the subject may be undergoing heart surgery, lung surgery, spinal surgery, brain surgery, vascular surgery, abdominal surgery, or organ transplantation surgery. The organ transplantation surgery may include heart, lung, pancreas, kidney or liver transplantation surgery. Moreover, the central nervous system ischemic condition may occur as a result of a trauma or injury to a part of the subject's body outside the central nervous system. By way of example, the trauma or injury may cause a degree of bleeding that significantly reduces the total volume of blood in the subject's body. Because of this reduced total volume, the amount of blood flow to the central nervous system is concomitantly reduced. By way of further example, the trauma or injury may also result in the formation of a vaso-occlusion that restricts blood flow to the central nervous system.

Of course it is contemplated that the sirtuin activating compounds may be employed to treat the central nervous system ischemic condition irrespective of the cause of the condition. In one embodiment, the ischemic condition results from a vaso-occlusion. The vaso-occlusion may be any type of occlusion, but is typically a cerebral thrombosis or an embolism. In a further embodiment, the ischemic condition may result from a hemorrhage. The hemorrhage may be any type of hemorrhage, but is generally a cerebral hemorrhage or a subararachnoid hemorrhage. In still another embodiment, the ischemic condition may result from the narrowing of a vessel. Generally speaking, the vessel may narrow as a result of a vasoconstriction such as occurs during vasospasms, or due to arteriosclerosis. In yet another embodiment, the ischemic condition results from an injury to the brain or spinal cord.

In yet another aspect, a sirtuin activating compound may be administered to reduce infarct size of the ischemic core following a central nervous system ischemic condition. Moreover, a sirtuin activating compound may also be beneficially administered to reduce the size of the ischemic penumbra or transitional zone following a central nervous system ischemic condition.

In one embodiment, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents. For example, one or more sirtuin-activating compounds can be combined with an effective amount of one or more of: L-DOPA; a dopamine agonist; an adenosine $A_2A$ receptor antagonist; a COMT inhibitor; a MAO inhibitor; an N-NOS inhibitor; a sodium channel antagonist; a selective N-methyl D-aspartate (NMDA) receptor antagonist; an AMPA/kainate receptor antagonist; a calcium channel antagonist; a GABA-A receptor agonist; an acetyl-choline esterase inhibitor; a matrix metalloprotease inhibitor; a PARP inhibitor; an inhibitor of p38 MAP kinase or c-jun-N-terminal kinases; TPA; NDA antagonists; beta-interferons; growth factors; glutamate inhibitors; and/or as part of a cell therapy.

Exemplary N-NOS inhibitors include 4-(6-amino-pyridin-2-yl)-3-methoxyphenol 6-[4-(2-dimethylamino-ethoxy)-2-methoxy-phenyl]-pyridin-2-yl-amine, 6-[4-(2-dimethylamino-ethoxy)-2,3-dimet-hyl-phenyl]-pyridin-2-yl-amine, 6-[4-(2-pyrrolidinyl-ethoxy)-2,3-dimethyl-phenyl]-pyridin-2-yl-amine, 6-[4-(4-(n-methyl) piperidinyloxy)-2,3-dimethyl-p-henyl]-pyridin-2-yl-amine, 6-[4-(2-dimethylamino-ethoxy)-3-methoxy-phenyl]-pyridin-2-yl-amine, 6-[4-(2-pyrrolidinyl-ethoxy)-3-methoxy-phenyl]-pyridin-2-yl-amine, 6-{4-[2-(6,7-dimethoxy-3,4-dihydro-1h-isoquinolin-2-yl)-ethoxy]-3-methoxy-phenyl}-pyridin-2-yl-amine, 6-{3-methoxy-4-[2-(4-phenethyl-piperazin-1-yl)-ethoxy]-phenyl}-pyridin-2-yl -amine, 6-{3-methoxy-4-[2-(4-methyl-piperazin-1-yl)-ethoxy]-phenyl}-pyridin-2-yl-amine, 6-{4-[2-(4-dimethylamin-o-piperidin-1-yl)-ethoxy]-3-methoxy-phenyl}-pyridin-2-yl-amine, 6-[4-(2-dimethylamino-ethoxy)-3-ethoxy-phenyl]-pyridin-2-yl-amine, 6-[4-(2-pyrrolidinyl-ethoxy)-3-ethoxy-phenyl]-pyridin-2-yl-amine, 6-[4-(2-dimethylamino-ethoxy)-2-isopropyl-phenyl]-pyridin-2-yl-amine, 4-(6-amino-pyridin-yl)-3-cyclopropyl-phenol 6-[2-cyclopropyl-4-(2-dimethylamino-ethoxy)-phenyl]-pyridin-2-yl-amine, 6-[2-cyclopropyl-4-(2-pyrrolidin-1-yl-ethoxy)-phenyl]-pyridin-2-yl-amine, 3-[3-(6-amino-pyridin-2yl)-4-cycl-opropyl-phenoxy]-pyrrolidine-1-carboxylic acid tert-butyl ester 6-[2-cyclopropyl-4-(1-methyl-pyrrolidin-3-yl-oxy)-phenyl]-pyridin-2-yl-amine, 4-(6-amino-pyridin-2-yl)-3-cyclobutyl-phenol 6-[2-cyclobutyl-4-(2-dime-thylamino-ethoxy)-phenyl]-pyridin-2-yl-amine, 6-[2-cyclobutyl-4-(2-pyrrolid-in-1-yl-ethoxy)-phenyl]-pyridin-2-yl-amine, 6-[2-cyclobutyl-4-(1-methyl-pyr-rolidin-3-yl-oxy)-phenyl]-pyridin-2-yl-amine, 4-(6-amino-pyridin-2-yl)-3-cyclopentyl-phenol 6-[2-cyclopentyl-4-(2-dimethylamino-ethoxy)-phenyl]-pyrid-in-2-yl-amine, 6-[2-cyclopentyl-4-(2-pyrrolidin-1yl-ethoxy)-phenyl]-pyridin-2-yl-amine, 3-[4-(6-amino-pyridin-2yl)-3-methoxy-phenoxy]-pyrrolidine-1-ca-rboxylic acid tert butyl ester 6-[4-(1-methyl-pyrrolidin-3-yl-oxy)-2-metho-xy-phenyl]-pyridin-2-yl-amine, 4-[4-(6-amino-pyridin-2yl)-3-methoxy-phenoxy-]-piperidine-1-carboxylic acid tert butyl ester 6-[2-methoxy-4-(1-methyl-p-iperidin-4-yl-oxy)-phenyl]-pyridin-2-yl-amine, 6-[4-(allyloxy)-2-methoxy-ph-enyl]-pyridin-2-yl-amine, 4-(6-amino-pyridin-2-yl)-3-methoxy-6-allyl-phenol 12 and 4-(6-amino-pyridin-2-yl)-3-methoxy-2-allyl-phenol 13 4-(6-amino-pyridin-2-yl)-3-methoxy-6-propyl-phenol 6-[4-(2-dimethylamino-ethoxy)-2-methoxy-5-propyl-phenyl]-pyridin-yl-amine, 6-[2-isopropyl-4-(pyrrolidin-3-yl-oxy)-phenyl]-pyridin-2-yl-amine, 6-[2-isopropyl-4-(piperidin-3-yl-oxy)-phenyl]-pyridin-2-yl-amine, 6-[2-i sopropyl-4-(1-methyl-azetidin-3-yl-oxy)-phenyl]-pyridin-2-yl-amine, 6-[2-isopropyl-4-(1-methyl-piperidin-4-yl-oxy)-phenyl]-pyridin-2-yl-amine, 6-[2-isopropyl-4-(1-methyl-pyrrolidin-3-yl-oxy)-phenyl]-pyridin-2-yl-amin-e 6-[2-isopropyl-4-(1-methyl-pyrrolidin-3-yl-oxy)-phenyl]-pyridin-2-yl-amine, 6-[2-isopropyl-4-(2-methyl-2-aza-bicyclo[2.2.1]hept-5-yl-oxy)-phenyl]-p-yridin-2-yl-amine, 6-[4-(2-dimethylamino-ethoxy)-2-methoxy-phenyl]-pyridin-2-yl-amine, 6-{4-[2-(benzyl-methyl-amino)-ethoxy]-2-methoxy-phenyl}-pyridin-2-yl-amine, 6-[2-methoxy-4-(2-pyrrolidin-1-yl-ethoxy)-phenyl]-pyridin-2-yl-amine, 2-(6-amino-pyridin-2-yl)-5-(2-dimethylamino-ethoxy)-phenol 2-[4-(6-amino-pyridin-2-yl)-3-methoxy-phenoxy]-acetamide 6-[4-(2-amino-ethoxy)-2-methoxy-phenyl]-pyridin-2-yl-amine, 6-{4-[2-(3,4-dihydro-1h-isoquinolin-2-yl)-ethoxy]-2-methoxy-phenyl}-pyrid-in-2-yl-amine, 2-[4-(6-amino-pyridin-2-yl)-3-methoxy-phenoxy]-ethanol 6-{2-methoxy-4-[2-(2,2,6,6-tetramethyl-piperidin-1-yl)-ethoxy]-phenyl}-py-ridin-2-yl-amine, 6-{4-[2-(2,5-dimethyl-pyrrolidin-1-yl)-ethoxy]-2-methoxy-phenyl}-pyridin-2-yl-amine, 6-{4-[2-(2,5-dimethyl-pyrrolidin-1-yl)-ethoxy]-2-methoxy-phenyl}-pyridin-2-yl-amine, 2-[4-(6-amino-pyridin-2-yl)-3-methoxy-phenoxy]-1-(2,2,6,6-tetramethyl-piperidin-1-yl)-ethanone 6-[2-methoxy-4-(1-methyl-pyrrolidin-2-yl-methoxy)-phenyl]-pyridin-2-yl-amine, 6-[4-(2-dimethylamino-ethoxy)-2-propoxy-phenyl]-pyridin-2-yl-amine, 6-{4-[2-(benzyl-methyl-amino)-ethoxy]-2-propoxy-phenyl}-pyridin-2-yl-amin-e 6-[4-(2-ethoxy-ethoxy)-2-methoxy-phenyl]-pyridin-2-yl-amine, 6-[4-(2-dimethylamino-ethoxy)-2-isopropoxy-phenyl]-pyridin-2-yl-amine, 6-[4-(2-ethoxy-ethoxy)-2-isopropoxy-phenyl]-pyridin-2-yl-amine, 6-[2-methoxy-4-(3-methyl-butoxy)-phenyl]-pyridin-2-yl-amine, 6-[4-(2-dimethylamino-ethoxy)-2-ethoxy-phenyl]-pyridin-2-yl-amine, 6-{4-[2-(benzyl-methyl-amino)-ethoxy]-2-ethoxy-phenyl}-pyridin-2-yl-amine, 6-[2-ethoxy-4-(3-methyl-butoxy)-phenyl]-pyridin-2-yl-amine, 1-(6-amino-3-aza-bicyclo[3.1.0]hex-3-yl)-2-[4-(6-amino-pyridin-2-yl)-3-et-hoxy-phenoxy]-ethanone 6-[2-ethoxy-4-(2-pyrrolidin-1-yl-ethoxy)-phenyl]-py-ridin-2-yl-amine, 3-{2-[4-(6-amino-pyridin-2-yl)-3-ethoxy-phenoxy]-ethyl}-3-aza-bicyclo[3.1.0]hex-6-yl-amine, 1-(6-amino-3-aza-bicyclo[3.1.0]hex-3-yl)-2-[4-(6-amino-pyridin-2-yl)-3-methoxy-phenoxy]-ethanone 3-{2-[4-(6-amino-pyridin-2-yl)-3-methoxy-phenoxy]-ethyl}-3-aza-bicyclo[3.1.0]hex-6-yl-amine, 6-[2-isopropoxy-4-(2-pyrrolidin-1-yl-ethoxy)-phenyl]-py-ridin-2-yl-amine, 6-{4-[2-(benzyl-methyl-amino)-ethoxy]-2-isopropoxy-phenyl-}-pyridin-2-yl-amine, 6-[4-(2-dimethylamino-ethoxy)-2-methoxy-5-propyl-phen-yl]-pyridin-2-yl-amine, 6-[5-allyl-4-(2-dimethylamino-ethoxy)-2-methoxy-phe-nyl]-pyridin-2-yl-amine, 6-[5-allyl-2-methoxy-4-(2-pyrrolidin-1-yl-ethoxy)-phenyl]-pyridin-2-yl-amine, 6-[3-allyl-4-(2-dimethylamino-ethoxy)-2-methoxy-phenyl]-pyridin-2-yl-amine, 6-[2-methoxy-4-(pyrrolidin-3-yl-oxy)-phenyl]-p-yridin-2-yl-amine, 6-[2-methoxy-4-(1-methyl-pyrrolidin-3-yl-oxy)-phenyl]-py-ridin-2-yl-amine, 6-[2-ethoxy-4-(pyrrolidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-methoxy-4-(piperidin-4-yl-oxy)-phenyl]-pyridin-2-yl-amine, 6-[2-methoxy-4-(2,2,6,6-tetramethyl-piperidin-4-yl-oxy)-phenyl]-pyridin-2-yl-amine, 6-[2-isopropoxy-4-(pyrrolidin-3-yl-oxy)-phenyl]-pyridin-2-yl-amine, 3-[4-(6-amino-pyridin-2-yl)-3-methoxy-phenoxy]-azetidine-1-carboxylic acid tert-butyl ester 6-[4-(azetidin-3-yl-oxy)-2-methoxy-phenyl]-pyridin-2-yl-amine, 6-[2-methoxy-4-(1-methyl-azetidin-3-yl-oxy)-phenyl]-pyridin-2-y-1-amine, 6-[2-isopropoxy-(pyrrolidin-3-yl-oxy)-phenyl]-pyridin-2-yl-amine, 6-[2-isopropoxy-4-(pyrrolidin-3-yl-oxy)-phenyl]-pyridin-2-yl-amine, 6-[2-methoxy-4-(pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-methoxy-4-(1-methyl-pyrrolidin-3-yl-oxy)-phenyl]-pyridin-2-yl-amine, 6-[2-methoxy-4-(2-methyl-2-aza-bicyclo[2.2.1]hept-5-yl-oxy)-phenyl]-pyrid-in-2-yl-amine, 6-[2-methoxy-4-(1-methyl-piperidin-4-yl-oxy)-phenyl]-pyridin-2-yl-amine, 6-[4-(1-ethyl-piperidin-4-yl-oxy)-2-methoxy-phenyl]-pyridin-2-yl-amine, 6-[5-allyl-2-methoxy-4-(1-methyl-pyrrolidin-3-yl-oxy)-phenyl]-pyr-idin-2-yl-amine, 6-[4-(2-dimethylamino-ethoxy)-2,6-dimethyl-phenyl]-pyridin-2-yl-amine, 6-[2,6-dimethyl-4-(3-piperidin-1-yl-propoxy)-phenyl]-pyridin-2-yl-amine, 6-[2,6-dimethyl-4-(2-pyrrolidin-1-yl-ethoxy)-phenyl]-pyridin-2-y-1-amine, 6-{2,6-dimethyl-4-[3-(4-methyl-piperazin-1-yl)-propoxy]-phenyl}-py-ridin-2-yl-amine, 6-[2,6-dimethyl-4-(2-morpholin-4-yl-ethoxy)-phenyl]-pyrid-in-2-yl-amine, 6-{4-[2-(benzyl-methyl-amino)-ethoxy]-2,6-dimethyl-phe-nyl}-p-pyridin-2-yl-amine, 2-[4-(6-amino-pyridin-2-yl)-3,5-dimethyl-phenoxy]-acetam-ide 6-[4-(2-amino-ethoxy)-2,6-dimethyl-phenyl]-pyridin-2-yl-amine, 6-[2-isopropyl-4-(2-pyrrolidin-1-yl-ethoxy)-phenyl]-pyridin-2-yl-amine, 2-(2,5-dimethyl-pyrrolidin-1-yl)-6-[2-isopropyl-4-(2-pyrrolidin-1-yl-etho-xy)-phenyl]-pyridine 6-{4-[2-(3,5-dimethyl-piperidin-1-yl)-ethoxy]-2-isopr-opyl-phenyl}-pyridin-2-yl-amine, 6-[4-(2-dimethylamino-ethoxy)-2-isopropyl-phenyl]-pyridin-2-yl-amine, 6-[2-tert-butyl-4-(2-dimethylamino-ethoxy)-phen-yl]-pyridin-2-yl-amine, 6-[2-tert-butyl-4-(2-pyrrolidin-1-yl-ethoxy)-phenyl-]-pyridin-2-yl-amine, 6-[4-(2-pyrrolidinyl-ethoxy)-2,5-dimethyl-phenyl]-pyr-idin-2-yl-amine, 6-[4-(2-dimethylamino-ethoxy)-2,5-dimethyl-phenyl]-pyridin-2-yl-amine, 6-[4-(2-(4-phenethylpiperazin-1-yl)-ethoxy)-2,5-dimethyl-pheny-1]-pyridin-2-yl-amine, 6-[2-cyclopropyl-4-(2-dimethylamino-1-methyl-ethoxy)-phenyl]-pyridin-2-yl-amine, 6-[cyclobutyl-4-(2-dimethylamino-1-methyl-etho-xy)-phenyl]-pyridin-2-yl-amine, 6-[4-(allyloxy)-2-cyclobutyl-phenyl]-pyridi-n-2ylamine, 2-allyl-4-(6-amino-pyridin-2-yl)-3-cyclobutyl-phenol and 4-allyl-4-(6-amino-pyridin-2-yl)-5-cyclobutyl-phenol 4-(6-amino-pyridin-2yl)-5-cyclobutyl-2-propyl-phenol 4-(6-amino-pyridin-2yl)-3-cyclobutyl-2-propyl-phenol 6-[2-cyclobutyl-4-(2-dimethylamino-1-methyl-ethoxy)-5-propyl-phenyl]-pyri-din-2-yl-amine, 6-[2-cyclobutyl-4-(2-dimethylamino-1-methyl-ethoxy)-3-propy-1-phenyl]-pyridin-2-yl-amine, 6-[2-cyclobutyl-4-(2-dimethylamino-ethoxy)-5-propyl-phe-nyl]-pyridin-2-yl-amine, 6-[2-cyclobutyl-4-(2-dimethy-lamino-ethox-y)-3-propyl-phenyl]-pyridin-2-yl-amine, 6-[2-cyclobutyl-4-(1-methyl-pyrroli-din-3-yl-oxy)-5-pro-pyl-phenyl]-pyridin-2-yl-amine, 6-[cyclobutyl-4-(1-methy-1-pyrrolidin-3-yl-oxy)-3-propyl-phenyl]-pyridin-2-yl-amine, 2-(4-benzyloxy-5-hydroxy-2-methoxy-phenyl)-6-(2,5-dimethyl-pyrrol-1-yl)-p-yridine 6-[4-(2-dimethylamino-ethoxy)-5-ethoxy-2-methoxy-phenyl]-pyridin-2-yl-amine, 6-[5-ethyl-2-methoxy-4-(1-methyl-piperidin-4-yl-oxy)-phe-nyl]-pyr-idin-2-yl-amine, 6-[5-ethyl-2-methoxy-4-(piperi-din-4-yl-oxy)-phenyl]-pyridi-n-2-yl-amine, 6-[2,5-dimethoxy-4-(1-methyl-pyrrolidin-3-yl-oxy)-phenyl]-pyr-idin-2-yl-amine, 6-[4-(2-dimethylamino-ethoxy)-5-ethyl-2-methoxy-phenyl]-py-ridin-2-yl-amine.

Exemplary NMDA receptor antagonist include (+)-(1S, 2S)-1-(4-hydroxy-phenyl)-2-(4-hydroxy-4-phenylpiperi-dino)-1-pro-panol, (1S, 2S)-1-(4-hydroxy-3-methoxyphe-nyl)-2-(4-hydroxy-4-phenylpiperi-dino)-1-propanol, (3R, 4S)-3-(4-(4-fluorophenyl)-4-hydroxypiperidin-1-yl-)-chro-man-4,7-diol, (1R*, 2R*)-1-(4-hydroxy-3-methylphenyl)-2-(4-(4-fluoro-phenyl)-4-hydroxypiperidin-1-yl)-propan-1-ol-mesylate or a pharmaceutically acceptable acid addition salt thereof.

Exemplary dopamine agonist include ropininole; L-dopa decarboxylase inhibitors such as carbidopa or benserazide, bromocriptine, dihydroergocryptine, etisulergine, AF-14, alaptide, pergolide, piribedil; dopamine D1 receptor ago-nists such as A-68939, A-77636, dihydrexine, and SKF-38393; dopamine D2 receptor agonists such as carbergoline, lisuride, N-0434, naxagolide, PD-118440, pramipexole, quinpirole and ropinirole; dopamine/β-adrenegeric receptor agonists such as DPDMS and dopexamine; dopamine/5-HT uptake inhibitor/5-HT-1A agonists such as roxindole; dopamine/opiate receptor agonists such as NIH-10494; α2-adrenergic antagonist/dopamine agonists such as terguride; α2-adrenergic antagonist/dopamine D2 agonists such as ergolines and talipexole; dopamine uptake inhibitors such as GBR-12909, GBR-13069, GYKI-52895, and NS-2141; monoamine oxidase-B inhibitors such as selegiline, N-(2-butyl)-N-methylpropargylamine, N-methyl-N-(2-pentyl) propargylamine, AGN-1133, ergot derivatives, lazabemide, LU-53439, MD-280040 and mofegiline; and COMT inhibitors such as CGP-28014.

Exemplary acetyl cholinesterase inhibitors include donepizil, 1-(2-methyl-1H-benzimida-zol-5-yl)-3-[1-(phenylmethyl)-4-piperidinyl]-1-propanone; 1-(2-phenyl-1H-benzimidazol-5-yl)-3-[1-(phenylmethyl)-4-piperidinyl]-1-propanone; 1-(1-ethyl-2-methyl-1H-benzimidazol-5-yl)-3-[1-(phenylmethyl)-4-p-iperidinyl]-1-propanone; 1-(2-methyl-6-benzothiazolyl)-3-[1-(phenylmethyl)-4-piperidinyl]-1-propanone; 1-(2-methyl-6-benzothiazolyl)-3-[1-[(2-methyl-4-thiazolyl)methyl]-4-piperidinyl]-1-propanone; 1-(5-methyl-benzo[b]thie-n-2-yl)-3-[1-(phenylmethyl)4-piperidinyl]-1-propanone; 1-(6-methyl-benzo[b]thien-2-yl)-3-[1-(phenylmethyl)-4-piperidinyl]-1-prop-anone; 1-(3,5-dimethyl-benzo[b]thien-2-yl)-3-[1-(phenylmethyl)-4-piperidin-yl]-1-propanone; 1-(benzo[b]thien-2-yl)-3-[1-(phenylmethyl)-4-piperidinyl]-1-propanone; 1-(benzofuran-2-yl)-3-[1-(phenylmethyl)-4-piperidinyl]-1-pro-panone; 1-(1-phenylsulfonyl-6-methyl-indol-2-yl)-3-[1-(phenylmethyl)-4-pip-eridinyl]-1-propanone; 1-(6-methyl-indol-2-yl)-3-[1-(phenylmethyl)-4-piper-idinyl]-1-propanone; 1-(1-phenylsulfonyl-5-amino-indol-2-yl)-3-[1-(phenylm-ethyl)-4-piperidinyl]-1-propanone; 1-(5-amino-indol-2-yl)-3-[1-(phenylmet-hyl)-4-piperidinyl]-1-propanone; and 1-(5-acetylamino-indol-2-yl)-3-[1-(ph-enylmethyl)-4-piperidinyl]-1-propanone. 1-(6-quinolyl)-3-[1-(phenylmethyl)-4-piperidinyl]-1-propanone; 1-(5-indolyl)-3-[1-(phenylmethyl)-4-piperidiny-1]-1-propanone; 1-(5-benzthienyl)-3-[1-(phenylmethyl)-4-piperidinyl]-1-pro-panone; 1-(6-quinazolyl)-3-[1-(phenylmethyl)-4-piperidinyl]-1-propanone; 1-(6-benzoxazolyl)-3-[1-(phenylmethyl)-4-piperidinyl]-1-propanone; 1-(5-benzofuryl)-3-[1-(phenylmethyl)-4-piperidinyl]-1-propanone; 1-(5-methyl-benzimidazol-2-yl)-3-[1-(phenylmethyl)-4-piperidinyl]-1-propa-none; 1-(6-methyl-benzimidazol-2-yl)-3-[1-(phenylmethyl)-4-piperidinyl]-1-propanone; 1-(5-chloro-benzo[b]thien-2-yl)-3-[1-(phenylmethyl)-4-piperidin-yl]-1-propanone; 1-(5-azaindol-2-yl)-3-[1-(phenylmethyl)4-piperidinyl]-1-p-ropanone; 1-(6-azabenzo[b]thien-2-yl)-3-[1-(phenylmethyl)-4-piperidinyl]-1-propanone; 1-(1H-2-oxo-pyrrolo[2',3',5,6]benzo[b]thieno-2-yl)-3-[1-(phenylmethyl)-4-piperidinyl]-1-pro-panone; 1-(6-methyl-benzothiazol-2-yl)-3-[1-(phenylmethyl)-4-piperidinyl]-1-propanone; 1-(6-methoxy-indol-2-yl)-3-[1-(phenylmethyl)-4-piperidinyl]-1-propanone; 1-(6-methoxy-benzo[b]thien-2-yl)-3-[1-(phenylmethyl)-4-piperidinyl]-11-pro-panone; 1-(6-acetylamino-benzo[b]thien-2-yl)-3-[1-(phenylmethyl)-4-piperid-inyl]-1-propanone; 1-(5-acetylamino-benzo[b]thien-2-yl)-3-[1-(phenylmethyl-)-4-piperidinyl]-1-propanone; 6-hydroxy-3-[2-[1-(phenylmethyl)-4-piperidin-yl]ethyl]-1,2-benzisoxazole; 5-methyl-3-[2-[1-(phenylmethyl)-4-piperidinyl-]ethyl]-1,2-benzisoxazole; 6-methoxy-3[2-[1(phenylmethyl)-4-piperidinyl]et-hyl]-1,2-benzisoxazole; 6-acetamide-3-[2-[1-(phenylmethyl)-4-piperidinyl]-ethyl]-1,2-benzisoxazole; 6-amino-3-[2-[1-(phenymethyl)-4-piperidinyl]ethy-l]-1,2-benzisoxazole; 6-(4-morpholinyl)-3-[2-[1-(phenylmethyl)-4-piperidin-yl] ethyl]-1,2-benzisoxazole; 5,7-dihydro-3-[2-[1-(phenylm-ethyl)-4-piperidi-nyl]ethyl]-6H-pyrrolo[4,5-f]-1,2-benzisoxazol-6-one; 3-[2-[1-(phenylmethyl)-4-piperidinyl] ethyl]-1,2-benzisothiazole; 3-[2-[1-(phenylmethyl)-4-piperidinyl]ethenyl]-1,2-benzisoxazole; 6-phenylamino-3-[2-[1-(phenylmethyl)-4-piperidinyl]ethyl]-1,2,-benzisoxaz-ole; 6-(2-thiazoly)-3-[2-[1-(phenylmethyl)-4-piperidinyl] ethyl]-1,2-benzis-oxazole; 6-(2-oxazolyl)-3-[2-[1-(phenylmethyl)-4-piperidinyl]ethyl]-1,2-be-nzisoxazole; 6-pyrrolidinyl-3-[2-[1-(phenylmethyl)-4-piperidinyl]ethyl]-1,2-benzisoxazole; 5,7-dihydro-5,5-dimethyl-3-[2-[1-(phe-nylmethyl)-4-piperid-inyl]ethyl]-6H-pyrrolo[4,5-f]-1,2-benzisoxazole-6-one; 6,8-dihydro-3-[2-[1-(phenylmethyl)-4-piperidinyl]ethyl]-7H-pyrrolo[5,4-g]-1,2-benzisoxazole-7-one; 3-[2-[1-(phenylmethyl)-4-piperidinyl]ethyl]-5,6,-8-trihydro-7H-isoxazolo[4,5-g]-quinolin-7-one; 1-benzyl-4-((5,6-dimethoxy-1-indanon)-2-yl)methylpiperidine, 1-benzyl-4-((5,6-dimethoxy-1-indanon)-2-ylidenyl)methylpiperidine, 1-benzyl-4-((5-methoxy-1-indanon)-2-yl)methylp-iperidine, 1-benzyl-4-((5,6-diethoxy-1-indanon)-2-yl)methylpiperidine, 1-benzyl-4-((5,6-methnylenedioxy-1-indanon)-2-yl)methylpiperidine, 1-(m-nitrobenzyl)-4-((5,6-dimethoxy-1-indanon)-2-yl)methylpiperidine, 1-cyclohexymethyl-4-((5,6-dimethoxy-1-indanon)-2-yl)methylpiperidine, 1-(m-florobenzyl)-4-((5,6-dimethoxy-1-indanon)-2-yl)methylpiperidine, 1-benzyl-4-((5,6-dimethoxy-1-indanon)-2-yl)propylpiperidine, and 1-benzyl-4-((5-isopropoxy-6-methoxy-1-indanon)-2-yl)methylpiperidine.

Exemplary calcium channel antagonists include diltiazem, omega-conotoxin GVIA, methoxyverapamil, amlodipine, felodipine, lacidipine, and mibefradil.

Exemplary GABA-A receptor modulators include clomethiazole; IDDB; gaboxadol (4,5,6,7-tetrahydroisoxazolo[5,4-c]pyridin-3-ol); ganaxolone (3α-hydroxy-3β-methyl-5α-pregnan-20-one); fengabine (2-[(butylimino)-(2-chlorophenyl)methyl]-4-chlorophenol); 2-(4-methoxyphenyl)-2,5,6,7,8,9-hexahydro-pyrazolo[4,3-c]cinnolin-3-one; 7-cyclobutyl-6-(2-methyl-2H-1,2,4-triazol-3-ylmethoxy)-3-phenyl-1,2,4-triazolo[4,3-b]pyridazine; (3-fluoro-4-methylphenyl)-N-({-1-[(2-methylphenyl)methyl]-benzimidazol-2-yl}methyl)-N-pentylcarboxamide; and 3-(aminomethyl)-5-methylhexanoic acid.

Exemplary potassium channel openers include diazoxide, flupirtine, pinacidil, levcromakalim, rilmakalim, chromakalim, PCO-400 and SKP-450 (2-[2"(1",3"-dioxolone)-2-methyl]-4-(2'-oxo-1'-pyrrolidinyl)-6-nitro-2H-1-benzopyra-n).

Exemplary AMPA/kainate receptor antagonists include 6-cyano-7-nitroquinoxalin-2,3-di-one (CNQX); 6-nitro-7-sulphamoylbenzo[f]quinoxaline-2,3-dione (NBQX); 6,7-dinitroquinoxaline-2,3-dione (DNQX); 1-(4-aminophenyl)-4-methyl-7,8-m-ethylenedioxy-5H-2,3-benzodiazepine hydrochloride; and 2,3-dihydroxy-6-nitro-7-sulfamoyl-benzo-[f]quinoxaline.

Exemplary sodium channel antagonists include ajmaline, procainamide, flecainide and riluzole.

Exemplary matrix-metalloprotease inhibitors include 4-[4-(4-fluorophenoxy)benzenesulfon-ylamino]tetrahydro-pyran-4-carboxylic acid hydroxyamide; 5-Methyl-5-(4-(4'-fluorophenoxy)-phenoxy)-pyrimidine-2,4,6-trione; 5-n-Butyl-5-(4-(4'-fluorophenoxy)-phenoxy)-pyrimidine-2,4,6-trione and prinomistat.

Poly(ADP ribose) polymerase (PARP) is an abundant nuclear enzyme which is activated by DNA strand single breaks to synthesize poly (ADP ribose) from NAD. Under normal conditions, PARP is involved in base excision repair caused by oxidative stress via the activation and recruitment of DNA repair enzymes in the nucleus. Thus, PARP plays a role in cell necrosis and DNA repair. PARP also participates in regulating cytokine expression that mediates inflammation. Under conditions where DNA damage is excessive (such as by acute excessive exposure to a pathological insult), PARP is over-activated, resulting in cell-based energetic failure characterized by NAD depletion and leading to ATP consumption, cellular necrosis, tissue injury, and organ damage/failure. PARP is thought to contribute to neurodegeneration by depleting nicotinamide adenine dinucleotide (NAD+) which then reduces adenosine triphosphate (ATP; Cosi and Marien, Ann. N.Y. Acad. Sci., 890:227, 1999) contributing to cell death which can be prevented by PARP inhibitors. Exemplory PARP inhibitors can be found in Southan and Szabo, Current Medicinal Chemistry, 10:321, 2003.

Exemplary inhibitors of p38 MAP kinase and c-jun-N-terminal kinases include pyridyl imidazoles, such as PD 169316, isomeric PD 169316, SB 203580, SB 202190, SB 220026, and RWJ 67657. Others are described in U.S. Pat. No. 6,288,089, and incorporated by reference herein.

In an exemplary embodiment, a combination therapy for treating or preventing MS comprises a therapeutically effective amount of one or more sirtuin-modulating compounds that increase the level and/or activity of a sirtuin protein and one or more of Avonex® (interferon beta-1a), Tysabri® (natalizumab), or Fumaderm® (BG-12/Oral Fumarate).

In another embodiment, a combination therapy for treating or preventing diabetic neuropathy or conditions associated therewith comprises a therapeutically effective amount of one or more sirtuin-modulating compounds that increase the level and/or activity of a sirtuin protein and one or more of tricyclic antidepressants (TCAs) (including, for example, imipramine, amytriptyline, desipramine and nortriptyline), serotonin reuptake inhibitors (SSRIs) (including, for example, fluoxetine, paroxetine, sertralene, and citalopram) and antiepileptic drugs (AEDs) (including, for example, gabapentin, carbamazepine, and topimirate).

In another embodiment, the invention provides a method for treating or preventing a polyglutamine disease using a combination comprising at least one sirtuin activating compound and at least one HDAC I/II inhibitor. Examples of HDAC I/II inhibitors include hydroxamic acids, cyclic peptides, benzamides, short-chain fatty acids, and depudecin.

Examples of hydroxamic acids and hydroxamic acid derivatives, but are not limited to, trichostatin A (TSA), suberoylanilide hydroxamic acid (SAHA), oxamflatin, suberic bishydroxamic acid (SBHA), m-carboxy-cinnamic acid bishydroxamic acid (CBHA), valproic acid and pyroxamide. TSA was isolated as an antifungi antibiotic (Tsuji et al (1976) J. Antibiot (Tokyo) 29:1-6) and found to be a potent inhibitor of mammalian HDAC (Yoshida et al. (1990) J. Biol. Chem. 265:17174-17179). The finding that TSA-resistant cell lines have an altered HDAC evidences that this enzyme is an important target for TSA. Other hydroxamic acid-based HDAC inhibitors, SAHA, SBHA, and CBHA are synthetic compounds that are able to inhibit HDAC at micromolar concentration or lower in vitro or in vivo. Glick et al. (1999) Cancer Res. 59:4392-4399. These hydroxamic acid-based HDAC inhibitors all possess an essential structural feature: a polar hydroxamic terminal linked through a hydrophobic methylene spacer (e.g. 6 carbon at length) to another polar site which is attached to a terminal hydrophobic moiety (e.g., benzene ring). Compounds developed having such essential features also fall within the scope of the hydroxamic acids that may be used as HDAC inhibitors.

Cyclic peptides used as HDAC inhibitors are mainly cyclic tetrapeptides. Examples of cyclic peptides include, but are not limited to, trapoxin A, apicidin and depsipeptide. Trapoxin A is a cyclic tetrapeptide that contains a 2-amino-8-oxo-9,10-epoxy-decanoyl (AOE) moiety. Kijima et al. (1993) J. Biol. Chem. 268:22429-22435. Apicidin is a fungal metabolite that exhibits potent, broad-spectrum antiprotozoal activitity and inhibits HDAC activity at nanomolar concentrations. Darkin-Rattray et al. (1996) Proc. Natl. Acad. Sci. USA. 93;13143-13147. Depsipeptide is isolated from Chromobacterium violaceum, and has been shown to inhibit HDAC activity at micromolar concentrations.

Examples of benzamides include but are not limited to MS-27-275. Saito et al. (1990) Proc. Natl. Acad. Sci. USA. 96:4592-4597. Examples of short-chain fatty acids include but are not limited to butyrates (e.g., butyric acid, arginine butyrate and phenylbutyrate (PB)). Newmark et al. (1994) Cancer Lett. 78:1-5; and Carducci et al. (1997) Anticancer Res. 17:3972-3973. In addition, depudecin which has been shown to inhibit HDAC at micromolar concentrations (Kwon et al. (1998) Proc. Natl. Acad. Sci. USA. 95:3356-3361) also falls within the scope of histone deacetylase inhibitor as described herein.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. After initiation of clotting, blood coagulation proceeds through the sequential activation of certain plasma proenzymes to their enzyme forms (see, for example, Coleman, R. W. et al. (eds.) *Hemostasis and Thrombosis, Second Edition*, (1987)). These plasma glycoproteins, including Factor XII, Factor XI, Factor IX, Factor X, Factor VII, and prothrombin, are zymogens of serine proteases. Most of these blood clotting enzymes are effective on a physiological scale only when assembled in complexes on membrane surfaces with protein cofactors such as Factor VIII and Factor V. Other blood factors modulate and localize clot formation, or dissolve blood clots. Activated protein C is a specific enzyme that inactivates procoagulant components. Calcium ions are involved in many of the component reactions. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place. It involves a cascade of complicated and regulated biochemical reactions between circulating blood proteins (coagulation factors), blood cells (in particular platelets), and elements of an injured vessel wall.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a sirtuin-modulating compound that increases the level and/or activity of a sirtuin protein. The compositions and methods disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites. Examples of thrombotic disorders include, but are not limited to, thromboembolism, deep vein thrombosis, pulmonary embolism, stroke, myocardial infarction, miscarriage, thrombophilia associated with anti-thrombin III deficiency, protein C deficiency, protein S deficiency, resistance to activated protein C, dysfibrinogenemia, fibrinolytic disorders, homocystinuria, pregnancy, inflammatory disorders, myeloproliferative disorders, arteriosclerosis, angina, e.g., unstable angina, disseminated intravascular coagulation, thrombotic thrombocytopenic purpura, cancer metastasis, sickle cell disease, glomerular nephritis, and drug induced thrombocytopenia (including, for example, heparin induced thrombocytopenia). In addition, sirtuin-modulating compounds that increase the level and/or activity of a sirtuin protein may be administered to prevent thrombotic events or to prevent re-occlusion during or after therapeutic clot lysis or procedures such as angioplasty or surgery.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents. For example, one or more sirtuin-modulating compounds can be combined with an effective amount of one or more of: aspirin, heparin, and oral Warfarin that inhibits Vit K-dependent factors, low molecular weight heparins that inhibit factors X and II, thrombin inhibitors, inhibitors of platelet GP IIbIIIa receptors, inhibitors of tissue factor (TF), inhibitors of human von Willebrand factor, inhibitors of one of more factors involved in hemostasis (in particular in the coagulation cascade). In addition, sirtuin-modulating compounds that increase the level and/or activity of a sirtuin protein can be combined with thrombolytic agents, such as t-PA, streptokinase, reptilase, TNK-t-PA, and staphylokinase.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem). Stunkard A J, Wadden T A. (Editors) Obesity: theory and therapy, Second Edition. New York: Raven Press, 1993. Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In other embodiments, a sirtuin-modulating compound that decreases the level and/or activity of a sirtuin protein may be used to stimulate appetite and/or weight gain. A method may comprise administering to a subject, such as a subject in need thereof, a pharmaceutically effective amount of a sirtuin-modulating agent that decreases the level and/or activity of a sirtuin protein, such as SIRT1 and/or SIRT3. A subject in need of such a treatment may be a subject who has cachexia or may be likely to develop cachexia. A combination of agents may also be administered. A method may further comprise monitoring in the subject the state of the disease or of activation of sirtuins, for example, in adipose tissue.

Methods for stimulating fat accumulation in cells may be used in vitro, to establish cell models of weight gain, which may be used, e.g., for identifying other drugs that prevent weight gain.

Also provided are methods for modulating adipogenesis or fat cell differentiation, whether in vitro or in vivo. In particular, high circulating levels of insulin and/or insulin like growth factor (IGF) 1 will be prevented from recruiting preadipocytes to differentiate into adipocytes. Such methods may be used to modulate obesity. A method for stimulating adipogenesis may comprise contacting a cell with a sirtuin-modulating agent that decreases the level and/or activity of a sirtuin protein.

In another embodiment, the invention provides methods of decreasing fat or lipid metabolism in a subject by administering a sirtuin-modulating compound that decreases the level and/or activity of a sirtuin protein. The method includes administering to a subject an amount of a sirtuin-modulating compound, e.g., in an amount effective to decrease mobilization of fat to the blood from WAT cells and/or to decrease fat burning by BAT cells.

Methods for promoting appetite and/or weight gain may include, for example, prior identifying a subject as being in need of decreased fat or lipid metabolism, e.g., by weighing the subject, determining the BMI of the subject, or evaluating fat content of the subject or sirtuin activity in cells of the subject. The method may also include monitoring the subject, e.g., during and/or after administration of a sirtuin-modulating compound. The administering can include one or more dosages, e.g., delivered in boluses or continuously. Monitoring can include evaluating a hormone or a metabolite. Exemplary hormones include leptin, adiponectin, resistin, and insulin. Exemplary metabolites include triglycerides, cholesterol, and fatty acids.

In one embodiment, a sirtuin-modulating compound that decreases the level and/or activity of a sirtuin protein may be used to modulate (e.g., increase) the amount of subcutaneous fat in a tissue, e.g., in facial tissue or in other surface-associated tissue of the neck, hand, leg, or lips. The sirtuin-modulating compound may be used to increase the rigidity, water retention, or support properties of the tissue. For example, the sirtuin-modulating compound can be applied topically, e.g., in association with another agent, e.g., for surface-associated tissue treatment. The sirtuin-modulating compound may also be injected subcutaneously, e.g., within the region where an alteration in subcutaneous fat is desired.

A method for modulating weight may further comprise monitoring the weight of the subject and/or the level of modulation of sirtuins, for example, in adipose tissue.

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents. Exemplary anti-obesity agents include, for example, phenylpropanolamine, ephedrine, pseudoephedrine, phentermine, a cholecystokinin-A agonist, a monoamine reuptake inhibitor (such as sibutramine), a sympathomimetic agent, a serotonergic agent (such as dexfenfluramine or fenfluramine), a dopamine agonist (such as bromocriptine), a melanocyte-stimulating hormone receptor agonist or mimetic, a melanocyte-stimulating hormone analog, a cannabinoid receptor antagonist, a melanin concentrating hormone antagonist, the OB protein (leptin), a leptin analog, a leptin receptor agonist, a galanin antagonist or a GI lipase inhibitor or decreaser (such as orlistat). Other anorectic agents include bombesin agonists, dehydroepiandrosterone or analogs thereof, glucocorticoid receptor agonists and antagonists, orexin receptor antagonists, urocortin binding protein antagonists, agonists of the glucagon-like peptide-1 receptor such as Exendin and ciliary neurotrophic factors such as Axokine.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention. Examples of medications that may cause weight gain, include for example, diabetes treatments, including, for example, sulfonylureas (such as glipizide and glyburide), thiazolidinediones (such as pioglitazone and rosiglitazone), meglitinides, nateglinide, repaglinide, sulphonylurea medicines, and insulin; anti-depressants, including, for example, tricyclic anti-depressants (such as amitriptyline and imipramine), irreversible monoamine oxidase inhibitors (MAOIs), selective serotonin reuptake inhibitors (SSRIs), bupropion, paroxetine, and mirtazapine; steroids, such as, for example, prednisone; hormone therapy; lithium carbonate; valproic acid; carbamazepine; chlorpromazine; thiothixene; beta blockers (such as propranolol); alpha blockers (such as clonidine, prazosin and terazosin); and contraceptives including oral contraceptives (birth control pills) or other contraceptives containing estrogen and/or progesterone (Depo-Provera, Norplant, Ortho), testosterone or Megestrol. In another exemplary embodiment, sirtuin-modulating compounds that increase the level and/or activity of a sirtuin protein may be administered as part of a smoking cessation program to prevent weight gain or reduce weight already gained.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compounds that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents. Exemplary anti-diabetic agents include, for example, an aldose reductase inhibitor, a glycogen phosphorylase inhibitor, a sorbitol dehydrogenase inhibitor, a protein tyrosine phosphatase 1B inhibitor, a dipeptidyl protease inhibitor, insulin (including orally bioavailable insulin preparations), an insulin mimetic, metformin, acarbose, a peroxisome proliferator-activated receptor-γ (PPAR-γ) ligand such as troglitazone, rosaglitazone, pioglitazone or GW-1929, a sulfonylurea, glipazide, glyburide, or chlorpropamide wherein the amounts of the first and second compounds result in a therapeutic effect. Other anti-diabetic agents include a glucosidase inhibitor, a glucagon-like peptide-1 (GLP-1), insulin, a PPAR α/γ dual agonist, a meglitimide and an αP2 inhibitor. In an exemplary embodiment, an anti-diabetic agent may be a dipeptidyl peptidase IV (DP-IV or DPP-IV) inhibitor, such as, for example LAF237 from Novartis (NVP DPP728; 1-[[[2-[(5-cyanopyridin-2-yl)amino]ethyl]amino] acetyl]-2-cyano-(S)-pyrrolidine) or MK-04301 from Merck (see e.g., Hughes et al., Biochemistry 38: 11597-603 (1999)).

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

Exemplary inflammatory conditions include, for example, multiple sclerosis, rheumatoid arthritis, psoriatic arthritis, degenerative joint disease, spondouloarthropathies, gouty arthritis, systemic lupus erythematosus, juvenile arthritis, rheumatoid arthritis, osteoarthritis, osteoporosis, diabetes (e.g., insulin dependent diabetes mellitus or juvenile onset diabetes), menstrual cramps, cystic fibrosis, inflammatory bowel disease, irritable bowel syndrome, Crohn's disease, mucous colitis, ulcerative colitis, gastritis, esophagitis, pancreatitis, peritonitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome. Exemplary inflammatory conditions of the skin include, for example, eczema, atopic dermatitis, contact dermatitis, urticaria, schleroderma, psoriasis, and dermatosis with acute inflammatory components.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases and/or inflammation associated with autoimmune diseases such as organ-tissue autoimmune diseases (e.g., Raynaud's syndrome), scleroderma, myasthenia gravis, transplant rejection, endotoxin shock, sepsis, psoriasis, eczema, dermatitis, multiple sclerosis, autoimmune thyroiditis, uveitis, systemic lupus erythematosus, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation. Exemplary anti-inflammatory agents include, for example, steroids (e.g., cortisol, cortisone, fludrocortisone, prednisone, 6α-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole, doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

Further examples of anti-inflammatory agents include, for example, aceclofenac, acemetacin, e-acetamidocaproic acid, acetaminophen, acetaminosalol, acetanilide, acetylsalicylic acid, S-adenosylmethionine, alclofenac, alclometasone, alfentanil, algestone, allylprodine, alminoprofen, aloxiprin, alphaprodine, aluminum bis(acetylsalicylate), amcinonide, amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antrafenine, apazone, beclomethasone, bendazac, benorylate, benoxaprofen, benzpiperylon, benzydamine, benzylmorphine, bermoprofen, betamethasone, betamethasone-17-valerate, bezitramide, α-bisabolol, bromfenac, p-bromoacetanilide, 5-bromosalicylic acid acetate, bromosaligenin, bucetin, bucloxic acid, bucolome, budesonide, bufexamac, bumadizon, buprenorphine, butacetin, butibufen, butorphanol, carbamazepine, carbiphene, carprofen, carsalam, chlorobutanol, chloroprednisone, chlorthenoxazin, choline salicylate, cinchophen, cinmetacin, ciramadol, clidanac, clobetasol, clocortolone, clometacin, clonitazene, clonixin, clopirac, cloprednol, clove, codeine, codeine methyl bromide, codeine phosphate, codeine sulfate, cortisone, cortivazol, cropropamide, crotethamide, cyclazocine, deflazacort, dehydrotestosterone, desomorphine, desonide, desoximetasone, dexamethasone, dexamethasone-21-isonicotinate, dexoxadrol, dextromoramide, dextropropoxyphene, deoxycorticosterone, dezocine, diampromide, diamorphone, diclofenac, difenamizole, difenpiramide, diflorasone, diflucortolone, diflunisal, difluprednate, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, enoxolone, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, fluazacort, flucloronide, flufenamic acid, flumethasone, flunisolide, flunixin, flunoxaprofen, fluocinolone acetonide, fluocinonide, fluocinolone acetonide, fluocortin butyl, fluocortolone, fluoresone, fluorometholone, fluperolone, flupirtine, fluprednidene, fluprednisolone, fluproquazone, flurandrenolide, flurbiprofen, fluticasone, formocortal, fosfosal, gentisic acid, glafenine, glucametacin, glycol salicylate, guaiazulene, halcinonide, halobetasol, halometasone, haloprednone, heroin, hydrocodone, hydrocortamate, hydrocortisone, hydrocortisone acetate, hydrocortisone succinate, hydrocortisone hemisuccinate, hydrocortisone 21-lysinate, hydrocortisone cypionate, hydromorphone, hydroxypethidine, ibufenac, ibuprofen, ibuproxam, imidazole salicylate, indomethacin, indoprofen, isofezolac, isoflupredone, isoflupredone acetate, isoladol, isomethadone, isonixin, isoxepac, isoxicam, ketobemidone, ketoprofen, ketorolac, p-lactophenetide, lefetamine, levallorphan, levorphanol, levophenacyl-morphan, lofentanil, lonazolac, lomoxicam, loxoprofen, lysine acetylsalicylate, mazipredone, meclofenamic acid, medrysone, mefenamic acid, meloxicam, meperidine, meprednisone, meptazinol, mesalamine, metazocine, methadone, methotrimeprazine, methylprednisolone, methylprednisolone acetate, methylprednisolone sodium succinate, methylprednisolone suleptnate, metiazinic acid, metofoline, metopon, mofebutazone, mofezolac, mometasone, morazone, morphine, morphine hydrochloride, morphine sulfate, morpholine salicylate, myrophine, nabumetone, nalbuphine, nalorphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paramethasone, paranyline, parsalmide, pentazocine, perisoxal, phenacetin, phenadoxone, phenazocine, phenazopyridine hydrochloride, phenocoll, phenoperidine, phenopyrazone, phenomorphan, phenyl acetylsalicylate, phenylbutazone, phenyl salicylate, phenyramidol, piketoprofen, piminodine, pipebuzone, piperylone, pirazolac, piritramide, piroxicam, pirprofen, pranoprofen, prednicarbate, prednisolone, prednisone, prednival, prednylidene, proglumetacin, proheptazine, promedol, propacetamol, properidine, propiram, propoxyphene, propyphenazone, proquazone, protizinic acid, proxazole, ramifenazone, remifentanil, rimazolium metilsulfate, salacetamide, salicin, salicylamide, salicylamide o-acetic acid, salicylic acid, salicylsulfuric acid, salsalate, salverine, simetride, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tixocortol, tolfenamic acid, tolmetin, tramadol, triamcinolone, triamcinolone acetonide, tropesin, viminol, xenbucin, ximoprofen, zaltoprofen and zomepirac.

In an exemplary embodiment, a sirtuin-modulating compound that increases the level and/or activity of a sirtuin protein may be administered with a selective COX-2 inhibitor for treating or preventing inflammation. Exemplary selective COX-2 inhibitors include, for example, deracoxib, parecoxib, celecoxib, valdecoxib, rofecoxib, etoricoxib, lumiracoxib, 2-(3,5-difluorophenyl)-3-[4-(methylsulfonyl)phenyl]-2-cyclopenten-1-one, (S)-6,8-dichloro-2-(trifluoromethyl)-2H-1-benzopyran-3-carboxylic acid, 2-(3,4-difluorophenyl)-4-(3-hydroxy-3-methyl-1-butoxy)-5-[4-(methylsulfonyl)phenyl]-3-(2H)-pyridazinone, 4-[5-(4-fluorophenyl)-3-(trifluoromethyl)-1H-pyrazol-1-yl]benzenesulfonamide, tert-butyl 1 benzyl-4-[(4-oxopiperidin-1-yl}sulfonyl]piperidine-4-carboxylate, 4-[5-(phenyl)-3-(trifluoromethyl)-1H-pyrazol-1-yl]benzenesulfonamide, salts and prodrugs thereof.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, faloxifene, antidepressants, anti-psychotics, chemotherapeutics, calcium channel blockers, and antibiotics.

In one embodiment, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

Nicotinic acid, 3-pyridinecarboxylic acid or niacin, is an antilipidemic agent that is marketed under, for example, the trade names Nicolar®, SloNiacin®, Nicobid® and Time Release Niacin®. Nicotinic acid has been used for many years in the treatment of lipidemic disorders such as hyperlipidemia, hypercholesterolemia and atherosclerosis. This compound has long been known to exhibit the beneficial effects of reducing total cholesterol, low density lipoproteins or "LDL cholesterol," triglycerides and apolipoprotein a (Lp(a)) in the human body, while increasing desirable high density lipoproteins or "HDL cholesterol".

Typical doses range from about 1 gram to about 3 grams daily. Nicotinic acid is normally administered two to four times per day after meals, depending upon the dosage form selected. Nicotinic acid is currently commercially available in two dosage forms. One dosage form is an immediate or rapid release tablet which should be administered three or four times per day. Immediate release ("IR") nicotinic acid formulations generally release nearly all of their nicotinic acid within about 30 to 60 minutes following ingestion. The other dosage form is a sustained release form which is suitable for administration two to four times per day. In contrast to IR formulations, sustained release ("SR") nicotinic acid formulations are designed to release significant quantities of drug for absorption into the blood stream over specific timed intervals in order to maintain therapeutic levels of nicotinic acid over an extended period such as 12 or 24 hours after ingestion.

As used herein, the term "nicotinic acid" is meant to encompass nicotinic acid or a compound other than nicotinic acid itself which the body metabolizes into nicotinic acid, thus producing essentially the same effect as nicotinic acid. Exemplary compounds that produce an effect similar to that of nicotinic acid include, for example, nicotinyl alcohol tartrate, d-glucitol hexanicotinate, aluminum nicotinate, niceritrol and d,1-alpha-tocopheryl nicotinate. Each such compound will be collectively referred to herein as "nicotinic acid."

In another embodiment, the invention provides a method for treating and/or preventing hyperlipidemia with reduced flushing side effects. The method comprises the steps of administering to a subject in need thereof a therapeutically effective amount of nicotinic acid and a sirtuin-modulating compound that increases the level and/or activity of a sirtuin protein in an amount sufficient to reduce flushing. In an exemplary embodiment, the nicotinic acid and/or sirtuin-modulating compound may be administered nocturnally.

In another representative embodiment, the method involves the use of sirtuin-modulating compounds that increase the level and/or activity of a sirtuin protein to reduce flushing side effects of raloxifene. Raloxifene acts like estrogen in certain places in the body, but is not a hormone. It helps prevent osteoporosis in women who have reached menopause. Osteoporosis causes bones to gradually grow thin, fragile, and more likely to break. Evista slows down the loss of bone mass that occurs with menopause, lowering the risk of spine fractures due to osteoporosis. A common side effect of raloxifene is hot flashes (sweating and flushing). This can be uncomfortable for women who already have hot flashes due to menopause.

In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, a 5HT2 receptor antagonist, an anticonvulsant, a norepinephrine reuptake inhibitor, an α-adrenoreceptor antagonist, an NK-3 antagonist, an NK-1 receptor antagonist, a PDE4 inhibitor, an Neuropeptide Y5 Receptor Antagonists, a D4 receptor antagonist, a 5HT1A receptor antagonist, a 5HT1D receptor antagonist, a CRF antagonist, a monoamine oxidase inhibitor, or a sedative-hypnotic drug.

In certain embodiments, sirtuin-modulating compounds that increase the level and/or activity of a sirtuin protein may be used as part of a treatment with a serotonin reuptake inhibitor (SRI) to reduce flushing. In certain preferred embodiments, the SRI is a selective serotonin reuptake inhibitor (SSRI), such as a fluoxetinoid (fluoxetine, norfluoxetine) or a nefazodonoid (nefazodone, hydroxynefazodone, oxonefazodone). Other exemplary SSRI's include duloxetine, venlafaxine, milnacipran, citalopram, fluvoxamine, paroxetine and sertraline. The sirtuin-modulating compound that increases the level and/or activity of a sirtuin protein can also be used as part of a treatment with sedative-hypnotic drug, such as selected from the group consisting of a benzodiazepine (such as alprazolam, chlordiazepoxide, clonazepam, chlorazepate, clobazam, diazepam, halazepam, lorazepam, oxazepam and prazepam), zolpidem, and barbiturates. In still other embodiments, a sirtuin-modulating compound that increases the level and/or activity of a sirtuin protein may be used as part of a treatment with a 5-HT1A receptor partial agonist, such as selected from the group consisting of buspirone, flesinoxan, gepirone and ipsapirone. Sirtuin-modulating compounds that increase the level and/or activity of a sirtuin protein can also used as part of a treatment with a norepinephrine reuptake inhibitor, such as selected from tertiary amine tricyclics and secondary amine tricyclics. Exemplary tertiary amine tricyclic include amitriptyline, clomipramine, doxepin, imipramine and trimipramine. Exemplary secondary amine tricyclic include amoxapine, desipramine, maprotiline, nortriptyline and protriptyline. In certain embodiments, sirtuin-modulating compounds that increase the level and/or activity of a sirtuin protein may be used as part of a treatment with a monoamine oxidase inhibitor, such as selected from the group consisting of isocarboxazid, phenelzine, tranylcypromine, selegiline and moclobemide.

In still another representative embodiment, sirtuin-modulating compounds that increase the level and/or activity of a sirtuin protein may be used to reduce flushing side effects of chemotherapeutic agents, such as cyclophosphamide, tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin. Levofloxacin is used to treat infections of the sinuses, skin, lungs, ears, airways, bones, and joints caused by susceptible bacteria. Levofloxacin also is frequently used to treat urinary infections, including those resistant to other antibiotics, as well as prostatitis. Levofloxacin is effective in treating infectious diarrheas caused by E. coli, campylobacter jejuni, and shigella bacteria. Levofloxacin also can be used to treat various obstetric infections, including mastitis.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

Glaucoma describes a group of disorders which are associated with a visual field defect, cupping of the optic disc, and optic nerve damage. These are commonly referred to as glaucomatous optic neuropathies. Most glaucomas are usually, but not always, associated with a rise in intraocular pressure. Exemplary forms of glaucoma include Glaucoma and Penetrating Keratoplasty, Acute Angle Closure, Chronic Angle Closure, Chronic Open Angle, Angle Recession, Aphakic and Pseudophakic, Drug-Induced, Hyphema, Intraocular Tumors, Juvenile, Lens-Particle, Low Tension, Malignant, Neovascular, Phacolytic, Phacomorphic, Pigmentary, Plateau Iris, Primary Congenital, Primary Open Angle, Pseudoexfoliation, Secondary Congenital, Adult Suspect, Unilateral, Uveitic, Ocular Hypertension, Ocular Hypotony, Posner-Schlossman Syndrome and Scleral Expansion Procedure in Ocular Hypertension & Primary Open-angle Glaucoma.

Intraocular pressure can also be increased by various surgical procedures, such as phacoemulsification (i.e., cataract surgery) and implanation of structures such as an artificial lens. In addition, spinal surgeries in particular, or any surgery in which the patient is prone for an extended period of time can lead to increased interoccular pressure.

Optic neuritis (ON) is inflammation of the optic nerve and causes acute loss of vision. It is highly associated with multiple sclerosis (MS) as 15-25% of MS patients initially present with ON, and 50-75% of ON patients are diagnosed with MS. ON is also associated with infection (e.g., viral infection, meningitis, syphilis), inflammation (e.g., from a vaccine), infiltration and ischemia.

Another condition leading to optic nerve damage is anterior ischemic optic neuropathy (AION). There are two types of AION. Arteritic AION is due to giant cell arteritis (vasculitis) and leads to acute vision loss. Non-arteritic AION encompasses all cases of ischemic optic neuropathy other than those due to giant cell arteritis. The pathophysiology of AION is unclear although it appears to incorporate both inflammatory and ischemic mechanisms.

Other damage to the optic nerve is typically associated with demyleination, inflammation, ischemia, toxins, or trauma to the optic nerve. Exemplary conditions where the optic nerve is damaged include Demyelinating Optic Neuropathy (Optic Neuritis, Retrobulbar Optic Neuritis), Optic Nerve Sheath Meningioma, Adult Optic Neuritis, Childhood Optic Neuritis, Anterior Ischemic Optic Neuropathy, Posterior Ischemic Optic Neuropathy, Compressive Optic Neuropathy, Papilledema, Pseudopapilledema and Toxic/Nutritional Optic Neuropathy.

Other neurological conditions associated with vision loss, albeit not directly associated with damage to the optic nerve, include Amblyopia, Bells Palsy, Chronic Progressive External Ophthalmoplegia, Multiple Sclerosis, Pseudotumor Cerebri and Trigeminal Neuralgia.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disrupton of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g. Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g. *Candida choroiditis, histoplasmosis*), protozoal infections (e.g. toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, a drug that raises intraocular pressure such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, retinal damage and the like, by administering to the subject in need of such treatment a therapeutic dosage of a sirtuin modulator disclosed herein.

The formation of cataracts is associated with several biochemical changes in the lens of the eye, such as decreased levels of antioxidants ascorbic acid and glutathione, increased lipid, amino acid and protein oxidation, increased sodium and calcium, loss of amino acids and decreased lens metabolism. The lens, which lacks blood vessels, is suspended in extracellular fluids in the anterior part of the eye. Nutrients, such as ascorbic acid, glutathione, vitamin E, selenium, bioflavonoids and carotenoids are required to maintain the transparency of the lens. Low levels of selenium results in an increase of free radical-inducing hydrogen peroxide, which is neutralized by the selenium-dependent antioxidant enzyme glutathione peroxidase. Lens-protective glutathione peroxidase is also dependent on the amino acids methionine, cysteine, glycine and glutamic acid. Cataracts can also develop due to an inability to properly metabolize galactose found in dairy products that contain lactose, a disaccharide composed of the monosaccharide galactose and glucose. Cataracts can be prevented, delayed, slowed and possibly even reversed if detected early and metabolically corrected.

Retinal damage is attributed, inter alia, to free radical initiated reactions in glaucoma, diabetic retinopathy and age-related macular degeneration (AMD). The eye is a part of the central nervous system and has limited regenerative capability. The retina is composed of numerous nerve cells which contain the highest concentration of polyunsaturated fatty acids (PFA) and subject to oxidation. Free radicals are generated by UV light entering the eye and mitochondria in the rods and cones, which generate the energy necessary to transform light into visual impulses. Free radicals cause peroxidation of the PFA by hydroxyl or superoxide radicals which in turn propagate additional free radicals. The free radicals cause temporary or permanent damage to retinal tissue.

Glaucoma is usually viewed as a disorder that causes an elevated intraocular pressure (IOP) that results in permanent damage to the retinal nerve fibers, but a sixth of all glaucoma cases do not develop an elevated IOP. This disorder is now perceived as one of reduced vascular perfusion and an increase in neurotoxic factors. Recent studies have implicated elevated levels of glutamate, nitric oxide and peroxynitirite in the eye as the causes of the death of retinal ganglion cells. Neuroprotective agents may be the future of glaucoma care. For example, nitric oxide synthase inhibitors block the formation of peroxynitrite from nitric oxide and superoxide. In a recent study, animals treated with aminoguanidine, a nitric oxide synthase inhibitor, had a reduction in the loss of retinal ganglion cells. It was concluded that nitric oxide in the eye caused cytotoxicity in many tissues and neurotoxicity in the central nervous system.

Diabetic retinopathy occurs when the underlying blood vessels develop microvascular abnormalities consisting primarily of microaneurysms and intraretinal hemorrhages. Oxidative metabolites are directly involved with the pathogenesis of diabetic retinopathy and free radicals augment the generation of growth factors that lead to enhanced proliferative activity. Nitric oxide produced by endothelial cells of the vessels may also cause smooth muscle cells to relax and result in vasodilation of segments of the vessel. Ischemia and hypoxia of the retina occur after thickening of the arterial basement membrane, endothelial proliferation and loss of pericytes. The inadequate oxygenation causes capillary obliteration or nonperfusion, arteriolar-venular shunts, sluggish blood flow and an impaired ability of RBCs to release oxygen. Lipid peroxidation of the retinal tissues also occurs as a result of free radical damage.

The macula is responsible for our acute central vision and composed of light-sensing cells (cones) while the underlying retinal pigment epithelium (RPE) and choroid nourish and help remove waste materials. The RPE nourishes the cones with the vitamin A substrate for the photosensitive pigments and digests the cones shed outer tips. RPE is exposed to high levels of UV radiation, and secretes factors that inhibit angiogenesis. The choroid contains a dense vascular network that provides nutrients and removes the waste materials.

In AMD, the shed cone tips become indigestible by the RPE, where the cells swell and die after collecting too much undigested material. Collections of undigested waste material, called drusen, form under the RPE. Photoxic damage also causes the accumulation of lipofuscin in RPE cells. The intracellular lipofuscin and accumulation of drusen in Bruch's membrane interferes with the transport of oxygen and nutrients to the retinal tissues, and ultimately leads to RPE and photoreceptor dysfunction. In exudative AMD, blood vessels grow from the choriocapillaris through defects in Bruch's membrane and may grow under the RPE, detaching it from the choroid, and leaking fluid or bleeding.

Macular pigment, one of the protective factors that prevent sunlight from damaging the retina, is formed by the accumulation of nutritionally derived carotenoids, such as lutein, the fatty yellow pigment that serves as a delivery vehicle for other important nutrients and zeaxanthin. Antioxidants such as vitamins C and E, beta-carotene and lutein, as well as zinc, selenium and copper, are all found in the healthy macula. In addition to providing nourishment, these antioxidants protect against free radical damage that initiates macular degeneration.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In one embodiment, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder. For example, one or more sirtuin-activating compounds can be combined with an effective amount of one or more of: an agent that reduces intraocular pressure, an agent for treating glaucoma, an agent for treating optic neuritis, an agent for treating CMV Retinopathy, an agent for treating multiple sclerosis, and/or an antibiotic, etc.

In one embodiment, a sirtuin modulator can be administered in conjunction with a therapy for reducing intraocular pressure. One group of therapies involves blocking aqueous production. For example, topical beta-adrenergic antagonists (timolol and betaxolol) decrease aqueous production. Topical timolol causes IOP to fall in 30 minutes with peak effects in 1-2 hours. A reasonable regimen is Timoptic 0.5%, one drop every 30 minutes for 2 doses. The carbonic anhydrase inhibitor, acetazolamide, also decreases aqueous production and should be given in conjunction with topical beta-antagonists. An initial dose of 500 mg is administered followed by 250 mg every 6 hours. This medication may be given orally, intramuscularly, or intravenously. In addition, alpha 2-agonists (e.g., Apraclonidine) act by decreasing aqueous production. Their effects are additive to topically administered beta-blockers. They have been approved for use in controlling an acute rise in pressure following anterior chamber laser procedures, but has been reported effective in treating acute closed-angle glaucoma. A reasonable regimen is 1 drop every 30 minutes for 2 doses.

A second group of therapies for reducing intraocular pressure involve reducing vitreous volume. Hyperosmotic agents can be used to treat an acute attack. These agents draw water out of the globe by making the blood hyperosmolar. Oral glycerol in a dose of 1 mL/kg in a cold 50% solution (mixed with lemon juice to make it more palatable) often is used. Glycerol is converted to glucose in the liver; persons with diabetes may need additional insulin if they become hyperglycemic after receiving glycerol. Oral isosorbide is a metabolically inert alcohol that also can be used as an osmotic agent for patients with acute angle-closure glaucoma. Usual dose is 100 g taken p.o. (220 cc of a 45% solution). This inert alcohol should not be confused with isosorbide dinitrate, a nitrate-based cardiac medication used for angina and for congestive heart failure. Intravenous mannitol in a dose of 1.0-1.5 mg/kg also is effective and is well tolerated in patients with nausea and vomiting. These hyperosmotic agents should be used with caution in any patient with a history of congestive heart failure.

A third group of therapies involve facilitating aqueous outflow from the eye. Miotic agents pull the iris from the iridocorneal angle and may help to relieve the obstruction of the trabecular meshwork by the peripheral iris. Pilocarpine 2% (blue eyes)-4% (brown eyes) can be administered every 15 minutes for the first 1-2 hours. More frequent administration or higher doses may precipitate a systemic cholinergic crisis. NSAIDS are sometimes used to reduce inflammation.

Exemplary therapeutic agents for reducing intraocular pressure include ALPHAGAN® P (Allergan) (brimonidine tartrate ophthalmic solution), AZOPT® (Alcon) (brinzolamide ophthalmic suspension), BETAGAN® (Allergan) (levobunolol hydrochloride ophthalmic solution, USP), BETIMOL® (Vistakon) (timolol ophthalmic solution), BETOPTIC S® (Alcon) (betaxolol HCl), BRIMONIDINE TARTRATE (Bausch & Lomb), CARTEOLOL HYDROCHLORIDE (Bausch & Lomb), COSOPT® (Merck) (dorzolamide hydrochloride-timolol maleate ophthalmic solution), LUMIGAN® (Allergan) (bimatoprost ophthalmic solution), OPTIPRANOLOL® (Bausch & Lomb) (metipranolol ophthalmic solution), TIMOLOL GFS (Falcon) (timolol maleate ophthalmic gel forming solution), TIMOPTIC® (Merck) (timolol maleate ophthalmic solution), TRAVATAN(® (Alcon) (travoprost ophthalmic solution), TRUSOPT® (Merck) (dorzolamide hydrochloride ophthalmic solution) and XALATAN® (Pharmacia & Upjohn) (latanoprost ophthalmic solution).

In one embodiment, a sirtuin modulator can be administered in conjunction with a therapy for treating and/or preventing glaucoma. An example of a glaucoma drug is DARANIDE® Tablets (Merck) (Dichlorphenamide).

In one embodiment, a sirtuin modulator can be administered in conjunction with a therapy for treating and/or preventing optic neuritis. Examples of drugs for optic neuritis include DECADRON® Phosphate Injection (Merck) (Dexamethasone Sodium Phosphate), DEPO-MEDROL® (Pharmacia & Upjohn)(methylprednisolone acetate), HYDROCORTONE® Tablets (Merck) (Hydrocortisone), ORAPRED® (Biomarin) (prednisolone sodium phosphate oral solution) and PEDIAPRED® (Celltech) (prednisolone sodium phosphate, USP).

In one embodiment, a sirtuin modulator can be administered in conjunction with a therapy for treating and/or preventing CMV Retinopathy. Treatments for CMV retinopathy include CYTOVENE® (ganciclovir capsules) and VALCYTE® (Roche Laboratories) (valganciclovir hydrochloride tablets).

In one embodiment, a sirtuin modulator can be administered in conjunction with a therapy for treating and/or preventing multiple sclerosis. Examples of such drugs include DANTRIUM® (Procter & Gamble Pharmaceuticals) (dantrolene sodium), NOVANTRONE® (Serono) (mitoxantrone), AVONEX® (Biogen Idec) (Interferon beta-1a), BETASERON® (Berlex) (Interferon beta-1b), COPAXONE® (Teva Neuroscience) (glatiramer acetate injection) and REBIF® (Pfizer) (interferon beta-1a).

In addition, macrolide and/or mycophenolic acid, which has multiple activities, can be co-administered with a sirtuin modulator. Macrolide antibiotics include tacrolimus, cyclosporine, sirolimus, everolimus, ascomycin, erythromycin, azithromycin, clarithromycin, clindamycin, lincomycin, dirithromycin, josamycin, spiramycin, diacetyl-midecamycin, tylosin, roxithromycin, ABT-773, telithromycin, leucomycins, and lincosamide.

Mitochondrial-Associated Diseases and Disorders

In certain embodiments, the invention provides methods for treating diseases or disorders that would benefit from increased mitochondrial activity. The methods involve administering to a subject in need thereof a therapeutically effective amount of a sirtuin activating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods for treating diseases or disorders that would benefit from increased mitochondrial activity may comprise identifying a subject suffering from a mitochondrial dysfunction. Methods for diagnosing a mitochondrial dysfunction may involve molecular genetic, pathologic and/or biochemical analysis are summarized in Cohen and Gold, Cleveland Clinic Journal of Medicine, 68: 625-642 (2001). One method for diagnosing a mitochondrial dysfunction is the Thor-Byrne-ier scale (see e.g., Cohen and Gold, supra; Collin S. et al., Eur Neurol. 36: 260-267 (1996)). Other methods for determining mitochondrial number and function include, for example, enzymatic assays (e.g., a mitochondrial enzyme or an ATP biosynthesis factor such as an ETC enzyme or a Krebs cycle enzyme), determination or mitochondrial mass, mitochondrial volume, and/or mitochondrial number, quantification of mitochondrial DNA, monitoring intracellular calcium homeostasis and/or cellular responses to perturbations of this homeostasis, evaluation of response to an apoptogenic stimulus, determination of free radical production. Such methods are known in the art and are described, for example, in U.S. Patent Publication No. 2002/0049176 and references cited therein.

Mitochondria are critical for the survival and proper function of almost all types of eukaryotic cells. Mitochondria in virtually any cell type can have congenital or acquired defects that affect their function. Thus, the clinically significant signs and symptoms of mitochondrial defects affecting respiratory chain function are heterogeneous and variable depending on the distribution of defective mitochondria among cells and the severity of their deficits, and upon physiological demands upon the affected cells. Nondividing tissues with high energy requirements, e.g. nervous tissue, skeletal muscle and cardiac muscle are particularly susceptible to mitochondrial respiratory chain dysfunction, but any organ system can be affected.

Diseases and disorders associated with mitochondrial dysfunction include diseases and disorders in which deficits in mitochondrial respiratory chain activity contribute to the development of pathophysiology of such diseases or disorders in a mammal. This includes 1) congenital genetic deficiencies in activity of one or more components of the mitochondrial respiratory chain; and 2) acquired deficiencies in the activity of one or more components of the mitochondrial respiratory chain, wherein such deficiencies are caused by a) oxidative damage during aging; b) elevated intracellular calcium; c) exposure of affected cells to nitric oxide; d) hypoxia or ischemia; e) microtubule-associated deficits in axonal transport of mitochondria, or f) expression of mitochondrial uncoupling proteins.

Diseases or disorders that would-benefit from increased mitochondrial activity generally include for example, diseases in which free radical mediated oxidative injury leads to tissue degeneration, diseases in which cells inappropriately undergo apoptosis, and diseases in which cells fail to undergo apoptosis. Exemplary diseases or disorders that would benefit from increased mitochondrial activity include, for example, AD (Alzheimer's Disease), ADPD (Alzheimer's Disease and Parkinsons's Disease), AMDF (Ataxia, Myoclonus and Deafness), auto-immune disease, cancer, CIPO (Chronic Intestinal Pseudoobstruction with myopathy and Ophthalmoplegia), congenital muscular dystrophy, CPEO (Chronic Progressive External Ophthalmoplegia), DEAF (Maternally inherited DEAFness or *aminoglycoside-induced DEAFness*), DEMCHO (Dementia and Chorea), diabetes mellitus (Type I or Type II), DIDMOAD (Diabetes Insipidus, Diabetes Mellitus, Optic Atrophy, Deafness), DMDF (Diabetes Mellitus and Deafness), dystonia, Exercise Intolerance, ESOC (Epilepsy, Strokes, Optic atrophy, and Cognitive decline), FBSN (Familial Bilateral Striatal Necrosis), FICP (Fatal Infantile Cardiomyopathy Plus, a MELAS-associated cardiomyopathy), GER (Gastrointestinal Reflux), HD (Huntington's Disease), KSS (Kearns Sayre Syndrome), "later-onset" myopathy, *LDYT* (*Leber's hereditary optic neuropathy and DYsTonia*), Leigh's Syndrome, LHON (Leber Hereditary Optic Neuropathy), LIMM (Lethal Infantile Mitochondrial Myopathy), MDM (Myopathy and Diabetes Mellitus), MELAS (Mitochondrial Encephalomyopathy, Lactic Acidosis, and Stroke-like episodes), MEPR (Myoclonic Epilepsy and Psychomotor Regression), MERME (MERRF/MELAS overlap disease), MERRF (Myoclonic Epilepsy and Ragged Red Muscle Fibers), MHCM (Maternally Inherited Hypertrophic CardioMyopathy), MICM (Maternally Inherited Cardiomyopathy), MILS (Maternally Inherited Leigh Syndrome), Mitochondrial Encephalocardiomyopathy, Mitochondrial Encephalomyopathy, MM (Mitochondrial Myopathy), MMC (Maternal Myopathy and Cardiomyopathy), MNGIE (Myopathy and external ophthalmoplegia, Neuropathy, Gastro-Intestinal, Encephalopathy), Multisystem Mitochondrial Disorder (myopathy, encephalopathy, blindness, hearing loss, peripheral neuropathy), NARP (Neurogenic muscle weakness, Ataxia, and Retinitis Pigmentosa; alternate phenotype at this locus is reported as *Leigh Disease*), PD (Parkinson's Disease), Pearson's Syndrome, PEM (Progressive Encephalopathy), PEO (Progressive External Ophthalmoplegia), PME (Progressive Myoclonus Epilepsy), PMPS (Pearson Marrow-Pancreas Syndrome), psoriasis, RTT (Rett Syndrome), schizophrenia, SIDS (Sudden Infant Death Syndrome), SNHL (Sensorineural Hearing Loss), Varied Familial Presentation (clinical manifestations range from spastic paraparesis to multisystem progressive disorder & fatal cardiomyopathy to truncal ataxia, dysarthria, severe hearing loss, mental regression, ptosis, ophthalmoparesis, distal cyclones, and diabetes mellitus), or Wolfram syndrome.

Other diseases and disorders that would benefit from increased mitochondrial activity include, for example, Friedreich's ataxia and other ataxias, amyotrophic lateral sclerosis (ALS) and other motor neuron diseases, macular degeneration, epilepsy, Alpers syndrome, Multiple mitochondrial DNA deletion syndrome, MtDNA depletion syndrome, Complex I deficiency, Complex II (SDH) deficiency, Complex III deficiency, Cytochrome c oxidase (COX, Complex IV) deficiency, Complex V deficiency, Adenine Nucleotide Translocator (ANT) deficiency, Pyruvate dehydrogenase (PDH) deficiency, Ethylmalonic aciduria with lactic acidemia, 3-Methyl glutaconic aciduria with lactic acidemia, Refractory epilepsy with declines during infection, Asperger syndrome with declines during infection, Autism with declines during infection, Attention deficit hyperactivity disorder (ADHD), Cerebral palsy with declines during infection, Dyslexia with declines during infection, materially inherited thrombocytopenia and leukemia syndrome, MARIAHS syndrome (Mitochondrial ataxia, recurrent infections, aphasia, hypouricemia/hypomyelination, seizures, and dicarboxylic aciduria), ND6 dystonia, Cyclic vomiting syndrome with declines during infection, 3-Hydroxy isobutryic aciduria with lactic acidemia, Diabetes mellitus with lactic acidemia, Uridine responsive neurologic syndrome (URNS), Dilated cardiomyopathy, Splenic Lymphoma, and Renal Tubular Acidosis/Diabetes/Ataxis syndrome.

In other embodiments, the invention provides methods for treating a subject suffering from mitochondrial disorders arising from, but not limited to, post-traumatic head injury and cerebral edema, stroke (invention methods useful for preventing or preventing reperfusion injury), Lewy body dementia, hepatorenal syndrome, acute liver failure, NASH (non-alcoholic steatohepatitis), Anti-metastasis/prodifferentiation therapy of cancer, idiopathic congestive heart failure, atrial fibrilation (non-valvular), Wolff-Parkinson-White Syndrome, idiopathic heart block, prevention of reperfusion injury in acute myocardial infarctions, familial migraines, irritable bowel syndrome, secondary prevention of non-Q wave myocardial infarctions, Premenstrual syndrome, Prevention of renal failure in hepatorenal syndrome, anti-phospholipid antibody syndrome, eclampsia/pre-eclampsia, oopause infertility, ischemic heart disease/angina, and Shy-Drager and unclassified dysautonomia syndromes.

In still another embodiment, there are provided methods for the treatment of mitochondrial disorders associated with pharmacological drug-related side effects. Types of pharmaceutical agents that are associated with mitochondrial disorders include reverse transcriptase inhibitors, protease inhibitors, inhibitors of DHOD, and the like. Examples of reverse transcriptase inhibitors include, for example, Azidothymidine (AZT), Stavudine (D4T), Zalcitabine (ddC), Didanosine (DDI), Fluoroiodoarauracil (FIAU), *Lamivudine* (3TC), Abacavir and the like. Examples of protease inhibitors include, for example, Ritonavir, Indinavir, Saquinavir, Nelfinavir and the like. Examples of inhibitors of dihydroorotate dehydrogenase (DHOD) include, for example, Leflunomide, Brequinar, and the like.

Reverse transcriptase inhibitors not only inhibit reverse transcriptase but also polymerase gamma which is required for mitochondrial function. Inhibition of polymerase gamma activity (e.g., with a reverse transcriptase inhibitor) therefore leads to mitochondrial dysfunction and/or a reduced mitochondrial mass which manifests itself in patients as hyperlactatemia. This type of condition may benefit from an increase in the number of mitochondria and/or an improvement in mitochondrial function, e.g., by administration of a sirtuin activating compound.

Common symptoms of mitochondrial diseases include cardiomyopathy, muscle weakness and atrophy, developmental delays (involving motor, language, cognitive or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, migraine, hepatic failure, lactic acidemia, and diabetes mellitus.

In certain embodiments, the invention provides methods for treating a disease or disorder that would benefit from increased mitochondrial activity that involves administering to a subject in need thereof one or more sirtuin activating compounds in combination with another therapeutic agent such as, for example, an agent useful for treating mitochondrial dysfunction (such as antioxidants, vitamins, or respiratory chain cofactors), an agent useful for reducing a symptom associated with a disease or disorder involving mitochondrial dysfunction (such as, an anti-seizure agent, an agent useful for alleviating neuropathic pain, an agent for treating cardiac dysfunction), a cardiovascular agent (as described further below), a chemotherapeutic agent (as described further below), or an anti-neurodegeneration agent (as described further below). In an exemplary embodiment, the invention provides methods for treating a disease or disorder that would benefit from increased mitochondrial activity that involves administering to a subject in need thereof one or more sirtuin activating compounds in combination with one or more of the following: coenzyme $Q_{10}$, L-carnitine, thiamine, riboflavin, niacinamide, folate, vitamin E, selenium, lipoic acid, or prednisone. Compositions comprising such combinations are also provided herein.

In exemplary embodiments, the invention provides methods for treating diseases or disorders that would benefit from increased mitochondrial acitivity by administering to a subject a therapeutically effective amount of a sirtuin activating disorders (e.g., Friedreich's Ataxia, muscular dystrophy, multiple sclerosis, etc.), disorders of neuronal instability (e.g., seizure disorders, migrane, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

A gene defect underlying Friedreich's Ataxia (FA), the most common hereditary ataxia, was recently identified and is designated "frataxin". In FA, after a period of normal development, deficits in coordination develop which progress to paralysis and death, typically between the ages of 30 and 40. The tissues affected most severely are the spinal cord, peripheral nerves, myocardium, and pancreas. Patients typically lose motor control and are confined to wheel chairs, and are commonly afflicted with heart failure and diabetes. The genetic basis for FA involves GAA trinucleotide repeats in an intron region of the gene encoding frataxin. The presence of these repeats results in reduced transcription and expression of the gene. Frataxin is involved in regulation of mitochondrial iron content. When cellular frataxin content is subnormal, excess iron accumulates in mitochondria, promoting oxidative damage and consequent mitochondrial degeneration and dysfunction. When intermediate numbers of GAA repeats are present in the frataxin gene intron, the severe clinical phenotype of ataxia may not develop. However, these intermediate-length trinucleotide extensions are found in 25 to 30% of patients with non-insulin dependent diabetes mellitus, compared to about 5% of the nondiabetic population. In certain embodiments, sirtuin activating compounds may be used for treating patients with disorders related to deficiencies or defects in frataxin, including Friedreich's Ataxia, myocardial dysfunction, diabetes mellitus and complications of diabetes like peripheral neuropathy.

Muscular dystrophy refers to a family of diseases involving deterioration of neuromuscular structure and function, often resulting in atrophy of skeletal muscle and myocardial dysfunction. In the case of Duchenne muscular dystrophy, mutations or deficits in a specific protein, dystrophin, are implicated in its etiology. Mice with their dystrophin genes inactivated display some characteristics of muscular dystrophy, and have an approximately 50% deficit in mitochondrial respiratory chain activity. A final common pathway for neuromuscular degeneration in most cases is calcium-mediated impairment of mitochondrial function. In certain embodiments, sirtuin activating compounds may be used for reducing the rate of decline in muscular functional capacities and for improving muscular functional status in patients with muscular dystrophy.

Multiple sclerosis (MS) is a neuromuscular disease characterized by focal inflammatory and autoimmune degeneration of cerebral white matter. Periodic exacerbations or attacks are significantly correlated with upper respiratory tract and other infections, both bacterial and viral, indicating that mitochondrial dysfunction plays a role in MS. Depression of neuronal mitochondrial respiratory chain activity caused by Nitric Oxide (produced by astrocytes and other cells involved in inflammation) is implicated as a molecular mechanism contributing to MS. In certain embodiments, sirtuin activating compounds may be used for treatment of patients with multiple sclerosis, both prophylactically and during episodes of disease exacerbation.

Epilepsy is often present in patients with mitochondrial cytopathies, involving a range of seizure severity and frequency, e.g. absence, tonic, atonic, myoclonic, and status epilepticus, occurring in isolated episodes or many times daily. In certain embodiments, sirtuin activating compounds may be used for treating patients with seizures secondary to mitochondrial dysfunction, including reducing frequency and severity of seizure activity.

Metabolic studies on patients with recurrent migraine headaches indicate that deficits in mitochondrial activity are commonly associated with this disorder, manifesting as impaired-oxidative phosphorylation and excess lactate production. Such deficits are not necessarily due to genetic defects in mitochondrial DNA. Migraineurs are hypersensitive to nitric oxide, an endogenous inhibitor of Cytochrome c Oxidase. In addition, patients with mitochondrial cytopathies, e.g. MELAS, often have recurrent migraines. In certain embodiments, sirtuin activating compounds may be used for treating patients with recurrent migraine headaches, including headaches refractory to ergot compounds or serotonin receptor antagonists.

Delays in neurological or neuropsychological development are often found in children with mitochondrial diseases. Development and remodeling of neural connections requires intensive biosynthetic activity, particularly involving synthesis of neuronal membranes and myelin, both of which require pyrimidine nucleotides as cofactors. Uridine nucleotides are involved inactivation and transfer of sugars to glycolipids and glycoproteins. Cytidine nucleotides are derived from uridine nucleotides, and are crucial for synthesis of major membrane phospholipid constituents like phosphatidylcholine, which receives its choline moiety from cytidine diphosphocholine. In the case of mitochondrial dysfunction (due to either mitochondrial DNA defects or any of the acquired or conditional deficits like exicitoxic or nitric oxide-mediated mitochondrial dysfunction) or other conditions resulting in impaired pyrimidine synthesis, cell proliferation and axonal extension is impaired at crucial stages in development of neuronal interconnections and circuits, resulting in delayed or arrested development of neuropsychological functions like language, motor, social, executive function, and cognitive skills. In autism for example, magnetic resonance spectroscopy measurements of cerebral phosphate compounds indicates that there is global undersynthesis of membranes and membrane precursors indicated by reduced levels of uridine diphospho-sugars, and cytidine nucleotide derivatives involved in membrane synthesis. Disorders characterized by developmental delay include Rett's Syndrome, pervasive developmental delay (or PDD-NOS "pervasive developmental delay not otherwise specified" to distinguish it from specific subcategories like autism), autism, Asperger's Syndrome, and Attention Deficit/Hyperactivity Disorder (ADHD), which is becoming recognized as a delay or lag in development of neural circuitry underlying executive functions. In certain embodiments, sirtuin activating compounds may be useful for treating treating patients with neurodevelopmental delays (e.g., involving motor, language, executive function, and cognitive skills), or other delays or arrests of neurological and neuropsychological development in the nervous system and somatic development in non-neural tissues like muscle and endocrine glands.

The two most significant severe neurodegenerative diseases associated with aging, Alzheimer's Disease (AD) and Parkinson's Disease (PD), both involve mitochondrial dysfunction in their pathogenesis. Complex I deficiencies in particular are frequently found not only in the nigrostriatal neurons that degenerate in Parkinson's disease, but also in peripheral tissues and cells like muscle and platelets of Parkinson's Disease patients. In Alzheimer's Disease, mitochondrial respiratory chain activity is often depressed, especially Complex IV (Cytochrome c Oxidase). Moreover, mitochondrial respiratory function altogether is depressed as a consequence of aging, further amplifying the deleterious sequelae of additional molecular lesions affecting respiratory chain function. Other factors in addition to primary mitochondrial dysfunction underlie neurodegeneration in AD, PD, and related disorders. Excitotoxic stimulation and nitric oxide are implicated in both diseases, factors which both exacerbate mitochondrial respiratory chain deficits and whose deleterious actions are exaggerated on a background of respiratory chain dysfunction. Huntington's Disease also involves mitochondrial dysfunction in affected brain regions, with cooperative interactions of excitotoxic stimulation and mitochondrial dysfunction contributing to neuronal degeneration. In certain embodiments, sirtuin activating compounds may be useful for treating and attenuating progression of age-related neurodegenerative diseases including AD and PD.

One of the major genetic defects in patients with Amyotrophic Lateral Sclerosis (ALS or Lou Gehrig's Disease) is mutation or deficiency in Copper-Zinc Superoxide Dismutase (SOD 1), an antioxidant enzyme. Mitochondria both produce and are primary targets for reactive oxygen species. Inefficient transfer of electrons to oxygen in mitochondria is the most significant physiological source of free radicals in mammalian systems. Deficiencies in antioxidants or antioxidant enzymes can result in or exacerbate mitochondrial degeneration. Mice transgenic for mutated SOD1 develop symptoms and pathology similar to those in human ALS. The development of the disease in these animals has been shown to involve oxidative destruction of mitochondria followed by functional decline of motor neurons and onset of clinical symptoms. Skeletal muscle from ALS patients has low mitochondrial Complex I activity. In certain embodiments, sirtuin activating compounds may be useful for treating ALS, for reversing or slowing the progression of clinical symptoms.

Oxygen deficiency results in both direct inhibition of mitochondrial respiratory chain activity by depriving cells of a terminal electron acceptor for Cytochrome c reoxidation at Complex IV, and indirectly, especially in the nervous system, via secondary post-anoxic excitotoxicity and nitric oxide formation. In conditions like cerebral anoxia, angina or sickle cell anemia crises, tissues are relatively hypoxic. In such cases, compounds that increase mitochondrial activity provide protection of affected tissues from deleterious effects of hypoxia, attenuate secondary delayed cell death, and accelerate recovery from hypoxic tissue stress and injury. In certain embodiments, sirtuin activating compounds may be useful for preventing delayed cell death (apoptosis in regions like the hippocampus or cortex occurring about 2 to 5 days after an episode of cerebral ischemia) after ischemic or hypoxic insult to the brain.

Acidosis due to renal dysfunction is often observed in patients with mitochondrial disease, whether the underlying respiratory chain dysfunction is congenital or induced by ischemia or cytotoxic agents like cisplatin. Renal tubular acidosis often requires administration of exogenous sodium bicarbonate to maintain blood and tissue pH. In certain embodiments, sirtuin activating compounds may be useful for treating renal tubular acidosis and other forms of renal dysfunction caused by mitochondrial respiratory chain deficits.

During normal aging, there is a progressive decline in mitochondrial respiratory chain function. Beginning about age 40, there is an exponential rise in accumulation of mitochondrial DNA defects in humans, and a concurrent decline in nuclear-regulated elements of mitochondrial respiratory activity. Many mitochondrial DNA lesions have a selection advantage during mitochondrial turnover, especially in postmitotic cells. The proposed mechanism is that mitochondria with a defective respiratory chain produce less oxidative damage to themselves than do mitochondria with intact functional respiratory chains (mitochondrial respiration is the primary source of free radicals in the body). Therefore, normally-functioning mitochondria accumulate oxidative damage to membrane lipids more rapidly than do defective mitochondria, and are therefore "tagged" for degradation by lysosomes. Since mitochondria within cells have a half life of about 10 days, a selection advantage can result in rapid replacement of functional mitochondria with those with diminished respiratory activity, especially in slowly dividing cells. The net result is that once a mutation in a gene for a mitochondrial protein that reduces oxidative damage to mitochondria occurs, such defective mitochondria will rapidly populate the cell, diminishing or eliminating its respiratory capabilities. The accumulation of such cells results in aging or degenerative disease at the organismal level. This is consistent with the progressive mosaic appearance of cells with defective electron transport activity in muscle, with cells almost devoid of Cytochrome c Oxidase (COX) activity interspersed randomly amidst cells with normal activity, and a higher incidence of COX-negative cells in biopsies from older subjects. The organism, during aging, or in a variety of mitochondrial diseases, is thus faced with a situation in which irreplaceable postmitotic cells (e.g. neurons, skeletal and cardiac muscle) must be preserved and their function maintained to a significant degree, in the face of an inexorable progressive decline in mitochondrial respiratory chain function. Neurons with dysfunctional mitochondria become progressively more sensitive to insults like excitotoxic injury. Mitochondrial failure contributes to most degenerative diseases (especially neurodegeneration) that accompany aging. Congenital mitochondrial diseases often involve early-onset neurodegeneration similar in fundamental mechanism to disorders that occur during aging of people born with normal mitochondria. In certain embodiments, sirtuin activating compounds may be useful for treating or attenuating cognitive decline and other degenerative consequences of aging.

Mitochondrial DNA damage is more extensive and persists longer than nuclear DNA damage in cells subjected to oxidative stress or cancer chemotherapy agents like cisplatin due to both greater vulnerability and less efficient repair of mitochondrial DNA. Although mitochondrial DNA may be more sensitive to damage than nuclear DNA, it is relatively resistant, in some situations, to mutagenesis by chemical carcinogens. This is because mitochondria respond to some types of mitochondrial DNA damage by destroying their defective genomes rather than attempting to repair them. This results in global mitochondrial dysfunction for a period after cytotoxic chemotherapy. Clinical use of chemotherapy agents like cisplatin, mitomycin, and cytoxan is often accompanied by debilitating "chemotherapy fatigue", prolonged periods of weakness and exercise intolerance which may persist even after recovery from hematologic and gastrointestinal toxicities of such agents. In certain embodiments, sirtuin activating compounds may be useful for treatment and prevention of side effects of cancer chemotherapy related to mitochondrial dysfunction.

A crucial function of the ovary is to maintain integrity of the mitochondrial genome in oocytes, since mitochondria passed onto a fetus are all derived from those present in oocytes at the time of conception. Deletions in mitochondrial DNA become detectable around the age of menopause, and are also associated with abnormal menstrual cycles. Since cells cannot directly detect and respond to defects in mitochondrial DNA, but can only detect secondary effects that affect the cytoplasm, like impaired respiration, redox status, or deficits in pyrimidine synthesis, such products of mitochondrial function participate as a signal for oocyte selection and follicular atresia, ultimately triggering menopause when maintenance of mitochondrial genomic fidelity and functional activity can no longer be guaranteed. This is analogous to apoptosis in cells with DNA damage, which undergo an active process of cellular suicide when genomic fidelity can no longer be achieved by repair processes. Women with mitochondrial cytopathies affecting the gonads often undergo premature menopause or display primary cycling abnormalities. Cytotoxic cancer chemotherapy often induces premature menopause, with a consequent increased risk of osteoporosis. Chemotherapy-induced amenorrhea is generally due to primary ovarian failure. The incidence of chemotherapy-induced amenorrhea increases as a function of age in premenopausal women receiving chemotherapy, pointing toward mitochondrial involvement. Inhibitors of mitochondrial respiration or protein synthesis inhibit hormone-induced ovulation, and furthermore inhibit production of ovarian steroid hormones in response to pituitary gonadotropins. Women with Down's syndrome typically undergo menopause prematurely, and also are subject to early onset of Alzheimer-like dementia. Low activity of cytochrome oxidase is consistently found in tissues of Down's patients and in late-onset Alzheimer's Disease. Appropriate support of mitochondrial function or compensation for mitochondrial dysfunction therefore is useful for protecting against age-related or chemotherapy-induced menopause or irregularities of menstrual cycling or ovulation. In certain embodiments, sirtuin activating compounds may be useful for treating and preventing amenorrhea, irregular ovulation, menopause, or secondary consequences of menopause.

In certain embodiments, sirtuin modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendelian inheritance pattern. Mutations in nuclear-encoded mitochondrial enzymes occur.

In certain embodiments, sirtuin activating compounds may be useful for treating patients suffering from toxic damage to mitochondria, such as, toxic damage due to calcium accumulation, excitotoxicity, nitric oxide exposure, drug induced toxic damage, or hypoxia.

A fundamental mechanism of cell injury, especially in excitable tissues, involves excessive calcium entry into cells, as a result of either leakage through the plasma membrane or defects in intracellular calcium handling mechanisms. Mitochondria are major sites of calcium sequestration, and preferentially utilize energy from the respiratory chain for taking up calcium rather than for ATP synthesis, which results in a downward spiral of mitochondrial failure, since calcium uptake into mitochondria results in diminished capabilities for energy transduction.

Excessive stimulation of neurons with excitatory amino acids is a common mechanism of cell death or injury in the central nervous system. Activation of glutamate receptors, especially of the subtype designated NMDA receptors, results in mitochondrial dysfunction, in part through elevation of intracellular calcium during excitotoxic stimulation. Conversely, deficits in mitochondrial respiration and oxidative phosphorylation sensitizes cells to excitotoxic stimuli, resulting in cell death or injury during exposure to levels of excitotoxic neurotransmitters or toxins that would be innocuous to normal cells.

Nitric oxide (about 1 micromolar) inhibits cytochrome oxidase (Complex IV) and thereby inhibits mitochondrial respiration; moreover, prolonged exposure to nitric oxide (NO) irreversibly reduces Complex I activity. Physiological or pathophysiological concentrations of NO thereby inhibit pyrimidine biosynthesis. Nitric oxide is implicated in a variety of neurodegenerative disorders including inflammatory and autoimmune diseases of the central nervous system, and is involved in mediation of excitotoxic and post-hypoxic damage to neurons.

Oxygen is the terminal electron acceptor in the respiratory chain. Oxygen deficiency impairs electron transport chain activity, resulting in diminished pyrimidine synthesis as well as diminished ATP synthesis via oxidative phosphorylation. Human cells proliferate and retain viability under virtually anaerobic conditions if provided with uridine and pyruvate (or a similarly effective agent for oxidizing NADH to optimize glycolytic ATP production).

In certain embodiments, sirtuin activating compounds may be useful for treating diseases or disorders associated with mitochondrial deregulation.

Transcription of mitochondrial DNA encoding respiratory chain components requires nuclear factors. In neuronal axons, mitochondria must shuttle back and forth to the nucleus in order to maintain respiratory chain activity. If axonal transport is impaired by hypoxia or by drugs like taxol which affect microtubule stability, mitochondria distant from the nucleus undergo loss of cytochrome oxidase activity. Accordingly, treatment with a sirtuin activating compound may be useful for promoting nuclear-mitochondrial interactions.

Mitochondria are the primary source of free radicals and reactive oxygen species, due to spillover from the mitochondrial respiratory chain, especially when defects in one or more respiratory chain components impairs orderly transfer of electrons from metabolic intermediates to molecular oxygen. To reduce oxidative damage, cells can compensate by expressing mitochondrial uncoupling proteins (UCP), of which several have been identified. UCP-2 is transcribed in response to oxidative damage, inflammatory cytokines, or excess lipid loads, e.g. fatty liver and steatohepatitis. UCPs reduce spillover of reactive oxygen species from mitochondria by discharging proton gradients across the mitochondrial inner membrane, in effect wasting energy produced by metabolism and rendering cells vulnerable to energy stress as a trade-off for reduced oxidative injury.

Muscle Performance

In other embodiments, the invention provides methods for enhancing muscle performance by administering a therapeutically effective amount of a sirtuin activating compound. For example, sirtuin activating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of a sirtuin activating compound that increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. An athlete may be hard training, that is, performs sports activities intensely more than three days a week or for competition. An athlete may also be a fitness enthusiast who seeks to improve general health and well-being, improve energy levels, who works out for about 1-2 hours about 3 times a week. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time. However, acute and intense anaerobic use of skeletal muscles often results in impaired athletic performance, with losses in force and work output, and increased onset of muscle fatigue, soreness, and dysfunction. It is now recognized that even a single exhaustive exercise session, or for that matter any acute trauma to the body such as muscle injury, resistance or exhaustive muscle exercise, or elective surgery, is characterized by perturbed metabolism that affects muscle performance in both short and long term phases. Both muscle metabolic/enzymatic activity and gene expression are affected. For example, disruption of skeletal muscle nitrogen metabolism as well as depletion of sources of metabolic energy occur during extensive muscle activity. Amino acids, including branched-chain amino acids, are released from muscles followed by their deamination to elevate serum ammonia and local oxidation as muscle fuel sources, which augments metabolic acidosis. In addition, there is a decline in catalytic efficiency of muscle contraction events, as well as an alteration of enzymatic activities of nitrogen and energy metabolism. Further, protein catabolism is initiated where rate of protein synthesis is decreased coupled with an increase in the degradation of non-contractible protein. These metabolic processes are also accompanied by free radical generation which further damages muscle cells.

Recovery from fatigue during acute and extended exercise requires reversal of metabolic and non-metabolic fatiguing factors. Known factors that participate in human muscle fatigue, such as lactate, ammonia, hydrogen ion, etc., provide an incomplete and unsatisfactory explanation of the fatigue/recovery process, and it is likely that additional unknown agents participate (Baker et al., J. Appl. Physiol. 74:2294-2300, 1993; Bazzarre et al., J Am. Coll. Nutr. 11:505-511, 1992; Dohm et al., Fed. Proc. 44:348-352, 1985; Edwards In: Biochemistry of Exercise, Proceedings of the Fifth International Symposium on the Biochemistry of Exercise (Kutrgen, Vogel, Poormans, eds.), 1983; MacDougall et al., Acta Physiol. Scand. 146:403-404, 1992; Walser et al., Kidney Int. 32:123-128, 1987). Several studies have also analyzed the effects of nutritional supplements and herbal supplements in enhancing muscle performance.

Aside from muscle performance during endurance exercise, free radicals and oxidative stress parameters are affected in pathophysiological states. A substantial body of data now suggests that oxidative stress contributes to muscle wasting or atrophy in pathophysiological states (reviewed in Clarkson, P. M. Antioxidants and physical performance. Crit. Rev. Food Sci. Nutr. 35: 31-41; 1995; Powers, S. K.; Lennon, S. L. Analysis of cellular responses to free radicals: Focus on exercise and skeletal muscle. Proc. Nutr. Soc. 58: 1025-1033; 1999). For example, with respect to muscular disorders where both muscle endurance and function are compensated, the role of nitric oxide (NO), has been implicated. In muscular dystrophies, especially those due to defects in proteins that make up the dystrophin-glycoprotein complex (DGC), the enzyme that synthesizes NO, nitric oxide synthase (NOS), has been associated. Recent studies of dystrophies related to DGC defects suggest that one mechanism of cellular injury is functional ischemia related to alterations in cellular NOS and disruption of a normal protective action of NO. This protective action is the prevention of local ischemia during contraction-induced increases in sympathetic vasoconstriction. Rando (Microsc Res Tech 55(4):223-35, 2001), has shown that oxidative injury precedes pathologic changes and that muscle cells with defects in the DGC have an increased susceptibility to oxidant challenges. Excessive lipid peroxidation due to free radicals has also been shown to be a factor in myopathic diseases such as McArdle's disease (Russo et al., Med Hypotheses. 39(2):147-51, 1992). Furthermore, mitochondrial dysfunction is a well-known correlate of age-related muscle wasting (sarcopenia) and free radical damage has been suggested, though poorly investigated, as a contributing factor (reviewed in Navarro, A.; Lopez-Cepero, J. M.;

Sanchez del Pino, M. L. Front. Biosci. 6: D26-44; 2001). Other indications include acute sarcopenia, for example muscle atrophy and/or cachexia associated with burns, bed rest, limb immobilization, or major thoracic, abdominal, and/or orthopedic surgery. It is contemplated that the methods of the present invention will also be effective in the treatment of muscle related pathological conditions.

In certain embodiments, the invention provides novel dietary compositions comprising sirtuin modulators, a method for their preparation, and a method of using the compositions for improvement of sports performance. Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases, including, for example, acyclovir, ganciclovir and zidovudine. In another embodiment, sirtuin-modulating compounds that increase the level and/or activity of a sirtuin protein may be administered as part of a combination drug therapy with another anti-fungal agent including, for example, topical anti-fungals such as ciclopirox, clotrimazole, econazole, miconazole, nystatin, oxiconazole, terconazole, and tolnaftate, or systemic anti-fungal such as fluconazole (Diflucan), itraconazole (Sporanox), ketoconazole (Nizoral), and miconazole (Monistat I.V.).

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In one embodiment, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods described herein may be applied to any organism, e.g., eukaryote, that may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bio-available to insect larvae, and not to plants.

At least in view of the link between reproduction and longevity (Longo and Finch, Science, 2002), sirtuin-modulating compounds that increase the level and/or activity of a sirtuin protein can be applied to affect the reproduction of organisms such as insects, animals and microorganisms.

4. Assays

Yet other methods contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In one embodiment, a screening assay comprises (i) contacting a sirtuin with a test agent and an acetylated substrate under conditions appropriate for the sirtuin to deacetylate the substrate in the absence of the test agent ; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

Methods for identifying an agent that modulates, e.g., stimulates or inhibits, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 µM to about 10 mM, preferably from about 10 µM to 1 mM, even more preferably from about 100 µM to 1 mM, such as about 200 µM. A preferred substrate is an acetylated lysine, e.g., $\epsilon$-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 µM, preferably from about 0.1 to 10 µM, such as 1 µM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

5. Pharmaceutical Compositions

The sirtuin-modulating compounds described herein may be formulated in a conventional manner using one or more physiologically acceptable carriers or excipients. For example, sirtuin-modulating compounds and their physiologically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In one embodiment, a sirtuin-modulating compound may be administered locally, at the site where the target cells are present, i.e., in a specific tissue, organ, or fluid (e.g., blood, cerebrospinal fluid, etc.).

Sirtuin-modulating compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), sirtuin-modulating compounds may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the compound and a suitable powder base such as lactose or starch.

Sirtuin-modulating compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

Sirtuin-modulating compounds may also be formulated in rectal compositions such as suppositories or retention enemas, e.g., containing conventional suppository bases such as cocoa butter or other glycerides.

In addition to the formulations described previously, sirtuin-modulating compounds may also be formulated as a depot preparation. Such long acting formulations may be administered by implantation (for example subcutaneously or intramuscularly) or by intramuscular injection. Thus, for example, sirtuin-modulating compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

One possibility to achieve sustained release kinetics is embedding or encapsulating the active compound into nanoparticles. Nanoparticles can be administrated as powder, as a powder mixture with added excipients or as suspensions. Colloidal suspensions of nanoparticles can easily be administrated through a cannula with small diameter.

Nanoparticles are particles with a diameter from about 5 nm to up to about 1000 nm. The term "nanoparticles" as it is used hereinafter refers to particles formed by a polymeric matrix in which the active compound is dispersed, also known as "nanospheres", and also refers to nanoparticles which are composed of a core containing the active compound which is surrounded by a polymeric membrane, also known as "nanocapsules". In certain embodiments, nanoparticles are preferred having a diameter from about 50 nm to about 500 nm, in particular from about 100 nm to about 200 nm.

Nanoparticles can be prepared by in situ polymerization of dispersed monomers or by using preformed polymers. Since polymers prepared in situ are often not biodegradable and/or contain toxicological serious byproducts, nanoparticles from preformed polymers are preferred. Nanoparticles from preformed polymers can be prepared by different techniques, e.g., by emulsion evaporation, solvent displacement, salting-out, mechanical grinding, microprecipitation, and by emulsification diffusion.

With the methods described above, nanoparticles can be formed with various types of polymers. For use in the method of the present invention, nanoparticles made from biocompatible polymers are preferred. The term "biocompatible" refers to material that after introduction into a biological environment has no serious effects to the biological environment. From biocompatible polymers those polymers are especially preferred which are also biodegradable. The term "biodegradable" refers to material that after introduction into a biological environment is enzymatically or chemically degraded into smaller molecules, which can be eliminated subsequently. Examples are polyesters from hydroxycarboxylic acids such as poly(lactic acid) (PLA), poly(glycolic acid) (PGA), polycaprolactone (PCL), copolymers of lactic acid and glycolic acid (PLGA), copolymers of lactic acid and caprolactone, polyepsilon caprolactone, polyhyroxy butyric acid and poly(ortho)esters, polyurethanes, polyanhydrides, polyacetals, polydihydropyrans, polycyanoacrylates, natural polymers such as alginate and other polysaccharides including dextran and cellulose, collagen and albumin.

Suitable surface modifiers can preferably be selected from known organic and inorganic pharmaceutical excipients. Such excipients include various polymers, low molecular weight oligomers, natural products and surfactants. Preferred surface modifiers include nonionic and ionic surfactants. Representative examples of surface modifiers include gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available Tweens™, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxy propylcellulose, hydroxypropylmethylcellulose phthalate, noncrystalline cellulose, magnesium aluminum silicate, triethanolamine, polyvinyl alcohol, and polyvinylpyrrolidone (PVP). Most of these surface modifiers are known pharmaceutical excipients and are described in detail in the Handbook of Pharmaceutical Excipients, published jointly by the American Pharmaceutical Association and The Pharmaceutical Society of Great Britain, the Pharmaceutical Press, 1986.

Further description on preparing nanoparticles can be found, for example, in U.S. Pat. No. 6,264,922, the contents of which are incorporated herein by reference.

Liposomes are a further drug delivery system which is easily injectable. Accordingly, in the method of invention the active compounds can also be administered in the form of a liposome delivery system. Liposomes are well-known by a person skilled in the art. Liposomes can be formed from a variety of phospholipids, such as cholesterol, stearylamine of phosphatidylcholines. Liposomes being usable for the method of invention encompass all types of liposomes including, but not limited to, small unilamellar vesicles, large unilamellar vesicles and multilamellar vesicles.

Liposomes are used for a variety of therapeutic purposes, and in particular, for carrying therapeutic agents to target cells. Advantageously, liposome-drug formulations offer the potential of improved drug-delivery properties, which include, for example, controlled drug release. An extended circulation time is often needed for liposomes to reach a target region, cell or site. In particular, this is necessary where the target region, cell or site is not located near the site of administration. For example, when liposomes are administered systemically, it is desirable to coat the liposomes with a hydrophilic agent, for example, a coating of hydrophilic polymer chains such as polyethylene glycol (PEG) to extend the blood circulation lifetime of the liposomes. Such surface-modified liposomes are commonly referred to as "long circulating" or "sterically stabilized" liposomes.

One surface modification to a liposome is the attachment of PEG chains, typically having a molecular weight from about 1000 daltons (Da) to about 5000 Da, and to about 5 mole percent (%) of the lipids making up the liposomes (see, for example, Stealth Liposomes, CRC Press, Lasic, D. and Martin, F., eds., Boca Raton, Fla., (1995)), and the cited references therein. The pharmacokinetics exhibited by such liposomes are characterized by a dose-independent reduction in uptake of liposomes by the liver and spleen via the mononuclear phagocyte system (MPS), and significantly prolonged blood circulation time, as compared to non-surface-modified liposomes, which tend to be rapidly removed from the blood and accumulated in the liver and spleen.

In certain embodiments, the complex is shielded to increase the circulatory half-life of the complex or shielded to increase the resistance of nucleic acid to degradation, for example degradation by nucleases.

As used herein, the term "shielding", and its cognates such as "shielded", refers to the ability of "shielding moieties" to reduce the non-specific interaction of the complexes described herein with serum complement or with other species present in serum in vitro or in vivo. Shielding moieties may decrease the complex interaction with or binding to these species through one or more mechanisms, including, for example, non-specific steric or non-specific electronic interactions. Examples of such interactions include non-specific electrostatic interactions, charge interactions, Van der Waals interactions, steric-hindrance and the like. For a moiety to act as a shielding moiety, the mechanism or mechanisms by which it may reduce interaction with, association with or binding to the serum complement or other species does not have to be identified. One can determine whether a moiety can act as a shielding moiety by determining whether or to what extent a complex binds serum species.

It should be noted that "shielding moieties" can be multifunctional. For example, a shielding moiety may also function as, for example, a targeting factor. A shielding moiety may also be referred to as multifunctional with respect to the mechanism(s) by which it shields the complex. While not wishing to be limited by proposed mechanism or theory, examples of such a multifunctional shielding moiety are pH sensitive endosomal membrane-disruptive synthetic polymers, such as PPAA or PEAA. Certain poly(alkylacrylic acids) have been shown to disrupt endosomal membranes while leaving the-outer cell surface membrane intact (Stayton et al. (2000) J. Controll. Release 65:203-220; Murthy et al. (1999) J. Controll. Release 61:137-143; WO 99/34831), thereby increasing cellular bioavailability and functioning as a targeting factor. However, PPAA reduces binding of serum complement to complexes in which it is incorporated, thus functioning as a shielding moiety.

Another way to produce a formulation, particularly a solution, of a sirtuin modulator such as resveratrol or a derivative thereof, is through the use of cyclodextrin. By cyclodextrin is meant α-, β-, or γ-cyclodextrin. Cyclodextrins are described in detail in Pitha et al., U.S. Pat. No. 4,727,064, which is incorporated herein by reference. Cyclodextrins are cyclic oligomers of glucose; these compounds form inclusion complexes with any drug whose molecule can fit into the lipophile-seeking cavities of the cyclodextrin molecule.

The cyclodextrin of the compositions according to the invention may be α-, β-, or γ-cyclodextrin, α-cyclodextrin contains six glucopyranose units; β-cyclodextrin contains seven glucopyranose units; and γ-cyclodextrin contains eight glucopyranose units. The molecule is believed to form a truncated cone having a core opening of 4.7-5.3 angstroms, 6.0-6.5 angstroms, and 7.5-8.3 angstroms in α-, β-, or γ-cyclodextrin respectively. The composition according to the invention may comprise a mixture of two or more of the α-, β-, or γ-cyclodextrins. Typically, however, the composition according to the invention will comprise only one of the α-, β-, or γ-cyclodextrins.

Most preferred cyclodextrins in the compositions according to the invention are amorphous cyclodextrin compounds.

By amorphous cyclodextrin is meant non-crystalline mixtures of cyclodextrins wherein the mixture is prepared from α-, β-, or γ-cyclodextrin. In general, the amorphous cyclodextrin is prepared by non-selective alkylation of the desired cyclodextrin species. Suitable alkylation agents for this purpose include but are not limited to propylene oxide, glycidol, iodoacetamide, chloroacetate, and 2-diethylaminoethlychloride. Reactions are carried out to yield mixtures containing a plurality of components thereby preventing crystallization of the cyclodextrin. Various alkylated cyclodextrins can be made and of course will vary, depending upon the starting species of cyclodextrin and the alkylating agent used. Among the amorphous cyclodextrins suitable for compositions according to the invention are hydroxypropyl, hydroxyethyl, glucosyl, maltosyl and maltotriosyl derivatives of β-cyclodextrin, carboxyamidomethyl-β-cyclodextrin, carboxymethyl-β-cyclodextrin, hydroxypropyl-β-cyclodextrin and diethylamino-β-cyclodextrin.

One example of resveratrol dissolved in the presence of a cyclodextrin is provided in Marier et al., *J. Pharmacol. Exp. Therap*. 302:369-373 (2002), the contents of which are incorporated herein by reference, where a 6 mg/mL solution of resveratrol was prepared using 0.9% saline containing 20% hydroxylpropyl-β-cyclodextrin.

As mentioned above, the compositions of matter of the invention comprise an aqueous preparation of preferably substituted amorphous cyclodextrin and one or more sirtuin modulators. The relative amounts of sirtuin modulators and cyclodextrin will vary depending upon the relative amount of each of the sirtuin modulators and the effect of the cyclodextrin on the compound. In general, the ratio of the weight of compound of the sirtuin modulators to the weight of cyclodextrin compound will be in a range between 1:1 and 1:100. A weight to weight ratio in a range of 1:5 to 1:50 and more preferably in a range of 1:10 to 1:20 of the compound selected from sirtuin modulators to cyclodextrin are believed to be the most effective for increased circulating availability of the sirtuin modulator.

Importantly, if the aqueous solution comprising the sirtuin modulators and a cyclodextrin is to be administered parenterally, especially via the intravenous route, a cyclodextrin will be substantially free of pyrogenic contaminants. Various forms of cyclodextrin, such as forms of amorphous cyclodextrin, may be purchased from a number of vendors including Sigma-Aldrich, Inc. (St. Louis, Mo., USA). A method for the production of hydroxypropyl-β-cyclodextrin is disclosed in Pitha et al., U.S. Pat. No. 4,727,064 which is incorporated herein by reference.

Additional description of the use of cyclodextrin for solubilizing compounds can be found in US 2005/0026849, the contents of which are incorporated herein by reference.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

To overcome such problems manufacturers have developed a number of fast melt solid dose oral formulations. These are available from manufacturers including Cima Labs, Fuisz Technologies Ltd., Prographarm, R. P. Scherer, Yamanouchi-Shaklee, and McNeil-PPC, Inc. All of these manufacturers market different types of rapidly dissolving solid oral dosage forms. See e.g., patents and publications by Cima Labs such as U.S. Pat. Nos. 5,607,697, 5,503,846, 5,223,264, 5,401,513, 5,219,574, and 5,178,878, WO 98/46215, WO 98/14179; patents to Fuisz Technologies, now part of BioVail, such as U.S. Pat. Nos. 5,871,781, 5,869,098, 5,866,163, 5,851,553, 5,622,719, 5,567,439, and 5,587,172; U.S. Pat. No. 5,464,632 to Prographarm; patents to R. P. Scherer such as U.S. Pat. Nos. 4,642,903, 5,188,825, 5,631,023 and 5,827,541; patents to Yamanouchi-Shaklee such as U.S. Pat. Nos. 5,576,014 and 5,446,464; patents to Janssen such as U.S. Pat. Nos. 5,807,576, 5,635,210, 5,595,761, 5,587,180 and 5,776,491; U.S. Pat. Nos. 5,639,475 and 5,709,886 to Eurand America, Inc.; U.S. Pat. Nos. 5,807,578 and 5,807,577 to L.A.B. Pharmaceutical Research; patents to Schering Corporation such as U.S. Pat. Nos. 5,112,616 and 5,073,374; U.S. Pat. No. 4,616,047 to Laboratoire L. LaFon; U.S. Pat. No. 5,501,861 to Takeda Chemicals Inc., Ltd.; and U.S. Pat. No. 6,316,029 to Elan.

In one example of fast melt tablet preparation, granules for fast melt tablets made by either the spray drying or pre-compacting processes are mixed with excipients and compressed into tablets using conventional tablet making machinery. The granules can be combined with a variety of carriers including low density, high moldability saccharides, low moldability saccharides, polyol combinations, and then directly compressed into a tablet that exhibits an improved dissolution and disintegration profile.

The tablets according to the present invention typically have a hardness of about 2 to about 6 Strong-Cobb units (scu). Tablets within this hardness range disintegrate or dissolve rapidly when chewed. Additionally, the tablets rapidly disentegrate in water. On average, a typical 1.1 to 1.5 gram tablet disintegrates in 1-3 minutes without stirring. This rapid disintegration facilitates delivery of the active material.

The granules used to make the tablets can be, for example, mixtures of low density alkali earth metal salts or carbohydrates. For example, a mixture of alkali earth metal salts includes a combination of calcium carbonate and magnesium hydroxide. Similarly, a fast melt tablet can be prepared according to the methods of the present invention that incorporates the use of A) spray dried extra light calcium carbonate/maltodextrin, B) magnesium hydroxide and C) a eutectic polyol combination including Sorbitol Instant, xylitol and mannitol. These materials have been combined to produce a low density tablet that dissolves very readily and promotes the fast disintegration of the active ingredient. Additionally, the pre-compacted and spray dried granules can be combined in the same tablet.

For fast melt tablet preparation, a sirtuin modulator useful in the present invention can be in a form such as solid, particulate, granular, crystalline, oily or solution. The sirtuin modulator for use in the present invention may be a spray dried product or an adsorbate that has been pre-compacted to a harder granular form that reduces the medicament taste. A pharmaceutical active ingredient for use in the present invention may be spray dried with a carrier that prevents the active ingredient from being easily extracted from the tablet when chewed.

In addition to being directly added to the tablets of the present invention, the medicament drug itself can be processed by the pre-compaction process to achieve an increased density prior to being incorporated into the formulation.

The pre-compaction process used in the present invention can be used to deliver poorly soluble pharmaceutical materials so as to improve the release of such pharmaceutical materials over traditional dosage forms. This could allow for the use of lower dosage levels to deliver equivalent bioavailable levels of drug and thereby lower toxicity levels of both currently marketed drug and new chemical entities. Poorly soluble pharmaceutical materials can be used in the form of nanoparticles, which are nanometer-sized particles.

In addition to the active ingredient and the granules prepared from low density alkali earth metal salts and/or water soluble carbohydrates, the fast melt tablets can be formulated using conventional carriers or excipients and well established pharmaceutical techniques. Conventional carriers or excipients include, but are not limited to, diluents, binders, adhesives (i.e., cellulose derivatives and acrylic derivatives), lubricants (i.e., magnesium or calcium stearate, vegetable oils, polyethylene glycols, talc, sodium lauryl sulphate, polyoxy ethylene monostearate), disintegrants, colorants, flavorings, preservatives, sweeteners and miscellaneous materials such as buffers and adsorbents.

Additional description of the preparation of fast melt tablets can be found, for example, in U.S. Pat. No. 5,939,091, the contents of which are incorporated herein by reference.

Pharmaceutical compositions (including cosmetic preparations) may comprise from about 0.00001 to 100% such as from 0.001 to 10% or from 0.1% to 5% by weight of one or more sirtuin-modulating compounds described herein.

In one embodiment, a sirtuin-modulating compound described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Sirtuin-modulating compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's (supra) ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Sirtuin-modulating compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor$^{RTM}$ from Beiersdorf, Inc. (Norwalk, Conn.).

Sirtuin-modulating compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Sirtuin-modulating compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Sirtuin-modulating compounds may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}$ MSO) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone$^{RTM}$ from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol$^{RTM}$) and diethylene glycol monoethyl ether oleate (available commercially as Softcutol$^{RTM}$); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol$^{RTM}$); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition as herein defined.

In an alternative embodiment, a pharmaceutical formulation is provided for oral or parenteral administration, in which case the formulation may comprises a modulating compound-containing microemulsion as described above, but may contain alternative pharmaceutically acceptable carriers, vehicles, additives, etc. particularly suited to oral or parenteral drug administration. Alternatively, a modulating compound-containing microemulsion may be administered orally or parenterally substantially as described above, without modification.

Phospholipids complexes, e.g., resveratrol-phospholipid complexes, and their preparation are described in U.S. Patent Application Publication No. 2004/116386. Methods for stabilizing active components using polyol/polymer microcapsules, and their preparation are described in US20040108608. Processes for dissolving lipophilic compounds in aqueous solution with amphiphilic block copolymers are described in WO 04/035013.

Conditions of the eye can be treated or prevented by, e.g., systemic, topical, intraocular injection of a sirtuin-modulating compound, or by insertion of a sustained release device that releases a sirtuin-modulating compound. A sirtuin-modulating compound that increases or decreases the level and/or activity of a sirtuin protein may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

Sirtuin-modulating compounds described herein may be stored in oxygen free environment according to methods in the art. For example, resveratrol or analog thereof can be prepared in an airtight capsule for oral administration, such as Capsugel from Pfizer, Inc.

Cells, e.g., treated ex vivo with a sirtuin-modulating compound, can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of sirtuin-modulating compounds can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Sirtuin-modulating compounds that exhibit large therapeutic indexes are preferred. While sirtuin-modulating compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

6. Kits

Also provided herein are kits, e.g., kits for therapeutic purposes or kits for modulating the lifespan of cells or modulating apoptosis. A kit may comprise one or more sirtuin-modulating compounds, e.g., in premeasured doses. A kit may optionally comprise devices for contacting cells with the compounds and instructions for use. Devices include syringes, stents and other devices for introducing a sirtuin-modulating compound into a subject (e.g., the blood vessel of a subject) or applying it to the skin of a subject.

Another type of kit contemplated by the invention are kits for identifying sirtuin-modulating compounds. Such kits contain (1) a sirtuin or sirtuin-containing material and (2) a sirtuin-modulating compound of the invention, which are in separate vessels. Such kits can be used, for example, to perform a competition-type assay to test other compounds (typically provided by the user) for sirtuin-modulating activity. In certain embodiments, these kits further comprise means for determining sirtuin activity (e.g., a peptide with an appropriate indicator, such as those disclosed in the Exemplification).

In yet another embodiment, the invention provides a composition of matter comprising a sirtuin modulator of this invention and another therapeutic agent [the same ones used in combination therapies and combination compositions] in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The agent and the sirtuin modulator are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a sirtuin modulator of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

Exemplification

The invention now being generally described, it will be more readily understood by reference to the following examples which are included merely for purposes of illustration of certain aspects and embodiments of the present invention, and are not intended to limit the invention in any way.

EXAMPLE 1

Synthesis and Characterization of Sirtuin Modulators General Schemes

Scheme 1:

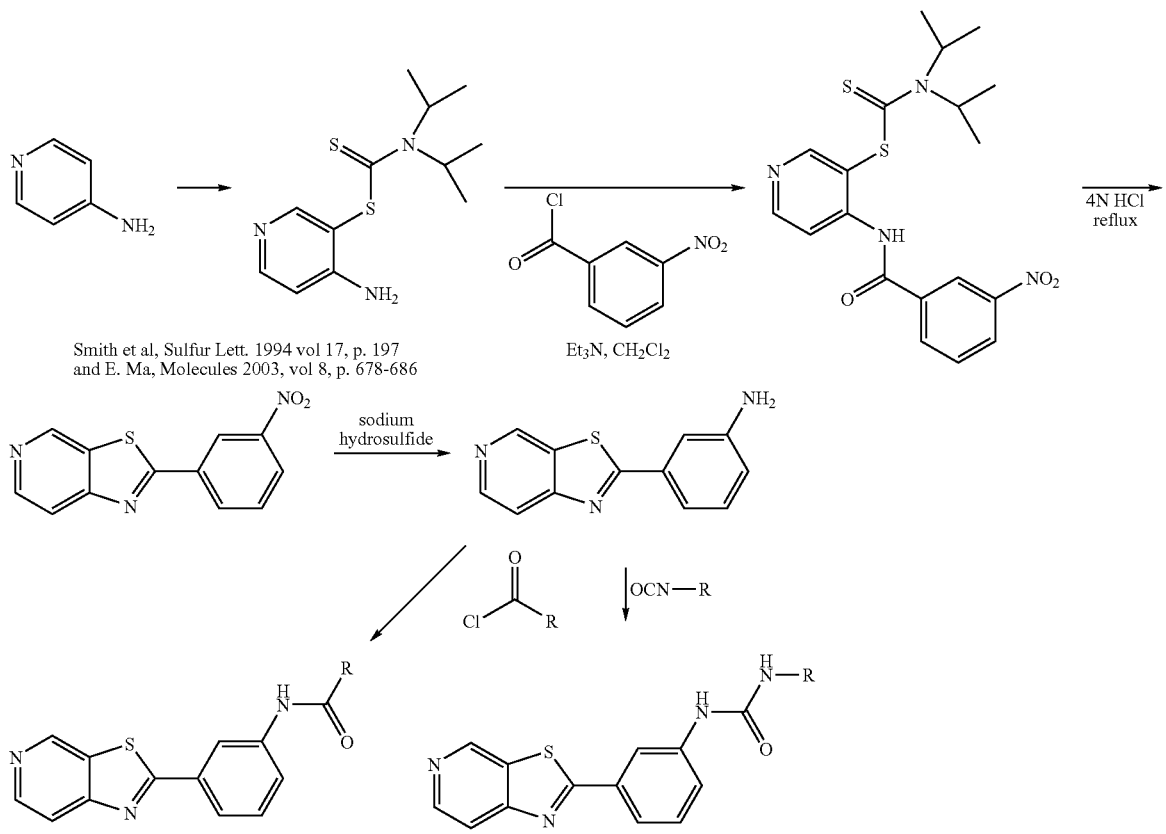

Scheme 2:
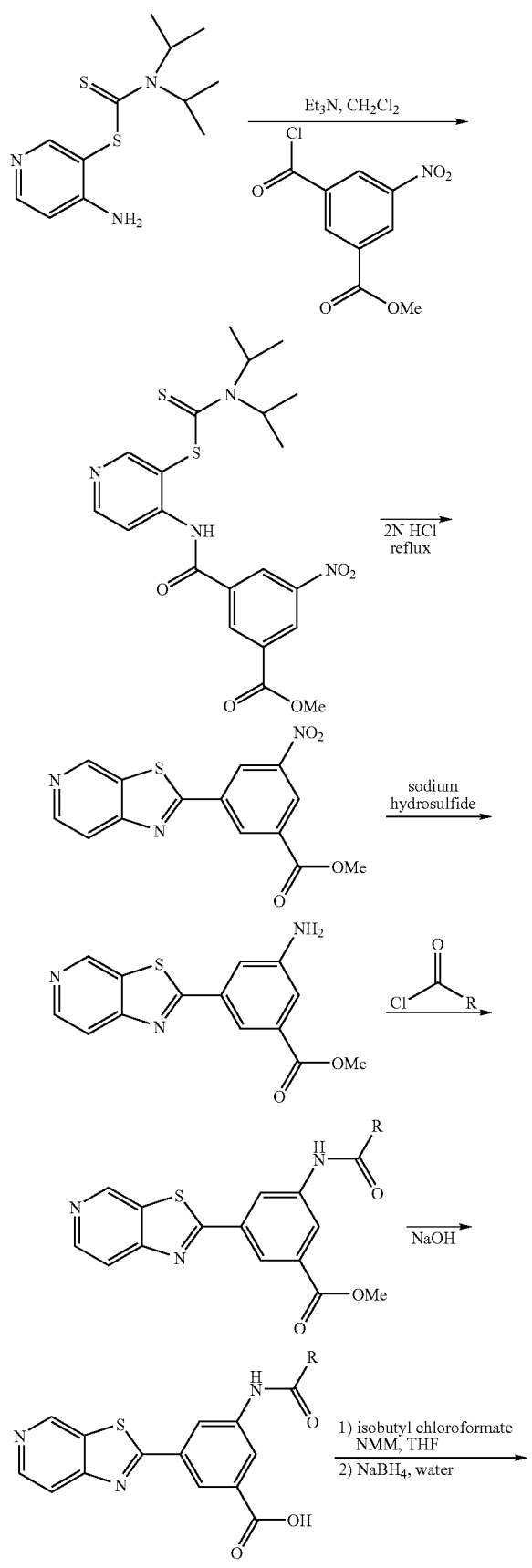
Scheme 3:
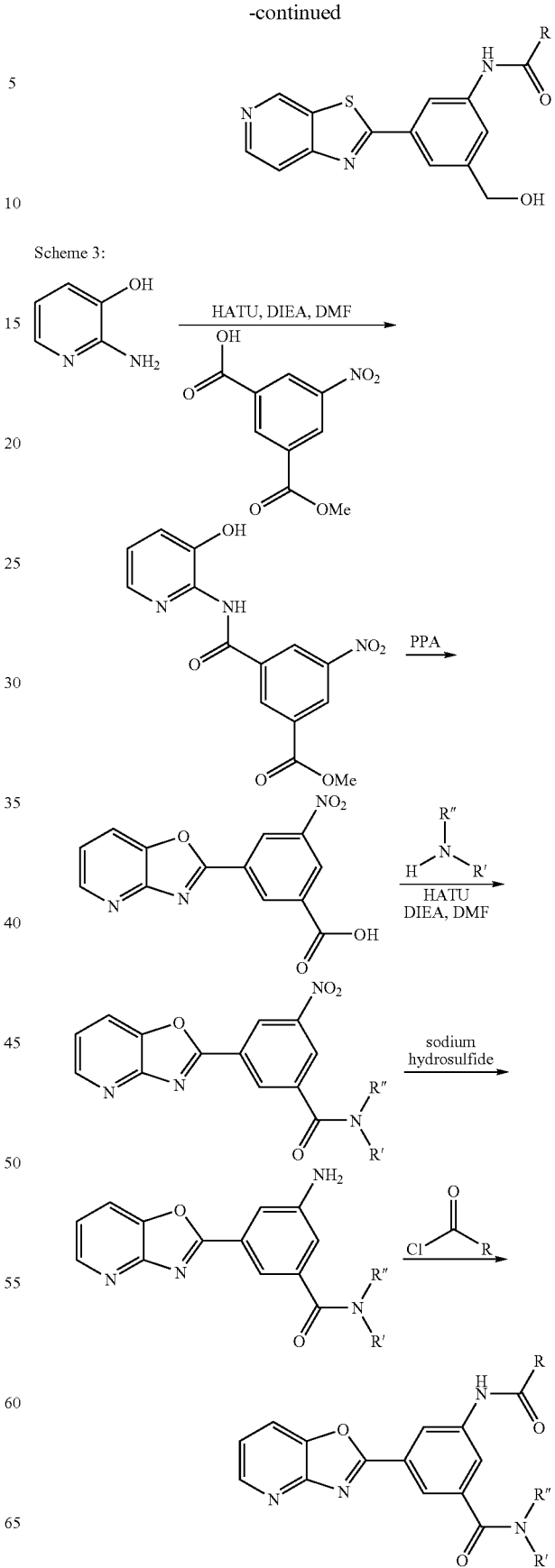

Scheme 4:

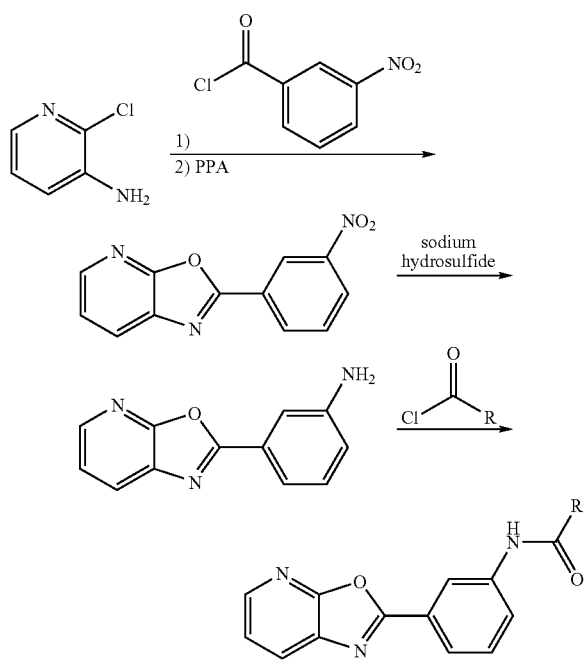

Experimental Section:
  Abbreviations used in experimental section:
  HATU=O-(7-Azabenzotriazol-1-yl)-N,N,N',N'-tetramethyluronium hexafluorophosphate
  NMM=4-Methylmorpholine
  DIEA=N,N-Diisopropylethylamine
  DMF=N,N-Dimethylformamide
  CH$_2$Cl$_2$=Dichloromethane
  EtOAc=Ethyl acetate
  MeOH=Methanol
  Na$_2$SO$_4$=Sodium sulfate
  PPA=Polyphosphoric acid
  Et$_3$N=Triethylamine
  rt=room temperature Preparation of 3-(thiazolo[5,4-c]pyridin-2-yl)benzenamine

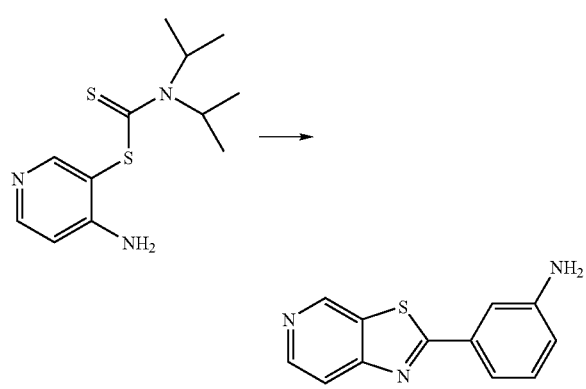

4-aminopyridin-3-yl diisopropylcarbamodithioate was prepared according to the procedures outlined in Smith et al, *Sulfur Lett.* 1994 vol 17, p. 197 and E. Ma, *Molecules* 2003, vol 8, p. 678-686.

220 mg of 4-aminopyridin-3-yl diisopropylcarbamodithioate (0.81 mmol) was dissolved in 6 mL of methylene chloride and cooled to 10 degrees C. (ice bath) along with triethylamine (0.175 mL, 1.5 eq). 3-Nitrobenzoyl chloride (150 mg, 1 eq, 0.81 mmol) was dissolved in 3 mL of methylene chloride and then added to the cooled solution of 4-aminopyridin-3-yl diisopropylcarbamodithioate. The reaction mixture was warmed to rt and stirred for 45 min. The reaction mixture was diluted with 5 mL of methylene chloride and washed with brine. The organic layer was dried (Na$_2$SO$_4$) and concentrated to afford 280 mg of compound of the intermediate amide (83% crude yield).

This intermediate amide (280 mg) was suspended in 5 mL of 4 N aq HCl and stirred under reflux for 30 min. The reaction mixture was cooled to rt and neutralized with 3 N NaOH and extracted with methylene chloride. The organic layer was dried (Na$_2$SO$_4$) and concentrated under reduced pressure to afford 200 mg of compound of 2-(3-nitrophenyl)thiazolo[5,4-c]pyridine (95% crude yield).

310 mg of 2-(3-nitrophenyl)thiazolo[5,4-c]pyridine (1.2 mmol) was mixed with 30 mL of MeOH along with 6 mL of water. Sodium hydrosulfide hydrate (6 eq, 7.24 mmol, 400 mg) was added and the reaction mixture was stirred under reflux for 3 hours. The reaction mixture was cooled to room temperature and concentrated. The aqueous layer was extracted with methylene chloride. The combined organic layers were dried (Na$_2$SO$_4$) and concentrated to afford 230 mg of 3-(thiazolo[5,4-c]pyridin-2-yl)benzenamine (84% crude yield) (MS, M$^+$+H=228).

Preparation of Compound 115

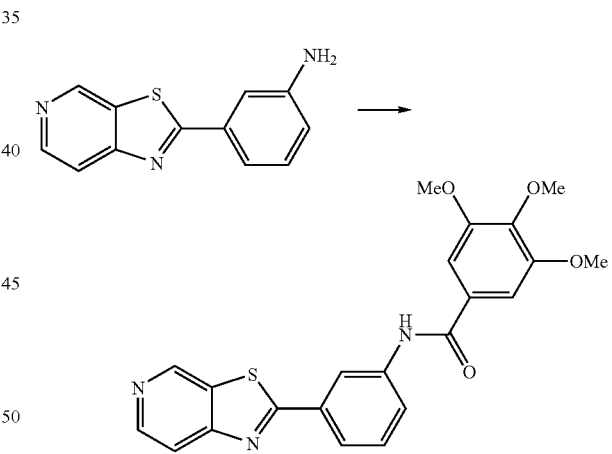

In a typical run, 40 mg of 3-(thiazolo[5,4-c]pyridin-2-yl)benzenamine (0.176 mmol) was suspended in 1 mL of pyridine along with 1 eq of 3,4,5-trimethoxybenzoyl chloride. The reaction mixture was then heated in a Biotage microwave reactor at 160 degree for 10 min. It was then cooled to room temperature and concentrated under reduced pressure. The resulting residue was purified by chromatography using a 9:1 mixture of CH$_2$Cl$_2$ to MeOH (MS, M$^+$+H=422)

Preparation of Compounds 113 and 114

The same procedure used in the preparation of Compound 115 was employed using the appropriate acid chloride.

Preparation of Compound 99

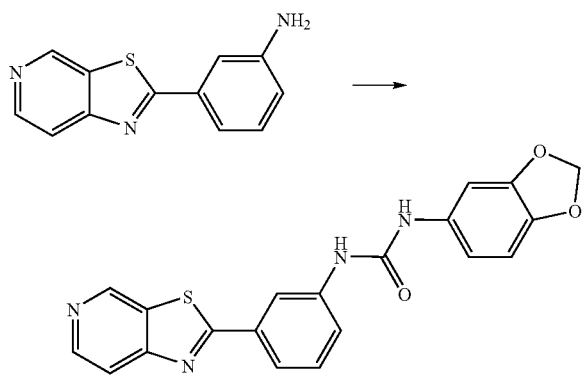

In a typical run, 3-(thiazolo[5,4-c]pyridin-2-yl)benzenamine (25 mg, 0.11 mmol) was suspended in 1 mL of pyridine along with 18 mg of 3,4-(methylenedioxy)phenyl isocyanate. The reaction mixture was then heated in a Biotage microwave reactor at 140 degree for 10 min. It was then cooled to room temperature and concentrated. The resulting residue was purified by chromatography using a 9:1 mixture of $CH_2Cl_2$ to MeOH (MS, $M^+ + H = 391$).

Preparation of methyl 3-amino-5-(thiazolo[5,4-c]pyridin-2-yl)benzoate

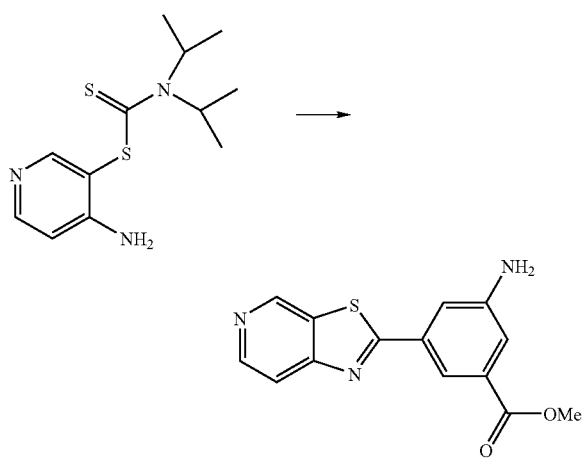

Mono-methyl 5-nitro-isophthlate (1.25 g, 5.58 mmol) was suspended in 25 mL of $CH_2Cl_2$ and oxalyl chloride (0.49 mL, 5.58 mmol) was added. After 3 drops of DMF was added, the reaction mixture was stirred at room temperature until all gas evolution had ceased and all the solids had dissolved. This freshly prepared solution of the acid chloride was then added dropwise to a solution of 4-aminopyridin-3-yl diisopropylcarbamodithioate (1.5 g, 5.58 mmol) and triethylamine (0.77 mL, 5.58 mmol) in 50 mL of $CH_2Cl_2$ at 0° C. The resulting reaction mixture was warmed to room temperature and stirred for 1 hour. It was then quenched with 25 mL of brine and the two layers were separated. The organic layer was dried ($Na_2SO_4$) and concentrated. The resulting residue was suspended in 25 mL of 2 N HCl and stirred under reflux for 30 min. It was then cooled to room temperature and the solids were collected by filtration and dried to afford 1.0 g of methyl 3-nitro-5-(thiazolo[5,4-c]pyridin-2-yl)benzoate. This material was then mixed with 20 mL of methanol and 3 mL of water along with 1 g of sodium hydrosulfide hydrate and stirred under reflux for 2 hours. The resulting reaction mixture was cooled and concentrated. The aqueous layer was extracted with $CH_2Cl_2$. The combined organic layers were dried ($Na_2SO_4$) and concentrated to afford 150 mg of methyl 3-amino-5-(thiazolo[5,4-c]pyridin-2-yl)benzoate (MS, $M^+ + H = 286$).

Preparation of Compound 133

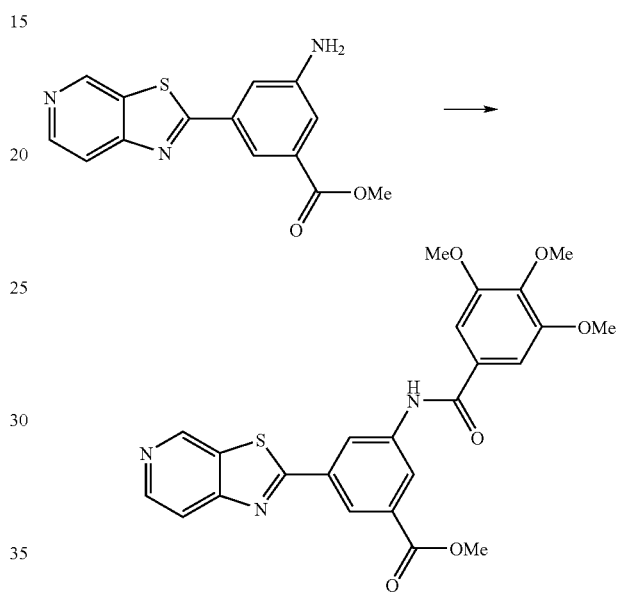

Methyl 3-amino-5-(thiazolo[5,4-c]pyridin-2-yl)benzoate (150 mg, 0.526 mmol) was mixed together with 3,4,5-trimethoxybenzoyl chloride (121 mg, 0.526 mmol) in 1 mL of pyridine. The reaction mixture was reacted in a Biotage microwave reactor at 160 degrees for 10 min. It was then cooled to room temperature and concentrated. The resulting residue was purified by chromatography using a 9:1 mixture of $CH_2Cl_2$ to MeOH to afford 90 mg of methyl 3-(thiazolo[5,4-c]pyridin-2-yl)-5-(3,4,5-trimethoxybenzamido)benzoate (36% yield) (MS, $M^+ + H = 480$).

Preparation of Compound 134

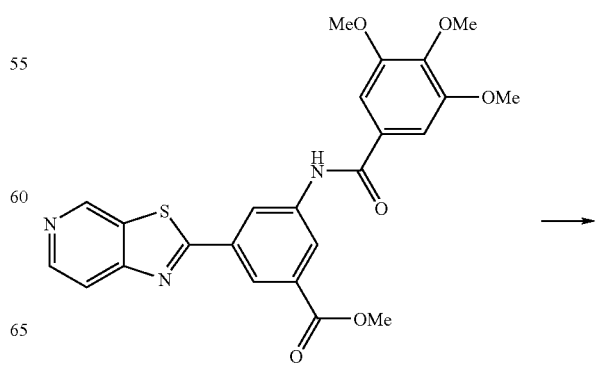

-continued

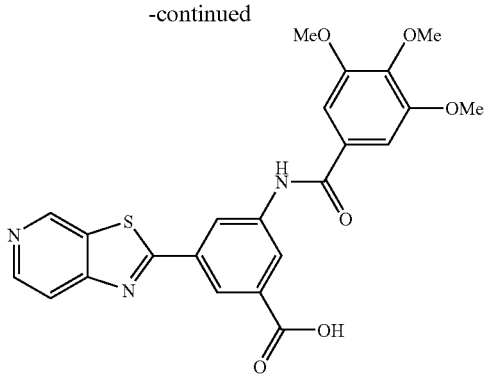

Methyl 3-(thiazolo[5,4-c]pyridin-2-yl)-5-(3,4,5-trimethoxybenzamido)benzoate (80 mg, 0.167 mmol) was dissolved in 5 mL of THF and 2 mL of water containing 30 mg of sodium hydroxide. The reaction mixture was stirred at room temperature for 1 hour. It was then acidified to pH 4 with 6 N HCl and concentrated. The solids were collected by filtration and dried to afford 60 mg of 3-(thiazolo[5,4-c]pyridin-2-yl)-5-(3,4,5-trimethoxybenzamido)benzoic acid (78% yield) (MS, M$^+$+H=466).

Preparation of Compound 135

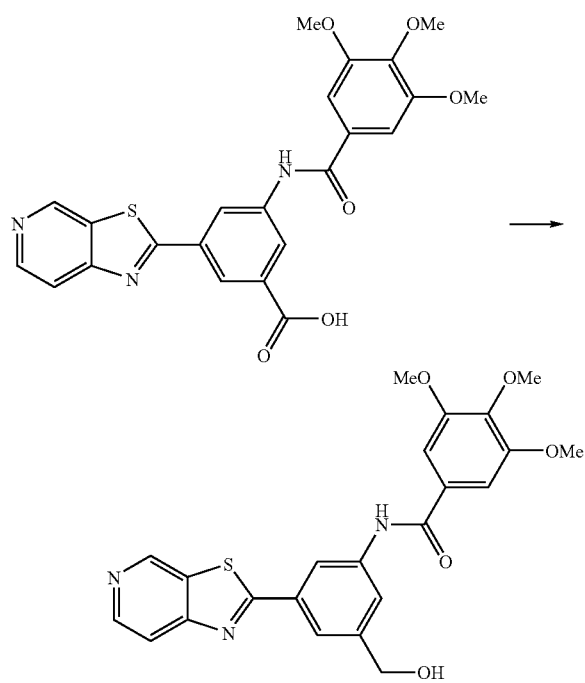

3-(thiazolo[5,4-c]pyridin-2-yl)-5-(3,4,5-trimethoxybenzamido)benzoic acid (50 mg, 0.108 mmol) was suspended in 2 mL of anhydrous THF and cooled to 0° C. along with 1 eq of NMM. Isobutyl chloroformate (1 eq) was added and the reaction mixture was stirred for 45 min. NaBH$_4$ (1 eq) was then added as a solution in 0.5 mL of water. The reaction mixture was stirred for 30 min and then warmed to room temperature and concentrated. The aqueous layer was extracted with CH$_2$Cl$_2$. The combined organic layers were dried (Na$_2$SO$_4$) and concentrated to afford the crude product. This was purified by chromatography using a 9:1 mixture of CH$_2$Cl$_2$ to MeOH (MS, M$^+$+H=452).

Preparation of 3-(oxazolo[5,4-b]pyridin-2-yl)benzenamine

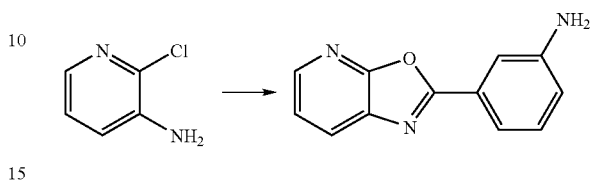

2-Chloropyridin-3-amine (3.20 g, 0.025 mol) was suspended in 15 mL of pyridine and added slowly to a suspension of 3-nitrobenzoyl chloride (4.64 g, 0.025 mol) in 15 mL of pyridine in an ice bath. The reaction mixture was slowly warmed to room temperature and stirred overnight. The next day, the reaction mixture was cooled in an ice bath and 30 mL of glacial acetic acid was added slowly. The resulting mixture was diluted with 200 mL of EtOAc and washed with water (3×20 mL). The organic layer was then dried (Na$_2$SO$_4$) and concentrated. The resulting residue was mixed with 10 mL of PPA and stirred at 160 degree for 6 hours. The reaction mixture was then poured carefully into 150 mL of water. The pH was brought to about 5 with solid NaOH and the solids were collected by filtration and dried. This material was mixed with 50 mL of MeOH and filtered. The filtrate was concentrated to afford 2.1 g of 2-(3-nitrophenyl)oxazolo[5,4-b]pyridine (35% yield) (MS, M$^+$+H=242).

2-(3-Nitrophenyl)oxazolo[5,4-b]pyridine (600 mg, 2.49 mmol) was mixed with 25 mL of MeOH and 4 mL of water along with 837 mg of sodium hydrosulfide hydrate (14.9 mmol). The reaction mixture was stirred under reflux for 3 hours. It was then cooled to room temperature and concentrated. The aqueous layer was extracted with CH$_2$Cl$_2$. The combined organic layers were dried (Na$_2$SO$_4$) and concentrated to afford 520 mg of 3-(oxazolo[5,4-b]pyridin-2-yl)benzenamine (quantitative crude yield) (MS, M$^+$+H=212).

Preparation of Compound 112

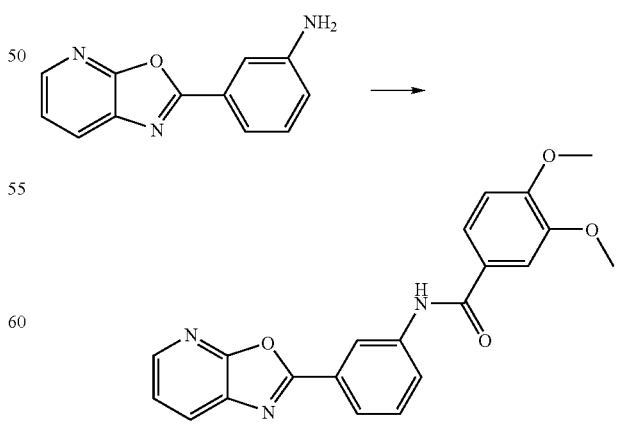

3-(Oxazolo[5,4-b]pyridin-2-yl)benzenamine was reacted with 3,4-dimethoxybenzoyl chloride under the microwave reaction conditions described earlier. The crude product was purified by chromatography using a 9:1 mixture of CH$_2$Cl$_2$ to MeOH (MS, M$^+$+H=376)

Preparation of Compound 74 and 111

The same procedure used in the preparation of Compound 112 was employed using 3,4-dimethoxyphenyl sulfonyl chloride and 3-dimethylaminobenzoyl chloride hydrochloride, respectively. The final product was purified by chromatography using a 9:1 mixture of CH$_2$Cl$_2$ to MeOH.

Preparation of 3-nitro-5-(oxazolo[4,5-b]pyridin-2-yl)benzoic acid and methyl 3-nitro-5-(oxazolo[4,5-b]pyridin-2-yl)benzoate

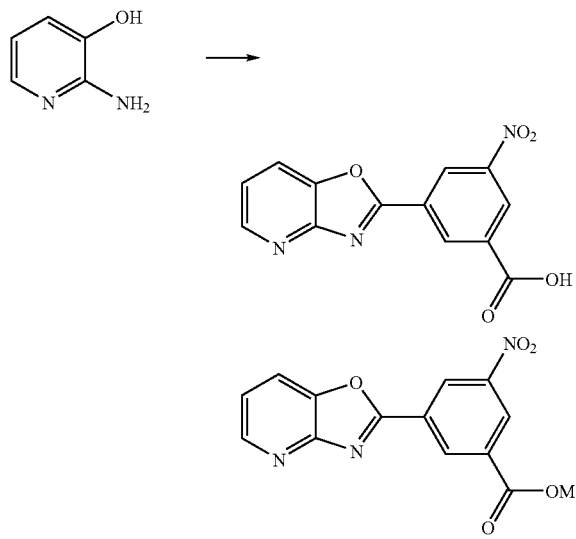

2-Amino-3-hydroxypyridine (1.00 g, 9.16 mmol) was dissolved in 20 mL of DMF along with 2.06 g of monomethyl 5-nitroisophthlate (9.16 mmol), 5.2 g of HATU (13.7 mmol) and 3.2 mL of DIEA (18.3 mmol). The reaction mixture was stirred at room temperature for 18 hours. It was then diluted with 200 mL of EtOAc and washed with water (3×25 mL). The organic layer was dried (Na$_2$SO$_4$) and concentrated. The resulting residue was mixed with 10 mL of PPA and stirred at 160 degree for 6 hours. The reaction mixture was then poured carefully into 200 mL of water and the pH was brought to 5 with solid NaOH. The solids were collected by filtration and dried to afford the product as a 1:1 mixture of the methyl ester and the acid. This mixture was separated by suspending in 150 mL of CH$_2$Cl$_2$ and then filtered. The filtrate was the methyl ester (MS, M$^+$+H=300) and the solids were the desired acid, namely, 3-nitro-5-(oxazolo[4,5-b]pyridin-2-yl)benzoic acid (MS, M$^+$+H=286).

Preparation of 3-amino-N-(2-(dimethylamino)ethyl)-5-(oxazolo[4,5-b]pyridin-2-yl)benzamide

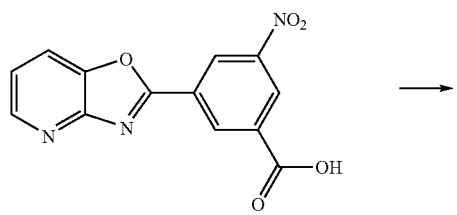

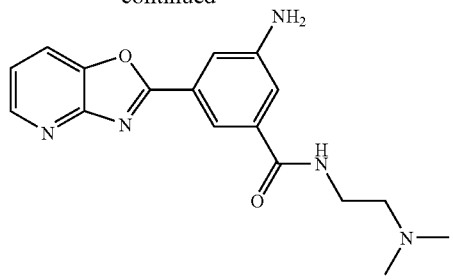

3-Nitro-5-(oxazolo[4,5-b]pyridin-2-yl)benzoic acid (250 mg, 0.877 mmol) was dissolved in 5 mL of DMF along with 1 eq of N,N-dimethylethylenediamine, 500 mg of HATU (1.5 eq) and 0.3 mL of DIEA (2 eq). The reaction mixture was stirred at room temperature for 18 hours. It was then diluted with 50 mL of EtOAc and washed with water. The organic layer was dried (Na$_2$SO$_4$) and concentrated to afford the nitro amide intermediate. This was dissolved in 50 mL of MeOH and 5 mL of water along with 200 mg of sodium hydrosulfide hydrate (4 eq). The reaction mixture was stirred under reflux for 1 hour. It was then concentrated to dryness and mixed with 50 mL of 1:1 CH$_2$Cl$_2$/MeOH and filtered. The filtrate was concentrated to afford essentially quantitative yield of 3-amino-N-(2-(dimethylamino)ethyl)-5-(oxazolo[4,5-b]pyridin-2-yl)benzamide (MS, M$^+$+H=326).

Preparation of Compound 153

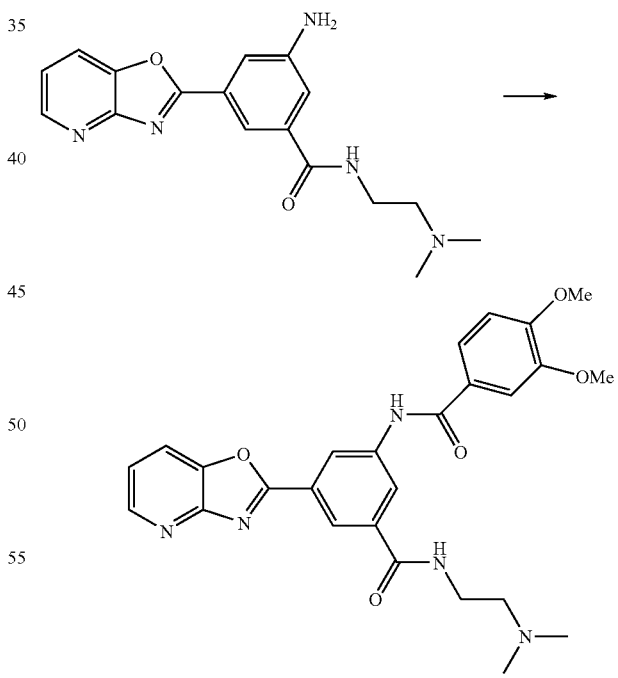

3-amino-N-(2-(dimethylamino)ethyl)-5-(oxazolo[4,5-b]pyridin-2-yl)benzamide was reacted with 3,4-dimethoxybenzoyl chloride under the same microwave conditions as described earlier. The crude product was purified by chromatography using a 9:1 mixture of CH$_2$Cl$_2$ to MeOH (MS, M$^+$+H=490).

Preparation of Compounds 154 and 155

The same procedure used in the preparation of Compound 153 was employed using the appropriate acid chloride.

Preparation of tert-butyl 4-(3-amino-5-(oxazolo[4,5-b]pyridin-2-yl)benzoyl)piperazine-1-carboxylate

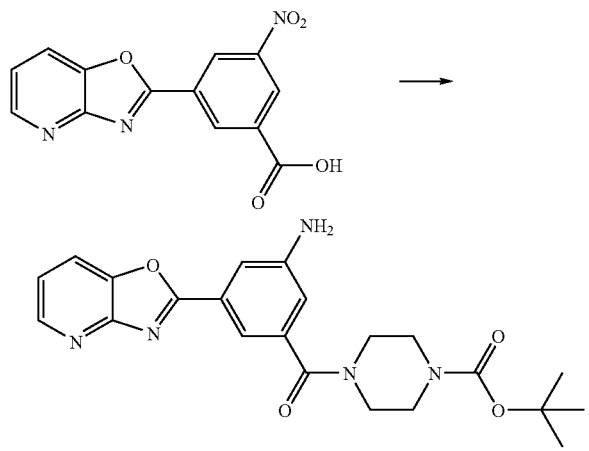

3-Nitro-5-(oxazolo[4,5-b]pyridin-2-yl)benzoic acid (250 mg, 0.877 mmol) was dissolved in 5 mL of DMF along with 1 eq of Boc-piperazine (163 mg), 500 mg of HATU (1.5 eq) and 0.3 mL of DIEA (2 eq). The reaction mixture was stirred at room temperature for 18 hours. It was then diluted with 50 mL of EtOAc and washed with water. The organic layer was dried ($Na_2SO_4$) and concentrated to afford the nitro amide intermediate. This was dissolved in 50 mL of MeOH and 5 mL of water along with 200 mg of sodium hydrosulfide hydrate (4 eq). The reaction mixture was stirred under reflux for 1 hour. The reaction mixture was concentrated and the aqueous layer was extracted with $CH_2Cl_2$. The combined organic layers were dried ($Na_2SO_4$) and concentrated to afford 300 mg of tert-butyl 4-(3-amino-5-(oxazolo[4,5-b]pyridin-2-yl)benzoyl)piperazine-1-carboxylate. (MS, $M^+ + H = 424$).

Preparation of Compound 107

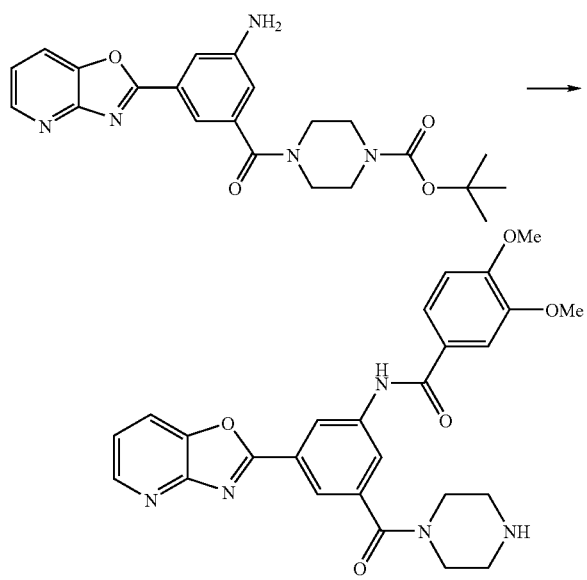

tert-Butyl 4-(3-amino-5-(oxazolo[4,5-b]pyridin-2-yl)benzoyl)piperazine-1-carboxylate (100 mg, 0.236 mmol) was dissolved in 1 mL of pyridine along with 47 mg of 3,4-dimethoxybenzoyl chloride (1 eq). The reaction mixture was heated in a Biotage microwave reactor for 10 min. It was then cooled to room temperature and concentrated. The resulting residue was purified by chromatography using a 9:1 mixture of $CH_2Cl_2$ to MeOH to afford 120 mg of the Boc-protected diamide derivative. This was treated with 2 mL of 25% TFA in $CH_2Cl_2$ and allowed to stand at room temperature for 1 hour. It was then concentrated and triturated with $Et_2O$ to afford 3,4-dimethoxy-N-(3-(oxazolo[4,5-b]pyridin-2-yl)-5-(piperazine-1-carbonyl)phenyl)benzamide as the TFA salt (MS, $M^+ + H = 488$).

Preparation of Compounds 138 and 139

The same procedure used in the preparation of Compound 107 was employed using the appropriate acid chloride.

Preparation of Compound 136

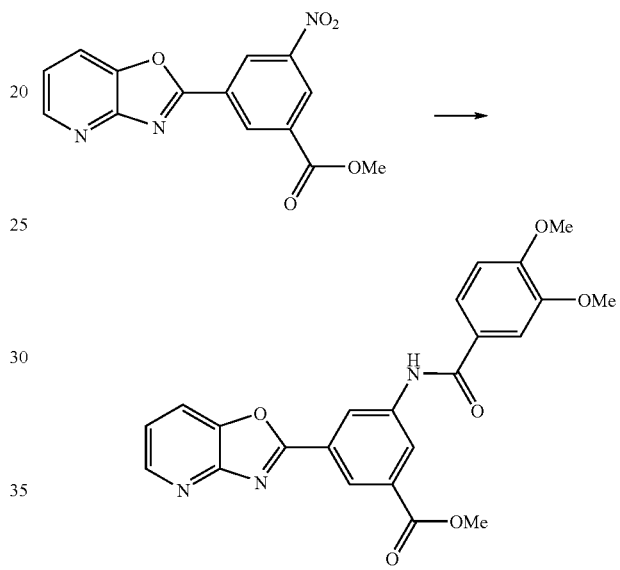

Methyl 3-nitro-5-(oxazolo[4,5-b]pyridin-2-yl)benzoate (2.70 g) was mixed with 100 mL of MeOH and 20 mL of water along with 3 g of sodium hydrosulfide hydrate (6 eq). The reaction mixture was stirred under reflux for 1 hour. It was then cooled to room temperature and concentrated. The aqueous layer was extracted with $CH_2Cl_2$. The combined organic layers were dried ($Na_2SO_4$) and concentrated to afford 600 mg of the intermediate amine. A portion of this intermediate amine (50 mg) was reacted with 1 eq of 3,4-dimethoxybenzoyl chloride under the same microwave reaction conditions described earlier. The crude product was purified by chromatography using a 9:1 mixture of $CH_2Cl_2$ to MeOH (MS, $M^+ + H = 434$).

Preparation of Compound 137

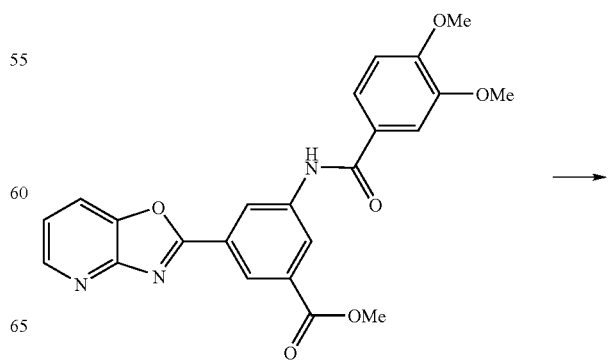

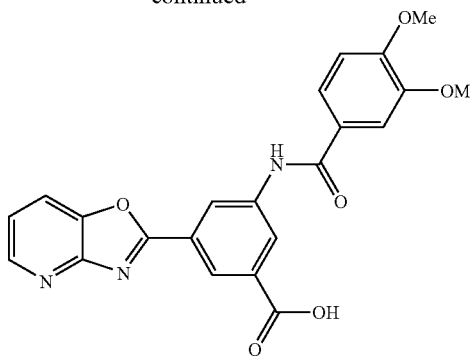

Methyl 3-(3,4-dimethoxybenzamido)-5-(oxazolo[4,5-b]pyridin-2-yl)benzoate (20 mg) was dissolved in 2 mL of THF and 1 mL of water containing 2 eq of NaOH. The reaction mixture was stirred at room temperature for 1 hour. It was then acidified to pH 5 with 6 N HCl and concentrated. The resulting solids were collected by filtration and dried to afford the acid (MS, $M^++H=420$).

Preparation of Compounds 79, 80 and 81

3-(2-Methylthiazol-4-yl)benzenamine (Aldrich) was subjected to the same microwave reaction conditions described earlier using the appropriate acid chloride. The final products were purified by chromatography using a 9:1 mixture of $CH_2Cl_2$ to MeOH.

Preparation of 2-amino-3-hydroxy-6-methylpyridine

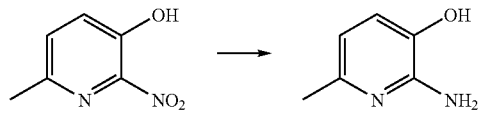

7.00 g of 3-hydroxy-6-methyl-2-nitropyridine (Aldrich, 0.045 mol) was dissolved in 250 mL of MeOH and 20 mL of $H_2O$ along with 15 g of sodium hydrosulfide hydrate (6 eq, 0.27 mol). The reaction mixture was stirred under reflux for 5 hours. The reaction mixture was cooled to room temperature and diluted with 300 mL of absolute EtOH and concentrated to dryness. The resulting residue was dissolved in 300 mL of $CH_2Cl_2$ and 10 mL of MeOH. The mixture was sonicated for 10 min and allowed to stand at room temperature for 3 hours. The resulting salts that precipitated out at this point were removed by filtration. The filtrate was concentrated to afford the crude amine. This was purified by passing through a short plug of silica gel and eluting with 95% $CH_2Cl_2$, 4% MeOH and 1% $Et_3N$. A total of 5.0 g of the desired amine was obtained (89% yield).

Preparation of 5-methyl-2-(3-nitro-phenyl)-oxazolo[4,5-b]pyridine

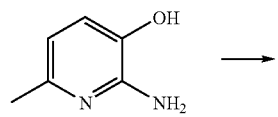

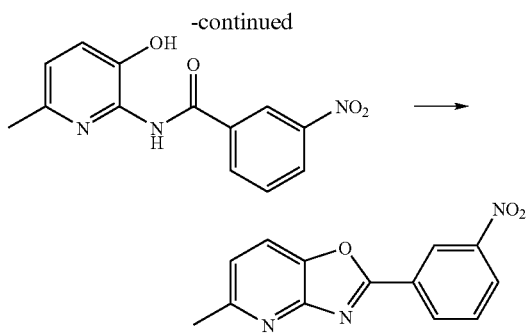

1.20 g of 2-amino-3-hydroxy-6-methyl pyridine (9.68 mmol) was dissolved in 20 mL of DMF along with 1.60 g of 3-nitrobenzoic acid (1 eq), 4.4 g of HATU (Novabiochem, 1.2 eq. 11.6 mmol) and 2.5 mL of DIEA.(1.5 eq, 14.5 mmol). The reaction mixture was stirred at room temperature for 18 hrs. It was then diluted with 250 mL of EtOAc and washed with water (4×15 mL). The organic layer was dried ($Na_2SO_4$) and concentrated to afford the crude product. Purification by chromatography (Isco, gradient elution, pentane to 80% EtOAc/pentane) afforded 1.10 g of the desired amide intermediate (42% yield).

This amide intermediate (1.10 g, 4.00 mmol) was mixed with 7 mL of PPA and stirred at 150° C. for 5 hrs. The reaction mixture was cooled to about 80° C. and diluted with 200 mL of water. This mixture was cooled in an ice bath and the pH was slowly brought to 5 using solid NaOH. The resulting solids were collected by filtration and dried to afford 600 mg of the desired product, namely, 5-methyl-2-(3-nitro-phenyl)-oxazolo[4,5-b]pyridine (24% overall yield for the 2 steps). LC/MS showed >95% purity.

Preparation of 5-bromomethyl-2-(3-nitro-phenyl)-oxazolo[4,5-b]pyridine

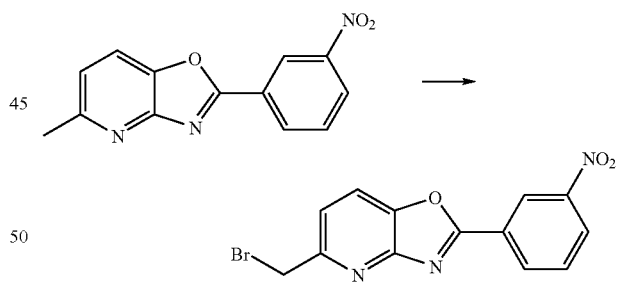

In a typical run, 400 mg of 5-methyl-2-(3-nitro-phenyl)-oxazolo[4,5-b]pyridine (1.57 mmol) was suspended in 50 mL of $CCl_4$ along with 280 mg (1.57 mmol) of NBS and 20 mg of benzoyl peroxide. The reaction mixture was stirred under reflux for 4 hours. LC/MS showed about 50% conversion to the desired bromide. After another 2 hours of reflux, no additional change was observed. Another 1 eq of NBS was added and reflux was continued for another 4 hours. LC/MS showed complete conversion. The reaction mixture was concentrated and the resulting crude product was purified by chromatography (Isco, gradient elution, $CH_2Cl_2$ to 9:1 $CH_2Cl_2$/MeOH) to afford essentially quantitative yield of 5-bromomethyl-2-(3-nitro-phenyl)-oxazolo[4,5-b]pyridine.

Preparation of 4-[2-(3-nitro-phenyl)-oxazolo[4,5-b]pyridin-5-ylmethyl]-piperazine-1-carboxylic acid tert-butyl ester

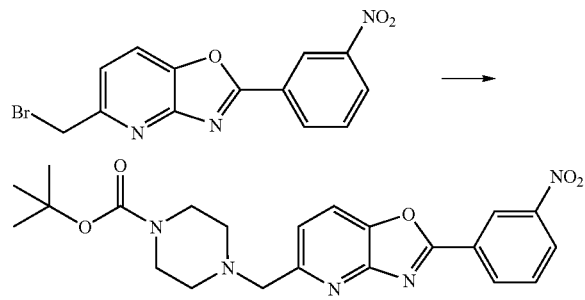

5-Bromomethyl-2-(3-nitro-phenyl)-oxazolo[4,5-b]pyridine (250 mg, 0.75 mmol) was dissolved in 5 mL of CH$_3$CN along with Et$_3$N (0.200 mL, 1.5 mmol) and 140 mg of Boc-piperazine. The reaction mixture was stirred at room temperature for 18 hours. It was then concentrated and the resulting residue was mixed with 25 mL of CH$_2$Cl$_2$ and washed with brine. The organic layer was dried (Na$_2$SO$_4$) and concentrated to afford essentially quantitative yield of 4-[2-(3-nitro-phenyl)-oxazolo[4,5-b]pyridin-5-ylmethyl]-piperazine-1-carboxylic acid tert-butyl ester.

Preparation of 4-[2-(3-amino-phenyl)-oxazolo[4,5-b]pyridin-5-ylmethyl]-piperazine-1-carboxylic acid tert-butyl ester

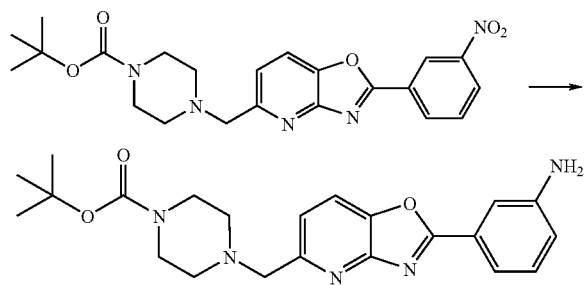

4-[2-(3-Nitro-phenyl)-oxazolo[4,5-b]pyridin-5-ylmethyl]-piperazine-1-carboxylic acid tert-butyl ester (330 mg, 0.75 mmol) was dissolved in 6 mL of MeOH and 2 mL of water along with 210 mg of sodium hydrosulfide hydrate (3.75 mmol). The reaction mixture was stirred under reflux for 4 hours. The reaction appeared to be complete based on LC/MS. The reaction mixture was cooled to room temperature and concentrated. The aqueous layer was extracted with CH$_2$Cl$_2$. The combined organic layers were dried (Na2SO$_4$) and concentrated to afford essentially quantitative yield of 4-[2-(3-amino-phenyl)-oxazolo[4,5-b]pyridin-5-ylmethyl]-piperazine-1-carboxylic acid tert-butyl ester.

Preparation of Compound 166

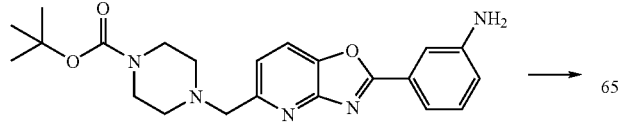

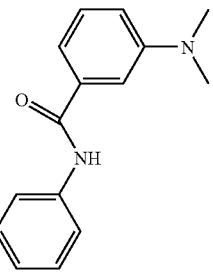

4-[2-(3-Amino-phenyl)-oxazolo[4,5-b]pyridin-5-ylmethyl]-piperazine-1-carboxylic acid tert-butyl ester (83 mg, 0.2 mmol) was dissolved in 1 mL of pyridine along with 1 eq of 3-dimethylamino benzoyl chloride hydrochloride (44 mg, 0.2 mmol). The reaction mixture was heated in a Biotage microwave reactor (160° C.) for 10 min. It was then cooled to room temperature and concentrated. The resulting residue was purified by chromatography (Isco, gradient elution, CH$_2$Cl$_2$ to 95% CH$_2$Cl$_2$, 4% MeOH and 1% Et$_3$N) to afford 25 mg of 4-{2-[3-(3-dimethylamino-benzoylamino)-phenyl]-oxazolo[4,5-b]pyridin-5-ylmethyl}-piperazine-1-carboxylic acid tert-butyl ester (23% yield).

4-{2-[3-(3-Dimethylamino-benzoylamino)-phenyl]-oxazolo[4,5-b]pyridin-5-ylmethyl}-piperazine-1-carboxylic acid tert-butyl ester (25 mg, 0.045 mmol) was dissolved in 1 mL of 25% TFA in CH$_2$Cl$_2$ and allowed to stand at room temperature for 1 hour. It was then concentrated and the resulting residue was triturated with Et$_2$O to afford essentially quantitative yield of 3-dimethylamino-N-[3-(5-piperazin-1-ylmethyl-oxazolo[4,5-b]pyridin-2-yl)-phenyl]-benzamide as the TFA salt.

Preparation of Compound 514

The preparation followed essentially the same procedure as detailed in the preparation of Compound 166 except that 2-quinoxaloyl chloride was used as the acid chloride component.

Preparation of 3-nitro-5-(oxazolo[4,5-b]pyridin-2-yl)benzoic acid and methyl 3-nitro-5-(oxazolo[4,5-b]pyridin-2-yl)benzoate

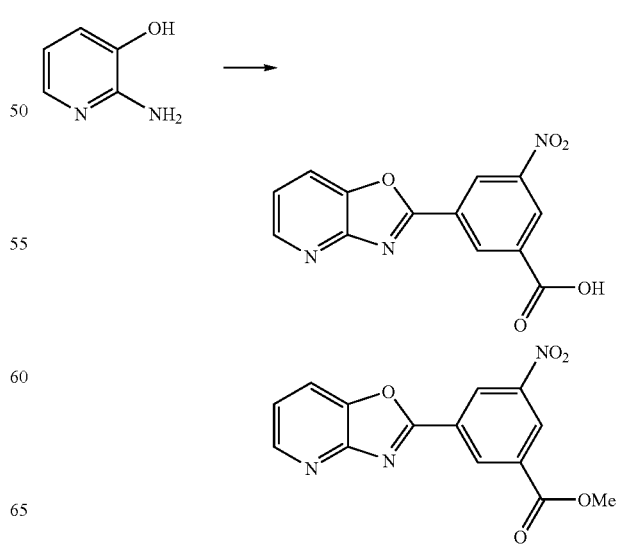

2-Amino-3-hydroxypyridine (1.00 g, 9.16 mmol) was dissolved in 20 mL of DMF along with 2.06 g of monomethyl 5-nitroisophthlate (9.16 mmol), 5.2 g of HATU (13.7 mmol) and 3.2 mL of DIEA (18.3 mmol). The reaction mixture was stirred at room temperature for 18 hours. It was then diluted with 200 mL of EtOAc and washed with water (3×25 mL). The organic layer was dried (Na$_2$SO$_4$) and concentrated. The resulting residue was mixed with 10 mL of PPA and stirred at 160 degree for 6 hours. The reaction mixture was then poured carefully into 200 mL of water and the pH was brought to 5 with solid NaOH. The solids were collected by filtration and dried to afford the product as a 1:1 mixture of the methyl ester and the acid. This mixture was separated by suspending it in 150 mL of CH$_2$Cl$_2$ and then filtering. The filtrate was the methyl ester (MS, M$^+$+H=300) and the solids were the desired acid, namely, 3-nitro-5-(oxazolo[4,5-b]pyridin-2-yl)benzoic acid (MS, M$^+$+H=286).

Preparation of 3-amino-N-(2-(dimethylamino)ethyl)-5-(oxazolo[4,5-b]pyridin-2-yl)benzamide

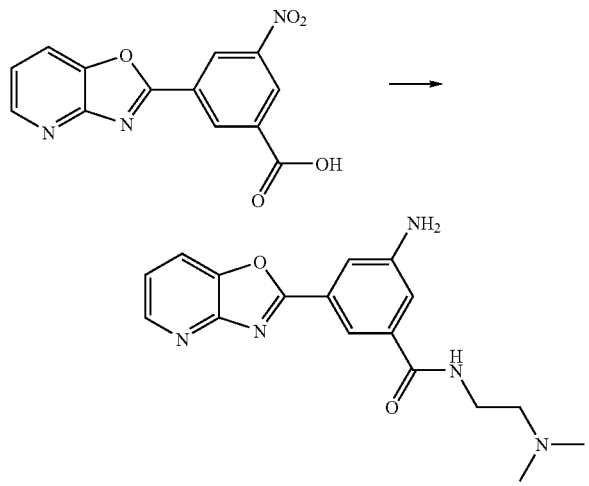

3-Nitro-5-(oxazolo[4,5-b]pyridin-2-yl)benzoic acid (250 mg, 0.877 mmol) was dissolved in 5 mL of DMF along with 1 eq of N,N-dimethylethylenediamine, 500 mg of HATU (1.5 eq) and 0.3 mL of DIEA (2 eq). The reaction mixture was stirred at room temperature for 18 hours. It was then diluted with 50 mL of EtOAc and washed with water. The organic layer was dried (Na$_2$SO$_4$) and concentrated to afford the nitro amide intermediate. This was dissolved in 50 mL of MeOH and 5 mL of water along with 200 mg of sodium hydrosulfide hydrate (4 eq). The reaction mixture was stirred under reflux for 1 hour. It was then concentrated to dryness and mixed with 50 mL of 1:1 CH$_2$Cl$_2$/MeOH and filtered. The filtrate was concentrated to afford essentially quantitative yield of 3-amino-N-(2-(dimethylamino)ethyl)-5-(oxazolo[4,5-b]pyridin-2-yl)benzamide (MS, M$^+$+H=326).

Preparation of tert-butyl 4-(3-amino-5-(oxazolo[4,5-b]pyridin-2-yl)benzoyl)piperazine-1-carboxylate

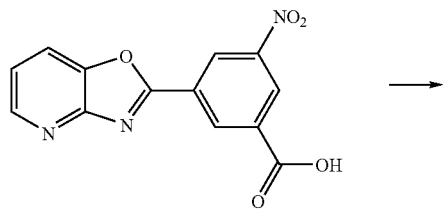

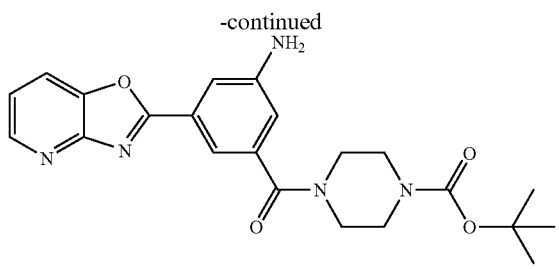

3-Nitro-5-(oxazolo[4,5-b]pyridin-2-yl)benzoic acid (250 mg, 0.877 mmol) was dissolved in 5 mL of DMF along with 1 eq of Boc-piperazine (163 mg), 500 mg of HATU (1.5 eq) and 0.3 mL of DIEA (2 eq). The reaction mixture was stirred at room temperature for 18 hours. It was then diluted with 50 mL of EtOAc and washed with water. The organic layer was dried (Na$_2$SO$_4$) and concentrated to afford the nitro amide intermediate. This was dissolved in 50 mL of MeOH and 5 mL of water along with 200 mg of sodium hydrosulfide hydrate (4 eq). The reaction mixture was stirred under reflux for 1 hour. The reaction mixture was concentrated and the aqueous layer was extracted with CH$_2$Cl$_2$. The combined organic layers were dried (Na$_2$SO$_4$) and concentrated to afford 300 mg of tert-butyl 4-(3-amino-5-(oxazolo[4,5-b]pyridin-2-yl)benzoyl)piperazine-1-carboxylate. (MS, M$^+$+H=424).

Preparation of Compound 164

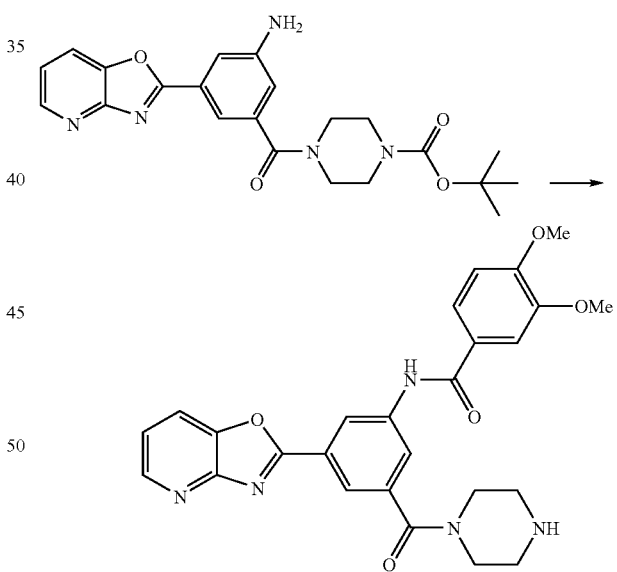

Tert-Butyl 4-(3-amino-5-(oxazolo[4,5-b]pyridin-2-yl)benzoyl)piperazine-1-carboxylate (100 mg, 0.236 mmol) was dissolved in 1 mL of pyridine along with 47 mg of 3,4-dimethoxybenzoyl chloride (I eq). The reaction mixture was heated in a Biotage microwave reactor for 10 min. It was then cooled to room temperature and concentrated. The resulting residue was purified by chromatography using a 9:1 mixture of CH$_2$Cl$_2$ to MeOH to afford 120 mg of the Boc-protected diamide derivative. This was treated with 2 mL of 25% TFA in CH$_2$Cl$_2$ and allowed to stand at room temperature for 1 hour. It was then concentrated and triturated with Et$_2$O to afford 3,4-dimethoxy-N-(3-(oxazolo[4,5-b]pyridin-2-yl)-5-(piperazine-1-carbonyl)phenyl)benzamide as the TFA salt (MS, M$^+$+H=488).

Preparation of (3-nitro-5-oxazolo[4,5-b]pyridin-2-yl-phenyl)-methanol

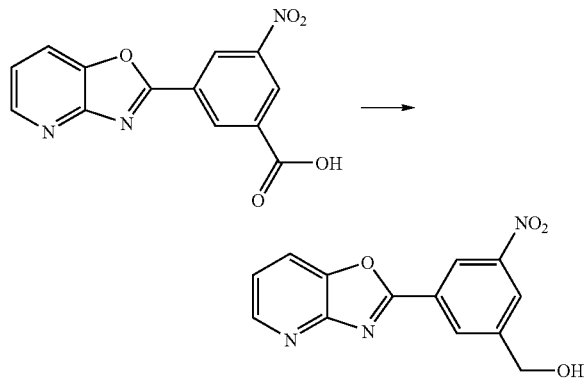

In a typical run, 3-nitro-5-(oxazolo[4,5-b]pyridin-2-yl) benzoic acid (770 mg, 2.70 mmol) was suspended in 50 mL of anhydrous THF and cooled in an ice bath along with NMM (0.3 mL, 2.70 mmol). Isobutyl chloroformate (0.35 mL, 2.70 mmol) was added and the reaction mixture was stirred at 0° C. for 1 hour. A solution of NaBH$_4$ (102 mg, 2.70 mmol) in 6 mL of water was then added at 0° C. and the reaction mixture was stirred at the same temperature for 45 min. It was then concentrated and the resulting residue was diluted with 10 mL of water. The aqueous layer was extracted with CH$_2$Cl$_2$. The organic layer was dried (Na$_2$SO$_4$) and concentrated to afford 500 mg of (3-nitro-5-oxazolo[4,5-b]pyridin-2-yl-phenyl)-methanol (68% yield, >95% pure by LC/MS).

Preparation of 4-(3-amino-5-oxazolo[4,5-b]pyridin-2-yl-benzyl)-piperazine-1-carboxylic acid tert-butyl ester

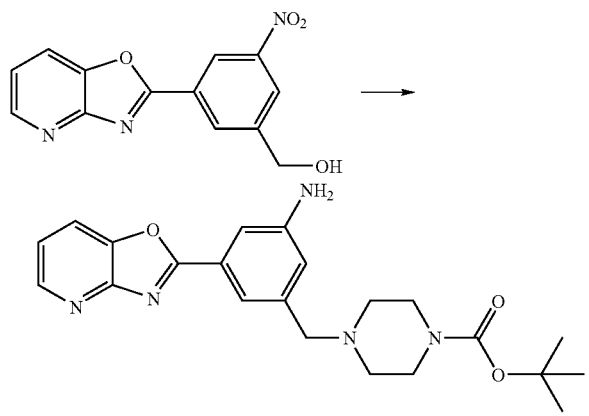

In a typical run, 250 mg of (3-nitro-5-oxazolo[4,5-b]pyridin-2-yl-phenyl)-methanol (0.923 mmol) was dissolved in 25 mL of CH$_2$Cl$_2$ along with 1 eq of Et$_3$N (130 μL). Methanesulfonyl chloride (1 eq, 70 μL) was added and the reaction mixture was warmed to room temperature and stirred for 15 min. It was then quenched with brine and extracted with CH$_2$Cl$_2$. The combined organic layers were dried (Na$_2$SO$_4$) and concentrated to afford the mesylate intermediate. This material was mixed with 4 mL of CH$_3$CN along with 130 μL of Et$_3$N and 172 mg of Boc-piperazine (0.923 mmol) and stirred at room temperature for 1 day. The reaction mixture was concentrated and the resulting residue was partitioned between CH$_2$Cl$_2$ and water. The organic layer was dried (Na$_2$SO$_4$) and concentrated to afford essentially quantitative yield of 4-(3-nitro-5-oxazolo[4,5-b]pyridin-2-yl-benzyl)-piperazine-1-carboxylic acid tert-butyl ester. This material was mixed with 6 mL of MeOH and 1 mL of water along with 200 mg of sodium hydrosulfide hydrate. The resulting reaction mixture was stirred under reflux for 1 hour. It was then cooled to room temperature and concentrated. The resulting residue was diluted with 2 mL of water and extracted with CH$_2$Cl$_2$. The combined organic layers were dried (Na$_2$SO$_4$) and concentrated to afford 280 mg of 4-(3-amino-5-oxazolo[4,5-b]pyridin-2-yl-benzyl)-piperazine-1-carboxylic acid tert-butyl ester.

Preparation of Compound 159

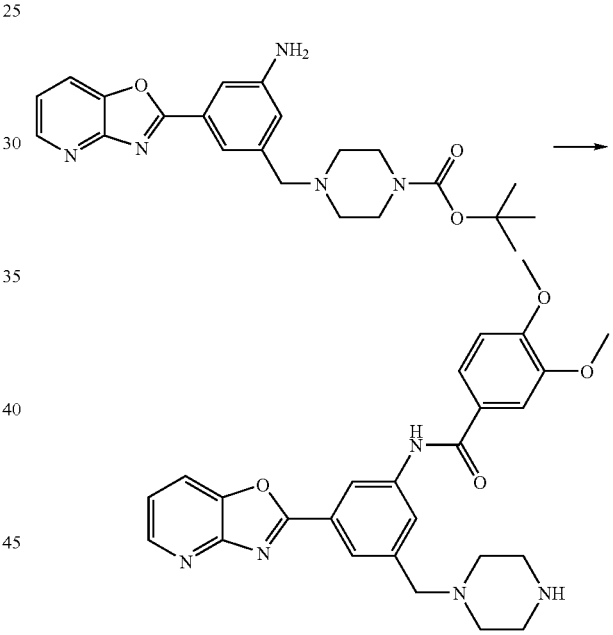

4-(3-Amino-5-oxazolo[4,5-b]pyridin-2-yl-benzyl)-piperazine-1-carboxylic acid tert-butyl ester (0.2 mmol) was mixed with 1 mL of pyridine along with 1 eq (40 mg) of 3,4-dimethoxybenzoyl chloride. The reaction mixture was reacted in a Biotage microwave reactor at 160° C. for 10 min. It was then cooed to room temperature and concentrated. The resulting crude product was purified by chromatography (Isco, gradient elution, CH$_2$Cl$_2$ to 95% CH$_2$Cl$_2$, 4% MeOH and 1% Et$_3$N). The purified product was then treated with 2 mL of 25% TFA in CH$_2$Cl$_2$ for 2 hours. It was then concentrated and the resulting residue was triturated with Et$_2$O to afford the desired product as the TFA salt (MS, M$^+$+H=474).

Preparation of Compound 160 and Compound 161

The same procedure used in the preparation of Compound 159 was employed using the appropriate acid chloride.

Preparation of 3-dimethylaminomethyl-5-oxazolo[4,5-b]pyridin-2-yl-phenylamine

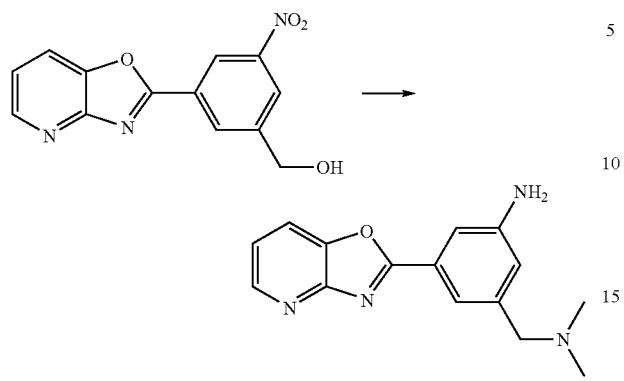

In a typical run, 250 mg of (3-nitro-5-oxazolo[4,5-b]pyridin-2-yl-phenyl)-methanol (0.923 mmol) was dissolved in 25 mL of $CH_2Cl_2$ along with 1 eq of $Et_3N$ (130 µL). Methanesulfonyl chloride (1 eq, 70 µL) was added and the reaction mixture was warmed to room temperature and stirred for 15 min. It was then quenched with brine and extracted with $CH_2Cl_2$. The combined organic layers were dried ($Na_2SO_4$) and concentrated to afford the mesylate intermediate. This material was dissolved in 5 mL of $CH_3CN$ along with 2 mL of 2 N-dimethylamine in THF. The reaction mixture was stirred at room temperature for 2 hours. It was then concentrated and the resulting residue was partitioned between $CH_2Cl_2$ and water. The organic layer was separated, dried ($Na_2SO_4$) and concentrated to afford the crude nitro derivative. This material was mixed with 6 mL of MeOH and 1 mL of water along with 200 mg of sodium hydrosulfide hydrate and stirred under reflux for 1 hour. The reaction mixture was cooled to room temperature and diluted with 100 mL of absolute EtOH and concentrated to dryness. The resulting residue was mixed with 10 mL of 9:1 $CH_2Cl_2$/MeOH and filtered. The filtrate was concentrated to afford 220 mg of 3-dimethylaminomethyl-5-oxazolo[4,5-b]pyridin-2-yl-phenylamine.

Preparation of Compound 156

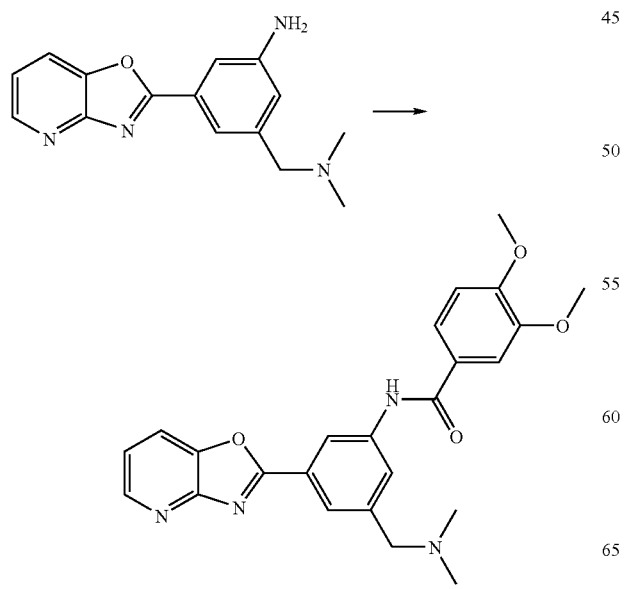

3-Dimethylaminomethyl-5-oxazolo[4,5-b]pyridin-2-yl-phenylamine (0.2 mmol) was mixed with 1 mL of pyridine along with 40 mg of 3,4-dimethoxybenzoyl chloride (0.2 mmol). The reaction mixture was reacted in a Biotage microwave reactor at 160° C. for 10 min. It was then cooled to room temperature and concentrated. The resulting residue was purified by chromatography (Isco, gradient elution, $CH_2Cl_2$ to 95% $CH_2Cl_2$, 4% MeOH and 1% $Et_3N$) to afford the desired product (MS, $M^+$+H=433).

Preparation of Compound 157 and Compound 158

The same procedure used in the preparation of Compound 156 was employed using the appropriate acid chloride.

Preparation of (3-nitro-5-thiazolo[5,4-c]pyridin-2-yl-phenyl)-methanol

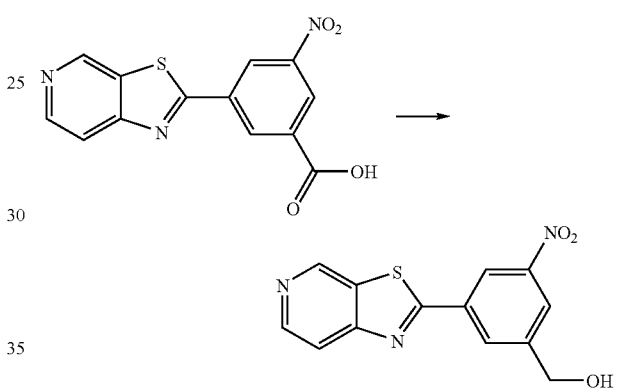

3-Nitro-5-thiazolo[5,4-c]pyridin-2-yl-benzoic acid (880 mg, 2.92 mmol) was suspended in 50 mL of anhydrous THF along with NMM (0.32 mL, 2.92 mmol). The reaction mixture was cooled in an ice bath and isobutyl chloroformate (0.38 mL, 2.92 mmol) was added. The reaction mixture was stirred at 0° C. for 40 min. $NaBH_4$ (110 mg, 2.92 mmol) was then added as a solution in 5 mL of water. The reaction mixture was stirred at 0° C. for 30 min and then warmed to room temperature. It was concentrated and then extracted with $CH_2Cl_2$. The combined organic layers were dried ($Na_2SO_4$) and concentrated to afford the crude product. Purification by chromatography (Isco, gradient elution, $CH_2Cl_2$ to 9:1 $CH_2Cl_2$/MeOH) afford 150 mg of (3-nitro-5-thiazolo[5,4-c]pyridin-2-yl-phenyl)-methanol.

Preparation of 3-dimethylaminomethyl-5-thiazolo[5,4-c]pyridin-2-yl-phenylamine

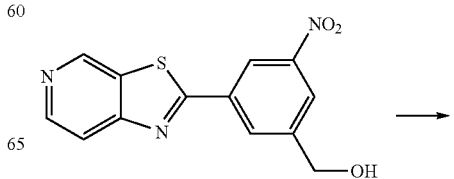

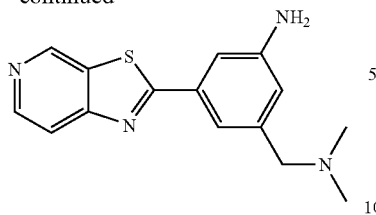

(3-Nitro-5-thiazolo[5,4-c]pyridin-2-yl-phenyl)-methanol (120 mg, 0.418 mmol) was suspended in 20 mL of CH$_2$Cl$_2$ along with Et$_3$N (87 μL, 1.5 eq) cooled in an ice bath. Methanesulfonyl chloride (32 μL, 0.418 mmol) was added and the reaction mixture was slowly warmed to room temperature. The reaction mixture was partitioned between CH$_2$Cl$_2$ and brine. The organic layer was separated, dried (Na$_2$SO$_4$) and concentrated to afford the crude mesylate intermediate. This material was dissolved in 2 mL of CH$_3$CN along with 2 mL of 2 N dimethylamine in THF. The resulting reaction mixture was stirred at room temperature for 2 hours. It was then concentrated. The resulting residue was mixed with 6 mL of MeOH and 2 mL of water containing 200 mg of sodium hydrosulfide hydrate. The reaction mixture was stirred under reflux for 3 hours. It was then cooled to room temperature, diluted with 100 mL of absolute EtOH, and concentrated to dryness. The resulting residue was mixed with 10 mL of 9:1 CH$_2$Cl$_2$/MeOH and filtered. The filtrate was concentrated to afford essentially quantitative yield of 3-dimethylaminomethyl-5-thiazolo[5,4-c]pyridin-2-yl-phenylamine.

Preparation of Compound 174

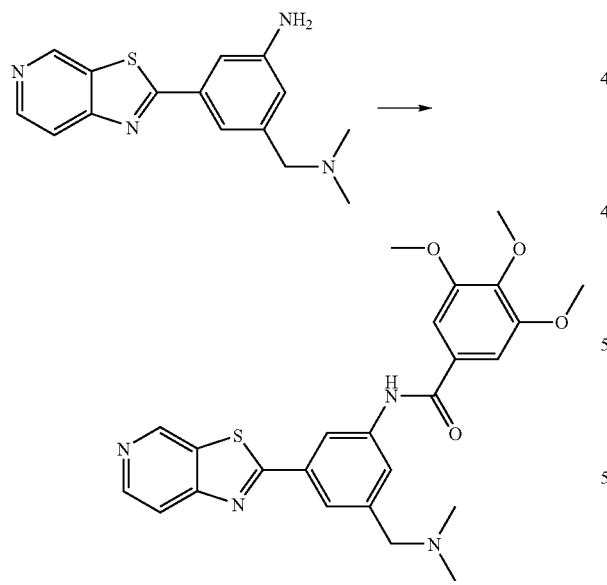

3-Dimethylaminomethyl-5-thiazolo[5,4-c]pyridin-2-yl-phenylamine (0.2 mmol) was mixed with 1 mL of pyridine along with 47 mg of 3,4,5-trimethoxybenzoyl chloride (0.2 mmol). The reaction mixture was reacted in a Biotage microwave reactor at 160° C. for 10 min. It was then cooled to room temperature and concentrated. The resulting residue was purified by chromatography (Isco, gradient elution, CH$_2$Cl$_2$ to 95% CH$_2$Cl$_2$, 4% MeOH and 1% Et$_3$N) to afford 30 mg of the desired product (MS, M$^+$+H=479).

Preparation of 3-(oxazolo[4,5-b]pyridin-2-yl)benzoic acid

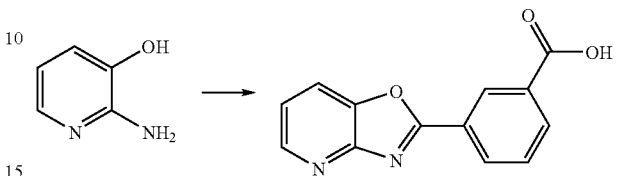

2-Amino-3-hydroxypyridine (1 g, 9.16 mmol) was dissolved in 25 mL of DMF along with 1.65 g of mono-methyl isophthalate (9.16 mmol), 5.2 g of HATU (1.5 eq) and 3.2 mL of DIEA. The reaction mixture was stirred at room temperature for 18 hrs. It was then diluted with 150 mL of ethyl acetate and washed with water (5×20 mL). The organic layer was dried (Na$_2$SO$_4$) and concentrated to afford 3.20 g of the intermediate amide. This material was mixed with 10 mL of PPA and stirred at 160 degree for 4 hrs. It was then cooled to room temperature and carefully poured into 150 mL of water. The pH was brought to about 5 with solid NaOH. The resulting precipitate was collected by filtration and dried to afford 380 mg of the desired acid, namely, 3-(oxazolo[4,5-b]pyridin-2-yl)benzoic acid.

Preparation of Compound 102

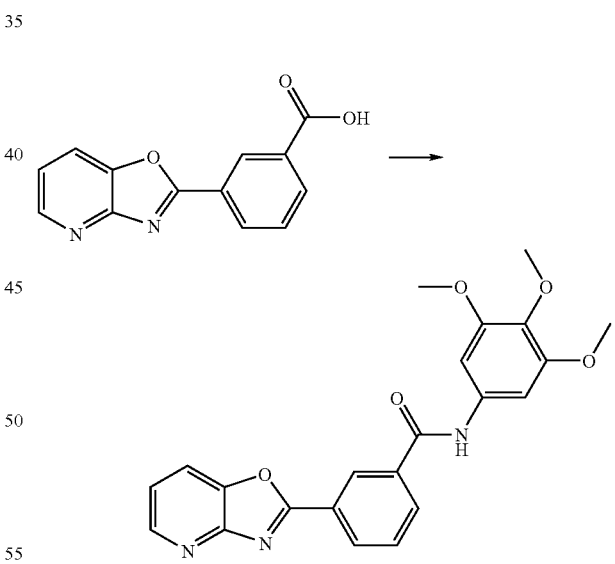

For amide formation, 3-(oxazolo[4,5-b]pyridin-2-yl)benzoic acid (30 mg, 0.125 mmol) was dissolved in 2 mL of DMF along with 3,4,5-trimethoxyaniline (23 mg, 1 eq) and 71 mg of HATU (1.5 eq). After 45 microliters of DIEA (2 eq) were added, the reaction mixture was stirred at room temperature for 18 hrs. It was then diluted with ethyl acetate and washed with water and concentrated. The resulting residue was purified by chromatography using a 9:1 mixture of CH$_2$Cl$_2$ to MeOH to afford 3-(oxazolo[4,5-b]pyridin-2-yl)-N-(3,4,5-trimethoxyphenyl)benzamide. (MS, M$^+$+H=406).

Preparation of Compound 100, Compound 101 and Compound 103

The same procedure used in the preparation of Compound 102 was employed using the appropriate amine.

Preparation of 5-oxazolo[4,5-b]pyridin-2-yl-pyridin-3-ylamine

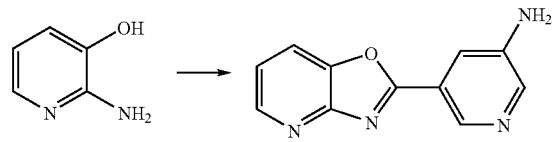

In a typical run, 790 mg of 2-amino-3-hydroxypyridine (7.24 mmol) and 1.00 g of 5-aminonicotinic acid (7.24 mmol) were mixed with 10 mL of PPA and stirred at 200° C. for 6 hours. The reaction mixture was cooled to about 100° C. and carefully poured into 100 mL of water. The pH was brought to 6 with solid NaOH and the solids were collected by filtration. After drying under high vacuum, a total of 180 mg of 5-oxazolo[4,5-b]pyridin-2-yl-pyridin-3-ylamine.

Preparation of Compound 73

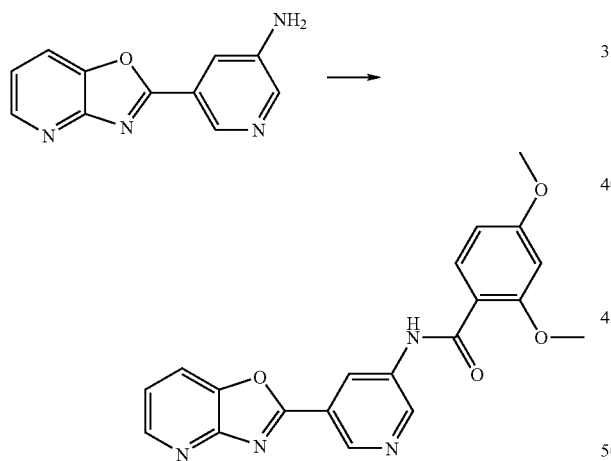

5-Oxazolo[4,5-b]pyridin-2-yl-pyridin-3-ylamine (25 mg, 0.118 mmol) was mixed with 1 mL of pyridine along with 24 mg of 2,4-dimethoxybenzoyl chloride (0.118 mmol). The reaction mixture was reacted in a Biotage microwave reactor at 160° C. for 10 min. It was then cooled to room temperature and concentrated. The resulting crude product was purified by chromatography (Isco, gradient elution, $CH_2Cl_2$ to 9:1 $CH_2Cl_2$/MeOH) to afford 11 mg of the product (MS, $M^+$+H=377).

Preparation of Compounds 66, 67 and 68

Essentially the same procedure as detailed for the preparation of Compound 73 was used employing the appropriate acid chloride.

Preparation of 2-imidazo[2,1-b]thiazol-6-yl-phenylamine

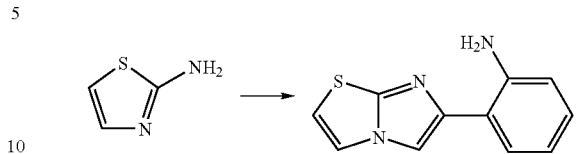

In a typical run, 123 mg of 2-aminothiazole (1.23 mmol) and 2-bromo-2'-nitroacetophenone (300 mg, 1.23 mmol) was mixed with 15 mL of methyl ethyl ketone and stirred under reflux for 18 hours. It was then cooled to room temperature and filtered. The filtrate was concentrated. The resulting solids were mixed with 20 mL of EtOH and 5 drops of concentrated HBr were added. The reaction mixture was stirred under reflux for 6 hours. Everything dissolved at this point and LC/MS showed formation of desired nitro intermediate (MS, $M^+$+H=246). The reaction mixture was concentrated and mixed with 20 mL of dilute aq. $NaHCO_3$. The resulting solids were collected by filtration and dried to afford 300 mg of the nitro intermediate. This material was mixed with 15 mL of MeOH and 3 mL of water along with 6 eq of sodium hydrosulfide hydrate. The reaction mixture was stirred under reflux for 8 hours. It was then cooled to room temperature and concentrated. The aqueous layer was extracted with $CH_2Cl_2$. The combined organic layers were dried ($Na_2SO_4$) and concentrated to afford 260 mg of 2-imidazo[2,1-b]thiazol-6-yl-phenylamine.

Preparation of Compound 203

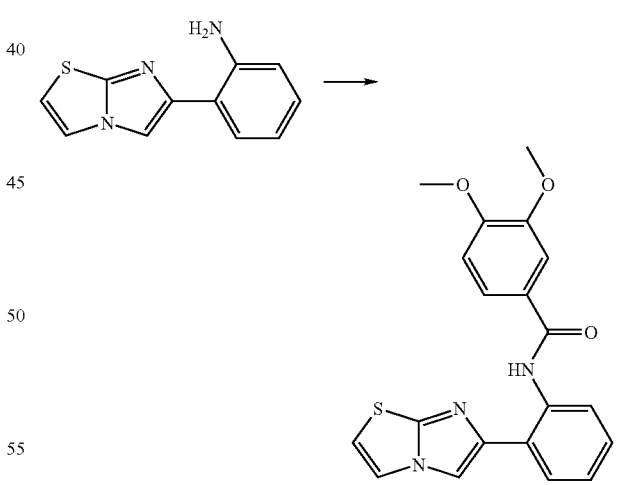

2-Imidazo[2,1-b]thiazol-6-yl-phenylamine (64 mg, 0.30 mmol) was mixed with 1 mL of pyridine along with 60 mg of 3,4-dimethoxybenzoyl chloride (0.30 mmol). The reaction mixture was reacted in the Biotage microwave reactor at 160° C. for 10 min. The reaction mixture was cooled to room temperature and concentrated. The resulting residue was purified by chromatography (Isco, gradient elution, $CH_2Cl_2$ to 9:1 $CH_2Cl_2$/MeOH) to afford the desired product (MS, $M^+$+H=380).

Preparation of Compound 204

The same procedure used in the preparation of Compound 203 was employed using the appropriate acid chloride.

Preparation of Compounds 707, 739 and 740

The same procedure used in the preparation of Compound 203 was employed except with 2-amino-4-methylthiazole at the beginning of the synthetic sequence, and the appropriate acid chloride at the last amide formation step.

Preparation of 6-(2-Nitro-phenyl)-imidazo[2,1-b]thiazole-3-carboxylic acid ethyl ester

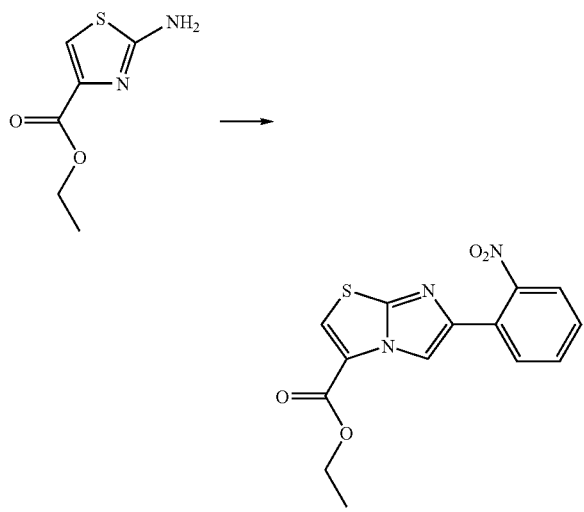

In a typical run, 2.1 g of ethyl 2-aminothiazole-4-carboxylate (Combi-Blocks, 0.0123 mol) was mixed with 25 mL of methyl ethyl ketone along with 2-bromo-2'-nitroacetophenone (3.0 g, 0.0123 mol). The reaction mixture was stirred under reflux for 18 hours. It was then cooled to room temperature and filtered to remove some of the solids. The filtrate was concentrated to afford 3.10 g of 6-(2-nitrophenyl)-imidazo[2,1-b]thiazole-3-carboxylic acid ethyl ester (MS, M$^+$+H=318).

Preparation of [6-(2-nitro-phenyl)-imidazo[2,1-b]thiazol-3-yl]-methanol

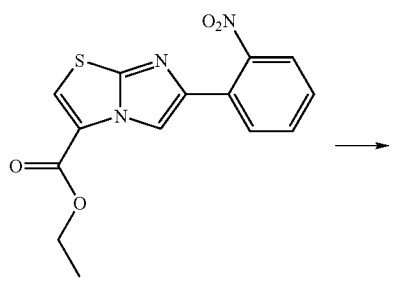

-continued

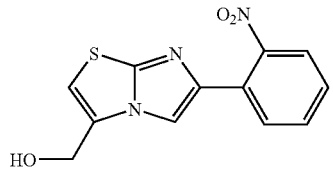

6-(2-Nitro-phenyl)-imidazo[2,1-b]thiazole-3-carboxylic acid ethyl ester (14.50 g, 0.0458 mol) was mixed with 100 mL of THF and 100 mL of water containing 7.3 g of NaOH (4 eq). The reaction mixture was stirred at room temperature for 18 hours. It was then concentrated. The aqueous layer was washed once with CH$_2$Cl$_2$ and then acidified with 6 N HCl. The solids were collected by filtration and dried to afford 7.4 g of the acid intermediate. This material (7.4 g, 0.0256 mol) was mixed with 200 mL of anhydrous THF along with NMM (2.8 mL, 0.0256 mol) and cooled to 0° C. Isobutyl chloroformate (3.35 mL, 0.0256 mol) was added and the reaction mixture was stirred in the ice bath for 3 hours. NaBH$_4$ (0.97 g, 0.0256 mol) was added as a solution in 30 mL of water. The reaction mixture was stirred at 0° C. for 45 min. It was then warmed to room temperature and concentrated. The aqueous layer was extracted with CH$_2$Cl$_2$. The combined organic layers were dried (Na$_2$SO$_4$) and concentrated to afford the crude product. Purification by chromatography (Isco, using a mixture of pentane/EtOAc) afforded 5.20 g of [6-(2-nitro-phenyl)-imidazo[2,1-b]thiazol-3-yl]-methanol (74% yield).

Preparation of 4-[6-(2-amino-phenyl)-imidazo[2,1-b]thiazol-3-ylmethyl]-piperazine-1-carboxylic acid tert-butyl ester

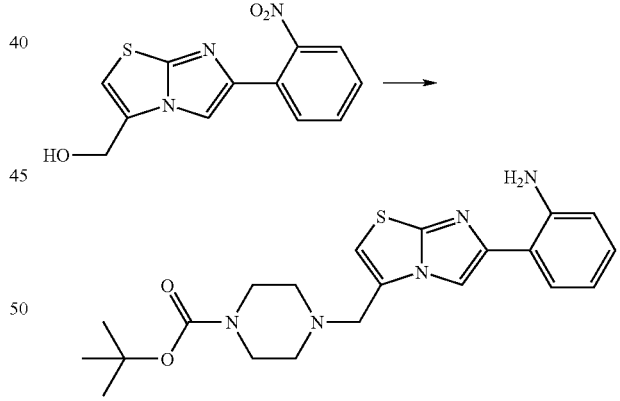

[6-(2-Nitro-phenyl)-imidazo[2,1-b]thiazol-3-yl]-methanol (1.0 g, 3.64 mmol) was dissolved in 100 mL of CH$_2$Cl$_2$ along with 1 eq of Et$_3$N (0.51 mL). Methanesulfonyl chloride (1 eq, 0.28 mL) was added and the reaction mixture was warmed to room temperature and stirred for 15 min. It was then quenched with brine and extracted with CH$_2$Cl$_2$. The combined organic layers were dried (Na$_2$SO$_4$) and concentrated to afford the mesylate intermediate. This material was mixed with 4 mL of CH$_3$CN along with 0.51 mL of Et$_3$N and 680 mg of Boc-piperazine (3.64 mmol) and stirred at room temperature for 1 day. The reaction mixture was concentrated and the resulting residue was partitioned between CH$_2$Cl$_2$ and water. The organic layer was dried (Na$_2$SO$_4$)

and concentrated to afford essentially quantitative yield of the product. This material was mixed with 6 mL of MeOH and 1 mL of water along with 200 mg of sodium hydrosulfide hydrate. The resulting reaction mixture was stirred under reflux for 24 hours. It was then cooled to room temperature and concentrated. The resulting residue was diluted with 2 mL of water and extracted with $CH_2Cl_2$. The combined organic layers were dried ($Na_2SO_4$) and concentrated to afford 0.90 g of 4-[6-(2-amino-phenyl)-imidazo[2,1-b]thiazol-3-ylmethyl]-piperazine-1-carboxylic acid tert-butyl ester.

Preparation of Compound 207

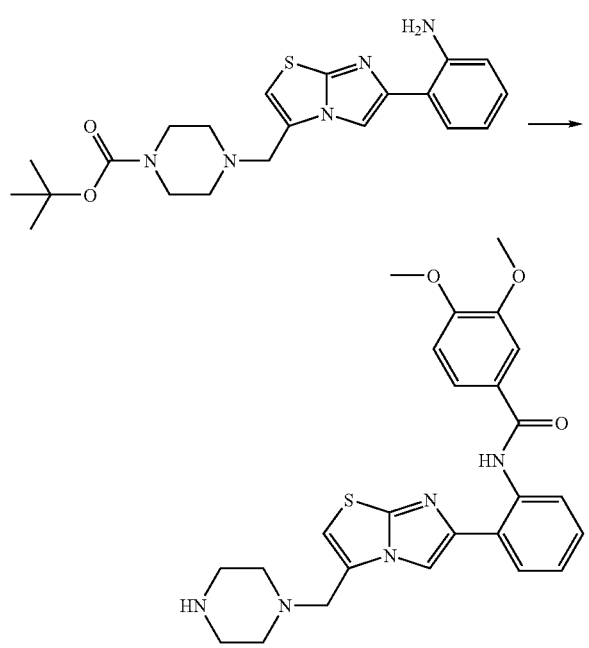

4-[6-(2-Amino-phenyl)-imidazo[2,1-b]thiazol-3-ylmethyl]-piperazine-1-carboxylic acid tert-butyl ester (0.3 mmol) was mixed with 1 mL of pyridine along with 1 eq (60 mg) of 3,4-dimethoxybenzoyl chloride. The reaction mixture was reacted in a Biotage microwave reactor at 160° C. for 10 min. It was then cooled to room temperature and concentrated. The resulting crude product was purified by chromatography (Isco, gradient elution, $CH_2Cl_2$ to 95% $CH_2Cl_2$, 4% MeOH and 1% $Et_3N$). The purified product was then treated with 2 mL of 25% TFA in $CH_2Cl_2$ for 2 hours. It was then concentrated and the resulting residue was triturated with $Et_2O$ to afford the desired product as the TFA salt (MS, $M^+ + H = 478$).

Preparation of Compounds 208, 326, 327, 328, 329, 330, 337, 338, 440, 441, 442, 443, 444, 445, 446, 447, 448, 510, 511, 512, 543, 544, 708, 709, 710, 733, 735, 736, 737, 738, 743 and 744

The same procedure used in the preparation of Compound 207 was employed using the appropriate acid chloride or sulfonyl chloride. Compounds 623, 624, 625, 644, 645, 692, 695, 697 and 698 were prepared according to the procedure used for the preparation of Compound 207, using the appropriate acid chloride. The acid chlorides were either commercially available or made from the carboxylic acids as follows: The carboxylic acid (1.0 mmol), thionyl chloride (2.0 mmol), and a catalytic amount of N,N-dimethylformamide (DMF) (2 drops) was refluxed in toluene (2 mL) for 1 hour. The reaction was cooled to room temperature and concentrated in vacuo to afford the desired acid chlorides.

Preparation of 2-(3-Dimethylaminomethyl-imidazo[2,1-b]thiazol-6-yl)-phenylamine

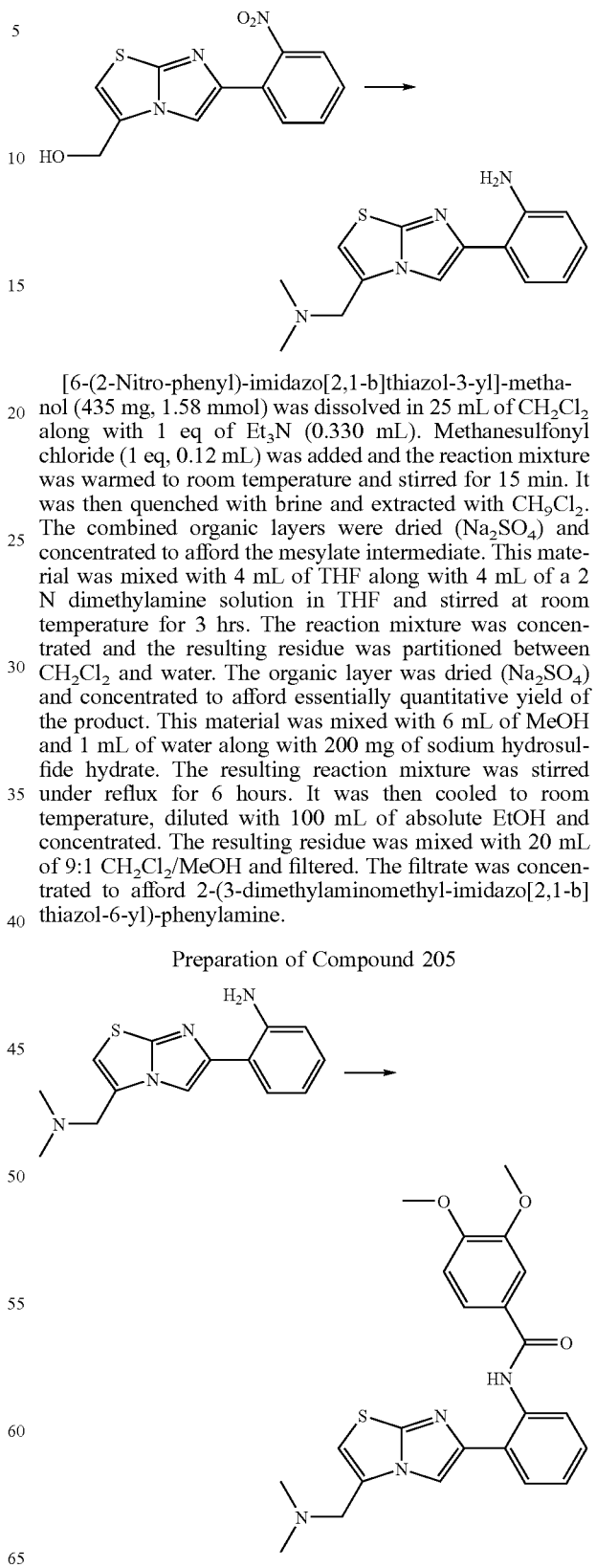

[6-(2-Nitro-phenyl)-imidazo[2,1-b]thiazol-3-yl]-methanol (435 mg, 1.58 mmol) was dissolved in 25 mL of $CH_2Cl_2$ along with 1 eq of $Et_3N$ (0.330 mL). Methanesulfonyl chloride (1 eq, 0.12 mL) was added and the reaction mixture was warmed to room temperature and stirred for 15 min. It was then quenched with brine and extracted with $CH_2Cl_2$. The combined organic layers were dried ($Na_2SO_4$) and concentrated to afford the mesylate intermediate. This material was mixed with 4 mL of THF along with 4 mL of a 2 N dimethylamine solution in THF and stirred at room temperature for 3 hrs. The reaction mixture was concentrated and the resulting residue was partitioned between $CH_2Cl_2$ and water. The organic layer was dried ($Na_2SO_4$) and concentrated to afford essentially quantitative yield of the product. This material was mixed with 6 mL of MeOH and 1 mL of water along with 200 mg of sodium hydrosulfide hydrate. The resulting reaction mixture was stirred under reflux for 6 hours. It was then cooled to room temperature, diluted with 100 mL of absolute EtOH and concentrated. The resulting residue was mixed with 20 mL of 9:1 $CH_2Cl_2$/MeOH and filtered. The filtrate was concentrated to afford 2-(3-dimethylaminomethyl-imidazo[2,1-b]thiazol-6-yl)-phenylamine.

Preparation of Compound 205

2-(3-Dimethylaminomethyl-imidazo[2,1-b]thiazol-6-yl)-phenylamine (0.3 mmol) was mixed with 1 mL of pyridine along with 1 eq (60 mg) of 3,4-dimethoxybenzoyl chloride. The reaction mixture was reacted in a Biotage microwave reactor at 160° C. for 10 min. It was then cooled to room temperature and concentrated. The resulting crude product was purified by chromatography (Isco, gradient elution, CH$_2$Cl$_2$ to 95% CH$_2$Cl$_2$, 4% MeOH and 1% Et$_3$N) to afford the desired product as a light yellow solid (MS, M$^+$+H=437).

Preparation of Compound 206

The same procedure used in the preparation of Compound 205 was employed using the appropriate acid chloride.

Preparation of 2-(3-morpholin-4-ylmethyl-imidazo[2,1-b]thiazol-6-yl)-phenylamine

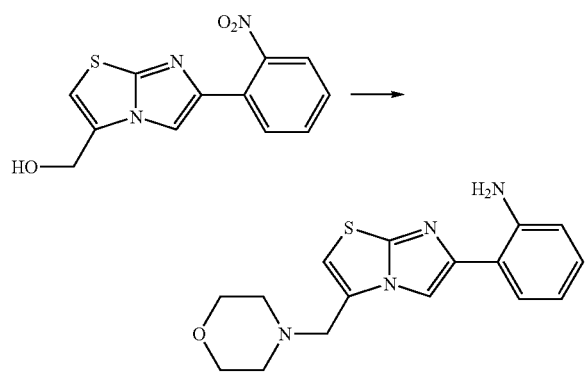

[6-(2-Nitro-phenyl)-imidazo[2,1-b]thiazol-3-yl]-methanol (435 mg, 1.58 mmol) was dissolved in 25 mL of CH$_2$Cl$_2$ along with 1 eq of Et$_3$N (0.330 mL). Methanesulfonyl chloride (1 eq, 0.12 mL) was added and the reaction mixture was warmed to room temperature and stirred for 15 min. It was then quenched with brine and extracted with CH$_2$Cl$_2$. The combined organic layers were dried (Na$_2$SO$_4$) and concentrated to afford the mesylate intermediate. This material was mixed with 6 mL of CH$_3$CN along with 0.33 mL of Et$_3$N and 0.14 mL of morpholine. The reaction mixture was stirred at room temperature for 18 hours. The next day, it was concentrated and the resulting residue was partitioned between CH$_2$Cl$_2$ and water. The organic layer was dried (Na$_2$SO$_4$) and concentrated to afford essentially quantitative yield of the product. This material was mixed with 6 mL of MeOH and 1 mL of water along with 200 mg of sodium hydrosulfide hydrate. The resulting reaction mixture was stirred under reflux for 6 hours. It was then cooled to room temperature, diluted with 100 mL of absolute EtOH and concentrated. The resulting residue was mixed with 20 mL of 9:1 CH$_2$Cl$_2$/MeOH and filtered. The filtrate was concentrated to afford 2-(3-morpholin-4-ylmethyl-imidazo[2,1-b]thiazol-6-yl)-phenylamine.

Preparation of Compound 209

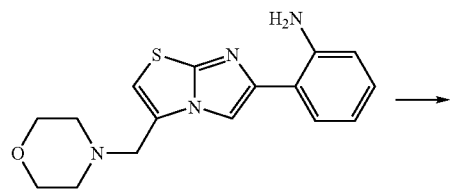

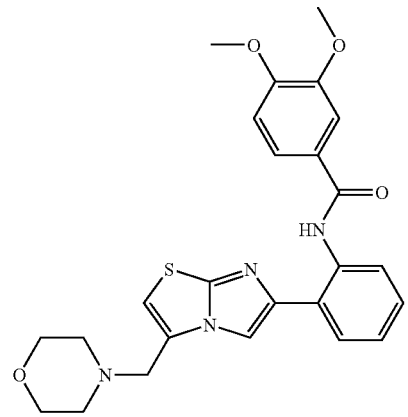

2-(3-Morpholin-4-ylmethyl-imidazo[2,1-b]thiazol-6-yl)-phenylamine (0.3 mmol) was mixed with 1 mL of pyridine along with 1 eq (60 mg) of 3,4-dimethoxybenzoyl chloride. The reaction mixture was reacted in a Biotage microwave reactor at 160° C. for 10 min. It was then cooled to room temperature and concentrated. The resulting crude product was purified by chromatography (Isco, gradient elution, CH$_2$Cl$_2$ to 95% CH$_2$Cl$_2$, 4% MeOH and 1% Et$_3$N) to afford the desired product as a light yellow solid (MS, M$^+$+H=479).

Preparation of Compound 210

The same procedure used in the preparation of Compound 209 was employed using the appropriate acid chloride.

Preparation of 6-(2-nitro-phenyl)-imidazo[2,1-b]thiazole-2-carboxylic acid ethyl ester

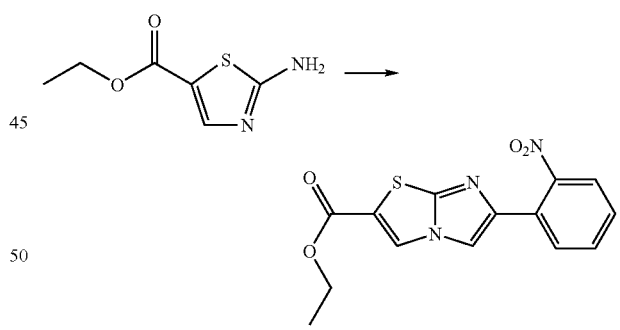

In a typical run, 1.0 g of ethyl 2-aminothiazole-5-carboxylate (Astatech, 5.81 mmol) was mixed with 50 mL of acetone along with 1.42 g of 2-bromo-2'-nitroacetophenone and stirred under reflux for 18 hours. It was then filtered. The filtrate was concentrated to afford the intermediate amide (MS, M$^+$+H=336). This material was mixed with 20 mL of EtOH along with 6 drops of concentrated HBr and stirred under reflux for 4 hours. The reaction mixture was cooled to room temperature and concentrated. The resulting residue was diluted with dilute aqueous NaHCO$_3$. The solids were collected by filtration and dried to afford 6-(2-nitro-phenyl)-imidazo[2,1-b]thiazole-2-carboxylic acid ethyl ester (MS, M$^+$+H=318).

Preparation of [6-(2-nitro-phenyl)-imidazo[2,1-b]thiazol-2-yl]-methanol

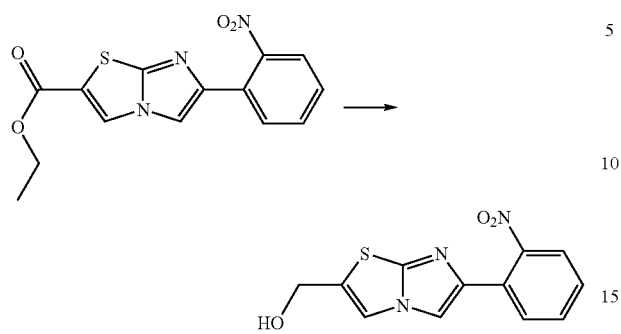

6-(2-Nitro-phenyl)-imidazo[2,1-b]thiazole-2-carboxylic acid ethyl ester (660 mg, 2.08 mmol) was dissolved in 12 mL of THF and NaOH (4 eq) was added as a solution in 10 mL of water. The reaction mixture was stirred at 50° C. for 12 hours. It was then cooled to room temperature and concentrated. The aqueous layer was acidified to pH 5 with 6 N HCl. The solids were collected by filtration and dried to afford essentially quantitative yield of the acid. This material (2.08 mmol) was mixed with 20 mL of anhydrous THF along with NMM (0.23 mL, 2.08 mmol) and cooled in an ice bath. Isobutyl chloroformate (0.27 mL, 2.08 mmol) was added and the reaction mixture was stirred at 0° C. for 30 min. NaBH$_4$ (80 mg, 2.08 mmol) was added as a solution in 5 mL of water. The reaction mixture was stirred at 0° C. for 30 min and then concentrated. The aqueous layer was extracted with CH$_2$Cl$_2$. The combined organic layers were dried (Na$_2$SO$_4$) and concentrated. Purification by chromatography (Isco, gradient elution using a mixture of CH$_2$Cl$_2$ and MeOH) afforded 190 mg of [6-(2-nitro-phenyl)-imidazo[2,1-b]thiazol-2-yl]-methanol.

Preparation of 2-(2-Dimethylaminomethyl-imidazo[2,1-b]thiazol-6-yl)-phenylamine

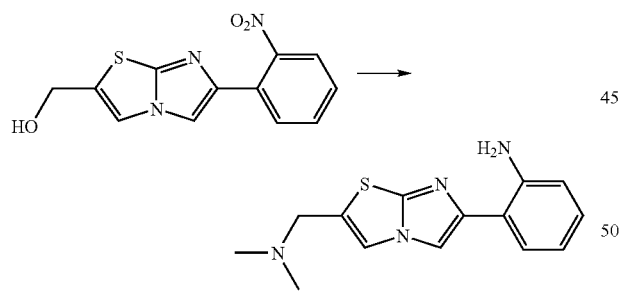

Essentially the same procedure used during the preparation of 2-(3-dimethylaminomethyl-imidazo[2,1-b]thiazol-6-yl)-phenylamine was employed, except that [6-(2-nitro-phenyl)-imidazo[2,1-b]thiazol-2-yl]-methanol was used as the starting material.

Preparation of Compound 178

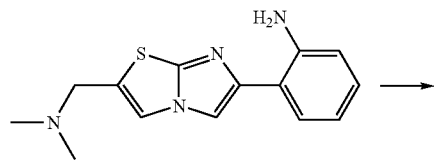

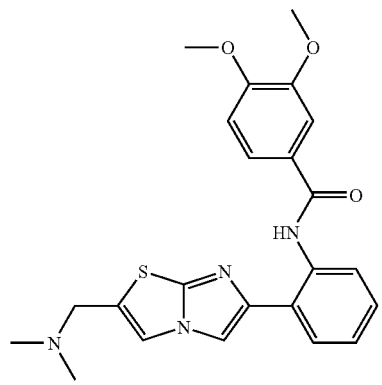

2-(2-Dimethylaminomethyl-imidazo[2,1-b]thiazol-6-yl)-phenylamine (0.3 mmol) was mixed with 1 mL of pyridine along with 1 eq (60 mg) of 3,4-dimethoxybenzoyl chloride. The reaction mixture was reacted in a Biotage microwave reactor at 160° C. for 10 min. It was then cooled to room temperature and concentrated. The resulting crude product was purified by chromatography (Isco, gradient elution, CH$_2$Cl$_2$ to 95% CH$_2$Cl$_2$, 4% MeOH and 1% Et$_3$N) to afford the desired product as a light yellow solid (MS, M$^+$+H=437).

Preparation of Compound 179

The same procedure used in the preparation of Compound 178 was employed using the appropriate acid chloride.

Preparation of 4-[6-(2-Amino-phenyl)-imidazo[2,1-b]thiazol-2-ylmethyl]-piperazine-1-carboxylic acid tert-butyl ester

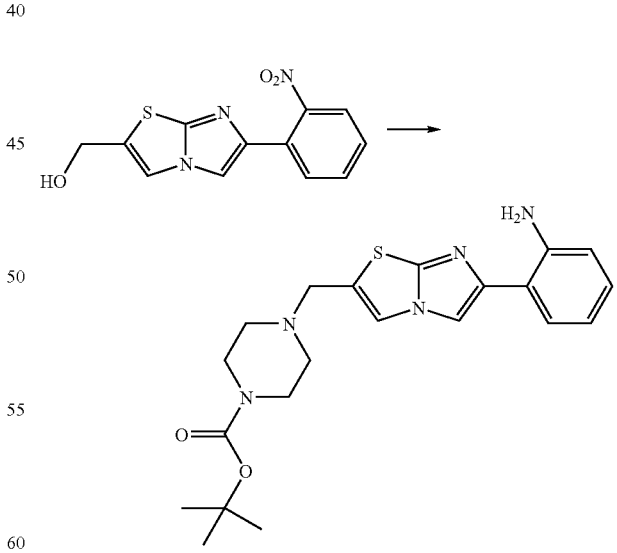

Essentially the same procedure used during the preparation of 4-[6-(2-amino-phenyl)-imidazo[2,1-b]thiazol-3-ylmethyl]-piperazine-1-carboxylic acid tert-butyl ester was employed, except that [6-(2-nitro-phenyl)-imidazo[2,1-b]thiazol-2-yl]-methanol was used as the starting material.

Preparation of Compound 270

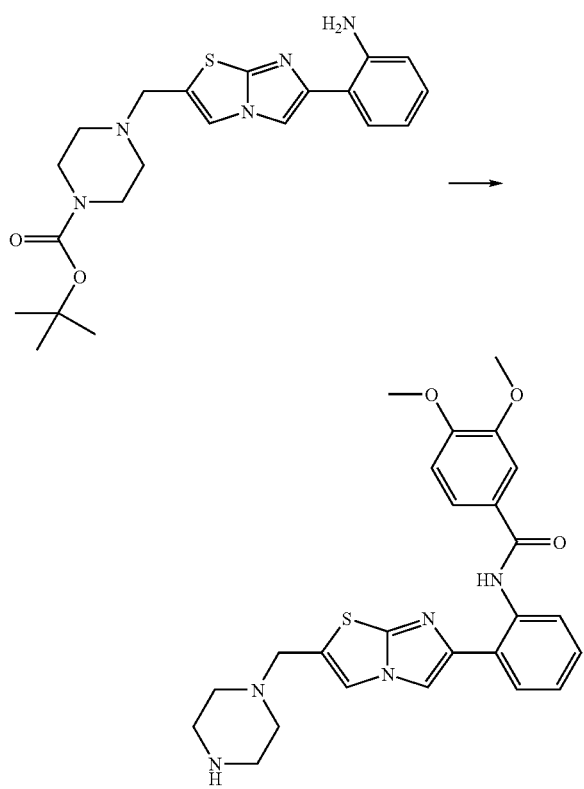

4-[6-(2-Amino-phenyl)-imidazo[2,1-b]thiazol-2-ylmethyl]-piperazine-1-carboxylic acid tert-butyl ester (0.2 mmol) was mixed with 1 mL of pyridine along with 1 eq (40 mg) of 3,4-dimethoxybenzoyl chloride. The reaction mixture was reacted in a Biotage microwave reactor at 160° C. for 10 min. It was then cooled to room temperature and concentrated. The resulting crude product was purified by chromatography (Isco, gradient elution, $CH_2Cl_2$ to 95% $CH_2Cl_2$, 4% MeOH and 1% $Et_3N$). The purified product was then treated with 2 mL of 25% TFA in $CH_2Cl_2$ for 2 hours. It was then concentrated and the resulting residue was triturated with $Et_2O$ to afford the desired product as the TFA salt (MS, $M^+ + H = 478$).

Preparation of Compound 271 and Compound 513

The same procedure used in the preparation of Compound 270 was employed using the appropriate acid chloride.

Preparation of 3-(2-nitro-phenyl)-imidazo[2,1-b]thiazole-6-carboxylic acid ethyl ester

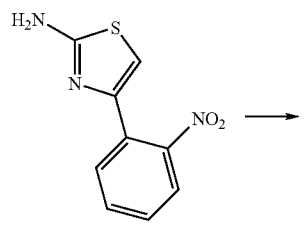

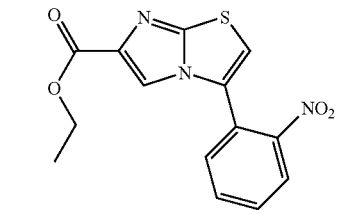

4-(2-Nitro-phenyl)-thiazol-2-ylamine was prepared as follows: 2-Bromo-2'-nitroacetophenone (1.75 g, 7.2 mmol) was mixed with 50 mL of absolute EtOH along with thiourea (1.09 g, 14.4 mmol) and stirred under reflux for 2 hours. The reaction mixture was cooled to room temperature and concentrated under reduced pressure. The resulting residue was basified with 20 mL of 1 N aqueous NaOH and extracted with $CH_2Cl_2$. The combined organic layers were dried ($Na_2SO_4$) and concentrated to afford essentially quantitative yield of 4-(2-nitro-phenyl)-thiazol-2-ylamine.

4-(2-Nitro-phenyl)-thiazol-2-ylamine (1.60 g, 7.2 mmol) was mixed with 50 mL of methyl ethyl ketone along 0.90 mL of ethyl bromopyruvate (7.2 mmol) and stirred under reflux for 24 hours. Another equivalent of ethyl bromopyruvate (0.90 mL, 7.2 mmol) was added and the reaction mixture was stirred under reflux for another 8 hours. The reaction mixture was cooled to room temperature and concentrated under reduced pressure. The resulting residue was purified by chromatography (Isco, gradient elution, $CH_2Cl_2$ to 95% $CH_2Cl_2$, 5% MeOH) to afford 1.2 g of 3-(2-nitro-phenyl)-imidazo[2,1-b]thiazole-6-carboxylic acid ethyl ester (52% yield).

Preparation of [3-(2-nitro-phenyl)-imidazo[2,1-b]thiazol-6-yl]-methanol

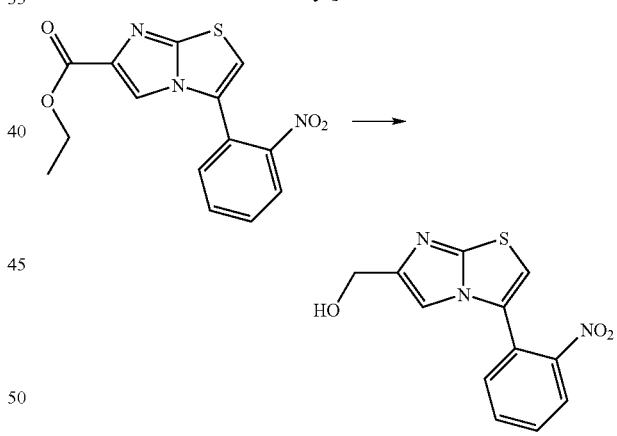

3-(2-Nitro-phenyl)-imidazo[2,1-b]thiazole-6-carboxylic acid ethyl ester (1.2 g, 3.78 mmol) was mixed with 50 mL of THF and 50 mL of water containing 600 mg of NaOH (4 eq). The reaction mixture was stirred at 50° C. for 8 hours. It was then cooled to room temperature and concentrated under reduced pressure. The aqueous layer was acidified to pH 6 with 6 N HCl. The resulting solids were collected by filtration and dried to afford 465 mg of the intermediate acid. This acid intermediate (465 mg, 1.61 mmol) was mixed with 50 mL of anhydrous THF along with NMM (0.18 mL, 1.61 mmol). The reaction mixture was cooled in an ice bath and isobutyl chloroformate (0.21 mL, 1.61 mmol) was added. After 30 minutes at 0° C., a solution of $NaBH_4$ (240 mg) in 2 mL of water was added. The resulting reaction mixture was stirred at 0° C. for 30 min and then concentrated. The aqueous layer was extracted with $CH_2Cl_2$. The combined organic layers were dried (Na$_2$SO$_4$) and concentrated to afford the crude alcohol. Purification by chromatography (Isco, gradient elution, CH$_2$Cl$_2$ to 95% CH$_2$Cl$_2$, 5% MeOH) afforded 200 mg of [3-(2-nitro-phenyl)-imidazo[2,1-b]thiazol-6-yl]-methanol (45% yield).

Preparation of 4-[3-(2-nitro-phenyl)-imidazo[2,1-b]thiazol-6-ylmethyl]-piperazine-1-carboxylic acid tert-butyl ester

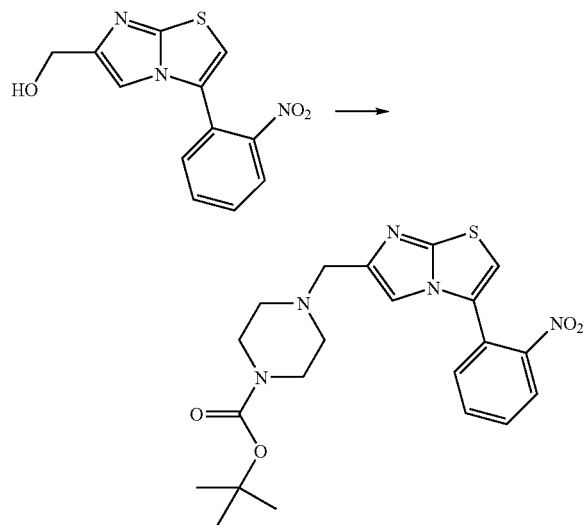

[3-(2-Nitro-phenyl)-imidazo[2,1-b]thiazol-6-yl]-methanol (200 mg, 0.727 mmol) was mixed with 50 mL of CH$_2$Cl$_2$ along with Et$_3$N (0.10 mL, 0.727 mmol) and cooled in an ice bath. Methanesulfonyl chloride (56 µL, 0.727 mmol) was added and the reaction mixture was warmed to room temperature and stirred for 30 min. The reaction mixture was quenched with brine and extracted with CH$_2$Cl$_2$. The combined organic layers were dried (Na$_2$SO$_4$) and concentrated to afford essentially quantitative yield of the mesylate intermediate. This material was dissolved in 10 mL of acetonitrile along with triethylamine (0.10 mL, 0.727 mmol) and Boc-piperazine. The reaction mixture was stirred at room temperature for 18 hours. It was then concentrated. The resulting residue was partitioned between water and CH$_2$Cl$_2$. The organic layer was separated, dried (Na$_2$SO$_4$) and concentrated to afford essentially quantitative yield of 4-[3-(2-nitro-phenyl)-imidazo[2,1-b]thiazol-6-ylmethyl]-piperazine-1-carboxylic acid tert-butyl ester.

Preparation of 4-[3-(2-amino-phenyl)-imidazo[2,1-b]thiazol-6-ylmethyl]-piperazine-1-carboxylic acid tert-butyl ester

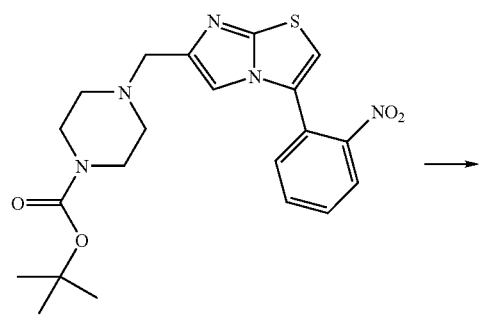

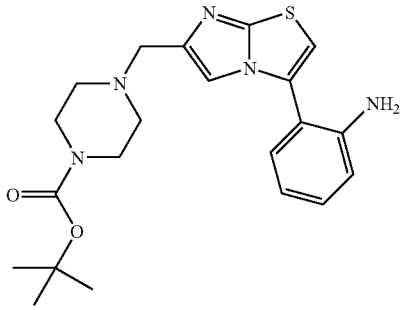

4-[3-(2-Nitro-phenyl)-imidazo[2,1-b]thiazol-6-ylmethyl]-piperazine-1-carboxylic acid tert-butyl ester (320 mg, 0.73. mmol) was mixed with 20 mL of MeOH and 5 mL of water containing sodium hydrosulfide hydrate (244 mg, 6 eq). The reaction mixture was stirred under reflux for 4 hours. It was then cooled to room temperature and concentrated. The aqueous layer was extracted with CH$_2$Cl$_2$. The combined organic layers were dried (Na$_2$SO$_4$) and concentrated to afford 280 mg of 4-[3-(2-amino-phenyl)-imidazo[2,1-b]thiazol-6-ylmethyl]-piperazine-1-carboxylic acid tert-butyl ester (92% yield).

Preparation of Compound 560

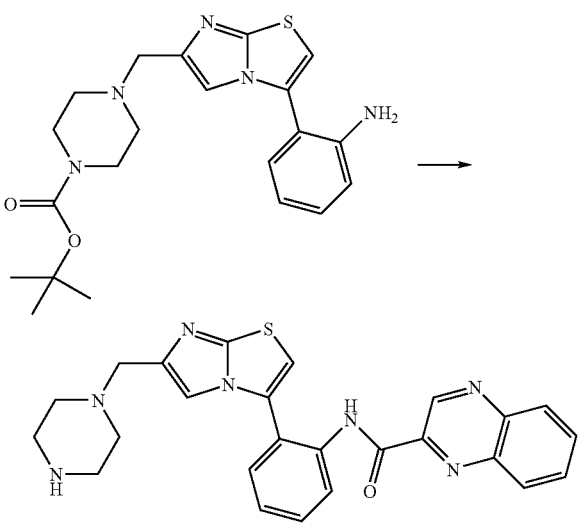

4-[3-(2-amino-phenyl)-imidazo[2,1-b]thiazol-6-ylmethyl]-piperazine-1-carboxylic acid tert-butyl ester (45 mg, 0.1 mmol) was mixed with 1 mL of pyridine along with 1 eq (40 mg) of 2-quinoxaloyl chloride. The reaction mixture was reacted in a Biotage microwave reactor at 160° C. for 10 min. It was then cooled to room temperature and concentrated. The resulting crude product was purified by chromatography (Isco, gradient elution, CH$_2$Cl$_2$ to 95% CH$_2$Cl$_2$, 4% MeOH and 1% Et$_3$N). The purified product was then treated with 2 mL of 25% TFA in CH$_2$Cl$_2$ for 2 hours. It was then concentrated and the resulting residue was triturated with Et$_2$O to afford the desired product as the TFA salt (MS, M$^+$+H=470).

Preparation of Compound 559

The same procedure used in the preparation of Compound 560 was employed using the appropriate acid chloride.

Preparation of a 1:1 mixture of 6-(2-Chloro-pyridin-3-yl)-imidazo[2,1-b]thiazole-3-carboxylic acid ethyl ester and 6-(2-bromo-pyridin-3-yl)-imidazo[2,1-b]thiazole-3-carboxylic acid ethyl ester

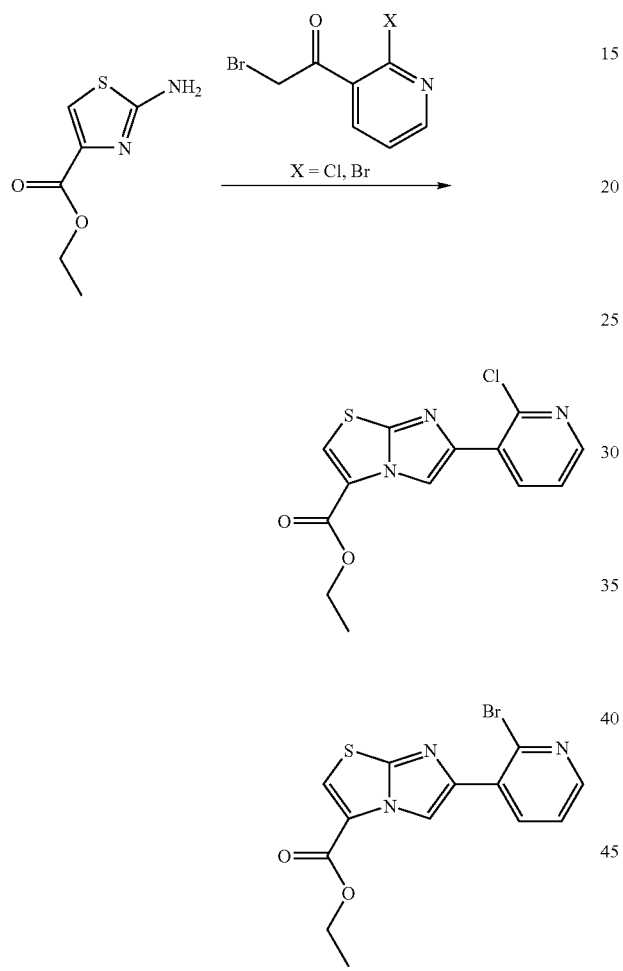

The 1:1 mixture of 2-bromo-1-(2-chloro-pyridin-3-yl)-ethanone and 2-bromo-1-(2-bromo-pyridin-3-yl)-ethanone was prepared according to the procedure outlined in WO 2005/061476. This mixture (5.6 g, approximately 0.0240 mol) was mixed with 150 mL of methyl ethyl ketone along with 2-amino-thiazole-4-carboxylic acid ethyl ester (4.6 g) and stirred under reflux for 18 hours. The reaction mixture was concentrated. The resulting residue was mixed with 150 mL of CH$_2$Cl$_2$ and filtered. The filtered solids were unreacted 2-amino-thiazole-4-carboxylic acid ethyl ester. The filtrate was concentrated to afford an essentially pure and 1:1 mixture of 6-(2-Chloro-pyridin-3-yl)-imidazo[2,1-b]thiazole-3-carboxylic acid ethyl ester and 6-(2-bromo-pyridin-3-yl)-imidazo[2,1-b]thiazole-3-carboxylic acid ethyl ester (3.0 g total).

Preparation of a 1:1 mixture of 6-(2-Chloro-pyridin-3-yl)-3-morpholin-4-ylmethyl-imidazo[2,1-b]thiazole and 6-(2-bromo-pyridin-3-yl)-3-morpholin-4-ylmethyl-imidazo[2,1-b]thiazole

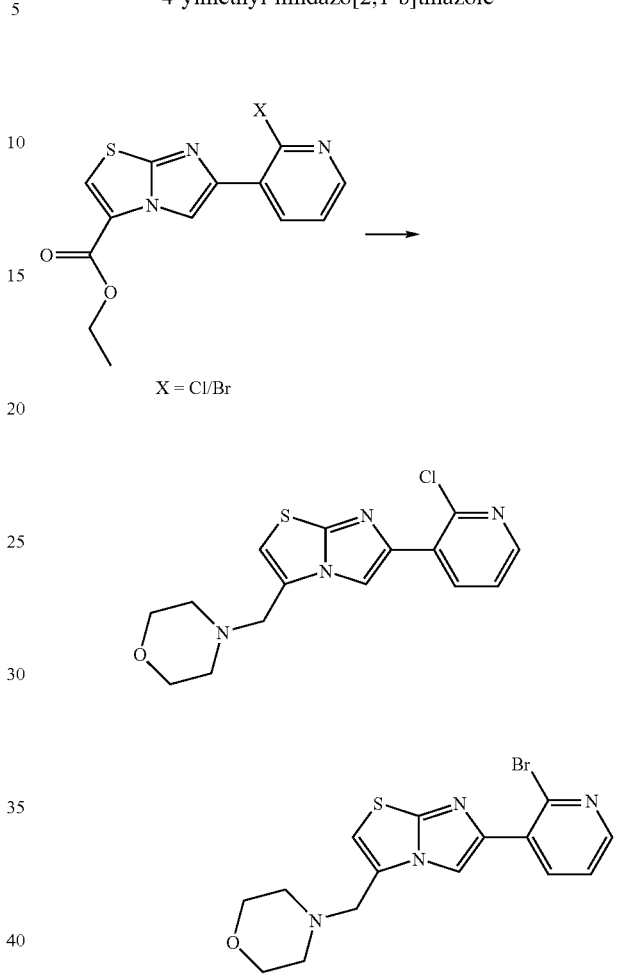

The 1:1 mixture of 6-(2-Chloro-pyridin-3-yl)-imidazo[2,1-b]thiazole-3-carboxylic acid ethyl ester and 6-(2-bromo-pyridin-3-yl)-imidazo[2,1-b]thiazole-3-carboxylic acid ethyl ester (3.0 g) was mixed with 100 mL of THF along with 25 mL of water containing 3 g of NaOH. The reaction mixture was stirred at 50° C. for 3 hours. It was then cooled to room temperature and concentrated. The aqueous layer was acidified to pH 5 with 6 N HCl and the resulting mixture was filtered. The solids were collected to afford 2.14 g the intermediate acid.

This 1:1 mixture of the acid (2.14 g) was mixed with 250 mL of anhydrous THF along with NMM (0.85 mL) and cooled in an ice bath. Isobutyl chloroformate (1.0 mL) was added and the reaction mixture was warmed to room temperature and stirred for 3 hours. The reaction mixture was cooled in an ice bath and NaBH$_4$ (0.29 g) was added as a solution in 20 mL of water. The reaction mixture was stirred for 30 min and then warmed to room temperature. It was concentrated and subsequently extracted with CH$_2$Cl$_2$. The combined organic layers were dried (Na2SO$_4$) and concentrated to afford 1.5 g of the intermediate alcohol.

This 1:1 mixture of the intermediate alcohol (1.5 g) was mixed with 100 mL of CH$_2$Cl$_2$ along with Et$_3$N (0.80 mL) and cooled in an ice bath. Methanesulfonyl chloride (0.44 mL) was added and the reaction mixture was warmed to room temperature. The reaction mixture was quenched with brine and the two layers were separated. The organic layer was dried (Na$_2$SO$_4$) and concentrated to afford the intermediate mesylate. This material was immediately mixed with 30 mL of CH$_3$CN along with 0.80 mL of Et$_3$N and 0.5 mL of morpholine. The reaction mixture was stirred at 50° C. for 3 hours. The reaction mixture was concentrated under reduced pressure and the resulting residue was partitioned between CH$_2$Cl$_2$ and brine. The organic layer was separated, dried (Na$_2$SO$_4$) and concentrated to afford the crude product. Purification by chromatography (Isco, gradient elution, CH$_2$Cl$_2$ to 95% CH$_2$Cl$_2$, 4% MeOH and 1% Et$_3$N) afforded 720 mg of a 1:1 mixture of 6-(2-Chloro-pyridin-3-yl)-3-morpholin-4-ylmethyl-imidazo[2,1-b]thiazole and 6-(2-bromo-pyridin-3-yl)-3-morpholin-4-ylmethyl-imidazo[2,1-b]thiazole.

Preparation of (4-methoxy-benzyl)-[3-(3-morpholin-4-ylmethyl-imidazo[2,1-b]thiazol-6-yl)-pyridin-2-yl]-amine

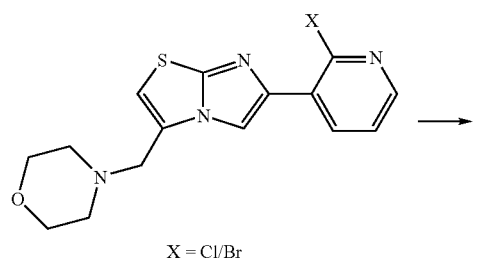

X = Cl/Br

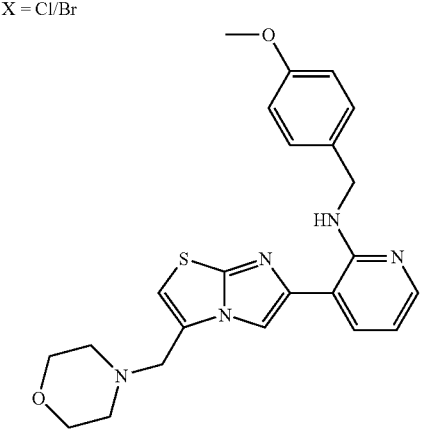

The 1:1 mixture of 6-(2-Chloro-pyridin-3-yl)-3-morpholin-4-ylmethyl-imidazo[2,1-b]thiazole and 6-(2-bromo-pyridin-3-yl)-3-morpholin-4-ylmethyl-imidazo[2,1-b]thiazole (600 mg) was mixed with 15 mL of toluene along with 0.47 mL of 4-methoxybenzylamine and stirred under reflux for 5 days. The reaction mixture was cooled to room temperature and partitioned between CH$_2$Cl$_2$ and brine. The organic layer was separated, dried (Na$_2$SO$_4$) and concentrated to afford the crude product. Purification by chromatography (Isco, gradient elution, CH$_2$Cl$_2$ to 95% CH$_2$Cl$_2$, 4% MeOH and 1% Et$_3$N) afforded 200 mg of (4-methoxy-benzyl)-[3-(3-morpholin-4-ylmethyl-imidazo[2,1-b]thiazol-6-yl)-pyridin-2-yl]-amine.

Preparation of 3-(3-morpholin-4-ylmethyl-imidazo[2,1-b]thiazol-6-yl)-pyridin-2-ylamine

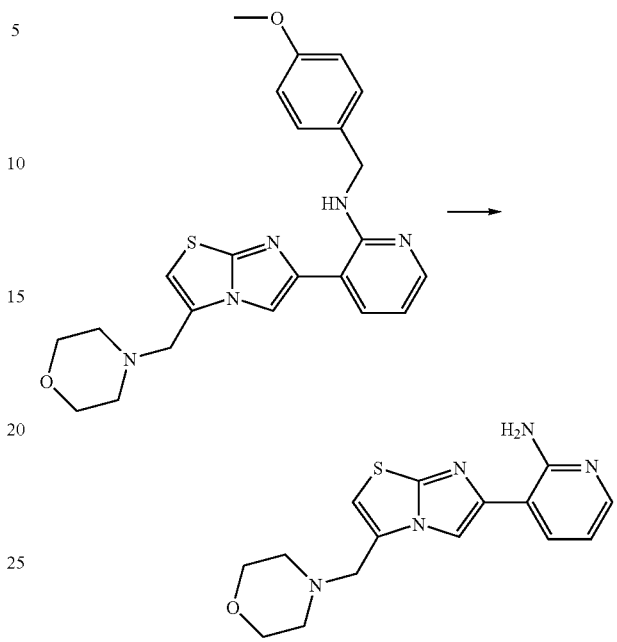

(4-Methoxy-benzyl)-[3-(3-morpholin-4-ylmethyl-imidazo[2,1-b]thiazol-6-yl)-pyridin-2-yl]-amine (100 mg, 0.23 mmol) was mixed with 2 mL of CH$_2$Cl$_2$ along with triethylsilane (0.11 mL, 2 eq). Trifluoroacetic acid (1 mL) was added and the reaction mixture was stirred at room temperature for 18 hours. The following day, the reaction mixture was concentrated. The resulting residue was triturated with Et$_2$O to afford essentially quantitative yield of 3-(3-morpholin-4-ylmethyl-imidazo[2,1-b]thiazol-6-yl)-pyridin-2-ylamine as the TFA salt.

Preparation of Compound 621

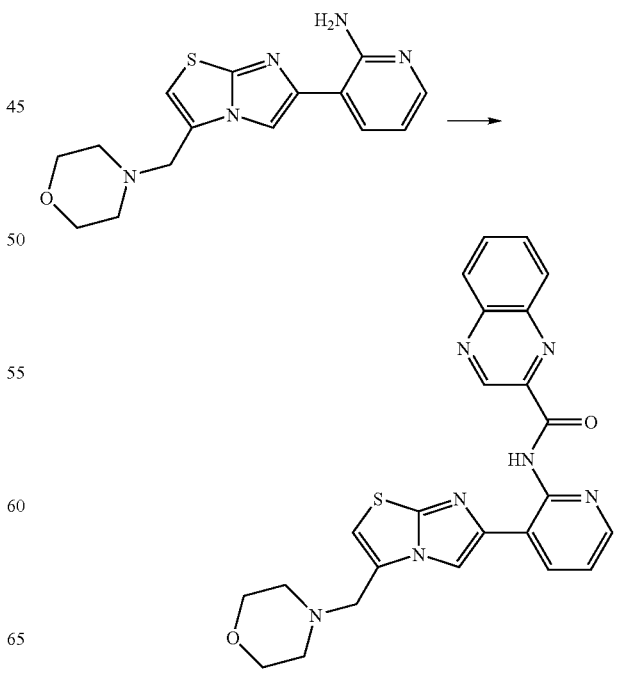

The TFA salt of 3-(3-morpholin-4-ylmethyl-imidazo[2,1-b]thiazol-6-yl)-pyridin-2-ylamine (0.1 mmol) was mixed with 1 mL of pyridine along with 0.1 mmol of 2-quinoxaloyl chloride. The reaction mixture was reacted in a microwave reactor at 160° C. for 10 min. It was then cooled to room temperature and concentrated to afford the crude product. Purification by preparative HPLC using a mixture of aqueous CH$_3$CN that has been buffered with 0.1% TFA afforded 18 mg of the desired product as the TFA salt (MS, M$^+$+H=472).

Preparation of
N-(4-hydroxypyridin-3-yl)-3-nitrobenzanide

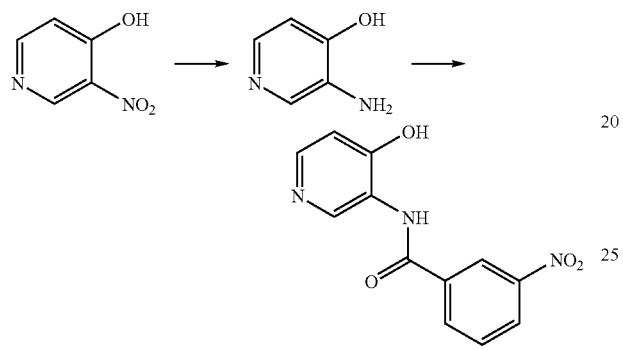

A suspension of 4-hydroxy-3-nitropyridine (40 g) and 10% Pd/C (4 g) in EtOH (700 mL) and dichloromethane (50 mL) was stirred under H$_2$ (1 atm) at room temperature for 4 days. TLC indicated completion of the reaction. The reaction mixture was filtered through a Celite pad, and the filtrate was concentrated in vacuo to give crude 3-amino-4-hydroxypyridine as a red foam (32 g, yield: 100%, confirmed by MS), which was used directly for the next step.

A solution of 3-nitrobenzoyl chloride (3.339 g, 18.0 mmol) in pyridine (54.0 mL) was added dropwise to a solution of 3-amino-4-hydroxypyridine (2.376 g, 21.6 mmol) in pyridine (36.0 mL) at 10° C. and the resultant mixture was stirred overnight. Na$_2$CO$_3$ (1.145 g, 10.8 mmol) was added and the mixture was stirred for 1 h. The solid was collected by filtration, washed with 10% HOAc (30 mL×3) and water (30 mL×3), and dried under vacuo to afford N-(4-hydroxypyridin-3-yl)-3-nitrobenzamide as yellow solid (3.70 g, yield: 66%). $^1$H-NMR (400 MHz, DMSO-d$_{6B}$) δ: 6.34 (1H, d, J=7.2 Hz), 7.74 (1H, d, J=8.0 Hz), 7.84 (1H, t, J=8.0 Hz), 8.34 (1H, d, J=7.2 Hz), 8.44 (1H, t, J=8.0 Hz), 8.66 (1H, s), 8.73 (1H, s), 9.66 (1H, s), 11.65 (1H, br s); MS (ESI) calcd. for C$_{12}$H$_9$N$_3$O$_4$ (m/z): 259, found: 260 [M+1]$^+$.

Preparation of
2-(3-nitrophenyl)oxazolo[4,5-c]pyridine

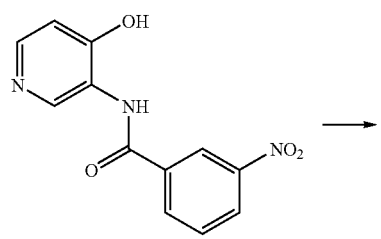

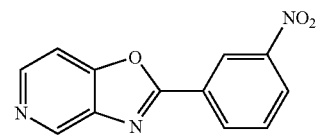

A solution of N-(4-hydroxypyridin-3-yl)-3-nitrobenzamide (1.554 g, 6 mmol) in polyphosphoric acid (12.0 mL) was stirred at 150° C. for 6 h. The reaction mixture was poured into distilled water and sodium hydroxide was added until pH=5. The precipitate was collected by filtration, washed with water until neutral and dried in vacuo oven (50° C.) to afford 2-(3-nitrophenyl)oxazolo[4,5-c]pyridine as a yellow solid (1.389 g, yield: 96%). MS (ESI) calcd. for C$_{12}$H$_7$N$_3$O (m/z): 241, found: 242 [M+1]$^+$.

Preparation of
3-(oxazolo[4,5-c]pyridin-2-yl)benzenamine

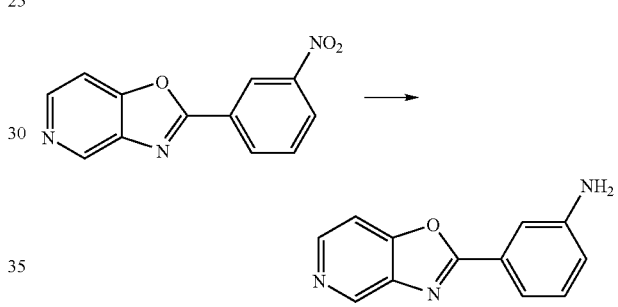

A suspension of 2-(3-nitrophenyl)oxazolo[4,5-c]pyridine (1.50 g, 6.2 mmol), iron powder (1.867 g, 31.8 mmol) and NH$_4$Cl (2.86 g, 53.5 mmol) in CH$_3$OH/H$_2$O (4: 1, 311.2 mL) was refluxed for 6 h. The mixture was filtered and the filtrate was evaporated in vacuo. The residue was purified by chromatography on silica gel (eluted with petroleum ether: EtOAc : Et$_3$N=160:40:1) to afford 3-(oxazolo[4,5-c]pyridin-2-yl)benzenamine as a white solid (1.107 g, yield: 85%). $^1$H NMR (400 MHz, DMSO-d$_6$) δ: 5.54 (2H, s), 6.82 (1H, d, J=8.0 Hz), 7.24 (1H, t, J=8.0 Hz), 7.35 (1H, d, J=8.0 Hz), 7.44 (1H, s), 7.86 (1H, d, J=5.6 Hz), 8.56 (1H, d, J=5.6 Hz), 9.07 (1H, s); MS (ESI) calcd. for C$_{12}$H$_9$N$_3$O (m/z): 211, found: 212 [M+1]$^+$.

General Procedure for Preparing Compounds 296, 297, 298, 299, 311, 343, 344, 345, 346, 347, and 348

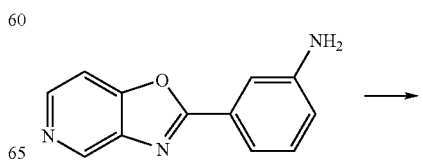

-continued

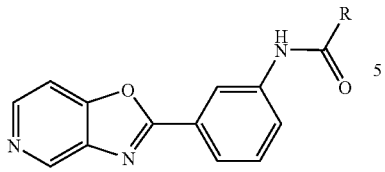

The acid chlorides, in turn, were either commercially available or prepared from the corresponding carboxylic acid as follows: 1.0 g of the carboxylic acid was refluxed in 10 mL of thionyl chloride and 0.1 mL of DMF for 2 hours. The reaction mixture was cooled to room temperature and concentrated under reduced pressure to afford the desired acid chloride. A mixture of the 3-(oxazolo[4,5-c]pyridin-2-yl)benzenamine (0.2 mmol each) and the appropriate acid chloride (0.24 mmol each) in pyridine (2 mL) was agitated at room temperature overnight. The reaction mixture was diluted with H$_2$O (5 mL each). The precipitates were collected by filtration and triturated with MeOH (5 mL) and dried to give library compounds, which were analyzed by HPLC & MS. The library compounds were further purified by passing through silica gel pad eluted with CH$_2$Cl$_2$/EtOAc or petroleum ether/EtOAc.

Preparation of
2-(3-nitrophenyl)thiazolo[4,5-c]pyridine

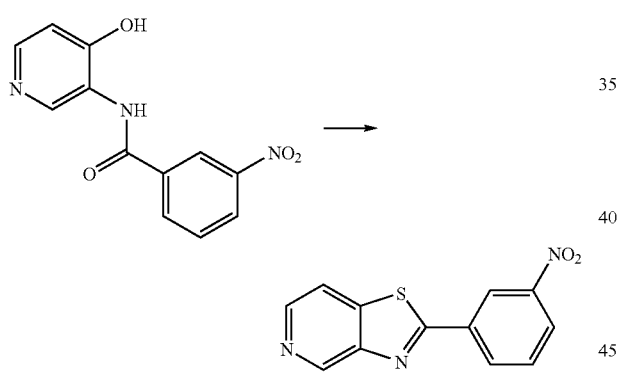

A mixture of N-(4-hydroxypyridin-3-yl)-3-nitrobenzamide (1.33 g, 5.2 mmol) and P$_2$S$_5$ (2.40 g, 10.4 mmol) in pyridine (6.0 mL) and p-xylene (24 mL) was stirred at 140° C. for 18 h. The solvent was removed under vacuo while hot and the residue was purified by recrystallization from EtOH to afford 2-(3-nitrophenyl)thiazolo[4,5-c]pyridine as a yellow solid (1.08 g, yield: 81%). MS (ESI) calcd. for C$_{12}$H$_7$N$_3$O$_2$S (m/z): 257, found: 258 [M+1]$^+$.

Preparation of
3-(thiazolo[4,5-c]pyridin-2-yl)benzenamine

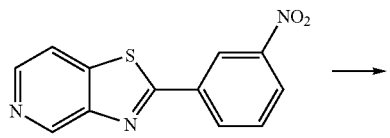

-continued

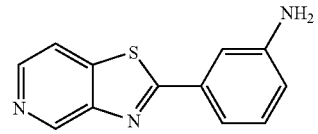

A mixture of 2-(3-nitrophenyl)thiazolo[4,5-c]pyridine (1.53 g, 5.9 mmol), NH$_4$Cl (2.76 g, 51.6 mmol), iron powder (1.80 g, 32.2 mmol), H$_2$O (30 mL) and methanol (120 mL) was heated to reflux for 5.5 h under N$_2$. The mixture was filtered and the filtrate was diluted with H$_2$O (400 mL). The precipitate was collected by filtration and dried in vacuo to afford 3-(thiazolo[4,5-c]pyridin-2-yl)benzenamine as a brown solid (841 mg, 63%). $^1$HNMR (400 MHz, DMSO-d$_6$) δ: 9.28 (1H, s); 8.52 (1H, s); 8.21(1H, s); 7.23-7.38 (3H, d), 6.79 (1H, s), 5.51 (2H, s); MS (ESI) calcd. for C$_{12}$H$_9$N$_3$S (m/z): 227, found: 228 [M+H]P General Procedure for Preparing Compounds 272, 273, 400, 401, 402, and 403

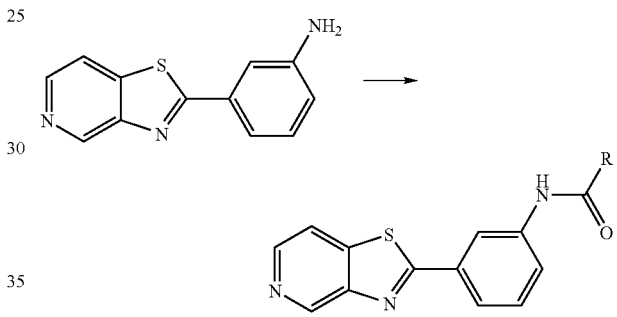

Essentially the same procedure as detailed above for the preparation of Compound 343 using 3-(thiazolo[4,5-c]pyridin-2-yl)benzenamine as the starting material and the appropriate acid chloride.

Preparation of
N-(4-hydroxypyridin-3-yl)-4-nitrobenzamide

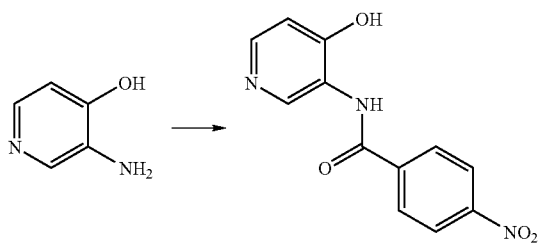

A solution of p-nitrobenzoyl chloride (4.8 g, 25.7 mmol) in pyridine (77.0 mL) was added dropwise to a solution of 3-amino-4-hydroxypyridine (3.4 g, 30.9 mmol) in pyridine (51.0 mL) at 10° C. and stirred overnight. A solution of Na$_2$CO$_3$ (1.7 g) in water (65 mL) was added and the resultant mixture was stirred for 1 h. The reaction mixture was neutralized with 10% AcOH. The precipitate was collected by filtration, washed with 10% AcOH, and dried in vacuo (50° C.) to afford N-(4-hydroxypyridin-3-yl)-4-nitrobenzamide as a light green powder (4.1 g, Yield: 62%).

¹HNMR (400 MHz, DMSO-d₆) δ: 11.64 (1H, br s), 9.57 (1H, s), 9.07 (1H, s), 8.75 (1H, d, J=4.4 Hz), 8.36 (1H, d, J=8.8 Hz), 8.20 (1H, d, J=8.8 Hz), 7.74 (1H, d, J=4.4 Hz), 6.33 (1H, s); MS(ESI) calcd for $C_{12}H_9N_3O$ (m/z): 211, found: 212 [M+1]⁺.

Preparation of 2-(4-nitrophenyl)oxazolo[4,5-c]pyridine

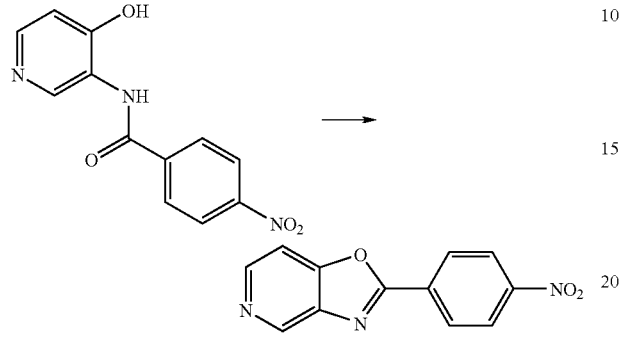

A solution of N-(4-hydroxypyridin-3-yl)-4-nitrobenzamide (2.59 g, 10.0 mmol) and polyphosphoric acid (20 mL) was stirred at 140° C. for 6 h. The reaction mixture was poured into distilled water (200 mL) and sodium hydroxide was added until pH=5. The precipitate was collected by filtration, washed with water until neutral and dried under vacuum to afford 2-(4-nitrophenyl)oxazolo[4,5-c]pyridine as a yellow solid (2.261 g, Yield: 94%). MS(ESI) calcd. for $C_{12}H_7NO_3$ (m/z): 241, found: 242 [M+1]⁺.

Preparation of 4-(oxazolo[4,5-c]pyridin-2-yl)benzenamine

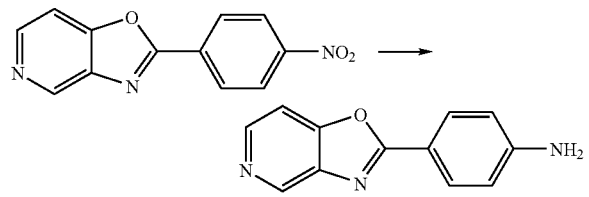

2-(4-Nitrophenyl)oxazolo[4,5-c]pyridine (2.261 g, 9.3 mmol), iron powder (2.814 g, 48.0 mmol) and NH₄Cl (4.314 g, 80.1 mmol) were refluxed in CH₃OH/H₂O (4:1, 469 mL) for 6 h. The mixture was filtered and the filtrate was evaporated in vacuo. The residue was purified by chromatography on silica gel eluted with petroleum ether:ethyl acetate: Et₃N=160:40:1 to afford 4-(oxazolo[4,5-c]pyridin-2-yl)benzenamine as a yellow solid (1.215 g, yield: 62%). ¹H NMR (400 MHz, DMSO-d₆) δ: 6.11 (2H, s), 6.69 (2H, d, J=8.4 Hz), 7.75 (1H, d, J=5.6 Hz), 7.87 (2H, d, J=8.4 Hz), 8.46 (1H, d, J=5.6 Hz), 8.94 (1H, s); MS(ESI) calcd. for $C_{12}H_9N_3O$ (m/z): 211, found: 212 [M+1]⁺.

General Procedure for Preparing Compounds 339, 340, 341, 342, 449, 410, 411, and 412

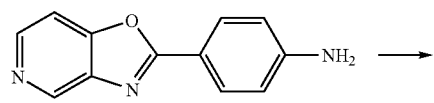

-continued

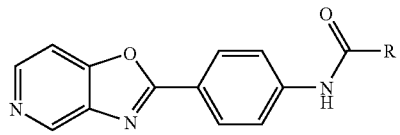

Compounds 339, 340, 341, 342, 449, 410, 411, and 412 were prepared by essentially the same procedure as detailed above for the preparation of Compound 343 using 4-(oxazolo[4,5-c]pyridin-2-yl)benzenamine as the starting material and the appropriate acid chloride.

Preparation of 2-(4-nitrophenyl)thiazolo[4,5-c]pyridine

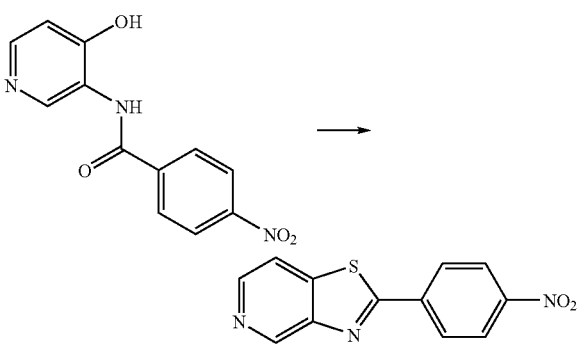

A mixture of N-(4-hydroxypyridin-3-yl)-4-nitrobenzamide (5.18 g, 0.02 mol) and P₂S₅ (8.90 g, 0.04 mol) in pyridine (25 mL) and p-xylene (100 mL) was stirred at 140° C. for 18 h. The solvent was removed under vacuo while hot and the residue was purified by recrystallization from EtOH to afford 2-(4-nitrophenyl)thiazolo[4,5-c]pyridine as a yellow solid (3.00 g, yield: 59%). MS (ESI), calcd for $C_{12}H_7N_3O_2S$ (m/z): 257, found: 258 [M+1]⁺.

Preparation of 4-(thiazolo[4,5-c]pyridin-2-yl)benzenamine

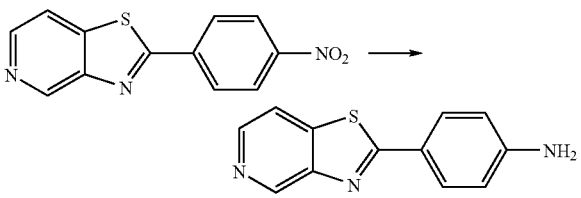

2-(4-nitrophenyl)thiazolo[4,5-c]pyridine (2.57 g, 0.01 mol), iron powder (2.8 g, 0.05 mmol) and NH₄Cl (4.32 g, 0.08 mol) were refluxed in CH₃OH/H₂O (4:1, 200 mL) for 6 h. The mixture was filtered and the filtrate was evaporated in vacuo. The residue was washed with water (30 ml) to give 4-(thiazolo[4,5-c]pyridin-2-yl)benzenamine as a white solid (1.37 g, Yield: 60%).

General Procedure for Preparing Compounds 322, 323, 324, 325, 409 and 450

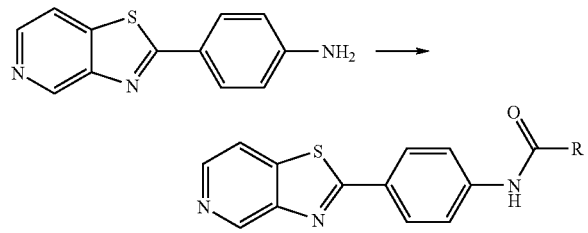

Compounds 322, 323, 324, 325, 409 and 450 were prepared by essentially the same procedure as detailed above for the preparation of Compound 343 using 4-(oxazolo[4,5-c]pyridin-2-yl)benzenamine as the starting material and the appropriate acid chloride.

Preparation of N-(4-hydroxypyridin-3-yl)-5-nitrothiophene-2-carboxamide

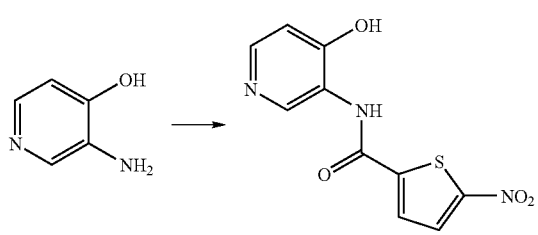

A mixture of 5-nitrothiophene-2-carboxylic acid (5.000 g, 28.9 mmol) in $SOCl_2$ (40 mL) was refluxed for 2 h. The excess $SOCl_2$ was evaporated in vacuo and 3-amino-4-hydroxypyridine (2.65 g, 24.1 mmol) in pyridine (150 mL) was added dropwise. The reaction mixture was stirred at 10° C. overnight. $Na_2CO_3$ (1.533 g, 14.5 mmol) in water (100 mL) was added and the resultant mixture was stirred for additional 1 h. The precipitate was collected by filtration, washed with 10% $Na_2CO_3$ (120 mL), and dried in vacuo to afford N-(4-hydroxypyridin-3-yl)-5-nitrothiophene-2-carboxamide as a yellow powder (5.87 g, yield: 92%).

Preparation of 2-(5-nitrothiophen-2-yl)oxazolo[4,5-c]pyridine

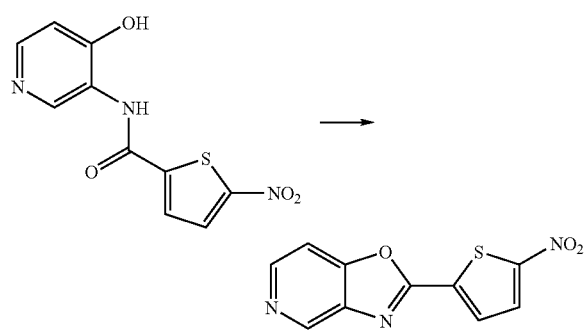

A solution of N-(4-hydroxypyridin-3-yl)-5-nitrothiophene-2-carboxamide (2.385 g, 9.0 mmol) in polyphosphoric acid (18 mL) was stirred at 140° C. for 6 h. The reaction mixture was poured into distilled water and sodium hydroxide was added until pH=5. The precipitate was collected by filtration, washed with water until neutral and dried to afford 2-(5-nitrothiophen-2-yl)oxazolo[4,5-c]pyridine as a yellow solid (1.775 g, yield: 80%). MS (ESI) calcd. for $C_{10}H_5N_3O_3S$ (m/z): 247, found: 248 $[M+1]^+$.

Preparation of 5-(oxazolo[4,5-c]pyridin-2-yl)thiophen-2-amine

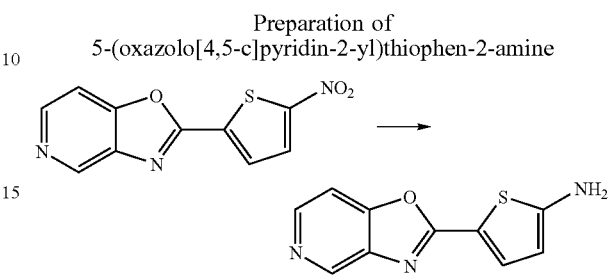

2-(5-nitrothiophen-2-yl)oxazolo[4,5-c]pyridine (1.775 g, 7.2 mmol), iron powder (2.108 g, 36.0 mmol) and $NH_4Cl$ (3.081 g, 57.6 mmol) were refluxed in $CH_3OH/H_2O$ (4:1, 360 mL) for 6 h. The mixture was filtered and the filtration was evaporated in vacuo. The residue was purified by chromatography on silica gel eluted with petroleum ether: ethyl acetate:$Et_3N$=160:40:1 to afford 5-(oxazolo[4,5-c]pyridin-2-yl)thiophen-2-amine as a yellow solid (1.1 g, yield: 70%). $^1$HNMR (400 MHz, DMSO-$d_6$) δ: 8.83 (1H, s), 8.41 (1H, d, J=4.8 Hz), 7.67 (1H, d, J=4.8 Hz), 7.57 (1H, d, J=4.4 Hz), 6.91 (2H, s), 6.03 (1H, d, J=4.4 Hz); MS (ESI) calcd. for $C_{10}H_7N_3OS$ (m/z): 217, found: 218 $[M+1]^+$.

Preparation of Compounds 422, 423, 424, 425, 426, 427 and 428

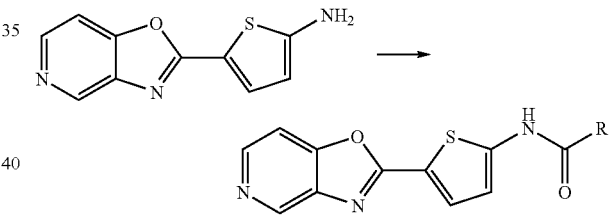

Compounds 422, 423, 424, 425, 426, 427 and 428 were prepared by essentially the same procedure as detailed above for the preparation of Compound 343 using 5-(oxazolo[4,5-c]pyridin-2-yl)thiophen-2-amine as the starting material and the appropriate acid chloride.

Preparation of 2-(5-nitrothiophen-2-yl)thiazolo[4,5-c]pyridine

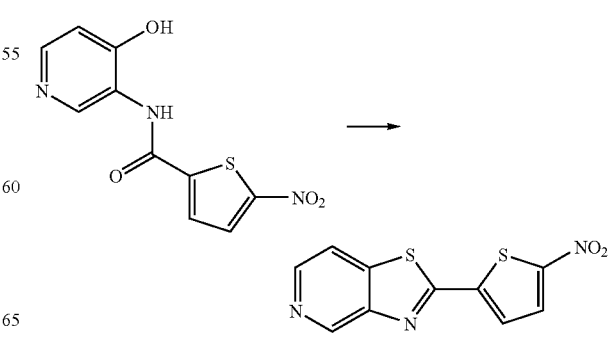

A mixture of compound 17 (1.97 g, 7.43 mmol) and P$_2$S$_5$ (3.30 g, 15 mmol) in pyridine (30 mL) and p-xylene (120 mL) was stirred at 140° C. for 18 h. The solvent was removed in vacuo while hot and the residue was purified by recrystallization from EtOH to afford compound 21 as a yellow solid (700 mg, yield: 35%, Lot#: MC0052-050-21). MS (ESI) calcd. for C$_{10}$H$_5$N$_3$O$_2$S$_2$ (m/z): 263, found: 264.1 [M+1]$^+$.

Preparation of
5-(thiazolo[4,5-c]pyridin-2-yl)thiophen-2-amine

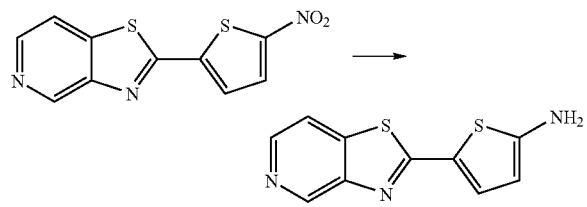

Compound 21 (700 mg, 2.66 mmol), iron powder (745 mg, 13.30 mmol) and NH$_4$Cl (1.36 g, 22 mmol) were refluxed in CH$_3$OH/H$_2$O (4:1, 150 mL) for 6 h. The mixture was filtered and the filtrate was evaporated in vacuo. The residue was washed with water (30 mL) and dried to afford compound 22 as a yellow solid (306 mg, yield: 50%).

Preparation of Compounds 515, 516, 517, 518, 519 and 520

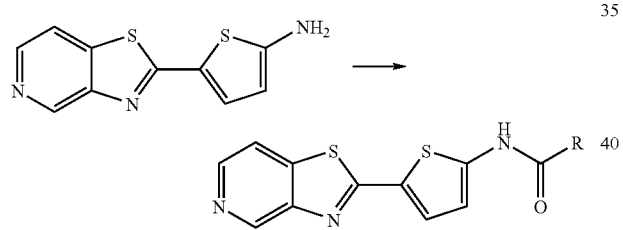

Compounds 515, 516, 517, 518, 519 and 520 were prepared by essentially the same procedure as detailed above for the preparation of Compound 343 using 5-(oxazolo[4,5-c]pyridin-2-yl)thiophen-2-amine as the starting material and the appropriate acid chloride.

Preparation of
N-(3-hydroxypyridin-4-yl)-3-methylbenzamide

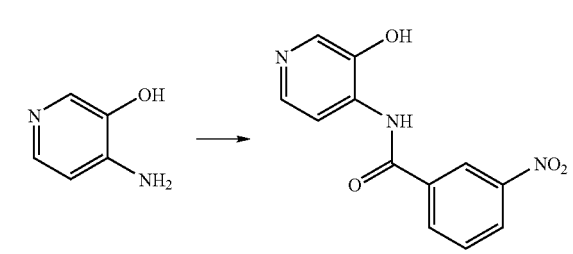

3-Amino-4-hydroxypyridine was prepared according to a procedure detailed in Journal of Organic Chemistry (1995), p. 5721. A solution of 3-nitrobenzoyl chloride (3.10 g, 16.7 mmol) in pyridine (50 mL) was added dropwise to a solution of 3-amino-4-hydroxypyridine (2.481 g, 21.6 mmol) in pyridine (40 mL) at 10° C. and the resultant mixture was stirred overnight. Na$_2$CO$_3$ (1 g) was added and the mixture was stirred for additional 1 hr. The solid was collected by filtration, washed with 10% acetic acid (30 mL×3) and water (30 mL×3) and dried under vacuo to afford N-(3-hydroxypyridin-4-yl)-3-methylbenzamide as yellow solid (1.057 g, yield: 43%).

Preparation of
2-(3-nitrophenyl)oxazolo[5,4-c]pyridine

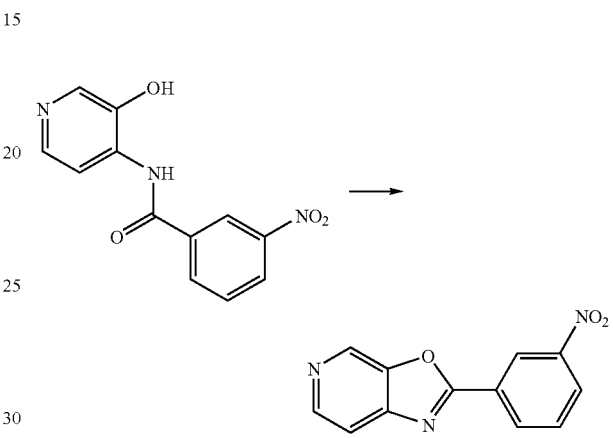

A solution of N-(3-hydroxypyridin-4-yl)-3-methylbenzamide (1.30 g, 5 mmol) in polyphosphoric acid (7.5 mL) was stirred at 150° C. for 6 hrs. The reaction mixture was poured into distilled water and sodium hydroxide was added until pH=5. The precipitate was collected by filtration, washed with water until neutral and dried in vacuo oven (50° C.) to afford 2-(3-nitrophenyl)oxazolo[5,4-c]pyridine as yellow solid (1.120 g, yield: 93%).

Preparation of
3-(oxazolo[5,4-c]pyridin-2-yl)benzenamine

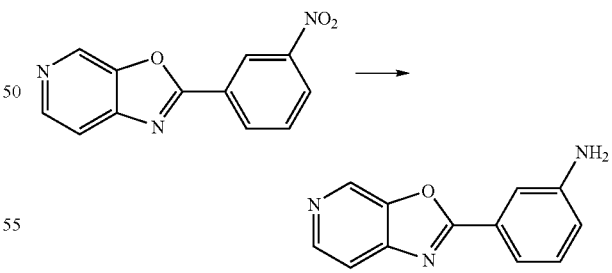

A suspension of 2-(3-nitrophenyl)oxazolo[5,4-c]pyridine (1.20 g, 5 mmol), iron powder (1.40 g, 25 mmol) and NH$_4$Cl (2.14 g, 40 mmol) in CH$_3$OH:H$_2$O (4:1, 60 mL) was refluxed for 6 hrs. The reaction mixture was filtered and the filtrate was evaporated in vacuo. The residue was poured into water. The precipitate was collected by filtration, and washed with water (20 mL×3) to afford 3-(oxazolo[5,4-c]pyridin-2-yl)benzenamine as a white solid (0.330 g, yield: 31%).

Preparation of Compounds 429, 430, 431, 451, 452, 453 and 454

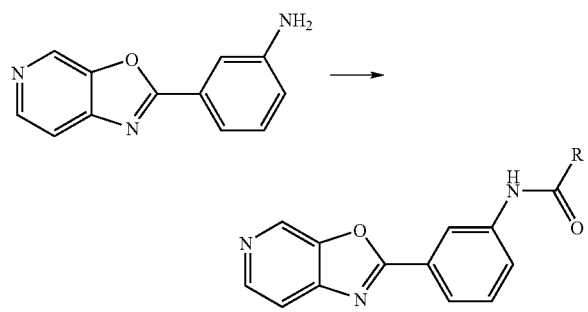

Compounds 429, 430, 431, 451, 452, 453 and 454 were prepared by essentially the same procedure as detailed above for the preparation of Compound 343 using 3-(oxazolo[5,4-c]pyridin-2-yl)benzenamine as the starting material and the appropriate acid chloride.

Preparation of N-(3-hydroxypyridin-4-yl)-4-nitrobenzamide

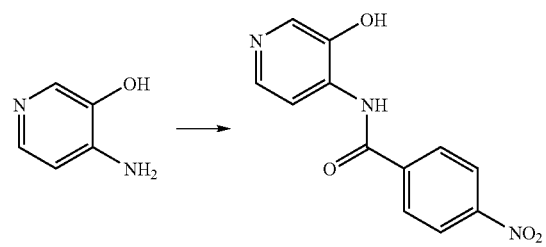

A solution of p-nitrobenzoyl chloride (4.8 g, 25.7 mmol) in pyridine (50 mL) was added to a solution of 4-amino-3-hydroxypyridine (2.5 g, 22.7 mmol) in pyridine (88 mL) at 10° C. and stirred at room temperature overnight. To the reaction mixture was added $Na_2CO_3$ (1.1 g, 10.4 mmol) in water (10 mL) and stirred for 1 hrs. 10% AcOH was added to neutralize the solution. The precipitate was collected by filtration, washed with 10% AcOH and dried to give N-(3-hydroxypyridin-4-yl)-4-nitrobenzamide as a yellow powder (2.27 g, yield: 52%). MS(ESI) calcd. for $C_{12}H_9N_3O_4$ (m/z): 259, found: 260 [M+H]$^+$.

Preparation of 2-(4-nitrophenyl)oxazolo[5,4-c]pyridine

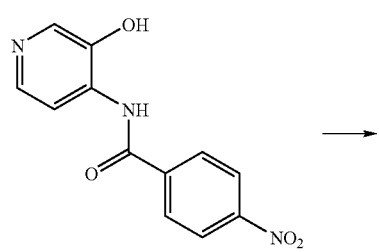

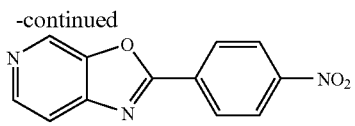

A mixture of N-(3-hydroxypyridin-4-yl)-4-nitrobenzamide (260 mg, 1 mmol) and polyphosphoric acid (1.5 mL) was stirred at 150° C. for 6 hrs. The reaction mixture was poured into water and sodium hydroxide was added until pH=5. The precipitate was collected by filtration, washed with water until neutral and dried to give 2-(4-nitrophenyl)oxazolo[5,4-c]pyridine as brown solid (177 mg, yield: 73%). $^1$HNMR (400 MHz, DMSO-d$_6$) δ: 9.21 (1H, s), 8.62 (1H, d, J=4.8 Hz), 8.51 (4H, d, J=18, 8.8 Hz), 7.95 (1H, d, J=5.2 Hz).

Preparation of 4-(oxazolo[5,4-c]pyridin-2-yl)benzenamine

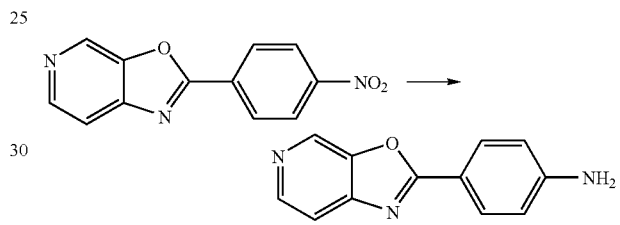

A mixture of 2-(4-nitrophenyl)oxazolo[5,4-c]pyridine (610 mg, 2.5 mmol), $NH_4Cl$ (1.2 g, 22.4 mmol), iron powder (0.76 g, 13.6 mmol), $H_2O$ (13 mL) and methanol (51 mL) was heated to reflux for 6 h under $N_2$. The mixture was concentrated in vacuo and purified by chromatography on silica gel (eluted with EA/PE=3:1) to give 4-(oxazolo[5,4-c]pyridin-2-yl)benzenamine as light brown powder (340 mg, yield 64%). $^1$H NMR (400 MHz, DMSO-d$_6$) δ:8.95 (1H, s); 8.46 (1H, d, J=5.2); 7.92 (2H, d, J=8.8); 7.69 (1H,d, J=5.6), 6.71 (2H,d, J=8.8), 6.19 (2H, s); MS(ESI) calcd for $C_{12}H_9N_3O$ (m/z): 211, found: 212 [M+H]$^+$.

Preparation of Compounds 408 and 419

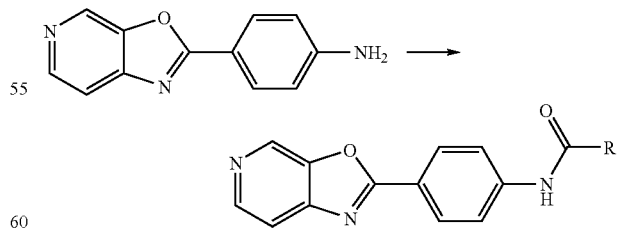

Compounds 408 and 419 were prepared by essentially the same procedure as detailed above for the preparation of Compound 343 using 4-(oxazolo[5,4-c]pyridin-2-yl)benzenamine as the starting material and the appropriate acid chloride.

Preparation of N-(3-hydroxypyridin-4-yl)-5-nitrothiophene-2-carboxamide

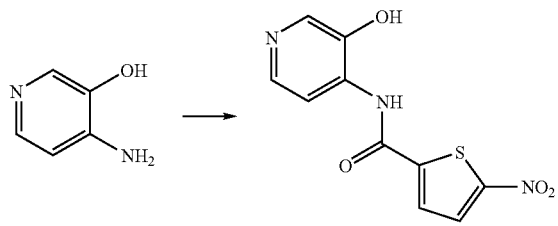

A solution of 5-nitrothiophene-2carboxylic acid (5.0 g, 28.9 mmol) and $SOCl_2$ (40 mL) was refluxed for 2 hrs. The solvent was removed in vacuo followed by addition of 4-amino-3-hydroxypyridine (2.65 g, 24.1 mmol) in pyridine (150 mL). The mixture was stirred at 10° C. overnight. $Na_2CO_3$ (1.53 g, 14.5 mmol) in water (100 mL) was added and stirred for 1 hr followed by adding AcOH to adjust pH=7. The precipitate was collected by filtration, washed with 10% AcOH (30 mL×2) and dried to give N-(3-hydroxypyridin-4-yl)-5-nitrothiophene-2-carboxamide as a yellow powder (5.0 g, yield 78%).

Preparation of 2-(5-nitrothiophen-2-yl)oxazolo[5,4-c]pyridine

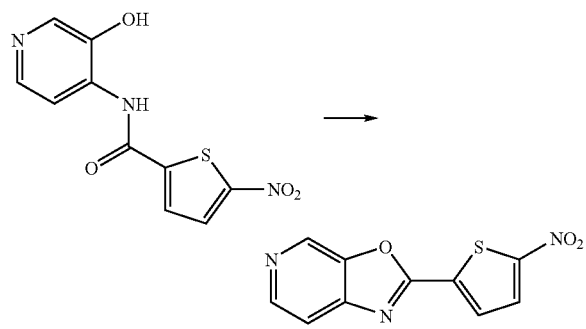

To a stirred solution of N-(3-hydroxypyridin-4-yl)-5-nitrothiophene-2-carboxamide (1.1 g, 4.1 mmol) in pyridine (5 mL) was added $P_2O_5$ (1.2 g, 8.3 mmol) and p-xylene (21 mL). After refluxing at 160° C. overnight, the reaction mixture was concentrated in vacuo and the residue was purified by chromatography on silica gel eluted with 5% of ethyl acetate in $CH_2Cl_2$ to give 2-(5-nitrothiophen-2-yl)oxazolo[5,4-c]pyridine as brown solid (174 mg, yield 17%). $^1H$ NMR (400 MHz, $CDCl_3$) δ: 8.97 (1H, s); 8.59 (1H, d, J=5.6); 7.94 (1H, d, J=4.4); 7.86 (1H, d, J=4.4), 7.69 (1H, d, J=5.6,0.8).

Preparation of 5-(oxazolo[5,4-c]pyridin-2-yl)thiophen-2-amine

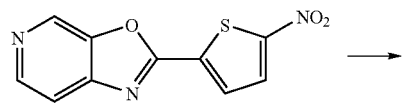

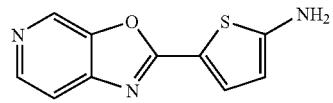

A mixture of 2-(5-nitrothiophen-2-yl)oxazolo[5,4-c]pyridine (170 mg, 0.69 mmol), $NH_4Cl$ (199 mg, 3.73 mmol), iron powder (328 mg, 5.87 mmol), $H_2O$ (10 mL) and methanol (40 mL) was heated to reflux for 6 hrs under $N_2$. The mixture was concentrated in vacuo followed by addition of 100 mL of water and left overnight at 4° C. The precipitate was collected by filtration and dried to give 5-(oxazolo[5,4-c]pyridin-2-yl)thiophen-2-amine as a brown solid (52 mg, yield 35%). $^1$HNMR (400 MHz, DMSO-$d_6$) δ: 8.84 (1H, s); 8.40 (1H, d, J=5.2); 7.64 (1H, d, J=4); 7.57 (1H, d, J=5.2), 7.06 (2H, s), 1.09 (1H, d, J=4.4).

Preparation of Compounds 561, 562 and 563

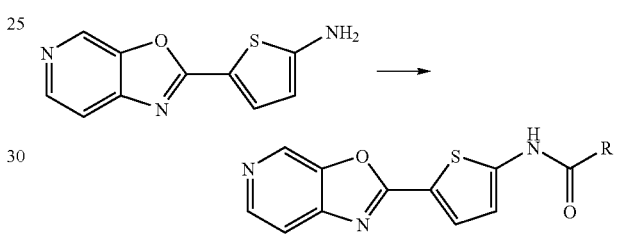

Compounds 561, 562 and 563 were prepared by essentially the same procedure as detailed above for the preparation of Compound 343 using 5-(oxazolo[5,4-c]pyridin-2-yl)thiophen-2-amine as the starting material and the appropriate acid chloride.

Preparation of 2-(oxazolo[4,5-c]pyridin-2-yl)benzenamine

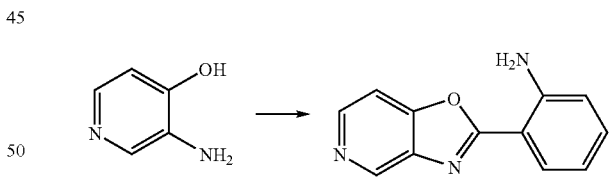

3-Amino-4-hydroxypyridine (2.225 g, 20.0 mmol) and 2-aminobenzoic acid (2.740 g, 20.0 mmol) were stirred in polyphosphoric acid (40 mL) at 140° C. for 6 hrs. The reaction mixture was poured into distilled water and sodium hydroxide was added until pH=8. The precipitate was collected by filtration and the crude product was purified by chromatography on silica gel eluting with petroleum ether: ethyl acetate:$Et_3N$ (160:40:1) to give 2-(oxazolo[4,5-c]pyridin-2-yl)benzenamine (1.659 g, Yield: 39%). $^1H$ NMR (400MHz, DMSO-$d_6$) δ: 6.68 (1H, t, J=7.6 Hz), 6.93 (1H, d, J=8.0 Hz), 7.17 (2H, s), 7.30 (1H, t, J=7.6 Hz), 7.83 (1H, d, J=5.6 Hz), 7.90 (1H, d, J=8.0 Hz), 8.55 (1H, d, J=5.6 Hz), 9.05 (1H, s); MS(ESI) calcd. for $C_{12}H_9N_3O$ (m/z): 211, found: 212 $[M+1]^+$.

Preparation of Compounds 404, 405, 406, 407, 420 and 421

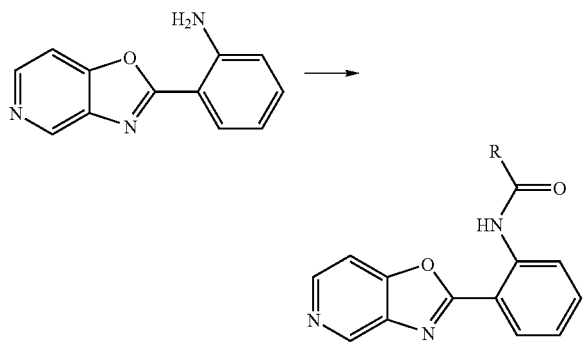

Compounds 404, 405, 406, 407, 420 and 421 were prepared by essentially the same procedure as detailed above for the preparation of Compound 343 using 2-(oxazolo[4,5-c]pyridin-2-yl)benzenamine as the starting material and the appropriate acid chloride.

Preparation of 2-(2-nitrophenyl)thiazolo[4,5-c]pyridine

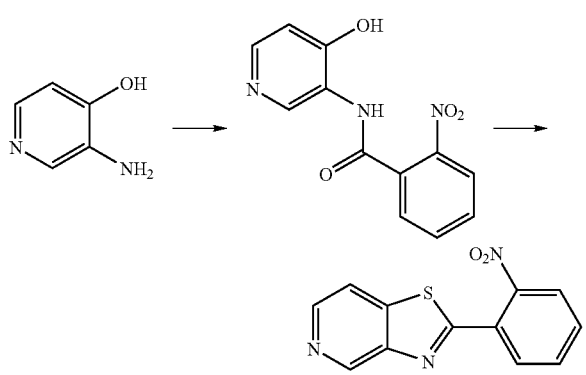

N-(4-Hydroxy-pyridin-3-yl)-2-nitro-benzamide was prepared using a procedure similar to that described above using 4-hydroxy-3-aminopyridine and 2-nitrobenzoyl chloride. A mixture of -(4-Hydroxy-pyridin-3-yl)-2-nitro-benzamide (2.6 g, 0.01 mol) and $P_2S_5$ (4.44 g, 0.02 mol) in pyridine (12.5 mL) and p-xylene (50 mL) was stirred at 140° C. for 18 hrs. The solvent was removed under vacuo and the residue was purified by recrystallization to give 2-(2-nitrophenyl)thiazolo[4,5-c]pyridine as a yellow solid (1.43 g, yield: 55%).

Preparation of 2-thiazolo[4,5-c]pyridin-2-yl-phenylamine

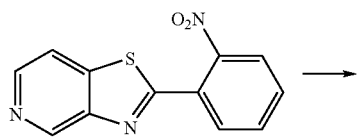

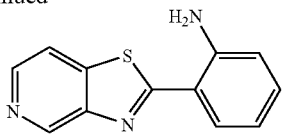

A suspension of 2-(2-nitrophenyl)thiazolo[4,5-c]pyridine (1.170 g, 4.6 mmol), Fe powder (1.26 g, 22.8 mmol) and $NH_4Cl$ (1.97 g, 36.8 mmol) in $CH_3OH : H_2O$ (4:1, 80 mL) was refluxed for 6 hrs. The mixture was filtered and the filtrate was evaporated in vacuo. The residue was poured into water. The precipitate was collected by filtration, and washed with water (20 mL×3) to afford 2-thiazolo[4,5-c]pyridin-2-yl-phenylamine as a yellow solid (0.760 g, yield: 73%).

Preparation of Compounds 317, 318, 319, 320, 321 and 349

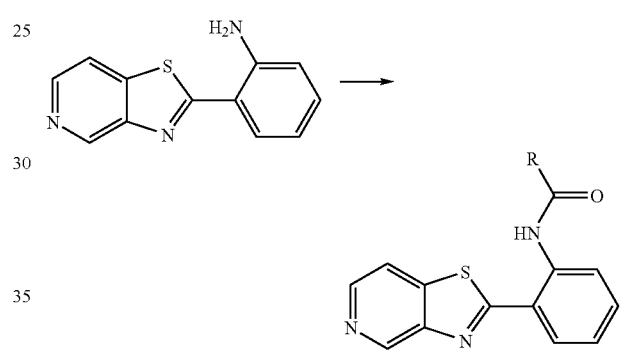

Compounds 317, 318, 319, 320, 321 and 349 were prepared by essentially the same procedure as detailed above for the preparation of Compound 343 using 2-(2-nitrophenyl)thiazolo[4,5-c]pyridine as the starting material and the appropriate acid chloride.

Preparation of 2-(oxazolo[5,4-c]pyridin-2-yl)benzenamine

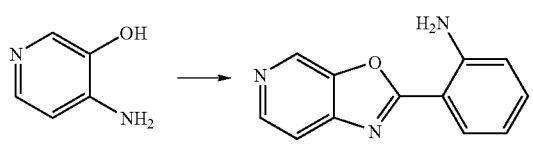

3-Hydroxy-4-aminopyridine (2.220 g, 20.0 mmol) and 2-aminobenzoic acid (2.740 g, 20.0 mmol) in polyphosphoric acid (40 mL) were stirred at 140° C. for 6 hrs. The reaction mixture was poured into distilled water and sodium hydroxide was added until pH=8. The precipitate was collected by filtration and further purified by chromatography on silica gel eluted with petroleum ether:ethyl acetate:$Et_3N$ (160:40:1) to give 2-(oxazolo[5,4-c]pyridin-2-yl)benzenamine as yellow solid (1.332 g, Yield: 31%). $^1$H NMR (400 MHz, DMSO-$d_6$) δ: 6.70 (1H, t, J=6.8 Hz), 6.94 (1H, d, J=8.4 Hz), 7.20 (2H, s), 7.33 (1H, t, J=6.8 Hz), 7.80 (1H, d, J=5.6 Hz), 7.95 (1H, d, J=8.4 Hz), 8.53 (1H, d, J=5.6 Hz), 9.05 (1H, s); MS(ESI) calcd. for $C_{12}H_9N_3O$ (m/z): 211, found: 212 [M+1]$^+$.

Preparation of Compounds 455, 456, 457, 458 and 459

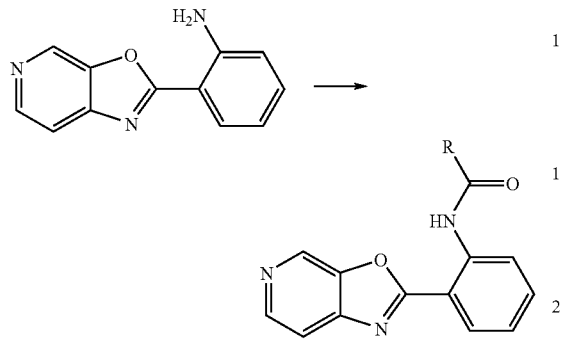

Compounds 455, 456, 457, 458 and 459 werer prepared by essentially the same procedure as detailed above for the preparation of Compound 343 using 2-(oxazolo[5,4-c]pyridin-2-yl)benzenamine as the starting material and the appropriate acid chloride.

Preparation of N-(2-chloro-5-methylpyridin-3-yl)-2-nitrobenzamide

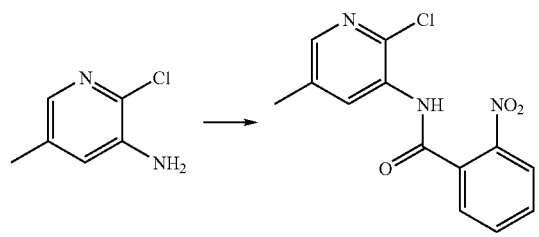

To a solution of 5-amino-6-chloro-3-picoline (9.54 g, 66.9 mmol) in pyridine (200 mL) was added 2-nitrobenzoyl chloride (13.65 g, 73.6 mmol) dropwise at 0° C. The resulting mixture was stirred at room temperature for 18 h. The dark mixture was then diluted with water (1500 mL) and sat. sodium bicarbonate solution was added until pH=8. The precipitate was collected by filtration, rinsed with water (30 mL×3) and dried in oven to afford N-(2-chloro-5-methylpyridin-3-yl)-2-nitrobenzamide as a pale solid (17.70 g, yield: 91%).

Preparation of 6-methyl-2-(2-nitrophenyl)thiazolo[5,4-b]pyridine

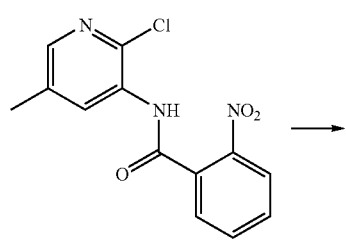

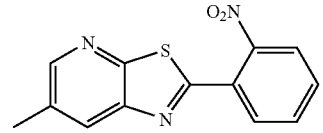

A mixture of N-(2-chloro-5-methylpyridin-3-yl)-2-nitrobenzamide (5.0 g, 17.1 mmol) and $P_2S_5$ (7.6 g, 34.2 mmol) in pyridine (50 mL) and p-xylene (200 mL) was stirred at 140° C. for 20 h. The hot solution was transferred to another flask and the solvent was removed in vacuo. The residue was purified by recrystallization from EtOH to afford 6-methyl-2-(2-nitrophenyl)thiazolo[5,4-b]pyridine as a yellow solid (3.5 g, yield: 75%).

Preparation of 6-(bromomethyl)-2-(2-nitrophenyl)thiazolo[5,4-b]pyridine

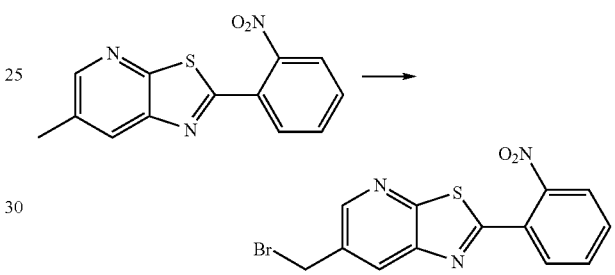

6-Methyl-2-(2-nitrophenyl)thiazolo[5,4-b]pyridine (2.9 g, 10.7 mmol), N-bromosuccinimide (NBS, 1.91 g, 10.7 mmol), $CCl_4$ (200 mL) and benzoyl peroxide (0.021 g) were added into a three-neck flask (500 mL) under argon. The resulting yellow mixture was refluxed for 2 h. Additional NBS (1.91 g) and benzoyl peroxide (0.021 g) were added. Two hours later, more NBS (0.95 g) and benzoyl peroxide (0.021 g) were added and the mixture was continually refluxed for 3 h. The mixture was then cooled to room temperature. The solution was transferred into another flask and concentrated in vacuo to afford crude 6-(bromomethyl)-2-(2-nitrophenyl)thiazolo[5,4-b]pyridine (4.0 g), which was directly used for next step.

Preparation of tert-butyl 4-((2-(2-nitrophenyl)thiazolo[5,4-b]pyridin-6-yl)methyl)piperazine-1-carboxylate

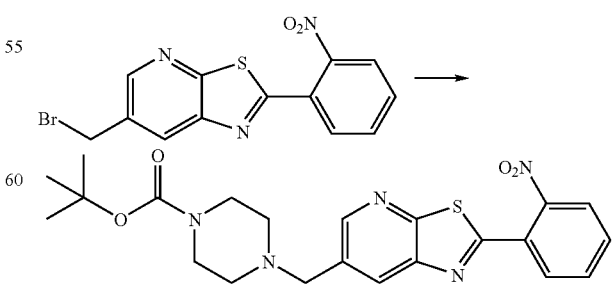

A solution of crude 6-(bromomethyl)-2-(2-nitrophenyl)thiazolo[5,4-b]pyridine (4.0 g), Boc-piperazine (1.99 g, 10.7 mmol), Et₃N (1.5 mL, 10.7 mmol) and acetonitrile (100 mL) was stirred at 50° C. for 4 h and then at room temperature for 60 h. TLC demonstrated that the reaction was complete. The mixture was concentrated in vacuo and purified by silica gel chromatography (petroleum ether: ethyl acetate: Et₃N=100:10:1) to afford tert-butyl 4-((2-(2-nitrophenyl)thiazolo[5,4-b]pyridin-6-yl)methyl)piperazine-1-carboxylate as a yellow solid (3.6 g, yield: 74% over 2 steps).

Preparation of tert-butyl 4-((2-(2-aminophenyl)thiazolo[5,4-b]pyridin-6-yl)methyl)piperazine-1-carboxylate

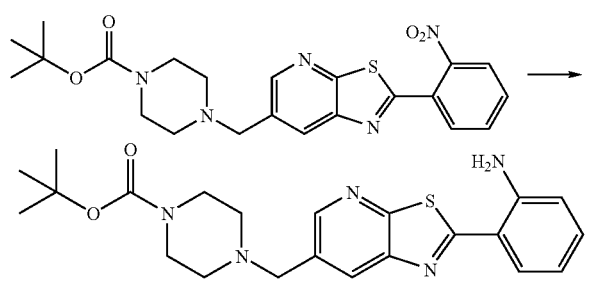

A mixture of tert-butyl 4-((2-(2-nitrophenyl)thiazolo[5,4-b]pyridin-6-yl)methyl)piperazine-1-carboxylate (2.13 g, 4.7 mmol), NH₄Cl (2.00 g, 37 mmol), iron powder (1.31 g, 23.5 mmol), H₂O (40 mL) and methanol (160 mL) was refluxed for 3 h under N₂. The reaction mixture was filtered, and the filtrate was concentrated in vacuo and purified by silica gel chromatography (petroleum ether: ethyl acetate: Et₃N=800:200:1) to afford tert-butyl 4-((2-(2-aminophenyl)thiazolo[5,4-b]pyridin-6-yl)methyl)piperazine-1-carboxylate as a yellow solid (1.63 g, yield: 81%).

General Procedure for Preparing Compounds 588, 589, 590, 591, 592, 593, 594, 622, 646, 681, 682, 683, 684, 685, 686, 687, 688, 689, 701, 702, 722, 723, 724, 725, 730, 731 and 732

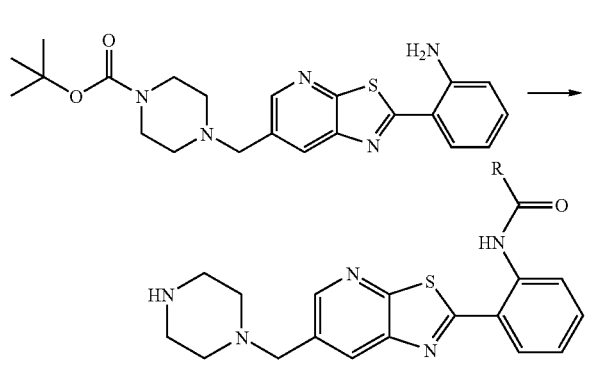

A mixture of the amino scaffold (tert-butyl 4-((2-(2-aminophenyl)thiazolo[5,4-b]pyridin-6-yl)methyl)piperazine-1-carboxylate, 0.141 mmol each) and the appropriate acid chloride (0.17 mmol) in pyridine (2 mL) was shaken at room temperature overnight. The reaction mixture was then diluted with sat. NaHCO₃ (5 mL each). The precipitates were collected by filtration and triturated with MeOH (5 mL) and dried to afford Boc-protected library compounds, which were analyzed by HPLC & MS. For those Boc-protected library compounds with purity below 95%, the compounds were further purified by passing through silica gel pad eluted with petroleum ether/EtOAc.

The Boc-protected compounds with were dissolved in 25% TFA/CH₂Cl₂ solution (1 or 2 mL) and shaken at room temperature and monitored by TLC or LC/MS. The mixtures were then concentrated in vacuo and co-evaporated with CH₂Cl₂ (1.0 mL×2) in vacuo to afford the desired products as the TFA salts, which were analyzed by ¹H NMR, HPLC and MS.

Preparation of Compounds 690, 726, 727, 728 and 729

Compounds 690, 726, 727, 728 and 729 were prepared by essentially the same procedure as detailed in the preparation of Compound 646 except that 3-amino-2-hydroxy-6-methylpyridine was used as the starting material.

General Procedure for Preparing Compounds 240, 608, 241, 221, 280, 222, 223, 225, 244, 245, 246, 247, 226, 303, 238, 227, 304, 228, 305, 306, 307, 308, 309, 310, 248, 249, and 396

Compounds 240, 608, 241, 221, 280, 222, 223, 225, 244, 245, 246, 247, 226, 303, 238, 227, 304, 228, 305, 306, 307, 308, 309, 310, 248, 249, and 396 were prepared by essentially the same procedure as detailed below for the preparation of Compound 241 using 3-Thiazolo[5,4-c]pyridin-2-yl-phenylamine as the starting material and the appropriate acid chloride.

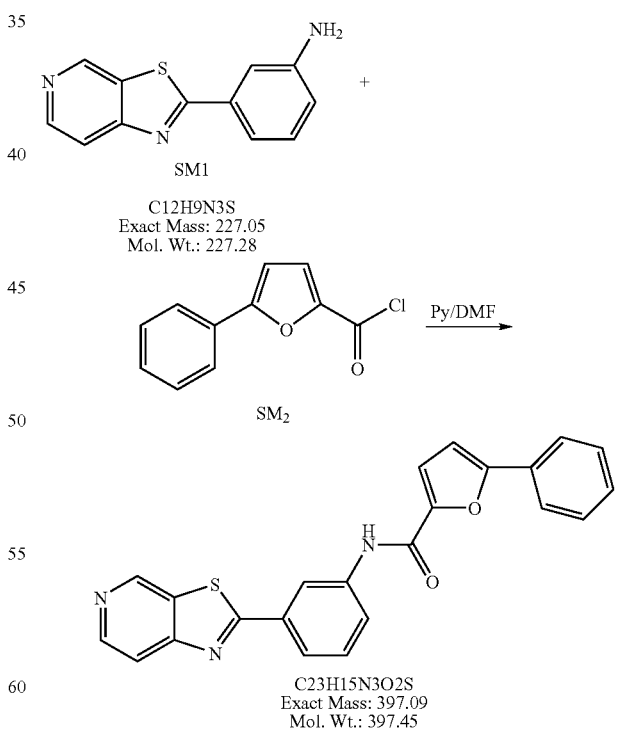

To a mixture of 3-thiazolo[5,4-c]pyridin-2-yl-phenylamine in 1.5 mL DMF was added 5-phenyl furan-2-carbonyl chloride (62 mg, MW=206.63, 0.3 mmol) in pyridine (0.25 mL). The reaction was kept for 72 hours at 40° C. and monitored with TLC. At the end of reaction, 5 mL H$_2$O was added, and the resulting suspension was filtered to collect the solid, which was then washed with H$_2$O and dried. The crude product was further purified by preparative TLC (acetone/petroleum ether=1/2) and washed with acetone to afford a white powder (43 mg, 36.1%). The product was confirmed by $^1$H NMR. $^1$H NMR (DMSO-d$_6$, 500 MHz), δ10.50 (1H, s), 9.45 (1H, s), 8.70 (1H, brs), 8.68 (1H, d, J=5.5 Hz), 8.13 (1H, d, J=7.8 Hz), 8.08 (1H, d, J=5.5 Hz), 8.02 (2H, d, J=7.6 Hz), 7.93 (1H, d, J=7.7 Hz), 7.63 (1H, t, J=7.9 Hz), 7.55 (3H, m), 7.43 (1H, t, J=7.3 Hz), 7.23 (1 H, d, J=3.4 Hz). EIMS m/z (%): 397.2 (M$^+$).

General Procedure for Preparing Compounds 466, 398, 229, 230, 282, 250, 231, 399, 251, 283, 232, 252, 284, 285, 287, 234, 235, 236, 237, 239, 289, 288, 290, 655, and 280

Compounds 466, 398, 229, 230, 282, 250, 231, 399, 251, 283, 232, 252, 284, 285, 287, 234, 235, 236, 237, 239, 289, 288, 290, 655, and 280 were by prepared by essentially the same procedure as detailed below for the preparation of Compound 398 using 3-Thiazolo[5,4-c]pyridin-2-yl-phenylamine as the starting material and the appropriate sulfonyl chloride.

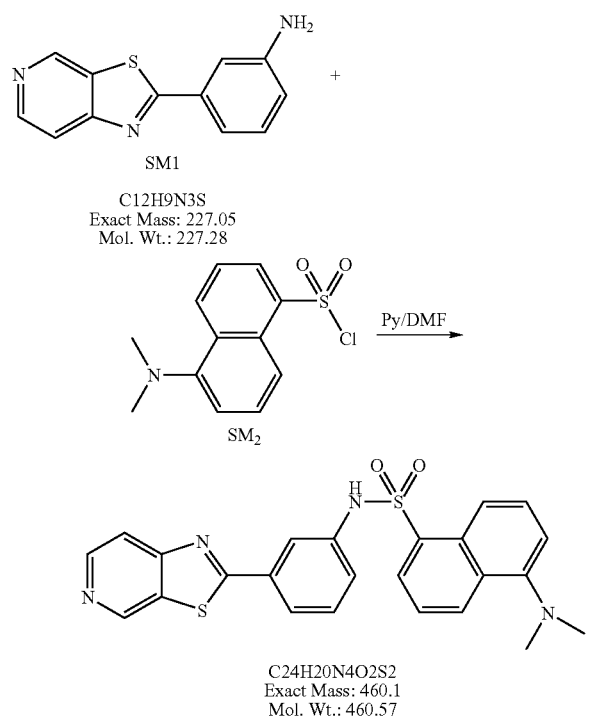

3-Thiazolo[5,4-c]pyridin-2-yl-phenylamine (68 mg, 0.3 mmol) in 2 mL pyridine was added to Dansyl chloride (81 mg, 0.3 mmol) while stirring. The reaction was kept at about 40° C. for 24 hours. Pyridine was evaporated in vacuum, and water was added.

The resulting suspension was filtered and washed by THF to afford the product as a yellow solid (29 mg, 21.0%). $^1$H NMR (DMSO-d$_6$, 500 MHz) δ 9.38 (1H,s), 8.64 (1H,d, J=2.8 Hz), 8.45 (1H,d, J=8.5 Hz), 8.38 (1H,d, J=8.6 Hz), 8.30 (1H,d, J=7.1 Hz), 8.03 (1H,d, J=5.4 Hz), 7.87(1H,s), 7.71(1H,d, J=7.6 Hz), 7.64 (2H,m), 7.40 (1H,t, J=7.9 Hz), 7.31(1H,d, J=8.1 Hz), 7.26 (1H,d, J=7.6 Hz), 2.77 (6H,s) m/z: 460.01 (M$^+$, 31).

General Procedure for Preparing Compounds 599, 600, 498, 610, 601, 611, 485, 484, 481, 612, 475, 473, 472, 613, and 491

Compounds 599, 600, 498, 610, 601, 611, 485, 484, 481, 612, 475, 473, 472, 613, and 491 were prepared by essentially the same procedure as detailed below for the preparation of Compound 599 using 3-Thiazolo[5,4-c]pyridin-2-yl-phenylamine as the starting material and the appropriate isothiocyanate.

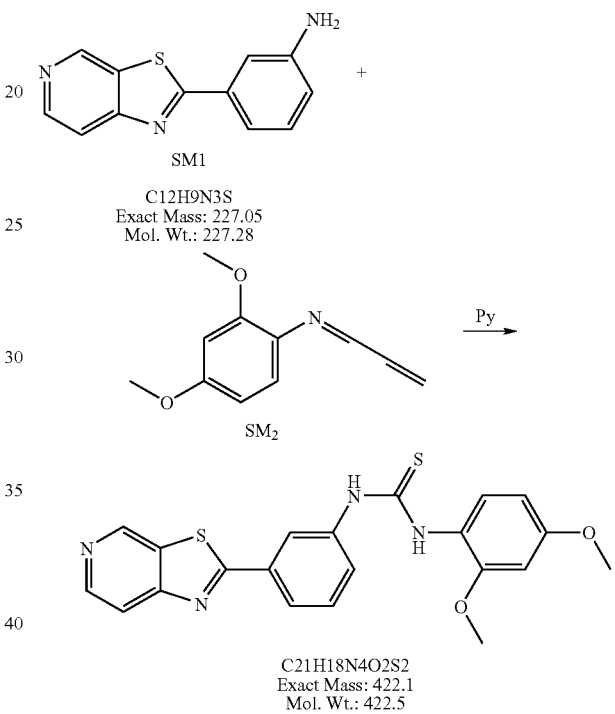

To a mixture of 3-thiazolo[5,4-c]pyridin-2-yl-phenylamine in 1 mL pyridine was added 2,4-Dimethoxyphenyl Isothiocyanate (59 mg, 0.3 mmol). The reaction was kept for 24 hours at 60° C. with stirring and the reaction was monitored by TLC. Once completed, to the crude mixture was added 5 mL H$_2$O, and the resulting suspension was filtered to collect the solid, which was then washed with H$_2$O and purified by preparative TLC (acetone/petroleum ether=1/2). The isolated solid was further washed with acetone and dried in air to provide the desired product 38 mg (30.3%). The product was confirmed by $^1$HNMR. $^1$H NMR (DMSO-d$_6$, 500 MHz) δ 9.40(1H,s), 8.65(1 H, d, J=5.4 Hz), 8.55(1H, s), 8.05 (1H, d, J=5.2 Hz), 7.90(1H, d, J=7.4 Hz), 7.77(1H, d, J=7.7 Hz), 7.55(1 H, t, J=7.8 Hz), 7.47(1H, d, J=6.6 Hz), 6.63(1H, s), 6.54(1H, d, J=7.8 Hz), 3.82(3H, s), 3.77(3H, s). MS: 422.26(M$^+$).

General Procedure for Preparing Compounds 604, 605 and 607

Compounds 604, 605 and 607 were prepared by essentially the same procedure as detailed below for the preparation of Compound 604 using using 3-Thiazolo[5,4-c]pyridin-2-yl-phenylamine as the starting material and the appropriate Chloroformate.

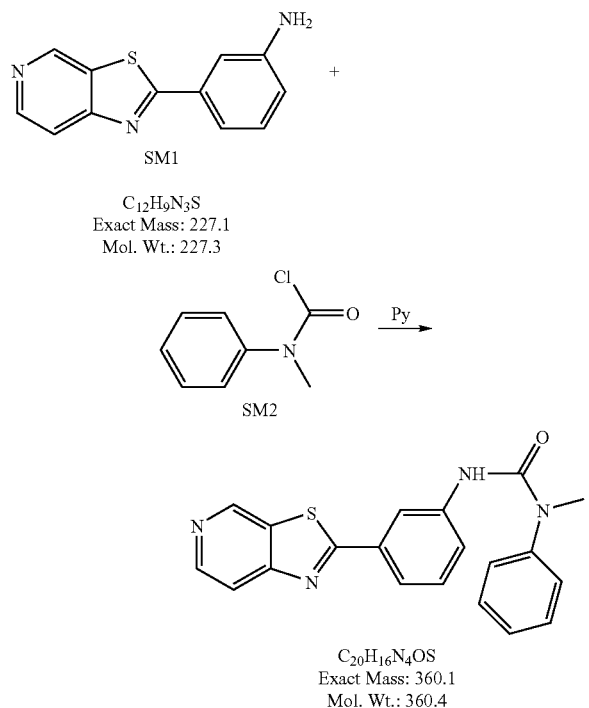

To a mixture of 3-thiazolo[5,4-c]pyridin-2-yl-phenylamine (68 mg, 0.3 mmol) in 2.5 mL Pyridine was added to N-Methyl-N-phenylcarbamoyl chloride (50.7 mg, 0.3 mmol). The reaction was kept at room temperature for 48 hours. To the mixture was then added water (5 mL) and the resulting suspension was filtered. The collected solid was further purified by preparative TLC (petroleum ether/acetone=2/1). The product was confirmed by $^1$H NMR. $^1$H NMR (500 MHz, Acetone-$d_6$) δ 9.34 (1H, s), 8.66 (1H, d, J=5.3 Hz), 8.43 (1H, s), 7.97 (1H, d, J=5.4 Hz), 7.79 (2H, d, J=7.9 Hz), 7.74 (1H, d, J=8.1 Hz), 7.50 (2H, t, J=8.1 Hz), 7.44 (2H, d, J=8.0 Hz), 7.37 (1H, d, J=7.2 Hz), 3.36 (3H, s).

General Procedure for Preparing Compounds 387, 609, 390, 391, 462, 392, 393, 436, 461, 460, 596, 465, and 463

Compounds 387, 609, 390, 391, 462, 392, 393, 436, 461, 460, 596, 465, and 463 were prepared by essentially the same procedure as detailed below for the preparation of Compound 385 using 2-Thiazolo[5,4-c]pyridin-2-yl-phenylamine as the starting material and the appropriate acid chloride.

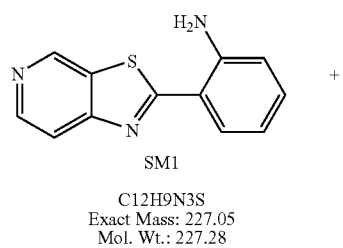

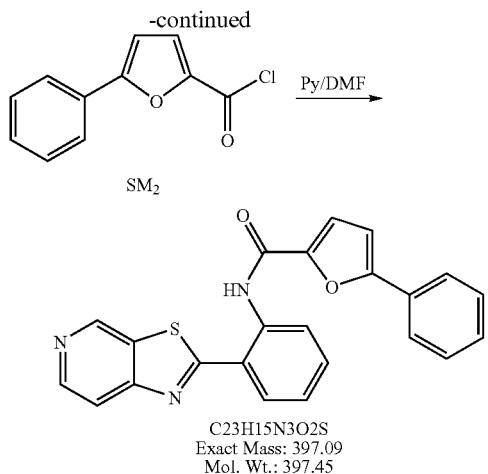

To a mixture of 2-thiazolo[5,4-c]pyridin-2-yl-phenylamine in 1.5 mL DMF was added 5-phenyl furan-2-carbonyl chloride (62 mg, 0.3 mmol) in pyridine (0.25 mL). The reaction was kept for 24 hours at 40° C. while stirring and monitored by TLC. Once completed, to the crude mixture was added 5 mL H$_2$O, and the resulting suspension was filtered to collect the solid product, which was subsequently washed with H$_2$O and dried. The crude product was further purified by preparative TLC (acetone/petroleum ether=1/2) to yield 38 mg product (36.80%), confirmed by $^1$H NMR: $^1$H NMR (500 MHz, DMSO-$d_6$) δ 8.44 (1H, s), 7.74 (4H, d, J=7.5 Hz), 7.41 (4H, t, J=7.7 Hz), 7.29 (1H, t, J=7.4 Hz), 6.87(2H, d, J=3.0 Hz), 6.75 (2H, d, J=2.6 Hz). EIMS m/z: 397.2 (M$^+$).

Preparation of Compounds 162 and 163

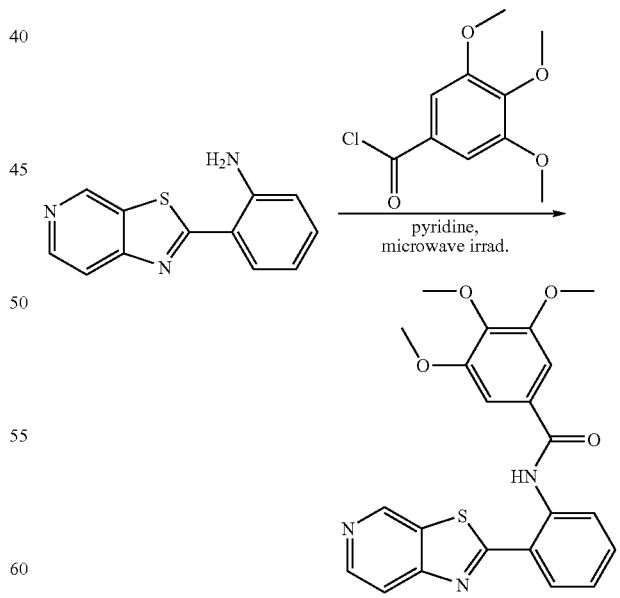

A microwave vial was charged with 2-thiazolo[5,4-c]pyridin-2-yl-phenylamine (40 mg, 0.2 mmol), 3,4,5-trimethoxybenzoylchloride (40.6 mg, 0.2 mmol) and 1 mL of pyridine. The mixture was subjected to microwave irradiation at 160° C. for 10 minutes. Upon cooling, MeOH was added to the solution, causing a precipitate to form. The solid was filtered, washed with MeOH and dried to afford the desired amide product. (Calc'd for C21H17N3O3S: 391.45, [M+H]+ found: 392.1).

General Procedure for Preparing Compounds 467, 394 and 469

Compounds 467, 394 and 469 were prepared by essentially the same procedure as detailed below for the preparation of Compound 467 using 2-Thiazolo[5,4-c]pyridin-2-yl-phenylamine as the starting material and the appropriate sulfonyl chloride.

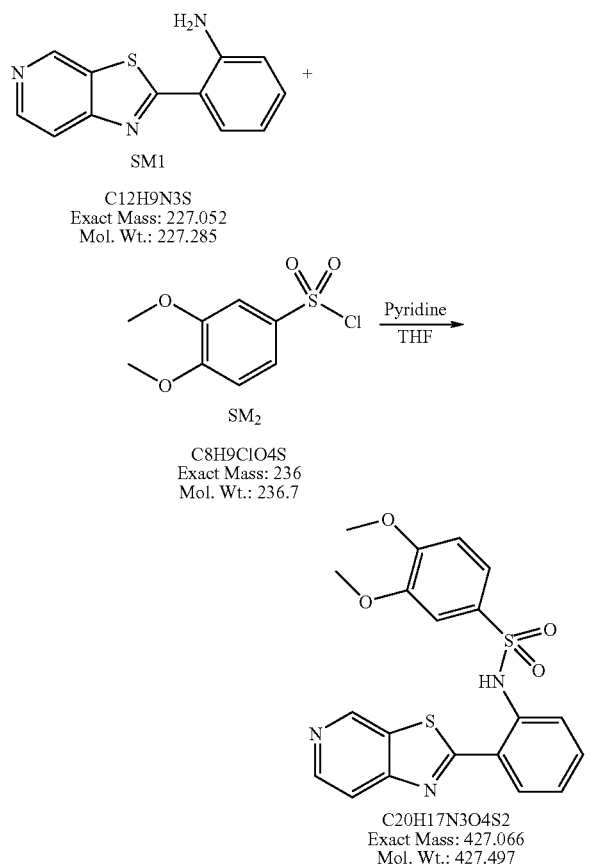

To a mixture of 2-thiazolo[5,4-c]pyridin-2-yl-phenylamine (71 mg, 0.3 mmol) in 1 mL THF was added SM2 (68 mg, 0.3 mmol ) in 2 mL pyridine with stirring at room temperature. The reaction was kept at 60° C. on oil-bath for 2 days and monitored via TLC till the starting material disappeared. 5 mL water was subsequently added and the resulting suspension was filtered to collect the crude product, which was washed by acetone to yield a fine yellow powder 13 mg (10.2%).

$^1$H NMR (500 MHz, DMSO-d$_6$) δ 9.43 (1H, s), 8.70 (1H, d, J=5.5 Hz), 8.12 (1H, d, J=5.4 Hz), 8.04 (1H, d, J=7.6 Hz), 7.58 (1H, t, J=7.5 Hz), 7.45 (1H, d, J=8.1 Hz), 7.38 (1H, t, J=7.1 Hz), 7.17 (1H, d, J=8.3 Hz), 7.00 (1H, s), 6.90 (1H, d, J=8.4 Hz), 3.71 (3H, s), 3.46 (3H, s). EIMS m/z: 427.17 (M+, 10).

General Procedure for Preparing Compounds 614, 615 and 616

Compounds 614, 615 and 616 were prepared by essentially the same procedure as detailed below for the preparation of Compound 614 using 2-Thiazolo[5,4-c]pyridin-2-yl-phenylamine as the starting material and the appropriate isothiocyanate.

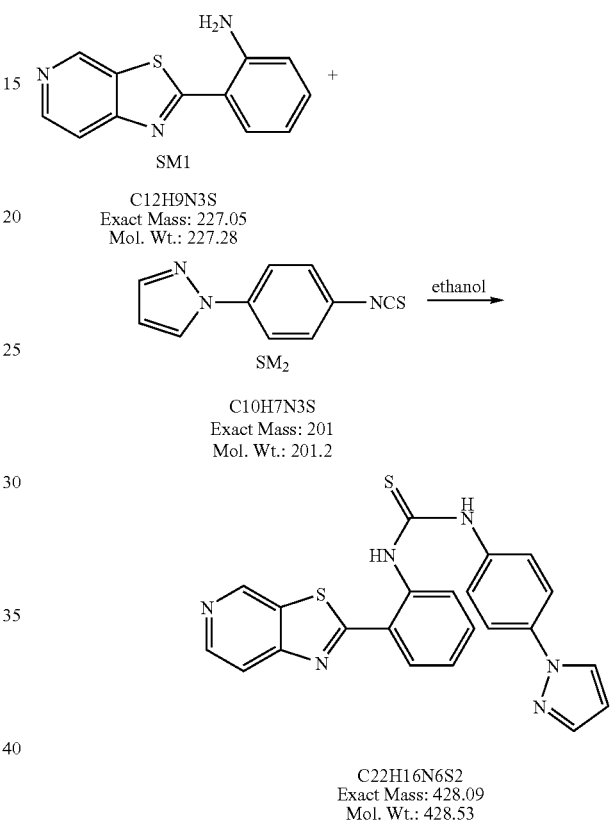

To a mixture of 2-Thiazolo[5,4-c]pyridin-2-yl-phenylamine (68 mg, 0.3 mmol), 4-(1H-pyrazol-1-yl)phenyl isothiocyanate (60 mg, 0.3 mmol) and a catalytic amount of DMAP was added 8 mL Ethanol. The reaction was kept at 50° C. for 48 hours. The suspension was filtered, and washed with acetone thoroughly to yield 10 mg (7%) of product. $^1$H NMR (500 MHz, DMSO-D6) δ 9.43(1H, s), 8.58(1H, d, J=5.5 Hz), 8.47(1H, m), 8.21(1H, d, J=7.9 Hz), 8.19(1H, d, J=7.4 Hz), 7.85(2H, d, J=8.9 Hz), 7.80(1H, d, J=8.9 Hz), 7.75(1H, d, J=6.7 Hz), 7.68(2H, m), 7.61(1H, m), 7.46(1H, m), 6.55(1H, m).

General Procedure for Preparing Compound 597

Compound 597 was prepared by essentially the same procedure as detailed below for the preparation of Compound 597 using 2-Thiazolo[5,4-c]pyridin-2-yl-phenylamine as the starting material and the appropriate Chloroformate.

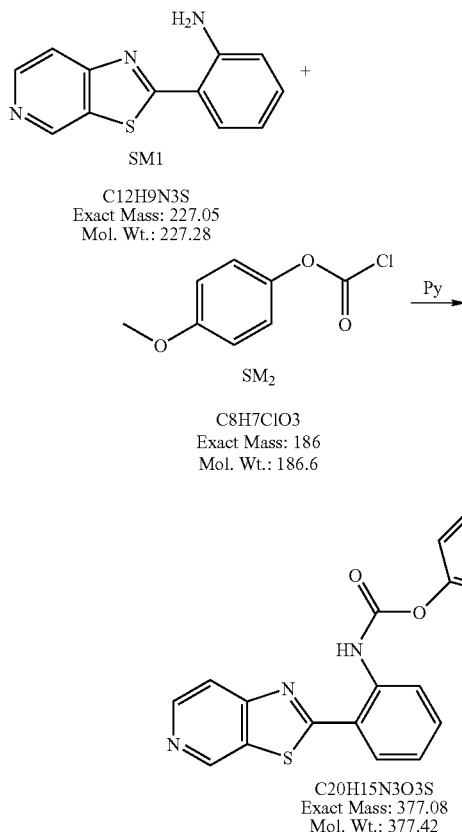

4-Methoxyphenyl chloroformate (56 mg, 0.3 mmol) was added to 2-Thiazolo[5,4-c]pyridin-2-yl-phenylamine (68 mg, 0.3 mmol) in 2.5 ml pyridine and the mixture was stirred at room temperature for 24 h. Water (5 mL) was added and the resulting mixture was filtered. The collected crude product was washed by water and dried to afford 11 mg (12%). $^1$H NMR (500 MHz, Acetone-d6) δ 9.27 (1H, s), 8.73 (1H, d, J=5.5 Hz), 8.62 (1H, d, J=8.4 Hz), 8.02(1H, d, J=5.5 Hz), 7.98(1H, d, J=7.8 Hz), 7.58 (1H, m), 7.23 (3H, m), 6.97 (2H, d, J=8.9 Hz), 3.87 (3H, s).

Preparation of 3-(5-dimethylaminomethyl-oxazolo [4,5-b]pyridin-2-yl)-phenylamine

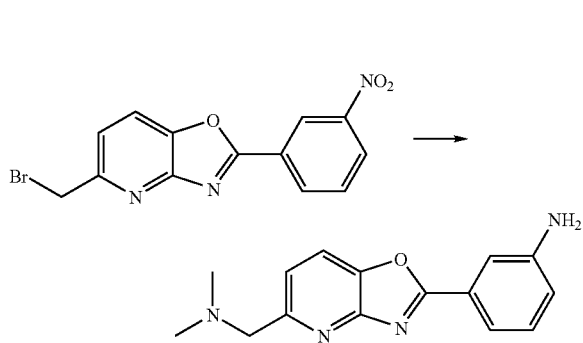

5-Bromomethyl-2-(3-nitro-phenyl)-oxazolo[4,5-b]pyridine (250 mg, 0.75 mmol) was dissolved in 5 mL of CH$_3$CN along 3 mL of a 2M solution of dimethylamine in THF. The reaction mixture was stirred at room temperature for 18 hours. It was then concentrated and the resulting residue was mixed with 25 mL of CH$_2$Cl$_2$ and washed with brine. The organic layer was dried (Na$_2$SO$_4$) and concentrated to afford essentially quantitative yield of the nitro intermediate. This was mixed with 6 mL of MeOH and 2 mL of water along with 200 mg of sodium hydrosulfide hydrate. The reaction mixture was stirred under reflux for 1 hour. It was then cooled to room temperature and concentrated to dryness. The resulting residue was mixed with 100 mL of a 9:1 CH$_2$Cl$_2$/MeOH mixture and filtered. The filtrate was concentrated to afford 120 mg of 3-(5-dimethylaminomethyl-oxazolo[4,5-b]pyridin-2-yl)-phenylamine (MS, M$^+$+H=269).

Preparation of Compound 165

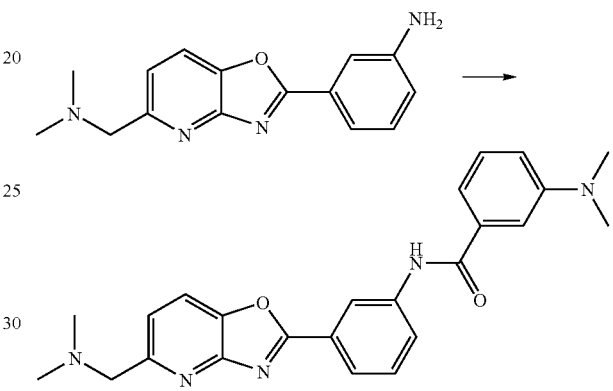

3-(5-Dimethylaminomethyl-oxazolo[4,5-b]pyridin-2-yl)-phenylamine (54 mg, 0.2 mmol) was reacted with 3-dimethylaminobenzoyl chloride in 1 mL of pyridine using the same microwave conditions detailed earlier. The reaction mixture was cooled to room temperature and concentrated. Purification by chromatography using a 9:1 mixture of CH$_2$Cl$_2$/MeOH buffered with 1% triethylamine afforded 7 mg of the desired product (MS, M$^+$+H=416).

Preparation of 3-(5-methyl-oxazolo[4,5-b]pyridin-2-yl)-phenylamine

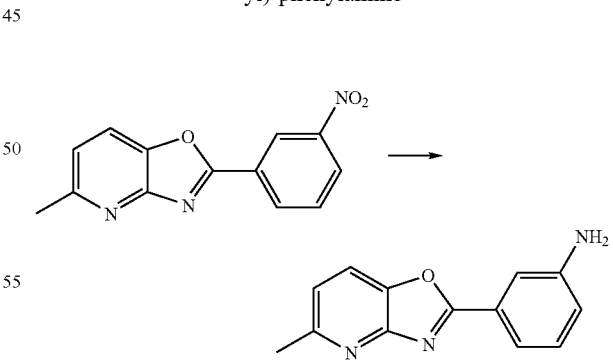

5-Methyl-2-(3-nitro-phenyl)-oxazolo[4,5-b]pyridine (50 mg, 0.196 mmol) was mixed with 6 mL of MeOH along with 2 mL of water and 66 mg of sodium hydrosulfide hydrate. The reaction mixture was stirred under reflux for 2 hours. It was then concentrated and extracted with CH$_2$Cl$_2$. The combined organic layers were dried (Na$_2$SO$_4$) and concentrated to afford 20 mg of 3-(5-methyl-oxazolo[4,5-b]pyridin-2-yl)-phenylamine.

Preparation of Compound 167

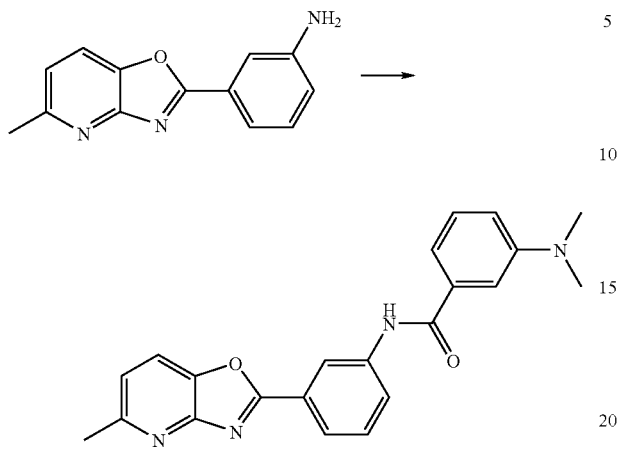

3-(5-Methyl-oxazolo[4,5-b]pyridin-2-yl)-phenylamine (20 mg, 0.0889 mmol) was reacted with 3-dimethylaminobenzoyl chloride in 1 mL of pyridine using the same microwave conditions detailed earlier. The reaction mixture was cooled to room temperature and concentrated. Purification by chromatography using a 9:1 mixture of $CH_2Cl_2$/MeOH buffered with 1% triethylamine afforded 7 mg of the desired product (MS, $M^++H=373$).

Preparation of 5-(2-nitro-phenyl)-thiazol-2-ylamine

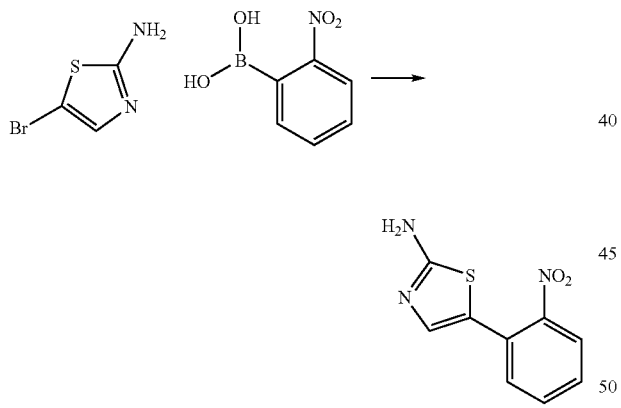

In a typical run, 2-amino-5-bromothiazole monohydrobromide (Aldrich, 5.00 g, 0.0192 mol) was mixed with 40 mL of toluene, 40 mL of ethanol, and 20 mL of water. 2-Nitrophenyl boronic acid (3.2 g, 0.0192 mol) was added, along with 2.35 g of [1,1'-bis(diphenylphosphino)ferrocene] dichloro-palladium(II) complex with $CH_2Cl_2$ (1:1) and 6.10 g of anhydrous sodium carbonate. The reaction mixture was stirred at 90° C. for 18 hours. It was then cooled to room temperature and concentrated. The resulting residue was mixed with 500 mL of EtOAc and washed with water (3×50 mL). The organic layer was filtered to remove the black precipitate. The filtrate was extracted with dilute 1N HCl. The combined aqueous layers were concentrated to near dryness. The resulting residue was purified by preparative HPLC using a mixture of aqueous acetonitrile that has been buffered with 0.1% TFA to afford 108 mg of 5-(2-nitrophenyl)-thiazol-2-ylamine (MS, $M^++H=222$).

Preparation of 2-(2-nitro-phenyl)-imidazo[2,1-b]thiazole-6-carboxylic acid ethyl ester

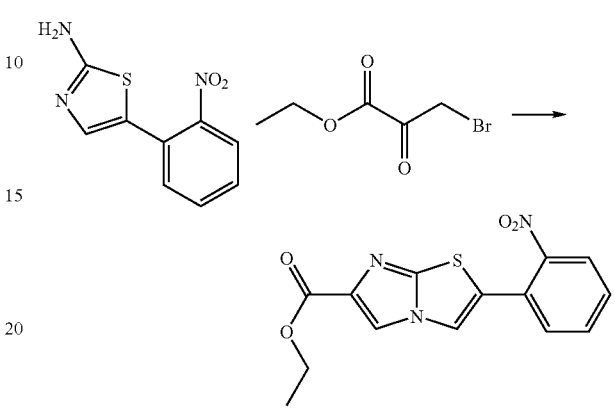

5-(2-Nitro-phenyl)-thiazol-2-ylamine (100 mg, 0.452 mmol) was mixed with 10 mL of methyl ethyl ketone along with 1.5 equivalents of ethyl bromopyruvate. The reaction mixture was stirred under reflux for 5 hours. The reaction mixture was cooled to room temperature and concentrated. The crude product was purified by chromatography (Isco, gradient elution, $CH_2Cl_2$ to 9:1 $CH_2Cl_2$/MeOH) to afford 60 mg of 2-(2-nitro-phenyl)-imidazo[2,1-b]thiazole-6-carboxylic acid ethyl ester (MS, $M^++H=318$).

Preparation of 2-(2-amino-phenyl)-imidazo[2,1-b]thiazole-6-carboxylic acid methyl ester

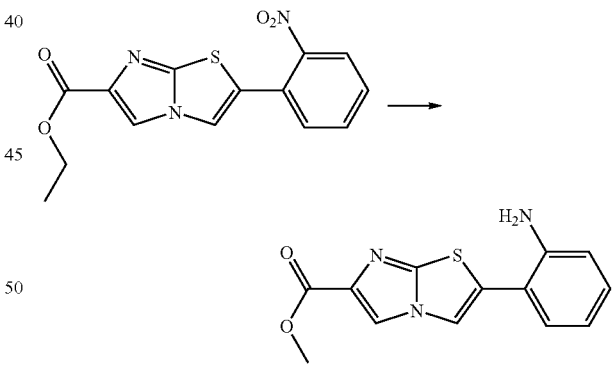

2-(2-Nitro-phenyl)-imidazo[2,1-b]thiazole-6-carboxylic acid ethyl ester (60 mg, 0.189 mmol) was mixed with 3 mL of MeOH along with sodium hydrosulfide hydrate (32 mg, 0.567 mmol) in 1 mL of water. The reaction mixture was stirred under reflux for 1 hour and monitored by LC/MS. Reduction of the nitro group was complete at this point and the ethyl ester group had been exchanged to the corresponding methyl ester derivative. The reaction mixture was cooled to room temperature and concentrated. The aqueous layer was extracted with $CH_2Cl_2$. The combined organic layers were dried ($Na_2SO_4$) and concentrated to afford essentially quantitative yield of 2-(2-amino-phenyl)-imidazo[2,1-b]thiazole-6-carboxylic acid methyl ester (MS, $M^++H=274$).

Preparation of Compound 703

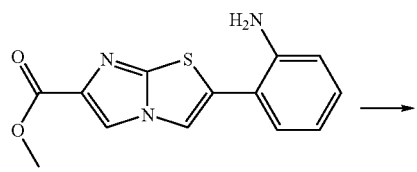

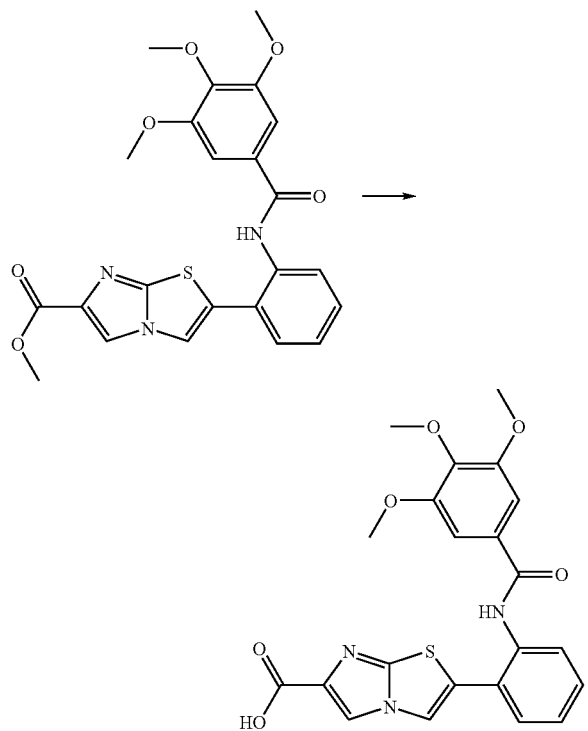

2-(2-Amino-phenyl)-imidazo[2,1-b]thiazole-6-carboxylic acid methyl ester (27 mg, 0.095 mmol) was mixed with 1 mL of pyridine along with 22 mg of 3,4,5-trimethoxybenzoyl chloride. The reaction mixture was reacted in a microwave reactor at 160° C. for 10 minutes. It was then cooled to room temperature and concentrated. The resulting crude product was purified by preparative HPLC using a mixture of aqueous acetonitrile that has been buffered with 0.1% TFA to afford 108 mg of 2-[2-(3,4,5-trimethoxybenzoylamino)-phenyl]-imidazo[2,1-b]thiazole-6-carboxylic acid methyl ester (MS, M⁺+H=468).

Preparation of Compound 704

2-[2-(3,4,5-trimethoxybenzoylamino)-phenyl]-imidazo[2,1-b]thiazole-6-carboxylic acid methyl ester (6 mg) was mixed with 1 mL of THF. Sodium hydroxide (10 mg) was added as a solution in 1 mL of water. The reaction mixture was stirred at room temperature for 4 hours and then concentrated. The resulting crude product was purified by preparative HPLC using a mixture of aqueous acetonitrile that has been buffered with 0.1% TFA to afford 108 mg of 2-[2-(3,4,5-trimethoxy-benzoylamino)-phenyl]-imidazo[2,1b]thiazole-6-carboxylic acid (MS, M⁺+H=454).

Preparation of Compound 108

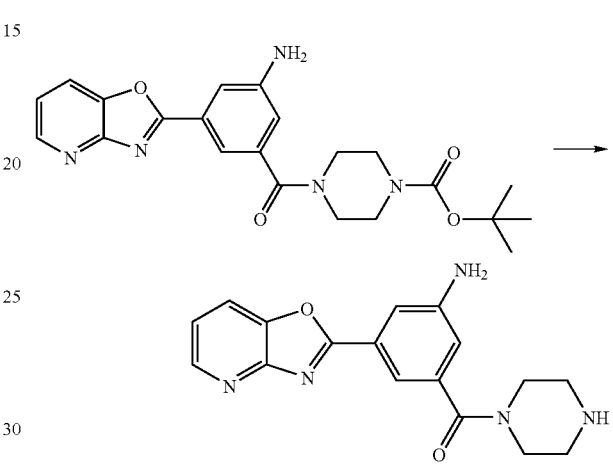

Tert-Butyl 4-(3-amino-5-(oxazolo[4,5-b]pyridin-2-yl)benzoyl)piperazine-1-carboxylate (25 mg) was treated with 1 mL of a solution containing 25% TFA in CH₂Cl₂ at room temperature for 30 min. It was then concentrated and Et₂O was added to precipitate out the product. After drying under vacuum, the desired product was obtained as the TFA salt (MS, M⁺+H=324).

Preparation of 2-(methylthio)oxazolo[4,5-b]pyridine

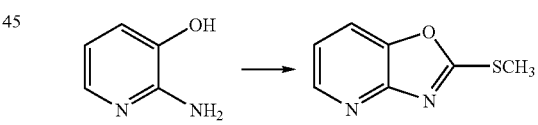

2-(Methylthio)oxazolo[4,5-b]pyridine was prepared according to the procedures of Chu-Moyer and Berger (*J. Org. Chem.* 1995, 60, 5721-5725) with minor modifications. To a suspension of 2-amino-3-hydroxypyridine (2.8 g, 25 mmol) in EtOH (62 mL, 0.4 M) was added potassium ethyl xanthogenate (8.0 g, 50 mmol, 2 equiv). The reaction mixture was heated to reflux (78° C.) and stirred for a period of 18 hours. The reaction mixture was concentrated to dryness and the resulting residue was dissolved in water (70 mL). Upon acidification to pH 5 with glacial acetic acid, a large quantity of solid precipitated out. The suspension was filtered, washed with water (3×), and dried on the high-vac line overnight to afford 2-thiooxazolo[4,5-b]pyridine as a brown solid (3.3 g, 21.6 mmol, 86%).

To a cooled solution of 2-thiooxazolo[4,5-b]pyridine (3.3 g, 21.6 mmol) in DMF (54 mL, 0.4 M) at 0° C. was added K₂CO₃ (3.0 g, 21.6 mmol) and iodomethane (1.6 mL, 25.9 mmol). After stirring at 0C for 2.5 hours, the reaction mixture was diluted with water (60 mL) and extracted with Et$_2$O (3×100 mL). The combined organic layers were washed with water and brine, dried (MgSO$_4$), filtered, and concentrated. Purification on silica (0% to 10% MeOH/ CH$_2$Cl$_2$) afforded 2-(methylthio)oxazolo[4,5-b]pyridine as a tan-colored solid (2.5 g, 14.7 mmol, 68%). MS, [M+1]$^+$=167.

Preparation of Boc-protected 1-oxazolo[4,5-b]pyridin-2-yl-piperidin-3-ylamine

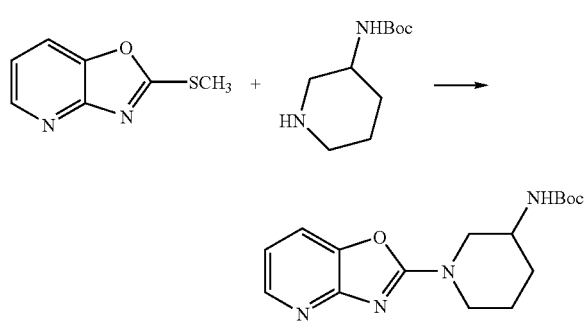

1-Oxazolo[4,5-b]pyridin-2-yl-piperidin-3-ylamine was prepared according to the procedures of Chu-Moyer and Berger (*J. Org. Chem.* 1995, 60, 5721-5725) with minor modifications. To a solution of 2-(methylthio)oxazolo[4,5-b]pyridine (1.9 g, 11.4 mmol) in toluene (1.1 M) was added 3-Boc-piperidine (2.3 g, 11.4 mmol). The reaction mixture was heated to 85° C. for 5.5 hours, cooled, then concentrated. The residue was dissolved in CH$_2$Cl$_2$, filtered, and concentrated. Purification on silica (0% to 10% MeOH/ CH$_2$Cl$_2$) afforded the desired products as a white solid (2.6 g, 8.3 mmol, 73%). MS, [M+1]$^+$=319.

Preparation of Meta-Pyridyl 6-(1H-benzo[d]imidazol-2-yl)pyridin-2-amine

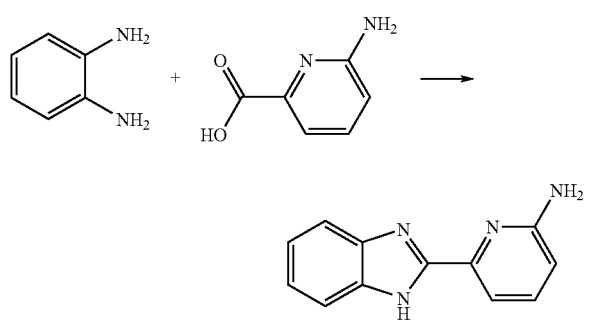

A suspension of 6-aminopyridine-2-carboxylic acid (1.12 g, 8.2 mmol) with 1,2-diaminobenzene (1.77 mg, 16.4 mmol) was heated in 8 mL of PPA at 180 degree for 2 h. The reaction mixture was poured into 250 mL of ice-water and neutralized with 2 N NaOH (chilled) while vigorously stirred. The resulting precipitate was filtered to collect an off-white solid, which was washed with 20 mL warm water, dried and purified by chromatography using a 9:1 mixture of CH$_2$Cl$_2$ to MeOH (MS, M$^+$+H=211).

Preparation of Compound 57

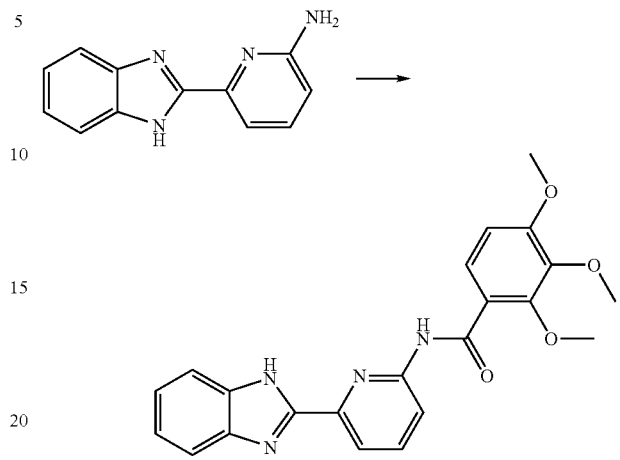

Meta-Pyridyl 6-(1H-benzo[d]imidazol-2-yl)pyridin-2-amine (25 mg, 0.118 mmol) was mixed with 1 mL of pyridine along with 24 mg of 2,3,4-trimethoxybenzoyl chloride (0.118 mmol). The reaction mixture was reacted in a Biotage microwave reactor at 160° C. for 10 min. It was then cooled to room temperature and concentrated. The resulting crude product was purified by chromatography (Isco, gradient elution, CH$_2$Cl$_2$ to 9:1 CH$_2$Cl$_2$/MeOH) to afford 11 mg of the product (MS, M$^+$+H=407.1).

Preparation of Compounds 58, 59, 60, 64, 69, 211 and 70

These compounds were prepared analogously to Compound 57, using the appropriate aromatic acid chlorides. The reaction mixture was either stirred at room temperature overnight or heated in a Biotage microwave reactor at 160 degrees for 10 minutes. It was then cooled to room temperature and concentrated under reduced pressure. The resulting residual crude products were purified either by recrystallization using acetonitrile or chromatography (Isco, gradient elution, CH$_2$Cl$_2$ to 9:1 CH$_2$Cl$_2$/MeOH).

Preparation of Compound 71

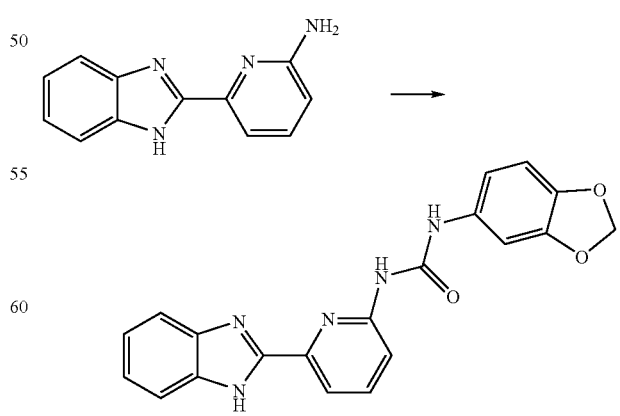

In a 2 mL vial, 6-(oxazolo[4,5-b]pyridin-2-yl)pyridin-2-amine (11 mg, 0.05 mmol) in 1 mL pyridine was added to 5-isocyanatobenzo[d][1,3]dioxole (9 mg, 0.05 mmol). The reaction was heated to 160° C. (MW) for 10 min. An aliquot was taken and diluted with MeOH. The pyridine was removed under vacuum. The crude product was suspended and magnetically stirred in 5 mL acetonitrile for half an hour and filtered to collect the product, which was subsequently dried under vacuum (MS, M$^+$+H=376.1).

Preparation of Compounds 72, 87 and 147

These compounds were prepared analogously to Compound 71, using the appropriate aromatic isocyanates or isothiocyanates. The reaction mixture was either stirred at room temperature overnight or heated in a Biotage microwave reactor at 160 degree for 10 minutes. It was then cooled to room temperature and concentrated under reduced pressure. The resulting residual crude products were purified either by recrystallization using acetonitrile or chromatography (Isco, gradient elution, CH$_2$Cl$_2$ to 9:1 CH$_2$Cl$_2$/MeOH).

Preparation of 2-(1,4-diazepan-1-yl)benzo[d]oxazole

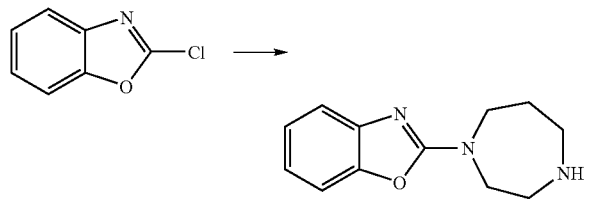

In a 40 mL vial at room temperature, 2-chlorobenzo[d]oxazole (760 mg, 5 mmol) was added to a solution of homopiperazine (2 g, 20 mmol) in CH$_3$CN. The reaction mixture gradually turned into a suspension. Upon standing for additional half an hour, solid was filtered off and the collected filtrate was directly subjected to chromatography (Isco, gradient elution, CH$_2$Cl$_2$ to 9:1 CH$_2$Cl$_2$/MeOH). 420 mg of the desired product was isolated (MS, M$^+$+H=218.1).

Preparation of Compound 85

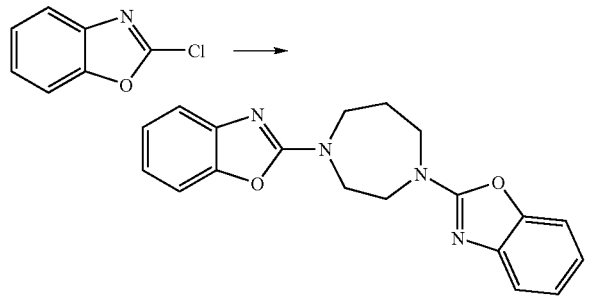

Compound 85 was obtained from the above reaction to prepare 2-(1,4-diazepan-1-yl)benzo[d]oxazole as a by product. 24 mg of product was obtained (MS, M$^+$+H=335.1).

Preparation of Compound 88

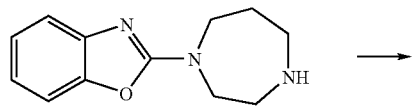

-continued

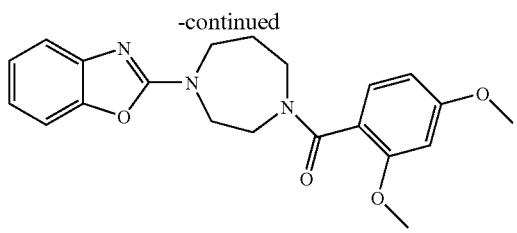

In a 2 mL vial, 2-(1,4-diazepan-1-yl)benzo[d]oxazole (43 mg, 0.2 mmol) in 1 mL pyridine was added 2,4-dimethoxybenzoyl chloride (40 mg, mw=230.6, 0.2 mmol). The reaction was heated to 160° C. (MW) for 10 min It was then cooled to room temperature and concentrated. The resulting crude product was purified by chromatography (Isco, gradient elution, CH$_2$Cl$_2$ to 9:1 CH$_2$Cl$_2$/MeOH) to afford 60 mg of the product (MS, M$^+$+H=382.1).

Preparation of Compounds 89, 90 and 91

These compounds were prepared analogously to Compound 88, using the appropriate aromatic acid chlorides and isocyanate. The reaction mixture was either stirred at room temperature overnight or heated in a Biotage microwave reactor at 160 degree for 10 minutes. It was then cooled to room temperature and concentrated under reduced pressure. The resulting residual crude products were purified either by recrystallization using acetonitrile or chromatography (Isco, gradient elution, CH$_2$Cl$_2$ to 9:1 CH$_2$Cl$_2$/MeOH)

Preparation of Compound 92

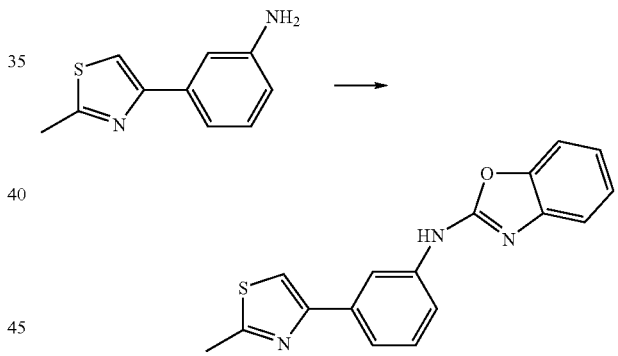

In a 2 mL vial, 3-(2-methylthiazol-4-yl)benzenamine (95 mg, 0.5 mmol, 1.5 eq) was added to 2-chlorobenzo[d]oxazole (51 mg, 0.33 mmol) in 2 mL CH3CN. The reaction was heated to 160° C. (MW) for 10 min. It was then cooled to room temperature and concentrated. The resulting crude product was purified by chromatography (Isco, gradient elution, CH$_2$Cl$_2$ to 9:1 CH$_2$Cl$_2$/MeOH) to afford 71 mg of the product (MS, M$^+$+H=308.1).

Preparation of Compounds 93, 94, 95, 104 and 105

These compounds were prepared analogously to Compound 92 using 3-(2-methylthiazol-4-yl)benzenamine, or 6-(oxazolo[4,5-b]pyridin-2-yl)pyridin-2-amine, or 6-(oxazolo[4,5-b]pyridin-2-yl)pyridin-2-amine to react with 2-chlorobenzo[d]oxazole or 2-chlorobenzo[d]thiazole. The reaction mixture was heated in a Biotage microwave reactor at 160 degree for 10 minutes. It was then cooled to room temperature and concentrated under reduced pressure. The resulting residual crude products were purified either by recrystallization using acetonitrile or chromatography (Isco, gradient elution, CH$_2$Cl$_2$ to 9:1 CH$_2$Cl$_2$/MeOH).

Preparation of Compound 142

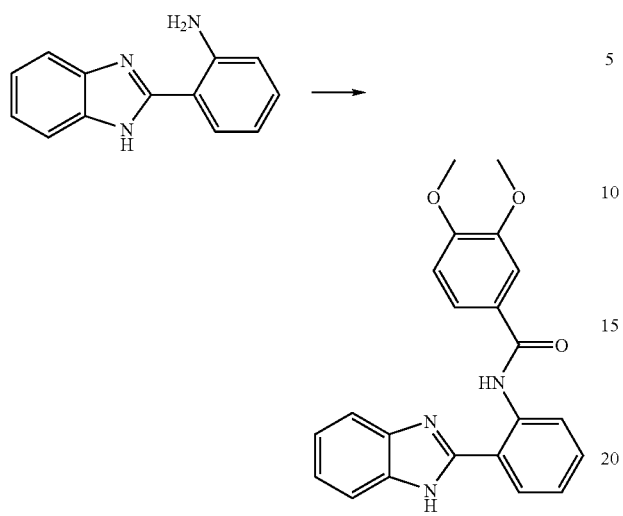

In a typical run, 2-(1H-benzo[d]imidazol-2-yl)benzenamine (105 mg, 0.5 mmol) in 5 mL pyridine was added to 3,4-dimethoxybenzoyl chloride (100 mg, mw=200, 0.5 mmol). The reaction was kept at room temperature overnight while stirring. Pyridine was then removed and 5 mL MeOH was then added to the crude mixture. The resulting suspension, upon stirring for half an hour, was filtered to collect off white solid, which was then washed with MeOH and dried under reduced pressure. TLC/HPLC/LC-Mass suggested that the purity of the product is greater than 95% (MS, $M^+ + H = 374.1$).

Preparation of 3-(1 H-benzo[d]imidazol-2-yl)pyridin-2-amine

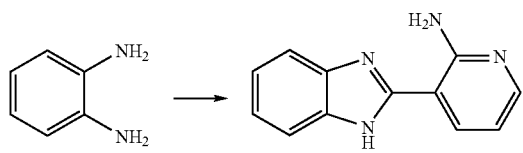

A suspension of 2-aminopyridine-3-carboxylic acid 2-amino nicotinic acid (1.12 g, 8.2 mmol) with 1,2-diaminobenzene (1.77 mg, 16.4 mmol) was heated in 8 mL of PPA at 180 degree for 2 h. The reaction mixture was poured into 250 mL ice-water and neutralized with 2 N ice-cold NaOH during vigorous stirring. The resulting precipitate was filtered and washed with 20 mL warm water to afford 1.1 grams of pure corresponding 3-(1H-benzo[d]imidazol-2-yl)pyridin-2-amine (MS, $M^+ + H = 211.1$).

Preparation of 6-(1H-benzo[d]imidazol-2-yl)pyridin-2-amine

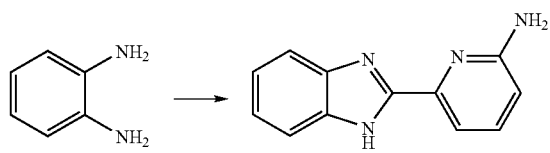

A suspension of 6-aminopyridine-2-carboxylic acid (112 mg), or 2-aminopyridine-4-carboxylic acid (112 mg, 0.82 mmol), or 5-aminopyridine-3-carboxylic acid (112 mg, 0.82 mmol) with 1,2-diaminobenzene (177 mg, 1.64 mmol) was heated in 4 mL of PPA (180 degree) for 2 h. The reaction mixture was each poured into 50 mL ice-water and neutralized with 2 N NaOH (chilled) during vigorous stirring. The resulting precipitate was filtered and washed with 20 mL warm water to afford 105 mg of desired 6-(1H-benzo[d] imidazol-2-yl)pyridin-2-amine (MS, $M^+ + H = 211.1$).

Preparation of 3-(1H-benzo[d]imidazol-2-yl)pyridin-4-amine

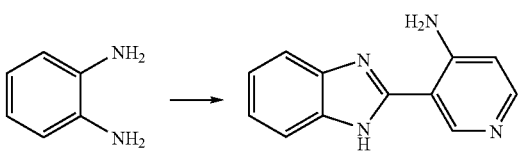

A suspension of 4-aminopyridine-3-carboxylic acid 4-amino nicotinic acid (1.12 g, 8.2 mmol) with 1,2-diaminobenzene (1.77 mg, 16.4 mmol) was heated in 8 mL of PPA at 180 degrees for 2 h. The reaction mixture was poured into 250 mL ice-water and neutralized with 2 N ice-cold NaOH during vigorous stirring. The resulting precipitate was filtered and washed with 20 mL warm water to afford 1.35 grams of pure corresponding 3-(1H-benzo[d]imidazol-2-yl) pyridin-2-amine (MS, $M^+ + H = 211.1$).

Preparation of 2-(1-methyl-1H-benzo[d]imidazol-2-yl)benzenamine

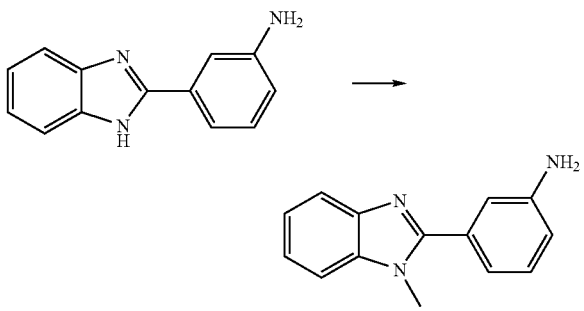

2-(1H-benzo[d]imidazol-2-yl)benzenamine (525 mg, 2.5 mmol) in 5 mL dry THF was cooled to −78 degrees before 1 mL n-Bu-Li (2.5 mmol, 2.5 N in hexanes) was added via a syringe. The reaction was stirred at −78 degrees for 20 min and MeI (360 mg, 2.6 mmol) was added. The reaction was warmed to r.t. gradually and kept at room temperature for another hour. The reaction crude was diluted with 25 mL ether and the resulted suspension was filtered off the solid. The crude product was isolated after the solvent was removed from the collected filtrate to product 510 mg of 2-(1-methyl-1H-benzo[d]imidazol-2-yl)benzenamine in greater than 95% purity (MS, $M^+ + H = 224.1$).

Preparation of Compounds 141, 143, 144, 145, 146, 168, 169, 175, 176, 177, 257, 258, 259, 260, 261, 276, 313, 314, 315, 507, 508, 556, and 293

These compounds were prepared analogously to Compound 142, using the appropriate substituted bicyclic aromatic benzenamines to react with corresponding aromatic acid chlorides, sulfonyl chlorides, chloroformates and isocyanate. The reaction mixture was either stirred at room temperature overnight or heated in a Biotage microwave reactor at 160 degree for 10 minutes. It was then cooled to room temperature and concentrated under reduced pressure. The resulting residual crude products were purified either by recrystallization using acetonitrile or chromatography using a 9:1 mixture of $CH_2Cl_2$ to MeOH.

Preparation of Compound 503

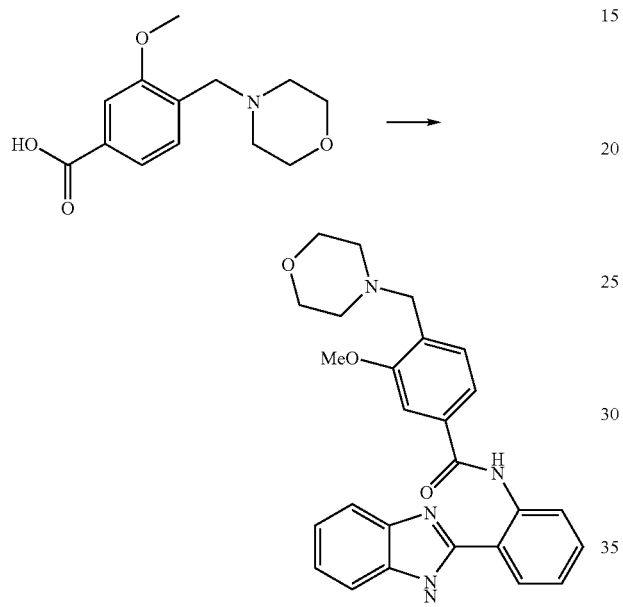

To 3-methoxy-4-(morpholinomethyl)benzoic acid (502 mg, 2 mmol) in $CH_2Cl_2$ (20 mL) was added $(COCl)_2$ (2 mL, 23 mmol), followed by one tiny drop of DMF. The resulting mixture was stirred at room temperature for 3 h, and evaporated in vacuo to give a yellow solid. This solid was then dissolved in 5 mL DMF. 2-(1H-benzo[d]imidazol-2-yl)benzenamine (420 mg, 2 mmol) in 5 mL pyridine was subsequently added and the reaction mixture was kept at room temperature overnight while stirring. The reaction was concentrated to provide the crude product, which was further purified by Shimadzu reverse prep HPLC to afford the desired product (103 mg) with >98% purity (MS, $M^++H=443.1$).

Preparation of Compound 587

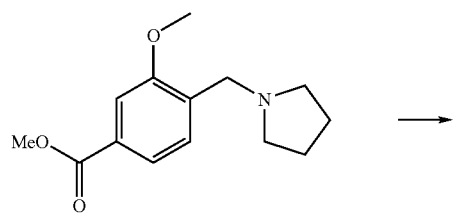

-continued

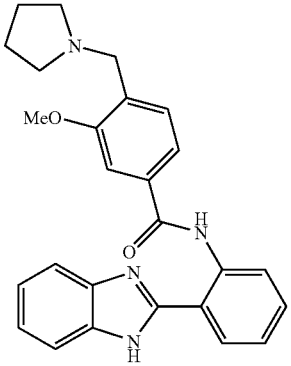

3-methoxy-4-((pyrrolidin-1-yl)methyl)benzoate (249 mg, 1 mmol) and 2-(1H-benzo[d]imidazol-2-yl)benzenamine (209 mg, 1 mmol) in toluene (5 mL) was cooled to 0° C. and then $AlMe_3$ was added (2 mL, 2 M in toluene, 4 eq). The resulting mixture was gradually warmed up to rt and stirred overnight. The reaction was then cooled again to 0° C. and carefully quenched with 5 mL MeOH. After warmed up to room temperature, the mixture was partitioned between saturated $NaHCO_3$ and AcOEt. Before the separation of the two layers, the mixture was filtered. Then, the biphasic filtrate was separated. The organic layer was collected and dried over $Na_2SO_4$, filtered and concentrated under reduced pressure. The product was purified by combiflash using amine RediSep column (68-2203-100, Teledyne Isco) (0-2% MeOH in DCM). The collected fractions were combined and concentrated to provide 25 mg of product (MS, $M^++H=427.1$).

Preparation of Compounds 557 and 558

These compounds were prepared analogously to Compound 587. The product was purified by combiflash using amine RediSep columns.

Preparation of 3-(chloromethyl)-6-(2-nitrophenyl)imidazo[2,1-b]thiazole

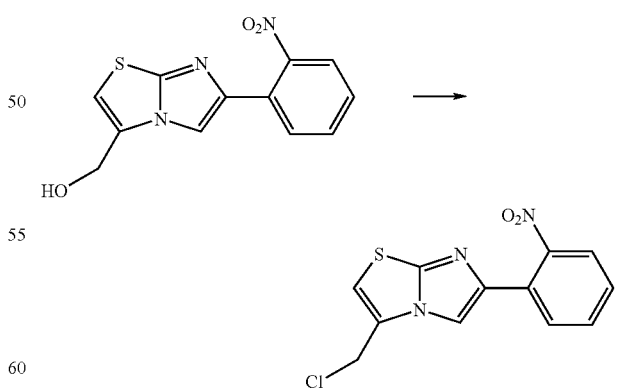

(3-Nitro-5-thiazolo[5,4-c]pyridin-2-yl-phenyl)-methanol (1.375 g, 5 mmol) was suspended in 25 mL of $CH_2Cl_2$ and cooled with an ice bath. Thionyl Chloride (3.6 mL, 10 eq) was added dropwise and the reaction mixture was slowly warmed to room temperature. After stirring overnight, to the reaction mixture was added 100 mL ether and the resulting suspension was filtered to collect 1.55 g of the desired product (MS, M++H=293.1).

Preparation of Compound 626

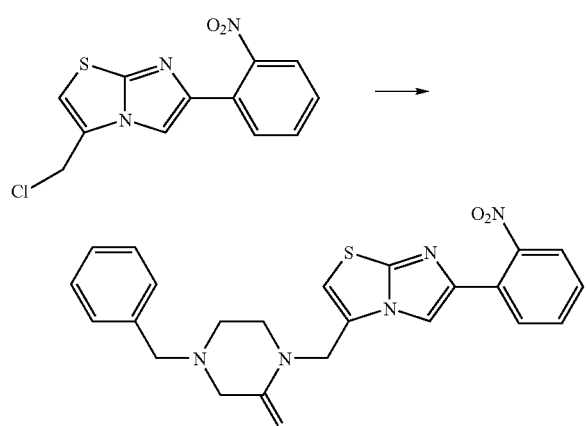

3-(chloromethyl)-6-(2-nitrophenyl)imidazo[2,1-b]thiazole (292 mg, 1 mmol), 4-benzylpiperazin-2-one (380 mg, 2 mmol) and NaH (88 mg, 2.2 eq) were suspended in 4 mL of dry DMF. The reaction was heated overnight at 100° C. After cooling to room temperature, the reaction mixture was partitioned between water and AcOEt. The organic layer was collected, dried and evaporated to provide crude product, which was further purified by reverse HPLC to give 211 mg of desired product 4-benzyl-1-((6-(2-nitrophenyl)imidazo[2,1-b]thiazol-3-yl)methyl)piperazin-2-one (MS, M++H=448.1).

Preparation of Compound 627

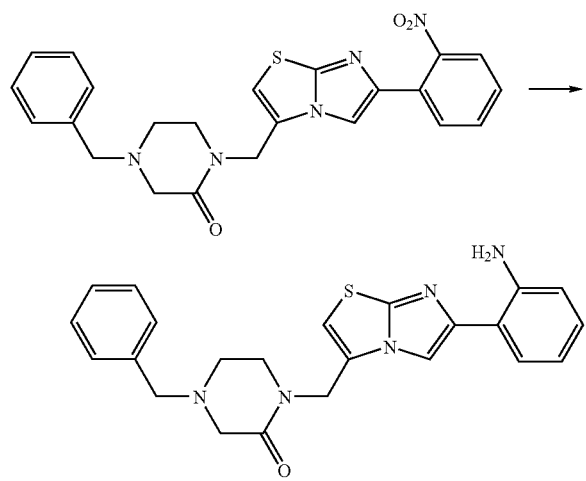

To a suspension of 200 mg of 1-((6-(2-nitrophenyl)imidazo[2,1-b]thiazol-3-yl)methyl)-4-benzylpiperazin-2-one in 5 mL MeOH was added 250 mg of sodium hydrosulfide hydrate. The reaction mixture was heated for 30 minutes at 135° C. (MW). After cooling to room temperature, the mixture was diluted with 50 mL of water and extracted with CH$_2$Cl$_2$. The combined organic layers were dried (Na$_2$SO$_4$) and concentrated to afford the crude product, which can be further purified via reverse phase HPLC to provide 135 mg of the targeted product 1-((6-(2-aminophenyl)imidazo[2,1-b]thiazol-3-yl)methyl)-4-benzylpiperazin-2-one (MS, M++H=418.1).

Preparation of Compound 628

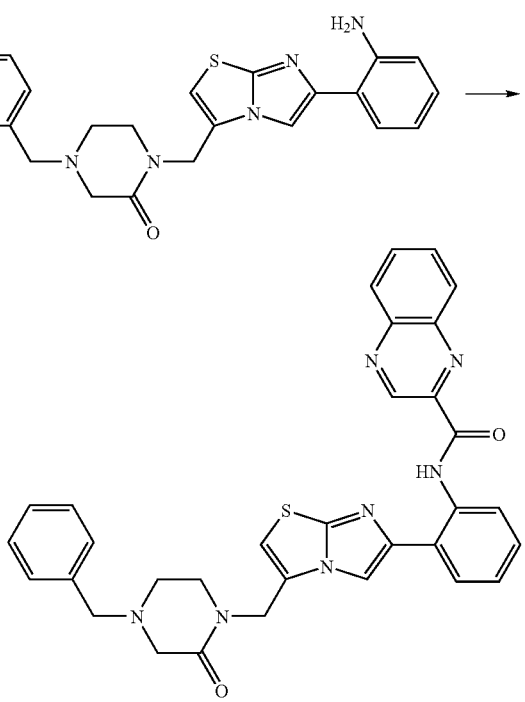

A mixture of 1-((6-(2-aminophenyl)imidazo[2,1-b]thiazol-3-yl)methyl)-4-benzylpiperazin-2-one (44 mg, 0.1 mmol) and 2-quinoxaloyl chloride (21 mg, 1.1 eq) in 2.5 mL pyridine was heated for 20 minutes at 160° C. (MW). After cooling to room temperature, pyridine was removed and the reaction crude was redissolved in methanol and purified via reverse phase HPLC to provide 22 mg desired product (MS, M++H=574.1).

Preparation of 617, 618, 647, 648, 676, 677, 678, 679, 699, 741, 742 and 711

These compounds were prepared analogously to Compound 628. Products were purified via reverse phase HPLC.

Preparation of Compound 42

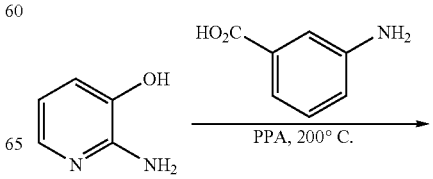

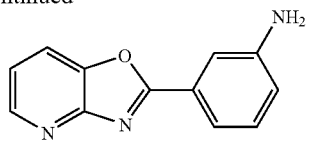

A 50 mL flask was charged with 2-amino-3-hydroxypyridine (1.0 g, 9.1 mmol), 3-aminobenzoic acid (1.24 g, 9.1 mmol) and 12 mL of polyphosphoric acid. The mixture was brought to 200° C. After 4 h, the reaction was cooled slightly and then quenched with ice-water. The mixture was neutralized to pH 7.5 with sat. $Na_2CO_3$. The product was extracted with EtOAc, and the combined organic extracts were washed with brine and dried over $MgSO_4$. Solvent evaporation afforded the desired aminophenyl-oxaolopyridine product. (Calc'd for C12H9N3O: 211.2, [M+H]+ found: 212)

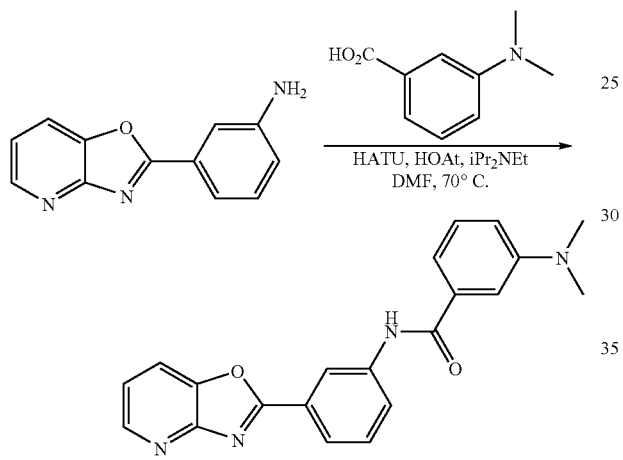

To a solution of the aniline (0.375 g, 1.8 mmol) in 6 mL of DMF was added 3-dimethylaminobenzoic acid (0.29 g, 1.8 mmol), HATU (1.0 g, 2.7 mmol), HOAt (0.36 g, 2.7 mmol) and diisopropylethylamine (0.69 g, 5.3 mmol). The reaction mixture was stirred overnight at 70° C. After dilution with $CH_2Cl_2$, the organic layer was washed with sat. $NaHCO_3$ and brine, and dried over $MgSO_4$. The crude material was purified by silica chromatography (0-10% MeOH/$CH_2Cl_2$) to afford the desired product. (Calc'd for C21H18N4O2: 358, [M+H]+ found: 359)

Compounds 19, 20, 21, 22, 23, 24, 25, 26, 27, 28, 29, 30, 31, 32, 33, 34, 35, 36, 37, 38, 39, 40, 41, 43, 44, 45, 46, 47, 48, 49, 50, 51, 52, 53, 54, 55, 56, 109 and 110 were prepared in an analogous manner to Compound 42.

Preparation of Compound 65

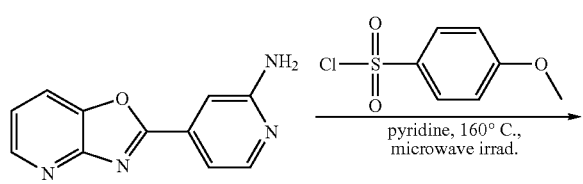

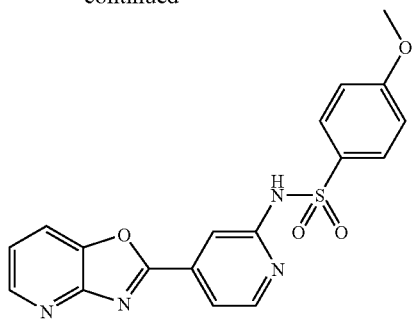

A microwave vial was charged with 4-oxazolo[4,5-b]pyridin-2-ylamine (50 mg, 0.2 mmol), 4-methoxybenzensulfonyl chloride (49 mg, 0.2 mmol) and 1 mL of pyridine. The mixture was subjected to microwave irradiation at 160° C. for 12 minutes. The pyridine was then evaporated, and the resulting brown solid was triturated with methanol/dichloromethane. The solid was filtered, washed with methanol/dichloromethane and dried to afford the desired product as an off-white powder. (Calc'd for C18H14N4O4S: 382.40, [M+H]+ found: 383.0).

Compounds 61, 63, 75, 76, 96, 97, 98, and 106 were prepared in an analogous manner to Compound 65.

Preparation Compound 77

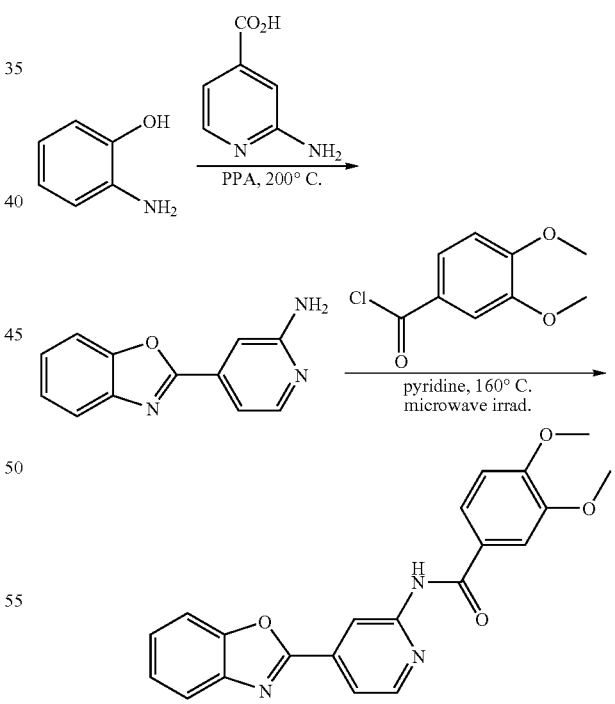

A 50 mL round bottom flask was charged with 2-aminophenol (0.24 g, 2.2 mmol), 2-aminopyridine-4-carboxylic acid (0.30 g, 2.2 mmol) and 2 mL of polyphosphoric acid. The mixture was brought to 200° C. and was stirred for 4 hours. The reaction was then quenched with ice and basified to pH 7.5 with saturated aqueous $Na_2CO_3$. The resulting precipitate was filtered, washed with water and dried to afford the desired product as a brown solid. (Calc'd for C12H9N3O: 211.23, [M+H]+ found: 212.1).

A microwave vial was charged with 4-benzoxazol-2-yl-pyridin-2-ylamine (0.050 g, 0.2 mmol), 3,4-dimethoxybenzoyl chloride (0.047 g, 0.2 mmol) and 1 mL of pyridine. The mixture was subjected to microwave irradiation at 160° C. for 12 minutes. Upon cooling, methanol was added to the mixture and a precipitate formed. The solid was filtered, washed with methanol and dried to afford the desired product as a red solid. (Calc'd for C21H17N3O4: 375.39, [M+H]+ found: 376.1)

Compound 78 was prepared in an analogous manner to Compound 77.

Preparation of 1-Benzo[1,3]dioxol-5-yl-3-(4-benzoxazol-2-yl-pyridin-2-yl)-urea; Compound 86

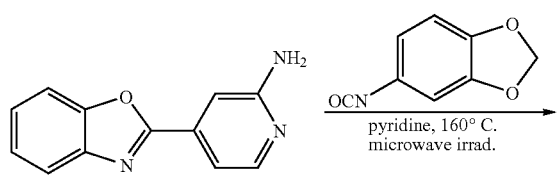

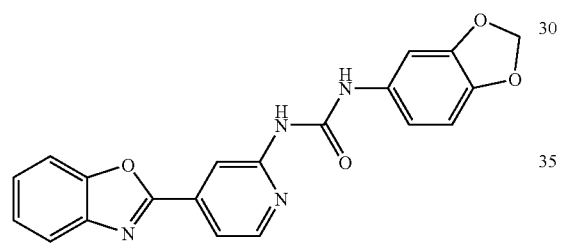

A microwave vial was charged with 4-benzoxazol-2-yl-pyridin-2-ylamine (0.05 g, 0.2 mmol), 3,4-(methylenedioxy) phenyl isocyanate (0.04 g, 0.2 mmol) and 1 mL of pyridine. The mixture was subjected to microwave irradiation at 160° C. for 15 minutes. Upon cooling, a precipitate formed. The solid was filtered and then triturated with hot methanol. The undissolved material was filtered, and the precipitate that formed in the mother liquor was filtered and dried to afford the desired product as a white solid. (Calc'd for C20H14N4O4: 374.36, [M+H]+ found: 375.1).

Preparation of 2-[1-(4-Fluoro-phenyl)-5-methyl-1H-imidazol-4-yl]-oxazolo[4,5-b]pyridine; Compound 62

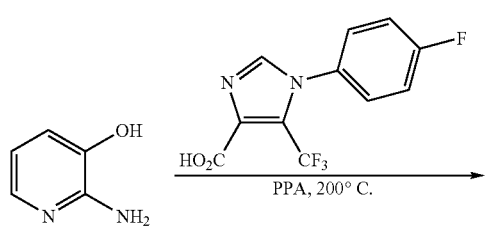

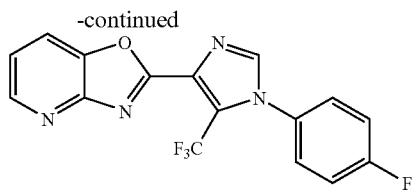

A 25 mL round bottom flask was charged with 1-(4-fluorophenyl)-5-(trifluoromethyl)pyrazole carboxylic acid (0.15 g, 0.5 mmol), 2-amino-3-hydroxypyridine (0.060 g, 0.5 mmol) and 1 mL of polyphosphoric acid. The mixture was brought to 200° C. and was stirred for 4 hours. The reaction was then quenched with ice and basified to pH 7.5 with saturated aqueous Na₂CO₃.

The resulting precipitate was filtered and washed with methanol. The crude product was purified by silica preparatory tlc plates, eluent 5% methanol/dichloromethane. The desired product was isolated and dried to afford a white powder. (Calc'd for C16H8F4N4O: 348.26, [M+H]+ found: 349.0).

Preparation of 3,4,5-Trimethoxy-N-methyl-N-(2-oxazolo[4,5-b]pyridin-2-yl-phenyl)-benzamide; Compound 292

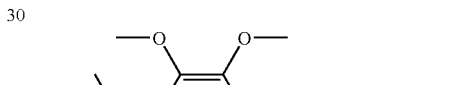

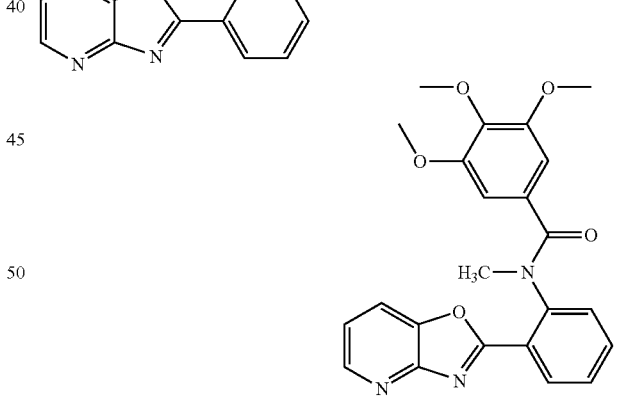

To a suspension of 3,4,5-trimethoxy-N-(2-oxazolo[4,5-b]pyridin-2-yl-phenyl)-benzamide (0.03 g, 0.1 mmol) in 3 mL of DMF was added sodium hydride (60% dispersion in mineral oil, 0.006 g, 0.2 mmol). The mixture was stirred at RT for 30 minutes, becoming homogeneous. To this was then added iodomethane, drop wise (0.040 g, 0.3 mmol, 0.02 mL). After an additional hour at RT, the reaction was quenched with water and then partitioned between saturated NH4Cl and EtOAc. The organic layer was washed with brine and dried over MgSO₄. The crude product was purified by silica chromatography, 0-5% methanol/dichloromethane.

The desired product was isolated as a yellow solid. (Calc'd for C23H21N3O5: 419.44, [M+H]+ found: 420.1)

Preparation of Compound 148

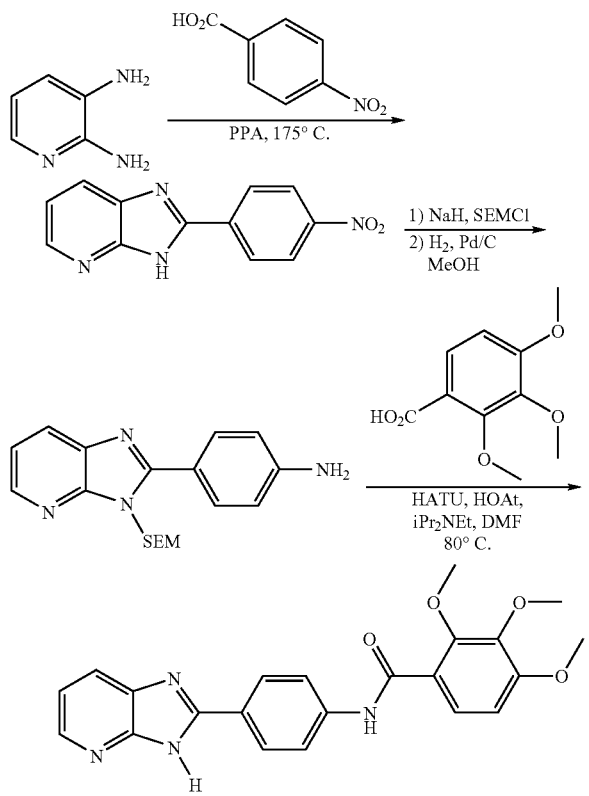

Para-nitrobenzoic acid (4.6 g, 27.5 mmol) and 2,3 diaminopyridine (3.0 g, 27.5 mmol) were added to polyphosphoric acid (27.5 mL) at room temperature with a mechanical stirrer. The reaction mixture was stirred at 175° C. for 2 h, cooled to rt, quenched with water and basified with NaHCO₃. The aqueous layer was left to precipitate overnight at rt. The resulting precipitate was filtered, washed with water, EtOAc and Et₂O and dried in vacuo to give the desired product as a brown solid. (Calc'd for C12H8N4O2: 240.22, [M+H]+ found: 241).

Dimethylformamide (30 mL) was added at 0° C. to sodium hydride (550 mg, 13.7 mmol) prewashed with hexane under an Argon atmosphere. 2-(4-Nitrophenyl)-3H-imidazo[4,5-b]pyridine (3.0 g, 12.43 mmol) was added portion-wise to this suspension at 0° C., and the reaction mixture was stirred at rt for 1 h 40 min. Then 2-(chloromethoxy)ethyltrimethylsilane (2.4 mL, 13.7 mmol) was added, and the reaction mixture was stirred at rt for 2.5 h and quenched with water. The aqueous layer was extracted with EtOAc and the combined organic layer was dried over Na₂SO₄, filtered and concentrated in vacuo. The crude product was purified by column chromatography on SiO2 with hexane/EtOAc (50:50) to (20:80) to give one fraction of pure isomer, and a second fraction which consisted of an 85:15 mixture of the two regioisomers. (Calc'd for C18H22N4O3Si: 370.48, [M+H]+ found: 371).

Palladium(0) on charcoal (10% w/w, 160 mg, 0.15 mmol) was added at rt to a mixture of the SEM-protected imidazopyridine (1.60 g, 4.30 mmol) in MeOH (8 mL), EtOAc (12 mL) and methoxyethanol (2 mL). The reaction mixture was placed under an H₂-atomsphere (vacuum/Argon three times; vacuum/H₂ three times) and stirred at rt until complete conversion (4 h). The reaction mixture was filtered over Celite and the filtrate was concentrated in vacuo to give the aniline as a brown solid. (Calc'd for C18H24N4OSi: 340.49, [M+H]+ found: 341).

To a solution of the imidazopyridine aniline (150 mg, 0.44 mmol) in 1.5 mL of DMF was added 2,3,4-trimethoxybenzoic acid (93 mg, 0.44 mmol), HATU (250 mg, 0.7 mmol), HOAt (90 mg, 0.7 mmol) and diisopropylethylamine (171 mg, 0.23 mL, 1.3 mmol). The reaction mixture was stirred overnight at 80° C. After dilution with ETOAc, the organic layer was washed with water, dried over Na₂SO₄, filtered and concentrated in vacuo. The obtained compound was then dissolved in EtOH (1 mL) and 5 N aq. HCl (1 mL). The reaction mixture was stirred at 70° C. for 2.5 h, cooled to rt and neutralized with 2N aq. NaOH and sat. aq. NaHCO₃ solution. The mixture was partially concentrated in vacuo and the resulting precipitate was filtered, washed with water and Et₂O and dried under vacuum to give the desired product.

Preparation of Compound 149, 150, 151, 180, 181, 182, 183, 184 and 185 were done in an analogous manner to Compound 148.

Preparation of Compound 190

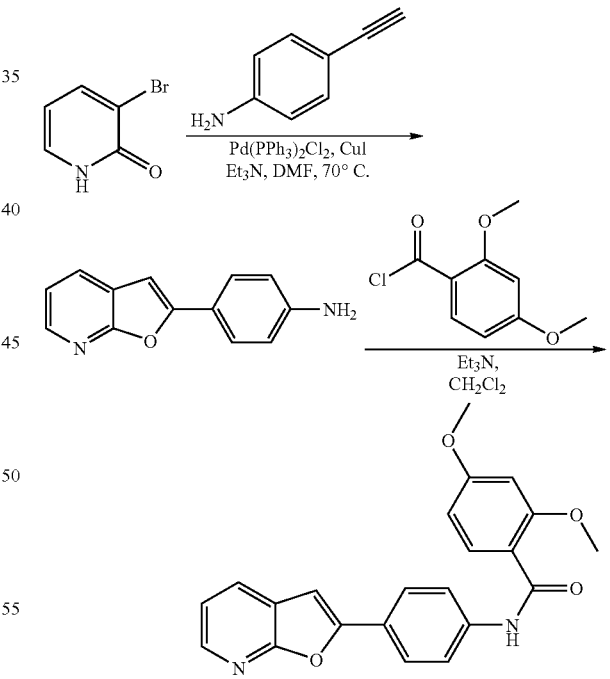

4-Ethynylaniline 15 (1.61 g, 13.79 mmol) was added at rt to a solution of 3-bromo-2-pyridinone 33 (2.0 g, 11.49 mmol), PdCl₂(PPh₃)₂ (403 mg, 0.574 mmol) and CuI (109 mg, 0.572 mmol) in degassed triethylamine (60 ml). The reaction mixture was degassed for 5 min, stirred at 100° C. for 6 h and concentrated in vacuo. The black residue was mixed with CH₂Cl₂/MeOH, filtered and concentrated in vacuo. The crude product was purified by column chromatography on SiO2 with CH₂Cl₂/MeOH (100:0) to (99:1) to afford the desired product. (Calc'd for C13H10N2O: 210.23, [M+H]+ found: 211).

To a solution of the N-(4-furo[2,3-b]pyridine-2-yl-phenyl-2,3-dimethoxybenzamide (30 mg, 0.143 mmol) and triethylamine (0.02 mL, 0.143 mmol) in CH₂Cl₂ (1 mL) was added 2,4-dimethoxybenzoyl chloride (44 mg, 0.219 mmol). The reaction mixture was stirred at rt overnight. After dilution with water, the aq. layer was extracted with CH₂Cl₂, and the combined organic layer was dried over Na2SO4, filtered and concentrated in vacuo. The crude product was purified by column chromatography on SiO₂ with Hexane/EtOAc (80:20 to 50:50) to afford the desired product. (Calc'd for C22H18N2O4: 374.39, [M+H]+ found: 375).

Preparation of Compounds 186, 187, 188, 189, 191, 192 and 193 was done in an analogous manner as Compound 190

Preparation of Compound 200

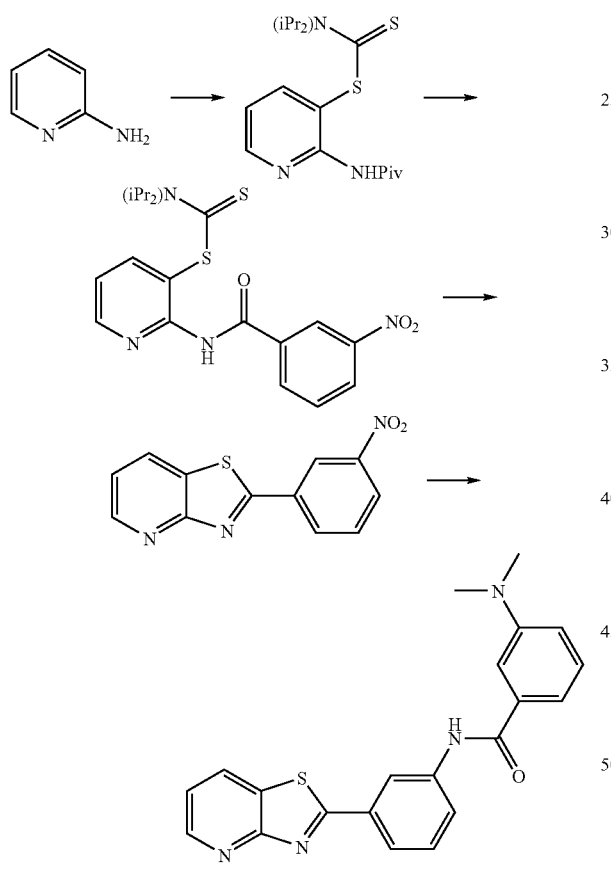

2-(3-Nitrophenyl)-thiazolo[4,5-b]pyridine was prepared from 2-amino-pyridine in six steps using the procedure described in *Sulfur Letters* 1995, 18 (2), 79-95. Palladium(0) on charcoal (10% w/w, 40 mg, 0.038 mmol) was added at rt to a mixture of 2-(3-nitrophenyl)-thiazolo[4,5-b]pyridine (403 mg, 1.57 mmol), toluene (2.5 ml), AcOH (2.5 ml) and methoxyethanol (2.5 ml). The reaction mixture was placed under an H2-atmosphere (vacuum/Argon three times; vacuum/H2 three times) and stirred at 50° C. for 3 h and at 60° C. for 1.5 h. As the reaction was not completed, another portion of palladium on charcoal (40 mg, 0.038 mmol) was added, and the reaction mixture was stirred at 60° C. for 20 h. The reaction mixture was cooled to rt, filtered over Celite, and the filtrate was concentrated in vacuo. The crude product was purified by column chromatography on SiO2 with EtOAc/hexane (80:20) to give the desired aniline as a brown solid. (Calc'd for C12H9N3S: 227.27, [M+H]+ found: 228.2).

To a solution of the thiazolo[4.5-b]pyridin-2-yl-phenylamine (40 mg, 0.176 mmol) and triethylamine (0.02 mL, 0.143 mmol) in CH₂Cl₂ (1 mL) was added 3-dimethylaminobenzoyl chloride hydrochloride (47 mg, 0.213 mmol). The reaction mixture was stirred at rt overnight. After dilution with water, the aq. layer was extracted with CH₂Cl₂, and the combined organic layer was dried over Na₂SO₄, filtered and concentrated in vacuo. The crude product was purified by preparative HPLC to afford the desired product. (Calc'd for C21H18N4OS3: 74.46, [M+H]+ found: 375).

Preparation of Compounds 152, 194, 195, 196, 197, 198, 199, 201 and 202 was done in an analogous manner to Compound 200

Preparation of Compound 286

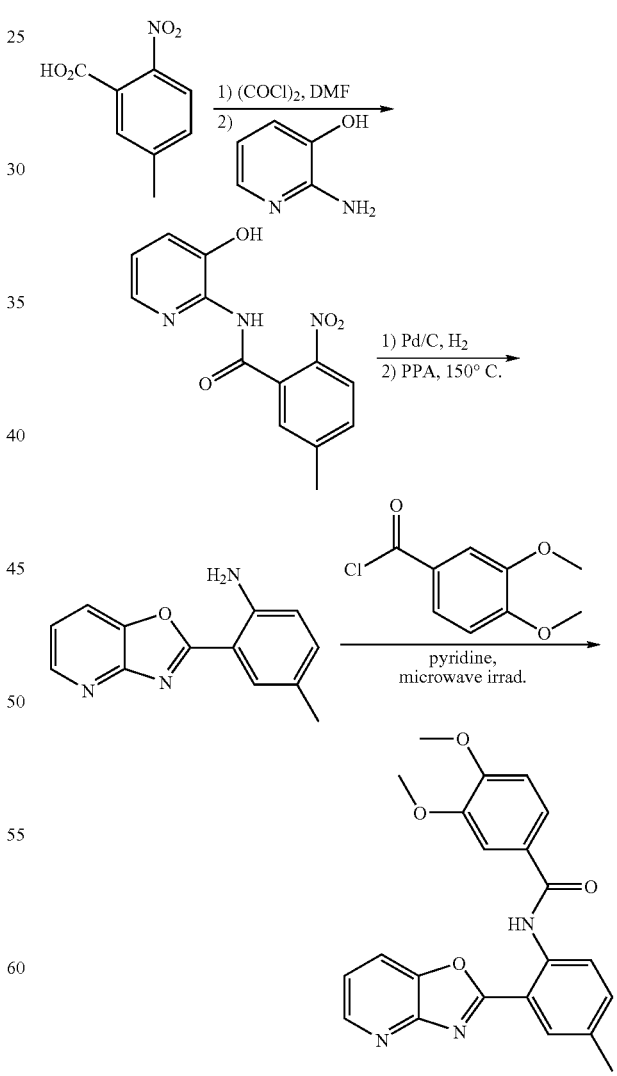

To a solution of 5-methyl-2-nitrobenzoic acid (2.0 g, 11.0 mmol) in 100 mL of CH₂Cl₂ was added oxalyl chloride (7.0 g, 4.8 mL, 55.2 mmol) and 3 drops of DMF. The mixture was stirred at rt for 40 minutes and the solvents were removed in vacuo. The resulting residue was put under high vacuum, and then dissolved in 10 mL of $CH_2Cl_2$. This solution was added to a solution of 2-amino-3-hydroxypyridine (1.21 g, 11.0 mmol) and diisopropylethylamine (2.1 g, 2.9 mL, 16.6 mmol) in 100 mL of $CH_2Cl_2$. The reaction was stirred at rt until completion, and was then partitioned between $CH_2Cl_2$ and brine. The organic layer was washed with brine and dried over $MgSO_4$. The crude product was purified by silica chromatography, EtOAc/Hexanes, (20:80 to 90:10) to afford the desired amide product. (Calc'd for C13H11N3O4: 273.25, [M+H]+ found: 274.1).

A slurry of palladium on carbon (10% w/w, 0.12 g) in 1 mL of EtOH was added to a solution of the pyridyl amide (1.2 g, 4.4 mmol) in 50 mL of MeOH. The reaction was placed under a $H_2$ atmosphere and was stirred at rt overnight. The mixture was purged with nitrogen and then filtered through Celite. The volatiles were removed in vacuo to afford the desired amine. (Calc'd for C13H13N3O2: 243.27, [M+H]+ found: 244).

2-Amino-N-(3-hydroxypyridin-2-yl)-5-methylbenzamide (0.2 g, 0,8 mmol) was combined with 1 mL of PPA, and the mixture was stirred at 150° C. for 2 h. The reaction was quenched with ice and basified with sat. Na2CO3. The resulting yellow solid was filtered, washed with water and dried to afford the desired aniline. (Calc'd for C13H11N3O: 225.25, [M+H]+ found: 226.1).

A microwave vial was charged with 4-methyl-2-oxazolo[4,5-b]pyridin-2-yl-phenyl amine (40 mg, 0.2 mmol), 3,4-dimethoxybenzoyl chloride (35 mg, 0.2 mmol) and 1 mL of pyridine. The mixture was subjected to microwave irradiation at 160° C. for 10 minutes. The resulting precipitate was filtered, washed with MeOH and dried to give the desired amide as a white solid. (Calc'd for C22H19N3O4: 389.41, [M+H]+ found: 390.1).

Preparation of Compound 295

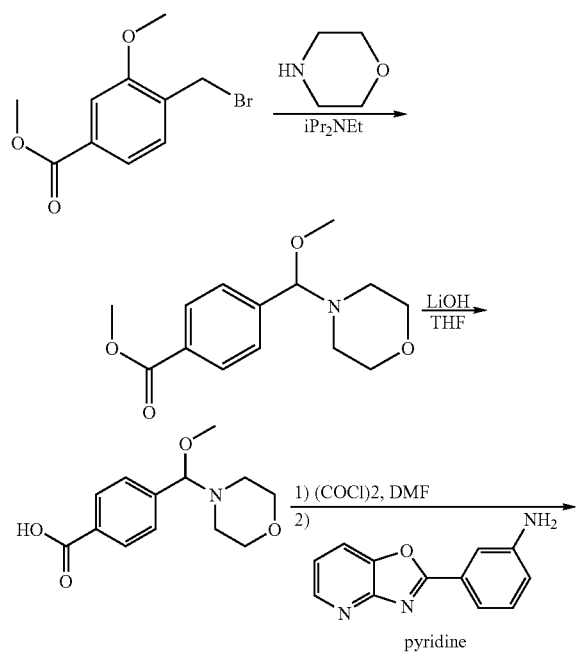

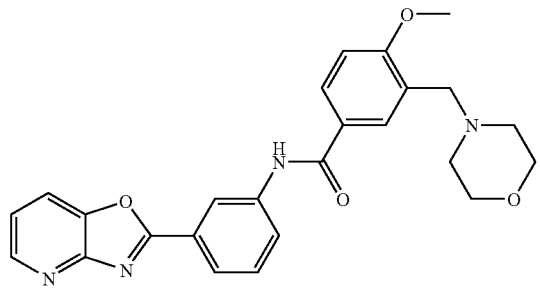

To a solution of methyl 4-(bromomethyl)-3-methoxybenzoate (10.0 g, 38.6 mmol) in 200 mL of $CH_2Cl_2$ was added morpholine (3.36 g, 38.6 mmol) and diisopropylethylamine (5.98 g, 8.1 mL, 46.3 mmol). The solution was stirred at rt overnight, and the reaction was then partitioned between $CH_2Cl_2$ and water. The organic extract was washed with brine and dried over $MgSO_4$. Solvent evaporation afforded the desired product as a sticky solid. (Calc'd for C14H19NO4: 265.31, [M+H]+ found: 266.1).

Methyl 4-(morpholinomethyl)-3-methoxybenzoate (10.4 g, 39.1 mmol) was dissolved in 150 mL of THF and to this was added a suspension of LiOH (4.68 g, 195.4 mmol) in 75 mL of water. The mixture was stirred overnight at rt, and the solvents were then removed in vacuo. The resulting solid was suspended in $CH_2Cl_2$ (200 mL) and MeOH (50 mL). This mixture was then filtered through Celite, and the solvent was evaporated from the mother liquor to afford the desired acid product. (Calc'd for C13H17NO4: 251.28, [M+H]+ found: 252.1)

The benzoic acid (0.1 g, 0.4 mmol) was suspended in $CH_2Cl_2$ (5 mL) and to this was added oxalyl chloride (0.25 g, 2.0 mmol, 0.17 mL) and 2 drops of DMF. After 1 h at rt, the solvents were removed in vacuo, and the resulting residue was placed under high vacuum for 30 minutes. It was then mixed with pyridine (2 mL) and added to a microwave vial charged with 3-oxazolo[4,5-b]pyridin-2-yl-phenylamine (0.084g, 0.4 mmol). The reaction mixture was subjected to microwave irradiation at 160° C. for 10 minutes. The solvents were then removed and the crude material was purified by silica chromatography (5-10% MeOH/$CH_2Cl_2$) and prep tlc (5% MeOH/$CH_2Cl_2$) to afford the desired amide product. (Calc'd for C25H24N4O4: 444.5, [M+H]+ found: 445.1).

Compounds 706, 571, 572, 585, 629, 630, 631, 632, 636, 637, 638, 642 and 643 was prepared in an analogous manner to Compound 295.

Preparation of Compound 468

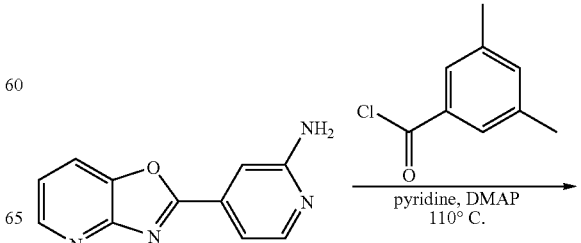

-continued

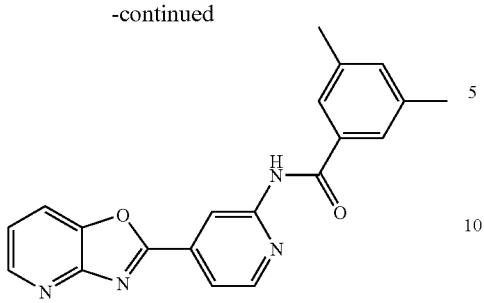

3,5-Dimethyl benzoic acid (0.3g, 2 mmol) and thionyl chloride (8 mL) were combined under a nitrogen atmosphere and heated to reflux for 3 h. The excess thionyl chloride was evaporated completely in vacuo. To this was then added 4-oxazolo[4,5-b]pyridin-2-yl pyridine-2-ylamine (0.318 g, 1.5 mmol), dry pyridine (8 mL) and a catalytic amount of DMAP, and the mixture was heated to reflux at 110° C. for 6 h. To this water (20 mL) was added and the compound was extracted into CH$_2$Cl$_2$ (2×25 mL). The organic layer was dried over anhydrous Na$_2$SO$_4$, filtered and concentrated. The crude compound was purified on silica (60-120 mesh) eluted with EtOAc: hexanes (1:5), to obtain the pure amide. (Calc'd for C20H16N4O2: 344.38, [M+H]+ found: 3445.1).

Preparation of Compounds 367, 369, 375, 376, 470, 482, 483, 566, 567, 576, 578, 579, 580 and 639 was done in an analogous manner as Compound 468.

Preparation of Compound 565

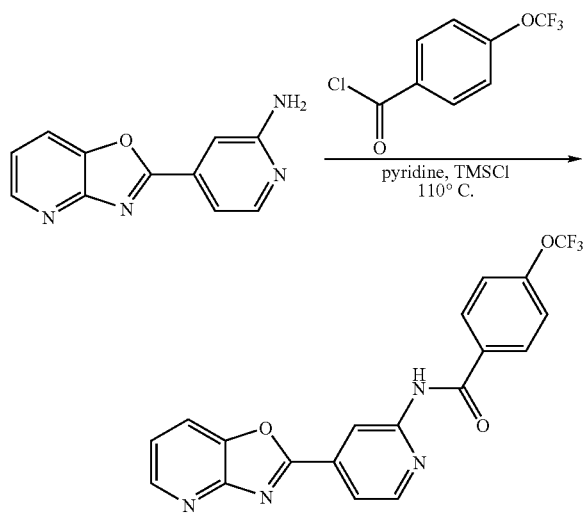

To a solution of 4-oxazolo[4,5-b]pyridin-2-yl pyridine-2-ylamine (0.192 g, 0.91 mmol) in dry pyridine (10 mL) was added TMSCl (1 mL 0.75 mmol) at 10-15° C. and the reaction mixture was stirred at room temperature for 4 h.

In a separate round bottomed flask, trifluoromethoxy benzoic acid (0.250 g, 1.21 mmol) and thionyl chloride (6 mL) were combined under a nitrogen atmosphere and heated to reflux for 3 h. The excess thionyl chloride was evaporated in vacuo. To this reaction mixture, the above prepared silylated amine was added at room temperature and the mixture was heated to reflux for 6 h. Water (20 mL) was added and the compound was extracted with dichloromethane (2×25 mL). The organic layer was dried over anhydrous Na$_2$SO$_4$, filtered and concentrated. The crude compound was purified on silica (60-120 mesh) eluted with EtOAc:hexanes, to obtain the pure amide. (Calc'd for C19H11F3N4O3: 400.32, [M+H]+ found: 400.8).

Preparation of Compounds 577, 581, 640, 641 and 668 was done in an analogous manner to Compound 565.

Preparation of Compound 705

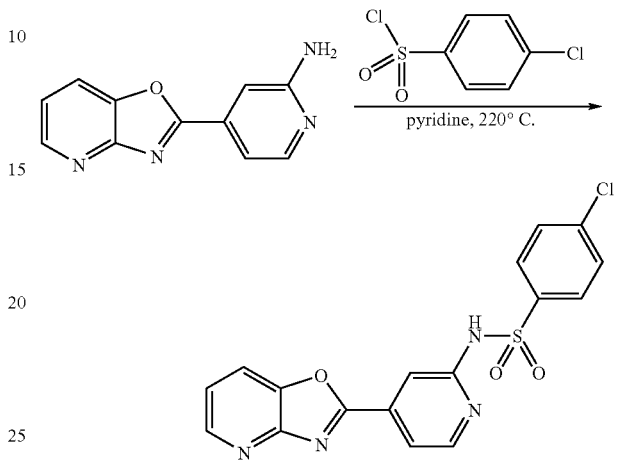

4-Oxazolo[4,5-b]pyridin-2-yl pyridine-2-ylamine (0.20 g, 0.9 mmol), dry pyridine (1 mL) and 4-chlorophenylsulphonyl chloride (0.9 g, 0.9 mmol) were mixed in a sealed tube and heated at 220° C. for 2 h. After completion of the reaction (monitored by TLC), the reaction mixture was cooled to room temperature, water (20 mL) was added, the compound was extracted into dichloromethane (2×30 mL), and the organic layer was dried (Na$_2$SO$_4$), filtered and concentrated. The crude compound was purified by silica column chromatography to obtain the pure sulfonamide. (Calc'd for C17H11ClN4O3S: 386.82, [M+H]+ found: 387.0).

Preparation of Compounds 370, 371, 372, 373, 374, 471, 474, 476, 477, 478, 479 and 653 was done in an analogous manner to Compound 705.

Preparation of Compound 379

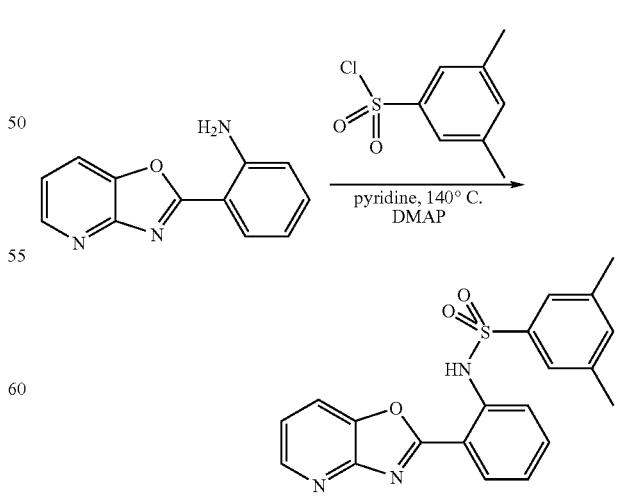

To a stirred solution of 2-oxazolo[4,5-b]pyridin-2-yl-phenylamine (0.2 g, 0.94 mmOl) in 2 mL of dry pyridine was added 3, 5-dimethyl sulfonyl chloride (0.193 g, 0.94 mmol) and a catalytic amount of DMAP. The mixture was stirred for 3 h at 140° C. (The progress of the reaction was monitored by TLC). The reaction mixture was diluted with water (20 mL), extracted with ethyl acetate (2×25mL). The combined organic layers were dried over Na₂SO₄ and evaporated in vacuo. The crude compound was purified by silica chromatography to obtain the corresponding sulfonamide (Calc'd for C20H17N3O3S: 379.44, [M+H]+ found: 380.0).

Preparation of Compounds 377, 378, 380, 381, 382, 383, 384, 486, 487, 488, 489, 490, 492, 493 and 494 was done in an analogous manner to Compound 379.

Preparation of Compound 495

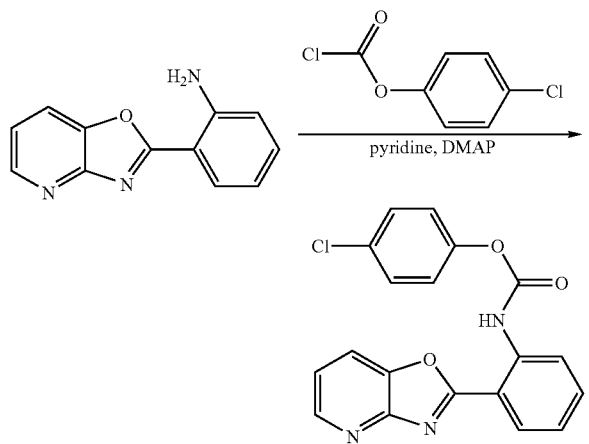

To a stirred solution of 2-oxazolo[4,5-b]pyridin-2-yl-phenylamine (0.15 g, 0.70 mmol) in 1.5 mL of pyridine was added 4-chlorophenyl choloroformate (0.16 g, 0.84 mmol) followed by a catalytic amount of DMAP at room temperature. The reaction was stirred for 2 h under a nitrogen atmosphere. (The progress of the reaction was monitored by TLC). The reaction mixture was diluted with water (10 mL), extracted with ethyl acetate (2×25 mL) and the combined organic layers were dried over anhydrous Na₂SO₄, filtered and concentrated in vacuo. The crude compound was purified by column chromatography to obtain the corresponding carbamate. (Calc'd for C19H12N3O3Cl: 365.7, [M+H]+ found: 366.0).

Preparation of Compounds 496, 497, 499, 500, 501, 502, 568 and 582 was done in an analogous manner to Compound 495.

Preparation of Compound 584

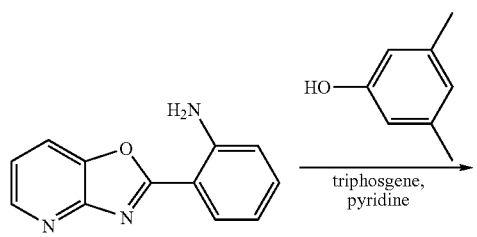

-continued

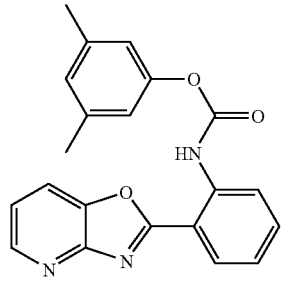

Triphosgene (0.72g, 2.4 mmol) was dissolved in dry dichloromethane and pyridine (1 equiv) was added at −78° C. The mixture was stirred for 10 min. To this reaction mixture was added 3,5-dimethyl phenol (0.5 g, 4 mmol) in 2 mL of DCM over a period of 10 min. and stirred for 2 h at room temperature. In another RB flask, 2-oxazolo[4,5-b] pyridin-2-yl-phenylamine (0.2 g, 0.9 mmol) was dissolved in pyridine (20 mL) and to this was added the above prepared phenyl chloroformate drop wise over a period of 5 min at room temperature. A catalytic amount of DMAP was added and the reaction was stirred overnight. After complete disappearance of the starting material (monitored by TLC), the reaction mixture was diluted with water (10 mL) and extracted with ethyl acetate (2×25 mL). The combined organic layers were dried over anhydrous Na₂SO₄, filtered and concentrated in vacuo. The crude compound was purified by silica column chromatography to obtain the pure compound. (Calc'd for C21H17N3O3: 359.38, [M+H]+ found: 360.0).

Preparation of Compounds 569, 570, 583, 655, 656, 657, 669, 670 and 671 was done in an analogous manner to Compound 584.

Preparation of Compound 672

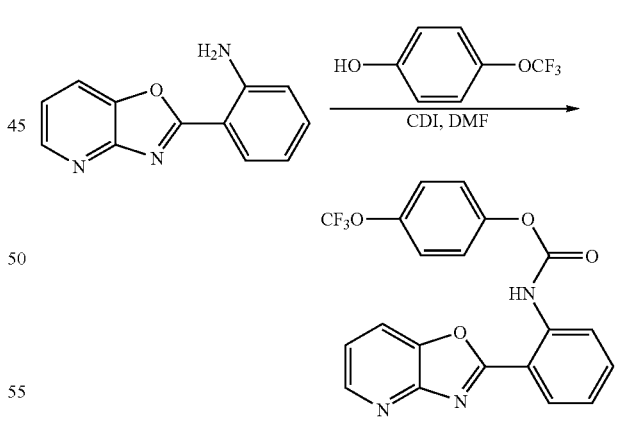

To a stirred solution of 4-trifluoromethoxy phenol (0.1 g, 0.56 mmol) in dry DMF (0.5 mL), was added N,N-carbonyl diimidazole (0.09 g, 0.56 mmol). The reaction was stirred for 30 min at room temperature under a nitrogen atmosphere. The reaction mixture was diluted with water (10 mL), extracted into ethyl acetate, dried over anhydrous Na₂SO₄, filtered and evaporated in vacuo. This crude compound was dissolved in pyridine (0.5 mL) and was added to a pre-stirred solution of 2-oxazolo[4,5-b]pyridin-2-yl-phenylamine (0.075 g, 0.35 mmol) in pyridine (0.5 mL) followed by the addition of a catalytic amount of DMAP. The mixture was stirred for 2 h at room temperature. After completion of the reaction (monitored by TLC), the reaction mixture was diluted with water (10 mL), extracted with ethyl acetate, dried over anhydrous Na₂SO₄, filtered and concentrated in vacuo. The crude compound was purified by column chromatography to afford the pure compound. (Calc'd for C20H12F3N3O4: 415.33, [M+H]+ found: 415.1).

Preparation of Compound 666

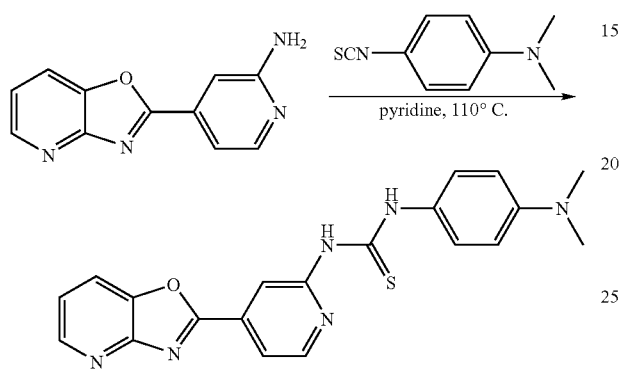

To a solution of 4-oxazolo[4,5-b]pyridin-2-yl pyridine-2-ylamine (0.24 g, 0.96 mmol) in pyridine (2 mL), trimethylsilyl chloride (0.6 mL, 4.33 mmol) was added drop wise at room temperature under a nitrogen atmosphere and the mixture was stirred for 6 h. To this was added 4-dimethyl aminophenyl isothiocyanate (0.251 g, 1.41 mmol) and a catalytic amount of dimethylamino pyridine. The reaction was refluxed for 12 h (progress of the reaction was monitored by TLC). The reaction mixture was diluted with water (50 mL) and the compound was extracted with DCM (2×50 mL). The combined organic layers were dried (Na₂SO₄) and evaporated in vacuo. The crude compound was purified by silica chromatography to afford the corresponding thiourea. (Calc'd for C20H18N6OS: 390.47, [M+H]+ found: 391.0).

Preparation of Compounds 573, 574, 575, 658, 659, 660, 661, 662, 663, 664, 665, 667, 673, 674 and 675 was done in an analogous manner to Compound 666.

Preparation of Compound 634

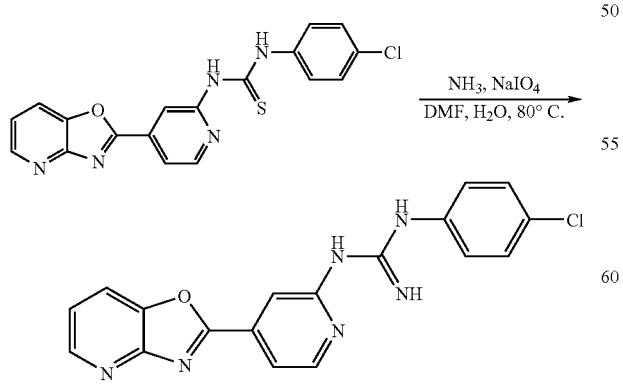

To a stirred solution of the thiourea (0.040 g, 1.05 mmol) in DMF:H₂O (4 mL, 2:2), was added an NH₃ solution (30%, 3 mL). The mixture was stirred for 30 min at room temperature. To this was added a NaIO₄ solution (0.033 g, in 2 mL water) and the reaction mixture was heated at 80° C. for 12 h. 10% NaOH solution (1 mL) was then added at room temperature. The resulting precipitate was filtered, washed with water (2×10 mL), hexanes (2×10 mL), and dried to obtain the required pure guanidine. (Calc'd for C18H13ClN6O: 364.8, [M+H]+ found: 364.9).

Preparation of Compounds 633 and 635 was done in an analogous manner to Compound 634.

Preparation of Compound 506

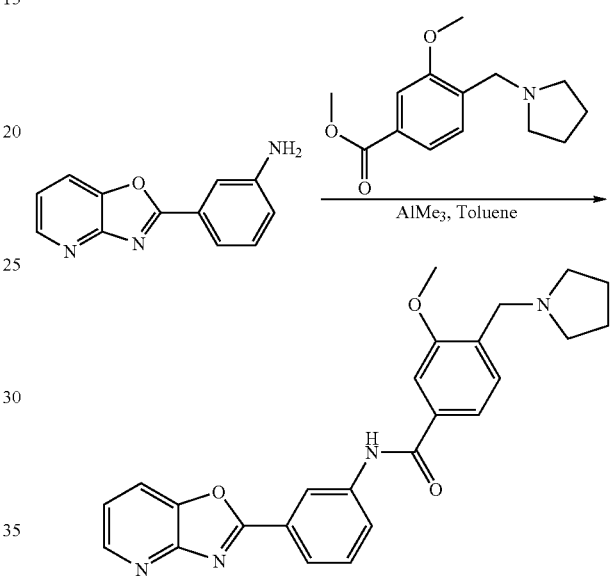

The methyl-4-methylpyrrolodine-3-methoxybenzoate was prepared following the same procedure as the methyl-4-methylmorpholine-3-methoxybenzoate was prepared.

To a suspension of 3-oxazolo[4,5-b]pyridin-2-yl-phenylamine (0.10 g, 0.5 mmol) in 1 mL of toluene was added trimethylaluminum (2.0 M in toluene, 0.2 mL, 0.5 mmol). This mixture was stirred for 1.5 h at rt. To this was then added a slurry of methyl-4-methylpyrrolodine-3-methoxybenzoate (0.12g 0.5 mmol) in 1 mL of toluene. The reaction was stirred at reflux for 17 h. Upon cooling, the mixture was partitioned between CH₂Cl₂ and brine. The aqueous layer was extracted with CH₂Cl₂, and the combined organic extracts were washed with brine and dried over MgSO₄. The crude product was purified by silica chromatography, 0 to 10% MeOH/CH₂Cl₂ to afford the desired amide. (Calc'd for C25H24N4O3: 428.50, [M+H]+ found: 429.1).

Preparation of Compound 525

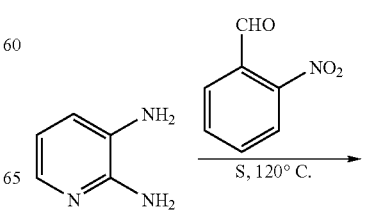

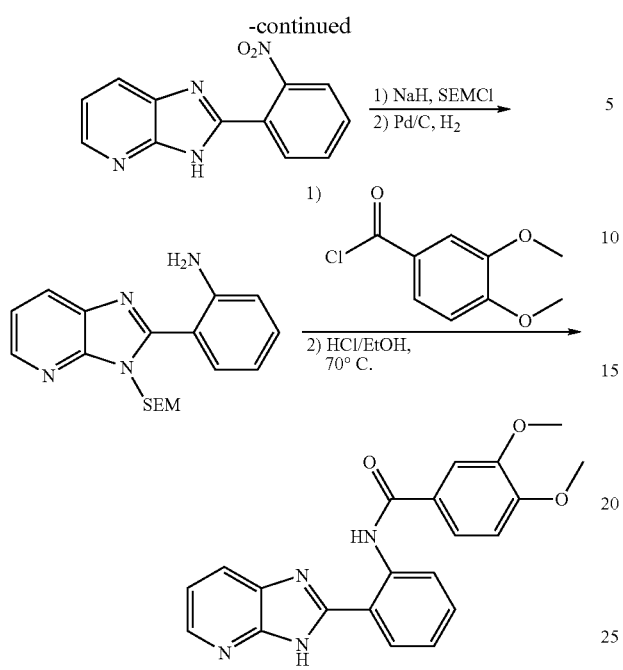

3.27 g (30 mmol) of 2,3-diaminopyridine, 4.53 g (30 mmol; 1.0 equiv) of 2-nitrobenzaldehyde and 1.92 g (60 mmol; 2.0 equiv) of sulfur were thoroughly mixed together and heated to 120° C. The mixture turned into a black liquid and was stirred for a further 3 h. After cooling to room temperature, the solid residue was dissolved in hot ethanol (400 ml) and filtered. The filtrate was concentrated, and the residue was purified by flash chromatography (gradient hexane/ethyl acetate 1:1 to 0:100) to give the pyridoimidazole product. (Calc'd for C12H8N4O2: 240.2, [M+H]+ found: 242).

In a two-necked 100 mL flask, 604 mg (13.8 mmol; 1.1 equiv) of sodium hydride (55% in paraffin) under nitrogen were washed with anhydrous hexane (2×5 ml) and suspended in anhydrous DMF (30 ml). 3.02 g (12.6 mmol) of imidazole 22 were added in portions at 0° C., leading to gas evolution and the formation of a deep red-brown solution. The mixture was stirred for 30 min at 0° C. and for 30 min at room temperature, cooled to 0° C., and 2.45 ml (13.8 mmol; 1.1 equiv) 2-(chloromethoxy)ethyltrimethylsilane were added drop wise. After stirring for 5.5 h at room temperature the orange-brown suspension was added to a mixture of saturated aq. Na2CO3-solution (150 ml), water (300 ml), ethyl acetate (200 ml), and brine (50 ml). The aqueous layer was extracted with ethyl acetate (4×100 ml); and the combined organic layer was washed with a mixture of brine and water (1:3; 2×100 ml) and brine (50 ml), dried (Na2SO4), and concentrated. The residue was purified by flash chromatography (gradient hexane/ethyl acetate 1:2 to 0:100), affording three isomers of the product: 1.90 g (5.13 mmol, 41%), 1.31 g (3.55 mmol; 28%), and 895 mg (2.41 mmol; 19%). (Calc'd for C18H22N4O3Si: 370.1, [M+H]+ found: 371.2).

The 2-(2-nitrophenyl)imidazopyridine 1.87 g (5.05 mmol) was dissolved in ethyl acetate (27 ml) and methanol (18 ml) in the presence of 10% palladium on charcoal (190 mg) at ambient pressure and temperature for 4 h. Purification of the crude product by flash chromatography (hexane/ethyl acetate 1:1) gave the desired aniline as a yellow-green oil. (Calc'd for C18H224N4OSi: 340.1, [M+H]+ found: 341.2).

The reaction of 2-[3-(2-trimethylsilanyl-ethoxymethyl)-3H-imidazo[4,5-b]pyridin-2-yl]phenylamine (85.1 mg; 0.25 mmol) with 3,4-dimethoxybenzoylchloride (60.2 mg; 1.2 equiv) and 38 μL (1.1 equiv) of NEt3 in dry CH2Cl2 (2 ml), followed by flash chromatography (hexane/ethyl acetate 2:1), afforded the desired amide as a colorless, highly viscous resin, which solidified upon addition of ethanol. (Calc'd for: C27H32N4O4Si: 504.2, [M+H]+ found: 505).

Preparation of Compounds 521, 522, 523, 524, 526, 527, 528, 529, 530, 531, 532, 533, 534, 535, 536, 537, 538, 539 and 540 was done in an analogous manner to Compound 525.

Preparation of Compound 253

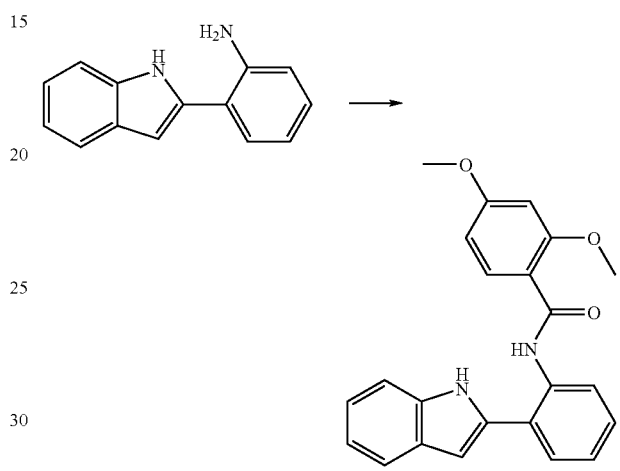

In a typical run, 2-(2-Aminophenyl)indole (104 mg, 0.5 mmol) in 4 mL pyridine was stirred with 2,4-dimethoxybenzoyl chloride (100 mg, 0.5 mmol). The reaction was stirred at room temperature overnight. Reaction completion was confirmed by LC-MS, and 15 mL of water was charged. The resulting suspension was stirred and sonicated until white precipitates were obtained. The white solid was collected by filtration, washed with water and air dried. The product was purified by flash chromatography on silica gel using CH2Cl2 as elluent (0 to 10% methanol gradient). TLC/HPLC/LC-Mass suggested that it was the clean product (MS, M++H=373.1).

Compounds 254, 255 and 256 were prepared in an analogous manner to Compound 253, using the appropriate acid chlorides.

Preparation of Compound 262

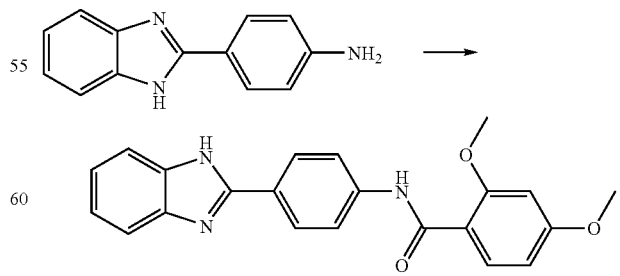

In a typical run, 4-(1H-Benzoimidazol-2-yl)-phenylamine (83 mg, 0.4 mmol) in 3 mL pyridine was added to 2,4-dimethoxybenzoyl chloride (80 mg, 0.4 mmol). The reaction was stirred overnight at room temperature. Reaction completion was confirmed by LC-MS, and 15 mL of water was charged. The resulting suspension, upon stirring for five hours, was filtered to collect an off white solid, which was washed with water and dried under reduced pressure. The product was purified by flash chromatography on silica gel using $CH_2Cl_2$ as eluent (0 to 10% methanol gradient). TLC/HPLC/LC-Mass suggested that it was the clean product (MS, $M^++H=374.1$).

Compounds 263, 264 and 294 were prepared in an analogous manner to Compound 262, using the appropriate acid chlorides, and purified either by recrystallization from acetonitrile or normal phase chromatography using a 9:1 mixture of $CH_2Cl_2$ to MeOH as eluent.

Preparation of Compound 332

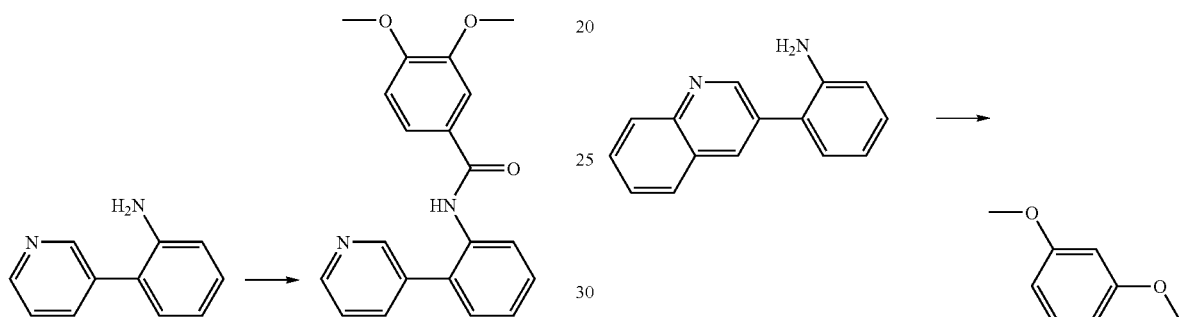

In a typical run to prepare Compound 332, in a vial was dissolved 2-Pyridin-3-yl-phenylamine (400 umol, 68 mg) in 2 ml of pyridine. 3,4-dimethoxybenzoyl chloride (400 umol, 80 mg) was added with stirring. The solution was stirred overnight at room temperature. 20 ml $H_2O$ was then added and the resulting white emulsion was stirred overnight with intermittent sonication until white precipitate was obtained in a clear solution. The solid was filtered, and air dried. Purification was done on silica gel with in $CH_2Cl_2$ (methanol gradient 0 to 10%), concentrated to dryness to obtain the product as a white solid. (MS, $M^++H=335.1$).

Compounds 331 and 333 were prepared in an analogous manner to Compound 332, using the appropriate acid chlorides. In the cases of Compounds 331 and 333, the crude product was isolated by extraction into $CH_2Cl_2$.

Preparation of Compound 334

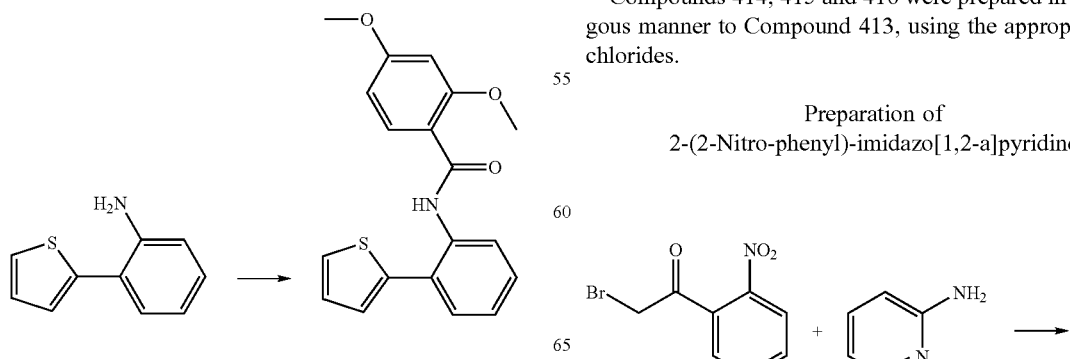

In a typical run to prepare Compound 332, in a vial was dissolved 2-Pyridin-3-yl-phenylamine (400 umol, 70 mg) in 2 ml of pyridine. 2,4-dimethoxybenzoyl chloride (400 umol, 80 mg) was added with stirring. The solution was stirred overnight at room temperature. 20 ml $H_2O$ was then added and the resulting white emulsion was stirred overnight with intermittent sonication until white precipitate was obtained in a clear solution. The solid was filtered, and air dried. Purification was performed on silica gel with $CH_2Cl_2$ (methanol gradient 0 to 10%), concentrated to dryness to obtain the product as a white solid. (MS, $M^++H=340.1$).

Compounds 335 and 336 were prepared in an analogous manner to Compound 332, using the appropriate acid chlorides. In the case of Compound 335, the crude product was isolated by extraction into $CH_2Cl_2$.

Preparation of Compound 413

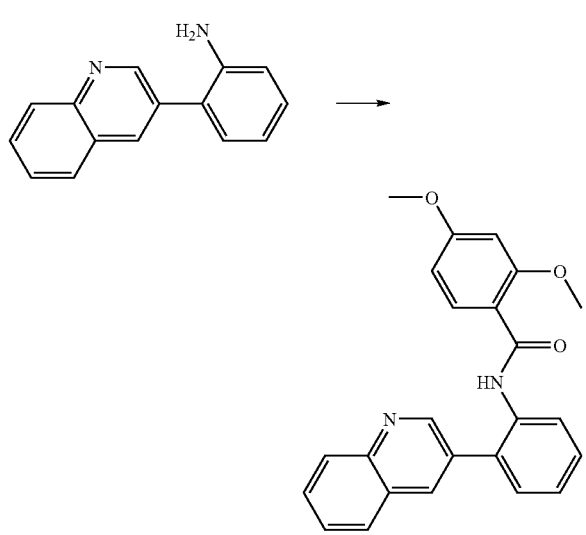

In a typical run to prepare Compound 413, in a vial was dissolved 2-Pyridin-3-yl-phenylamine (300 umol, 66 mg) in 1 ml of pyridine. 2,4-dimethoxybenzoyl chloride (300 umol, 60 mg) was added with stirring. The solution was stirred overnight at room temperature, concentrated to dryness, and chased with pentane (2×5 ml) to obtain the crude product as an orange solid. The crude was purified by silica gel chromatography (0% to 70% Ethyl Acetate in Pentane) to obtain the desired product (77 mg). (MS, $M^++H=385.1$)

Compounds 414, 415 and 416 were prepared in an analogous manner to Compound 413, using the appropriate acid chlorides.

Preparation of 2-(2-Nitro-phenyl)-imidazo[1,2-a]pyridine

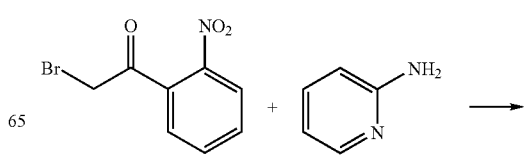

-continued

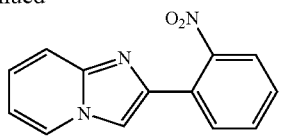

2-Bromo-2'-nitroacetophenone (7.65 g, 31.3 mmol) and 2-aminopyridine (2.95 g, 31.3 mmol) were dissolved in acetone (50 ml) and brought to reflux. After 10 minutes a light yellow/white precipitate forms in addition to strong boiling. Refluxing was continued for 3 hours and cooled to room temperature. The volume was reduced ½ by evaporation and the intermediate solids were collected by filtration and washed with acetone (20 ml) and air dried (7.26 g of intermediate). The intermediate (7.20 g) was dissolved in MeOH (100 ml) with HBr (4 drops, catalytic) and brought to reflux. The reaction was monitored by TLC (10% MeOH in $CH_2Cl_2$). After 70 minutes, the reaction mixture was cooled to room temperature, adjusted to pH=12 with 1 M NaOH, and concentrated to remove the methanol. The yellow product was collected by filtration, washed with water and air dried. 5.54 g (74%) of 2-(2-Nitro-phenyl)-imidazo[1,2-a]pyridine was obtained as a yellow crystalline solid (MS, $M^++H=240.1$).

Preparation of
2-Imidazo[1,2-a]pyridin-2-yl-phenylamine

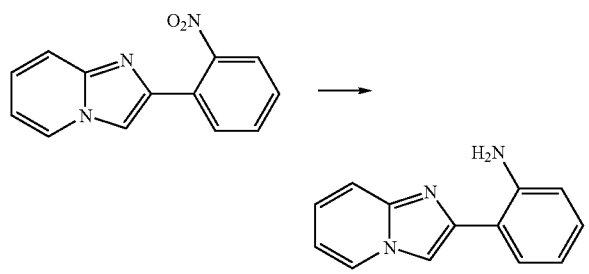

2-Imidazo[1,2-a]pyridin-2-yl-phenylamine was prepared with two reductive methods.

1) Catalytic hydrogenation. 2-(2-Nitro-phenyl)-imidazo[1,2-a]pyridine (250 mg, 1.04 mmol) was dissolved in THF (15 mL). The flask was charged 20 mg of 10% Palladium on Carbon, flushed with nitrogen and stirred over $H_2$ balloon (1 atm.) O/W. The reaction was monitored by either HPLC or TLC (5% MeOH in $CH_2Cl_2$). The reaction mixture was filtered over a bed of Celite to remove the catalyst, the bed was washed with THF (2×10 ml) and the combined organics were concentrated to dryness to obtain an amber oil. The white solid product was obtained by careful roto-evaporation of a 50% Aqueous ethanol solution, and collected by filtration (MS, $M^++H=210.1$).

2) Sulfide reduction. Into a round bottom flask was charged 2-(2-Nitro-phenyl)-imidazo[1,2-a]pyridine (250 mg, 1.04 mmol), Sodium hydrogensulfide (351 mg, 6.24 mmol), methanol (6 ml) and water (2 ml). The reaction mixture was refluxed overnight. TLC indicated that the reaction was complete (5% MeOH in $CH_2Cl_2$). The mixture was cooled to room temperature, concentrated to dryness and to the white/yellow salts was added water (1 mL), $CH_2Cl_2$ (10 mL) and MeOH (1 mL). The layers were separated and the aqueous layer was back extracted with $CH_2Cl_2$ (2×10 ml). The combined organic layers were dried over $Na_2SO_4$, and concentrated to dryness to obtain the product as a tan solid (MS, $M^++H=210.1$).

Preparation of Compound 265

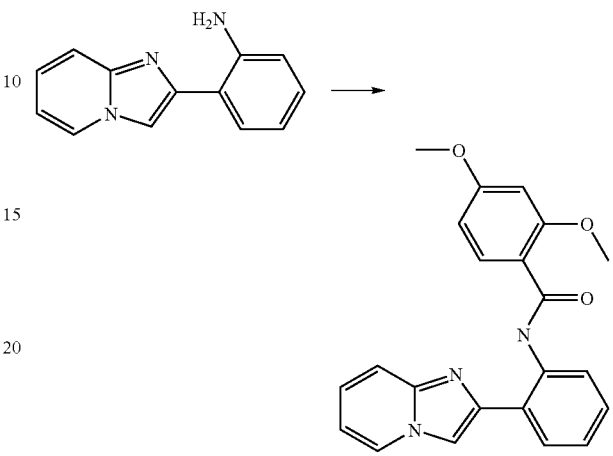

In a typical run to prepare Compound 265, in a vial was dissolved 2-Imidazo[1,2-a]pyridin-2-yl-phenylamine (400 umol, 84 mg) in 3 ml of pyridine. 2,4-dimethoxybenzoyl chloride (400 umol, 80 mg) was added with stirring. The solution was stirred overnight at room temperature. 15 ml $H_2O$ was then added and the resulting white emulsion was stirred for 5 hours with intermittent sonication until a white precipitate was obtained in a clear solution. The solid was filtered, and air dried. Purification was performed on silica gel with $CH_2Cl_2$ as eluent (methanol gradient 0 to 10%), concentrated to dryness and triturated with Pentane to obtain the product as an off white solid (MS, $M^++H=374.1$).

Compounds 266, 267 and 268 were prepared in an analogous manner to Compound 265, using the appropriate acid chlorides.

Preparation of 2-(2-Nitro-phenyl)-imidazo[1,2-a]pyridine-3-carbaldehyde

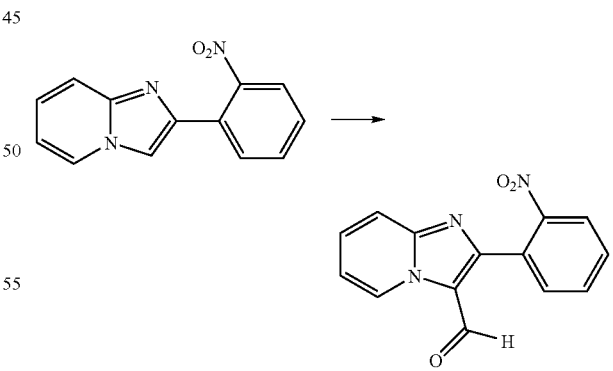

In a dry flask charged with DMF (2.7 g, 37 mmol) and cooled to 0° C. was added slowly $POCl_3$ over 5 minutes. The solution was stirred for 10 min at 0° C. was warmed to room temperature over 1 hour. To the deep red color solution recooled to 0° C. was added 2-(2-Nitro-phenyl)-imidazo[1,2-a]pyridine (1.0 g, 4.18 mmol) in DMF (8 ml). The reaction was stirred for 5.5 hours; LC-MS indicated some product formation. A second addition of the Vilsmeier complex (from 2.7 g of DMF and 1.47 g POCl₃) was charged and the reaction stirred overnight, then heated to 50° C. for 3 hours until reaction completion. The reaction was cooled to room temperature, poured onto ice, adjusted to pH=7 with 1N NaOH. The product was extracted into CH₂Cl₂ (3×50 ml), washed with brine, dried over Na₂SO₄ and concentrated to obtain the product as a white solid (1.03 g, 92% yield). (MS, M⁺+H=268.0)

Preparation of Compound 316

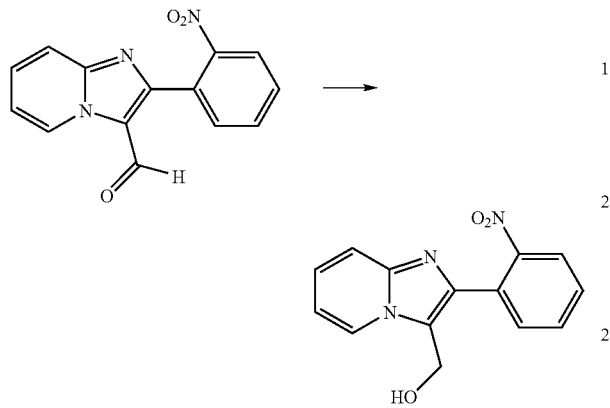

To 2-(2-Nitro-phenyl)-imidazo[1,2-a]pyridine (700 mg, 2.62 mmol) suspended in methanol (30 ml) cooled to 0° C. was charged a solution of NaBH₄ (99 mg, 2.62 mmol) in methanol (2 ml). After stirring at 0° C. for 15 min, the solution was warmed to room temperature and stirred for 1.5 hours. The pH was adjusted to 6 with 4 N HCl, and the solution concentrated to remove the methanol. The yellow solid was colleted by filtration, washed with water and dried thoroughly to obtain the product as a yellow solid (539 mg, 76% yield). (MS, M⁺+H=270.1)

Preparation of 3-Chloromethyl-2-(2-nitro-phenyl)-imidazo[1,2-a]pyridine

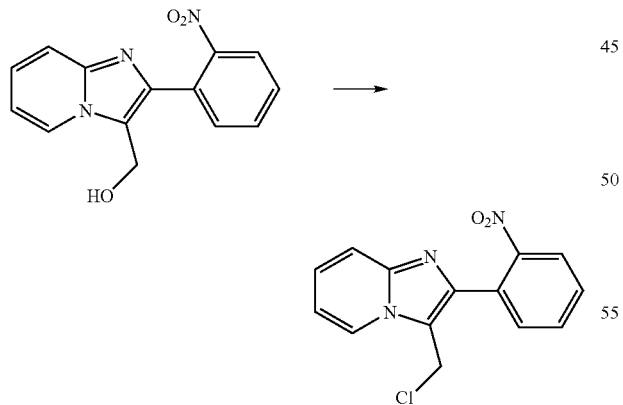

To [2-(2-Nitro-phenyl)-imidazo[1,2-a]pyridin-3-yl]-methanol (500 mg, 1.86 mmol) suspended in CH₂Cl₂ (25 ml) was added dropwise thionyl chloride (662 mg, 3 eq). The reaction was stirred at room temperature for 3.5 hours, concentrated to dryness, chased with CH₂Cl₂ and dried under reduced pressure to obtain the product as a white solid in quantitative yield. (MS, M⁺+H=270.1, reacts with water diluent.

Preparation of 2-(3-Dimethylaminomethyl-imidazo[1,2-a]pyridin-2-yl)-phenylamine

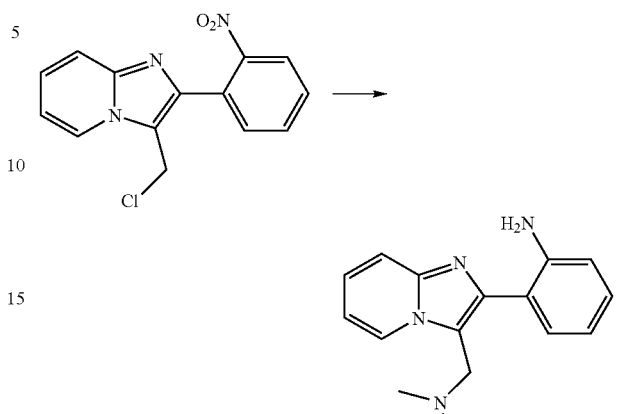

To 3-Chloromethyl-2-(2-nitro-phenyl)-imidazo[1,2-a]pyridine (324 mg, 1.0 mmol) suspended in CH₂Cl₂ (20 ml) cooled to 0° C. was added dropwise triethylamine (303 mg, 3 eq), followed by 2 M dimethylamine in THF (8 mmol, 4 ml) in two portions over a 5 hour period. The reaction mixture was concentrated to dryness, dissolved in CH₂Cl₂ (20 ml) washed with water, brine, dried over Na₂SO₄, concentrated and purified by chromatography using a 9:1 mixture of CH₂Cl₂/MeOH. The fractions were concentrated, dissolved in THF (15 ml), and stirred over H₂ balloon with 10% Pd/C (10 mg) overnight. The reaction mixture was filtered through Celite and concentrated to obtain the product as a yellow solid (164 mg). (MS, M⁺+H=267.1)

Preparation of Compound 350

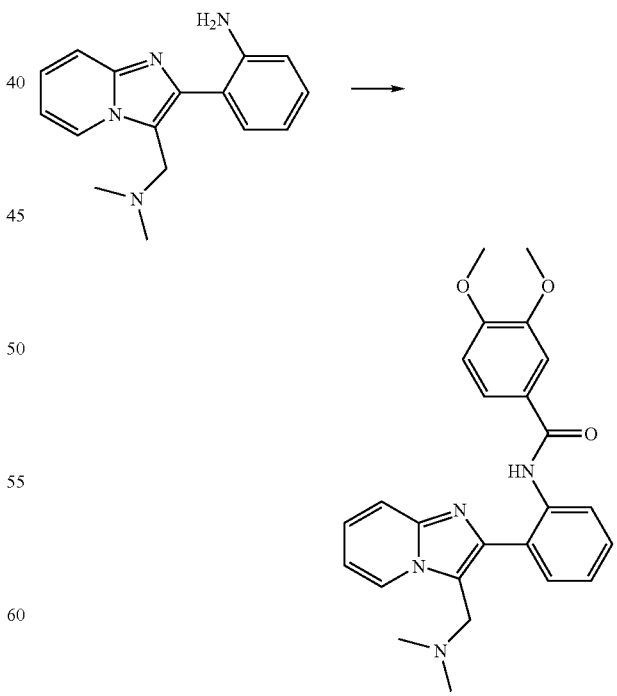

In a typical run to prepare Compound 350, 2-(3-Dimethylaminomethyl-imidazo[1,2-a]pyridin-2-yl)-phenylamine (200 umol, 53 mg) in 2 ml of pyridine was stirred with 3,4-dimethoxybenzoyl chloride (200 umol, 40 mg) at room temperature overnight. The reaction mixture was quenched by the addition of 10 ml H₂O, concentrated and purified by chromatography using a 90:9:1 mixture of CH₂Cl₂/Methanol/Triethylamine. Trituration with pentane gave the product as a tan solid. Higher purity can be achieved with additional silica gel column chromatography (100% EtOAc) and/or prep TLC (5% MeOH in CH₂Cl₂ w/7M NH₃). (MS, M⁺+H=431.1)

Compound 351 was prepared in an analogous manner to Compound 350, using the appropriate acid chlorides.

Preparation of 4-[2-(2-Amino-phenyl)-imidazo[1,2-a]pyridin-3-ylmethyl]-piperazine-1-carboxylic acid tert-butyl ester

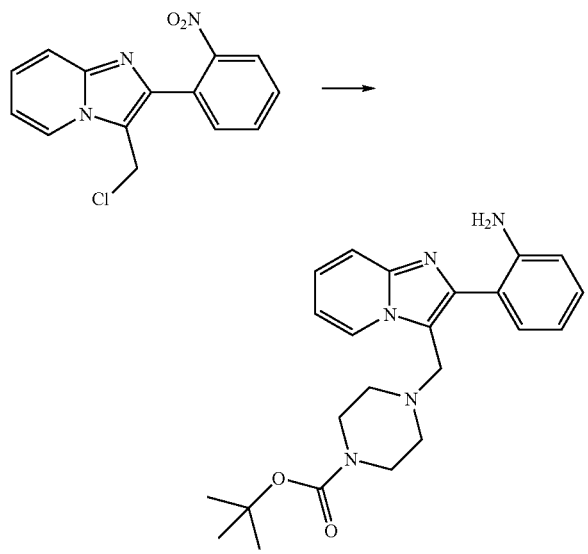

To 3-Chloromethyl-2-(2-nitro-phenyl)-imidazo[1,2-a]pyridine (298 mg, 0.92 mmol) suspended in CH₂Cl₂ (15 ml) cooled to 0° C. was added dropwise triethylamine (279 mg, 3 eq), followed by 1-Boc-piperazine (1.3 eq, 221 mg) in two portions over a 24 hour period. The reaction mixture was concentrated to dryness and purified by chromatography using a 9:1 mixture of CH₂Cl₂ to MeOH. The fractions were concentrated, dissolved in Ethanol (20 ml), and stirred over H₂ atmosphere with 10% Pd/C (10 mg) for 48 hours. The reaction mixture was filtered through Celite and concentrated, and dried under high vacuum to obtain 250 mg of the desired product. (MS, M⁺+H=408.2)

Preparation of Compound 359

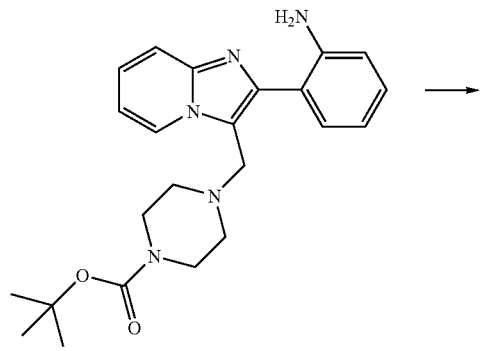

-continued

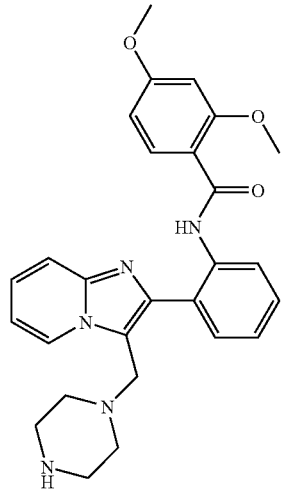

In a typical run to prepare Compound 359, 4-[2-(2-Amino-phenyl)-imidazo[1,2-a]pyridin-3-ylmethyl]-piperazine-1-carboxylic acid tert-butyl ester (150 umol, 61 mg) in 2 ml of pyridine was stirred with 2,4-dimethoxybenzoyl chloride (150 umol, 30 mg) for 3 hours at room temperature. The reaction was quenched with 1 ml H₂O, concentrated and purified by silica gel chromatography (0 to 5% MeOH in CH₂Cl₂). The fractions were concentrated, treated with TFA/CH₂Cl₂ for 5 hours, concentrated to dryness, chased with CH₂Cl₂ (2×10 mL), pumped under high vacuum and triturated with 1:1 Pentane/Ether to obtain the Bis TFA salt as a white solid, (46 mg). (MS, M⁺+H=472.1)

Compounds 362 and 364 were prepared in an analogous manner to Compound 359, using the appropriate acid chlorides.

Preparation of 2-(2-Nitro-phenyl)-imidazo[1,2-a]pyrimidine

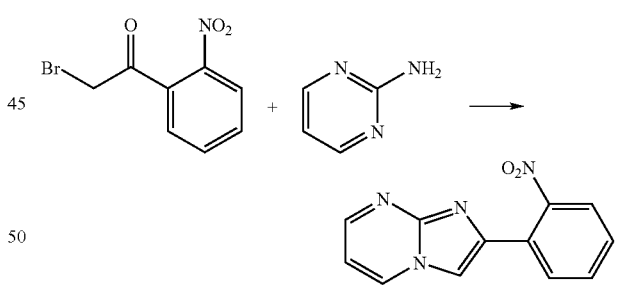

2-Bromo-2'-nitroacetophenone (5.0 g, 20.4 mmol) and 2-aminopyrimidine (1.94 g, 20.4 mmol) were dissolved in acetone (50 ml) and brought to reflux. After 60 minutes a light white precipitate developed. Refluxing was continued for 5.5 hours and cooled to room temperature. The volume was reduced 1 by evaporation and the intermediate solids were collected by filtration, washed with acetone (20 ml) and air dried (2.84 g of intermediate). A second crop was collected by concentration of the combined mother liquors, and refluxing the residue in fresh acetone (20 ml) for 1.5 hours. Upon cooling, and reducing the volume by 1 by evaporation, 3.11 g of solids were collected. The combined solid intermediate (5.95 g) was dissolved in MeOH (70 ml) with 5 drops of conc. HBr and refluxed for 2 hours. After cooling the volume was reduced by ½, water (40 ml) was added solution was made basic (pH=10) with 1N NaOH. Roto-evaporation to remove methanol resulted in the product crystallizing. The product was filtered, washed with water and air dried to obtain 5.03g of the desired product. (MS, M⁺+H=241.0)

Preparation of
2-Imidazo[1,2-a]pyrimidin-2-yl-phenylamine

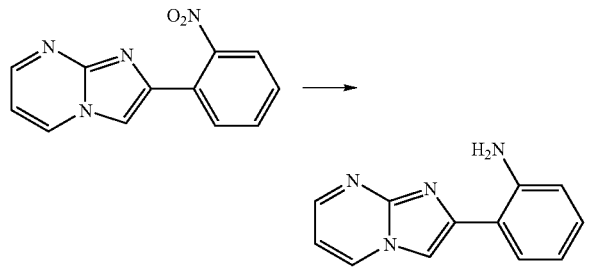

2-(2-Nitro-phenyl)-imidazo[1,2-a]pyrimidine (2 g, 8.33 mmol) and NaHS (2.8 g, 6 eq) were refluxed in 25% aqueous methanol (40 ml) water overnight. The reaction mixture was cooled to room temperature, and concentrated to dryness. Methanol (10 ml) and water (30 ml) were added, and the product was extracted with CH₂Cl₂ (3×100 ml). The combined organic layers were concentrated to dryness, chased with 10% MeOH:CH₂Cl₂ and dried under high vacuum at 45° C. to obtain the product as an orange solid (1.34 g, 76% yield). (MS, M⁺+H=211.1)

Preparation of Compound 437

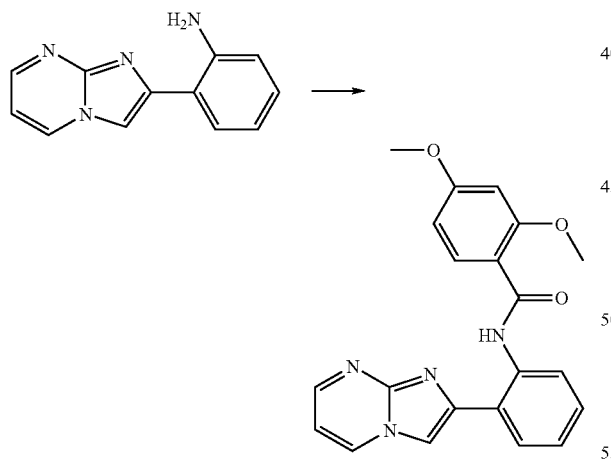

In a typical run to prepare Compound 437, 2-Imidazo[1,2-a]pyrimidin-2-yl-phenylamine (200 umol, 42 mg) in 2 ml of pyridine was stirred with 2,4-dimethoxybenzoyl chloride (200 umol, 40 mg) overnight at room temperature. The following morning the reaction mixture was concentrated to dryness, chased with CH₂Cl₂ and Pentane. Purification was performed on silica gel with a 30% to 70% EtOAc gradient in Pentane. (MS, M⁺+H=375.1)

Compounds 438, 439, 504 and 505 were prepared in an analogous manner to Compound 437, using the appropriate acid chlorides.

Preparation of 2-(5,6,7,8-Tetrahydro-imidazo[1,2-a]pyridin-2-yl)-phenylamine

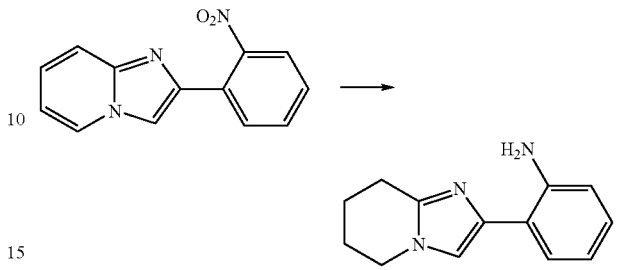

In a dry flask was charged 2-(2-Nitro-phenyl)-imidazo[1,2-a]pyridine (239 mg, 1 mmol), 10% Pd/C (15 mg), Ethanol (25 ml), water (1.5 ml) and 4M HCl (0.5 ml). The atmosphere was flushed with nitrogen and stirred over 1 atm. hydrogen over 5 days with an additional charge of Pd/C catalyst (15 mg) and 4 N HCl (4.5 ml) until reaction completion was obtained. The reaction mixture was filtered through Celite, and neutralized to pH=6 with a saturated NaHCO₃ solution. The solution was roto-evaporated to remove the ethanol, the aqueous layer was extracted with CH₂Cl₂ (2×5 ml), and the combined organic layer dried over Na₂SO₄ and concentrated to obtain the product as an oil in quantitative yield (205 mg). (MS, M⁺+H=214.1)

Preparation of Compound 545

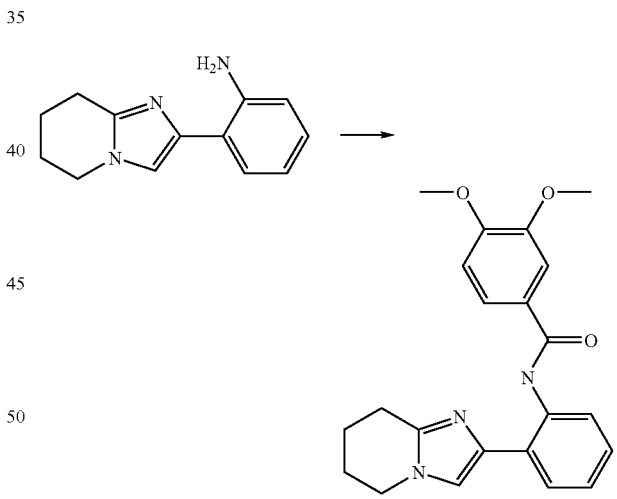

In a vial was added 2-(5,6,7,8-Tetrahydro-imidazo[1,2-a]pyridin-2-yl)-phenylamine (200 umol, 42 mg) and triethylamine (3.5 eq, 100 ul) in anhydrous CH₂Cl₂ (3 ml) followed by 3,4-dimethoxybenzoyl chloride (200 umol, 40 mg) with stirring. The reaction was stirred overnight at room temperature, concentrated to 10 dryness, and purified on silica gel with a 0% to 100% EtOAc gradient in Pentane to obtain the product as a white solid (30 mg) after trituration with pentane. (MS, M⁺+H=378.1)

Compounds 546, 547 and 548 were prepared in an analogous manner to Compound 545, using the appropriate acid chlorides.

Preparation of Compound 541

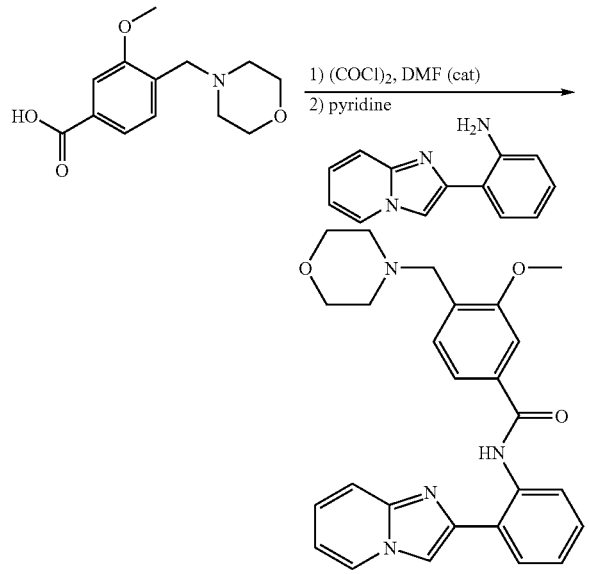

In a vial charged with 3-Methoxy-4-morpholin-4-ylmethyl-benzoic acid (125 mg, 500 umol) dissolved in anhydrous $CH_2Cl_2$ (5 mL) was added oxalyl chloride (0.5 mL, 11 eq) and 1 drop of DMF. After stirring for 3 hours the reaction was concentrated to dryness to obtain the acid chloride. To the acid chloride was added a solution of 2-Imidazo[1,2-a]pyridin-2-yl-phenylamine (500 mmol, 104 mg) in anhydrous Pyridine (5 ml). After stirring for 2 hours the reaction mixture was concentrated to dryness, suspended in EtOAc, and washed with 50% saturated $NaHCO_3$ solution. The aqueous layer was back extracted with EtOAc and the combined organic layers were dried over $Na_2SO_4$ and concentrated to obtain the crude yellow solid. Column chromatography (40 g silica, 0% to 5% MeOH gradient in $CH_2Cl_2$), concentration and triturating in methanol gave the product as a white solid (57 mg). (MS, $M^++H=443.1$)

Compounds 542 was prepared in an analogous manner to Compound 541, using 2-Imidazo[1,2-a]pyrimidin-2-yl-phenylamine.

Preparation of 2-(3-Pyrrolidin-1-ylmethyl-imidazo[2,1-b]thiazol-6-yl)-phenylamine

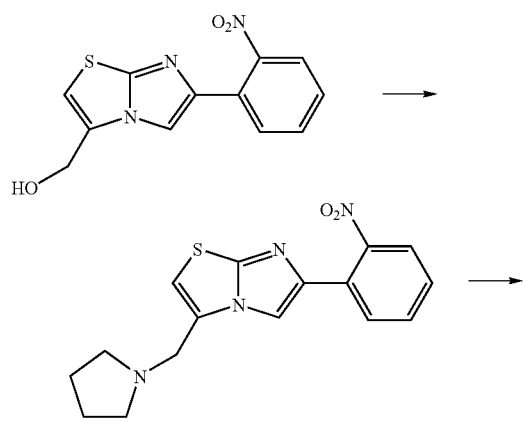

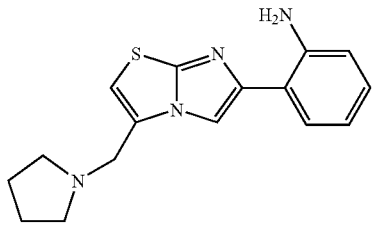

[6-(2-Nitro-phenyl)-imidazo[2,1-b]thiazol-3-yl]-methanol (110 mg, 0.4 mmol) in $CH_2Cl_2$ (5 ml) with triethylamine (56 ul, 1 eq) was cooled to 0° C. Methylsulfonyl chloride (31 ul, 1 eq) was added dropwise, stirred at 0° C. for 10 min, warmed to room temperature, and stirred for 15 min. The reaction was quenched by the addition of brine, and the mesylate was extracted with $CH_2Cl_2$, dried over $Na_2SO_4$ and concentrated. The residue was dissolved in acetonitrile (3 ml), and added triethylamine (31 ul, 1 eq), followed by pyrrolidine (66 ul, 2 eq). The reaction mixture was stirred for 2 hours, concentrated and chased with pentane. Column chromatography in $CH_2Cl_2$ (0 to 4% MeOH gradient) gave 6-(2-Nitro-phenyl)-3-pyrrolidin-1-ylmethyl-imidazo[2,1-b]thiazole. This material was dissolved in methanol (16 ml) and a solution of sodium hydrogen sulfide (112 mg, 5 eq) in water (4 ml) was added. The reaction mixture was refluxed for 2 days with additional charges of NaHS (2×112 mg). The reaction was concentrated to remove the methanol, and the aqueous solution was extracted with $CH_2Cl_2$ (3×40 ml). The organic layer was dried over $Na_2SO_4$, and concentrated to obtain the product as a yellow film, 109 mg. (MS, $M^++H=299.1$)

Preparation of Compound 620

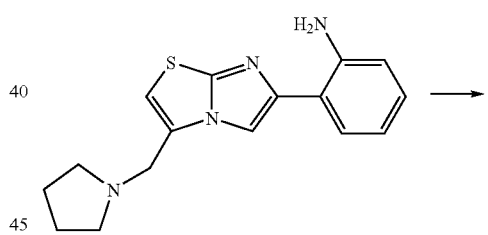

2-(3-Pyrrolidin-1-ylmethyl-imidazo[2,1-b]thiazol-6-yl)-phenylamine (200 umol) in 2 ml of pyridine was stirred with 3,4,5-trimethoxybenzoyl chloride (200 umol, 46 mg). The solution was stirred for 3 hours, concentrated to dryness, chased with Methanol and purified by prep-HPLC. The fractions were lyophilized to obtain 36 mg of the product as a TFA salt. (MS, M+H=493.1.)

Compound 619 was prepared in an analogous manner to Compound 620, using the appropriate acid chlorides.

Preparation of 6-(2-Nitro-phenyl)-imidazo[2,1-b] thiazole-3-carboxylic acid ethyl ester

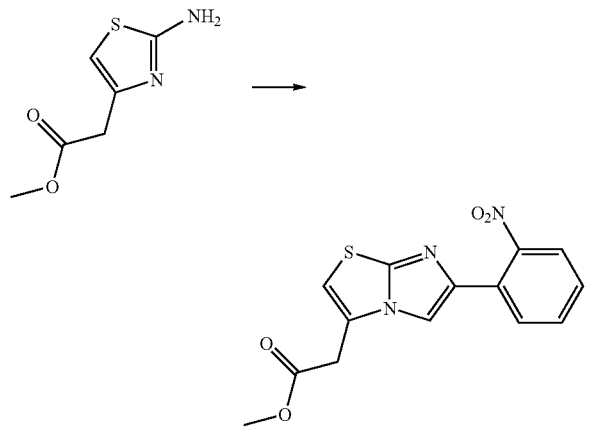

In a typical run, ethyl (2-Amino-thiazol-4-yl)-acetic acid methyl ester (1.0 g, 5.8 mmol) was mixed with 30 mL of methyl ethyl ketone along with 2-bromo-2'-nitroacetophenone (1.42 g, 5.8 mmol). The reaction mixture was refluxed for 1 hour and stirred at 90° C. overnight. It was then cooled to room temperature and concentrated to a red oil. Efforts to precipitate the product by dissolution in methanol and adding water resulted in an emulsion. Methanol was removed by roto-evaporation and the aqueous emulsion was charged to a sepratory funnel. The pH was adjusted to 9 with NaHCO$_3$, and the mixture was extracted with CH$_2$Cl$_2$ (3×50 ml). The combined organic layer was dried over Na$_2$SO$_4$, concentrated to a red oil and purified on silica gel chromatography (CH$_2$Cl$_2$ with 0 to 5% MeOH gradient). The product was obtained as a red solid (0.59 g, 32% yield). (MS, M+H=318.0.)

Preparation of [6-(2-Nitro-phenyl)-imidazo[2,1-b] thiazol-3-yl]-acetic acid

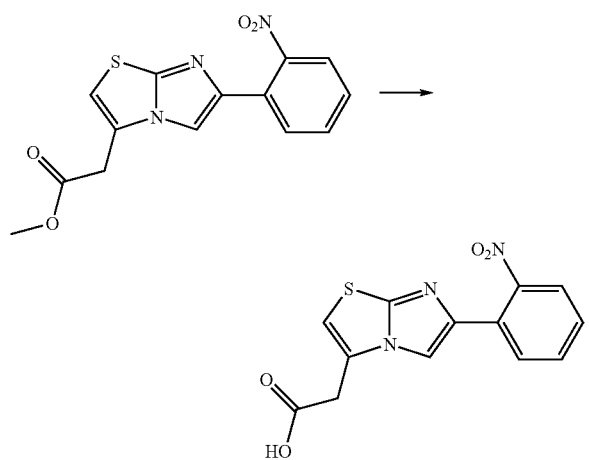

6-(2-Nitro-phenyl)-imidazo[2,1-b]thiazole-3-carboxylic acid ethyl ester (466 mg, 1.47 mmol) in 2:1 THF/Water was combined with 4 eq of NaOH (234 mg). The reaction mixture was heated to 50° C. for 3 hours. The reaction mixture was concentrated to dryness, the residue dissolved in water (20 ml), washed with CH$_2$Cl$_2$, and the aqueous layer was adjusted to pH=3 with 4N HCl. The solids were collected by filtration, washed with water and air dried to obtain the acid product was a brown solid (442 mg, 99% yield) (MS, M+H=304.0)

Preparation of Compound 649

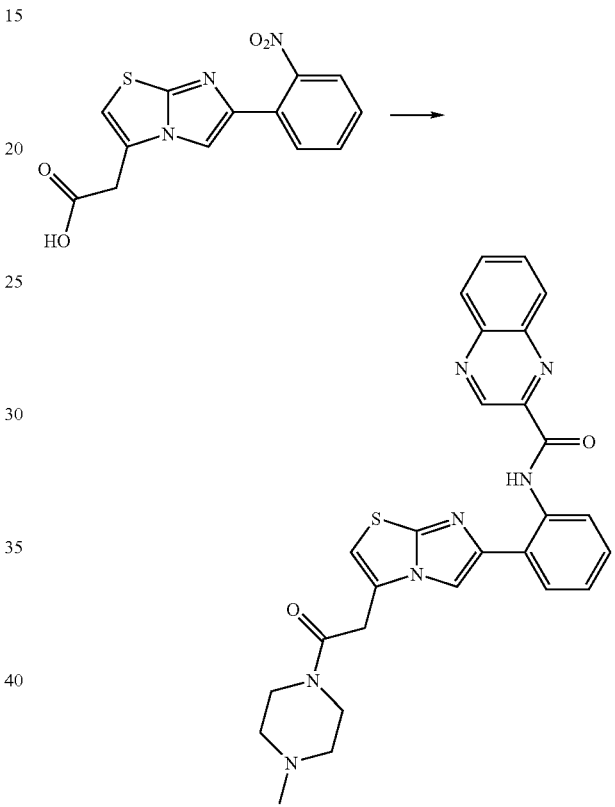

In a vial [6-(2-Nitro-phenyl)-imidazo[2,1-b]thiazol-3-yl]-acetic acid (30 mg, 100 uMol), N-methylpiperzine (10 mg, 1.0 eq), and N,N-Diisopropylethylamine (52 uL, 3.0 eq) were dissolved in CH$_2$Cl$_2$. HOAT (16 mg, 1.2 eq) was added to the reaction mixture followed by EDCI (29 mg, 1.5 eq). The reaction was stirred overnight. After adding 50% saturated NaHCO$_3$ (2 ml) and extracting with CH$_2$Cl$_2$ (3×3 mL), the organic layer was dried over Na$_2$SO$_4$, and concentrated. Trituration with Pentane gave the amide product as a brown solid.

The amide from above was dissolved in methanol (4 ml) with NaHS (34 mg, 6 eq) and microwave heated at 150° C. for 30 min. MgSO$_4$ was charged to the reaction mixture, and upon filtering, concentration, and chasing with CH$_2$Cl$_2$ (2×) the desired aniline was obtained as a red film.

The aniline from above was dissolved in pyridine (2 ml) and 2-Quinoxaloyl chloride (38 mg, 2.0 eq) was charged as a solid. After stirring overnight, the reaction was concentrated to dryness and purified on prep-HPLC to obtain the title compound as an orange solid (32.2 mg, 44% yield over 3 steps). (MS, M+H=512.2)

Preparation of Compound 650

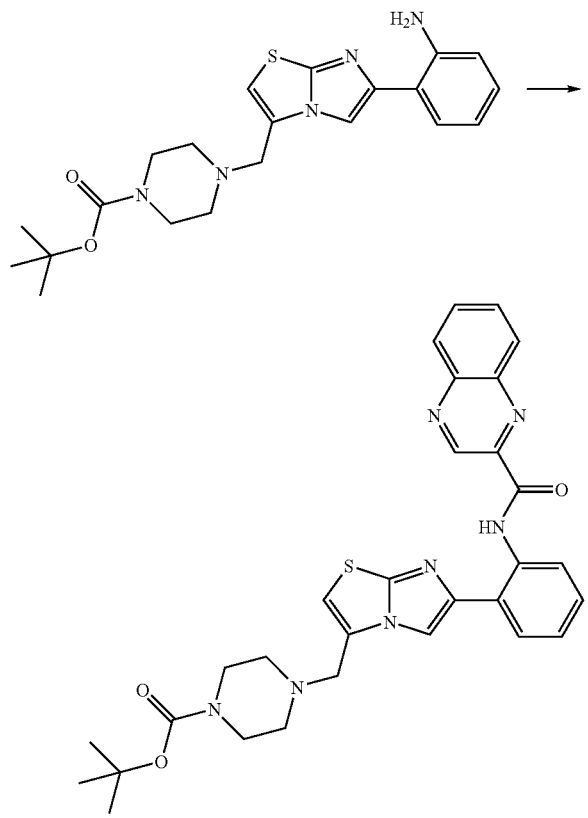

To a vial was added 4-[6-(2-Amino-phenyl)-imidazo[2,1-b]thiazol-3-ylmethyl]-piperazine-1-carboxylic acid tert-butyl ester (82 mg, 0.2 mmol), Triethylamine (56 ul, 2 eq) and anhydrous $CH_2Cl_2$ (3 ml). 2-quinoxaloyl chloride (40 mg, 1.0 eq) was added as a solid. The reaction mixture was stirred for 18 hours, concentrated and chased with $CH_2Cl_2$. Purification on silica gel with a $CH_2Cl_2$ eluent (with 95:4:1 $CH_2Cl_2$:MeOH:$Et_3N$ gradient) gave Compound 650 as a yellow solid. (MS, $M^+$+H=570.2)

Preparation of Compound 651

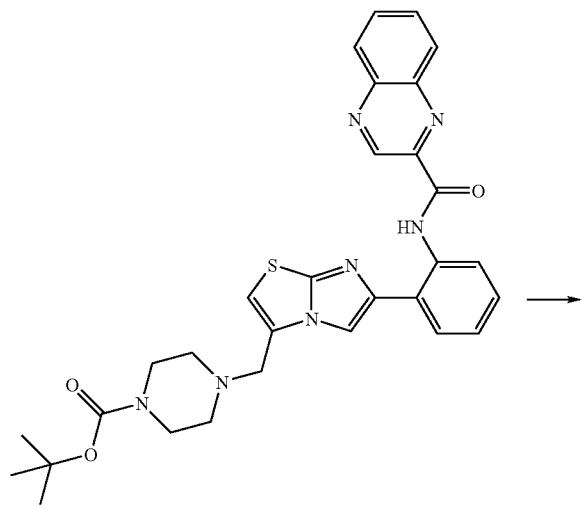

-continued

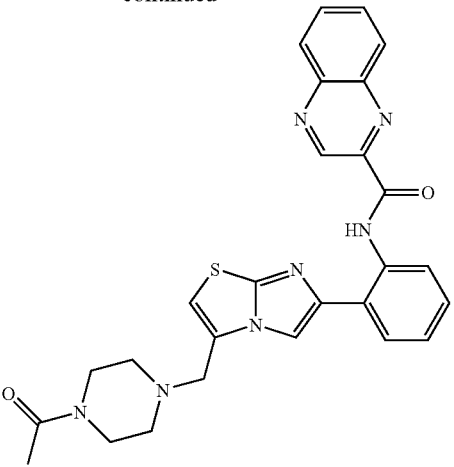

Compound 650 (105 mg, 0.185 mmol) was treated with 30% TFA in $CH_2Cl_2$ (4 ml) for 2 hours, chased with $CH_2Cl_2$ (3×) and Ether (3×), to obtain crude Compound 441. Half of the material (92 umol) was dissolved in $CH_2Cl_2$ (5 ml), along with $Et_3N$ (70 ul) and cooled to 0° C. Acetic anhydride (10 ul, 1 eq) was added and the reaction mixture was warmed to room temperature over 1 hour. The reaction was quenched by the addition of methanol and water, and concentrated to dryness. Purification on reverse phase prep HPLC and lyophilization gave Compound 651 as a TFA salt. (MS, $M^+$+H=512.2)

Preparation of 2-[6-(2-Nitro-phenyl)-imidazo[2,1-b]thiazol-3-yl]-ethanol

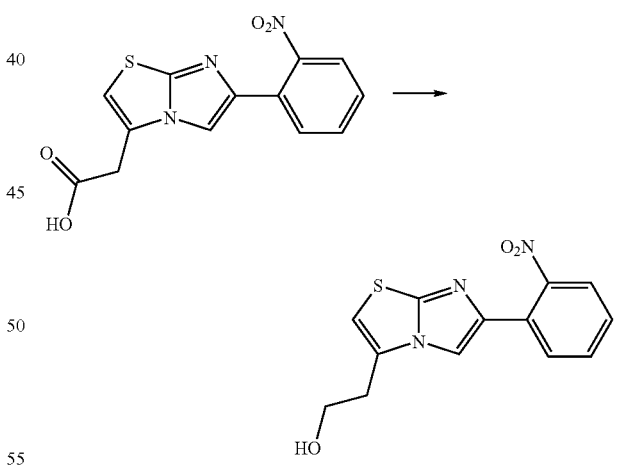

[6-(2-Nitro-phenyl)-imidazo[2,1-b]thiazol-3-yl]-acetic acid (300 mg, 1.0 mmol) was suspended in THF (20 ml), and stirred with NMM (110 ul, 1 eq) at room temperature for 1 hour. The reaction mixture was cooled to 0° C. and isobutylchloroformate (131 ul, 1 eq) was charged and the reaction mixture was stirred at 0° C. for 2 hours at which time the mixed anhydride formation was complete. A mixture of $NaBH_4$ (38 mg) in water (5 ml) was added dropwise at 0° C. and warmed to room temperature and stirred for 1 hour. The reaction did not proceed to completion with 1 eq.; therefore the $NaBH_4$ addition was repeated with 3 eq of $NaBH_4$. The

313 reaction was not complete after 1 hour, therefore the reaction mixture was concentrated to dryness, charged with fresh THF, followed by NaBH$_4$ (1 eq) and stirred overnight. LC-MS indicated the reaction was complete, therefore the mixture was concentrated to dryness, and CH$_2$Cl$_2$ (50 ml) and water (20 ml) were added. The layers were split, and the aqueous layer was extracted with CH$_2$Cl$_2$ (3×50 ml), and the combined organic layers were dried over Na$_2$SO$_4$ and concentrated to dryness. The product was purified on silica gel (Pentane with 15% to 100% EtOAc gradient), concentrated and lyophilized from CH$_3$CN:H$_2$O (160 mg, 55% yield). (MS, M$^+$+H=290.0)

Preparation of 4-{2-[6-(2-Nitro-phenyl)-intidazo[2,1-b]thiazol-3-yl]-ethyl}-piperazine-1-carboxylic acid tert-butyl ester

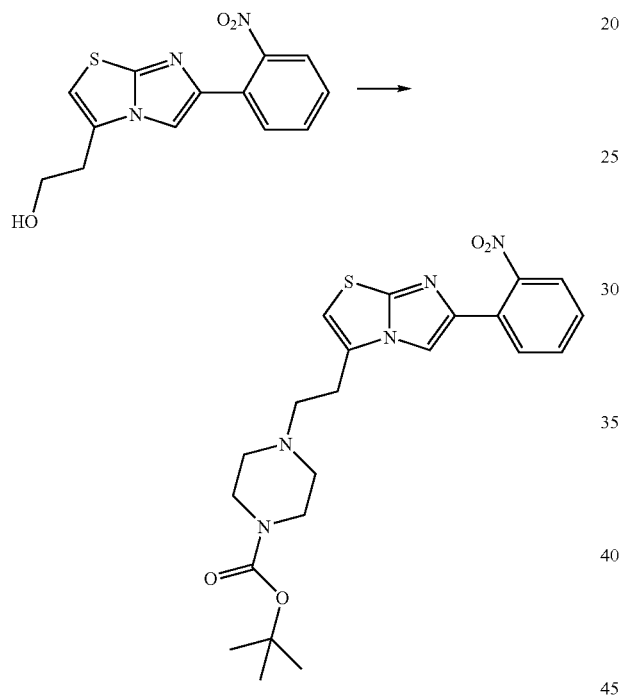

2-[6-(2-Nitro-phenyl)-imidazo[2,1-b]thiazol-3-yl]-ethanol (40 mg, 0.14 mmol) was dissolved in anhydrous CH$_2$Cl$_2$ and cooled to 0° C. Triethylamine (19 ul, 1 eq) was added followed by Methanesulfonyl chloride (11 ul, 1 eq). The reaction mixture was warmed to room temperature and stirred for 30 min. LC-MS indicated the reaction was incomplete, therefore the addition of Triethylamine (19 ul, 1 eq) and methanesulfonyl chloride (11 ul, 1 eq) was repeated. The reaction mixture was quenched with the addition of 2 ml of brine, extracted with CH$_2$Cl$_2$ (2×2 ml), dried over Na$_2$SO$_4$ and concentrated to obtain the mesylate as a yellow film.

The mesylate was dissolved in anhydrous acetonitrile (2 ml), Triethylamine (38 ul, 2 eq) and stirred with N-Boc-piperazine (26 mg, 2 eq) overnight. The reaction mixture was still exclusively the mesylate. The reaction mixture was charged with sodium iodide (41 mg) and stirred for 6 days and purified by reverse phase prep HPLC. The fractions were made alkaline with NaHCO$_3$ (sat), concentrated to remove CH$_3$CN and the aqueous layer was extracted with CH$_2$Cl$_2$. The organic layer was dried and concentrated to obtain the product as a yellow film. (MS, M$^+$+H=458.2)

314

Preparation of Compound 680

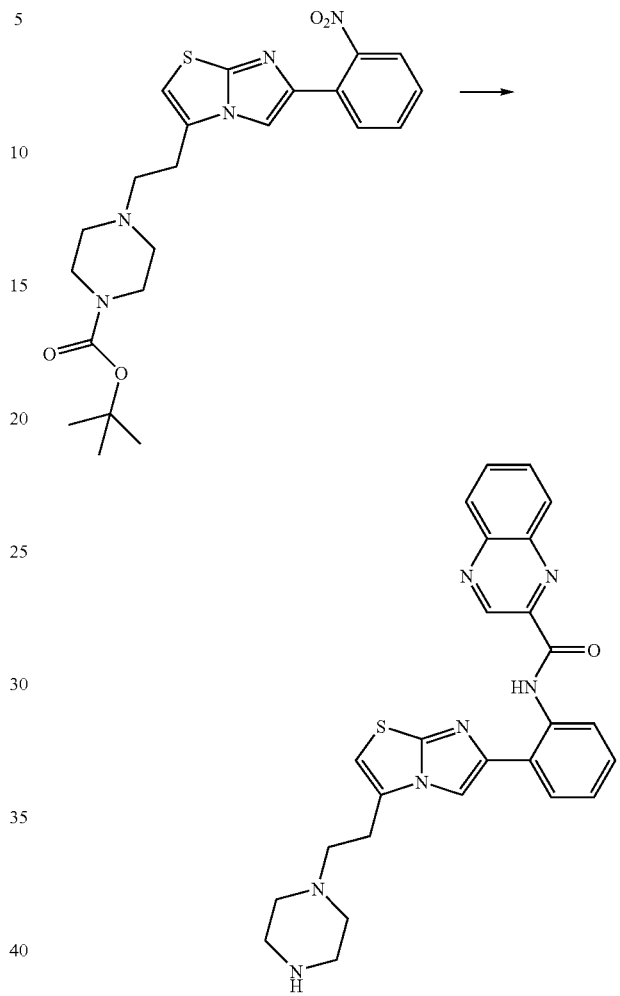

In a microwave tube was added 4-{2-[6-(2-Nitro-phenyl)-imidazo[2,1-b]thiazol-3-yl]-ethyl}-piperazine-1-carboxylic acid tert-butyl ester (24 mg, 0.05 mmol), NaHS (30 mg, 10 eq) and 5 ml of methanol. The reaction mixture was microwave heated at 150° C. for 30 min. The reaction proceeded, but was not complete. An additional 30 mg of NaHS was charged, and the reaction mixture was microwave heated at 150° C. for 30 minutes. Again, charged 15 mg of NaHS and microwave heated at 160° C. for 20 minutes. The solids were removed by filtration; the solution was dried over MgSO$_4$, and concentrated to obtain the amine intermediate. This amine (0.05 mmol) was mixed with pyridine (3 ml), with 2-quinoxaloyl chloride (20 mg, 2 eq) and microwave heated at 160° C. for 10 min. The reaction was partially complete, therefore after charging another two equivalents of 2-quinoxaloyl chloride (20 mg) the reaction was microwave heated for 20 minutes at 160° C. The reaction mixture was concentrated to dryness, and purified on silica gel chromatography (CH$_2$Cl$_2$ elluent, 0 to 5% MeOH gradient). The residue was treated with 25% TFA/CH$_2$Cl$_2$ for 3 hours, concentrated and purified on reverse phase prep HPLC. (MS, M$^+$+H=484.2).

Preparation of 3-Chloromethyl-6-(2-nitro-phenyl)-imidazo[2,1-b]thiazole

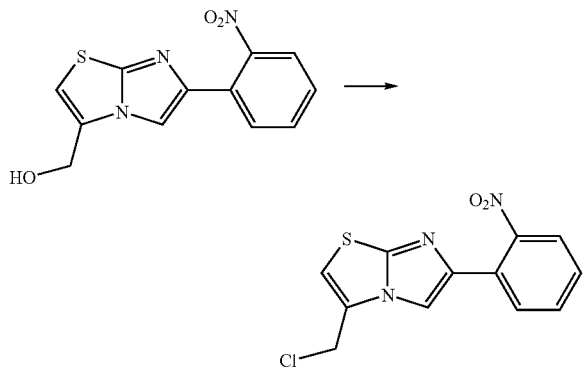

To a stirred solution of [6-(2-Nitro-phenyl)-imidazo[2,1-b]thiazol-3-yl]-methanol (1.0 g, 3.63 mmol) in anhydrous dichloromethane (15 ml) was slowly added thionyl chloride (2 ml, 7.5 eq). The solution turned homogenous, followed by development of a yellow precipitate. After 5 minutes, a catalytic amount of DMF (1 drop) was added and the mixture was stirred for 1 hour, concentrated to dryness, chased with $CH_2Cl_2$ (2×) then Ether (1×), and dried under reduced pressure. 1.53 g of yellow solid was obtained, and assumed to be quantitative yield. (MS, $M^++H=294.0$)

Preparation of Compound 700

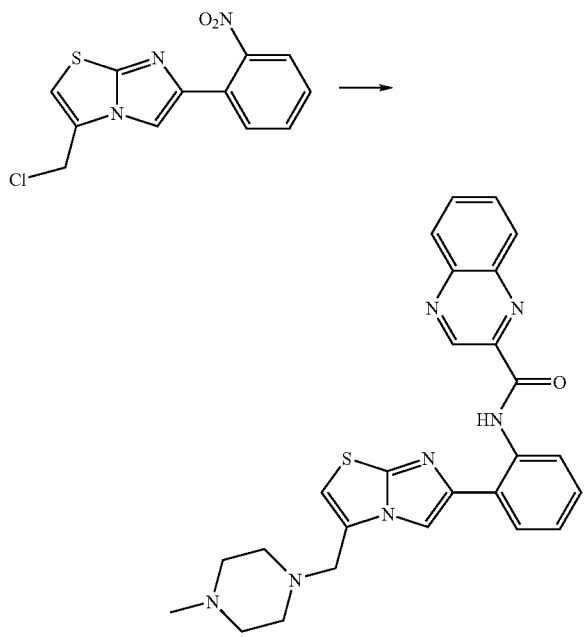

Displacement: 3-Chloromethyl-6-(2-nitro-phenyl)-imidazo[2,1-b]thiazole (126 mg, 0.300 mmol) in 2 ml of 1-methyl-piperazine was microwave heated at 110° C. for 30 minutes. The reaction mixture was concentrated to dryness, and chased with methanol to obtain crude 3-(4-Methyl-piperazin-1-ylmethyl)-6-(2-nitro-phenyl)-imidazo[2,1-b] thiazole.

Nitro reduction: The above residue was dissolved in ethanol (20 ml), and 10% Palladium on carbon was added with stirring. The atmosphere was evacuated and backfilled with Nitrogen (3×) and stirred over $H_2$ balloon (1 atm.) for 18 hours. The reaction mixture was filtered through Celite, concentrated to dryness, and chased with $CH_2Cl_2$ and pentane to obtain the amine as a red oil.

Amide Formation: The amine from above was dissolved in pyridine (3 ml), added to a microwave tube containing 2-quinoxalyl chloride (64 mg, 1.1 eq) and microwave heated for 30 minutes at 160° C. Reaction was only 50% complete, therefore another portion of 2-quinoxalyl chloride was charged and heating was continued for 30 minutes at 160° C. The reaction mixture was concentrated to dryness and purified by reverse phase prep-HPLC. (MS, $M^++H=512.2$)

Compounds 714, 715, 716, and 717 were prepared in an analogous manner to Compound 700, using the appropriate amines. (Boc protecting groups were removed by treatment with 25% TFA in $CH_2Cl_2$ for 3 hours, prior to purification.)

Preparation of Compound 718

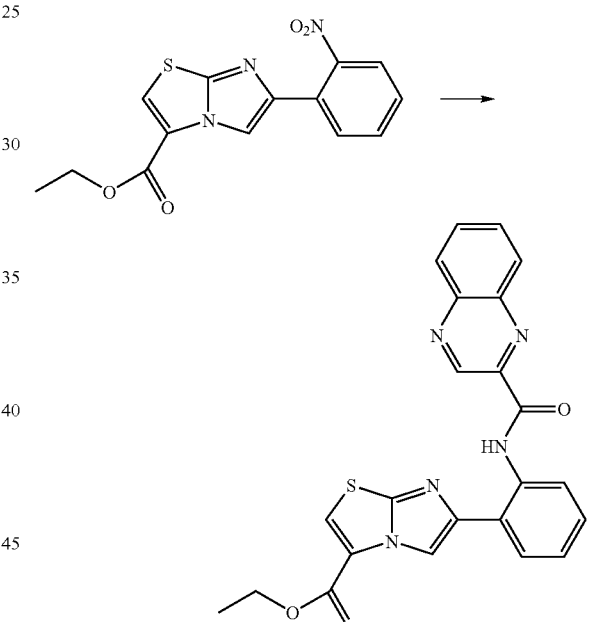

6-(2-Nitro-phenyl)-imidazo[2,1-b]thiazole-3-carboxylic acid ethyl ester (0.342 g, 1 mmol) was dissolved in 3:1 Ethanol:THF (80 ml). To the reaction mixture was added 10% Pd/C (30 mg) and the reaction mixture was stirred over $H_2$ balloon (1 atm) for 7 days with periodic charges of additional catalyst. The reaction mixture was filtered through Celite, concentrated to dryness and chased with pentane to obtain the aniline as an orange solid, 289 mg.

A portion of the aniline from above (56 mg, 200 umol) was dissolved in pyridine (4 ml) and stirred with 2-quinoxalyl chloride (46 mg 1.2 eq) overnight at room temperature. The reaction mixture was quenched with ethanol, concentrated to dryness, and chased with $CH_2Cl_2$/pentane. The residue was dissolved in $CH_2Cl_2$ and washed with 50% saturated aqueous $NaHCO_3$, dried over $Na_2SO_4$. The product was purified on silica gel ($CH_2Cl_2$ with 0 to 5% methanol gradient). (MS, $M^++H=444.1$)

Compound 720 was prepared in an identical manner to Compound 718, using [6-(2-Nitro-phenyl)-imidazo[2,1-b]thiazol-3-yl]-acetic acid methyl ester as the starting material.

Preparation of Compound 719

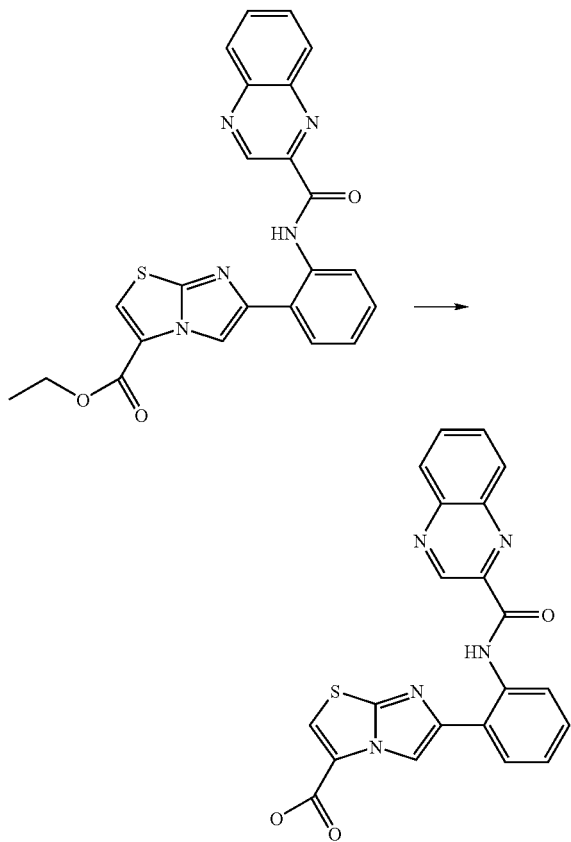

6-{2-[(Quinoxaline-2-carbonyl)-amino]-phenyl}-imidazo[2,1-b]thiazole-3-carboxylic acid ethyl ester was dissolved in 1:10 THF:Methanol (33 ml) and stirred with 1 M aqueous NaOH (4 ml) overnight. The reaction was complete by LC-MS. The reaction mixture was concentrated to remove the organics, and charged with water (20 ml). The alkaline (pH=13) aqueous layer was washed with $CH_2Cl_2$ (2×20 ml). The aqueous layer was acidified (pH=2) with 4 M HCl, and extracted with $CH_2Cl_2$ (3×20 ml). The combined organic layers were dried over $Na_2SO_4$, filtered, concentrated and triturated with pentane to obtain the desired product as an orange solid. (MS, M$^+$+H=416.0)

Compound 721 was prepared in an identical manner to Compound 719, using the analogous methyl ester starting material.

Preparation of Compound 745

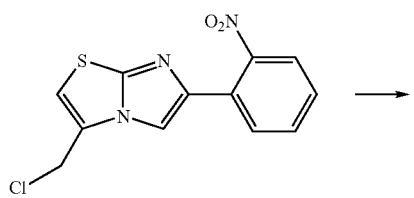

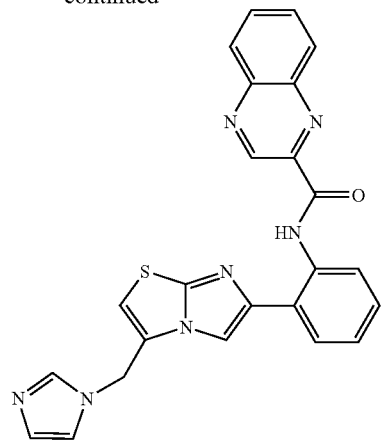

Displacement: 3-Chloromethyl-6-(2-nitro-phenyl)-imidazo[2,1-b]thiazole (0.200 mmol), imidazole (68 mg, 5 eq), and triethylamine (140 ul) in acetonitrile (3 ml) were heated at 110° C. for 30 minutes in a microwave. The reaction mixture was concentrated to dryness.

Nitro reduction: The above residue was dissolved in methanol (6 ml), and a mixture of NaHS (67 mg, 6 eq) in water (1 ml) was added, and the reaction was stirred at 60° C. overnight. The following morning another portion of NaHS (67 mg, 6 eq) was charged and the reaction was heated to 85° C. for 3 hours. The reaction was cooled, concentrated to dryness, diluted with $CH_2Cl_2$ and water and extracted with $CH_2Cl_2$ (2×40 ml). The combined organic layers were dried ($Na_2SO_4$), and concentrated.

Amide Formation: The amine from above, was dissolved in pyridine (3 ml), and stirred with 2-quinoxalyl chloride (46 mg, 1.2 eq) at room temperature for 3 hours. The reaction mixture was concentrated to dryness and purified by reverse phase prep-HPLC. And lyophilized with HCl to obtain the HCl salt. (MS, M$^+$+H=452.1)

EXAMPLE 2

Identification of Sirtuin Modulators

A fluorescence polarization or mass spectrometry based assay was used to identify modulators of SIRT1 activity. The same assay may be used to identify modulators of any sirtuin protein. The fluorescence polarization assays utilizes one of two different peptides based on a fragment of p53, a known sirtuin deacetylation target. Compounds 1-18 were tested using a substrate containing peptide 1 having 14 amino acid residues as follows: GQSTSSHSK(Ac)NleSTEG (SEQ ID NO: 1) wherein K(Ac) is an acetylated lysine residue and Nle is a norleucine. The peptide is labeled with the fluorophore MR121 (excitation 635 nm/emission 680 nm) at the C-terminus and biotin at the N-terminus. The sequence of the peptide substrate is based on p53 with several modifications. In particular, all arginine and leucine residues other than the acetylated lysine have replaced with serine so that the peptide is not susceptible to trypsin cleavage in the absence of deacetylation. In addition, the methionine residue naturally present in the sequence has been replaced with the norleucine because the methionine may be susceptible to oxidation during synthesis and purification. Compounds 19-56 were tested using a substrate containing peptide 2 having 20 amino acid residues as follows: EE-K(biotin)-GQSTSSHSK(Ac)NleSTEG-K(MR121)-EE-NH$_2$ (SEQ ID NO: 2) wherein K(biotin) is a biotinolated lysine residue, K(Ac) is an acetylated lysine residue, Nle is norleucine and K(MR121) is a lysine residue modified by an MR121 fluorophore. This peptide is labeled with the fluorophore MR121 (excitation 635 nm/emission 680 nm) at the C-termini and biotin at the N-termini. The sequence of the peptide substrates are based on p53 with several modifications. In particular, all arginine and leucine residues other than the acetylated lysine residues have replaced with serine so that the peptides are not susceptible to trypsin cleavage in the absence of deacetylation. In addition, the methionine residues naturally present in the sequences have been replaced with the norleucine because the methionine may be susceptible to oxidation during synthesis and purification. As an alternative substrate in the assay, the following peptide 3 has also been used for testing Compounds 19 through 56: Ac-EE-K(biotin)-GQSTSSHSK(Ac)NleSTEG-K(5TMR)-EE-NH2 (SEQ ID NO: 3) wherein K(Ac) is an acetylated lysine residue and Nle is a norleucine. The peptide is labeled with the fluorophore 5TMR (excitation 540 nm/emission 580 nm) at the C-terminus. The sequence of the peptide substrate is also based on p53 with several modifications. In addition, the methionine residue naturally present in the sequence was replaced with the norleucine because the methionine may be susceptible to oxidation during synthesis and purification.

The peptide substrates were exposed to a sirtuin protein in the presence of NAD$^+$ to allow deacetylation of the substrate and render it sensitive to cleavage by trypsin. Trypsin was then added and the reaction was carried to completion (i.e., the deacetylated substrate is cleaved) releasing the MR121 or 5TMR fragment. Streptavidin is then added to the reaction where it can bind both the uncleaved substrate (i.e., any remaining acetylated substrate) and the non-fluorescent portion of the cleaved peptide substrate (i.e., the biotin containing fragment). The fluorescence polarization signal observed for the full length peptide substrates bound to streptavidin was higher than the fluorescence polarization signal observed for the released MR121 or 5TMR C-terminal fragment. In this way, the fluorescence polarization obtained is inversely proportional to the level of deacetylation (e.g., the signal is inversely proportional to the activity of the sirtuin protein). Results were read on a microplate fluorescence polarization reader (Molecular Devices Spectramax MD) with appropriate excitation and emission filters.

The fluorescence polarization assays using peptide 1 was conducted as follows: 0.5 µM peptide substrate and 150 µM βNAD$^+$ is incubated with 0.1 µg/mL of SIRT1 for 60 minutes at 37° C. in a reaction buffer (25 mM Tris-acetate pH8, 137 mM Na-Ac, 2.7 mM K-Ac, 1 mM Mg-Ac, 0.05% Tween-20, 0.1% Pluronic F127, 10 mM CaCl$_2$, 5 mM DTT, 0.025% BSA, 0.15 mM Nicotinamide). Test compounds 1-18 were solubilized in DMSO and added to the reaction at 11 concentrations ranging from 0.7 µM to 100 µM.

Fluorescence polarization assays using peptide 2 may be conducted as follows: 0.5 µM peptide substrate and 120 µM βNAD$^+$ were incubated with 3 nM SIRT1 for 20 minutes at 25° C. in a reaction buffer (25 mM Tris-acetate pH8, 137 mM Na-Ac, 2.7 mM K-Ac, 1 mM Mg-Ac, 0.05% Tween-20, 0.1% Pluronic F127, 10 mM CaCl$_2$, 5 mM DTT, 0.025% BSA). Test compounds 19-56 were solubilized in DMSO and added to the reaction at 10 concentrations ranging from 300 µM to 0.15 µM in three-fold dilutions.

After the incubation with SIRT1, nicotinamide was added to the reaction to a final concentration of 3 mM to stop the deacetylation reaction and 0.5 µg/mL of trypsin was added to cleave the deacetylated substrate. The reaction was incubated for 30 minutes at 37° C. in the presence of 1 µM streptavidin. Fluorescent polarization was determined at excitation (650 nm) and emissions (680 nm) wavelengths. The level of activity of the sirtuin protein in the presence of the various concentrations of test compound is then determined and may be compared to the level of activity of the sirtuin protein in the absence of the test compound, and/or the level of activity of the sirtuin proteins in the negative control (e.g., level of inhibition) and positive control (e.g., level of activation) described below.

For the Fluorescence Polarization assays, a control for inhibition of sirtuin activity is conducted by adding 1 µL of 500 mM nicotinamide as a negative control at the start of the reaction (e.g., permits determination of maximum sirtuin inhibition). A control for activation of sirtuin activity was conducted using 3 nM of sirtuin protein, with 1 µL of DMSO in place of compound, to reach baseline deacetylation of the substrate (e.g., to determine normalized sirtuin activity).

The mass spectrometry based assay utilizes a peptide having 20 amino acid residues as follows: Ac-EE-K(biotin)-GQSTSSHSK(Ac)NleSTEG-K(5TMR)-EE-NH2 (SEQ ID NO: 3) wherein K(Ac) is an acetylated lysine residue and Nle is a norleucine. The peptide is labeled with the fluorophore 5TMR (excitation 540 nm/emission 580 nm) at the C-terminus. The sequence of the peptide substrate is based on p53 with several modifications. In addition, the methionine residue naturally present in the sequence was replaced with the norleucine because the methionine may be susceptible to oxidation during synthesis and purification.

The mass spectrometry assay is conducted as follows: 0.5 µM peptide substrate and 120 µM βNAD$^+$ is incubated with 10 nM SIRT1 for 25 minutes at 25° C. in a reaction buffer (50 mM Tris-acetate pH 8, 137 mM NaCl, 2.7 mM KCl, 1 mM MgCl$_2$, 5 mM DTT, 0.05% BSA). Test compounds may be added to the reaction as described above. The SirT1 gene is cloned into a T7-promoter containing vector and transformed into BL21(DE3). After the 25 minute incubation with SIRTI, 10 µL of 10% formic acid is added to stop the reaction. Reactions are sealed and frozen for later mass spec analysis. Determination of the mass of the substrate peptide allows for precise determination of the degree of acetylation (i.e. starting material) as compared to deacetylated peptide (product).

For the mass spectrometry based assay, a control for inhibition of sirtuin activity is conducted by adding 1 µL of 500 mM nicotinamide as a negative control at the start of the reaction (e.g., permits determination of maximum sirtuin inhibition). A control for activation of sirtuin activity is conducted using 10 nM of sirtuin protein, with 1 µL of DMSO in place of compound, to determinine the amount of deacteylation of the substrate at a given timepoint within the linear range of the assay. This timepoint is the same as that used for test compounds and, within the linear range, the endpoint represents a change in velocity.

For each of the above assays, SIRT1 protein was expressed and purified as follows. The SirT1 gene was cloned into a T7-promoter containing vector and transformed into BL21 (DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl] phosphine (TCEP), 10 μM $ZnCl_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

Sirtuin modulating compounds that activated SIRT1 were identified using the assay described above and are shown below in Table 4. Sirtuin modulating compounds that inhibited SIRT1 were identified using the assay described above and are shown below in Table 5. The $ED_{50}$ values for the activating compounds in the fluorescence polarization assay (FP) or mass spectrometry assay (MS) are represented by A' ($ED_{50}$=<5 μM), A ($ED_{50}$=5-50 μM), B ($ED_{50}$=51-100 μM), C ($ED_{50}$=101-150 μM), and D ($ED_{50}$=>150 μM). NT means that the compound was not tested using the indicated assay. NA means that the compound was not active in the indicated assay. Fold activation, as determined by MS is represented by A (Fold activation >250%), B (Fold Activation <250%), or C (no fold activation). The $ED_{50}$ of resveratrol for activation of SIRT1 is 16 μM and the fold activation of resveratrol for SIRT1 in the MS assay is approximately 200%. Similarly, the $IC_{50}$ values for the inhibiting compounds are represented by A ($IC_{50}$=<50 μM), B ($IC_{50}$=51-100 μM), C ($IC_{50}$=101-150 μM), and D ($IC_{50}$=>150 μM).

TABLE 4

Sirt1 Activators

| COMPOUND NO | [M + H]+ | STRUCTURE | $ED_{50}$ FP ASSAY | $ED_{50}$ MS ASSAY | FOLD ACT. MS |
|---|---|---|---|---|---|
| 1 | | 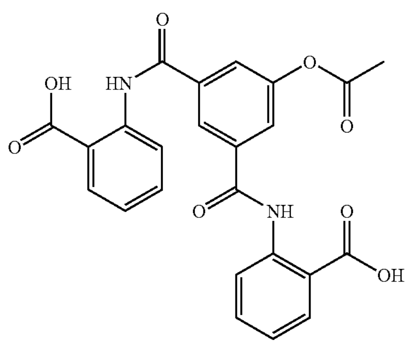 | A | NT | |
| 2 | | 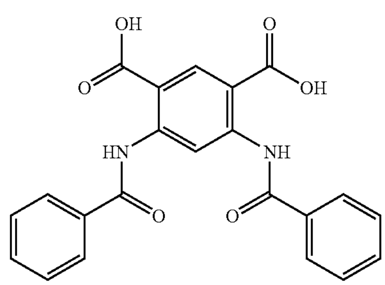 | D | NT | |
| 3 | | 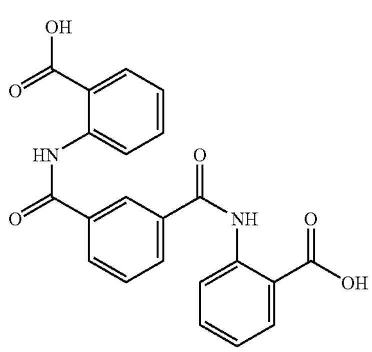 | B | NT | |

TABLE 4-continued

Sirt1 Activators

| COMPOUND NO | [M + H]+ | STRUCTURE | $ED_{50}$ FP ASSAY | $ED_{50}$ MS ASSAY | FOLD ACT. MS |
|---|---|---|---|---|---|
| 4 | | 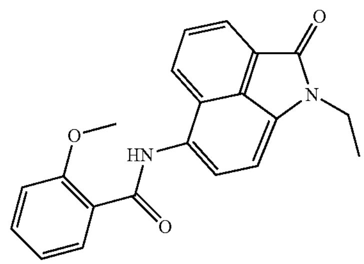 | N/A | NT | |
| 5 | | 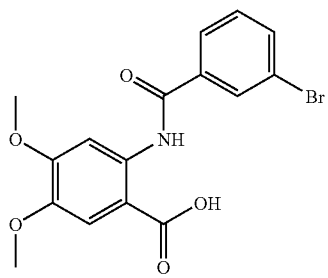 | B | NT | |
| 6 | | 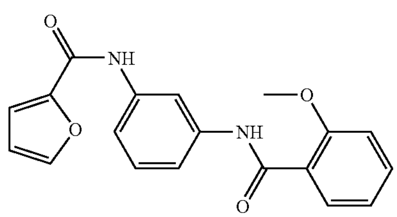 | D | NT | |
| 7 | 346 | 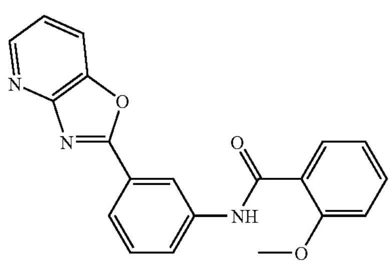 | A | NT | |
| 8 | | 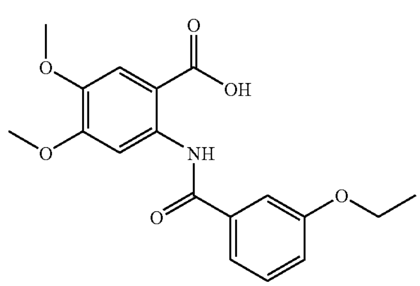 | B | NT | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 9 | | 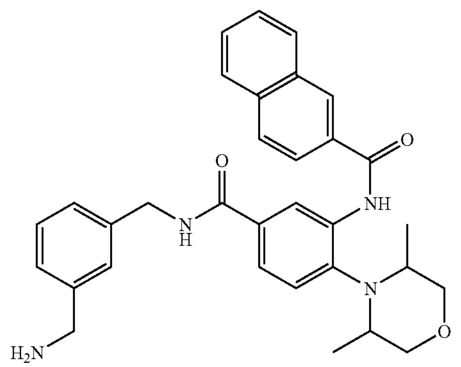 | C | NT | |
| 10 | | 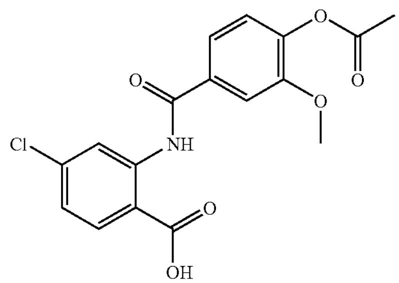 | D | NT | |
| 19 | 409.6 | 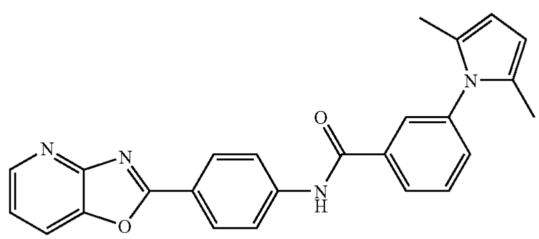 | D | D | C |
| 20 | 401.3 | 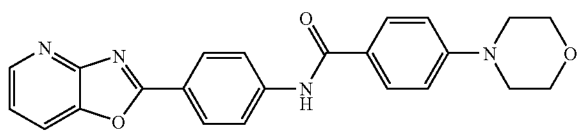 | D | D | C |
| 21 | 399.1 | 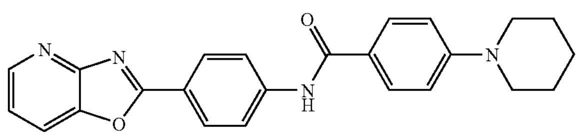 | D | D | C |
| 22 | 414.0 | 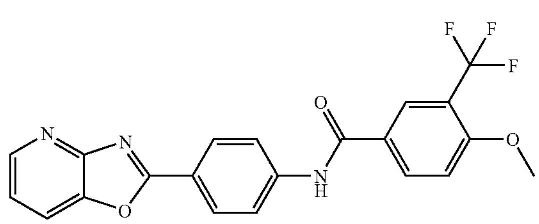 | D | D | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 24 | 359.4 | 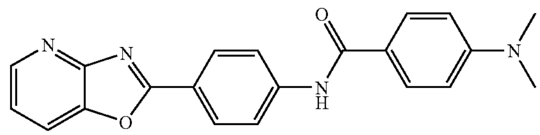 | D | D | C |
| 27 | 376.1 | 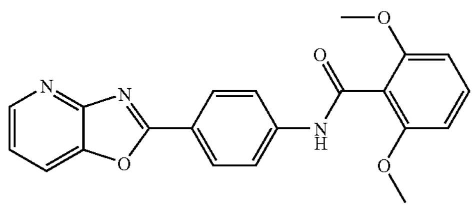 | D | D | C |
| 29 | 385.1 | 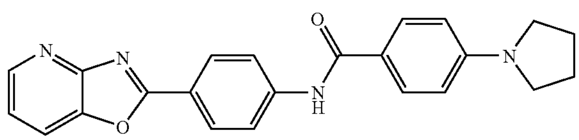 | D | D | C |
| 31 | 360.1 | 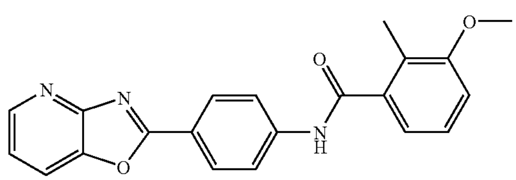 | D | D | C |
| 32 | 400.0 | 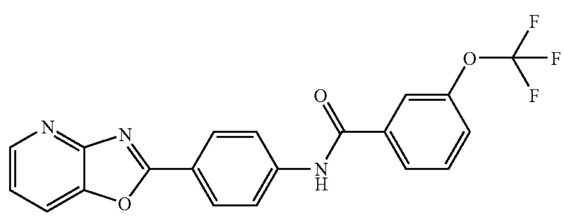 | D | D | C |
| 33 | 376.1 | 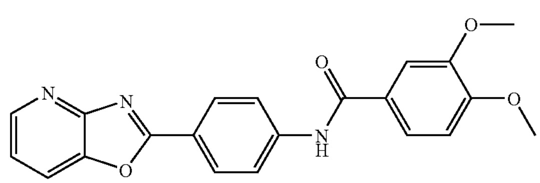 | D | D | C |
| 34 | 406.3 | 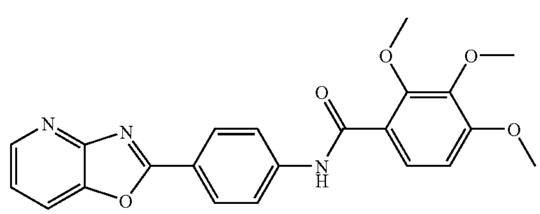 | D | D | C |
| 35 | 346.5 | 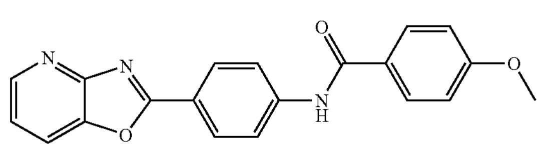 | D | D | C |

TABLE 4-continued

Sirt1 Activators

| COMPOUND NO | [M + H]+ | STRUCTURE | $ED_{50}$ FP ASSAY | $ED_{50}$ MS ASSAY | FOLD ACT. MS |
|---|---|---|---|---|---|
| 36 | 376.7 | 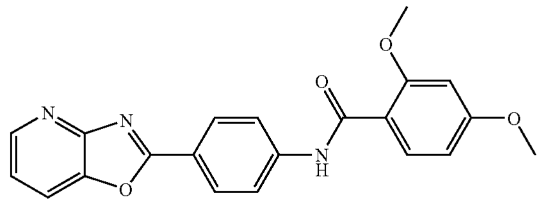 | D | D | C |
| 37 | 316.4 | 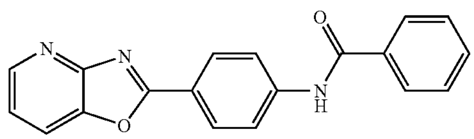 | D | D | C |
| 38 | 401.0 | 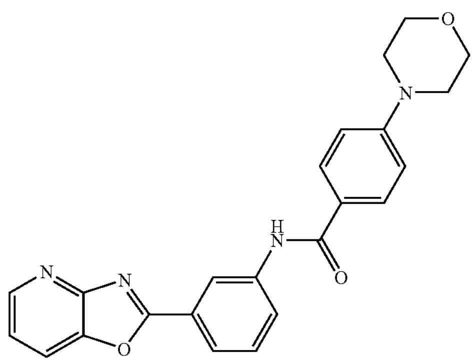 | D | D | C |
| 39 | 399.1 | 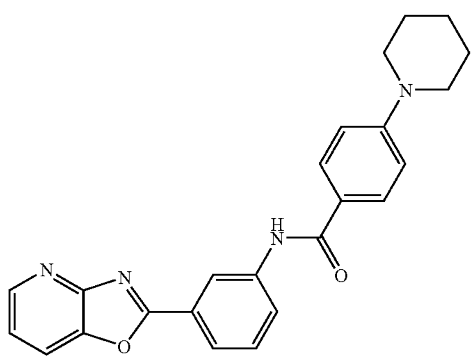 | D | D | C |
| 40 | 414.2 | 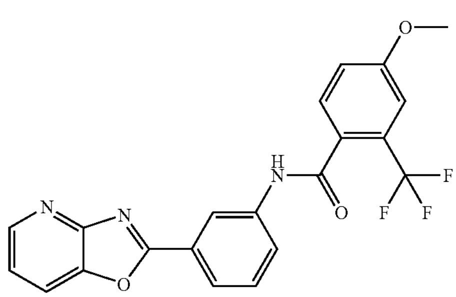 | D | D | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 41 | 414.2 | 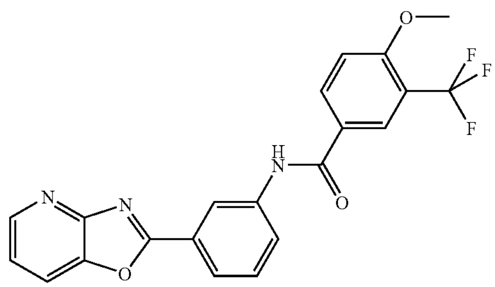 | D | D | C |
| 42 | 359.1 | 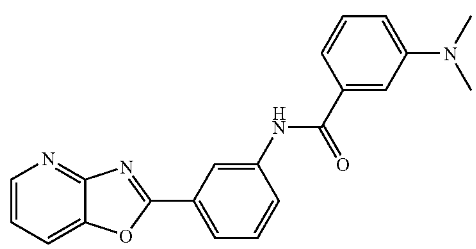 | A | A | B |
| 43 | 359.1 | 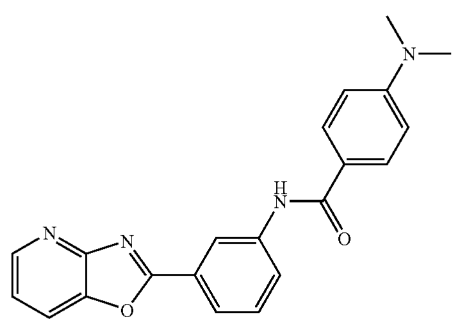 | A | A | B |
| 45 | 341.0 | 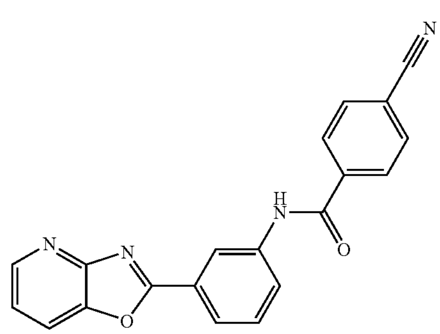 | D | D | C |
| 46 | 376.1 | 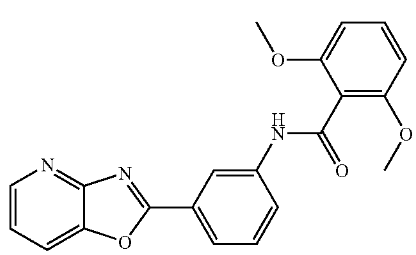 | D | D | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 48 | 406.3 | | D | D | C |
| 49 | 360.1 | | D | A | B |
| 50 | 400.0 | | NT | D | |
| 51 | 360.1 | | A | A | B |
| 52 | 376.1 | | A | A | B |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 53 | 406.1 | 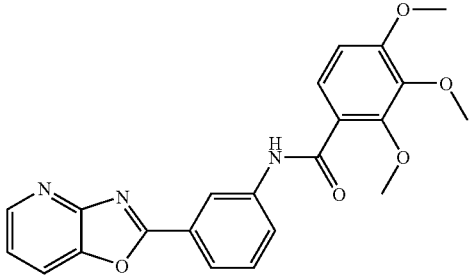 | D | D | C |
| 54 | 346.4 | 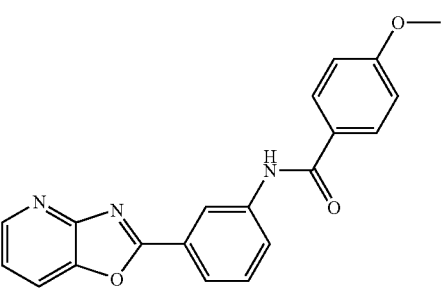 | NT | D | |
| 55 | 376.1 | 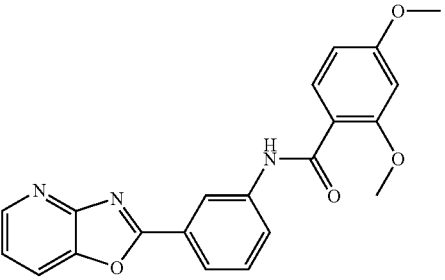 | A | A | B |
| 56 | 316.0 | 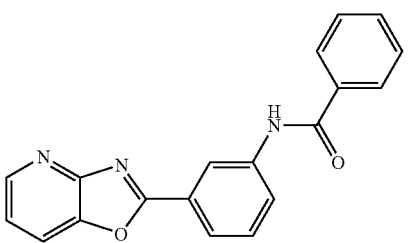 | D | A | B |
| 57 | 407.1 | 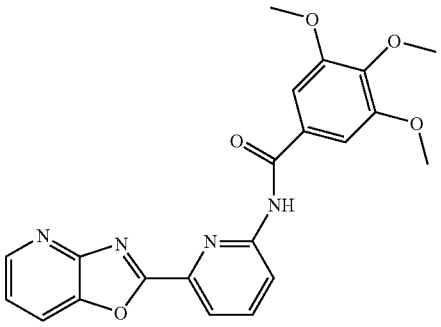 | | | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 58 | 377.1 | 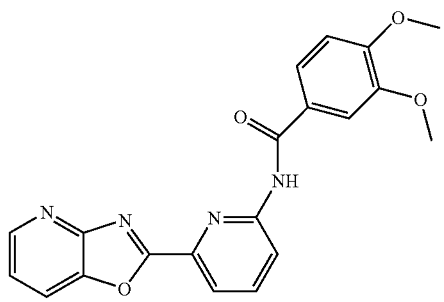 | | NA | |
| 59 | 318.1 | 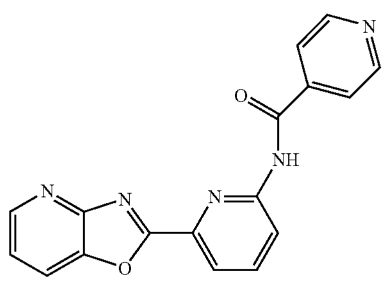 | | NA | |
| 60 | 413.1 | 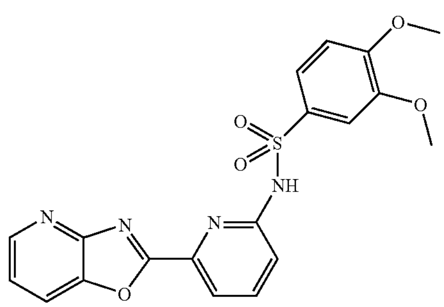 | | A | |
| 61 | 413.1 | 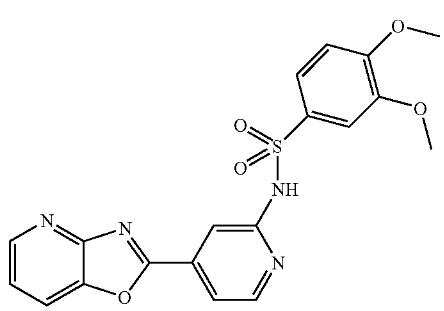 | | NA | |
| 62 | 349.0 | 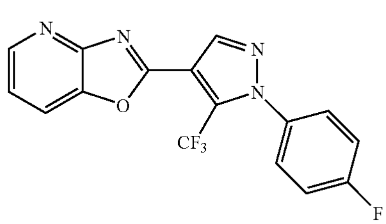 | | NA | |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 63 | 377.1 | 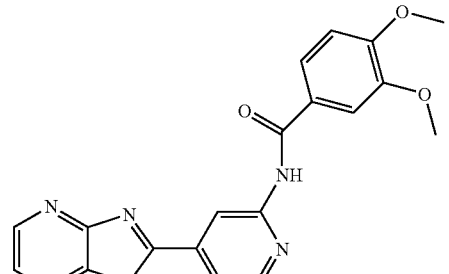 | | | A |
| 64 | 360.1 | 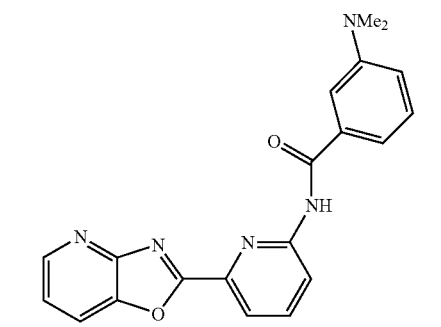 | | | A |
| 65 | 383.0 | 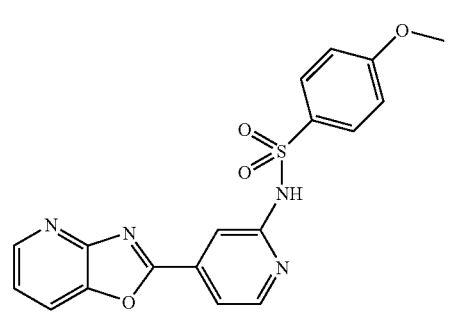 | | | NA |
| 66 | 407 | 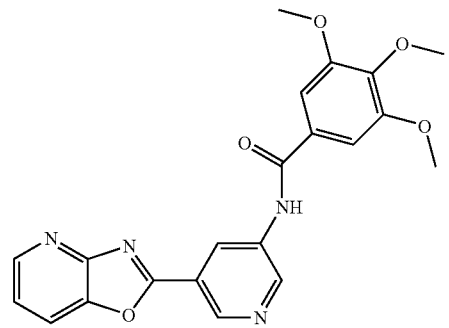 | | | A |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 67 | 377 | 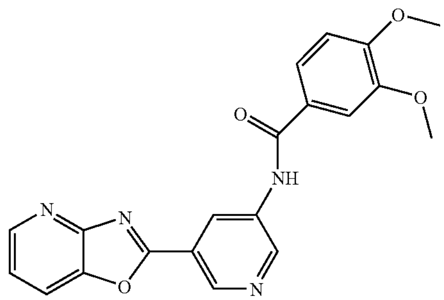 | | A | |
| 68 | 360 | 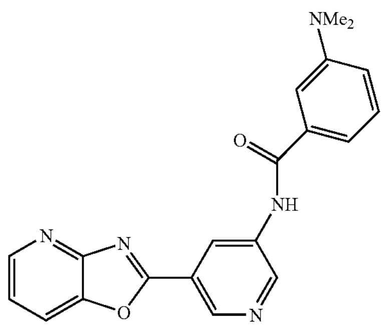 | | A | |
| 69 | 377.1 | 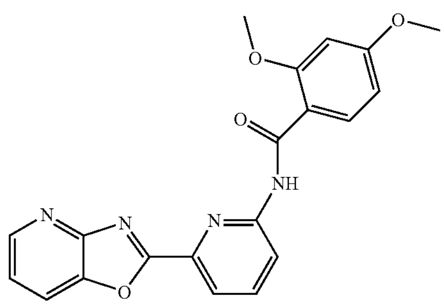 | | A | B |
| 70 | 360.1 | 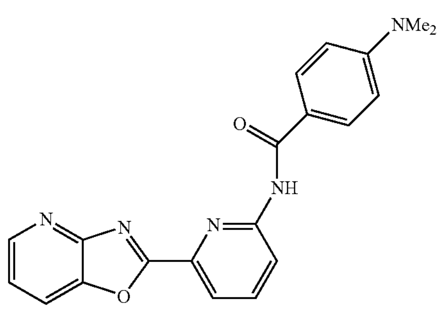 | | A | B |
| 71 | 376.1 | 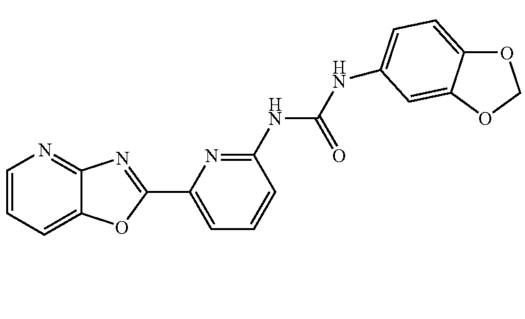 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 72 | 422.1 | 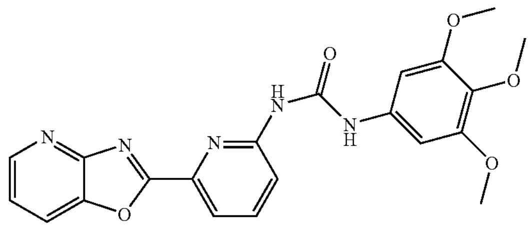 | | NT | |
| 73 | 377 | 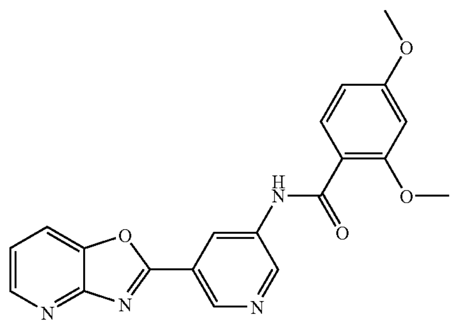 | | NT | |
| 74 | 412 | 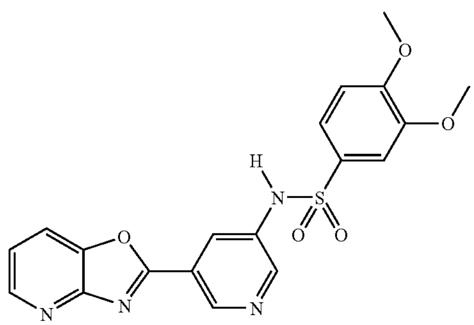 | | D | C |
| 75 | 407.1 | 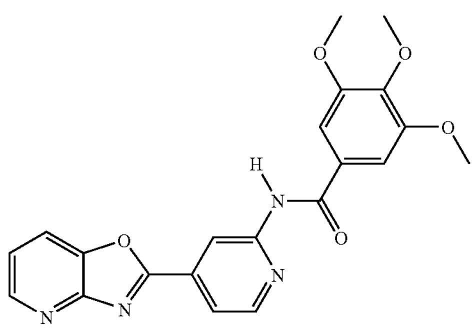 | | A | B |
| 76 | 360.1 | 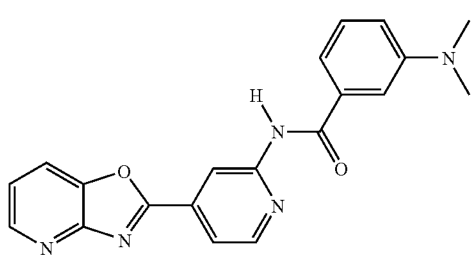 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 77 | 376.1 | 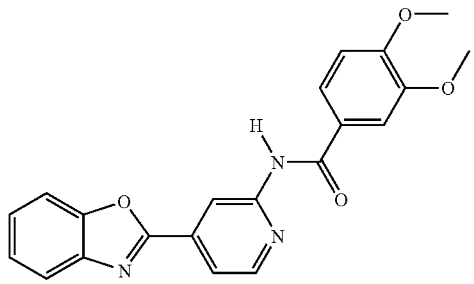 | | A | B |
| 78 | 445.1 | 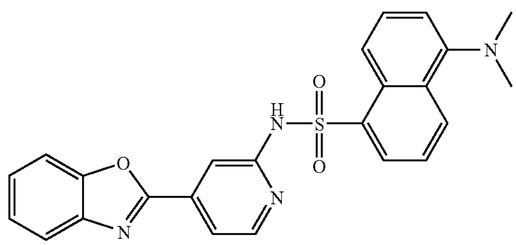 | | | |
| 79 | 338 | 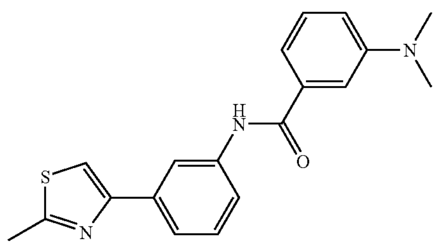 | | D | C |
| 80 | 355 | 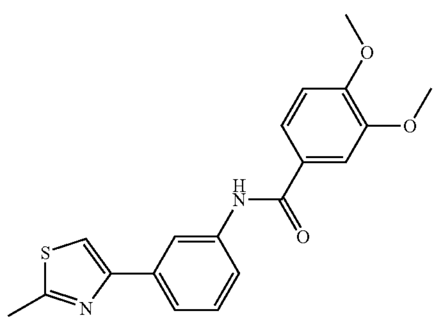 | | A | B |
| 81 | 354.5 | 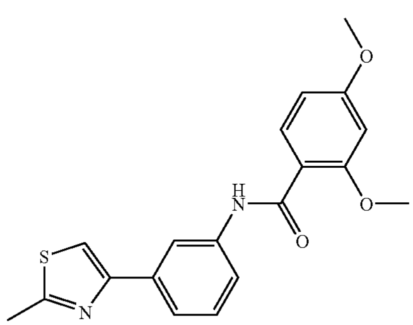 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 82 | 402 | 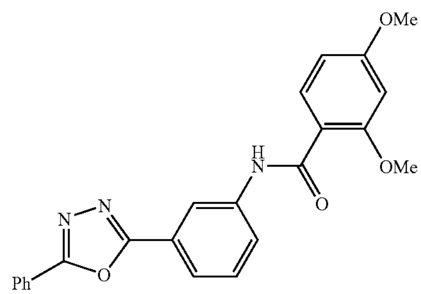 | | C | |
| 83 | 355 | 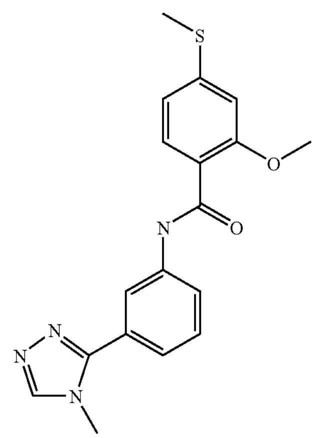 | A | B | |
| 84 | 417 | 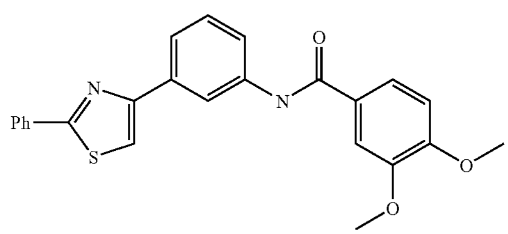 | A | B | |
| 85 | 335.1 | 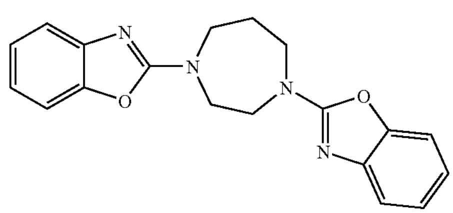 | D | C | |
| 86 | 375.1 | 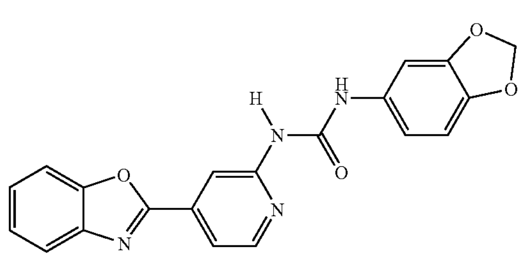 | D | C | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 87 | 375.1 | 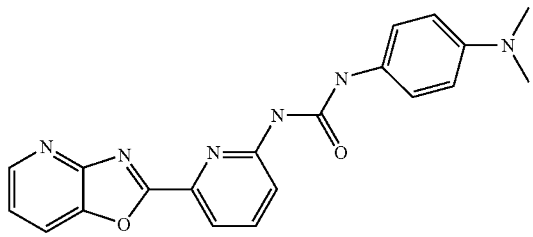 | | D | C |
| 88 | 382.1 | 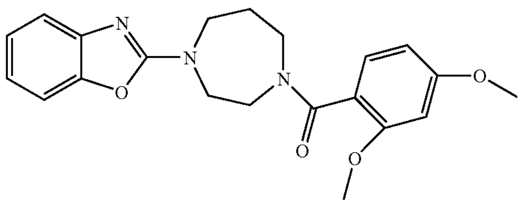 | | D | C |
| 89 | 365.1 | 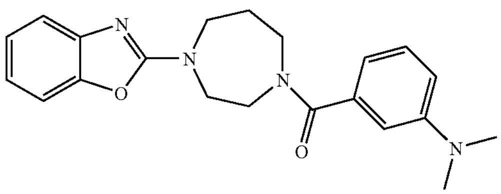 | | D | C |
| 90 | 381.1 | 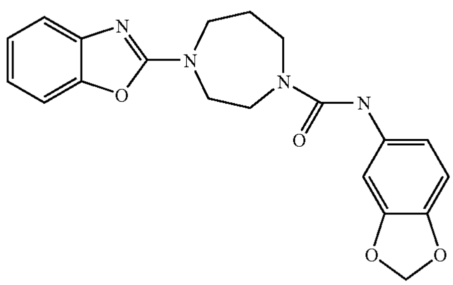 | | | |
| 91 | 412.1 | 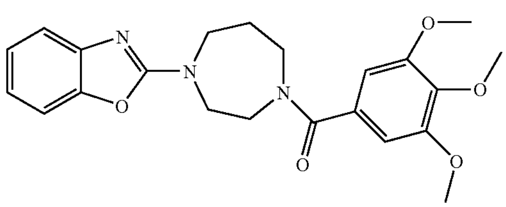 | | D | C |
| 92 | 308.1 | 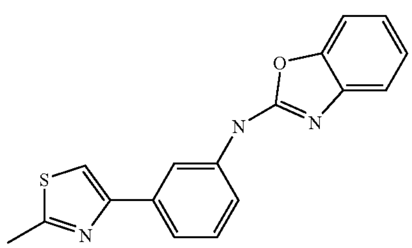 | | A | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 93 | 329.1 | 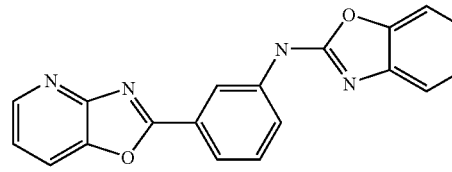 | | A | B |
| 94 | 434.1 | 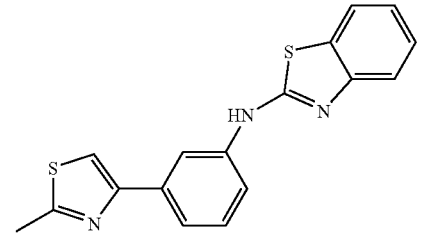 | | A | B |
| 95 | 345.1 | 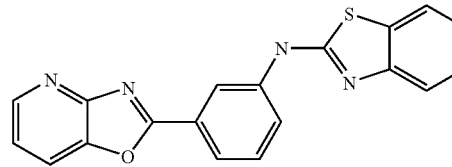 | | A' | B |
| 96 | 376.1 | 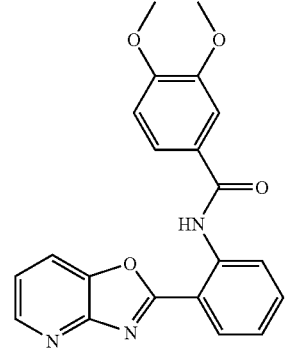 | | A' | B |
| 97 | 359.1 | 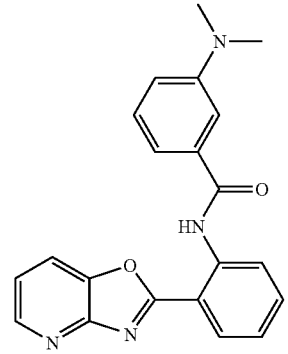 | | A' | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 98 | 408.1 | 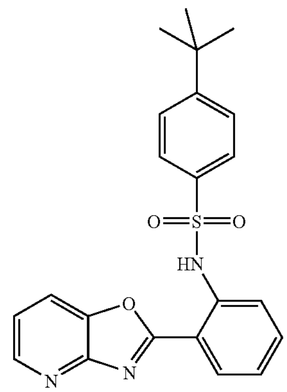 | | D | C |
| 99 | 391 | 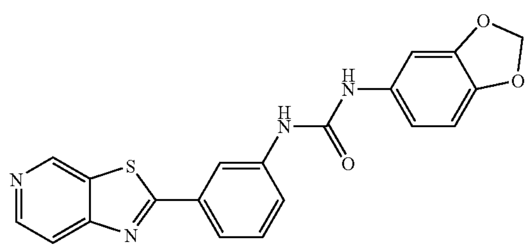 | A' | | A |
| 100 | 376 | 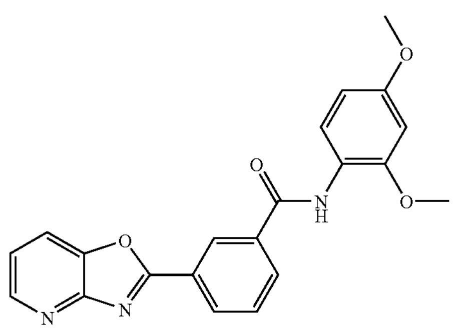 | A | | B |
| 101 | 376 | 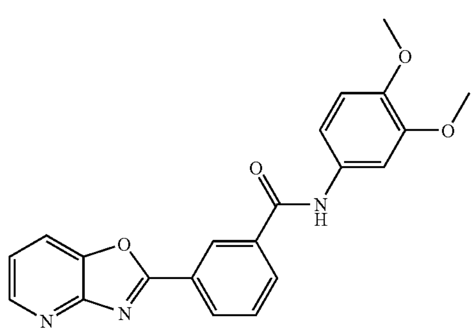 | A | | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 102 | 406 | 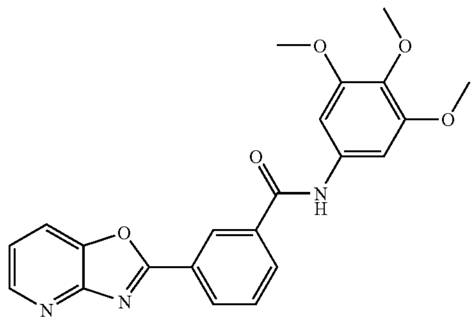 | | A | A |
| 103 | 374 | 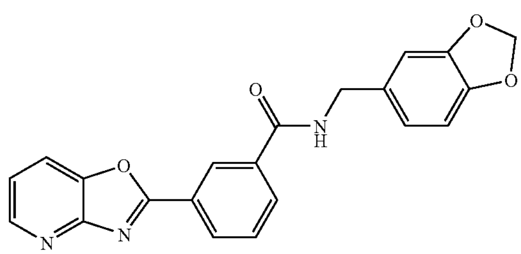 | | D | C |
| 104 | 346.1 | 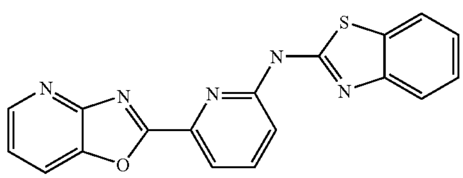 | | A' | B |
| 105 | 330.1 | 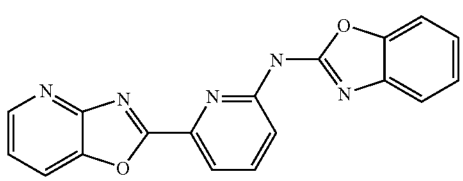 | | A' | B |
| 106 | 406.1 | 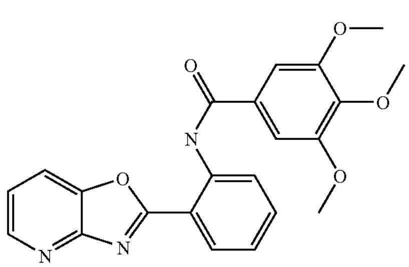 | | A' | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 107 | 488 | 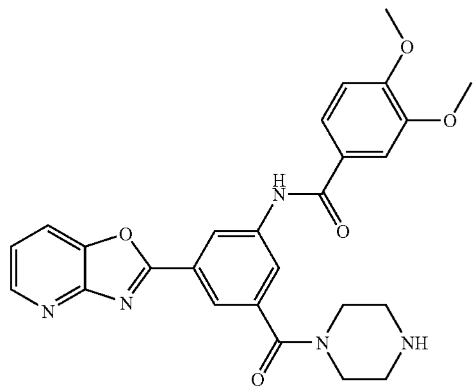 | | A | B |
| 108 | 324 | 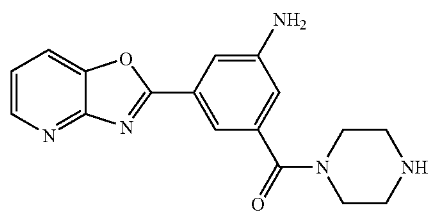 | | NA | |
| 109 | 401 | 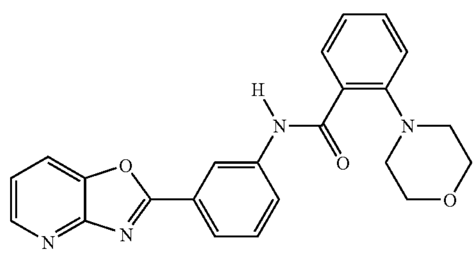 | | A | B |
| 110 | 381 | 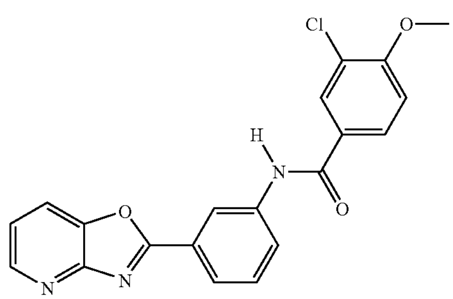 | | C | |
| 111 | 359 | 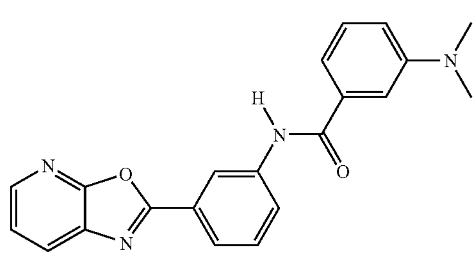 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 112 | 376 | 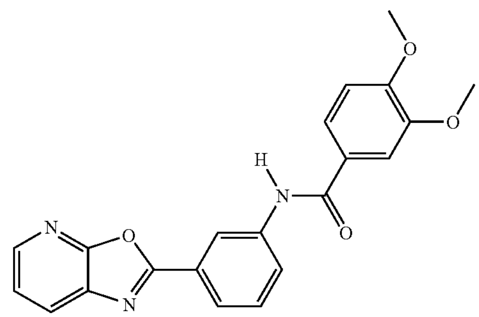 | | A | B |
| 113 | 375 | 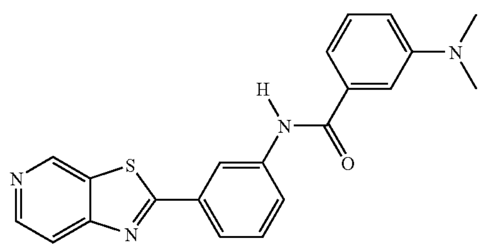 | | A | B |
| 114 | 392 | 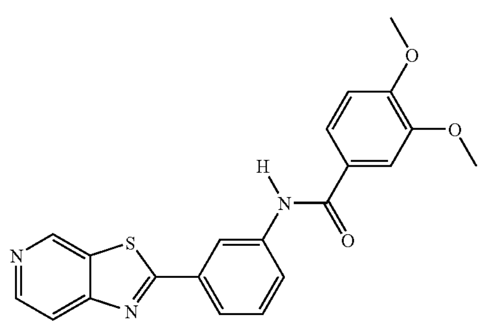 | | A' | A |
| 115 | 422 | 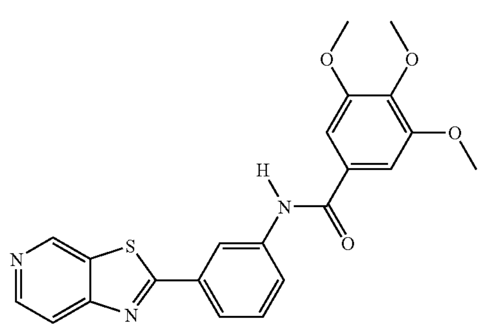 | | A | A |
| 116 | 386 | 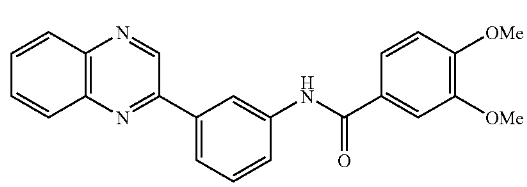 | | | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 117 | 388 | 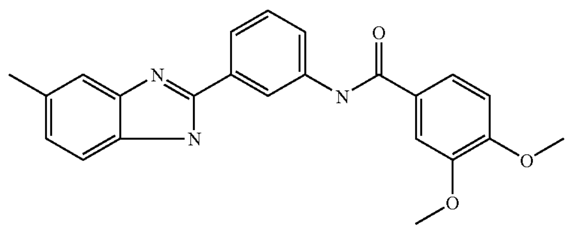 | | A | A |
| 118 | 410 | 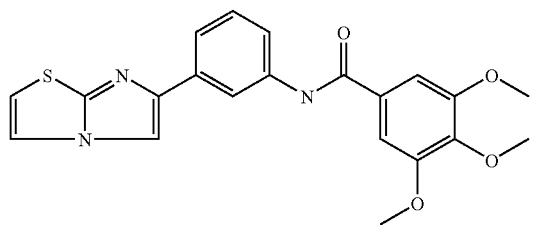 | | A | A |
| 119 | 375 | 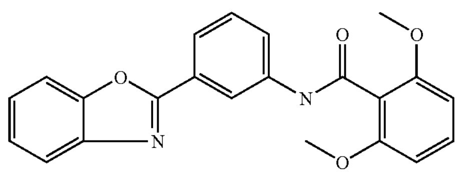 | | A | B |
| 120 | 391 | 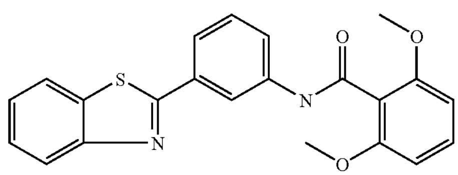 | | NT | |
| 121 | 414 | 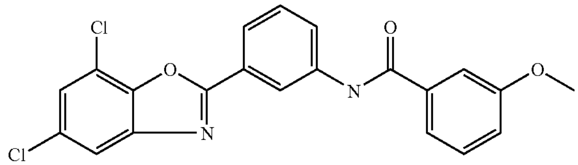 | | D | C |
| 122 | 417 | 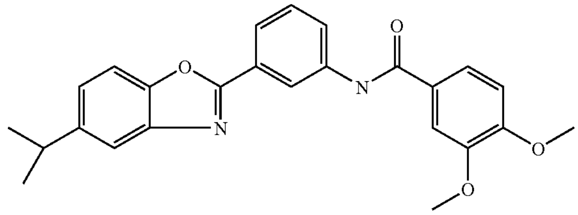 | | C | |
| 123 | 474 | 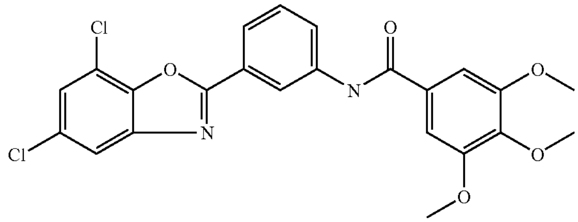 | | NT | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 124 | 391 | 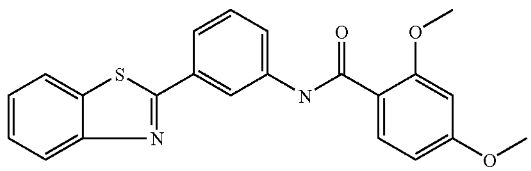 | A | | B |
| 125 | 433 | 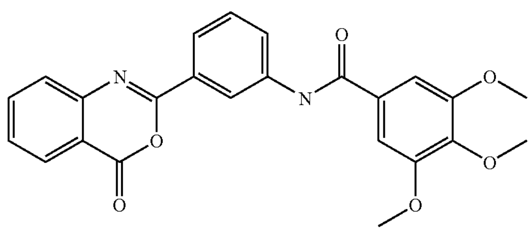 | B | | B |
| 126 | 374 | 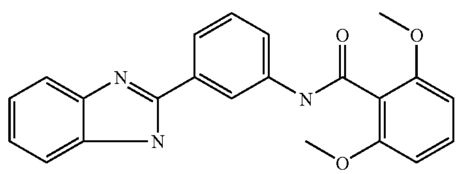 | A | | B |
| 127 | 355 | 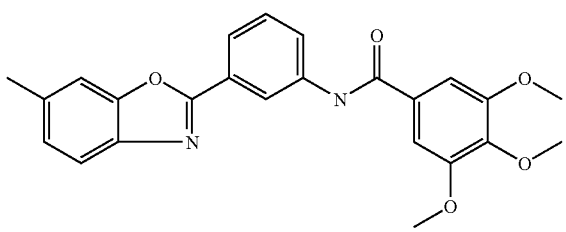 | A | | A |
| 128 | 388 | 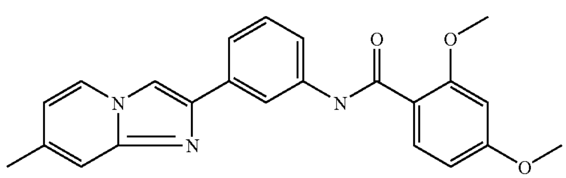 | A | | B |
| 129 | 418 | 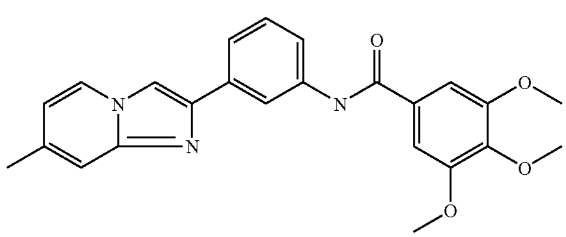 | A' | | A |
| 130 | 358 | 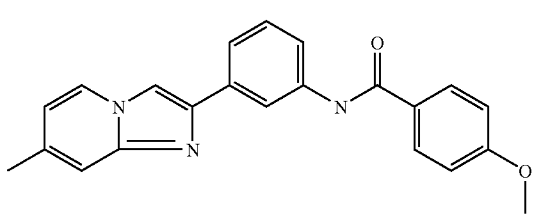 | A | | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 131 | 418 | 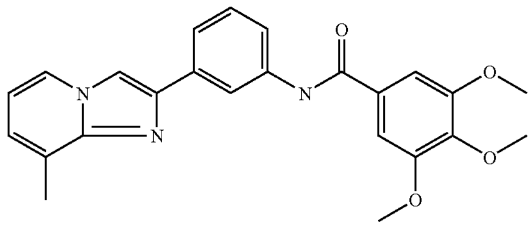 | | A | A |
| 132 | 350 | 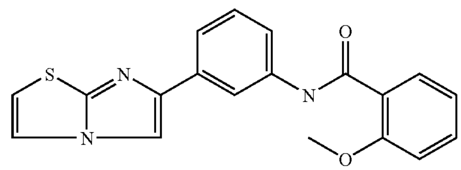 | | A | A |
| 133 | 480 | 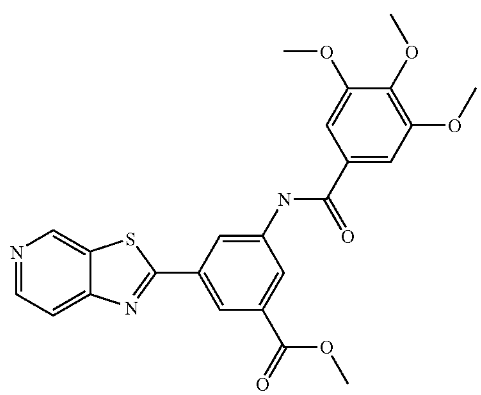 | | A' | B |
| 134 | 466 | 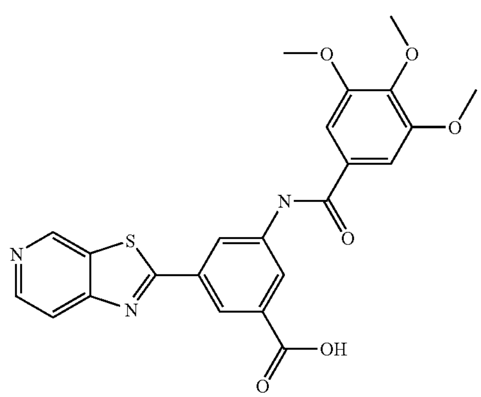 | | A' | B |

US 7,345,178 B2
367                                                                 368
TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 135 | 452 | 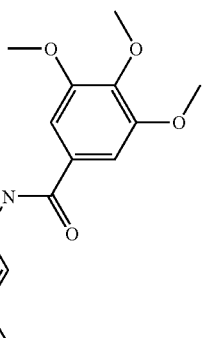 | A' | B | |
| 136 | 434 | 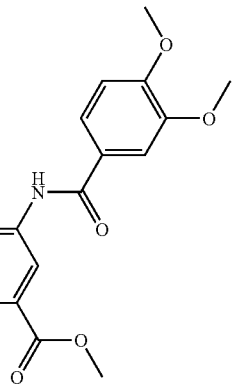 | D | C | |
| 137 | 420 | 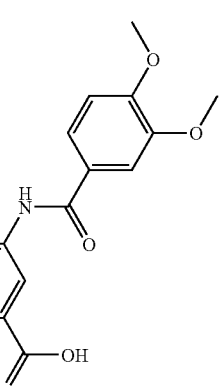 | D | | |
| 138 | 471 | 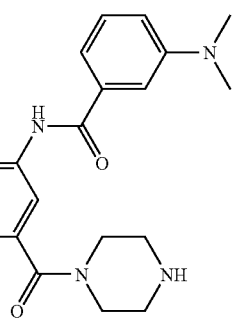 | A | B | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 139 | 488 | 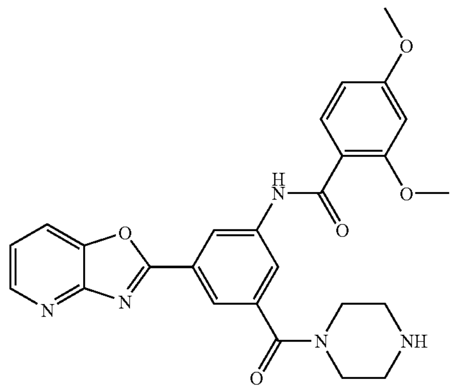 | | A | B |
| 141 | 374.1 | 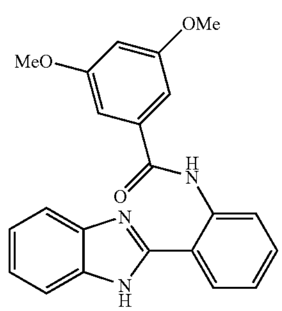 | | A' | B |
| 142 | 374.1 | 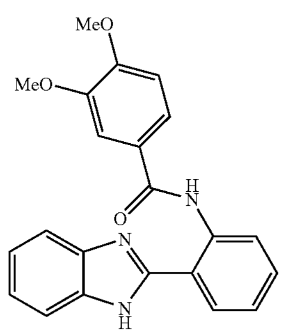 | | A' | A |
| 143 | 410.1 | 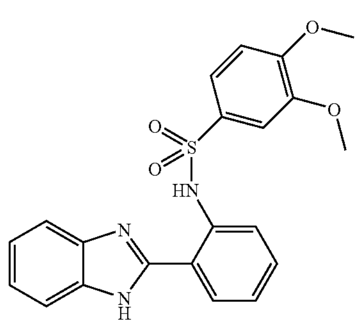 | | D | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 144 | 427.1 | 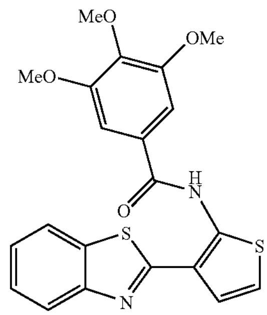 | | D | C |
| 145 | 397.1 | 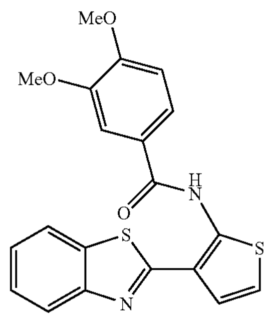 | | A' | B |
| 146 | 397.1 | 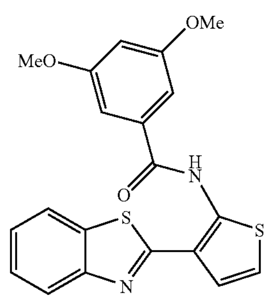 | | A' | B |
| 147 | 392.1 | 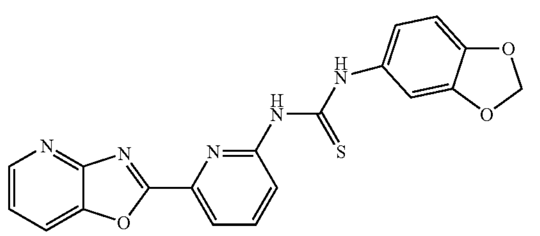 | | D | |
| 148 | 405.2 | 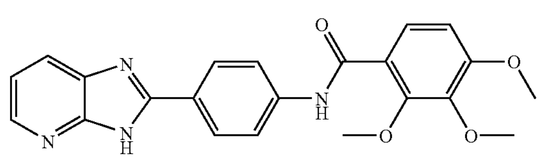 | | D | |
| 149 | 359.0 | 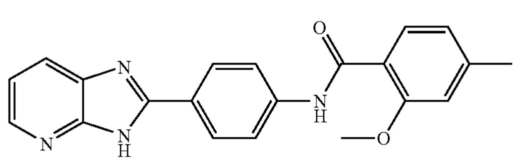 | | A' | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 150 | 375.0 | 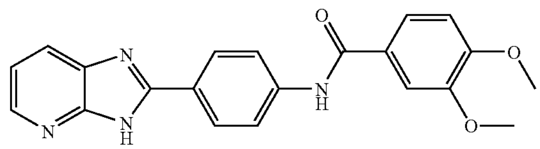 | | A' | B |
| 151 | 375.0 | 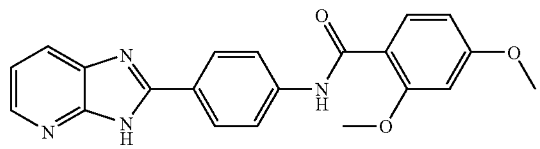 | | D | C |
| 152 | 392.1 | 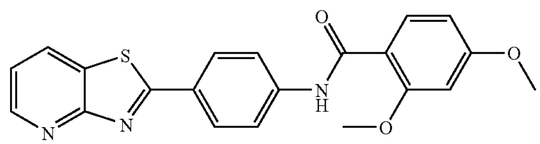 | | D | C |
| 153 | 490 | 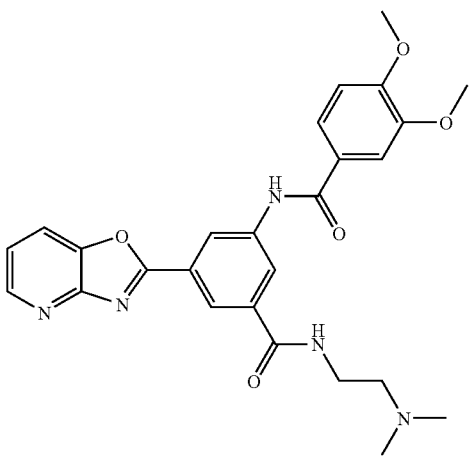 | | A | B |
| 154 | 473 | 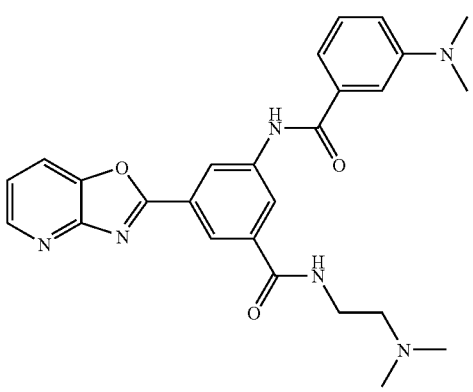 | | C | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 155 | 490 | 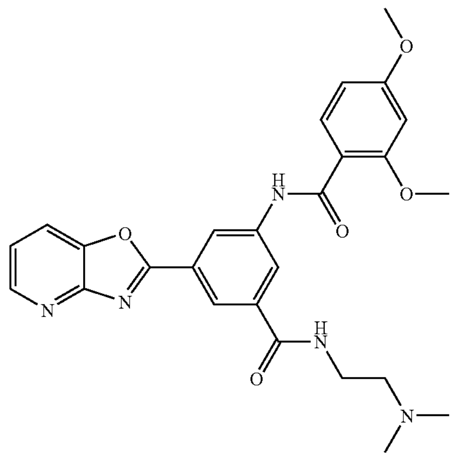 | | A | B |
| 156 | 433 | 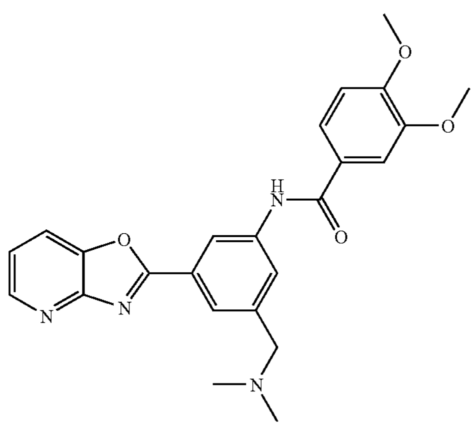 | | A | B |
| 157 | 416 | 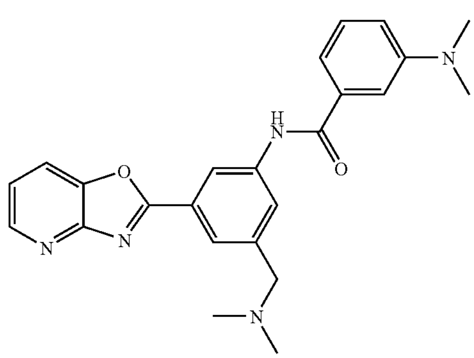 | | D | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 158 | 433 | 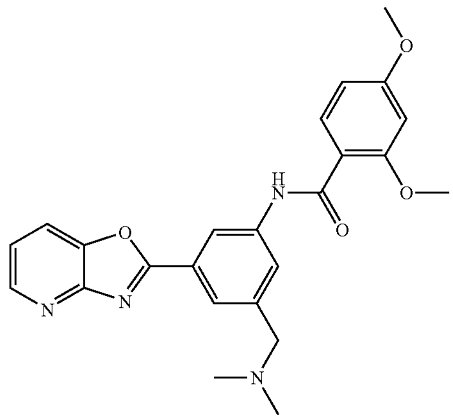 | A | B | |
| 159 | 474 | 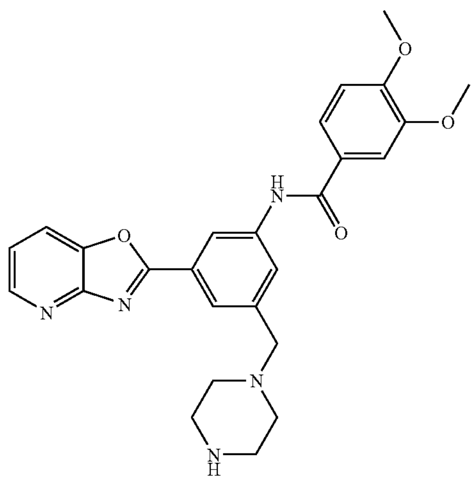 | A | B | |
| 160 | 457 | 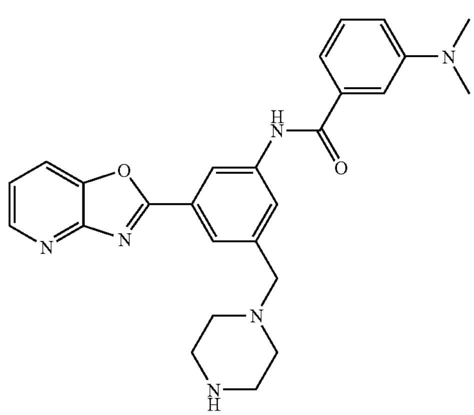 | B | A | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 161 | 474 | 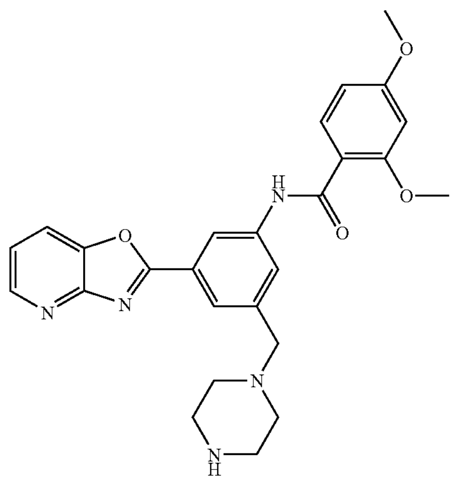 | | A | A |
| 162 | 392.1 | 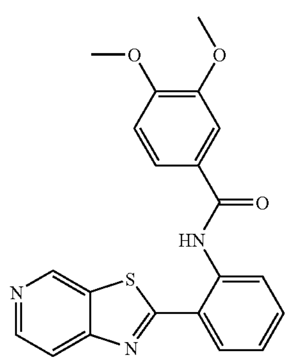 | | A' | B |
| 163 | 422.1 | 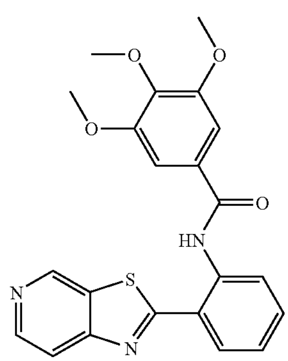 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 164 | 488 | 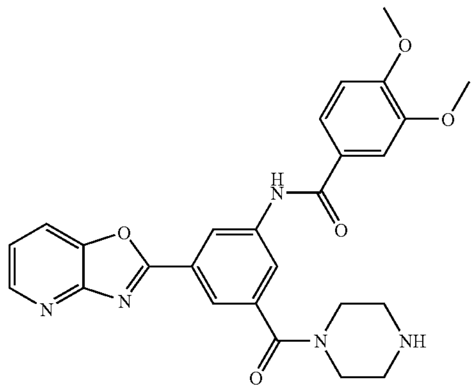 | | A | B |
| 165 | 416 | 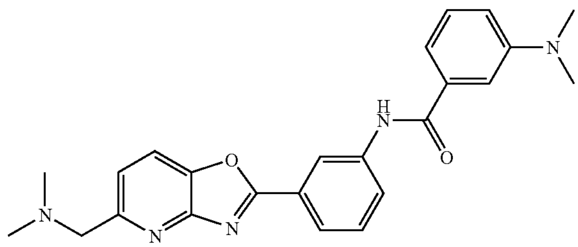 | | D | A |
| 166 | 457 | 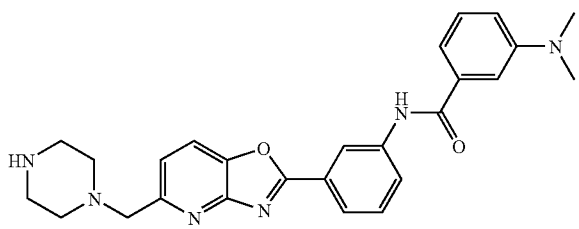 | | A | B |
| 167 | 373 | 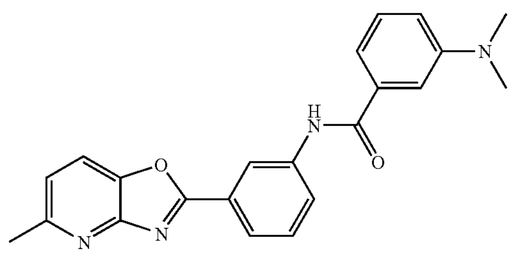 | | A | B |
| 168 | 388.1 | 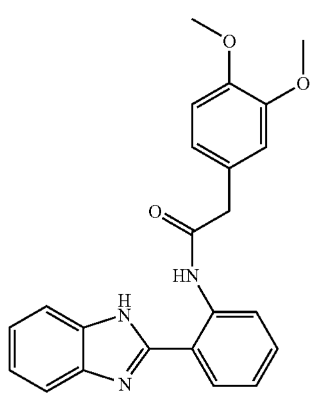 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 169 | 343.1 | 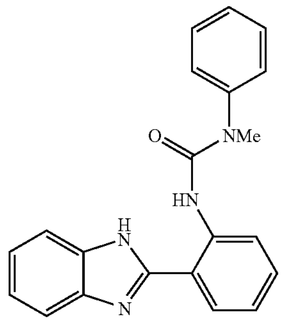 | A' | | B |
| 174 | 479 | 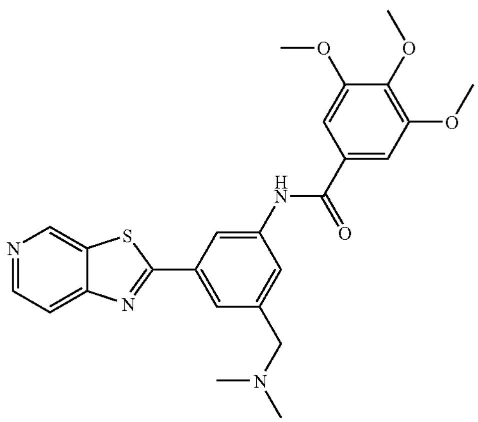 | B | | A |
| 175 | 323.1 | 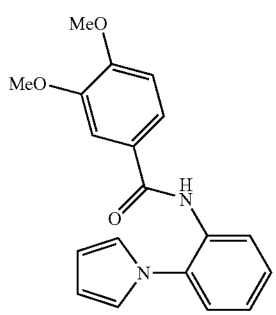 | B | | B |
| 176 | 354.1 | 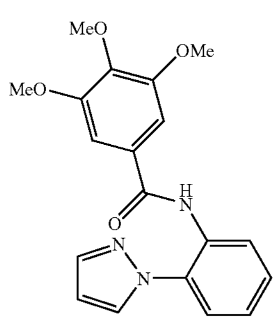 | B | | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 177 | 324.1 | 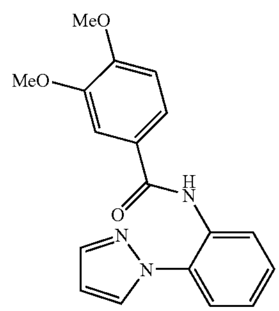 | | D | B |
| 178 | 437 | 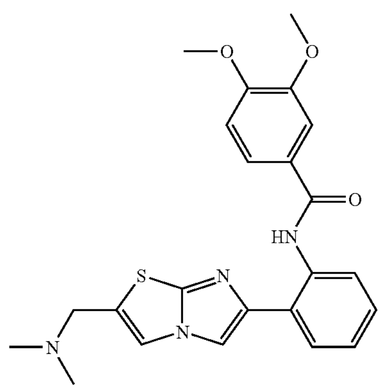 | | A | A |
| 179 | 467 | 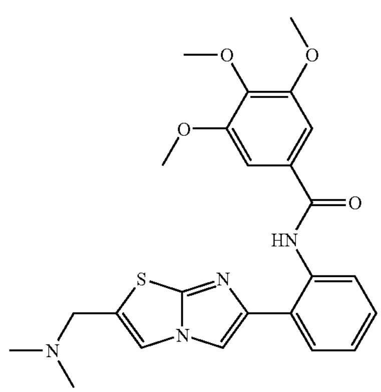 | | A' | A |
| 180 | 358.0 | 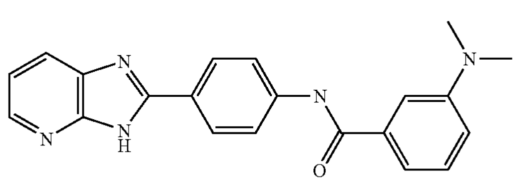 | | A | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 181 | 405.0 | 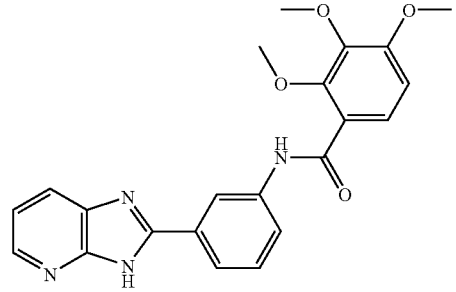 | | A' | A |
| 182 | 359.0 | 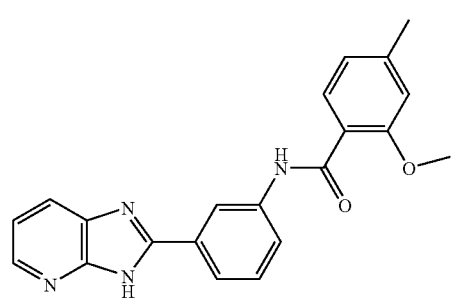 | | A' | A |
| 183 | 358.0 | 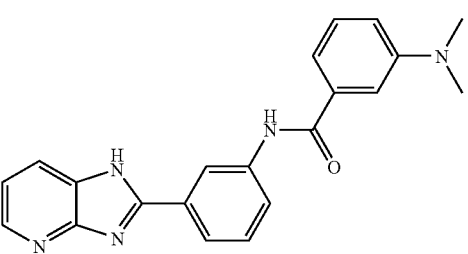 | | A | A |
| 184 | 375.0 | 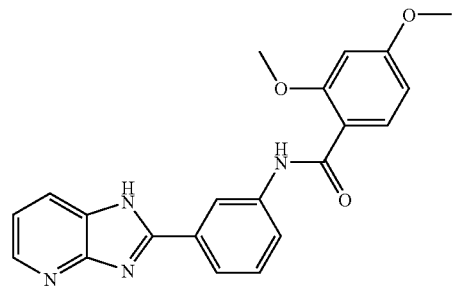 | | A' | B |
| 185 | 374.9 | 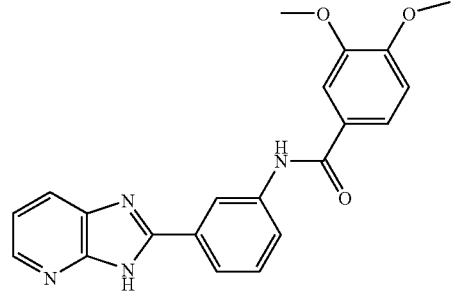 | | A' | A |

TABLE 4-continued

Sirt1 Activators

| COMPOUND NO | [M + H]+ | STRUCTURE | $ED_{50}$ FP ASSAY | $ED_{50}$ MS ASSAY | FOLD ACT. MS |
|---|---|---|---|---|---|
| 186 | 405.3 | 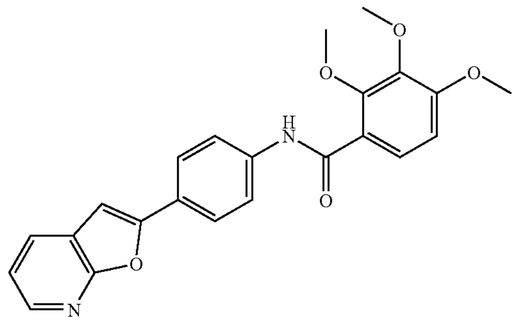 | | NA | C |
| 187 | 358.9 | 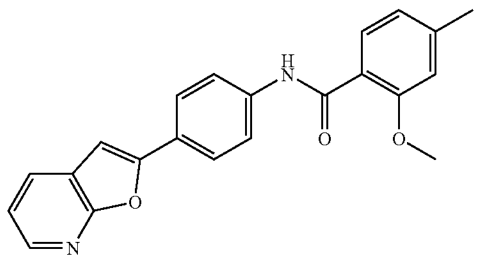 | | A | B |
| 188 | 358.9 | 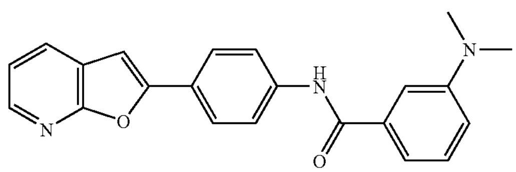 | | NA | C |
| 189 | 375.2 | 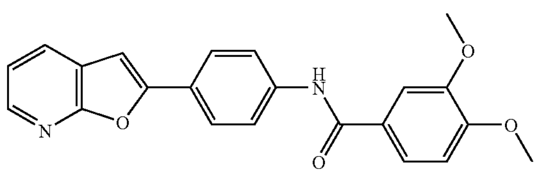 | | NA | C |
| 190 | 375.3 | 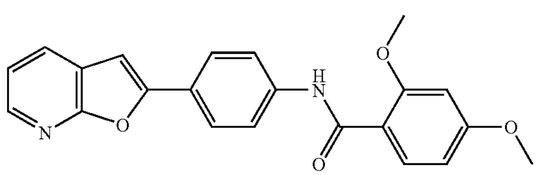 | | A' | B |
| 191 | 375.0 | 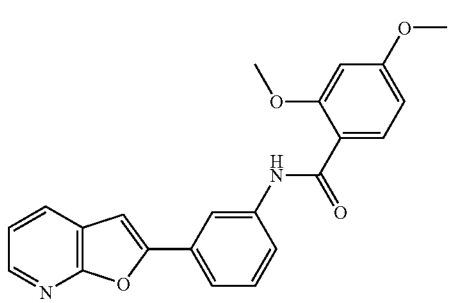 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 192 | 375.0 | 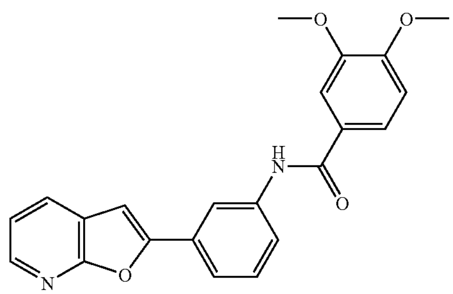 | | A | B |
| 193 | 358.0 | 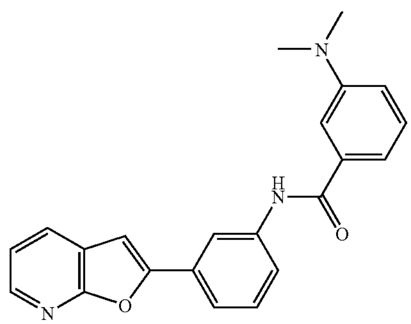 | | NA | C |
| 194 | 422.3 | 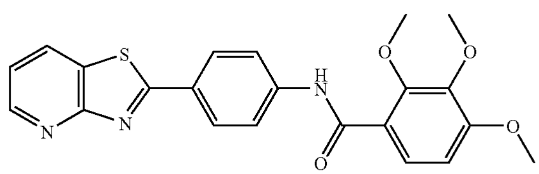 | | NA | C |
| 195 | 375.9 | 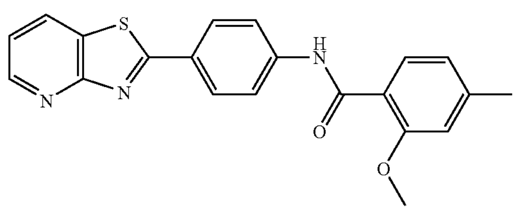 | | NA | C |
| 196 | 374.9 | 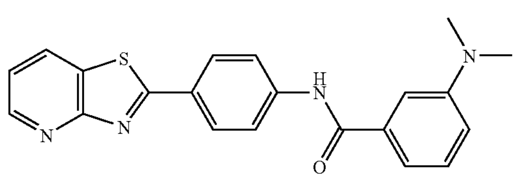 | | A | B |
| 197 | 391.1 | 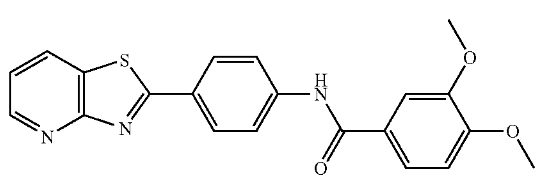 | | A' | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 198 | 422.4 | 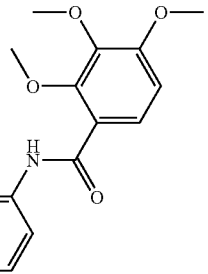 | | A | B |
| 199 | 375.9 | 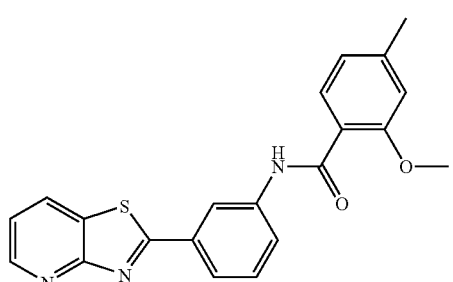 | | A' | B |
| 200 | 375.4 | 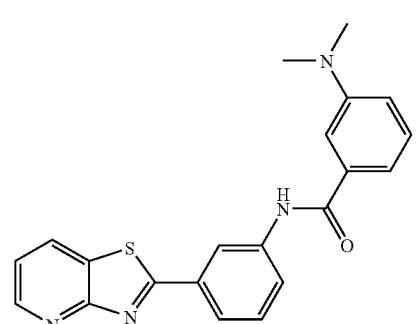 | | A' | B |
| 201 | 391.9 | 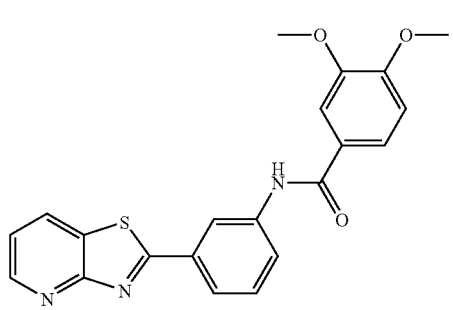 | | A | B |
| 202 | 392.4 | 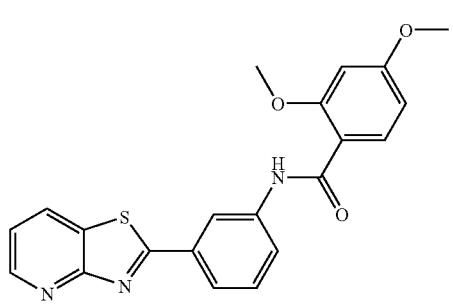 | | A' | B |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 203 | 380 | 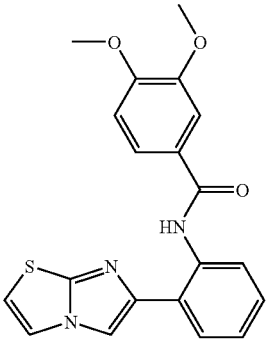 | | A' | B |
| 204 | 410 | 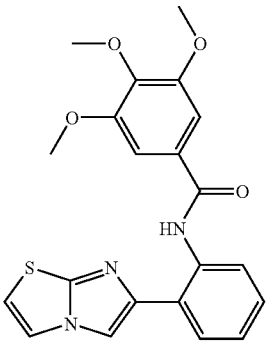 | | A' | A |
| 205 | 437 | 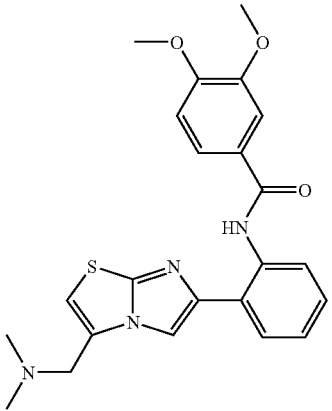 | | A | A |
| 206 | 467 | 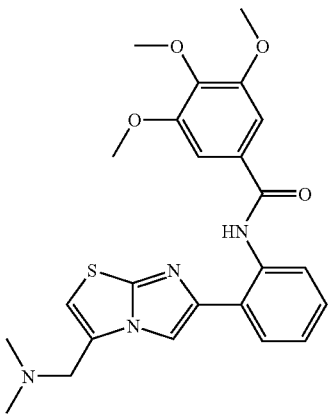 | | A | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 207 | 478 | 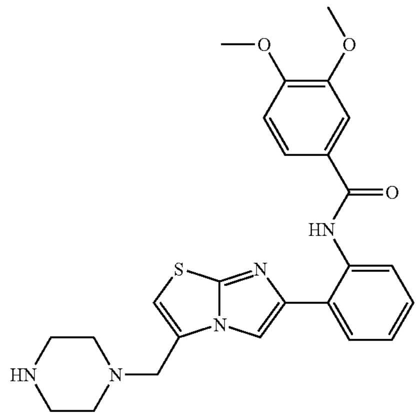 | | A | A |
| 208 | 508 | 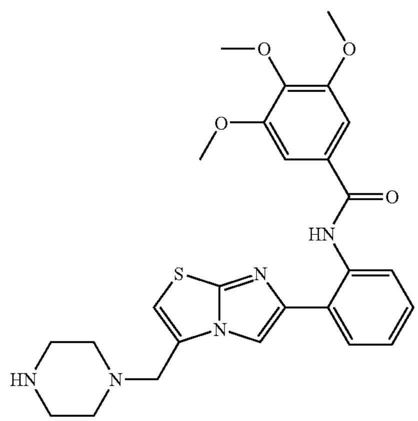 | | A | A |
| 209 | 479 | 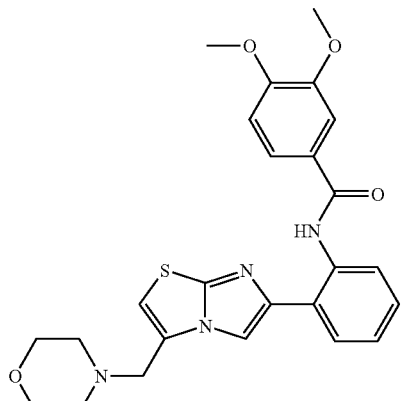 | | A | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 210 | 509 | 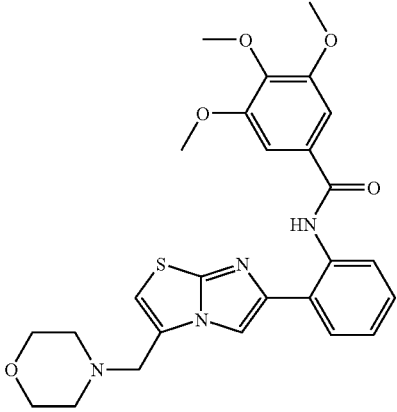 | | A | B |
| 211 | | 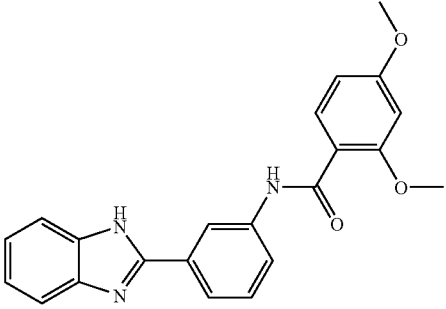 | | A' | B |
| 212 | 362 | 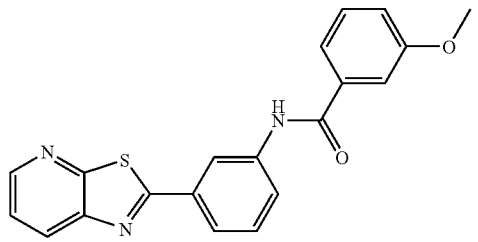 | | A | B |
| 213 | 392 | 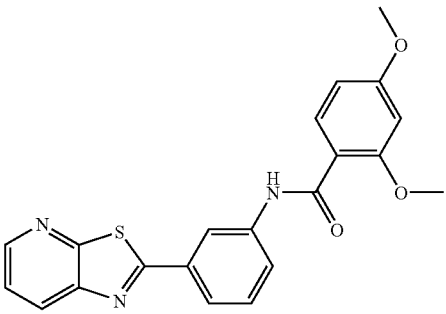 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 214 | 392 | 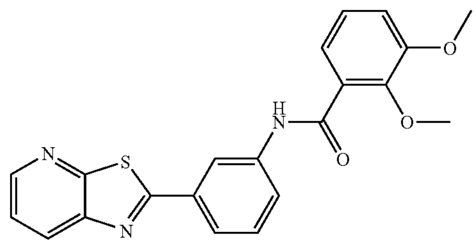 | | A | B |
| 215 | 392 | 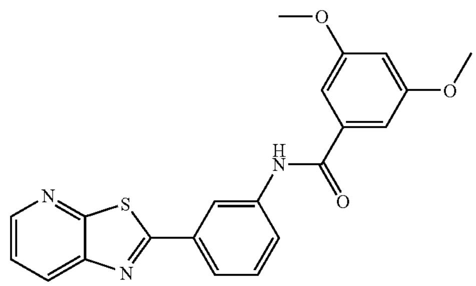 | | A' | B |
| 216 | 362 | 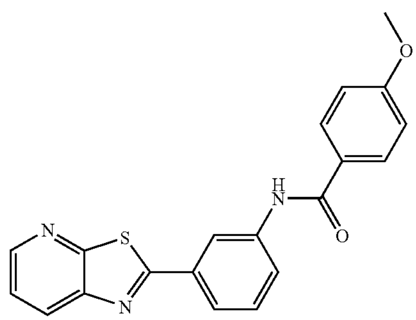 | | A' | B |
| 217 | 422 | 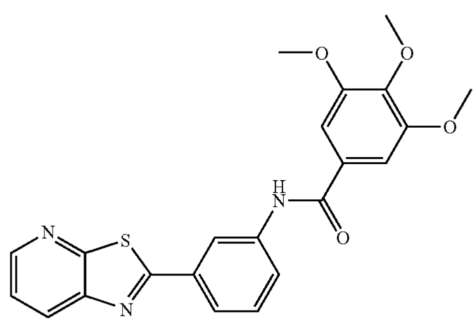 | | A' | A |
| 218 | 405 | 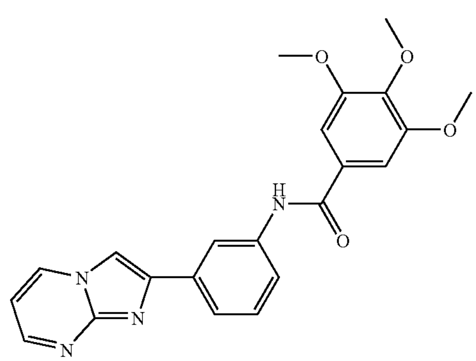 | | A' | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 219 | 419 | 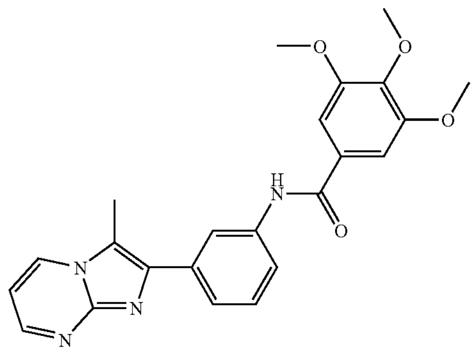 | | A | A |
| 220 | 423 | 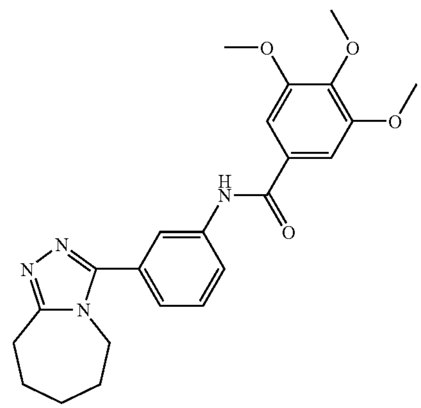 | | NA | C |
| 221 | 321.4 | 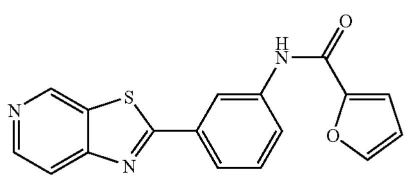 | | A | B |
| 222 | 366.8 | 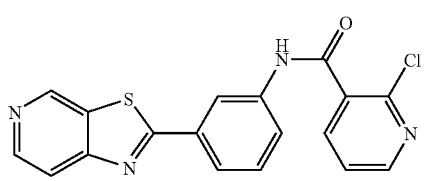 | | A | B |
| 223 | 337.4 | 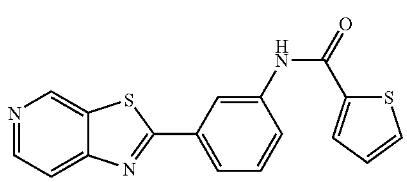 | | A' | B |
| 225 | 332.4 | 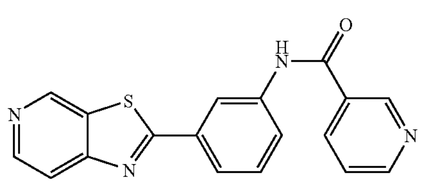 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 226 | 412.5 | 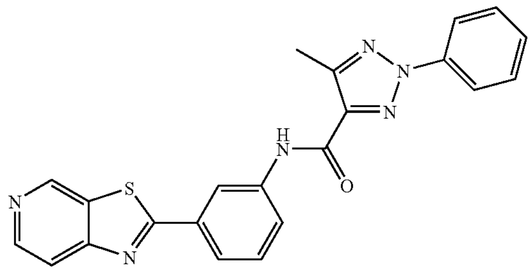 | | | |
| 227 | 333.4 | 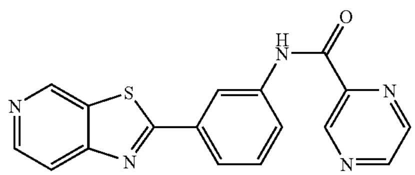 | | NA | C |
| 228 | 391.5 | 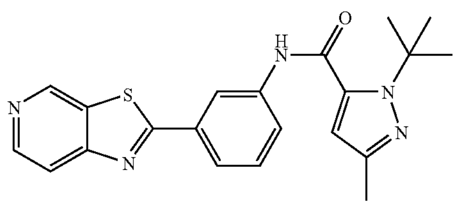 | | A | A |
| 229 | 418.5 | 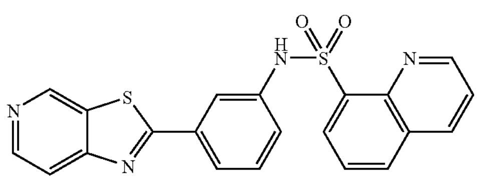 | | NA | C |
| 230 | 459.5 | 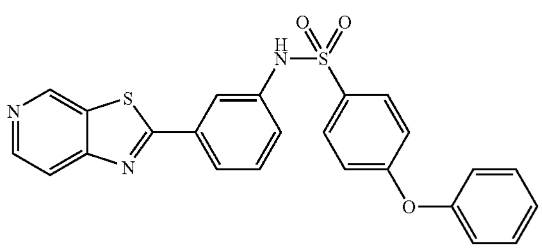 | | NA | C |
| 231 | 425.5 | 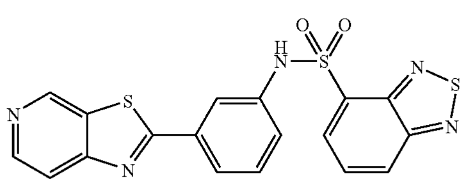 | | NA | C |
| 232 | 423.5 | 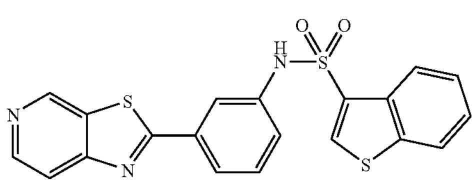 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 234 | 449.5 | 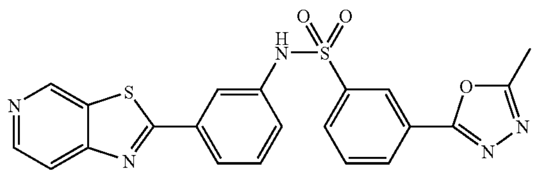 | | NA | C |
| 235 | 436.3 | 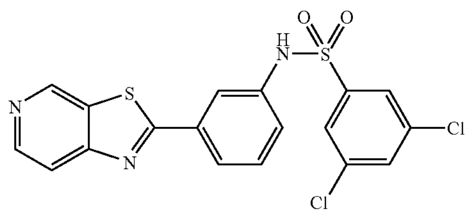 | | NA | C |
| 236 | 423.5 | 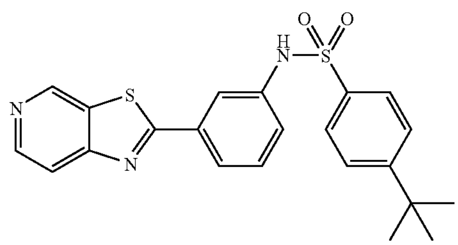 | | NA | C |
| 237 | 450.5 | 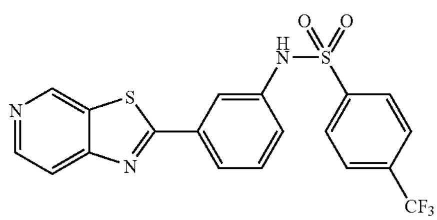 | | NA | C |
| 238 | 480.5 | 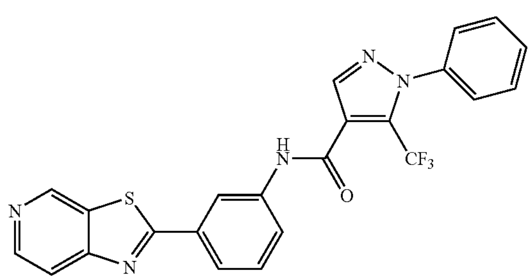 | | A' | B |
| 239 | 466.5 | 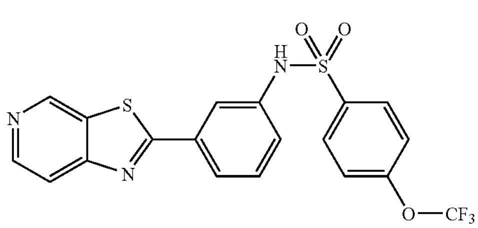 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 240 | 392.4 | 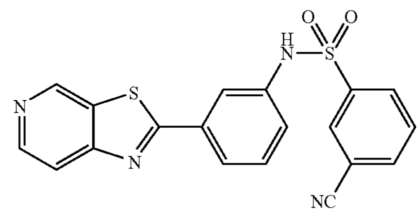 | | NA | C |
| 241 | 397.2 | 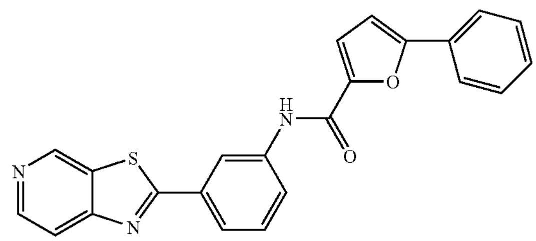 | | A' | B |
| 244 | 332.4 | 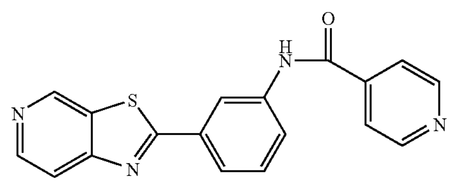 | | NA | C |
| 245 | 423.5 | 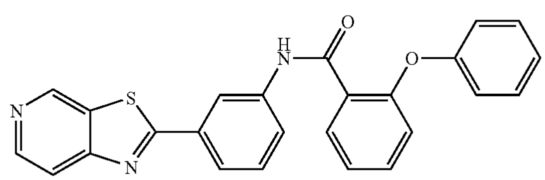 | | A' | B |
| 246 | 391.5 | 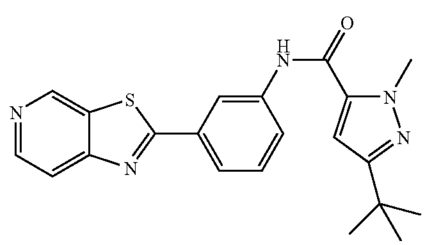 | | A' | B |
| 247 | 413.5 | 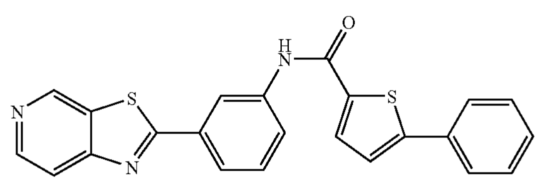 | | NA | C |
| 248 | 467.4 | 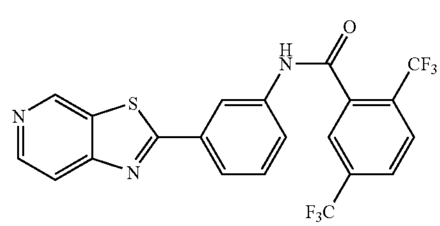 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 249 | 395.9 | 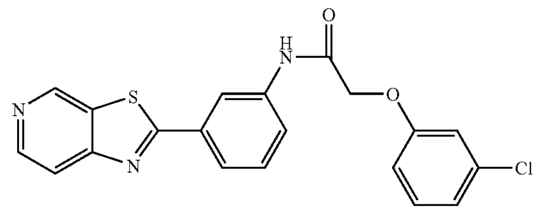 | | NA | C |
| 250 | 385.5 | 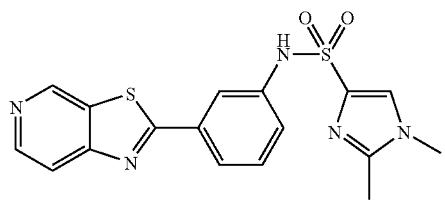 | | NA | C |
| 251 | 425.5 | 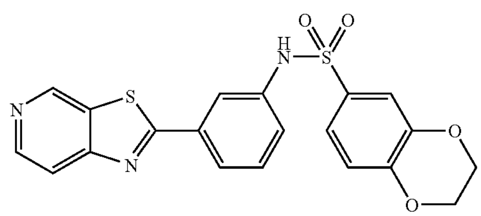 | | NA | C |
| 252 | 453.5 | 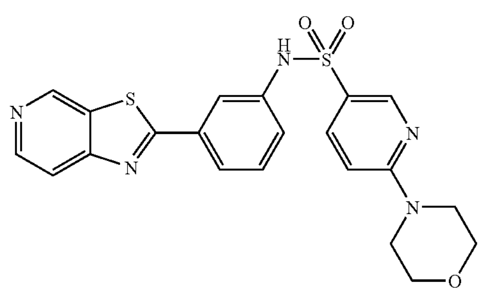 | | NA | C |
| 253 | 373.1 | 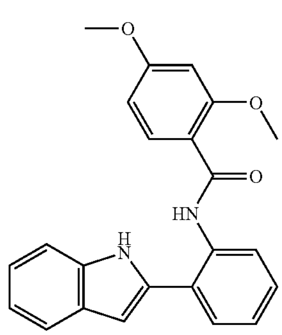 | | NA | C |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 254 | 373 | 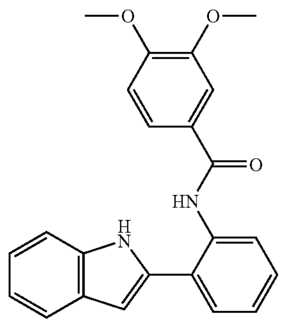 | | A' | B |
| 255 | 403 | 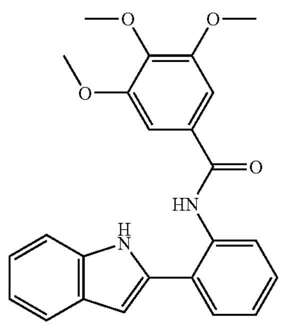 | | A' | B |
| 256 | 356 | 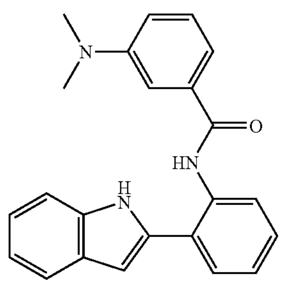 | | NA | C |
| 257 | 413.1 | 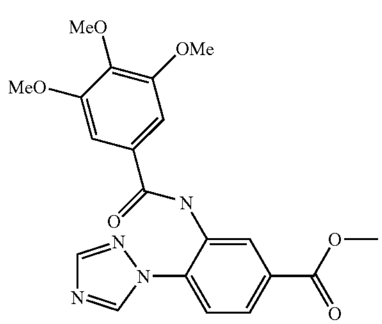 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 258 | 383.1 | | | A | B |
| 259 | 405.1 | | | A' | A |
| 260 | 375.1 | | | A' | A |
| 261 | 375.1 | | | A' | A |
| 262 | 374.1 | | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 263 | 404 | 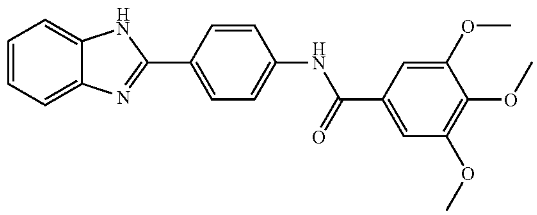 | A | B | |
| 264 | 357 | 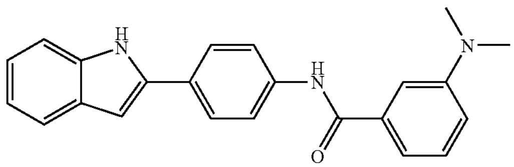 | A' | B | |
| 265 | 374.1 | 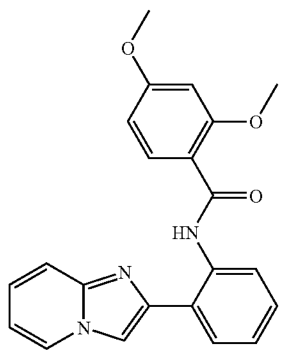 | A | B | |
| 266 | 374 | 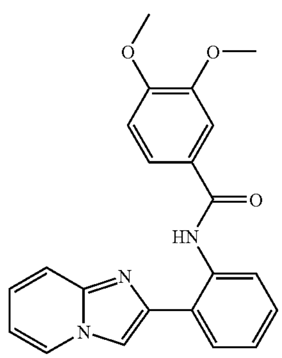 | A' | A | |
| 267 | 404 | 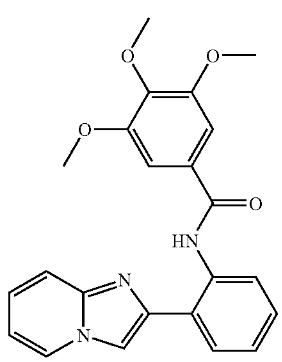 | A' | B | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 268 | 357 | 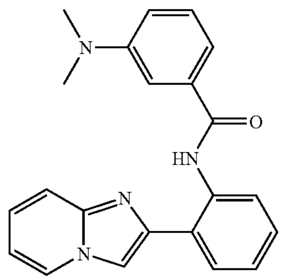 | | A' | B |
| 270 | 478 | 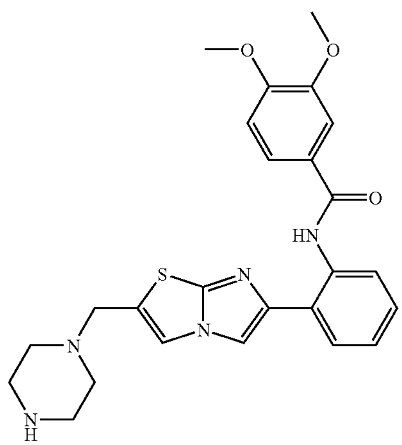 | | A | A |
| 271 | 508 | 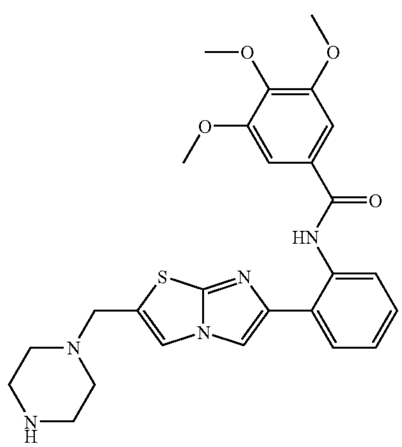 | | A' | A |
| 272 | 392 | 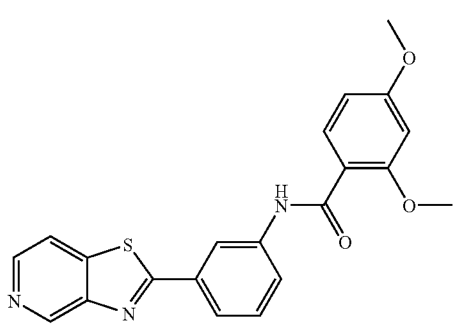 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 273 | 422 | 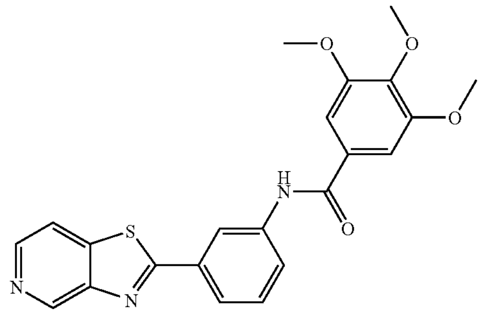 | | A | A |
| 276 | 375.1 | 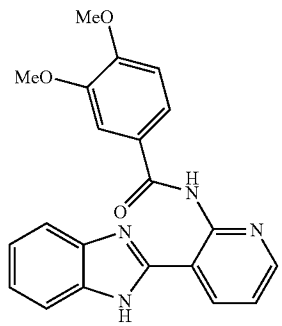 | | A' | B |
| 280 | 381.5 | 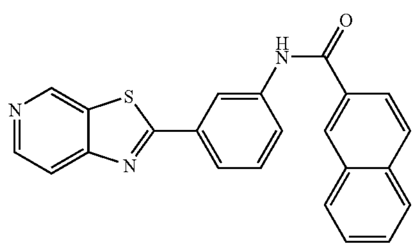 | | | |
| 282 | 386.5 | 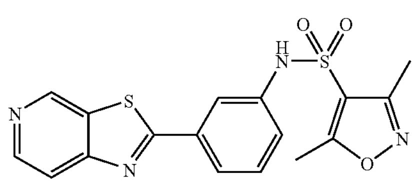 | | NA | C |
| 283 | 451.6 | 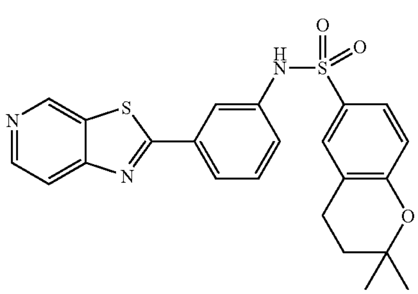 | | NA | C |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 284 | 439.5 | 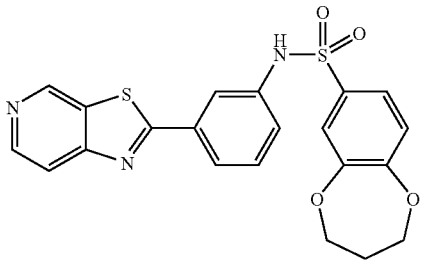 | | NA | C |
| 285 | 440.5 | 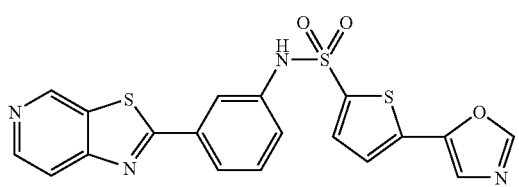 | | NA | C |
| 286 | 390.1 | 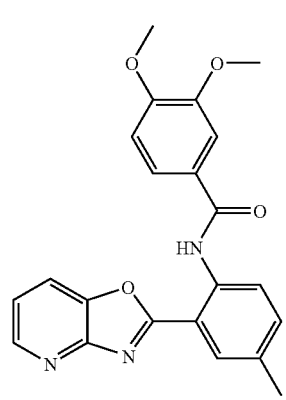 | | NA | C |
| 287 | 457.6 | 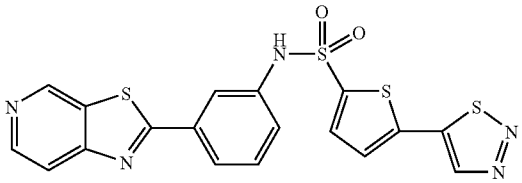 | | | |
| 288 | 424.5 | 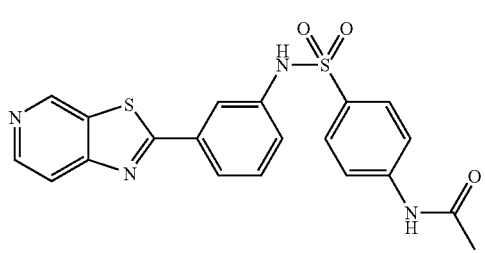 | | A | B |
| 289 | 427.5 | 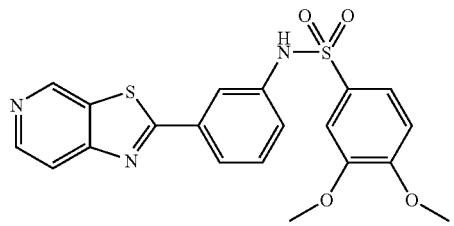 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 290 | 445.5 | | | NA | C |
| 292 | 420.1 | | | | D |
| 293 | 404.1 | | | A' | A |
| 294 | 374 | | | A' | B |
| 295 | 252.1 | | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 296 | 376 | 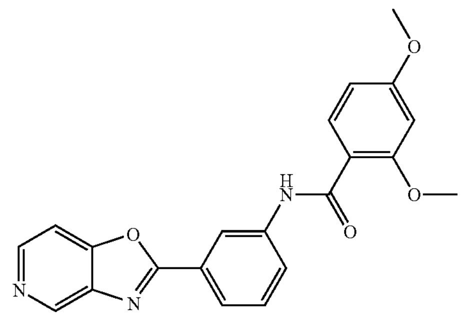 | | A | B |
| 297 | 376 | 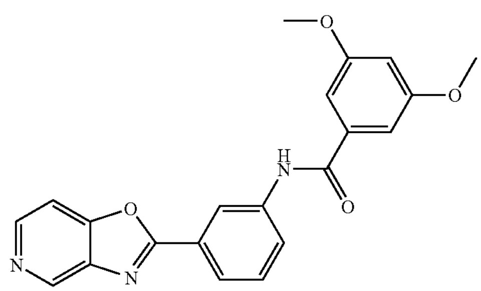 | | A | B |
| 298 | 406 | 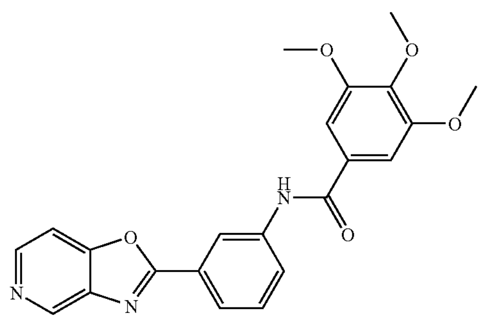 | | A | B |
| 299 | 359 | 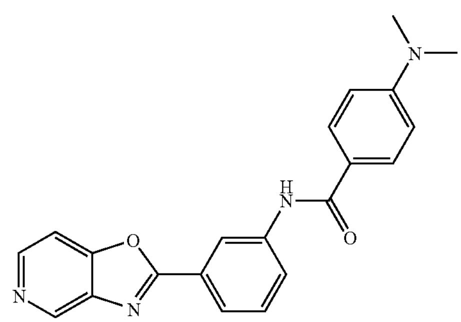 | | A | B |
| 303 | 437.5 | 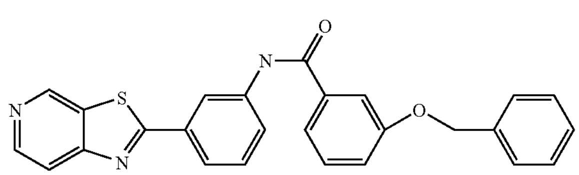 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 304 | 336.4 | 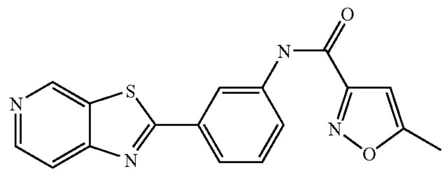 | | A' | B |
| 305 | 414.5 | 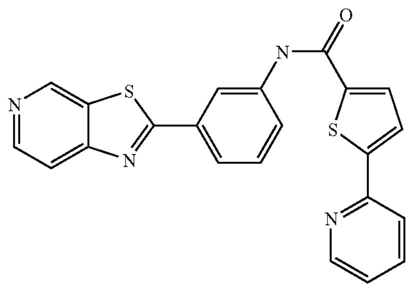 | | NA | |
| 306 | 424.5 | 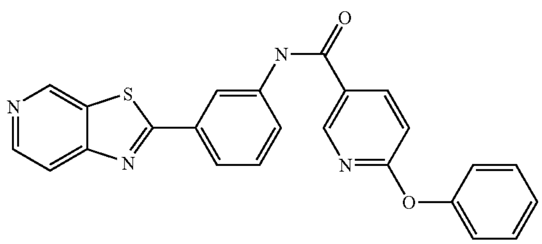 | | A | B |
| 307 | 382.4 | 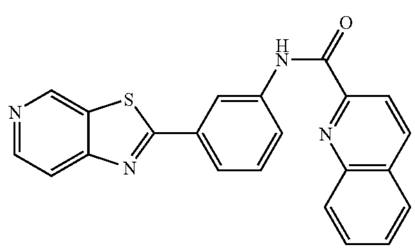 | | A' | A |
| 308 | 400.3 | 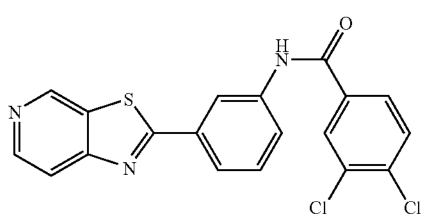 | | NA | |
| 309 | 367.4 | 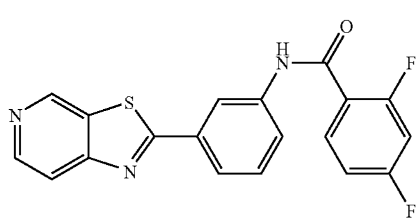 | | NA | |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 310 | 387.5 | 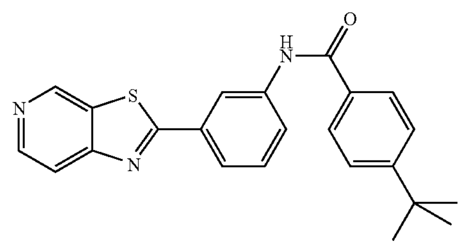 | | NA | |
| 311 | 359 | 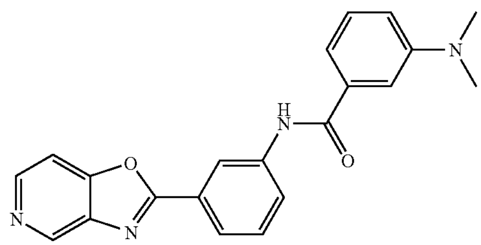 | | A | B |
| 313 | 418.1 | 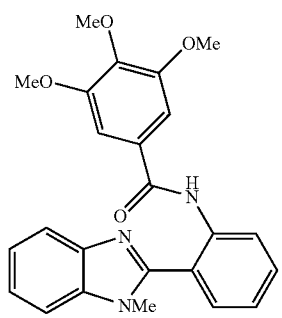 | | A | B |
| 314 | 388.1 | 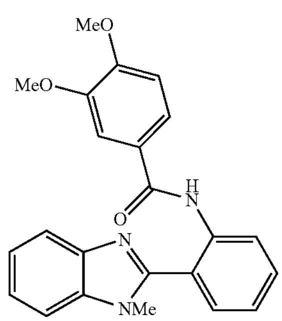 | | A' | B |
| 315 | 388.1 | 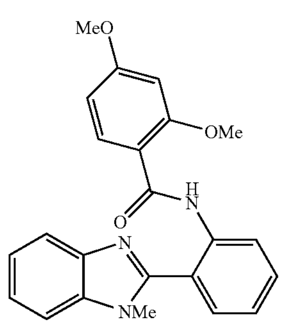 | | NA | |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 317 | 392 | 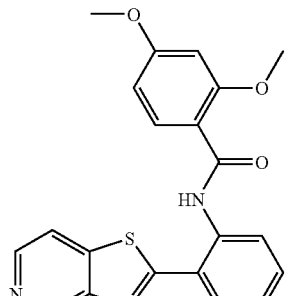 | | A' | B |
| 318 | 392 | 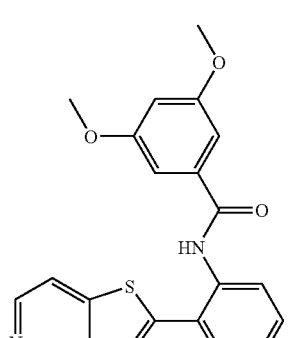 | | A | B |
| 319 | 422 | 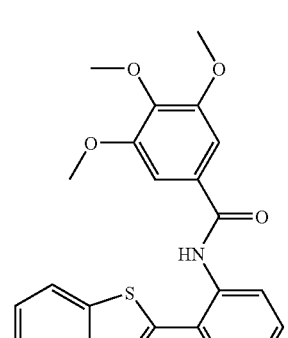 | | A' | B |
| 320 | 375 | 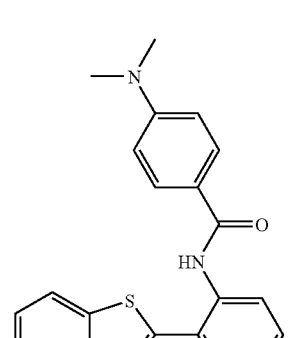 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 321 | 375 | 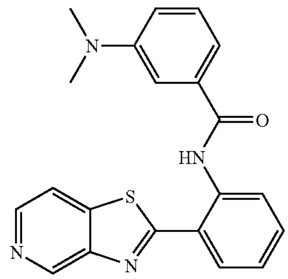 | | A' | B |
| 322 | 392 | 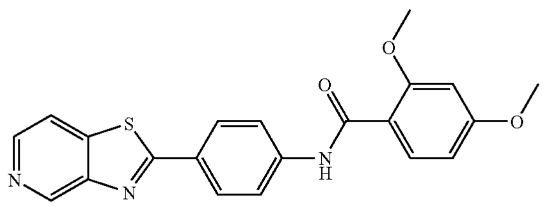 | | NA | |
| 323 | 392 | 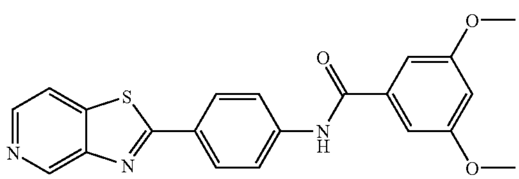 | | A | B |
| 324 | 422 | 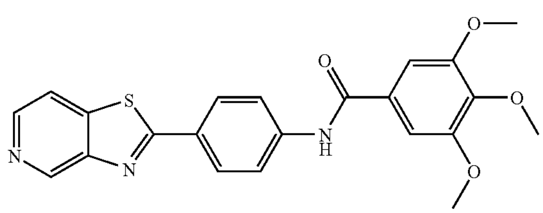 | | NA | |
| 325 | 375 | 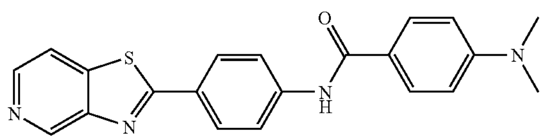 | | NA | |
| 326 | 478 | 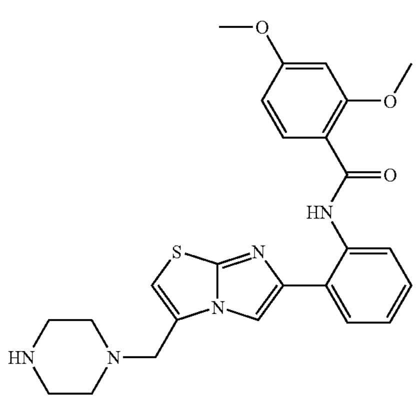 | | A | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 327 | 461 | 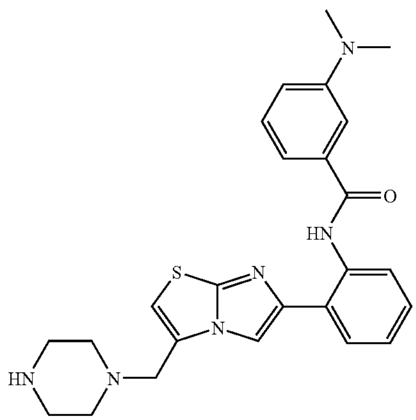 | | A | A |
| 328 | 418 | 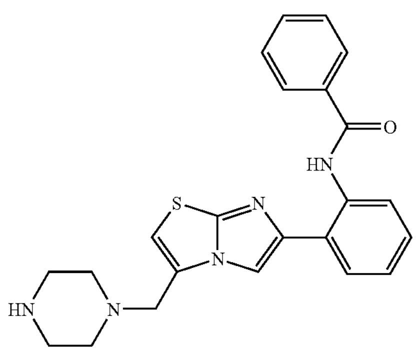 | | B | A |
| 329 | 462 | 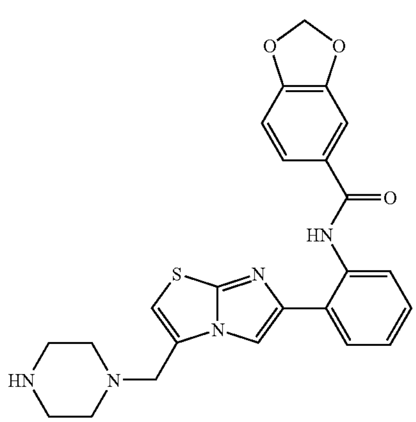 | | A | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 330 | 443 | 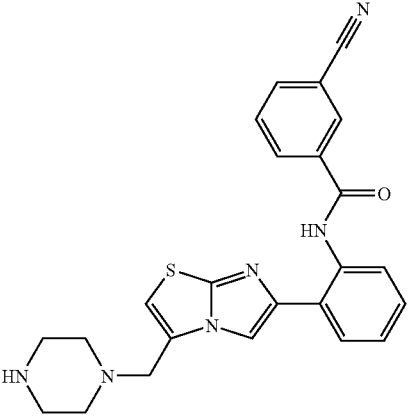 | | A | A |
| 331 | 335 | 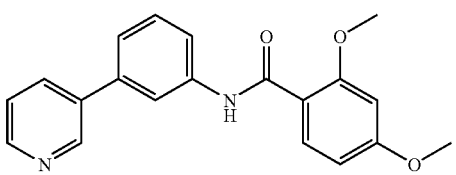 | | A | B |
| 332 | 335.1 | 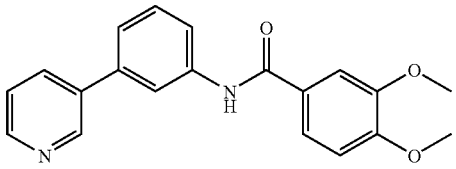 | | A | B |
| 333 | 365 | 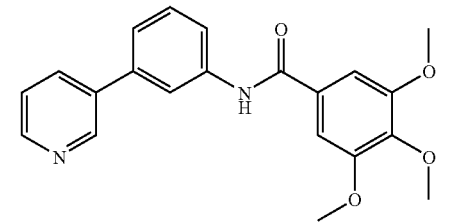 | | A | B |
| 334 | 340.1 | 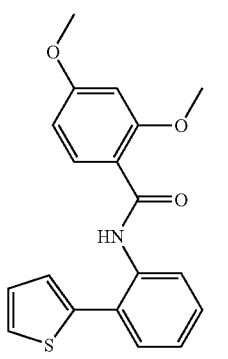 | | A | B |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 335 | 340 | 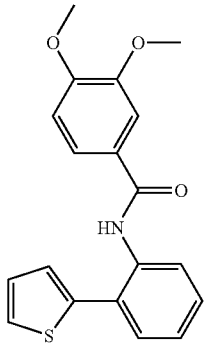 | | A | B |
| 336 10 | 370 | 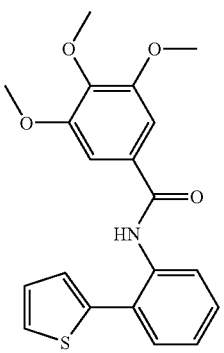 | | A | B |
| 337 | 443 | 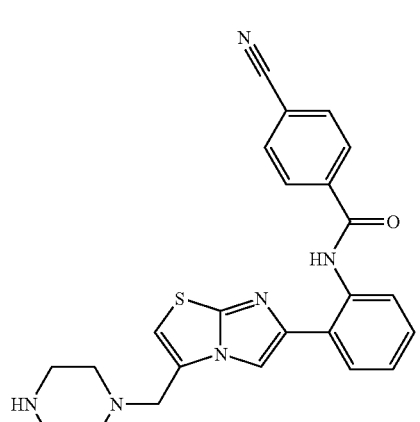 | | | NA |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 338 | 458 | 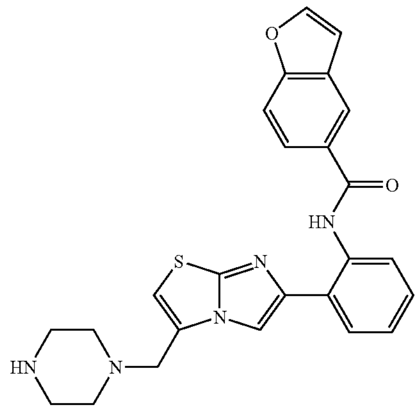 | | A | A |
| 339 | 376 | 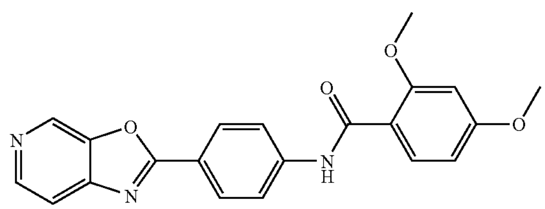 | | NA | |
| 340 | 376 | 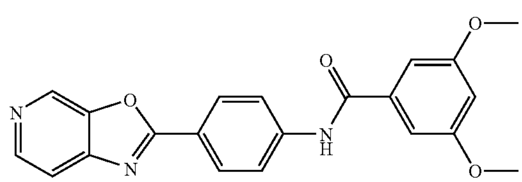 | | NA | |
| 341 | 406 | 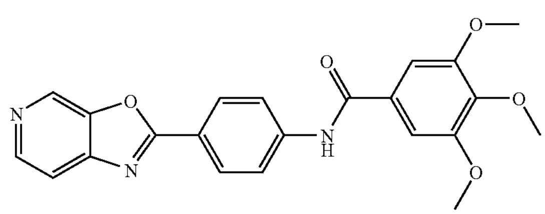 | | A' | B |
| 342 | 359 | 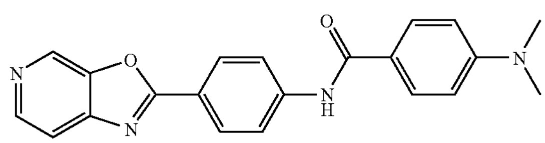 | | NA | |
| 343 | 406 | 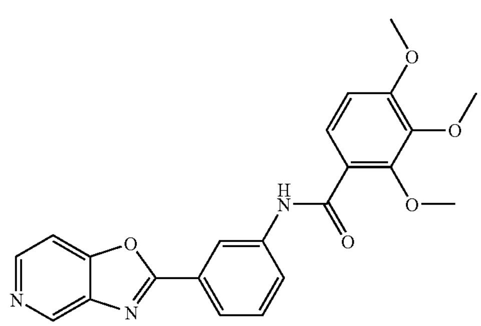 | | A | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 344 | 375 | 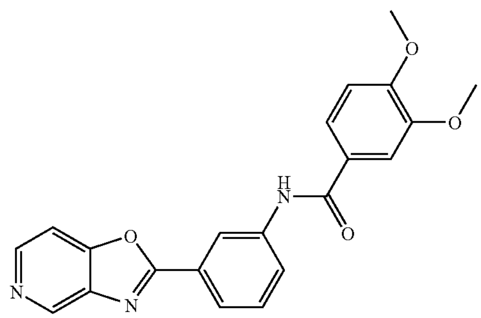 | | A' | B |
| 345 | 376 | 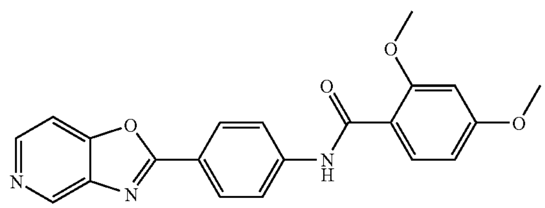 | | NA | |
| 346 | 376 | 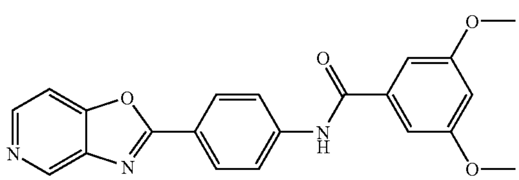 | | NA | |
| 347 | 406 | 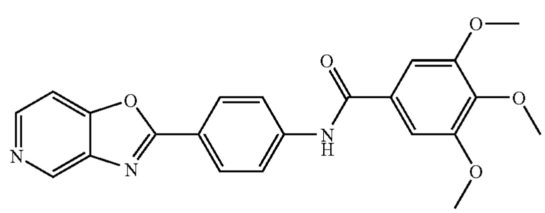 | | A' | B |
| 348 | 359 | 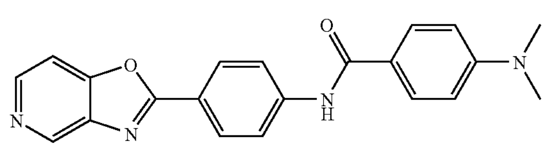 | | NA | |
| 349 | 375 | 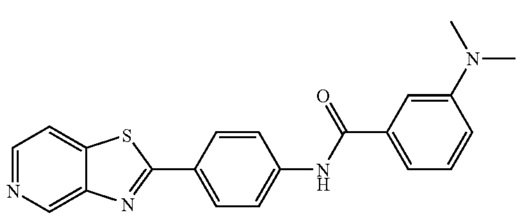 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 350 | 431.1 | | | B | B |
| 351 | 461 | | | A | B |
| 359 | 472.1 | | | NA | |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 362 | 502 | 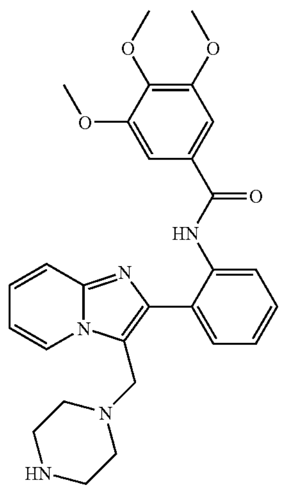 | | B | B |
| 364 | 472 | 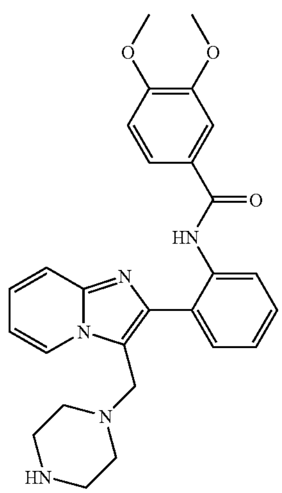 | | D | A |
| 367 | 359.1 | 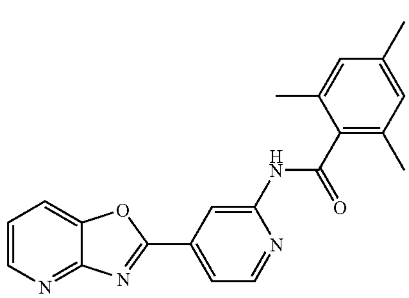 | | NA | |

: 451 :
TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 369 | 350.8 | 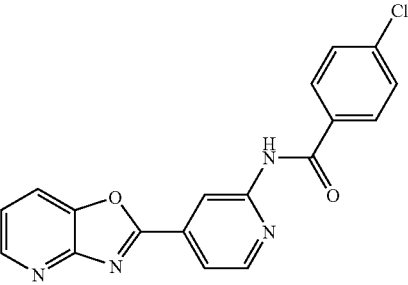 | | NA | |
| 370 | 437.0 | 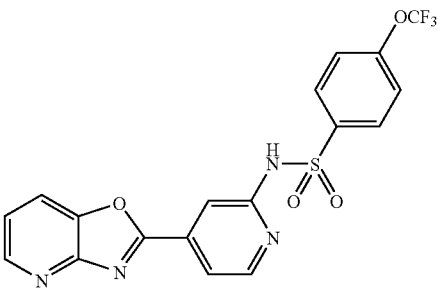 | | NA | |
| 371 | 381.1 | 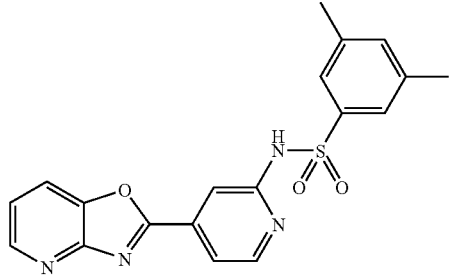 | | NA | |
| 372 | 431.1 | 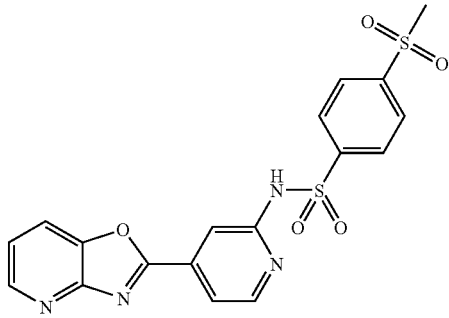 | | NA | |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 373 | 445.0 | 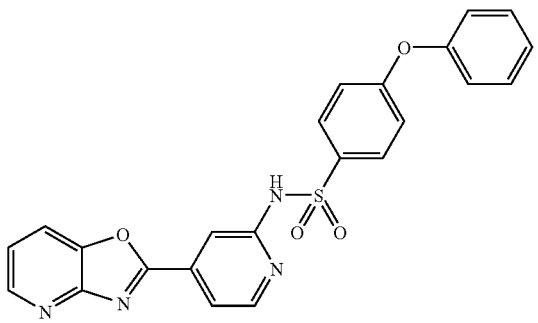 | | NA | |
| 374 | 421.1 | 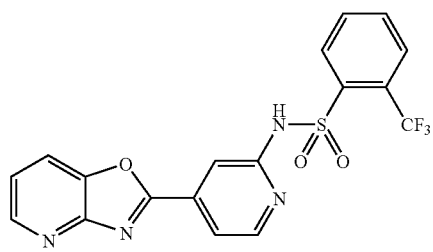 | | NA | |
| 375 | 358.2 | 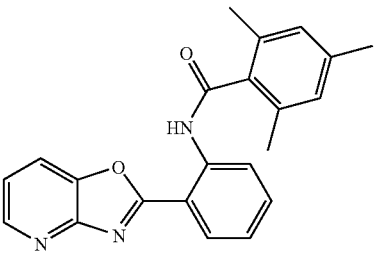 | | NA | |
| 376 | 350.0 | 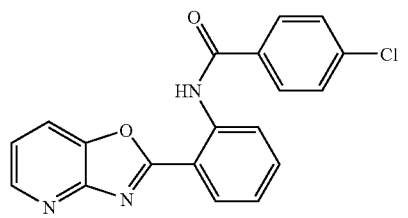 | | NA | |
| 377 | | 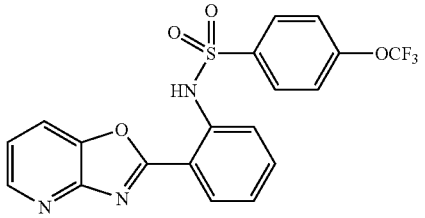 | | NA | |

455 456
TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 378 | 412.1 | 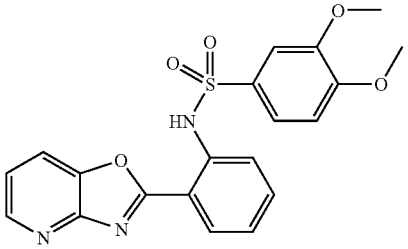 | | NA | |
| 379 | 380.0 | 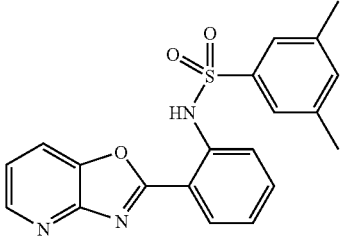 | | NA | |
| 380 | 429.9 | 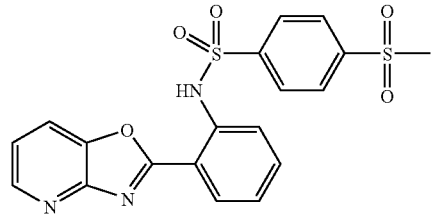 | | NA | |
| 381 | 444.1 | 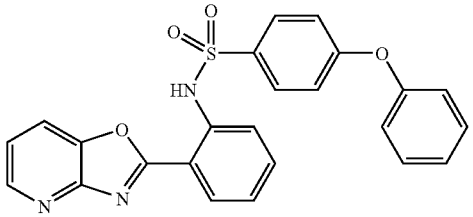 | | NA | |
| 382 | 420.0 | 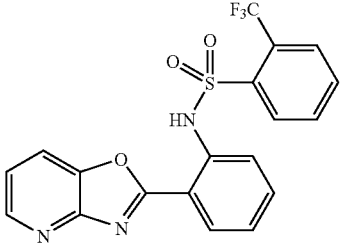 | | NA | |
| 383 | 515.7 | 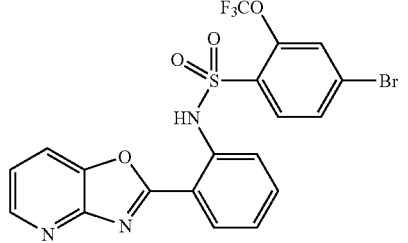 | | NA | |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 384 | 487.8 | 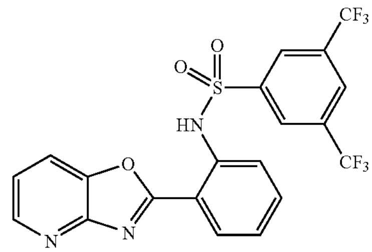 | | NA | |
| 385 | 397.2 | 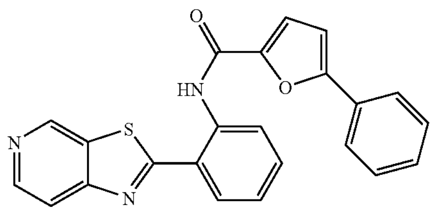 | | NA | |
| 387 | 366.8 | 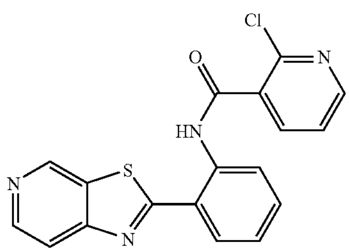 | | NA | |
| 390 | 412.5 | 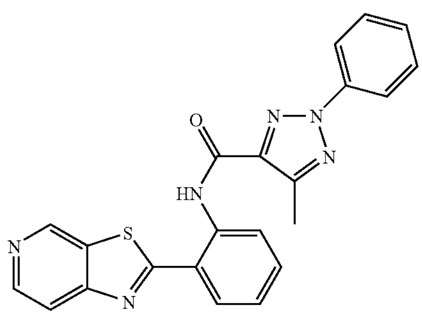 | | A | B |
| 391 | 333.4 | 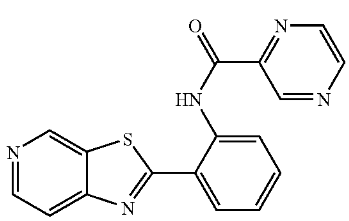 | | A | B |
| 392 | 424.5 | 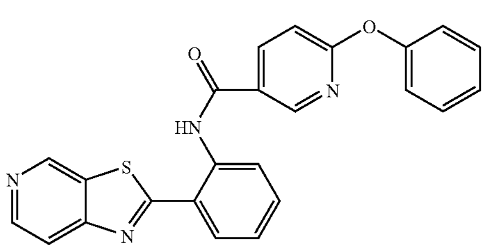 | | A | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 393 | 400.3 | 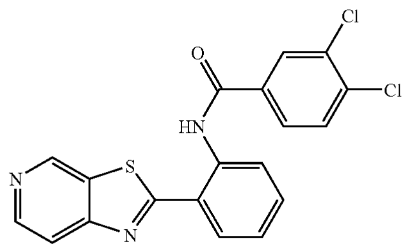 | | NA | |
| 394 | 457.6 | 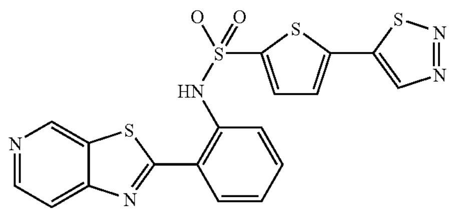 | | NA | |
| 396 | 389.5 | 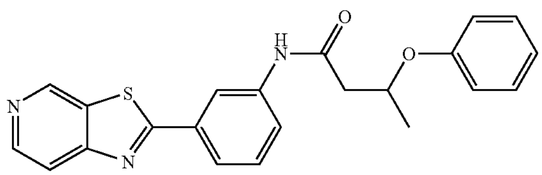 | | A | B |
| 398 | 460.1 | 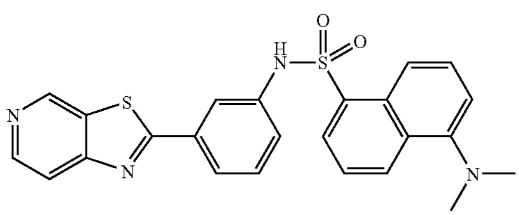 | | A | B |
| 399 | 424.5 | 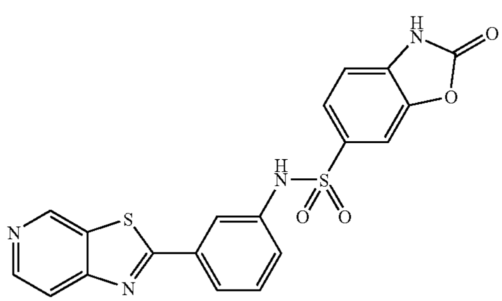 | | A | B |
| 400 | 392 | 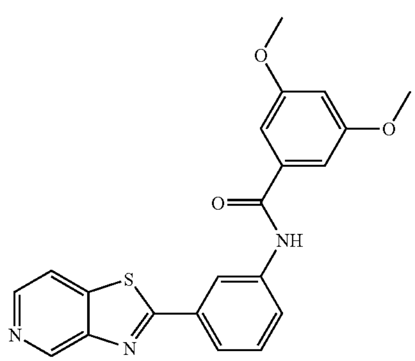 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 401 | 422 | 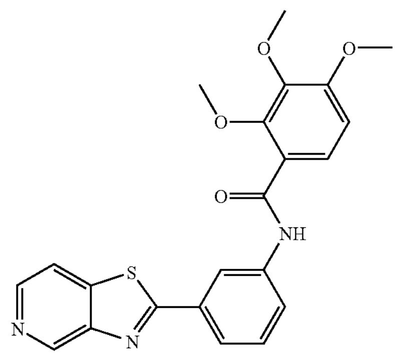 | | A | B |
| 402 | 375 | 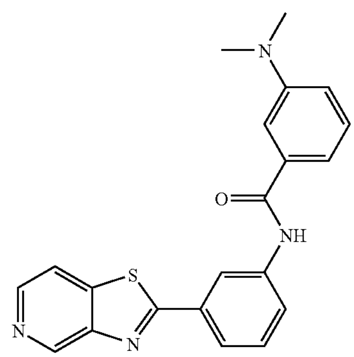 | | A' | B |
| 403 | 375 | 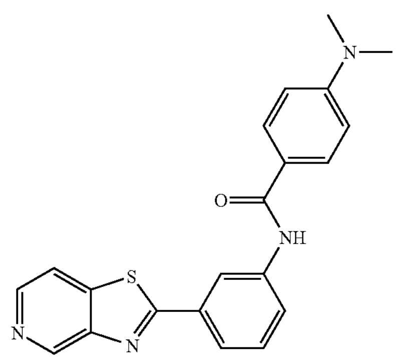 | | A' | B |
| 404 | 376 | 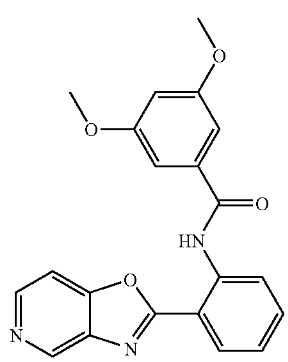 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 405 | 406 | 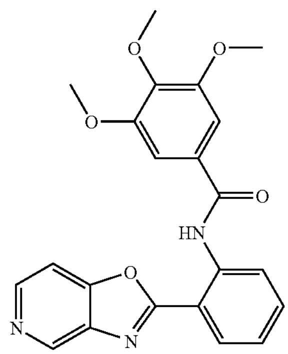 | | A' | B |
| 406 | 359 | 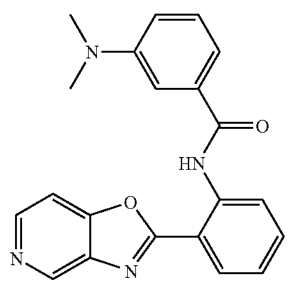 | | A' | B |
| 407 | 359 | 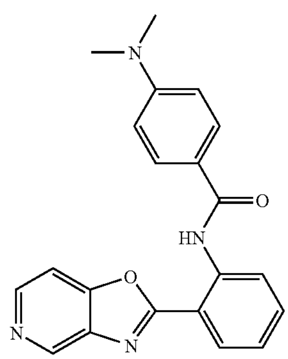 | | A' | B |
| 408 | 359 | 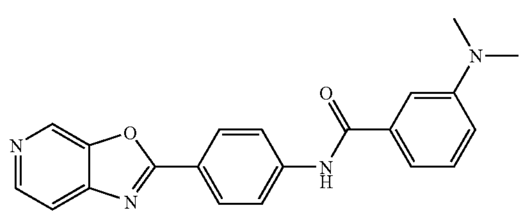 | | B | B |
| 409 | 422 | 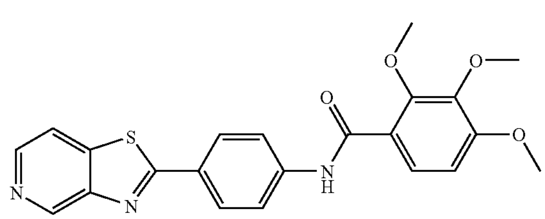 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 410 | 359 | 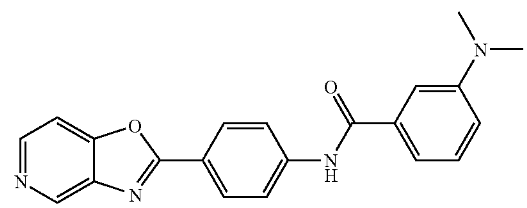 | | NA | |
| 411 | 422 | 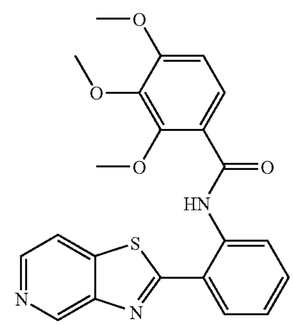 | | A | B |
| 412 | 406 | 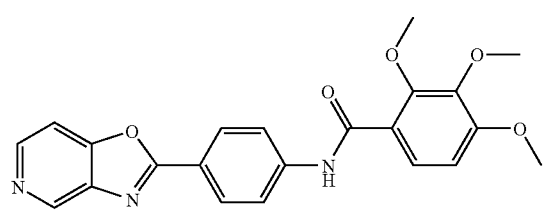 | | NA | |
| 413 | 385.1 | 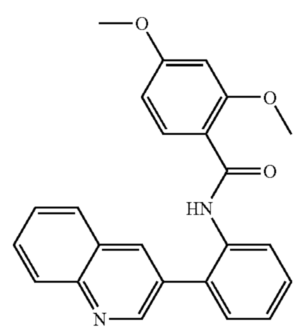 | | B | B |
| 414 | 385 | 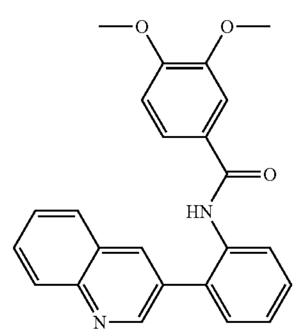 | | A | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 415 | 415 | 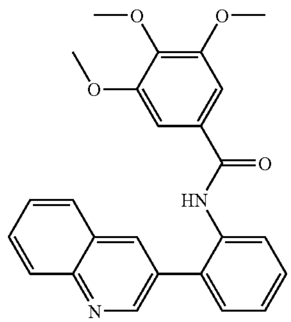 | | B | B |
| 416 | 368 | 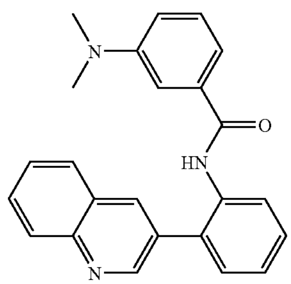 | | NA | |
| 419 | 406 | 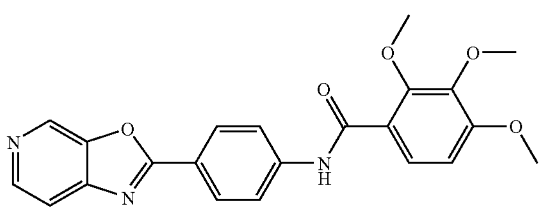 | | NA | |
| 420 | 376 | 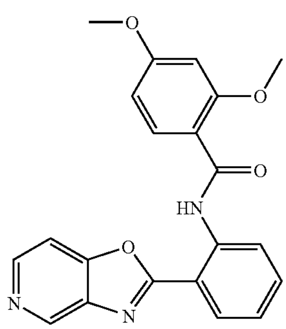 | | NA | |
| 421 | 406 | 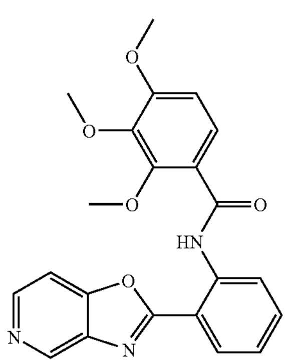 | A | | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 422 | 382 | 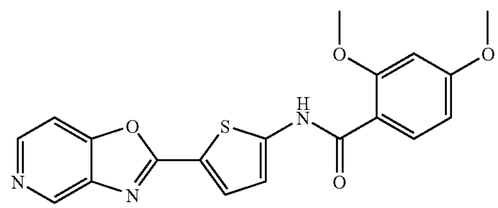 | | A | B |
| 423 | 382 | 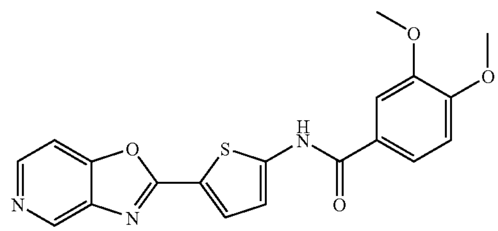 | | A' | B |
| 424 | 382 | 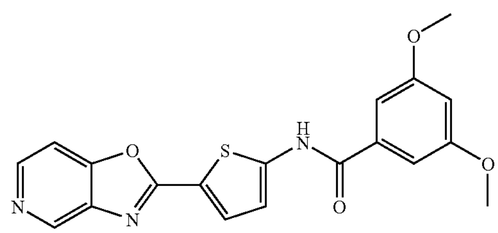 | | NA | |
| 425 | 412 | 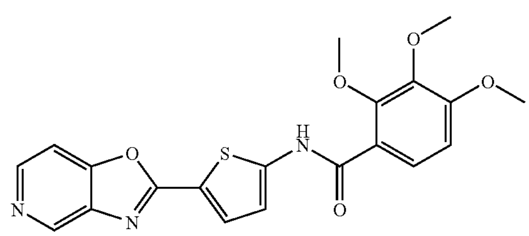 | | NA | |
| 426 | 412 | 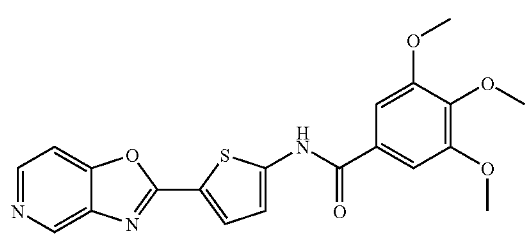 | | A' | B |
| 427 | 365 | 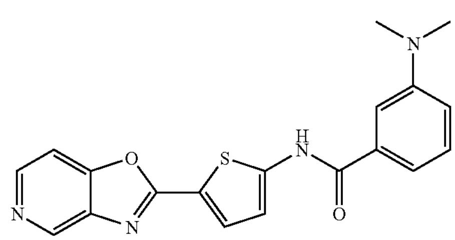 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 428 | 365 | 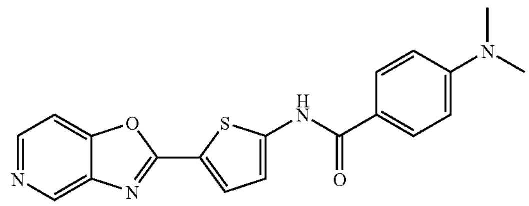 | | NA | |
| 429 | 376 | 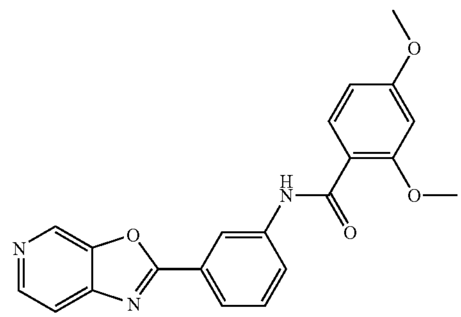 | | A' | B |
| 430 | 406 | 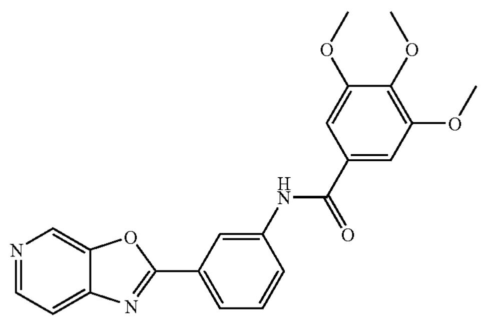 | | A | A |
| 431 | 359 | 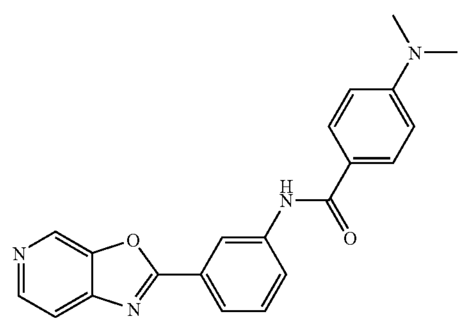 | | A | B |
| 436 | 445.1 | 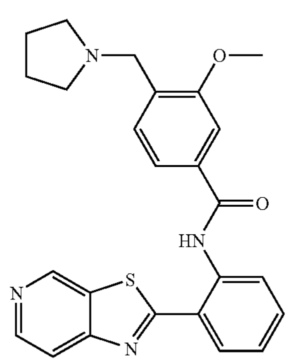 | | A | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 437 | 375.1 | 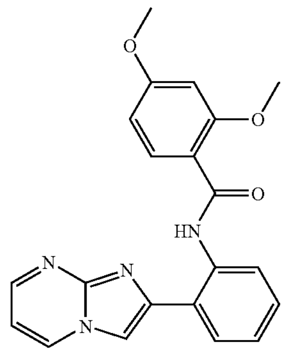 | | A | B |
| 438 | 375 | 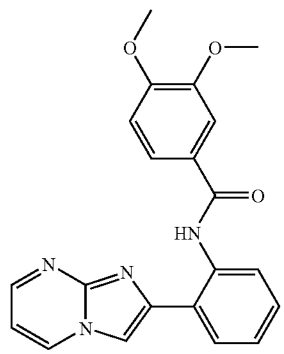 | | A' | A |
| 439 | 405 | 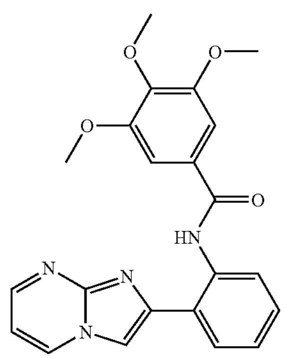 | | A' | B |
| 440 | 468 | 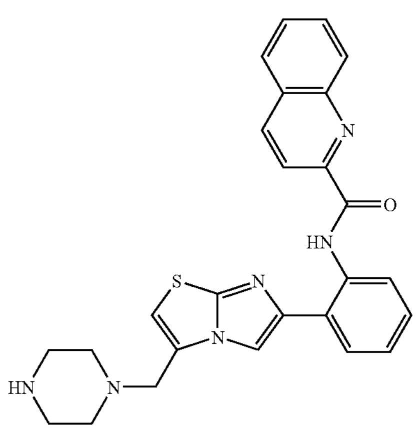 | | A' | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 441 | 470 | 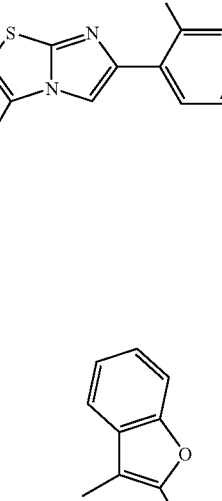 | | A' | A |
| 442 | 472 | 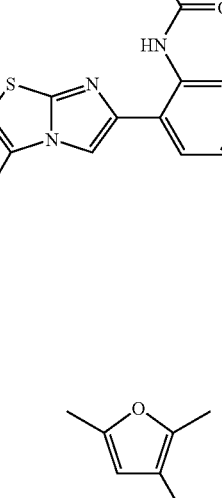 | | A' | A |
| 443 | 436 | 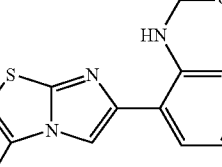 | | A | A |

TABLE 4-continued
Sirt1 Activators
| COMPOUND NO | [M + H]+ | STRUCTURE | ED50 FP ASSAY | ED50 MS ASSAY | FOLD ACT. MS |
|---|---|---|---|---|---|
| 444 | 464 | 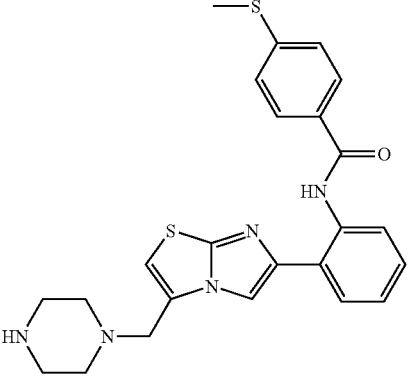 | | A | A |
| 445 | 432 | 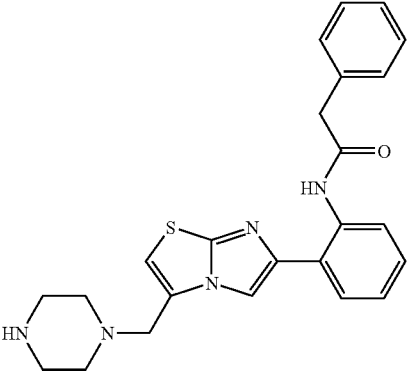 | | A | B |
| 446 | 424 | 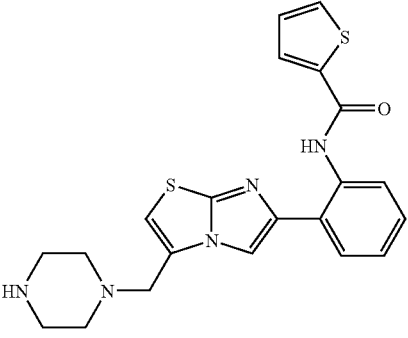 | | A | B |
| 447 | 484 | 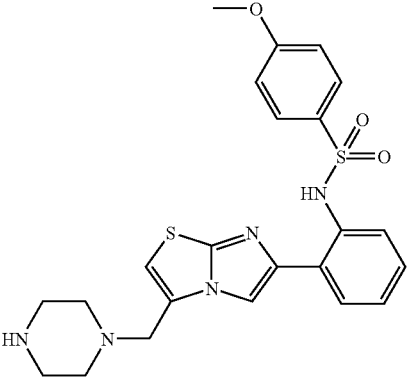 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 448 | 510 | 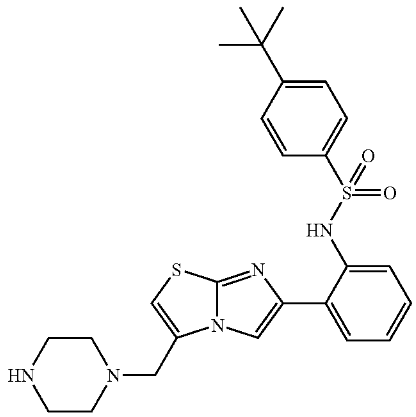 | | NA | |
| 449 | 376 | 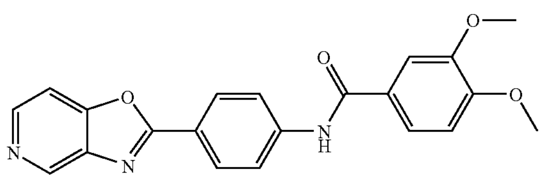 | | NA | |
| 450 | 392 | 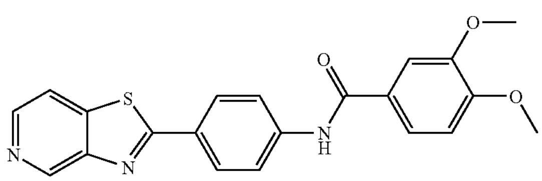 | | NA | |
| 451 | 376 | 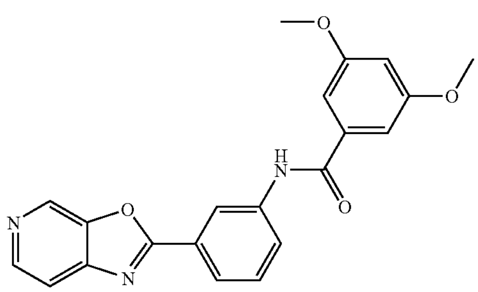 | | A | B |
| 452 | 406 | 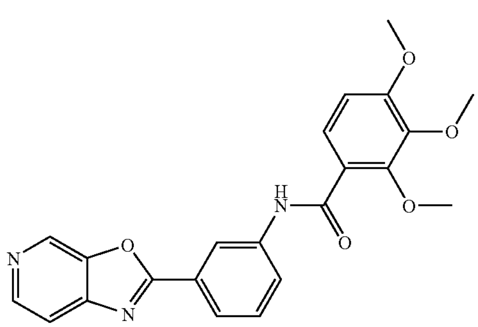 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 453 | 359 | | | A | B |
| 454 | 376 | | | A | B |
| 455 | 376 | | | A' | B |
| 456 | 376 | | | A' | B |

TABLE 4-continued

Sirt1 Activators

| COMPOUND NO | [M + H]+ | STRUCTURE | ED50 FP ASSAY | ED50 MS ASSAY | FOLD ACT. MS |
|---|---|---|---|---|---|
| 457 | 406 | 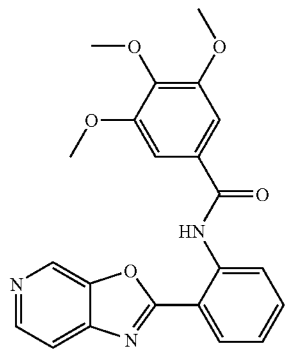 | | A | B |
| 458 | 359 | 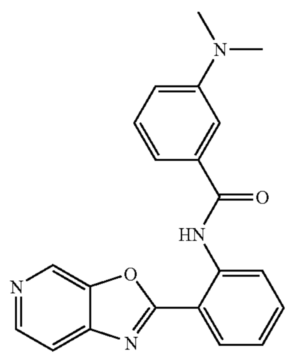 | | A' | B |
| 459 | 359 | 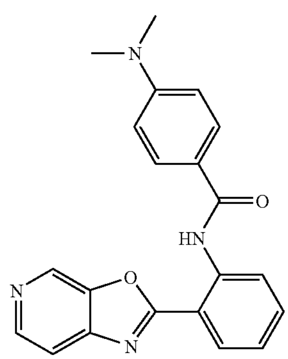 | | A' | B |
| 460 | 359.4 | 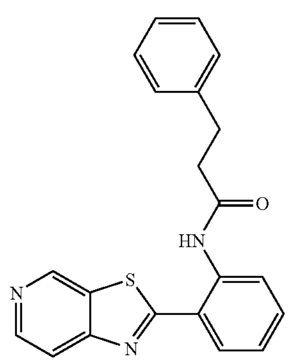 | | A | B |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 461 | 367.4 | 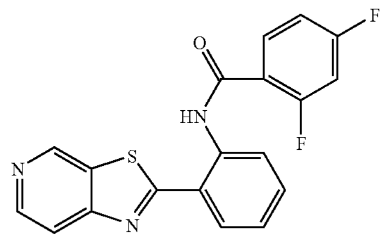 | | NA | |
| 462 | 391.5 | 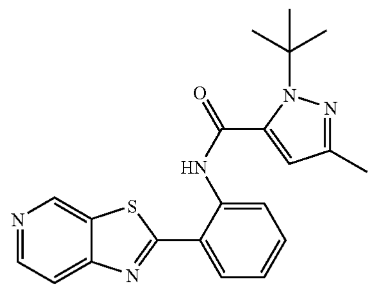 | | A' | B |
| 463 | 375.4 | 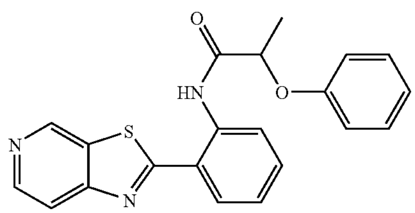 | | A | B |
| 465 | 395.9 | 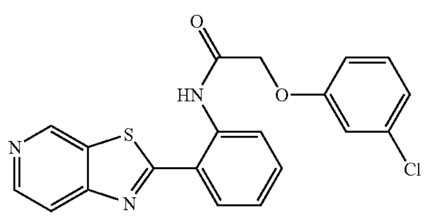 | | NA | |
| 466 | 445.5 | 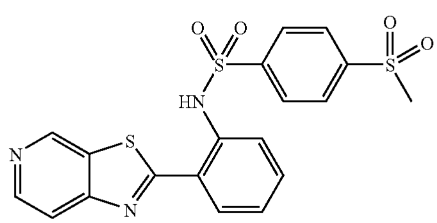 | | NA | |
| 467 | 427.2 | 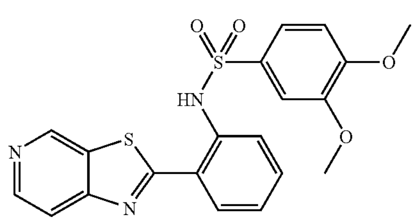 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 468 | 345.0 | 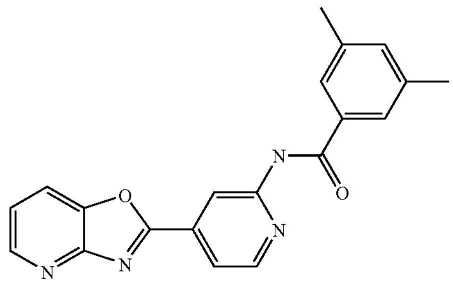 | | A | B |
| 469 | 435.4 | 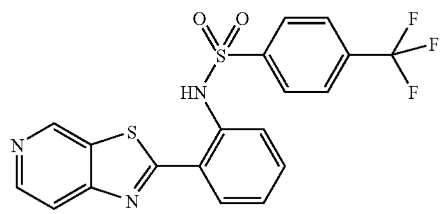 | | NA | |
| 470 | 365.0 | 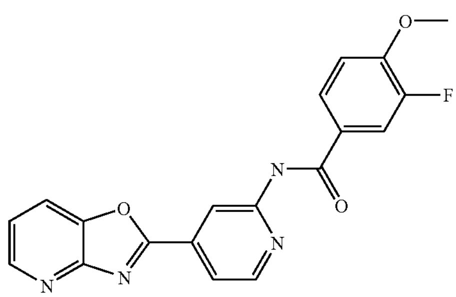 | | NA | |
| 471 | 488.9 | 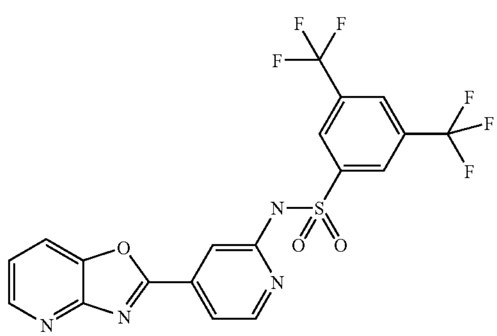 | | NA | |
| 472 | 437.5 | 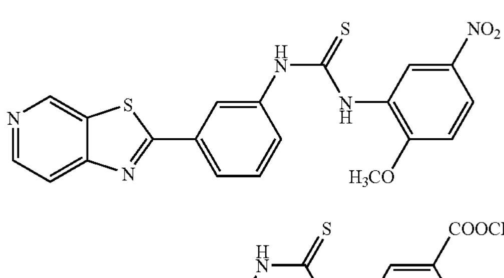 | | NA | |
| 473 | 420.5 | 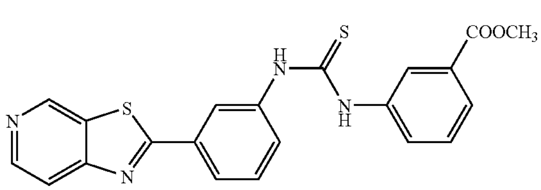 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 474 | | 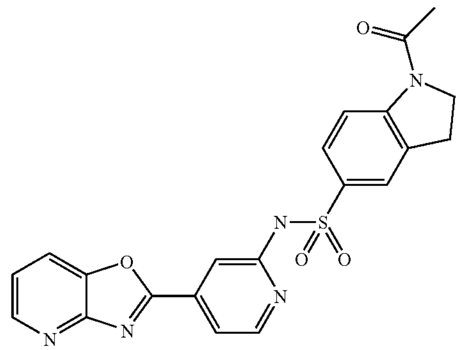 | | NA | |
| 475 | 408.6 | 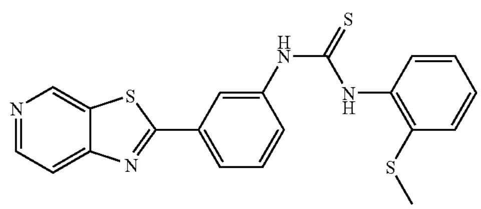 | | NA | |
| 476 | 410.9 | 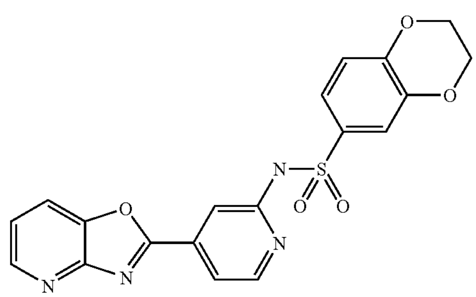 | | NA | |
| 477 | 435.9 | 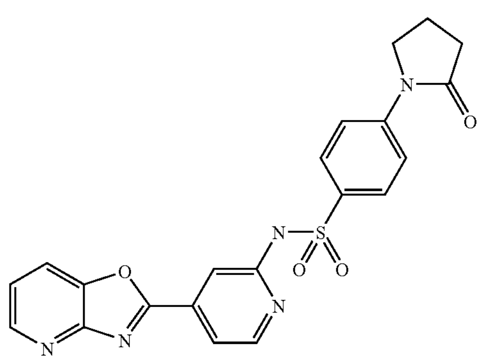 | | NA | |
| 478 | 404.8 | 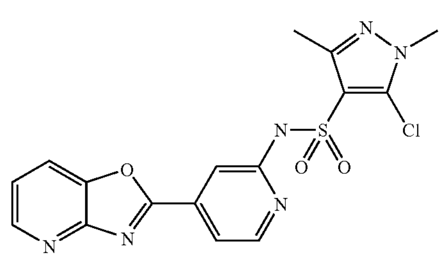 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 479 | 420.9 | | | NA | |
| 481 | 428.5 | | | A | B |
| 482 | 344.1 | | | A' | B |
| 483 | 364.1 | | | NA | |
| 484 | 448.6 | | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 485 | 363.5 | 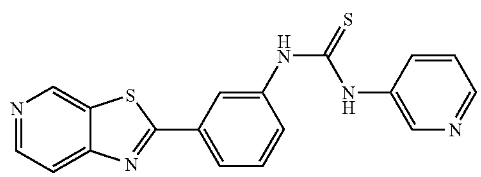 | | A | A |
| 486 | 385.9 | 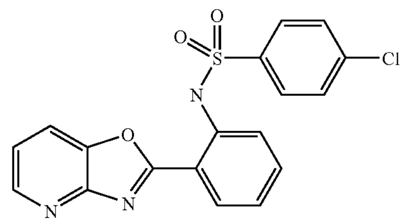 | | NA | |
| 487 | 396.1 | 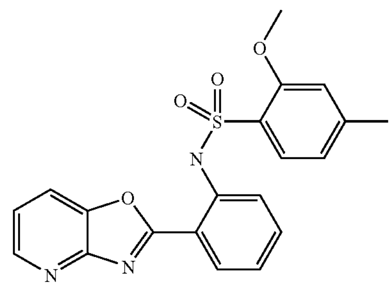 | | NA | |
| 488 | 435.1 | 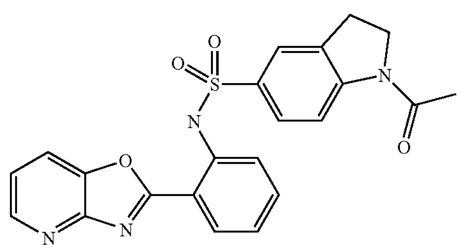 | | NA | |
| 489 | 410.1 | 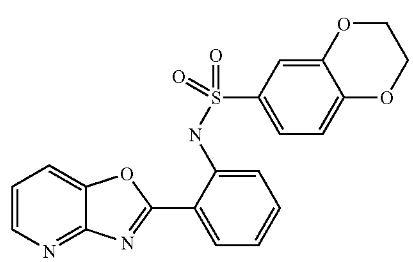 | | NA | |
| 490 | 434.9 | 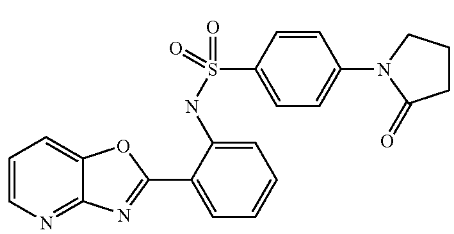 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 491 | 420.5 | 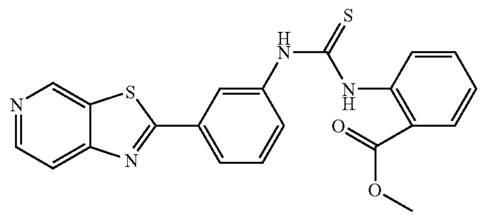 | | NA | |
| 492 | 404.0 | 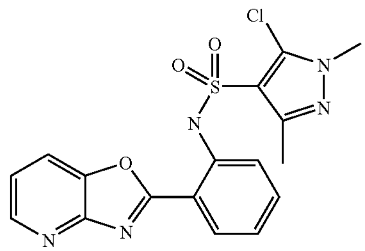 | | NA | |
| 493 | | 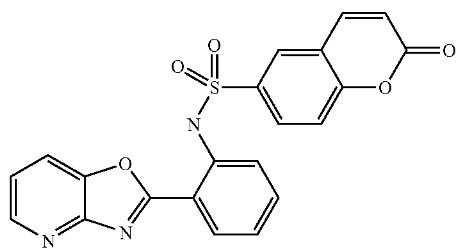 | | NA | |
| 494 | 422.9 | 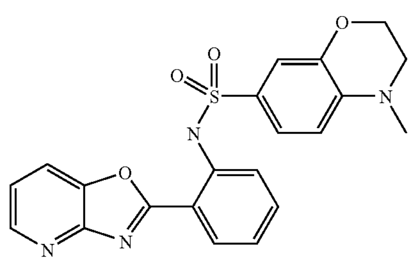 | | NA | |
| 495 | 366.0 | 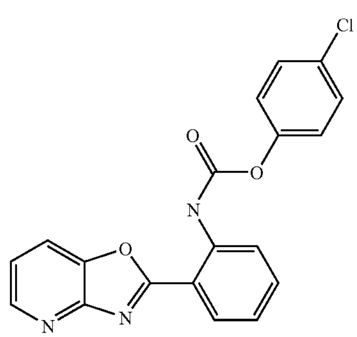 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 496 | 349.9 | 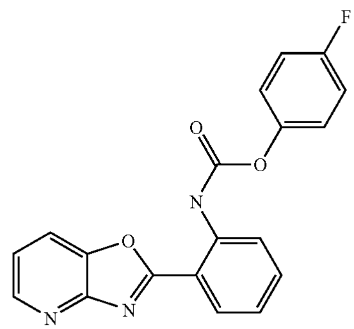 | | NA | |
| 497 | 346.0 | 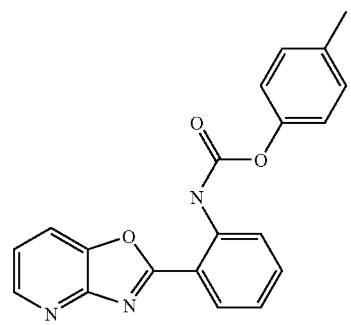 | | NA | |
| 498 | 406.5 | 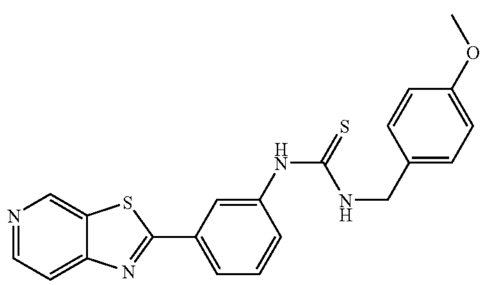 | | A | B |
| 499 | 362.1 | 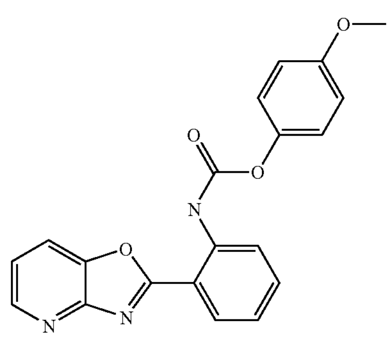 | | NA | |
| 500 | | 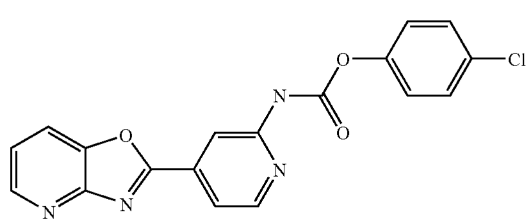 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 501 | 347.1 | 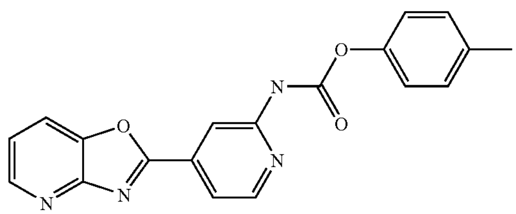 | | NA | |
| 502 | 363.1 | 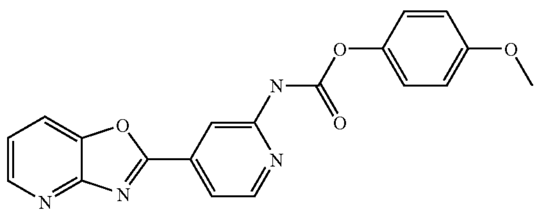 | | NA | |
| 503 | 443.1 | 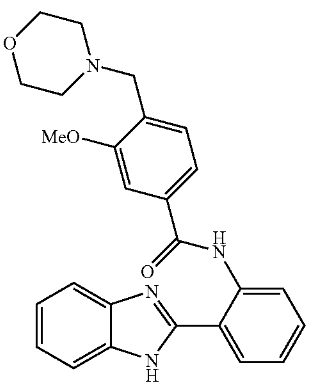 | | A' | A |
| 504 | 358 | 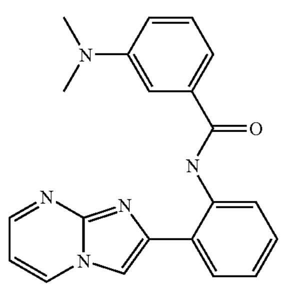 | | A | B |
| 505 | 359 | 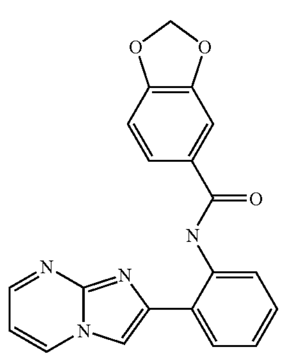 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 506 | 429.1 | 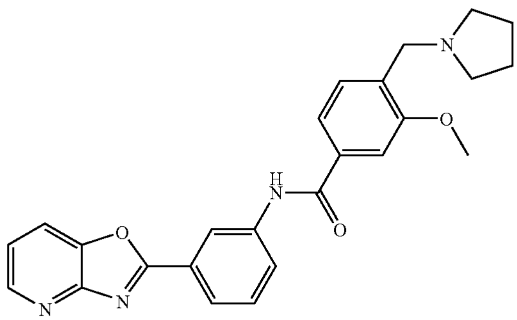 | | A | A |
| 507 | 388.1 | 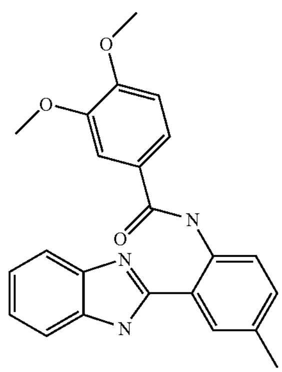 | | A' | A |
| 508 | 366.1 | 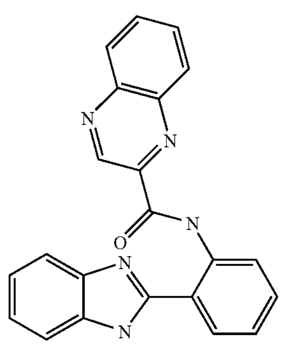 | | A' | A |
| 510 | 457 | 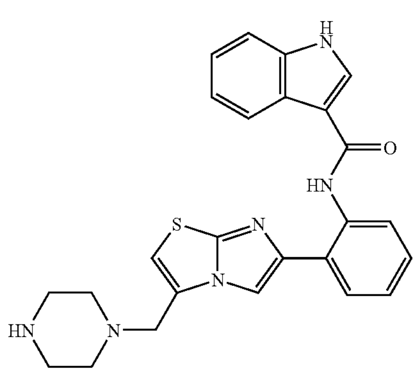 | | A' | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 511 | 460 | 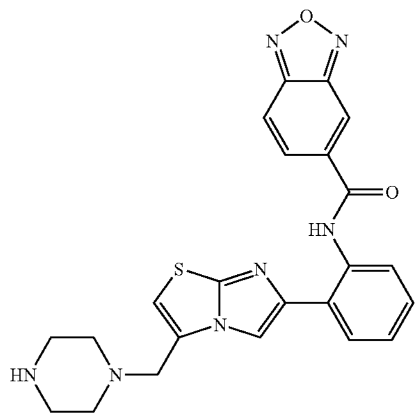 | | NA | |
| 512 | 484 | 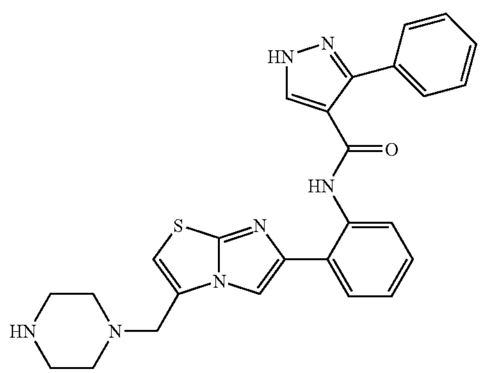 | | A' | A |
| 513 | 470 | 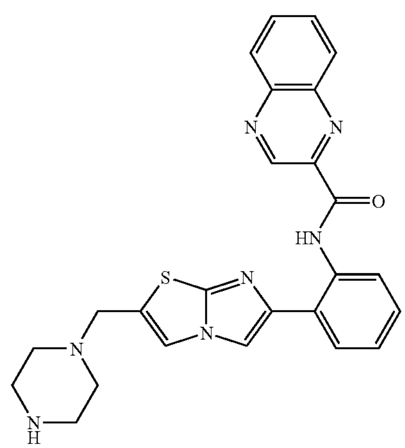 | | A' | A |
| 514 | 466 | 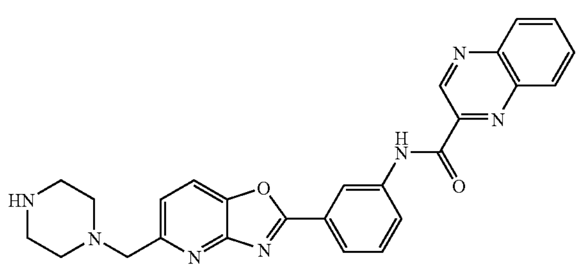 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 515 | 398 | 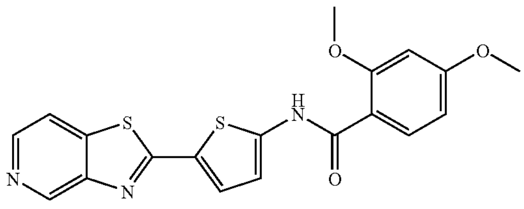 | | A' | B |
| 516 | 398 | 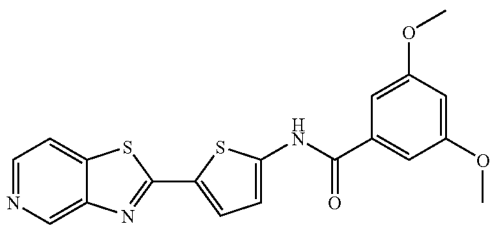 | | NA | |
| 517 | 428 | 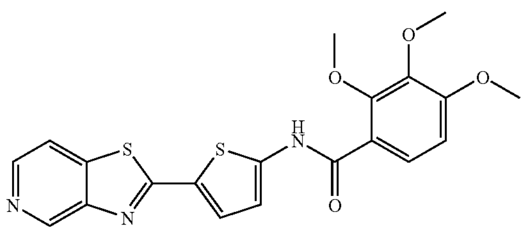 | | NA | |
| 518 | 381 | 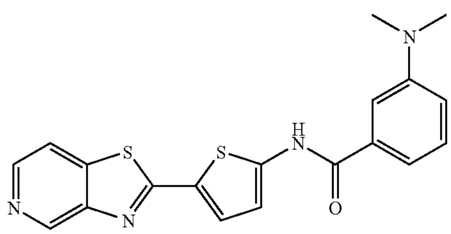 | | A' | B |
| 519 | 381 | 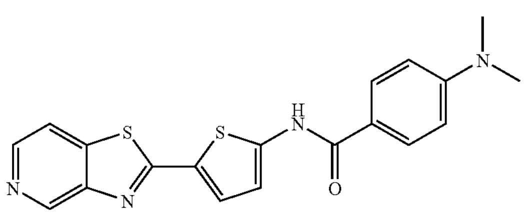 | | A' | B |
| 520 | 428 | 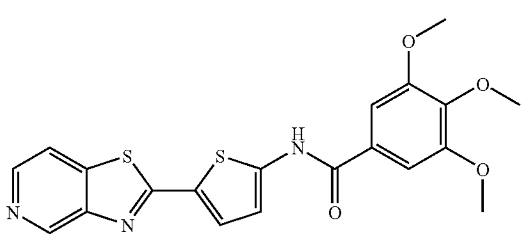 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 521 | 375.0 | 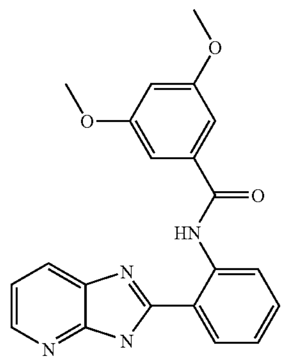 | | A' | B |
| 522 | 405.0 | 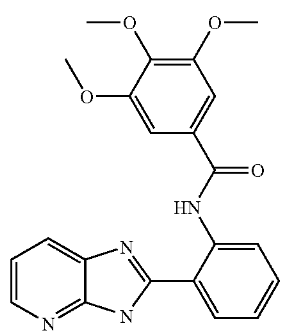 | | A | A |
| 523 | 359.0 | 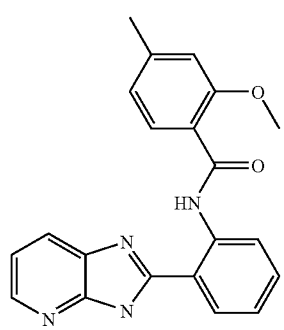 | | A | B |
| 524 | 358.0 | 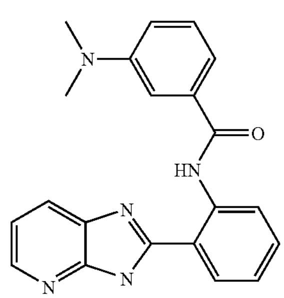 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 525 | 375.0 | 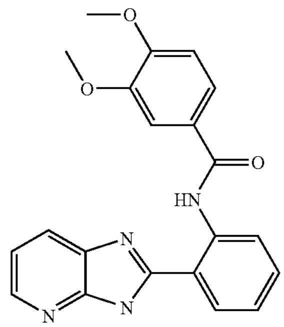 | | A' | B |
| 526 | 400.0 | 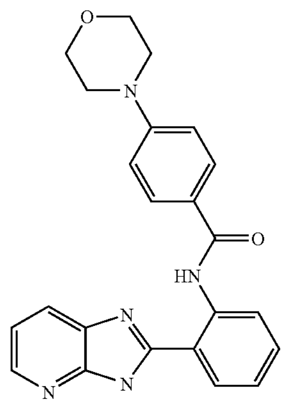 | | A' | A |
| 527 | 398.0 | 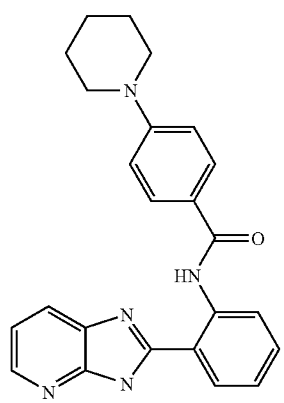 | | A' | B |
| 528 | 412.9 | 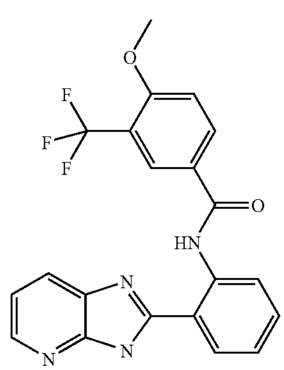 | | A' | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 529 | 399.1 | 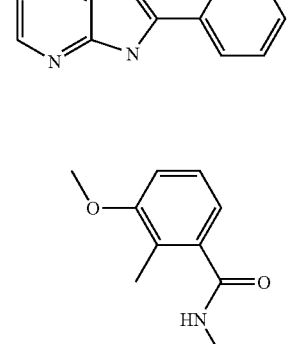 | | A' | B |
| 530 | 359.0 | 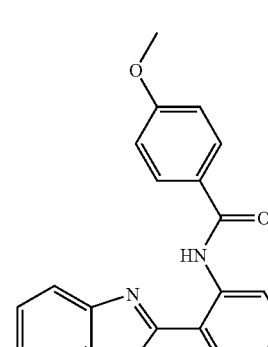 | | A' | B |
| 531 | 345.0 | 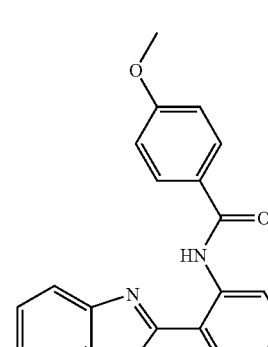 | | A' | B |
| 532 | 345.0 | 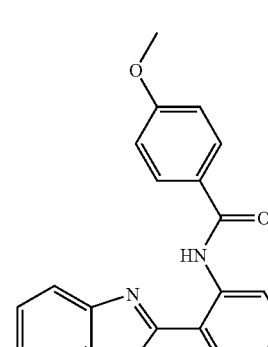 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 533 | 315.0 | 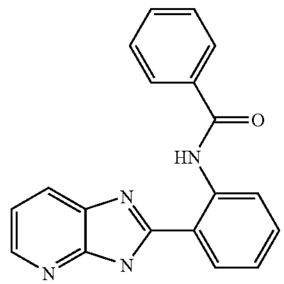 | | A' | B |
| 534 | 358.0 | 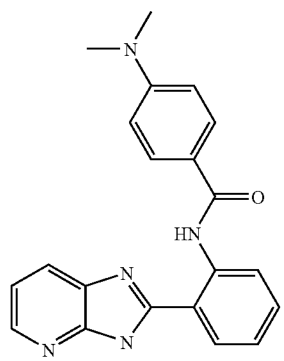 | | A' | B |
| 535 | 428.1 | 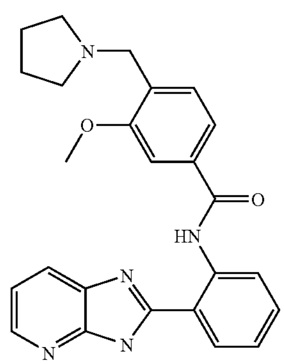 | | A | A |
| 536 | 442.1 | 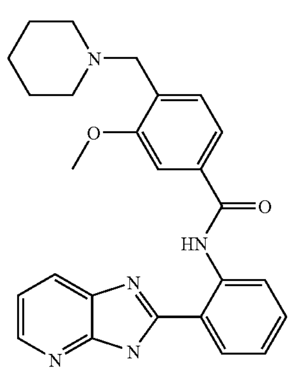 | | A | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 537 | 444.0 | 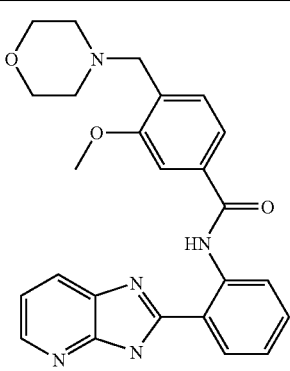 | | A' | A |
| 538 | 443.1 | 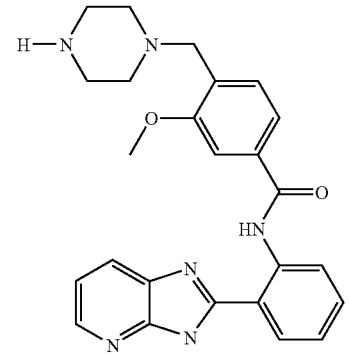 | | A | A |
| 539 | 457.1 | 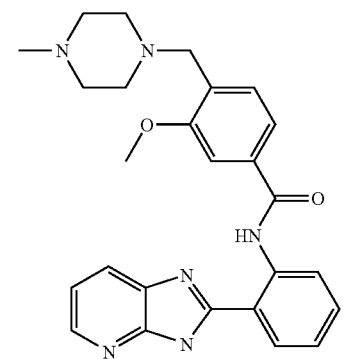 | | A' | A |
| 540 | 402.1 | 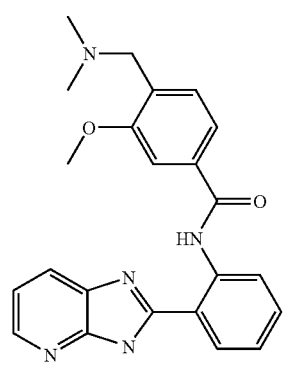 | | A | A |

TABLE 4-continued
Sirt1 Activators
| COMPOUND NO | [M + H]+ | STRUCTURE | ED50 FP ASSAY | ED50 MS ASSAY | FOLD ACT. MS |
|---|---|---|---|---|---|
| 541 | 443.1 | 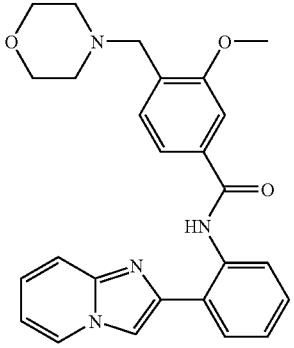 | | A | B |
| 542 | 444 | 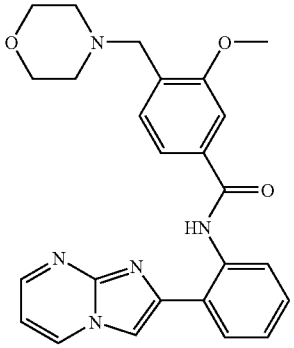 | | A | A |
| 543 | 420 | 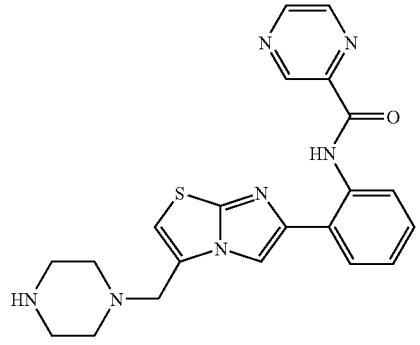 | | A' | A |
| 544 | 474 | 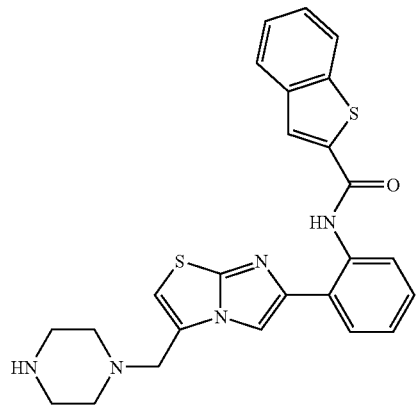 | | A | A |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 545 | 378.1 | 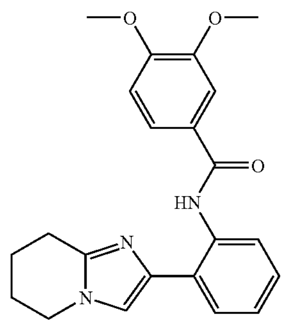 | | A | B |
| 546 | 408 | 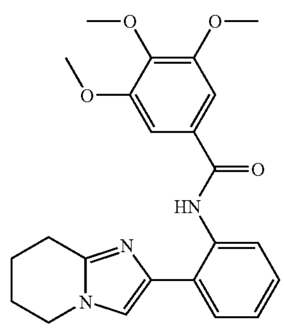 | | A | B |
| 547 | 369 | 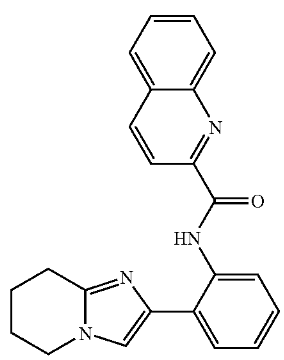 | | A' | B |
| 548 | 370 | 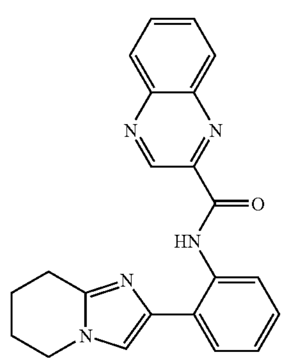 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 556 | 365.1 | 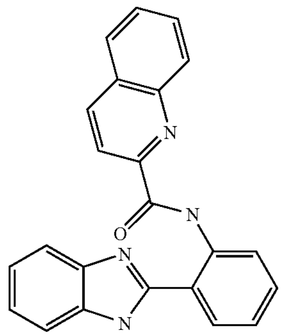 | | A' | A |
| 557 | 542.1 | 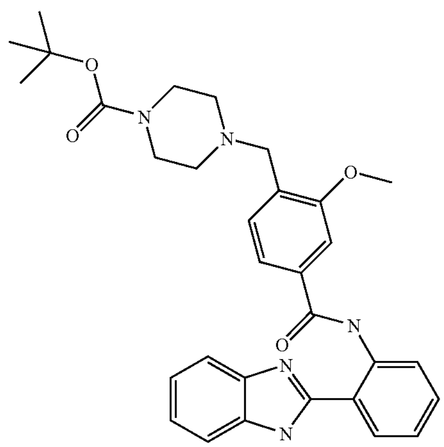 | | NA | |
| 558 | 442.1 | 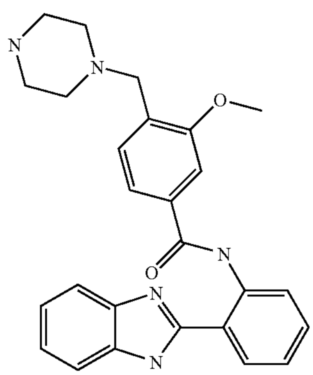 | | A' | A |
| 559 | 508 | 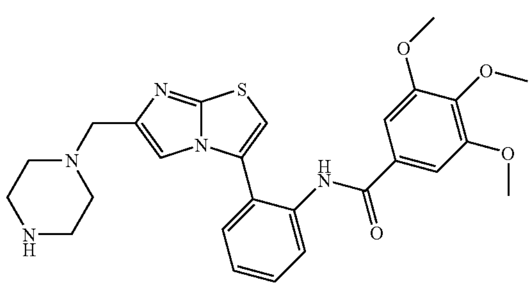 | | NA | |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 560 | 470 | 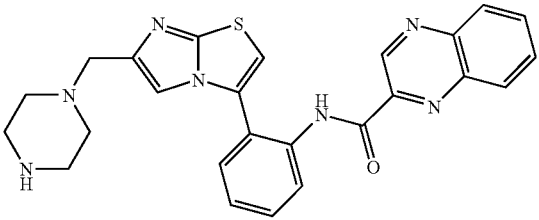 | | NA | |
| 561 | 382 | 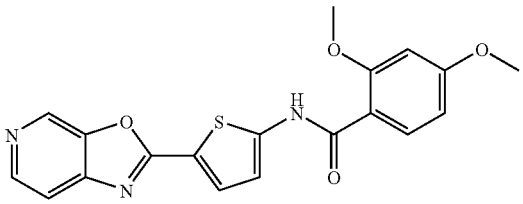 | | A' | B |
| 562 | 382 | 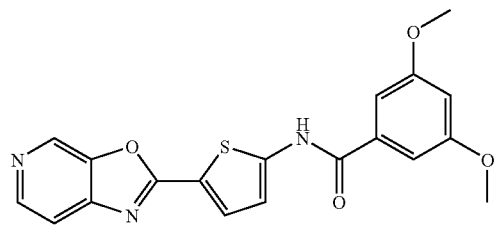 | | A' | B |
| 563 | 412 | 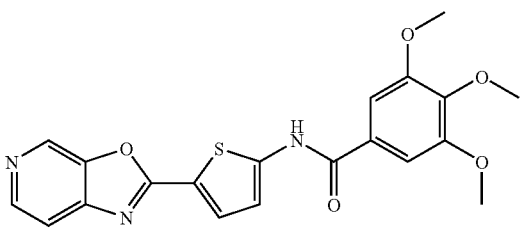 | | A | B |
| 565 | 400.8 | 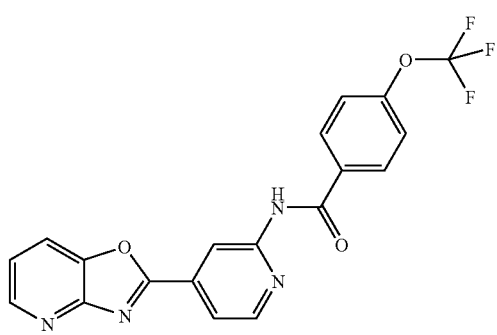 | | NA | |
| 566 | 409.9 | 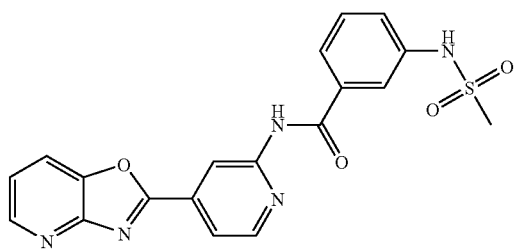 | | A | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 567 | 374.9 | 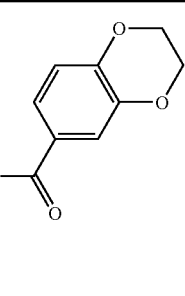 | | NA | |
| 568 | 367.0 | 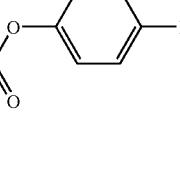 | | NA | |
| 569 | 374.9 | 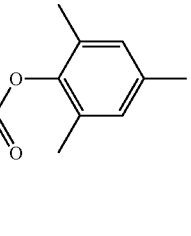 | | NA | |
| 570 | 361.0 | 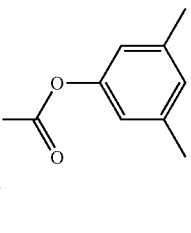 | | NA | |
| 571 | 444.0 | 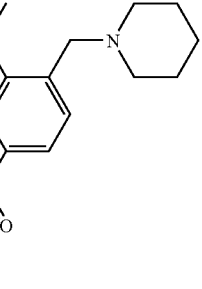 | | A | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 572 | 429.9 | 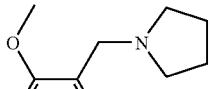 | | B | B |
| 573 | 431.8 | 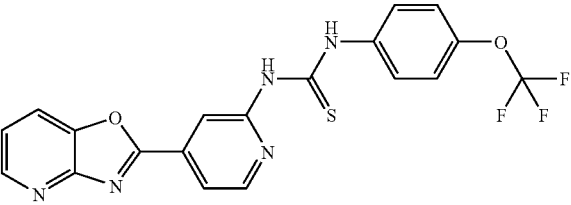 | | NA | |
| 574 | 376.2 | 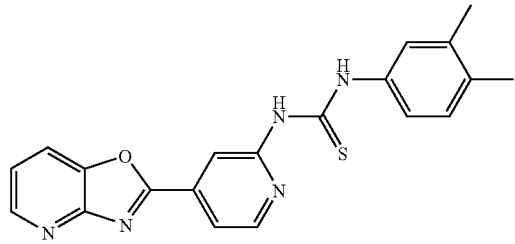 | | NA | |
| 575 | 439.9 | 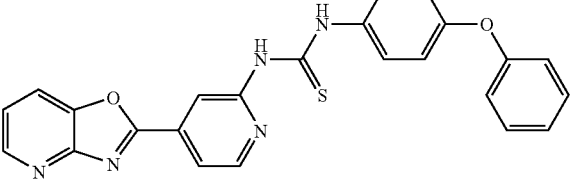 | | NA | |
| 576 | 376.1 | 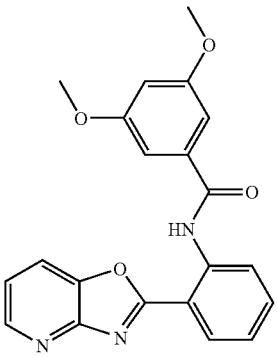 | | NA | |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 577 | 400.1 | 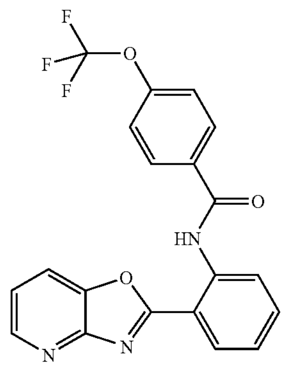 | | | NA |
| 578 | 368.1 | 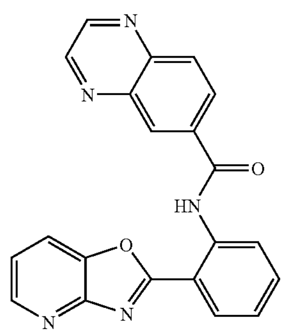 | | | NA |
| 579 | 401.1 | 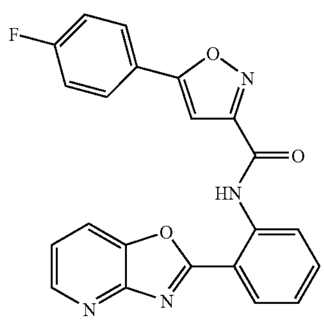 | | | NA |
| 580 | 374.0 | 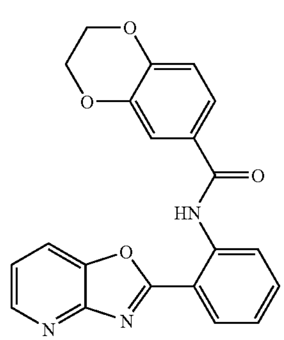 | | | NA |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 581 | 334.0 | 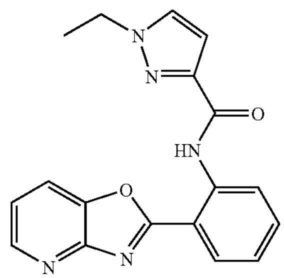 | | A | B |
| 582 | 400.0 | 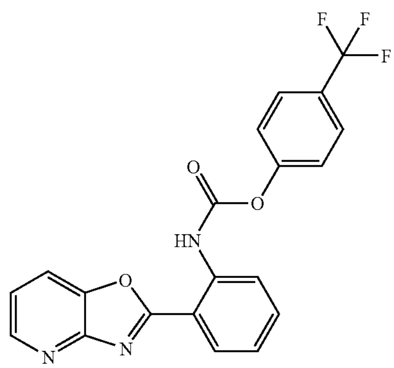 | | NA | |
| 583 | 374.1 | 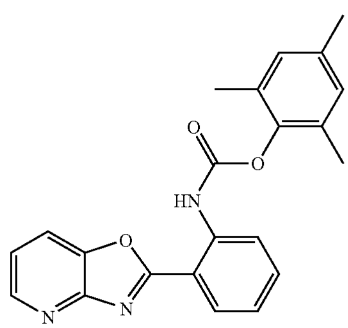 | | NA | |
| 584 | 360.0 | 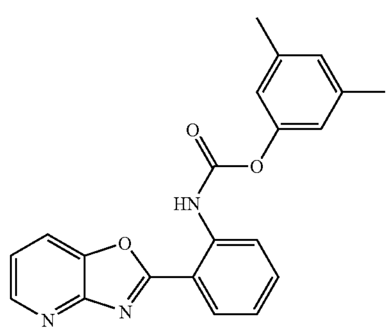 | | NA | |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 585 | 443.1 | 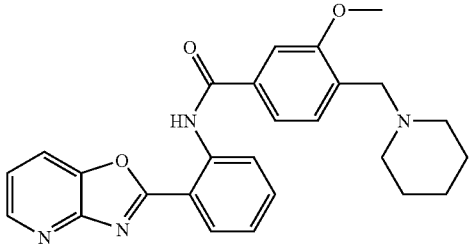 | | A | B |
| 587 | 427.1 | 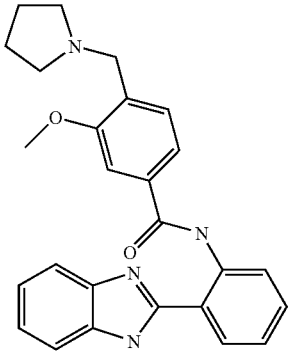 | | A' | B |
| 588 | 520 | 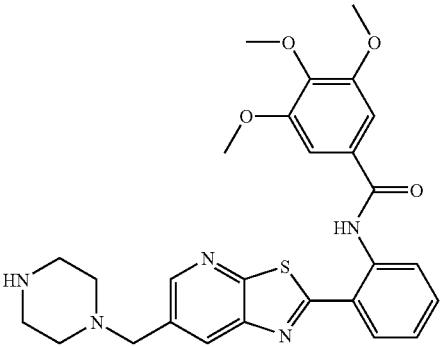 | | A | A |
| 589 | 490 | 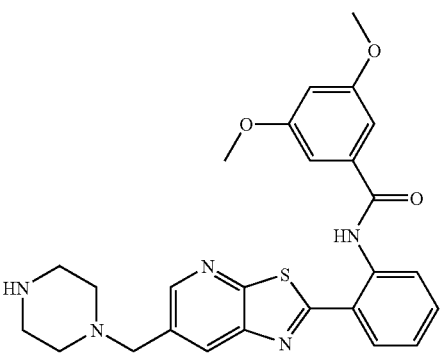 | | A' | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 590 | 474 | 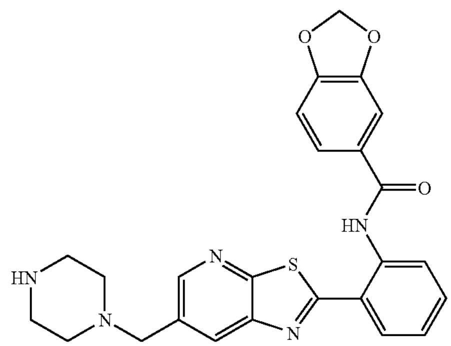 | | A | B |
| 591 | 458 | 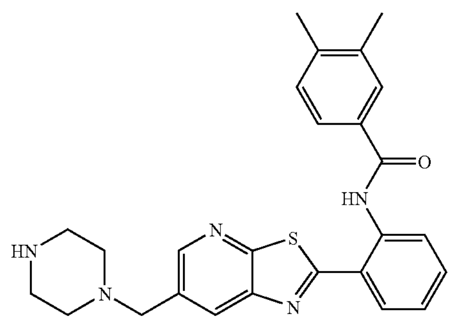 | | A' | A |
| 592 | 455 | 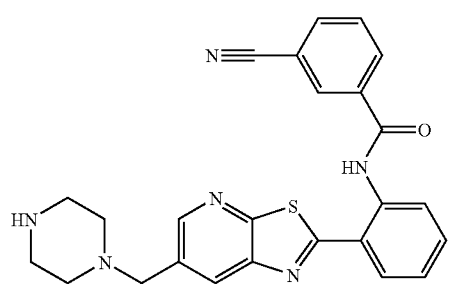 | | A' | B |
| 593 | 473 | 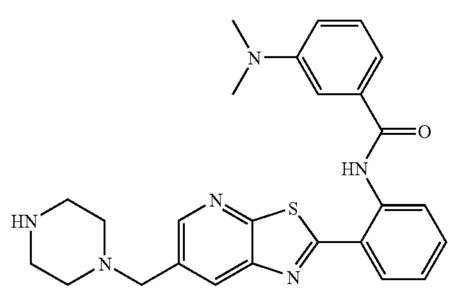 | | A' | A |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 594 | 466 | 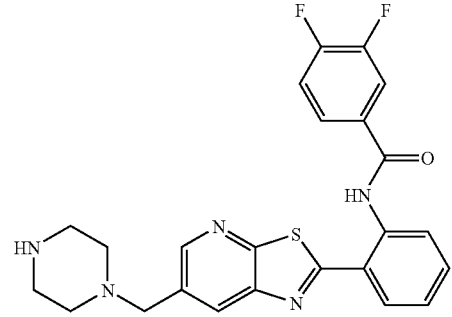 | | A | B |
| 596 | 467.4 | 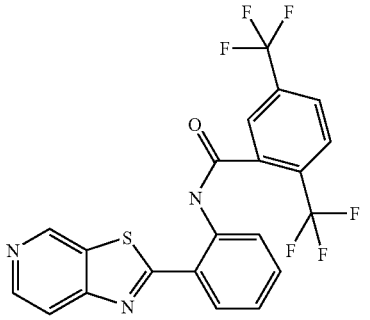 | | A' | B |
| 597 | 377.2 | 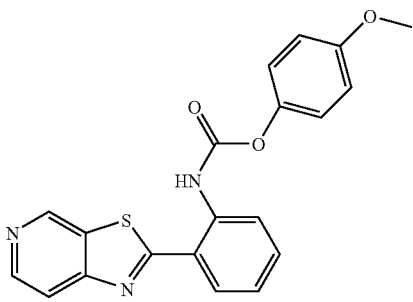 | | A' | B |
| 599 | 422.3 | 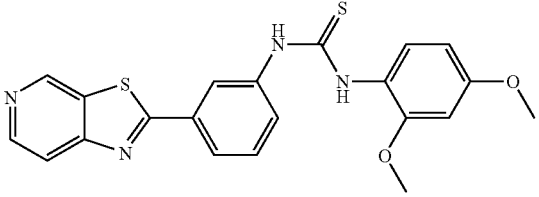 | | A' | B |
| 600 | 422.5 | 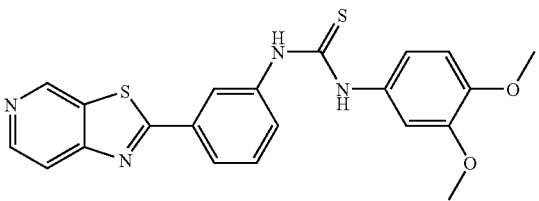 | | D | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 601 | 405.5 | 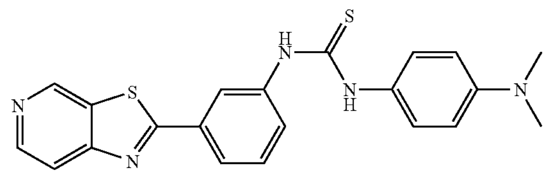 | | NA | |
| 604 | 360.4 | 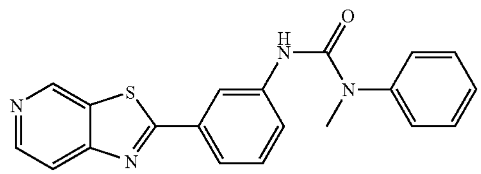 | | NA | |
| 605 | 377.4 | 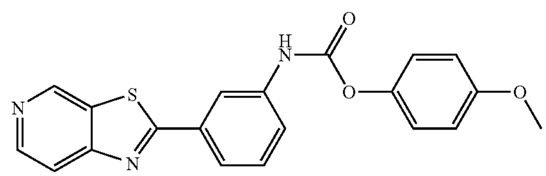 | | NA | |
| 607 | 415.4 | 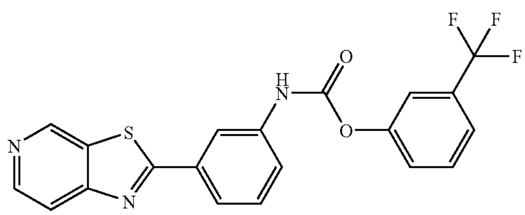 | | NA | |
| 608 | 332.4 | 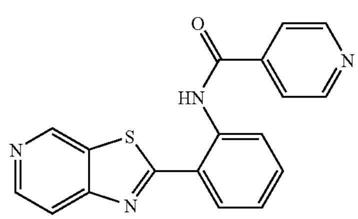 | | NA | |
| 609 | 439.3 | 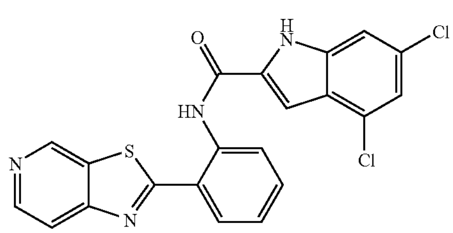 | | NA | |
| 610 | 418.6 | 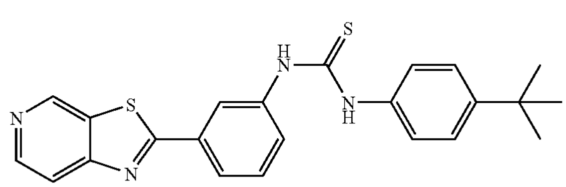 | | NA | |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 611 | 465.6 | 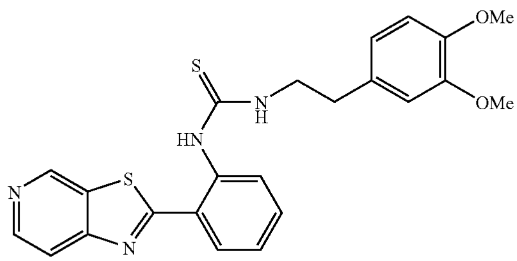 | | A' | B |
| 612 | 402.5 | 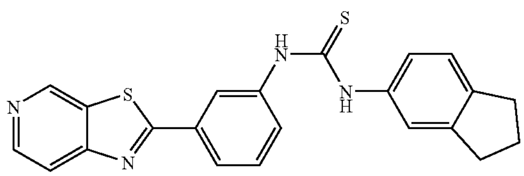 | | NA | |
| 614 | 428.5 | 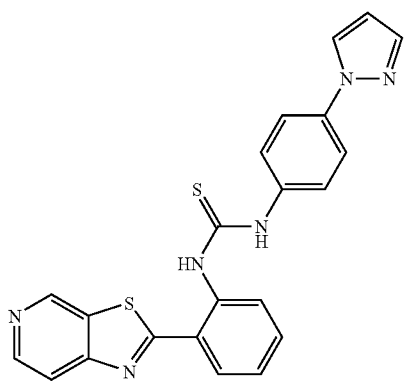 | | NA | |
| 615 | 408.6 | 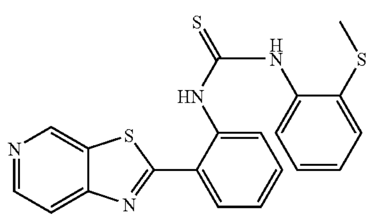 | | NA | |
| 616 | 437.5 | 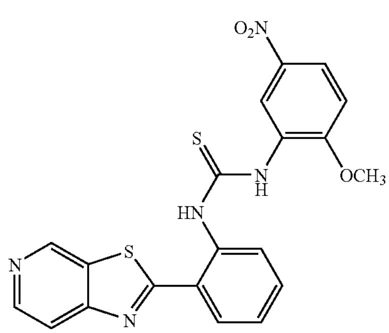 | | | |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 617 | 471.1 | 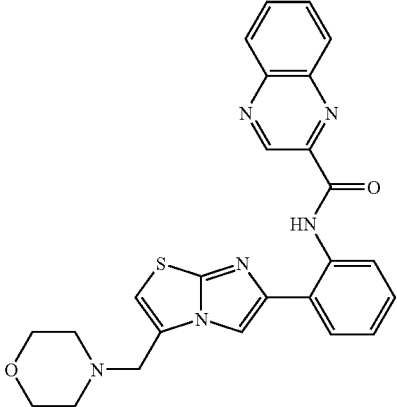 | | A' | A |
| 618 | 469.1 | 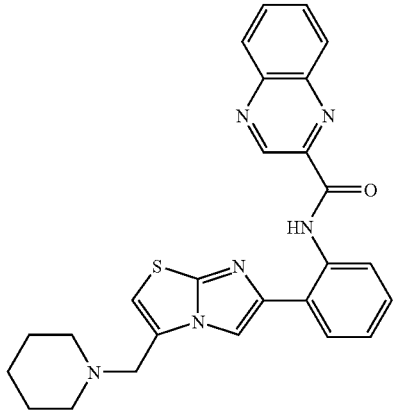 | | A' | B |
| 619 | 455 | 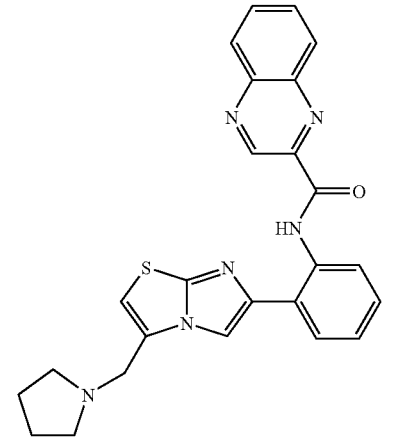 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 620 | 493.1 | 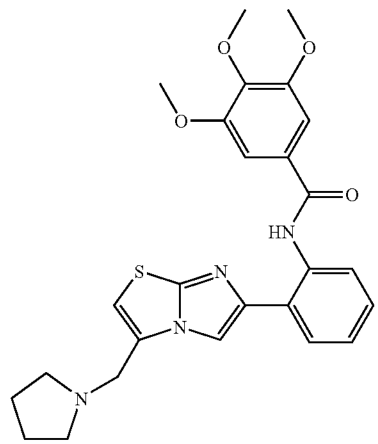 | | A' | B |
| 621 | 472 | 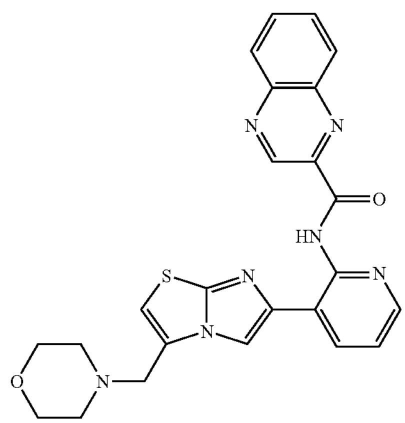 | | A' | A |
| 622 | 482 | 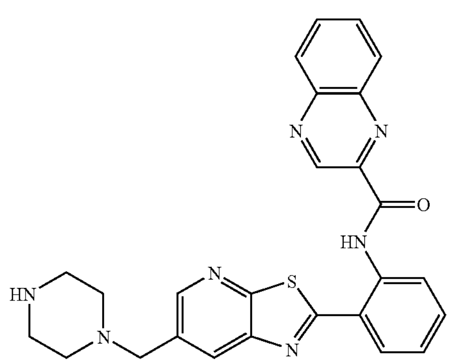 | | A' | A |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 623 | 437 | 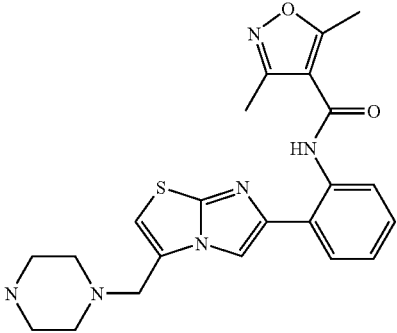 | | NA | C |
| 624 | 458 | 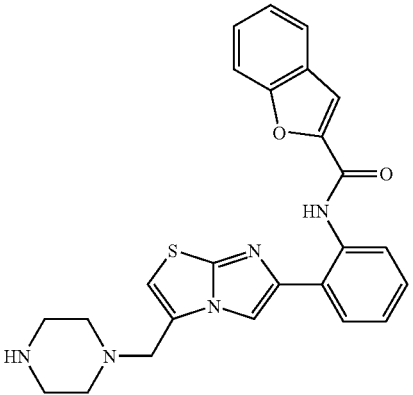 | | A' | A |
| 625 | 496 | 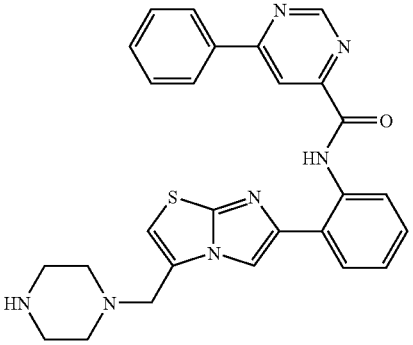 | | A' | A |

TABLE 4-continued

Sirt1 Activators

| COMPOUND NO | [M + H]+ | STRUCTURE | $ED_{50}$ FP ASSAY | $ED_{50}$ MS ASSAY | FOLD ACT. MS |
|---|---|---|---|---|---|
| 628 | 574.1 | 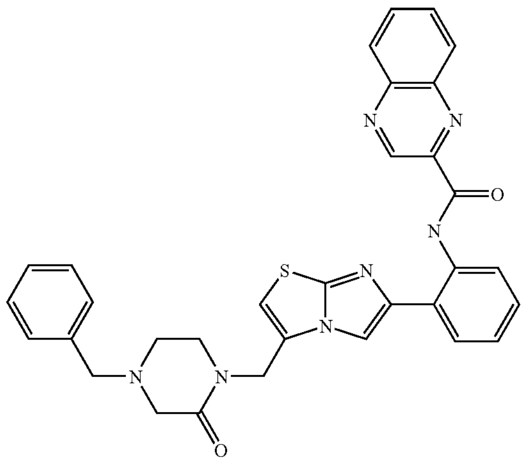 | | A' | B |
| 629 | 429.0 | 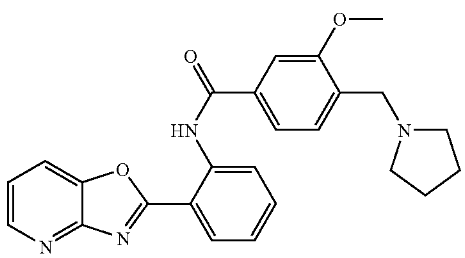 | | A | A |
| 630 | 403.1 | 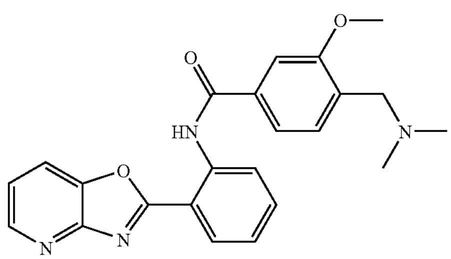 | | A | A |
| 631 | 445.0 | 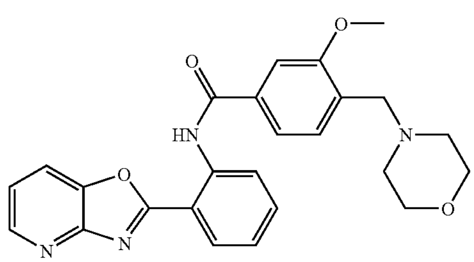 | | A' | B |
| 632 | 458.1 | 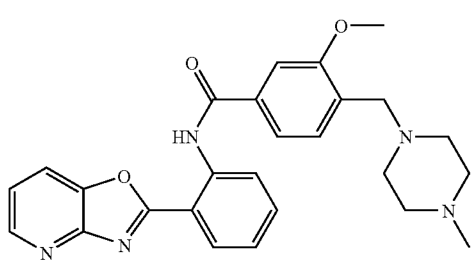 | | A | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 633 | 423.3 | 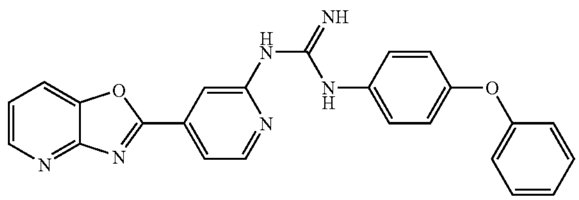 | | NA | C |
| 634 | 364.9 | 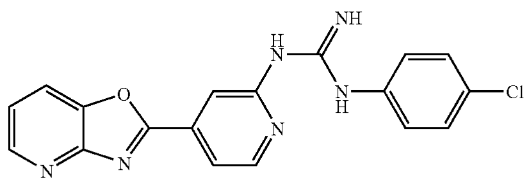 | | D | B |
| 635 | 421.1 | 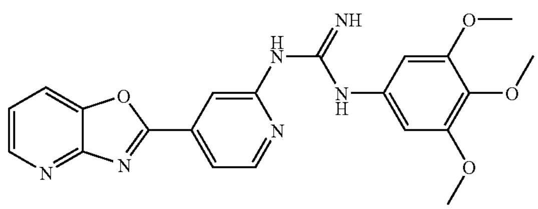 | | D | A |
| 636 | 359.9 | 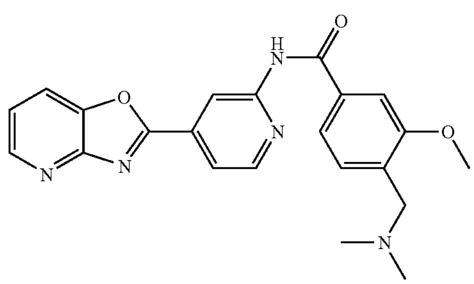 | | B | B |
| 637 | 459.3 | 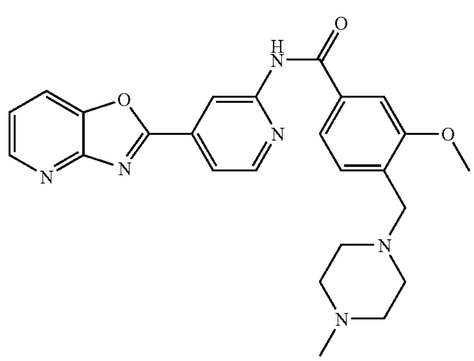 | | D | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 638 | 445.2 | 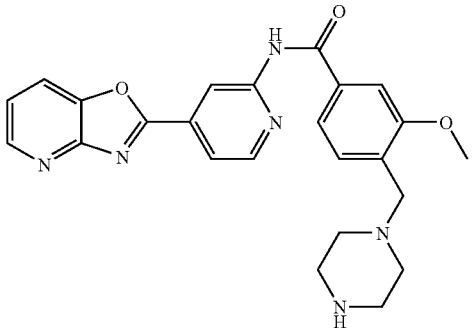 | | D | B |
| 639 | 378.9 | 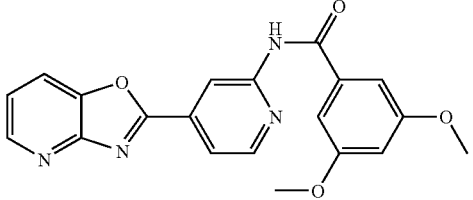 | | A | B |
| 640 | 368.9 | 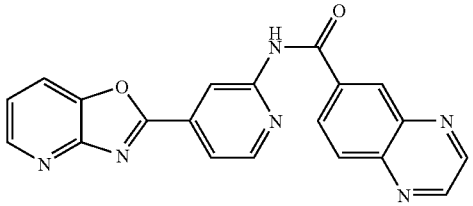 | | NA | C |
| 641 | 334.9 | 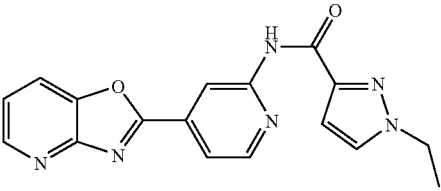 | | D | B |
| 642 | 446.2 | 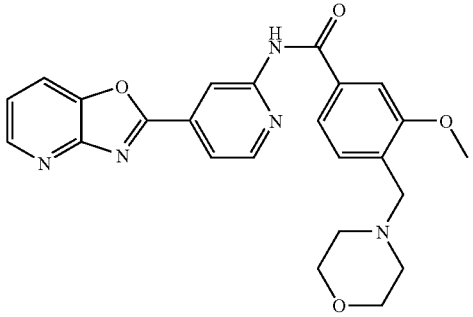 | | D | B |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 643 | 535.1 | 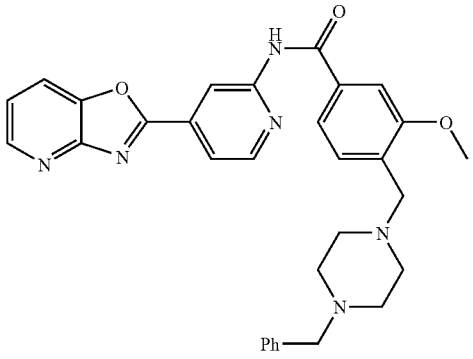 | | A | B |
| 644 | 434 | 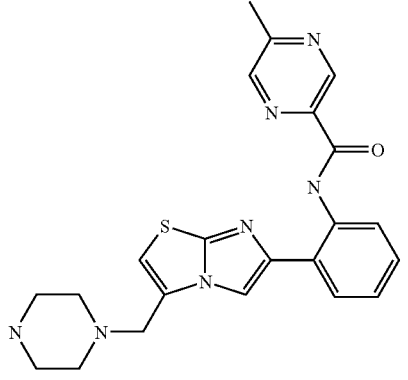 | | A | A |
| 645 | 469 | 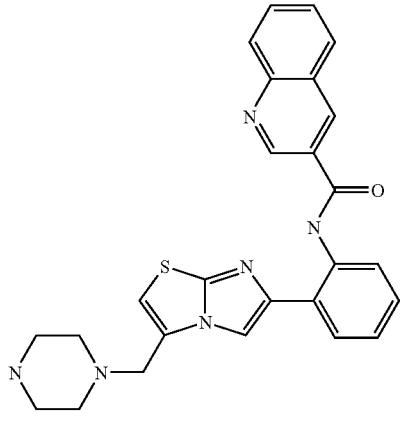 | | A' | A |
| 646 | 481 | 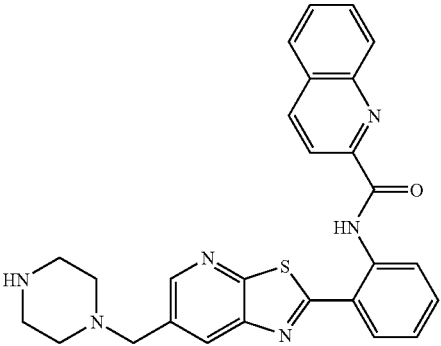 | | A | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 647 | 473.1 | 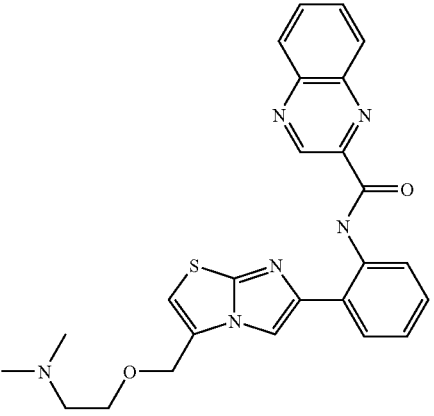 | | A' | A |
| 648 | 402.1 | 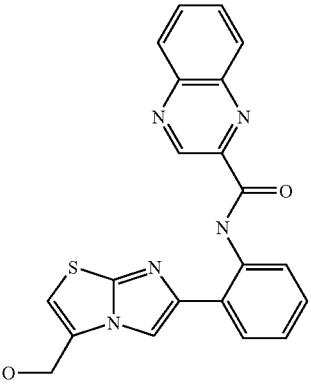 | | A' | B |
| 649 | 512.2 | 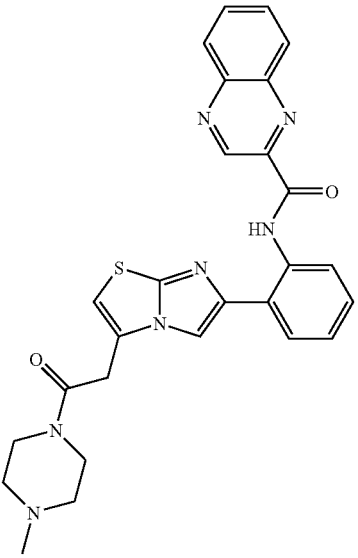 | | A' | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 650 | 570.2 | 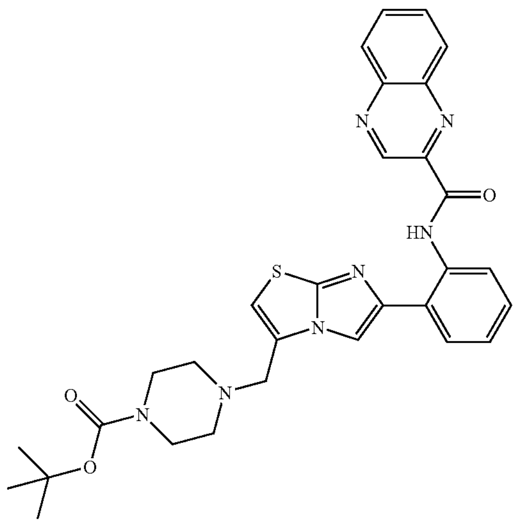 | | NA | |
| 651 | 512.2 | 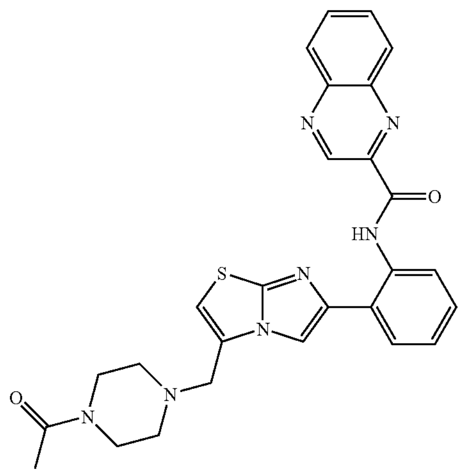 | | A' | A |
| 655 | 393.0 | 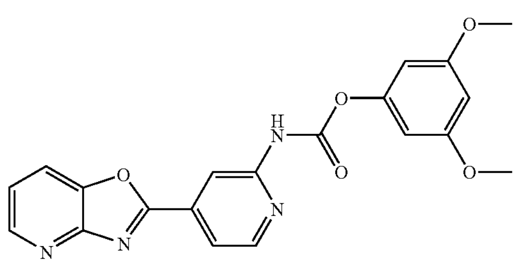 | | NA | C |
| 656 | 393.2 | 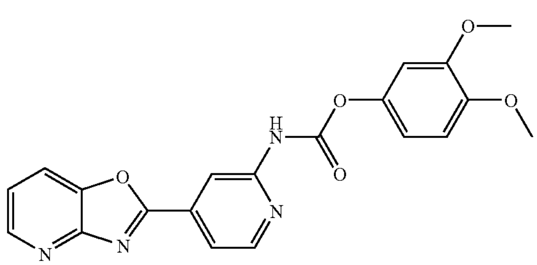 | | NA | C |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 657 | 423.1 | 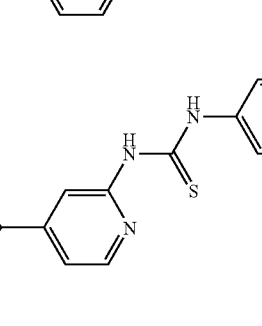 | | NA | C |
| 658 | 382.1 | 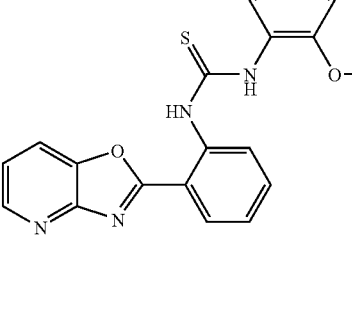 | | NA | C |
| 659 | 509.2 | 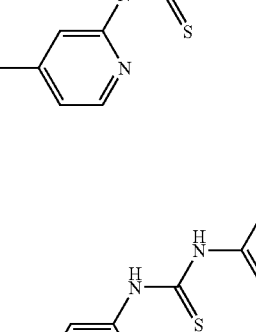 | | NA | C |
| 660 | 408.1 | 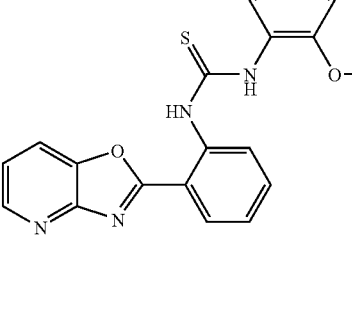 | | A | B |
| 661 | 408.2 | 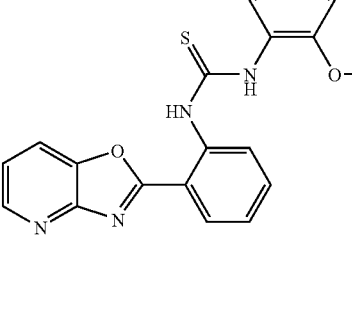 | | A' | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 662 | 378.2 | 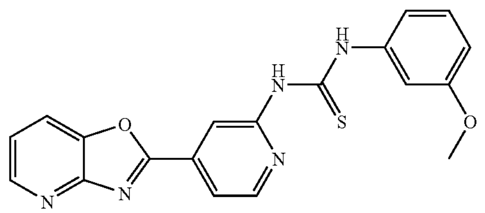 | | NA | C |
| 663 | 438.0 | 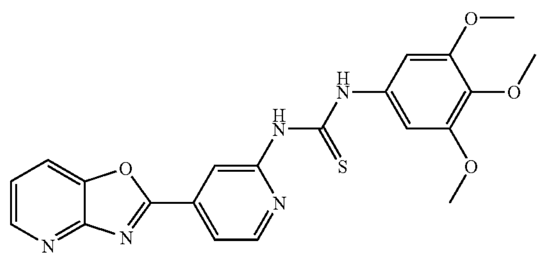 | | A | B |
| 664 | 477.8 | 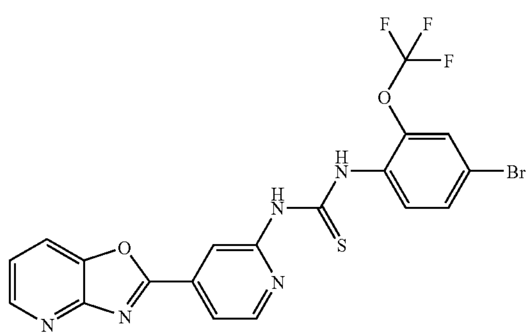 | | NA | C |
| 665 | 406.1 | 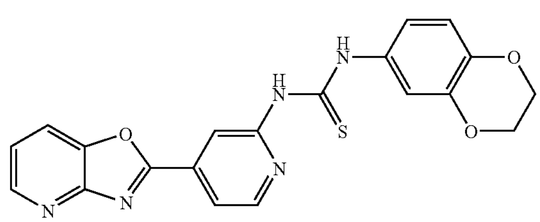 | | NA | C |
| 666 | 391.0 | 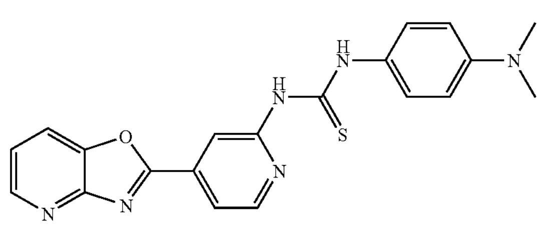 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 667 | 448.0 | 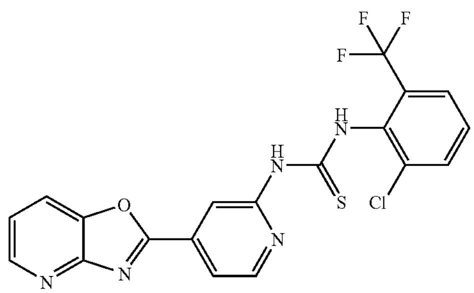 | | A | A |
| 668 | 410.0 | 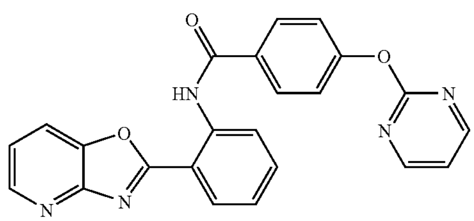 | | A | B |
| 669 | 392.0 | 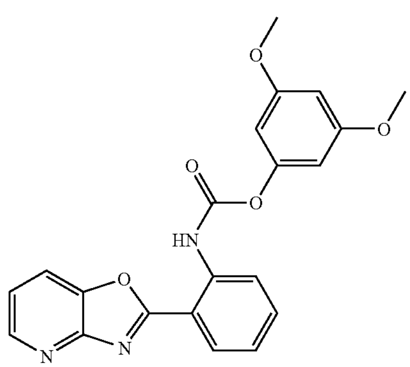 | | NA | C |
| 670 | 392.0 | 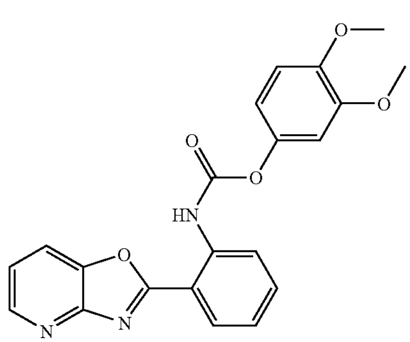 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 671 | 422.0 | 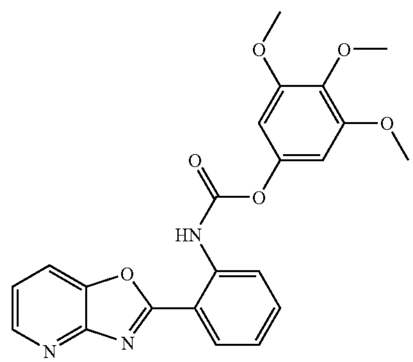 | | NA | C |
| 672 | 415.1 | 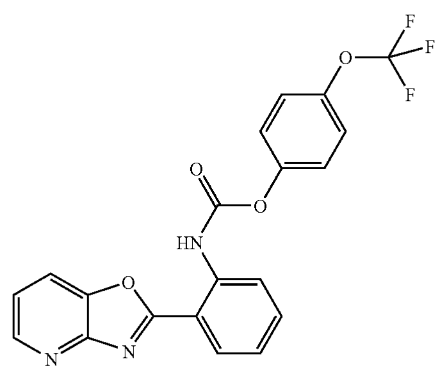 | | NA | C |
| 673 | | 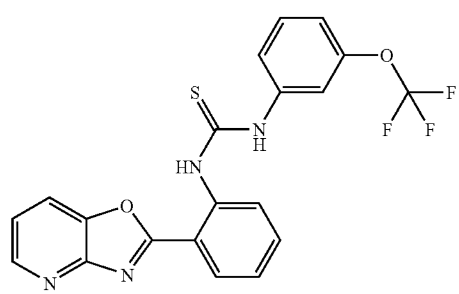 | | NA | C |
| 674 | | 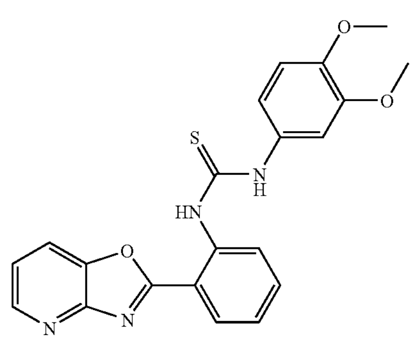 | | NA | C |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 675 | 407.1 | 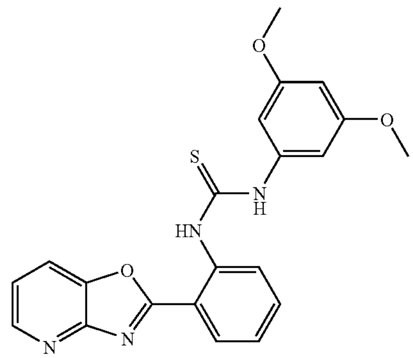 | | NA | C |
| 676 | | 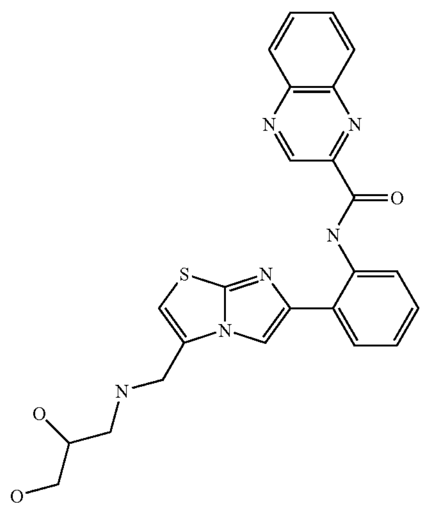 | | A' | A |
| 677 | | 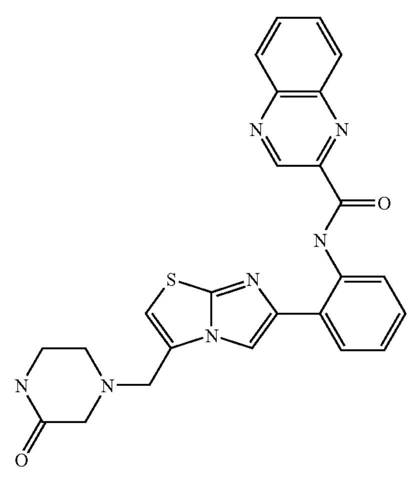 | | A' | A |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 678 | | 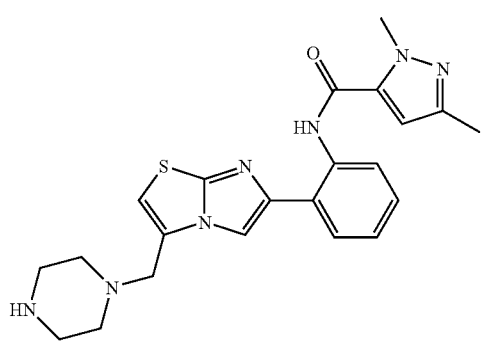 | | A | B |
| 679 | | 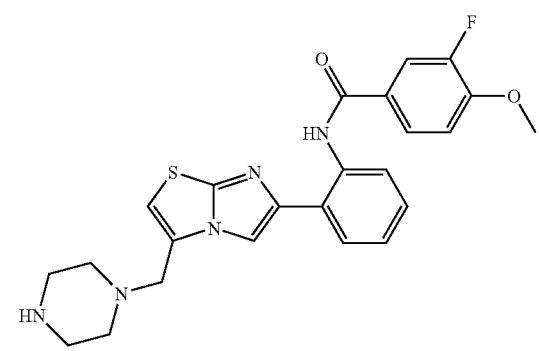 | | A | B |
| 680 | 484.2 | 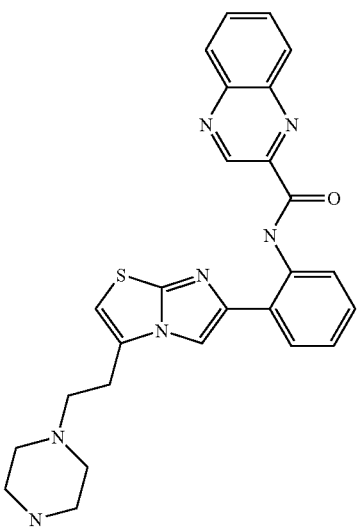 | | A' | A |

TABLE 4-continued
Sirt1 Activators
| COMPOUND NO | [M + H]+ | STRUCTURE | $ED_{50}$ FP ASSAY | $ED_{50}$ MS ASSAY | FOLD ACT. MS |
|---|---|---|---|---|---|
| 681 | 522 | 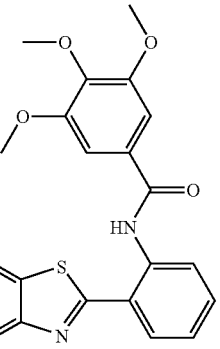 | | A | A |
| 682 | 492 | 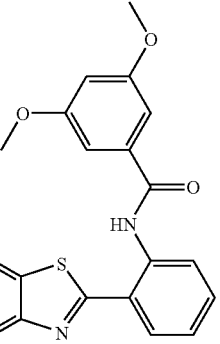 | | A' | A |
| 683 | 475 | 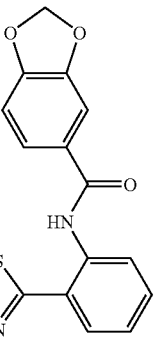 | | A | B |
| 684 | 460 | 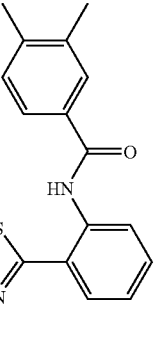 | | A | B |

TABLE 4-continued
Sirt1 Activators
| COMPOUND NO | [M + H]+ | STRUCTURE | ED50 FP ASSAY | ED50 MS ASSAY | FOLD ACT. MS |
|---|---|---|---|---|---|
| 685 | 456 | 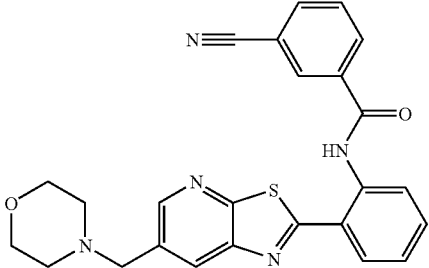 | | A' | A |
| 686 | 475 | 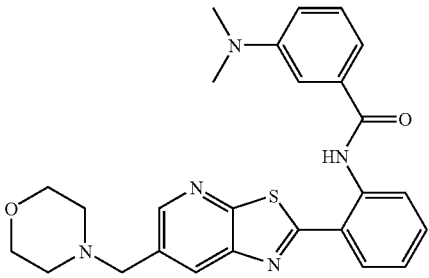 | | A' | A |
| 687 | 467 | 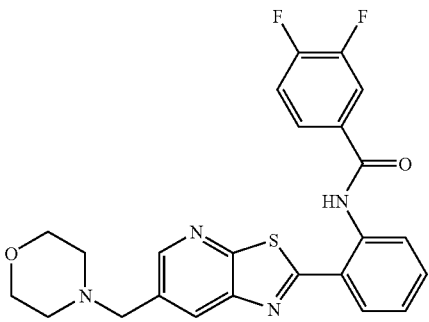 | | NA | C |
| 688 | 483 | 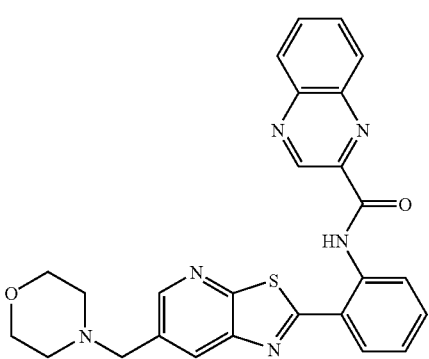 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 689 | 479 | 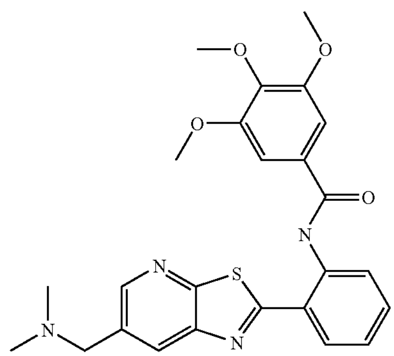 | | A | A |
| 690 | 483 | 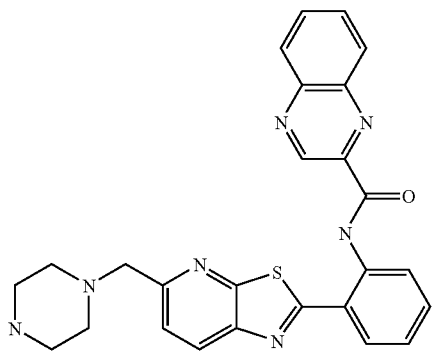 | | A' | A |
| 692 | 469 | 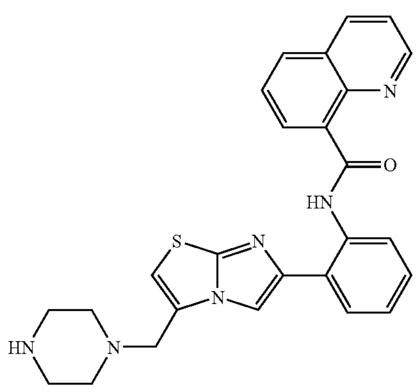 | | C | B |
| 695 | 454 | 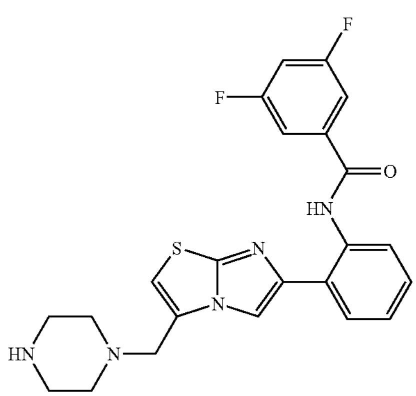 | | A' | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 697 | 596 | 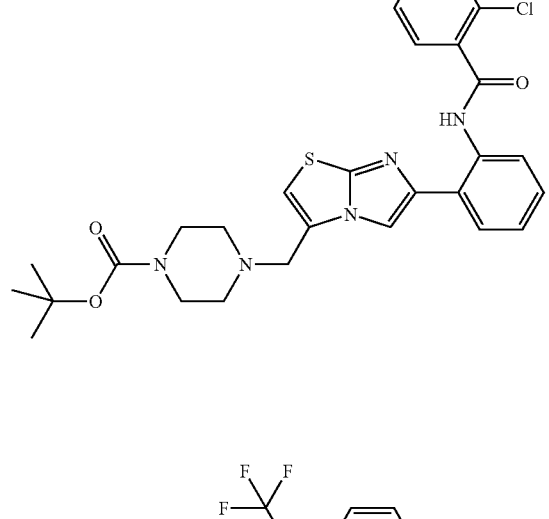 | | NA | C |
| 698 | 502 | 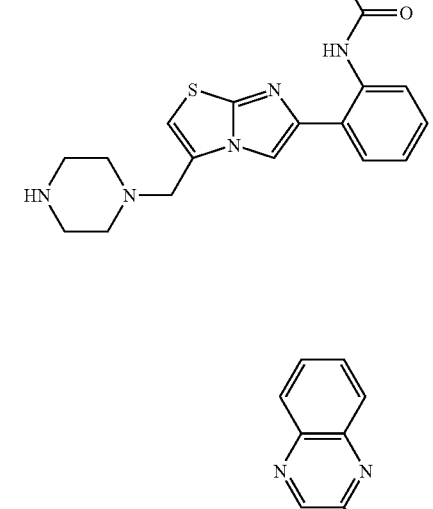 | A' | | A |
| 699 | | 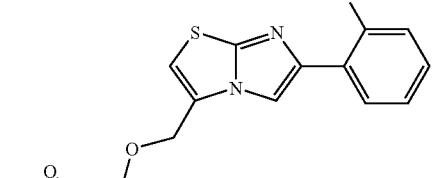 | A | | A |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 700 | 512.2 | 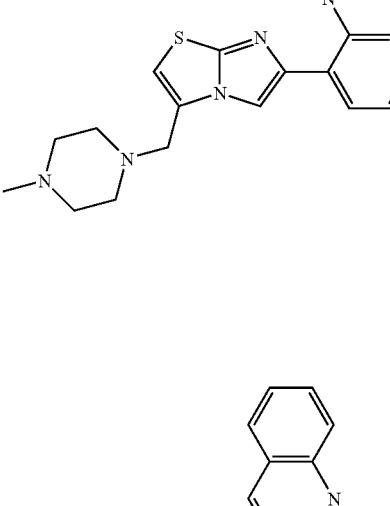 | | A' | A |
| 701 | 477 | 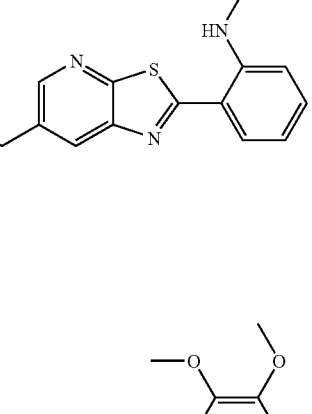 | | A' | A |
| 702 | 534 | 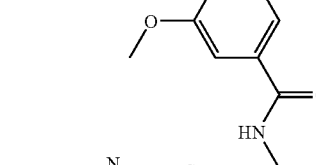 | | A | A |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 703 | 468 | 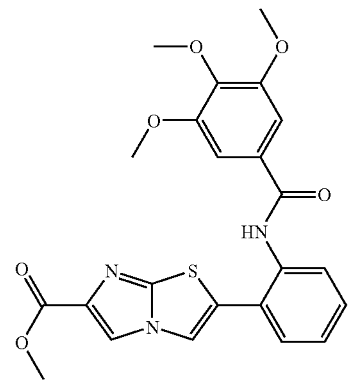 | | NA | C |
| 704 | 454 | 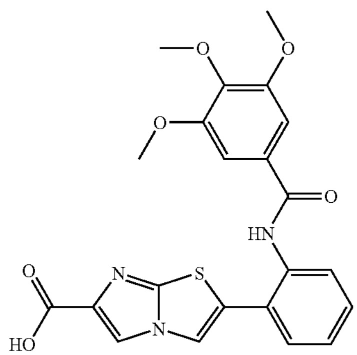 | | NA | C |
| 705 | 387 | 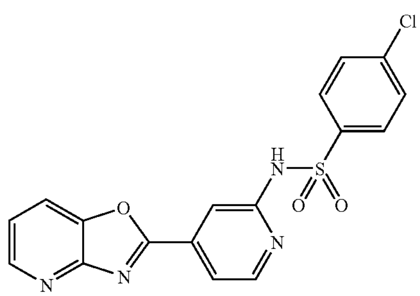 | | | |
| 706 | 445.1 | 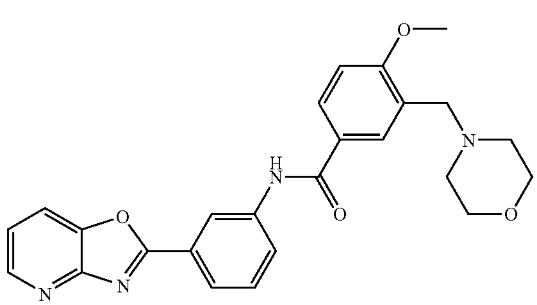 | | | |

TABLE 4-continued
Sirt1 Activators
| COMPOUND NO | [M + H]+ | STRUCTURE | ED₅₀ FP ASSAY | ED₅₀ MS ASSAY | FOLD ACT. MS |
|---|---|---|---|---|---|
| 707 | 386.1 | 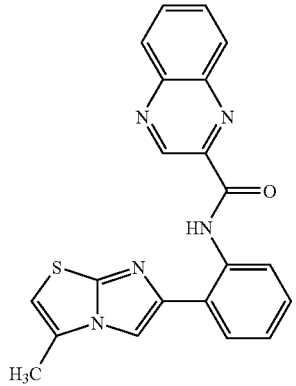 | | A' | A |
| 708 | 494.2 | 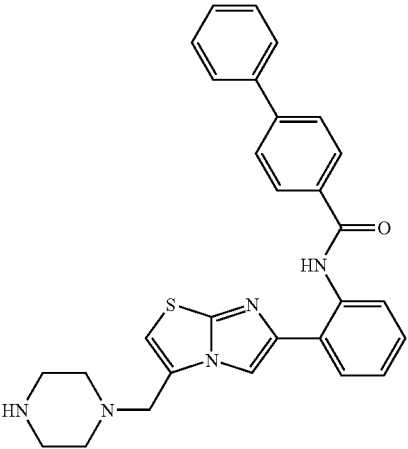 | | A' | A |
| 709 | 494.1 | 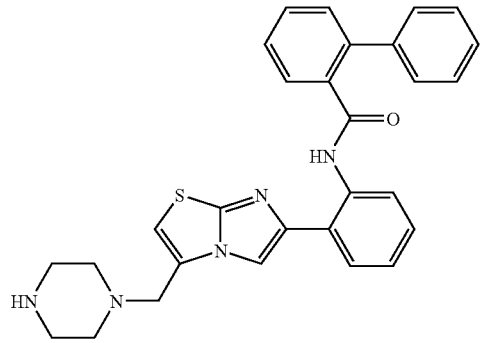 | | NA | C |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 710 | 494.1 | 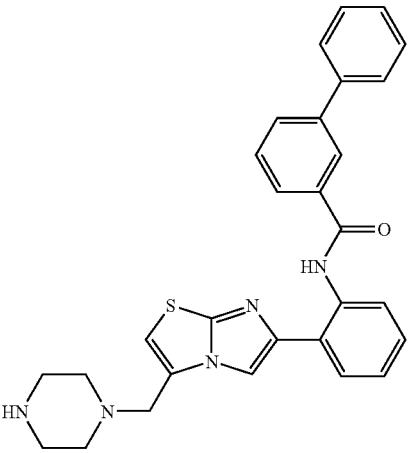 | | A' | A |
| 711 | | 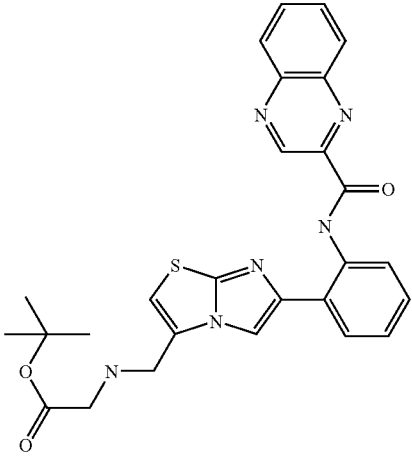 | | A | B |
| 714 | | 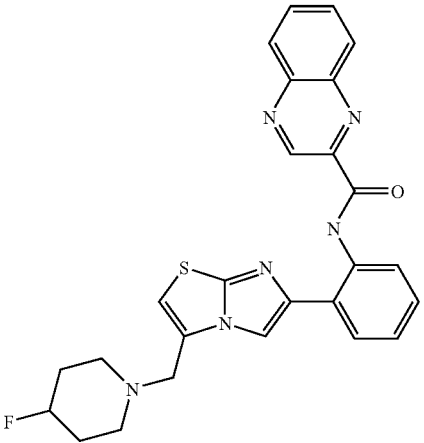 | | A | B |

TABLE 4-continued
Sirt1 Activators
| COMPOUND NO | [M + H]+ | STRUCTURE | ED$_{50}$ FP ASSAY | ED$_{50}$ MS ASSAY | FOLD ACT. MS |
|---|---|---|---|---|---|
| 715 | | 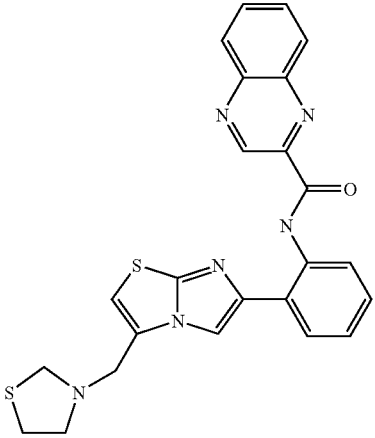 | | A' | B |
| 716 | | 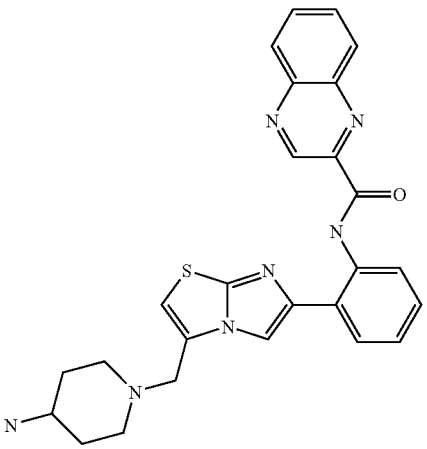 | | A' | A |
| 717 | | 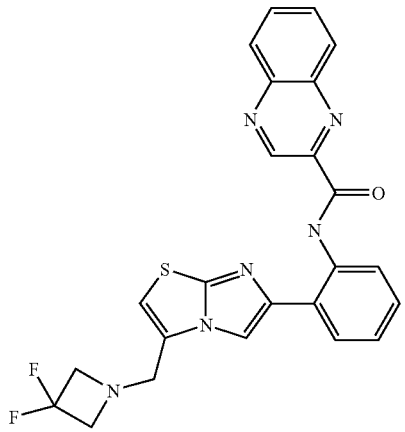 | | A | B |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 718 | 444.1 | 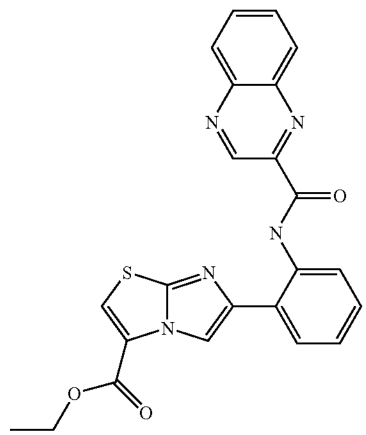 | | NA | C |
| 719 | 416 | 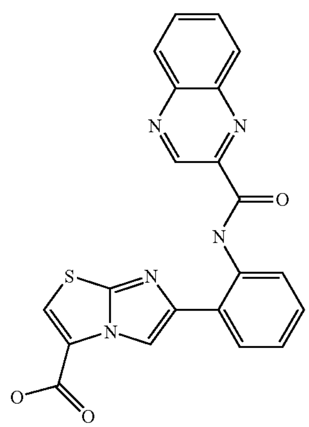 | | A | A |
| 720 | | 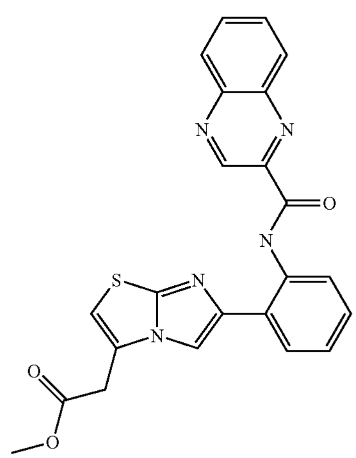 | | NA | C |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 721 | | 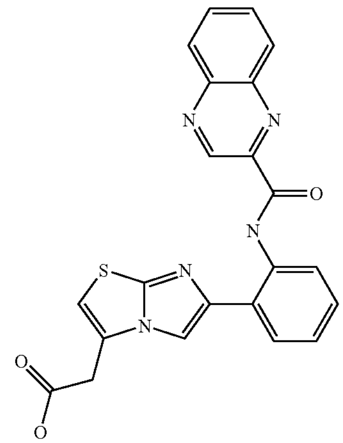 | | A | A |
| 722 | 449 | 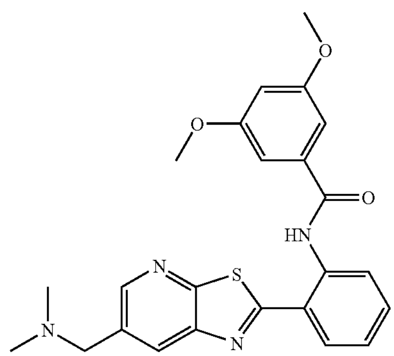 | | A' | A |
| 723 | 490 | 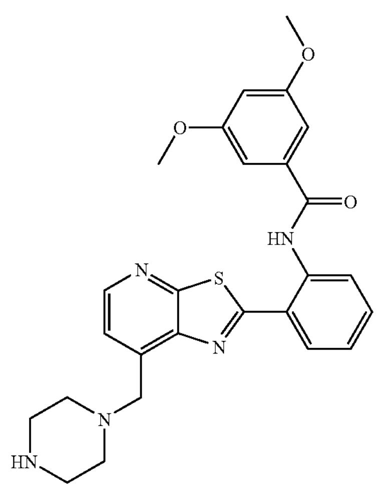 | | A | A |

TABLE 4-continued

Sirt1 Activators

| COMPOUND NO | [M + H]+ | STRUCTURE | $ED_{50}$ FP ASSAY | $ED_{50}$ MS ASSAY | FOLD ACT. MS |
|---|---|---|---|---|---|
| 724 | 482 | | | A' | A |
| 725 | 505 | | | A' | A |
| 726 | 491 | | | A' | A |
| 727 | 458 | | | A' | A |

TABLE 4-continued
Sirt1 Activators
| COMPOUND NO | [M + H]+ | STRUCTURE | ED50 FP ASSAY | ED50 MS ASSAY | FOLD ACT. MS |
|---|---|---|---|---|---|
| 728 | 466 | 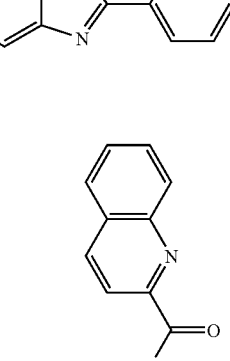 | | A | A |
| 729 | 481 | 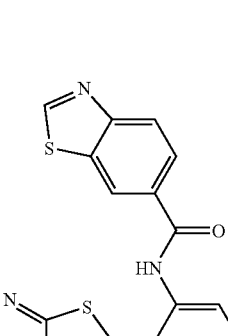 | | A' | A |
| 730 | 488 | 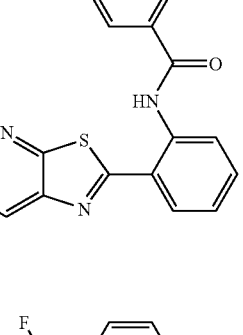 | | A | A |
| 731 | 498 | 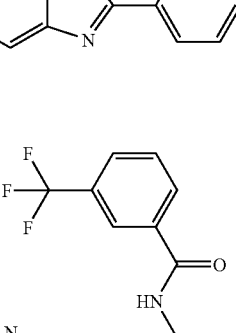 | | A | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 732 | 497 | 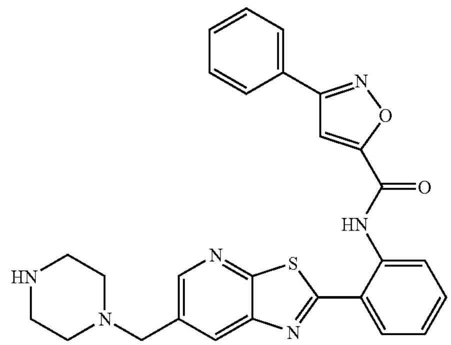 | A' | | B |
| 733 | 484.2 | 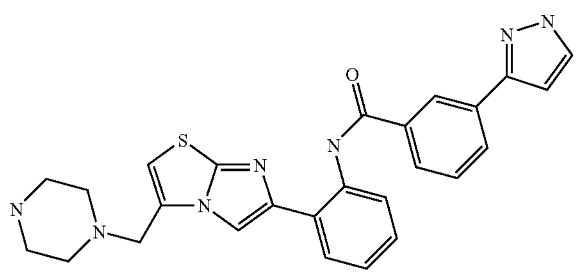 | A' | | A |
| 735 | 514.2 | 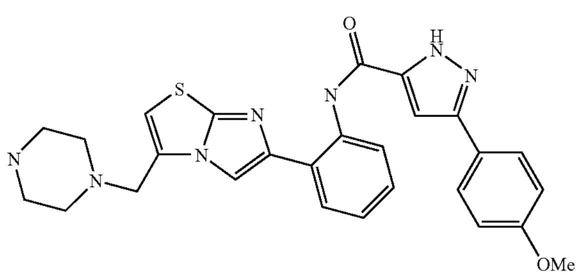 | A' | | A |
| 736 | 514.2 | 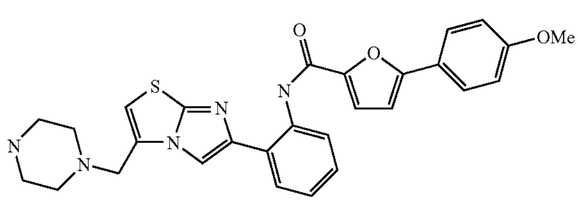 | A' | | A |
| 737 | 500.1 | 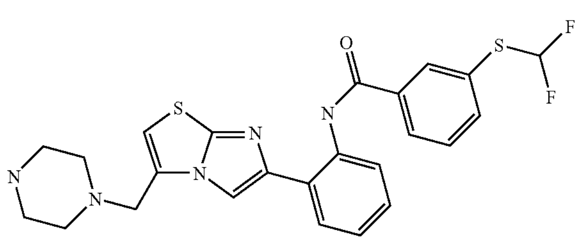 | A' | | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 738 | 448.1 | | A | A |
| 739 | 424.1 | | A' | A |
| 740 | 377.1 | | A' | B |
| 741 | 498.1 | | A' | A |

TABLE 4-continued

Sirt1 Activators

| COMPOUND NO | [M + H]+ | STRUCTURE | ED$_{50}$ FP ASSAY | ED$_{50}$ MS ASSAY | FOLD ACT. MS |
|---|---|---|---|---|---|
| 742 | 487.1 | | | A' | B |
| 743 | 466.1 | | | A | A |
| 744 | 437.1 | | | B | A |

TABLE 4-continued

Sirt1 Activators

| COMPOUND NO | [M + H]+ | STRUCTURE | ED₅₀ FP ASSAY | ED₅₀ MS ASSAY | FOLD ACT. MS |
|---|---|---|---|---|---|
| 745 | 452.1 | 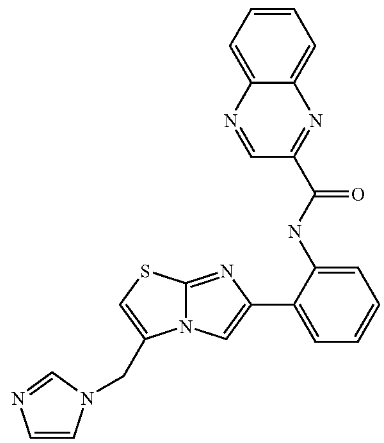 | | A' | A |

TABLE 5

Sirt1 Inhibitors

| COMPOUND NO | [M + H]+ | STRUCTURE | IC₅₀ FP ASSAY | IC₅₀ MS ASSAY |
|---|---|---|---|---|
| 13 | | 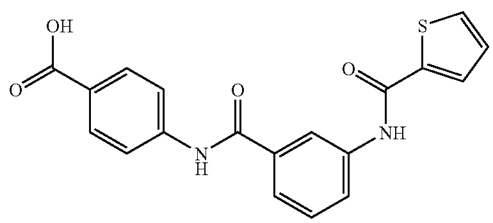 | A | |
| 14 | | 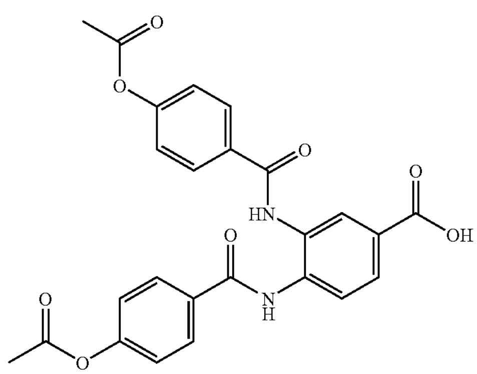 | B | |
| 15 | | 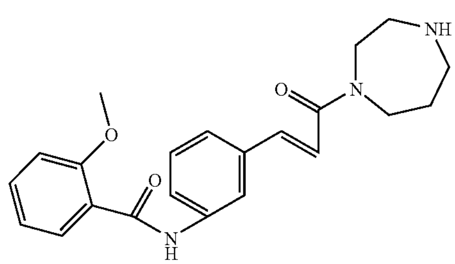 | C | |

TABLE 5-continued

Sirt1 Inhibitors

| COMPOUND NO | [M + H]+ | STRUCTURE | IC$_{50}$ FP ASSAY | IC$_{50}$ MS ASSAY |
|---|---|---|---|---|
| 23 | 359.4 | 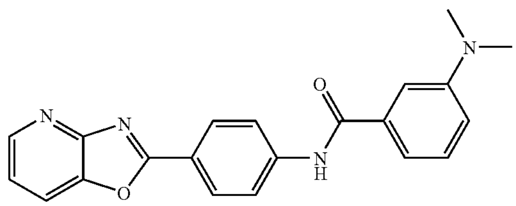 | | D |
| 25 | 341.3 | 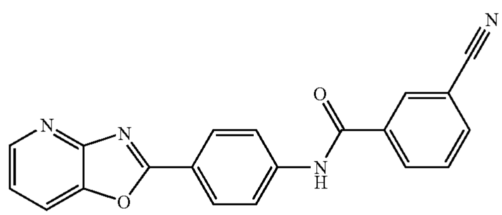 | | B |
| 26 | 341.4 | 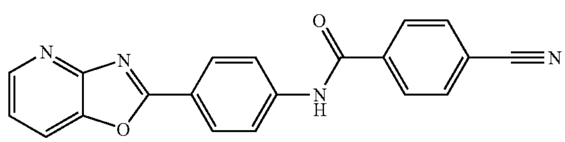 | | B |
| 28 | 401.1 | 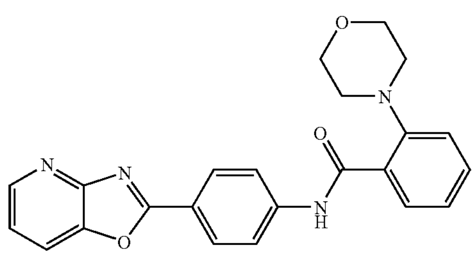 | | D |
| 30 | 380.0 | 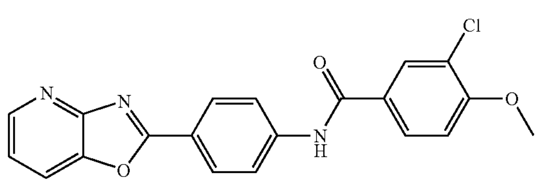 | | D |
| 44 | 341.0 | 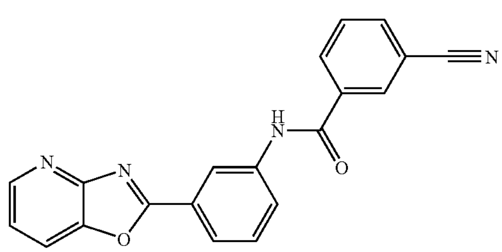 | | D |

TABLE 5-continued

Sirt1 Inhibitors

| COMPOUND NO | [M + H]+ | STRUCTURE | IC$_{50}$ FP ASSAY | IC$_{50}$ MS ASSAY |
|---|---|---|---|---|
| 47 | 385.0 | 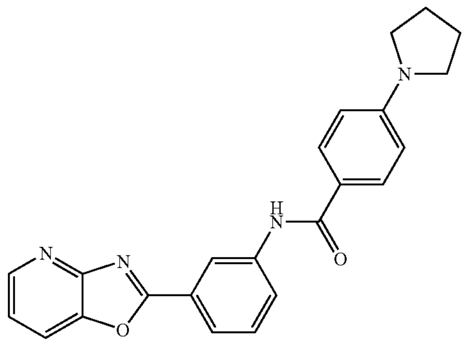 | | B |
| 291 | | 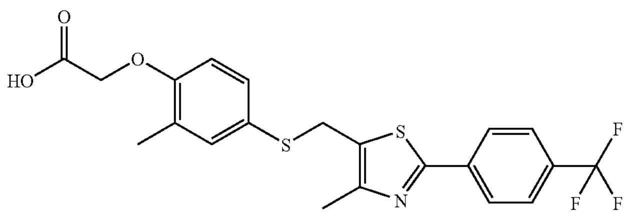 | | B |
| 652 | | 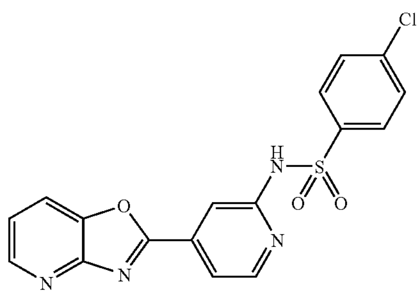 | | B |
| 653 | | 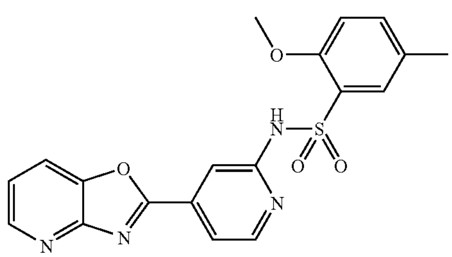 | | C |
| 654 | | 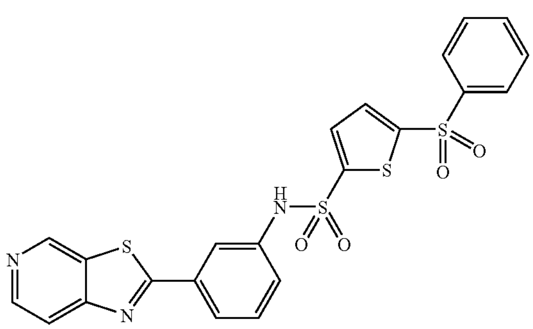 | | D |

EXAMPLE 3

Identification of Sirtuin Modulators Using SIRT3

A fluorescence polarization assay was used to identify modulators of SIRT3 activity. The same assay may be used to identify modulators of any sirtuin protein. The assay utilizes a peptide substrate based on a fragment of Histone H4, a known sirtuin deacetylation target. The substrate contains a peptide having 14 amino acid residues as follows: Biotin-GASSHSK(Ac)VLK(MR121) (SEQ ID NO: 4) wherein K(Ac) is an acetylated lysine residue. The peptide is labeled with the fluorophore MR121 (excitation 635 nm/emission 680 nm) at the C-terminus and biotin at the N-terminus.

The peptide substrate is exposed to a sirtuin protein in the presence of $NAD^+$ to allow deacetylation of the substrate and render it sensitive to cleavage by trypsin. Trypsin is then added and the reaction is carried to completion (i.e., the deacetylated substrate is cleaved) releasing the MR121 fragment. Streptavidin is then added to the reaction where it can bind both the uncleaved substrate (i.e., any remaining acetylated substrate) and the non-fluorescent portion of the cleaved peptide substrate (i.e., the biotin containing fragment). The fluorescence polarization signal observed for the full length peptide substrate bound to streptavidin is higher than the fluorescence polarization signal observed for the released MR121 C-terminal fragment. Therefore, the fluorescence polarization obtained is inversely proportional to the level of deacetylation (e.g., the signal is inversely proportional to the activity of the sirtuin protein). Results are read on a microplate fluorescence polarization reader (Molecular Devices Spectramax Md.) with appropriate excitation and emission filters.

The fluorescence polarization assays may be conducted as follows: 0.5 µM peptide substrate and 50 µM βNAD$^+$ is incubated with 2 nM of SIRT3 for 60 minutes at 37° C. in a reaction buffer (25 mM Tris-acetate pH8, 137 mM Na-Ac, 2.7 mM K-Ac, 1 mM Mg-Ac, 0.1% Pluronic F127, 10 mM $CaCl_2$, 1 mM TCEP, 0.025% BSA). Test compounds are solubilized in DMSO and are added to the reaction at 11 concentrations ranging from 0.7 µM to 100 µM. The SIRT3 protein used in the assays corresponded to amino acid residues 102-399 of human SIRT3 with an N-terminal His-tag. The protein was overexpressed in *E. coli* and purified on a nickel chelate column using standard techniques. After the 60 minute incubation with SIRT3, nicotinamide is added to the reaction to a final concentration of 3 mM to stop the deacetylation reaction and 0.5 µg/mL of trypsin is added to cleave the deacetylated substrate. The reaction is incubated for 30 minutes at 37° C. in the presence of 1 mM streptavidin. Fluorescent polarization is determined at excitation (650 nm) and emissions (680 nm) wavelengths.

The level of activity of the sirtuin protein in the presence of the various concentrations of test compound are then determined and may be compared to the level of activity of the sirtuin protein in the absence of the test compound, and/or the level of activity of the sirtuin proteins in the negative control (e.g., level of inhibition) and positive control (e.g., level of activation) described below.

A control for inhibition of sirtuin activity is conducted by adding 30 mM nicotinamide at the start of the reaction (e.g., permits determination of maximum sirtuin inhibition). A control for activation of sirtuin activity is conducted using 0.5 µg/mL of sirtuin protein to reach baseline deacetylation of the substrate (e.g., to determine normalized sirtuin activity).

Sirtuin modulating compounds that activated SIRT3 were identified using the assay described above and are shown below in Table 6. Sirtuin modulating compounds that inhibited SIRT3 were identified using the assay described above and are shown below in Table 7. The $ED_{50}$ values for the activating compounds are represented by A ($ED_{50}$=<50 µM), B ($ED_{50}$=51-100 µM), C ($ED_{50}$=101-150 µM), and D ($ED_{50}$=>150 µM). The $ED_{50}$ of resveratrol for activation of SIRT3 is >300 uM. Similarly, the $IC_{50}$ values for the inhibiting compounds are represented by A ($IC_{50}$=<50 µM), B ($IC_{50}$=51-100 µM), C ($IC_{50}$=101-150 µM), and D ($IC_{50}$=>150 µM).

TABLE 6

| COMPOUND NO | STRUCTURE | $ED_{50}$ |
|---|---|---|
| 11 | 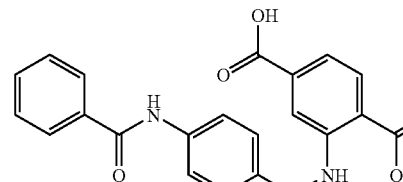 | N/A |
| 12 | 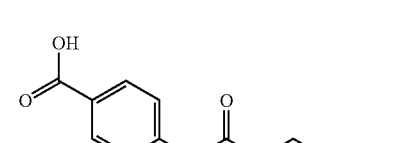 | N/A |

TABLE 7

| COMPOUND NO | STRUCTURE | IC$_{50}$ |
|---|---|---|
| 1 | 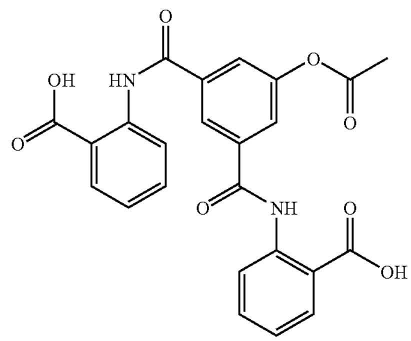 | N/A |
| 2 | 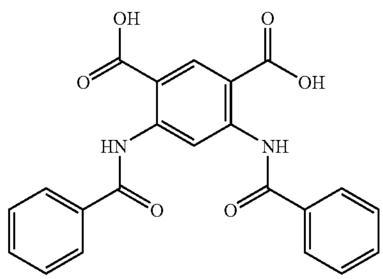 | N/A |
| 15 | 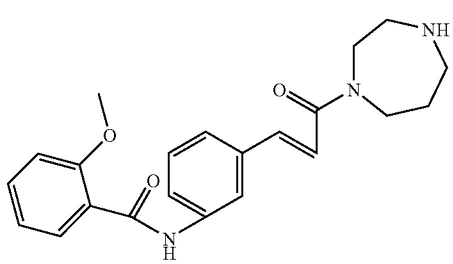 | B |
| 16 | 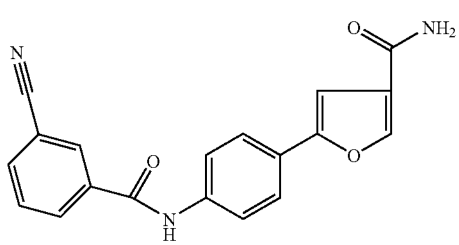 | C |
| 17 | 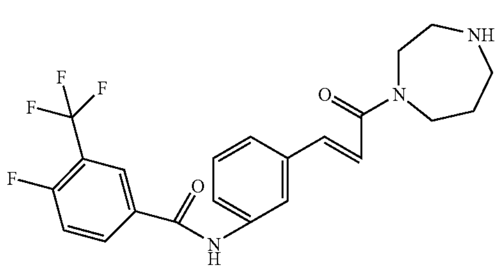 | B |

TABLE 7-continued

| COMPOUND NO | STRUCTURE | IC$_{50}$ |
|---|---|---|
| 18 | (structure) | B |

EXAMPLE 4

Cell-Based Assays of Sirtuin Activity

Fat mobilization assay. 3T3 L1 cells are plated with 2 ml of 30,000 cells/ml in Dulbecco's Modified Eagle Medium (DMEM)/10% newborn calf serum in 24-well plates. Individual wells are then allowed to differentiate by addition of 100 nM Rosiglitazone. Undifferentiated control cells are maintained in fresh DMEM/10% newborn calf serum throughout the duration of the assay. At 48 hours (2 days), adipogenesis is initiated by addition of DMEM/10% fetal calf serum/0.5 mM 3-isobutyl-1-methylxanthine (IBMX)/1 µM dexamethasone. At 96 hours (4 days), adipogenesis is allowed to progress by removal of the media and adding 2 ml of DMEM/10% fetal calf serum to each well along with either 10 µg/mL insulin or 100 nM Rosiglitazone. At 144 hours (6 days) and 192 hours (8 days), all wells are changed to DMEM/10% fetal calf serum.

At 240 hours (10 days from the original cell plating), test compounds at a range of concentrations are added to individual wells in triplicate along with 100 nM Rosiglitazone. Three wells of undifferentiated cells are maintained in DMEM/10% newborn calf serum and three wells of differentiated control cells are maintained in fresh DMEM/10% newborn calf serum with 100 nM Rosiglitazone. As a positive control for fat mobilization, resveratrol (a SIRT1 activator) is used at concentrations ranging in three fold dilutions from 100 µM to 0.4 µM.

At 312 hours (13 days), the media is removed and cells are washed twice with PBS. 0.5 mL of Oil Red O solution (supplied in Adipogenesis Assay Kit, Cat.# ECM950, Chemicon International, Temecula, Calif.) is added per well, including wells that have no cells as background control. Plates are incubated for 15 minutes at room temperature, and then the Oil Red O staining solution is removed and the wells are washed 3 times with 1 mL wash solution (Adipogenesis Assay Kit). After the last wash is removed, stained plates are visualized, scanned or photographed. Dye is extracted (Adipogenesis Assay Kit) and quantified in a plate reader at 520 nM. Quantitative and visual results are shown in FIG. 16.

Primary dorsal root ganglion (DRG) cell protection assay. Test compounds are tested in an axon protection assay as described (Araki et al. (2004) Science 305(5686):1010-3). Briefly, mouse DRG explants from E12.5 embryos are cultured in the presence of 1 nM nerve growth factor. Non-neuronal cells are removed from the cultures by adding 5-fluorouracil to the culture medium. Test compounds are added 12 to 24 hours prior to axon transections. Transection of neurites was performed at 10-20 days in vitro (DIV) using an 18-guage needle to remove the neuronal cell bodies.

EXAMPLE 5

ATP Cell-Based Assay

This example describes the effect of the SIRT1 activator, resveratrol on cellular ATP levels in NCI-H358 cells. Cellular ATP levels are an indirect measurement of cellular metabolic rates and, by extension, mitochondrial function. As SIRT1 activation has been linked to increased mitochondrial biogenesis in vivo, this study is designed to determine if resveratrol increases mitochondrial function, using cellular ATP levels as the readout. The ATP assay is combined with a cellular viability assay so that cellular ATP levels can be normalized to viable cells. Cellular ATP levels were measured using the ATPLite 1Step Kit (PerkinElmer) and cellular viability was measured using the cell permeable dye, AlamarBlue™.

The Cellular ATP Assay is a multiplexed assay that measures both ATP levels and viability of a given cell sample. This assay is run in a 96-well Assay Plate and data are reported as the [ATP]/viability for each well in the Assay Plate.

The ATPLite 1Step™ Kit is a single-step luminescent cell-based assay for detection of ATP. The kit contains lyophilized substrate mixture, comprised of D-luciferin and the firefly (*Photinus pyralis*) enzyme luciferase. Additionally, the kit contains a detergent-based reconstitution buffer that induces the lysis of cellular membranes. The luciferase in the assay mixture catalyzes a reaction between the free cellular ATP and D-luciferin to produce bioluminescence according to the schematic reaction outlined below. The amount of light produced is proportional to the cellular ATP concentration.

The AlamarBlue™ Assay is a single-step assay that utilizes a soluble, non-toxic, cell permeable dye that is added to cell growth media. This dye undergoes electron reduction in viable cells but not dead cells. The reduced dye product gives a fluorescent signal which can be monitored with a fluorescence plate reader (excitation 545 nm and emission 575 nm). The amount of fluorescence generated in a given well is proportional to the number of viable cells. The viability signal generated by this assay is used to normalize the ATP signal from the ATPLite 1 Step™ assay results.

Preparation of Test Substance for Cellular ATP Assay: Resveratrol was weighed and placed in a brown vial. The material was dissolved in 100% vehicle (DMSO) to yield a final concentration of 10 mM (stock solution). The stock solution was serially diluted with 100% DMSO as described in SOP 7.10. The final concentrations of resveratrol in the compound plate were 0.008, 0.023, 0.069, 0.206, 0.617, 1.852, 5.556, 16.667, 50 and 150 μM.

The effect of resveratrol on cellular ATP levels in NCI-H358 cells (100 μL) was examined using the Cellular ATP Assay as described. The experimental design is summarized in FIG. 1. In this assay NCI-H358 cells (obtained from the American Tissue Culture Collection, ATCC) were seeded in 96 well microplates ($10^4$ cells/well). The NCI-H358 Growth Culture Media consists of RPMI 1640 Media supplemented with 10% FBS, 100 mg/mL streptomycin, and 100 units/mL penicillin. Three replicate cell microplates were treated with 15 μL of 10 concentrations of resveratrol (0.008, 0.023, 0.069, 0.206, 0.617, 1.852, 5.556, 16.667, 50 and 150 μM) or 15 μL vehicle (DMSO; final concentration of 0.5%; 12 replicates per plate). After 48 hours of compound treatment under cell growth conditions, plates were removed from incubator, and 15 μl of AlamarBlue™ dye was added to each well. Cell microplates were incubated with dye for 2 hours under growth conditions, and fluorescence was subsequently measured using a plate reader. Media containing AlamarBlue™ was removed, and plates were washed in 100 μl of PBS per well. This wash was removed, and 200 μl of 1× ATPLite 1Step reagent was added to each well. Luminescence was then measured using a plate reader. The ATP signal for each well, measured by the luminescence scan, was normalized to its coresponding cell viability value, measured by the fluorescence scan, to generate the average ATP level per viable cell unit (ATP/vCell). The ATP/vCell for each treatment was then normalized to the average vehicle ATP/vCell for its respective cell microplate, yielding the normalized ATP/vCell (norm. ATP/vCell). Finally, the norm. ATP/vCell for each unique treatment was averaged across plate replicates, generating the average norm. ATP/vCell. Doses of resveratrol that increase cellular ATP levels have normalized ATP/vCell values greater than 1.0. The concentration of resveratrol which gives the 50% of the maximum increase in normalized ATP/vCell (EC50 ATP) was determined by a best-fit curve analysis using a sigmoidal dose-response curve model.

The ATP levels of cells treated with 10 concentrations of resveratrol or vehicle alone were measured. Each of these ATP levels was normalized to the cell viability in the corresponding treatment well, generating the ATP/vCell value. Each ATP/vCell value was subsequently normalized to its average Vehicle ATP/vCell values for its respective cell microplate.

Figure 2:
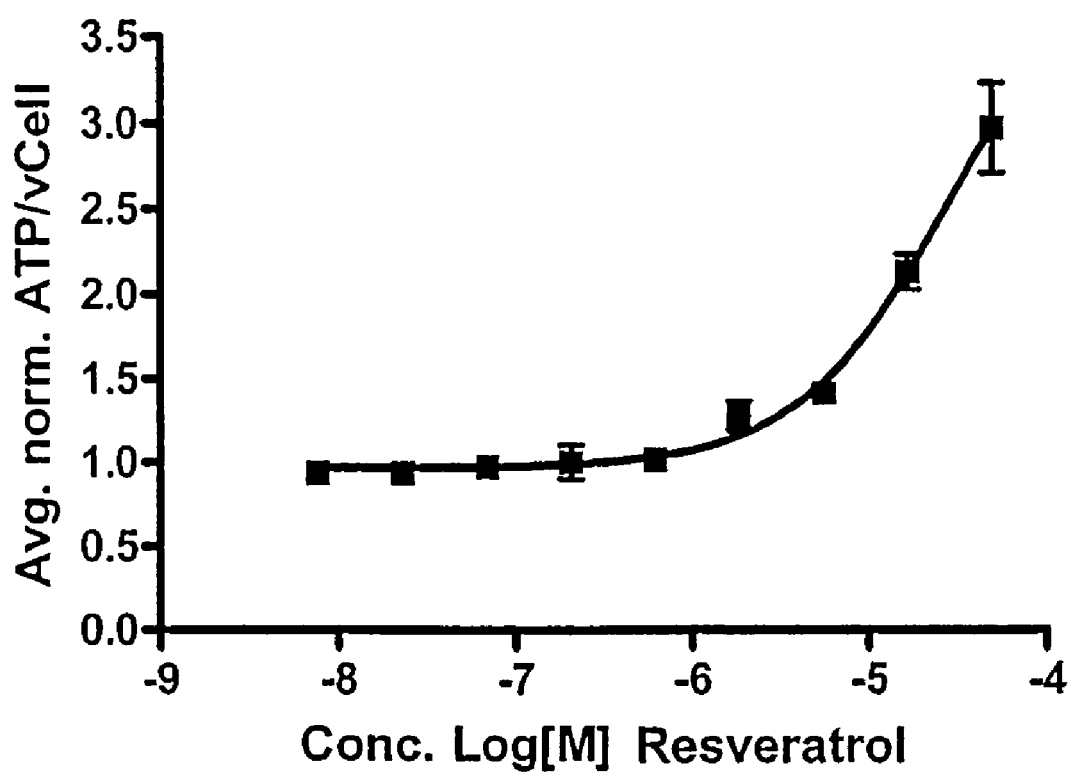
FIG. 2 shows a dose-response curve for ATP levels in cells following resveratrol treatment.

Data are represented as the normalized ATP/vCell (arbitrary units). FIG. 2 shows the best-fit, sigmoidal dose-response curve for the 10 concentrations of resveratrol plotted against their corresponding normalized ATP/vCell values. These values represent an average of three plate replicates. Resveratrol increases cellular ATP levels in NCI-H358 cells in a dose-dependent manner. The maximum increase in cellular ATP levels was 3.0 fold and occurred with treatment of 50 μM resveratrol. The EC50 ATP for resveratrol was determined to be 29 μM.

EXAMPLE 6

Screening of Test Compounds in ATP Cell-Based Assay

A number of compounds were screened for their affect on ATP levels in the assay as described in Example 5. Results are shown in Table 8. The $ED_{50}$ values for compounds that raised intracellular ATP levels are represented by A ($ED_{50}$=<50 μM), B ($ED_{50}$=51-100 μM), C ($ED_{50}$=101-150 μM), and D ($ED_{50}$=>150 μM). NA means that the compound was not tested using the indicated assay. Similarly, the $IC_{50}$ values for the compounds that lowered intracellular ATP levels are represented by A ($IC_{50}$=<50 μM), B ($IC_{50}$=51-100 μM), C ($IC_{50}$=101-150 μM), and D ($IC_{50}$=>150 μM).

TABLE 8

| COMPOUND NO | STRUCTURE | $ED_{50}$ ATP ASSAY | $IC_{50}$ ATP ASSAY |
|---|---|---|---|
| 52 | 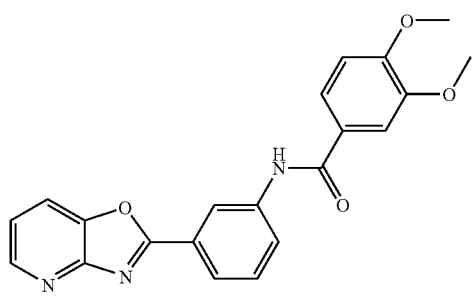 | A | |
| 42 | 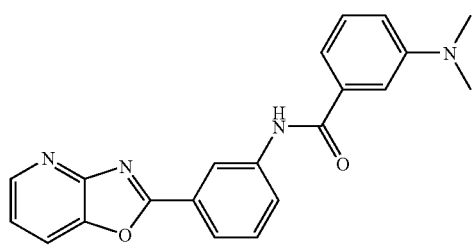 | A | |

TABLE 8-continued

| COMPOUND NO | STRUCTURE | ED$_{50}$ ATP ASSAY | IC$_{50}$ ATP ASSAY |
|---|---|---|---|
| 49 | 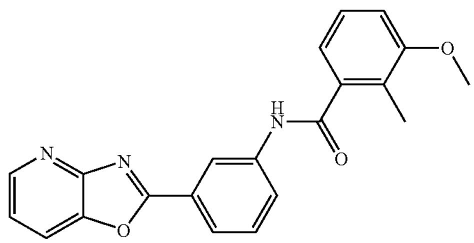 | A | |
| 115 | 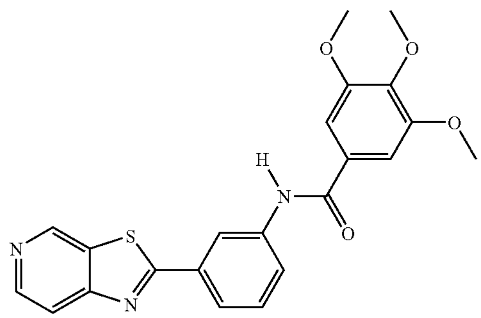 | D | |
| 79 | 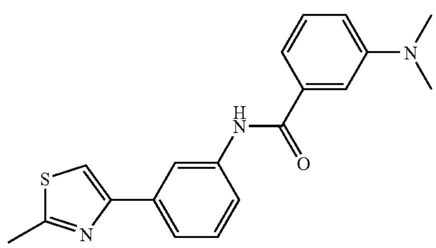 | A | |
| 117 | 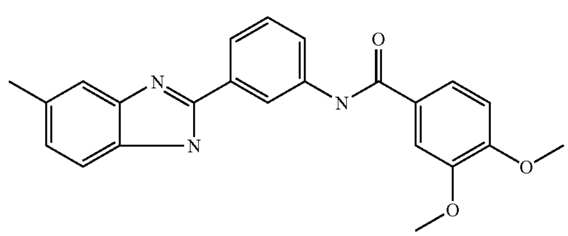 | | B |
| 120 | 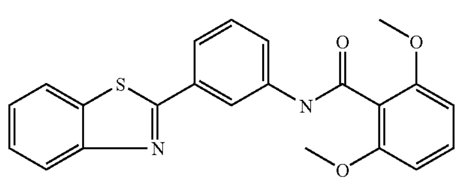 | A | |
| 121 | 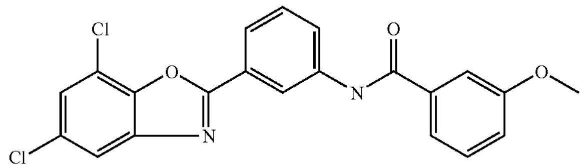 | NA | |

TABLE 8-continued

| COMPOUND NO | STRUCTURE | ED$_{50}$ ATP ASSAY | IC$_{50}$ ATP ASSAY |
|---|---|---|---|
| 123 | 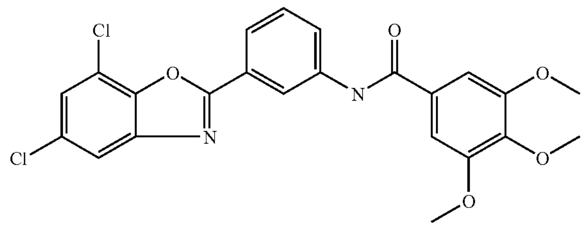 | | D |
| 85 | 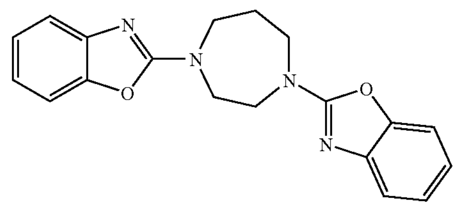 | | NA |
| 86 | 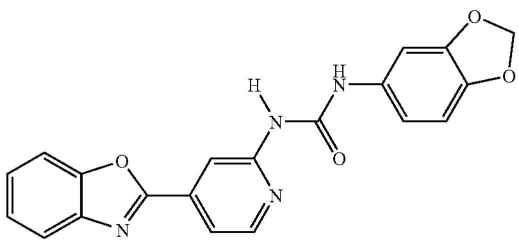 | | A |
| 87 | 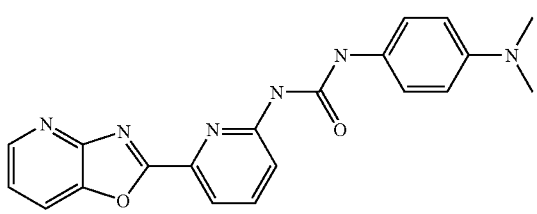 | | NA |
| 88 | 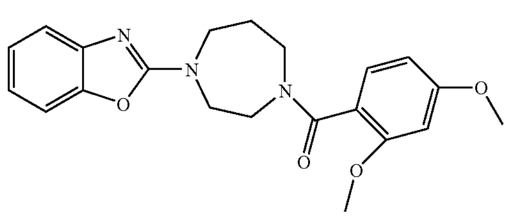 | | NA |
| 89 | 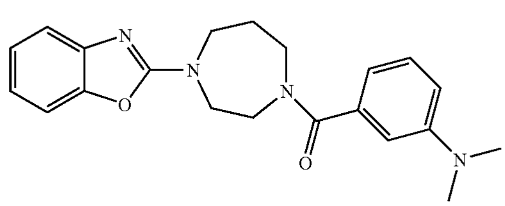 | | A |

TABLE 8-continued

| COMPOUND NO | STRUCTURE | ED$_{50}$ ATP ASSAY | IC$_{50}$ ATP ASSAY |
|---|---|---|---|
| 90 | 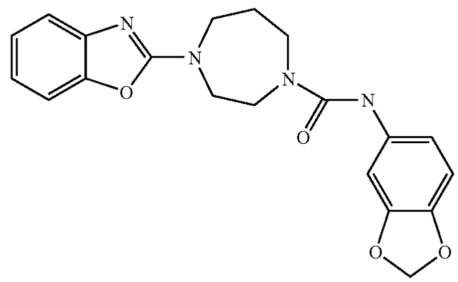 | | D |
| 91 | 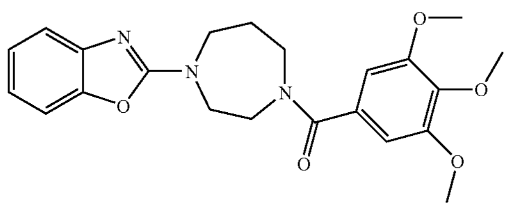 | | A |
| 92 | 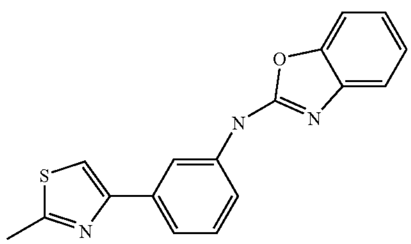 | | B |
| 93 | 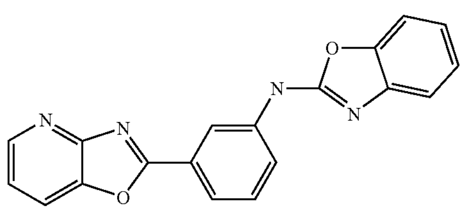 | | D |
| 94 | 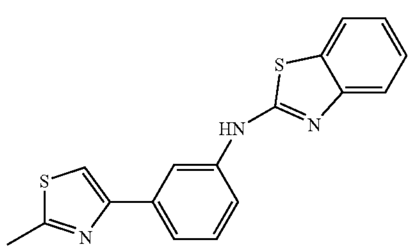 | | D |
| 95 | 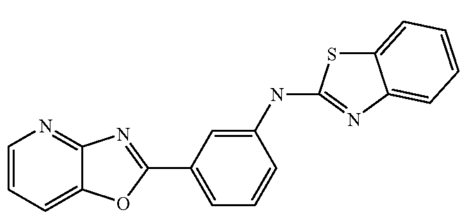 | | NA |

TABLE 8-continued

| COMPOUND NO | STRUCTURE | ED$_{50}$ ATP ASSAY | IC$_{50}$ ATP ASSAY |
|---|---|---|---|
| 97 | 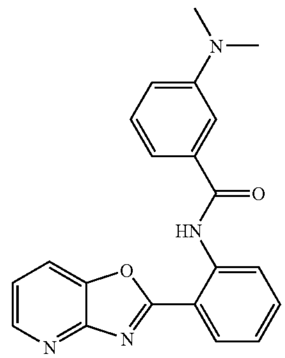 | A | |
| 98 | 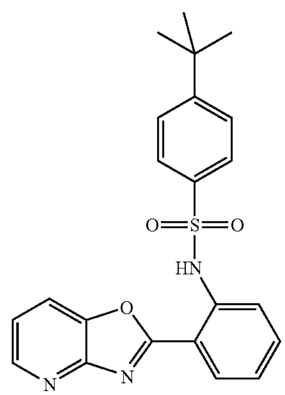 | NA | |
| 99 | 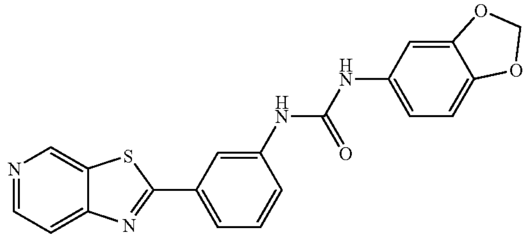 | A | |
| 100 | 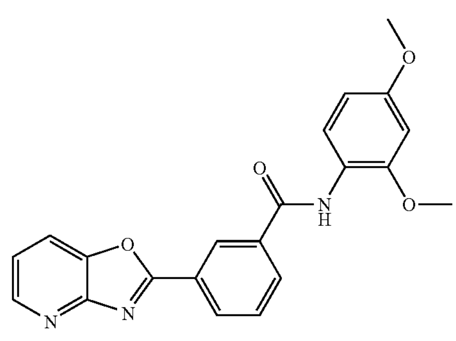 | A | |

TABLE 8-continued

| COMPOUND NO | STRUCTURE | ED$_{50}$ ATP ASSAY | IC$_{50}$ ATP ASSAY |
|---|---|---|---|
| 101 | 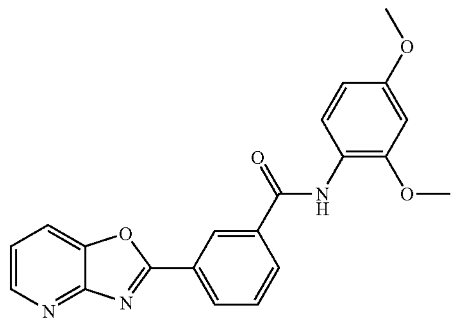 | | C |
| 102 | 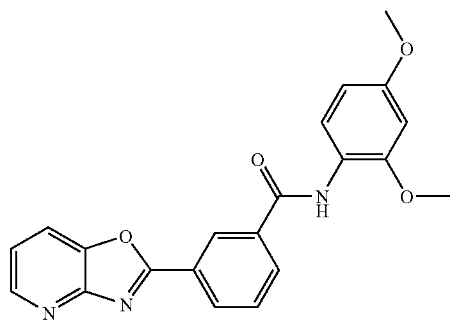 | | NA |
| 103 | 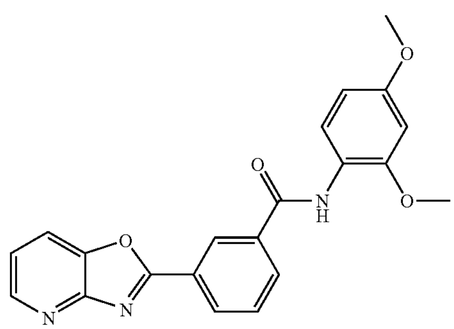 | | A |
| 104 | 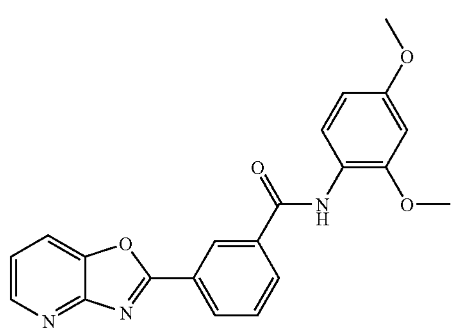 | | A |

TABLE 8-continued
| COMPOUND NO | STRUCTURE | ED$_{50}$ ATP ASSAY | IC$_{50}$ ATP ASSAY |
|---|---|---|---|
| 105 | 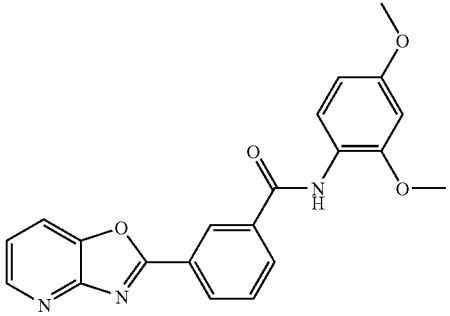 | NA | |
| 133 | 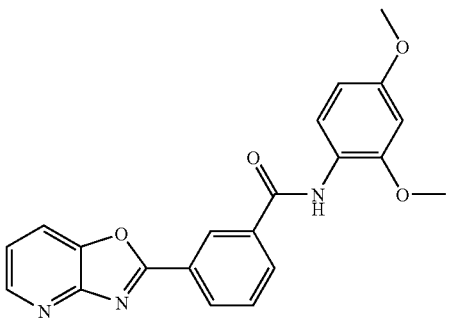 | NA | |
| 134 | 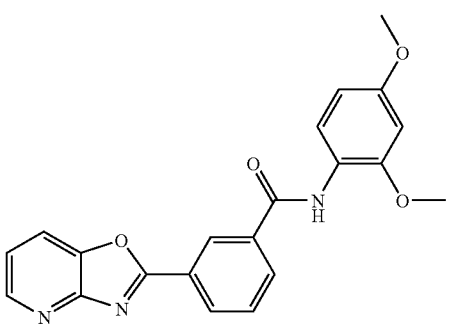 | A | |
| 135 | 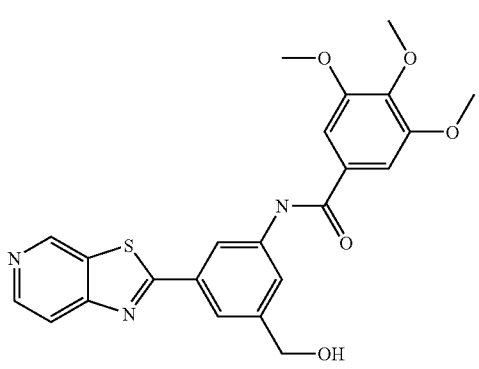 | A | |

TABLE 8-continued

| COMPOUND NO | STRUCTURE | ED$_{50}$ ATP ASSAY | IC$_{50}$ ATP ASSAY |
|---|---|---|---|
| 106 | 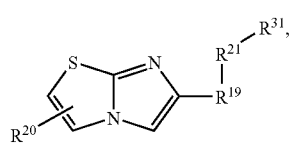 | A | |

Equivalents

The present invention provides among other things sirtuin-activating compounds and methods of use thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

Also incorporated by reference are the following: PCT Publications WO 2005/002672; 2005/002555; and 2004/016726.

What is claimed is:

1. A compound of the formula:

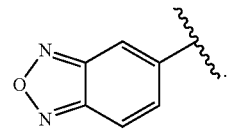 (XVIII)

or a salt thereof, wherein
R$^{19}$ is

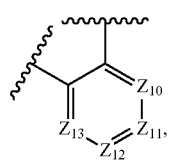

wherein:
each $Z_{10}$, $Z_{11}$, $Z_{12}$ and $Z_{13}$ is independently selected from $CR^{20}$ or $CR_1'$;

wherein:
zero to one $R^{20}$ is a solubilizing group; and
zero to one $R_1'$ is an optionally substituted $C_1$-$C_3$ straight or branched alkyl;
each $R^{20}$ is independently selected from H or a solubilizing group;
$R^{21}$ is —NR$_1'$—C(O)—;
each $R_1'$ is independently selected from H or optionally substituted $C_1$-$C_3$ straight or branched alkyl; and
$R^{31}$ is selected from an optionally substituted monocyclic or bicyclic aryl, or an optionally substituted monocyclic or bicyclic heteroaryl, with the proviso that $R^{31}$ is not 4-cyanophenyl or

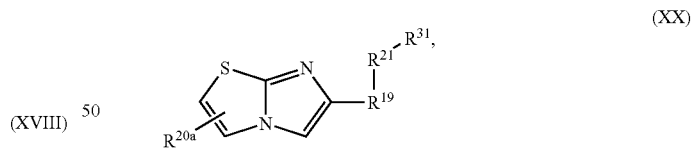

2. A compound of the formula:

(XX)

or a salt thereof wherein
R$^{19}$ is

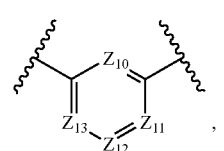

wherein:
each $Z_{10}$, $Z_{11}$, $Z_{12}$ and $Z_{13}$ is independently selected from $CR^{20}$ or $CR_1'$;

wherein:
  zero to one $R^{20}$ is a solubilizing group; and
  zero to one $R_1'$ is an optionally substituted $C_1$-$C_3$ straight or branched alkyl;
  each $R^{20}$ is independently selected from H or a solubilizing group;
  $R^{20a}$ is independently selected from H or a solubilizing group;
  $R^{21}$ is —$NR_1'$—C(O)—;
wherein
  each $R_1'$ is independently selected from H or optionally substituted $C_1$-$C_3$ straight or branched alkyl; and
  $R^{31}$ is selected from an optionally substituted monocyclic or bicyclic aryl, or an optionally substituted monocyclic or bicyclic heteroaryl, wherein when $Z_{10}$, $Z_{11}$, $Z_{12}$ and $Z_{13}$ are each CH, $R^{20a}$ is a solubilizing group.

3. A compound of the formula:

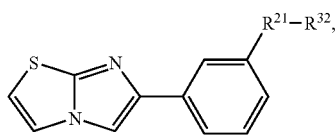

(XXI)

or a salt thereof, wherein
  $R^{21}$ is —$NR_1'$—C(O)—;
wherein
  $R_1'$ is H or optionally substituted $C_1$-$C_3$ straight or branched alkyl; and
  $R^{32}$ is an optionally substituted monocyclic or bicyclic heteroaryl, or an optionally substituted bicyclic aryl, wherein:
    when $R^{21}$ is —NH—C(O)—, $R^{32}$ is not furan-2-yl, 5-bromofuran-2-yl, or 2-phenyl-4-methylthiazol-5-yl.

4. A compound of the formula:

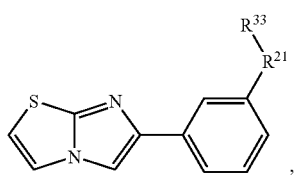

(XXII)

or a salt thereof, wherein:
  $R^{21}$ is —$NR_1'$—C(O)—,
wherein $R_1'$ is optionally substituted $C_1$-$C_3$ straight or branched alkyl; and
  $R^{33}$ is an optionally substituted phenyl.

5. A compound of the formula:

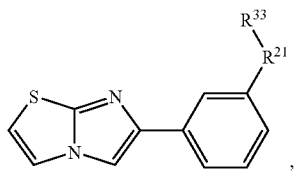

(XXII)

or a salt thereof wherein:
  $R^{21}$ is —NH—C(O)—; and
  $R^{33}$ is phenyl substituted with
    a) one —$N(CH_3)_2$ group;
    b) one CN group at the 3 position;
    c) one —$S(CH_3)$ group; or
    d)

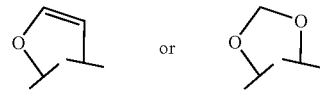

bridging the 3 and 4 positions.

6. A composition comprising a compound of the formula:

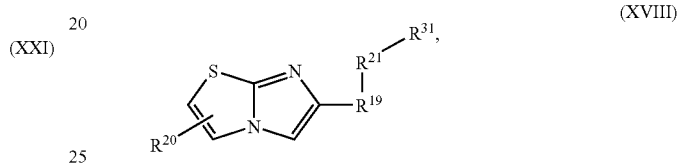

(XVIII)

or a salt thereof, wherein
  $R^{19}$ is selected from:

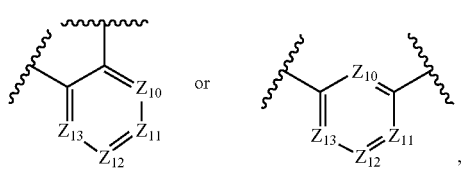

wherein:
  each $Z_{10}$, $Z_{11}$, $Z_{12}$ and $Z_{13}$ is independently selected from $CR^{20}$ or $CR_1'$;
wherein:
  zero to one $R^{20}$ is a solubilizing group; and
  zero to one $R_1'$ is an optionally substituted $C_1$-$C_3$ straight or branched alkyl;
  each $R^{20}$ is independently selected from H or a solubilizing group;
  $R^{21}$ is —$NR_1'$—C(O)—;
  each $R_1'$ is independently selected from H or optionally substituted $C_1$-$C_3$ straight or branched alkyl; and
  $R^{31}$ is selected from an optionally substituted monocyclic or bicyclic aryl, or an optionally substituted monocyclic or bicyclic heteroaryl, with the proviso that when $R^{19}$ is

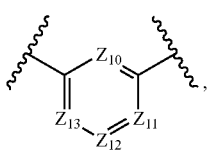

$Z_{10}$, $Z_{11}$, $Z_{12}$ and $Z_{13}$ are each CH, $R^{20}$ is H, and $R^{21}$ is —NHC(O)—, $R^{31}$ is not an optionally substituted phenyl, wherein the composition is pyrogen-free.

7. A pharmaceutical composition comprising:
a) a compound of the formula:

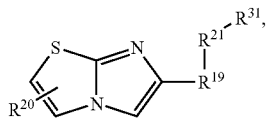  (XVIII)

or a pharmaceutically acceptable salt thereof, wherein $R^{19}$ is selected from:

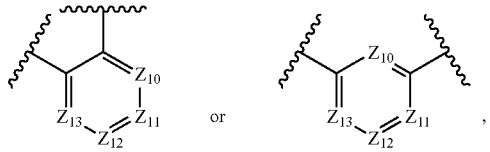

wherein:
each $Z_{10}$, $Z_{11}$, $Z_{12}$ and $Z_{13}$ is independently selected from $CR^{20}$ or $CR_1'$;
wherein:
zero to one $R^{20}$ is a solubilizing group; and
zero to one $R_1'$ is an optionally substituted $C_1$-$C_3$ straight or branched alkyl;
each $R^{20}$ is independently selected from H or a solubilizing group;
$R^{21}$ is —$NR_1'$—C(O)—;
each $R_1'$ is independently selected from H or optionally substituted $C_1$-$C_3$ straight or branched alkyl; and
$R^{31}$ is selected from an optionally substituted monocyclic or bicyclic aryl, or an optionally substituted monocyclic or bicyclic heteroaryl, with the proviso that when $R^{19}$ is

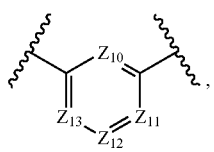

$Z_{10}$, $Z_{11}$, $Z_{12}$ and $Z_{13}$ are each CH, $R^{20}$ is H, and $R^{21}$ is —NHC(O)—, $R^{31}$ is not an optionally substituted phenyl; and
b) a pharmaceutically acceptable carrier or diluent.

8. A packaged pharmaceutical comprising a compound of the formula:

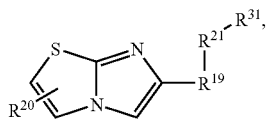  (XVIII)

or a pharmaceutically acceptable salt thereof, wherein $R^{19}$ is selected from:

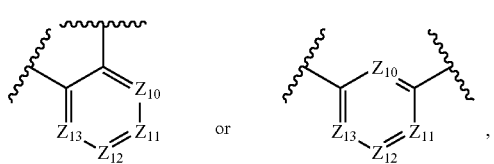

wherein:
each $Z_{10}$, $Z_{11}$, $Z_{12}$ and $Z_{13}$ is independently selected from $CR^{20}$ or $CR_1'$;
zero to one $R^{20}$ is a solubilizing group; and
zero to one $R_1'$ is an optionally substituted $C_1$-$C_3$ straight or branched alkyl;
each $R^{20}$ is independently selected from H or a solubilizing group;
$R^{21}$ is —$NR_1'$—C(O)—;
each $R_1'$ is independently selected from H or optionally substituted $C_1$-$C_3$ straight or branched alkyl; and
$R^{31}$ is selected from an optionally substituted monocyclic or bicyclic aryl, or an optionally substituted monocyclic or bicyclic heteroaryl, with the proviso that when $R^{19}$ is

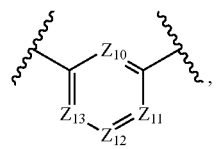

$Z_{10}$, $Z_{11}$, $Z_{12}$ and $Z_{13}$ are each CH, $R^{20}$ is H and $R^{21}$ is —NHC(O)—, $R^{31}$ is not an optionally substituted phenyl.

9. The compound of claim 1, having the formula:

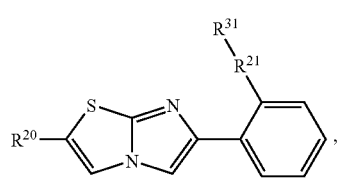  (XIX)

wherein
$R^{20}$ is selected from H or a solubilizing group;
$R^{21}$ is —NH—C(O)—; and
$R^{31}$ is selected from an optionally substituted monocyclic or bicyclic aryl, or an optionally substituted monocyclic or bicyclic heteroaryl.

10. The compound according to claim 1, wherein:

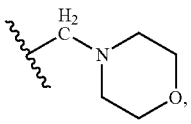 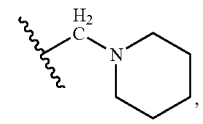

$R^{20}$ is selected from H, —$CH_2$—N($CH_3$)$_2$,

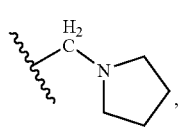 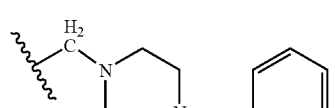

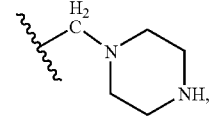 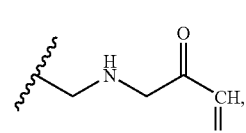

-continued

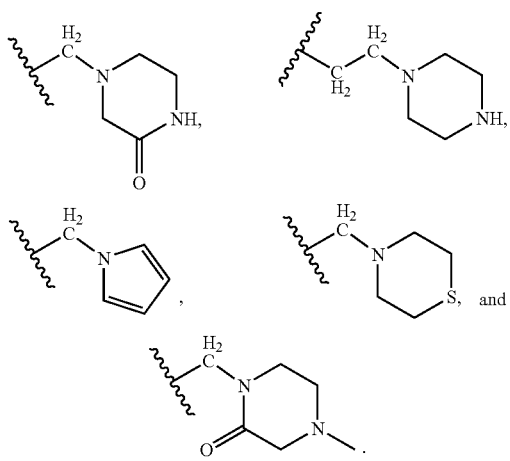

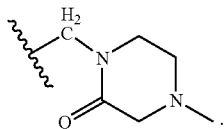

11. The compound according to claim 1, wherein:

$R^{31}$ is selected from phenyl, pyrazolyl, furyl, pyridyl, pyrimidinyl, thienyl, naphthyl, benzopyrazolyl, benzofuryl, quinolinyl, quinoxalinyl, or benzothienyl and wherein $R^{31}$ is optionally substituted.

12. The compound according to claim 2, wherein:

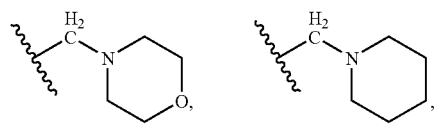

$R^{20a}$ is selected from H, —CH$_2$—N(CH$_3$)$_2$,

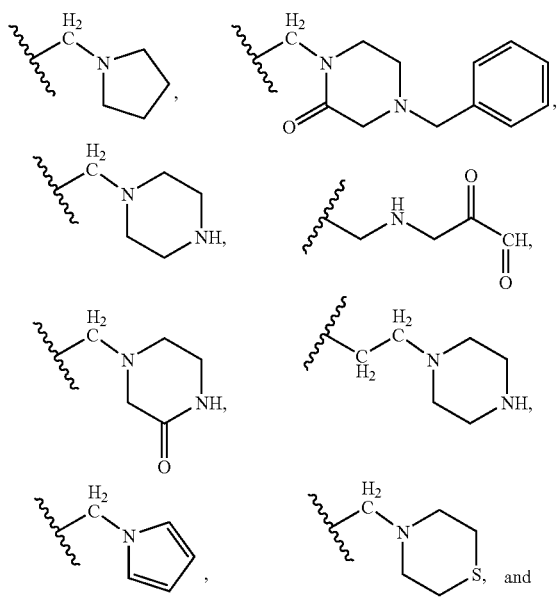

13. The compound according to claim 2, wherein:

$R^{31}$ is selected from phenyl, pyrazolyl, furyl, pyridyl, pyrimidinyl, thienyl, naphthyl, benzopyrazolyl, benzofuranyl, quinolinyl, quinoxalinyl, or benzothienyl and wherein $R^{31}$ is optionally substituted.

14. The compound according to claim 3, wherein:

$R^{32}$ is selected from pyrrolyl, pyrazolyl, pyrazinyl, furyl, pyridyl, pyrimidinyl, or thienyl, and $R^{32}$ is optionally substituted and is optionally benzofused.

15. The compound according to claim 3, wherein $R^{32}$ is selected from benzofuryl, methylfuryl, benzothienyl, pyridyl, pyrazinyl, pyrimidinyl, pyrazolyl, wherein said methyfuryl, pyridyl, pyrazinyl, pyrimidinyl or pyrazolyl is optionally benzofused and wherein $R^{32}$ is optionally substituted or further substituted.

16. A composition comprising a compound of claim 1, wherein the composition is pyrogen-free.

17. A composition comprising a compound of claim 2, wherein the composition is pyrogen-free.

18. A composition comprising a compound of claim 3, wherein the composition is pyrogen-free.

19. A composition comprising a compound of claim 4, wherein the composition is pyrogen-free.

20. A composition comprising a compound of claim 5, wherein the composition is pyrogen-free.

21. A pharmaceutical composition comprising a pharmaceutically acceptable carrier or diluent and a compound of claim 1.

22. A pharmaceutical composition comprising a pharmaceutically acceptable carrier or diluent and a compound of claim 2.

23. A pharmaceutical composition comprising a pharmaceutically acceptable carrier or diluent and a compound of claim 3.

24. A pharmaceutical composition comprising a pharmaceutically acceptable carrier or diluent and a compound of claim 4.

25. A pharmaceutical composition comprising a pharmaceutically acceptable carrier or diluent and a compound of claim 5.

26. A packaged pharmaceutical comprising a compound of claim 1.

27. A packaged pharmaceutical comprising a compound of claim 2.

28. A packaged pharmaceutical comprising a compound of claim 3.

29. A packaged pharmaceutical comprising a compound of claim 4.

30. A packaged pharmaceutical comprising a compound of claim 5.

* * * * *